(12) United States Patent
Subasinghe et al.

(10) Patent No.: US 7,109,354 B2
(45) Date of Patent: Sep. 19, 2006

(54) THIOPHENE AMIDINES, COMPOSITIONS THEREOF, AND METHODS OF TREATING COMPLEMENT-MEDIATED DISEASES AND CONDITIONS

(75) Inventors: Nalin Subasinghe, West Chester, PA (US); Ehab Khalil, West Chester, PA (US); Kristi Leonard, West Chester, PA (US); Farah Ali, Exton, PA (US); Heather Rae Hufnagel, Glenmoore, PA (US); Jeremy M. Travins, Newtown Square, PA (US); Shelley K. Ballentine, Lansdale, PA (US); Kenneth T. Wilson, West Grove, PA (US); Maxwell D. Cummings, Wayne, PA (US); Wenxi Pan, Glenmoore, PA (US); Joan Gushue, Collegeville, PA (US); Sanath Meegalla, Boothwyn, PA (US); Mark Wall, Harleysville, PA (US); Jinsheng Chen, Exton, PA (US); M. Jonathan Rudolph, Exton, PA (US); Hui Huang, Belle Mead, NJ (US)

(73) Assignee: 3-Dimensional Pharmaceuticals, Inc., Yardley, PA (US)

( * ) Notice: Subject to any disclaimer, the term of this patent is extended or adjusted under 35 U.S.C. 154(b) by 70 days.

(21) Appl. No.: 10/445,817

(22) Filed: May 28, 2003

(65) Prior Publication Data

US 2004/0009995 A1 Jan. 15, 2004

Related U.S. Application Data

(60) Provisional application No. 60/383,130, filed on May 28, 2002.

(51) Int. Cl.
*C07D 333/02* (2006.01)
*C07D 333/32* (2006.01)
(52) U.S. Cl. .......................... 549/29; 549/64; 549/70; 549/83
(58) Field of Classification Search ................ 549/29, 549/64, 70, 83
See application file for complete search history.

(56) References Cited

U.S. PATENT DOCUMENTS

| 4,510,130 A | 4/1985 | Platt et al. ....................... 514/2 |
| 4,634,783 A | 1/1987 | Fujii et al. |
| 4,722,890 A | 2/1988 | Sanders et al. ................. 435/7 |
| 4,727,064 A | 2/1988 | Pitha ............................ 514/58 |
| 4,764,604 A | 8/1988 | Mueller ...................... 536/103 |
| 4,916,219 A | 4/1990 | Linhardt et al. ............... 536/21 |
| 5,024,998 A | 6/1991 | Bodor ........................... 514/58 |
| 5,268,363 A | 12/1993 | Nicholson-Weller ......... 514/21 |
| 5,466,811 A | 11/1995 | Alexander ................... 546/283 |
| 5,472,939 A | 12/1995 | Fearon et al. ................... 514/8 |
| 6,410,587 B1 | 6/2002 | Grainger et al. ............ 514/445 |
| 6,410,733 B1 | 6/2002 | Pastor et al. ................. 546/168 |
| 6,562,840 B1 | 5/2003 | Illig et al. .................... 514/312 |

FOREIGN PATENT DOCUMENTS

| EP | 0 983 982 B1 | 3/2000 |
| WO | WO 99/20608 | 4/1999 |
| WO | WO 00/47578 | * 8/2000 |

OTHER PUBLICATIONS

Adachi, H. et al., "Effects of cyclosporine, aspirin, and cobra venom factor on discordant cardiac xenograft survival in rats," *Trans. Proc.*, Feb. 1987, 19(1), 1145-1148.

Ahrenstedt, Ö., et al., "Enhanced local production of complement components in the small intestines of patients with Crohn's disease," *New Engl. J. Med.*, 1990, 322, 1345-1349.

Ashworth, R. De B., et al., "Synthetic antimalarials. Part XXXVII. Some $N^1$-p-Chlorophenyl-$N^2$ : $N^4$ : $N^5$-trialkyldiguanides and other related miscellaneous diguanide types," *J. Chem. Soc.*, 1949, 475-482.

Badalamente, M.A., et al., "Neuromuscular recovery using calcium protease inhibition after median nerve repair in primates," *Proc. Natl. Acad. Sci. USA*, Aug. 1989, 86, 5983-5987.

Biesecker, G., et al., "Renal localization of the membrane attack complex in systemic lupus erythematosus nephritis," *J. Exp. Med.*, Dec. 1981, 154, 1779-1794.

Biesecker, G., et al., "Cutaneous localization of the membrane attack complex in discoid and systemic lupus erythematosus," *N. Engl. J. Med.*, Feb. 1982, 306, 264-270.

(Continued)

*Primary Examiner*—James O. Wilson
*Assistant Examiner*—Paul V. Ward

(57) ABSTRACT

Disclosed is a method for treating the symptoms of an acute or chronic disorder mediated by the classical pathway of the complement cascade, comprising administering to a mammal in need of such treatment a therapeutically effective amount of a compound of Formula I

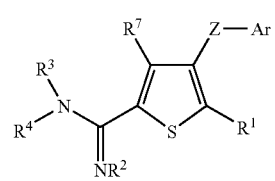

or a solvate, hydrate or pharmaceutically acceptable salt thereof; wherein $R^1$, $R^2$, $R^3$, $R^4$ and $R^7$ are defined in the specification, Z is SO or $SO_2$, and Ar is an aromatic or heteroaromatic group as defined herein.

16 Claims, No Drawings

OTHER PUBLICATIONS

Bone, R.C., "Modulators of coagulation," *Arch. Intern. Med.*, Jul. 1992, 152, 1381-1389.

Carvalho, A.C., et al., "Activation of the contact system of plasma proteolysis in the adult respiratory distress syndrome," *J. Lab. Med.*, 1988, 112, 270-277.

Chavez-Cartaya, RE., et al., "Regulation of the complement cascade by soluble complement receptor type 1," *Transplantation*, Apr. 15, 1995, 59(7), 1047-1052.

Chenoweth, D.E., et al., "Anaphylatoxin formation in extracorporeal circuits," *Complement*, 1986, 3, 152-165.

Cochrane, C.G., "The role of complement in experimental disease models," *Springer Seminar Immunopathol.*, 1984, 7, 263-270.

Colman, R.W., "The role of plasma proteases in septic shock," *New Engl. J. Med.*, May 4, 1989, 320(18), 1207-1209.

Couser, W.G., et al., "Complement and the direct mediation of immune glomerular injury: a new perspective," *Kidney Inst.*, 1985, 28, 879-890.

Curran, D.P., et al., Stille couplings with fluorous tin reactants: attractive features for preparative organic synthesis and liquid-phase combinatorial synthesis, *J. Org. Chem.*, 1996, 61(19), 6480-6481.

Dahl, M.V., et al., "Membrane attack complex of complement in dermatitis herpetiformis," *Arch. Dermatol.*, Jan. 1985, 121, 70-72.

Dahl, M.V., et al., "Deposition of the membrane attack complex of complement in bullous pemphigoid," *J. Invest. Dermatol.*, 1984, 82(2), 132-135.

Dai, C., et al., "The first general method for palladium-catalyzed negishi cross-coupling of aryl and vinyl chlorides: use of commercially available Pd(P9t-Bu)$_3$)$_2$ as a catalyst," *J. Am. Chem. Soc.*, 2001, 123, 2719-2724.

Dell'Erba, C., et al., "A 13C N.M.R. study of 5-Cyano-, 5-Methoxycarbonyl-, 5-Carbamoyl-, and 5-Acetyl-3-nitro-2-X-thiophenes: substituent effects and their relation to the charge distribution in corresponding 2,2-dimethoxy meisenheimer adducts," *J. Chem. Soc., Perkins Trans.*, 1989, 2, 1779-1782.

Dell'Erba, C., et al., "Thiophene Series—VI* Substituent effect on the rate of nucleophilic substitution: kinetics of the reaction between 2-Bromo-3-Nitro-5-X-Thiophenes and piperidine in ethanol," *Tetrahedron*, 1965, 21, 1061-1066.

Demling, R.H., et al., "The lung inflammatory response to thermal injury: relationship between physiologic and histologic changes," *Surgery*, 1989, 106, 52-59.

Deppisch, R., et al., "Fluid phase generation of terminal complement complex as a novel index of bioincompatibility," *Kidney Inst.*, 1990, 37, 696-706.

Doyle, M.P., et al., "Alkyl nitrite—metal halide deamination reactions. 2. substitutive deamination of arylamines by alkyl nitrites and copper(II)halides. A direct and remarkably efficient conversion of arylamines to aryl halides," *J. Org. Chem.*, 1977, 42(14), 2426-2431.

Eisen, H.N., "An introduction to molecular and cellular principles of the immune responses," *Immunology*, Harper & Row Publishers, Inc., Hager stown, MD, 1974, 512-525.

Falk, R.J., et al., "radioimmunoassay of the attack complex of complement in sera from patients with glomerulonephritis," *Clin. Research*, 1984, 32(2), 503A (abstract).

Falk, R.J., et al., "Neoanigen of e polymerized nin omponen of omplemen," *J. Clin. Invest.*, Aug. 1983, 72, 560-573.

Fearon, D.T., "Ani-inflammatory and immunosuppressive effects of recombinant soluble complement receptors," *Clin. Exp. Immunol.*, 1991, 86(Suppl. 1), 43-46.

Feasby, T.E., et al., "Complement depletion suppresses Lewis rat experimental allergic neuritis," *Brain Res.*, 1987, 419, 97-103.

Field, L., et al., "Methyl *p*-tolyl sulfone," *Organic Synthesis*, John Wiley & Sons, 1963, vol. IV, 674-677.

Frost, C.G., et al., "Recent development in aromatic heteroatom coupling reactions," *J. Chem. Soc., Perkins Trans.*, 1998, 1, 2615-2623.

Gelfand, J.A., et al., "Alternative complement pathway activation increases mortality in a model of burn injury in mice," *J. Clin. Invest.*, Dec. 1982, 70, 1170-1176.

Guttman, R.D., "Genetics of acute rejection of rat cardiac allografts and a model of hyperacute rejection," *Transplantation*, 1974, 17(4), 383-387.

Hack, C.E., et al., "Elevated plasma levels of the anaphylatoxins C3a and C4a are associated with a fatal outcome in sepsis," *Am. J. Med.*, Jan. 1989, 86, 20-26.

Hazelton, C.J., et al., "2H-benzimidazoles (Isobenzimidazoles). Part 9.[1] Synthesis and reactions of 4,6-dibromo-2H-benzimidazole-2-spirocyclohexane," *Tetrahedron*, 1995, 51(19), 5597-5608.

Hill, J., et al., "Soluble complement receptor type 1 ameliorates the local and remote organ injury after intestinal ischemia-reperfusion in the rat," *J. Immunol.*, Sep. 1, 1992, 149(5), 1723-1728.

Ho, T.-L, et al., "Reduction of aromatic nitro compounds by titanium(III) chloride," *Synthesis*, Jan. 1974, p. 45 (abstract).

Huang, J., et al., "Neuronal protection in stroke by an sLe$^x$-glycosylated complement inhibitory protein," *Science*, Jul. 23, 1999, 285, 595-599.

Ishiyama, T., et al., "Palladium(0)-catalyzed cross-coupling reaction of alkoxydiboron with haloarenes: a direct procedure for arylboronic esters," *J. Org. Chem.*, 1995, 60, 7508-7510.

Jiang, G., et al., "GnRH antagonists: a new generation of long acting analogues incorporating p-ureido-phenylalanines at positions 5 and 6," *J. Med. Chem.*, 2001, 44, 453-467.

Kim, S., et al., 1,1'-thiocarbonyldi-2,2'-pyridone. A new useful reagent for functional group conversions under essentially neutral conditions, *J. Org. Chem.*, 1986, 51, 2613-2615.

Knechtle, S.J., et al., "The effect of cyclosporine, total lymphoid irradiation, and cobra venom factor on hyperacute rejection," *J. Heart Transplant*, Sep./Oct. 1985, 4(5), 541-545.

Kojima, H., et al., "Terminal complement complex: Activation of complement by hemodialysis membrane," *Nippon Jenzo Gakkai Shi*, 1989, 31, 91-97 (English Abstract).

Krutosikova, A., et al., "Synthesis of 2-arylfuro[3,2-c]pyridines and their derivatives," *Collect. Czech. Chem. Commun.*, 1996, 61, 1627-1636.

Lam, P.Y.S., et al., "Copper-catalyzed C-N and C-O bond cross-coupling with arylboronic acid," *Tetrahedron Letters*, 2001, 42, 3415-3418.

Langlois, P.F., et al., "Accentuated complement activation in patient plasma during the adult respiratory distress syndrome: a potential mechanism for pulmonary inflammation," *Heart Lung*, Jan. 1989, 18(1), 71-84.

Liebeskind, L.S., et al., "3-stannylcyclobutenediones as nucleophilic cyclobutenedione equivalents. Synthesis of substituted cyclobutenediones and cyclobutenedione monoacetals and the beneficial effect of catalytic copper iodide on the stille reaction," *J. Org. Chem.*, 1990, 55, 5359-5364.

Linney, I.D., et al., "Design, synthesis, and structure—activity relationships of novel non-imidazole histamine H$_3$ receptor antagonists," *J. Med. Chem.*, 2000, 43, 2362-2370.

Liszewski, M.K., et al., "Novel complement inhibitors," *Exp. Opin. Invest. Drugs*, 1998, 7(3), 323-331.

Littke, A.F., et al., "Versatile catalysts for the Suzuki cross-coupling of arylboronic acids with aryl and vinyl halides and triflates under mild conditions," *J. Am. Chem. Soc.*, 2000, 122, 4020-4028.

Makrides, S.C., "Therapeutic inhibition of the complement system," *Am. Soc. For Pharmacol. Experi. Therap.*, 1998, 50(1), 59-87.

Martinez-Brotons, F., et al., "Plasma kallikrein-kinin system in patients with uncomplicated sepsis and septic shock—comparison with cardiogenic shock," *Thromb Haemostas.*, 1987, 58(2), 709-713.

Miyaura, N., et al., "Palladium-catalyzed cross-coupling reactions of organoboron compounds," *Chem. Rev.*, 1995, 95(70, 2457-2483).

Monache, G.D., et al., "Novel hypotensive agents from *verbesina caracasana*. 2. Synthesis and pharmacology of caracasanamide," *J. Med. Chem.*, 1993, 36, 2956-2963.

Mundla, S.R., et al., "A novel method for the efficient synthesis of 2-arylamino-2-imidazolines," *Tetrahedron Lett.*, 2000, 41, 6563-6566.

Murata, M., et al., "Palladium-catalyzed borylation of aryl halides or triflates with dialkoxyborane: a novel and facile synthetic route to arylboronates," *J. Org. Chem.*, 2000, 65, 164-168.

Naka, Y., et al., "Complement activation as a cause for primary graft failure in an isogeneic rat model of hypothermic lung preservation and transplantation," *Transplantation*, Nov. 15, 1997, 64(9), 1248-1255.

Negishi, E., et al., "Selective carbon-carbon bond formation via transition metal catalysis, 3. A highly selective synthesis of unsymmetrical biaryls and diarylmethanes by the nickel-or-palladium-catalyzed reaction of aryl-and benzylzinc derivatives with aryl halides," *J. Org. Chem.*, 1977, 42(10), 1821-1823.

Parillo, J.E., et al., "Septic shock in humans; Advances in the understanding of pathogenesis, cardiovascular dysfunction, and therapy," *Ann. Of Int. Med.*, 1990, 113, 227-242.

Paterson, I., et al., "1,6-asymmetic induction in boron-nmediated aldol reactions: application to a practical total synthesis of(+)-discodermolide," *Org. Lett.*, 2003, 5(1), 35-38.

Pemberton, M., et al., "Microvascular effects of complement blockade with soluble recombinant CR1 on ischemia/reperfusion Injury of skeletal muscle," *J. of Immunol.*, Jun. 1, 1993, 150(11), 5104-5113.

Phillion, D.P., et al., "Synthesis and reactivity of diethyl phosphonomethyltriflate," *Tetrahedron Lett.*, 1986, 27(13), 1477-1480.

Ramsay, G.C., et al., "Effects of quenchers on photoreduction of p-benzoylbenzenesulfonic acid in aqueous 2-propanol," *J. Am. Chem. Soc.*, Mar. 10, 1971, 93(5), 1166-1171.

Reike, R.D., "New organometallic reagents using highly reactive metals," *Tetrahedron*, 1997, 53(6), 1925-1956.

Roitt, I.M., et al., "Complement," *Immunology*, Gower Medical Publishing, London, NY, 1985, Chapter 7, 7.1-7.14.

Rousselet, G., et al., "Copper(I)-induced addition of amines to unactivated nitriles: the first general one-step synthesis of alkyl amidines," *Tetrahedron Lett.*, 1993, 34(40), 6395-6498.

Ruzziconi, R., et al., "First general approach to cyclohex-3-ene-1,1-bis(phosphonates) by diels-alder cycloaddition of tetraethyl vinylidenebis(phosphonate) to 1,3-dienes," *J. Org. Chem.*, 2003, 68, 736-742.

Salama, A., et al., "Deposition of terminal C5b-9 complement complexes on erythrocytes and leukocytes during cardiopulmonary bypass," *N. Engl. J. Med.*, Feb. 18, 1988, 318, 408-414.

Sanders, M.E., et al., "The terminal complement cascade is activated in cerebrospinal fluid (CSF) in Guillan-Barre syndrome (GBS) and multiple sclerosis (MS)," *Clin. Research*, 1985, 33, 388A (abstract).

Sanders, P.W., et al., "Catabolism of human complement factor D (D) by the rat proximal tubule," *Clin. Research*, 1985, 33, 388A (abstract).

Saulnier, M.G., et al., "An efficient method for the synthesis of guanidine prodrugs," *Bioorg. Med. Chem. Lett.*, 1994, 4(16), 1985-1990.

Schmiechel, C.J., et al., "Septic shock what do physicians want?," *BioTechnol.*, Mar. 1990, 10, 264-267.

Sidler, D.R., et al., Aluminum-amine complexes for the conversion of carboxylic esters to amides. Application to the synthesis of $LTD_4$ antagonist*J. Org. Chem.*, Mar. 25, 1994, 59(6), 1231-1233.

Spiegel, K., et al., "Strategies for inhibition of complement activation in the treatment of neurodegenerative diseases," in *Neuroinflammation: Mechanisms and Management*, Wood (Ed.), Humana Press, Inc., Totowa, NJ, Chapter 5, 129-176.

Stanetty, P., et al., "synthesis of thieno[3,2-d] [1,2,3] *thiadiazoles. New mechanistic aspects of the hurd-mori reaction,"* Heterocycles, 1998, 48(2), 259-266.

Staubli, U., et al., "Chronic administration of a thiol-proteinase inhibitor blocks long-term potentiation of synaptic responses," *Brain Research*, 1988, 444, 153-158.

Stille, J.K., "The palladium-catalyzed cross-coupling reactions of organotin reagents with organic electrophiles," *Angew. Chem., Int. Ed. Engl.*, 1986, 25, 508-524.

Thijs, L.G., et al., "Activation of the complement system during immunotherapy with recombinant IL-2," *J. Immunol.*, Mar. 15, 1990, 144, 2419-2424.

Towsend, C.A., et al., "Studies of methoxymethyl-directed metalation," *Tetrahedron Lett.*, 1981, 22(40), 3923-3924.

Wakefield, B.J. Organolithium Methods, Academic, San Diego, 1990.

Wakefield, B.J., The Chemistry of Organolithium Compounds, Pergamon, Oxford, 1974.

Watson, W.C., et al., "Genetic susceptibility to murine collagen II autoimmune arthritis," *J. Exp. Med.*, Dec. 1985, 162, 1878-1891.

Weisman, H.F., et al., "Soluble human complement receptor type 1: in vivo inhibitor of complement suppressing post-ischemic myocardial inflammation and necrosis," *Science*, Jul. 13, 1990, 249, 146-151.

Winkle, M.R., "Regioselective metalation reactions of some substituted (Methoxymethoxy) arenes," *J. Am. Chem. Soc.*, 1982, 47(11), 2101-2108.

Wolfe, J.P., et al., "Simple, efficient catalyst system for the palladium-catalyzed amination of aryl chlorides, bromides, and triflates," *J. Org. Chem.*, 2000, 65, 1158-1174.

Wolfe, J.P., et al., "Rational development of practical catalysts for aromatic carbon—nitrogen bond formation," *Acc. Chem. Res.*, 1998, 31, 815-818.

Wolfe, J.P., et al., "Nickel-catalyzed amination of aryl chlorides," *J. Am. Chem. Soc.*, 1997, 119, 6054-6058.

Wolfe, J.P., et al., "Highly active palladium catalysts for Suzuki coupling reactions," *J. Am. Chem. Soc.*, 1999, 121, 9550-9561.

Xu, Y., et al., "preparation of new wittig reagents and their application to the synthesis of α,β-unsaturated phosphonates," *J. Org. Chem.*, 1996, 61, 7697-7701.

Yamanaka, H., et al., "Studies on pyrimidine derivatives, XXXIX[1]) site-selectivity in the reaction of 5-substituted and 4,5-disubstituted pyrimidine N-oxides with trimethylsilyl cyanide," *Chem. Pharm. Bull.*, 1987, 35(8), 3119-3126.

Zilow, G., et al., "Complement activation and the prognostic value of C3a in patients at the risk of adult respiratory distress syndrome," *Clin. Exp. Immunol.*, 1990, 79, 151-157.

Copy of the PCT International Search Report dated Oct. 24, 2003 (PCT/US03/16888).

European Search Report dated Sep. 26, 2005, for corresponding EP application 03755527.3.

* cited by examiner

THIOPHENE AMIDINES, COMPOSITIONS THEREOF, AND METHODS OF TREATING COMPLEMENT-MEDIATED DISEASES AND CONDITIONS

This application claims priority under 35 U.S.C. §119(e) to U.S. Provisional Application No. 60/383,130, filed May 28, 2002, which is fully incorporated by reference herein.

BACKGROUND OF THE INVENTION

1. Field of the Invention

The present invention is in the field of medicinal chemistry. In particular, the invention is directed to novel heterocyclic amidines and their use for inhibiting the enzyme C1s, a protease in the classical pathway of the complement system; and the use of this inhibition to treat or ameliorate acute or chronic disorders in mammals.

2. Related Art

The immune system of the human body is equipped with several defense mechanisms to respond to bacterial, viral, or parasitic infection and injury. One such defense mechanism involves the complement system. Complement consists of a complex series of approximately 30 plasma and membrane protein components, many of which are proteinases. Once activated, this system of enzymes non-specifically complements the immunologically specific effects of antibody by modulating the immune response, lysing target cells, stimulating vascular and other smooth muscle cells, facilitating the transport of immune complexes, producing anaphylatoxins which cause degranulation of mast cells and release of histamine, stimulating chemotaxis (migration) of leukocytes toward the area of complement activity, activating B lymphocytes and macrophages, and inducing phagocytosis and lysis of cells (Eisen, H. N., *Immunology*, Harper & Row Publishers, Inc., Hagerstown, Md., p. 512 (1974); Roitt, I. et al., *Immunology*, Gower Medical Publishing, London, N.Y., pp. 7.1–7.14 (1985); U.S. Pat. Nos. 5,472,939 and 5,268,363).

The complement system functions as a "cascade." The enzyme cascades are initiated when inactive enzyme precursor molecules are activated, through limited proteolysis, by membrane-bound enzymes. A small fragment is lost from the enzyme precursor and a nascent membrane binding site is revealed. The major fragment then binds to the membrane as the next functionally active enzyme of the complement cascade. Since each enzyme is able to activate many enzyme precursors, the system forms an amplifying cascade, resembling the reactions seen in blood clotting and fibrinolysis (Roitt, I. et al., *Immunology*, Gower Medical Publishing, London, N.Y., pp. 7.1–7.14 (1985)).

The proteins of the complement system form two interrelated enzyme cascades, termed the classical and alternative pathways. The classical pathway is usually initiated by antigen-antibody complexes, while the alternative pathway is activated by specific polysaccharides, often found on bacterial, viral, and parasitic cell surfaces. The classical pathway consists of components C1–C9, while the alternative pathway consists of components C3–C9 (excluding C4) and several factors, such as Factor B, Factor D, and Factor H.

The sequence of events comprising the classical complement pathway consists of three stages: recognition, enzymatic activation, and membrane attack leading to cell death. The first phase of complement activation begins with C1. C1 is made up of three distinct proteins: a recognition subunit, C1q, and the serine proteinase subcomponents, C1r and C1s, which are bound together in a calcium-dependent tetrameric complex, $C1r_2s_2$. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, which in turn cleaves C3 to form C3a and C3b (Makrides, *Pharmacol. Rev.* 50:59–87 (1998); and U.S. Pat. No. 5,268,363). Both the classical and alternative pathways are capable of individually inducing the production of the C3 convertase to convert C3 to C3b, the generation of which is the central event of the complement pathway. C3b binds to C3b receptors present on neutrophils, eosinophils, monocytes and macrophages, thereby activating the terminal lytic complement sequence, C5–C9 (Roitt, I. et al., *Immunology*, Gower Medical Publishing, London, N.Y., pp. 7.1–7.14 (1985)).

Complement is designed to fight infection and injury; however, this same mechanism, if inappropriately activated, can cause a significant amount of inflammation and tissue damage as a result of the rapid and aggressive enzyme activity. Complement-induced inflammation and tissue damage has been implicated in a number of disease states, including: the intestinal inflammation of Crohn's disease which is characterized by the lymphoid infiltration of mononuclear and polymorphonuclear leukocytes (Ahrenstedt et al., *New Engl. J. Med.* 322:1345–9 (1990)), thermal injury (burns, frostbite) (Gelfand et al., *J. Clin. Invest.* 70:1170 (1982); Demling et al., *Surgery* 106:52–9(1989)), hemodialysis (Deppisch et al., *Kidney Inst.* 37:696–706 (1990); Kojima et al., *Nippon Jenzo Gakkai Shi* 31:91–7 (1989)), post pump syndrome in cardiopulmonary bypass (Chenoweth et al., *Complement. Inflamm.* 3:152–165 (1981); Chenoweth et al., *Complement* 3:152–165 (1986); Salama et al., *N. Engl. J. Med.* 318:408–14 (1988)), and ischaemia (Huang et al., *Science* 285:595 (1999); Naka et al., *Transplantation* 64:1248 (1997); Pemberton et al., *J. Immunol.* 150:5104 (1993); Chavez-Cartaya et al., *Transplantation* 59:1047 (1995); Hill et al., *J. Immunol.* 149:1723 (1992); Weisman et al., *Science* 249:146 (1990)). Both complement and leukocytes are reported to be implicated in the pathogenesis of adult respiratory distress syndrome (Zilow et al., *Clin. Exp. Immunol.* 79:151–57 (1990); Langlois et al., *Heart Lung* 18:71–84 (1989)). Activation of the complement system is suggested to be involved in the development of fatal complications in sepsis (Hack et al., *Am. J. Med.* 86:20–26 (1989)) and causes tissue injury in animal models of autoimmune diseases such as immune-complex-induced vasculitis (Cochrane, *Springer Seminar Immunopathol.* 7:263 (1984)), glomerulonephritis (Couser et al., *Kidney Inst.* 29:879 (1985)), type II collagen-induced arthritis (Watson & Townes, *J. Exp. Med.* 162:1878 (1985)), and experimental allergic neuritis (Feasby et al., *Brain Res.* 419:97 (1987)). The complement system is also involved in hyperacute allograft and hyperacute xenograft rejection (Knechtle et al., *J. Heart Transplant* 4(5):541 (1985); Guttman, *Transplantation* 17:383 (1974); Adachi et al.,*Trans. Proc.* 19(1): 1145 (1987)). Complement activation during immunotherapy with recombinant IL-2 appears to cause the severe toxicity and side effects observed from IL-2 treatment (Thijs et al., *J. Immunol.* 144:2419 (1990)).

Complement fragments generated by the classical portion of the complement cascade have been found to be present in the immune complexes formed against indigenous tissue in autoimmune diseases. Such diseases include, but are not limited to: Hashimoto's thyroiditis, glomerulonephritis and cutaneous lesions of systemic lupus erythematosus, other glomerulonephritides, bullous pemphigoid, dermatitis herpetiformis, Goodpasture's syndrome, Graves' disease, myasthenia gravis, insulin resistance, autoimmune hemolyic anemia, autoimmune thrombocytopenic purpura, and rheumatoid arthritis (Biesecker et al. *J. Exp. Med.* 154: 1779 (1981); Biesecker et al., *N. Engl. J. Med.* 306: 264 (1982); Falk et al., *Clin. Research* 32:503A (Abstract) (1984); Falk et al., *J. Clin. Invest.* 72:560 (1983); Dahl et al., *J. Invest. Dermatol.* 82:132 (1984); Dahl et al., *Arch. Dermatol.* 121:70 (1985); Sanders et al., *Clin. Research* 33:388A (Abstract) (1985); and U.S. Pat. Nos. 5,268,363 and 4,722,890).

Compounds that potently and selectively inhibit complement will have therapeutic applications in several acute and chronic immunological and non-immunological disorders, and a variety of neurodegenerative diseases. Evidence from both human and animal studies shows that activation of the classical complement pathway is primarily involved in neurodegenerative diseases of the central nervous system (CNS). Autoimmune diseases in which these inhibitors of the complement cascade system will be therapeutically useful include myasthenia gravis (MG), rheumatoid arthritis, and systemic lupus erythematosus. Neurodegenerative diseases in which inhibitors of the complement cascade system will be therapeutically useful include the demyelinating disorder multiple sclerosis (MS), the neuropathies Guillain-Barré syndrome (GBS) and Miller-Fisher syndrome (MFS), Alzheimer's disease (AD), and prion-related disease (variant Creutzfeld Jacob disease). Other diseases and conditions include hereditary and acquired angioedema (in which a deficiency in complement inhibitory protein leads to an active complement consumption and repeated episodes of life-threatening angiodema), septic shock, paroxysmal nocturnal hemoglobinuria, organ rejection (transplantation), bums (wound healing), brain trauma, soft tissue trauma, asthma, platelet storage, hemodialysis, ischemia-reperfusion injury, and cardiopulmonary bypass equipment (Makrides, *Pharmacol. Rev.* 50:59–87 (1998); Spiegel et al., Strategies for Inhibition of Complement Activation in the Treatment of Neurodegenerative Diseases in: *Neuroinflammation: Mechanisms and Management*, Wood (ed.), Humana Press, Inc., Totowa, N.J., Chapter 5, pp. 129–176; and U.S. Pat. No. 4,916,219).

A number of strategies have been proposed for the inhibition of primarily the classical complement pathway. Efforts to directly inhibit complement activation have focused on chemical compounds that inhibit complement components such as C1r and C1s. Small peptide inhibitors of convertases, such as the C3 and C5 convertases, have also been described (Liszewski and Atkinson, *Exp. Opin. Invest. Drugs* 7: 323–332 (1998). So far, the best studied 'designer' complement inhibitor for treatment of CNS disorders is soluble recombinant human complement receptor Type 1 (sCR1). sCR1 has proven effective in animal models of CNS diseases and is under investigation for use in man (Fearon, *Clin. Exp. Immunol.* 86 (Suppl.1):43–46 (1991)). However, there are several drawbacks to the use of sCR1 in disorders of the CNS: the agent is expensive, must be administered systemically, and has a short half-life in vivo. The next generation of complement inhibitors are likely to solve many of these drawbacks (Spiegel et al., Strategies for Inhibition of Complement Activation in the Treatment of Neurodegenerative Diseases in: *Neuroinflammation: Mechanisms and Management*, Wood (ed.), Humana Press, Inc., Totowa, N.J., Chapter 5, pp. 129–176).

A need continues to exist for non-peptidic compounds that are potent inhibitors of complement, specifically C1s, and which possess greater bioavailability and fewer side-effects than currently available C1s inhibitors. Accordingly, novel C1s inhibitors, characterized by potent inhibitory capacity, are potentially valuable therapeutic agents for a variety of conditions.

SUMMARY OF THE INVENTION

The present invention provides a novel class of thienyl amidines. The thienyl amides of Formula I inhibit the enzyme C1s, a protease in the classical pathway of the complement system, and thus, can be used to treat or ameliorate complement-mediated acute or chronic disorders in mammals.

Thus, a first aspect of the present invention is directed to novel compounds of Formula I.

In a second embodiment, the present invention provides a pharmaceutical composition comprising a compound of Formula I and a pharmaceutically acceptable carrier or diluent.

The present invention further provides a method for treating acute and chronic disorders associated with activation of the classical pathway of the complement system by administering to a mammal in need of such treatment a therapeutically effective amount of a compound of Formula I. These acute and chronic conditions are caused either in whole or in part by inflammation and tissue damage that result from aberrant activation of the complement cascade.

In one embodiment, compounds of Formula I can be administered to a mammal to treat complement-mediated inflammation and tissue damage. Examples of conditions that can be treated include intestinal inflammation of Crohn's disease, thermal injury (burns, frostbite), post pump syndrome in cardiopulmonary bypass, and ischaemia (stroke, myocardial infarction, ischaemic colitis, hemorrhagic shock, trauma, post-surgical tissue damage and delayed or impaired function of organ or graft following transplant).

The complement system is activated in hyperacute allograft and hyperacute xenograft rejection, and in acute humoral rejection mediated by donor-specific antibodies. Thus, in yet another embodiment, compounds of Formula I can be administered to a mammal before, during or after the transplant of an organ or a graft to ameliorate the rejection of such organ or graft by the mammal. Grafts can include an allograft or xenograft.

Complement activation during immunotherapy with recombinant IL-2 appears to cause acute vascular leak syndrome that results in the severe toxicity and side effects observed from IL-2 treatment and other conditions such as bone marrow transplantation and acute pancreatitis. In another embodiment of the present invention, a compound of Formula I is administered to a mammal before, during or after treatment of said mammal with IL-2, bone marrow transplantation, or onset of pancreatitis, in an amount effective to reduce the vascular leak syndrome that causes toxicity and side-effects associated with the treatment or disorders.

In another embodiment, compounds of Formula I can be administered to a mammal to treat complement-mediated tissue injury associated with autoimmune diseases. Examples of autoimmune diseases that are treatable according to the present invention include Hashimoto's thyroiditis, Addison's disease, glomerulonephritis and cutaneous lesions of systemic lupus erythematosus, other glomerulonephritides, bullous pemphigoid, pemphigus, Goodpasture's syndrome, Graves' disease, immune-complex-induced vasculitis, hemolytic anemia, myasthenia gravis, allergic neuritis, myasthenia gravis, Type I diabetes mellitus, autoimmune hemolytic anemia, autoimmune thrombocytopenic purpura, type II collagen-induced arthritis, and rheumatoid arthritis. Autoimmune diseases preferred for treatment by inhibitors of the present invention include myasthenia gravis (MG), rheumatoid arthritis, and systemic lupus erythematosus.

Another embodiment of the present invention is directed to administering a therapeutically effective amount of a compound of Formula I to a mammal that has been diagnosed with a neurodegenerative disease. Neurodegenerative diseases in which inhibitors of the complement cascade system will be therapeutically useful include the demyelinating disorder multiple sclerosis (MS), the neuropathies Guillain-Barré syndrome (GBS) and Miller-Fisher syndrome (MFS), Alzheimer's disease (AD), and variant Creutzfeldt-Jakob disease.

In another embodiment, compounds of the present invention can be administered to a mammal to treat complement-mediated complications in sepsis, or symptoms of adult respiratory distress syndrome.

Other diseases and conditions that can be treated include hereditary and acquired angioedema, paroxysmal nocturnal hemoglobinuria, brain trauma and other soft tissue trauma, asthma and hemodialysis.

Compounds of Formula I can also be employed in vitro for human organ and graft storage as well as platelet storage.

DETAILED DESCRIPTION OF THE INVENTION

Compounds useful in the present invention have the general Formula I:

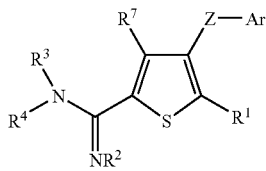

I or a solvate, hydrate or pharmaceutically acceptable salt thereof; wherein:

Z is —S(O)— or —S(O$_2$)—;

$R^1$ is $C_{1-4}$ alkyl, halo, amino, $C_{1-6}$ alkylthio, $C_{2-6}$ alkenylthio, $C_{1-6}$ alkoxy, trifluoromethyl, methylsulfonyl, or benzylthio; preferably halo, $C_{1-4}$ alkylthio or $C_{2-4}$ alkenylthio;

Ar is phenyl, naphthyl, pyridyl, imidazolyl, thiazolyl, furanyl, thienyl, benzothiazolyl, pyrazolyl, pyrimidinyl, benzimidazolyl, benzofuranyl, indolyl, benzothiophenyl or benzo[c]chromenyl, any of which is optionally substituted;

$R^2$, $R^3$ and $R^4$ are independently hydrogen, $C_{1-4}$ alkyl, $C_{6-10}$ aryl, $C_{1-4}$ hydroxyalkyl, $C_{1-4}$ aminoalkyl, mono $(C_{1-4})$alkylamino$(C_{2-6})$alkyl, di$(C_{1-4})$alkylamino$(C_{2-6})$alkyl, carboxy$(C_{1-4})$alkyl, cyano, amino, nitro, $C_{1-4}$ alkoxy, or hydroxy, or —CO$_2$R$^w$, where $R^w$ is hydrogen, hydroxy, $C_{1-4}$ alkoxy, cyano, $C_{1-4}$ alkoxycarbonyl, $C_{1-4}$ alkyl, $C_{3-8}$ cycloalkyl, phenyl, benzyl,

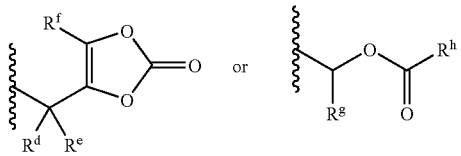

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is $C_{6-10}$ ar($C_{1-4}$)alkyl or $C_{1-6}$ alkyl; and $R^7$ is hydrogen, chloro, fluoro or amino.

A first preferred group of compounds falling within the scope of the present invention include compounds of Formula I wherein Ar is naphthyl or phenyl substituted by one or two of $C_{1-6}$ alkyl, $C_{1-6}$ alkoxy, $C_{2-6}$ alkenyl, halo, hydroxy, phenyl, phenoxy, amino or phenylamino. Useful values of Ar in this aspect of the invention include 2-phenylphenyl, naphth-2-yl, 2-methoxyphenyl, 4-methoxyphenyl, 4-chlorophenyl, 2-bromophenyl, 3,4-dimethylphenyl, 3-methoxyphenyl, 3-bromophenyl, 4-ethylphenyl, 4-bromophenyl, 4-phenylphenyl, 3,4-dimethoxyphenyl, 2-isopropylphenyl, 3,5-dichlorophenyl, 3-hydroxyphenyl, 2-methyl-5-t-butylphenyl, 4-t-butylphenyl, 3-bromo-5-t-butoxyphenyl, 3-bromo-5-hydroxyphenyl, 3-bromo-5-methoxyphenyl, 3-bromo-5-vinyloxyphenyl, 3-phenoxyphenyl, 5-bromo-3-methylphenyl and 2-aminophenyl.

Another group of compounds falling within the scope of the present invention include compounds of Formula I wherein Ar is phenyl substituted by one or two of $C_{1-6}$ alkyl, $C_{1-6}$ alkoxy, $C_{2-6}$ alkenyl, halo, hydroxy, phenyl, phenoxy, amino, phenylamino, hydroxytetrahydropyranyl, ($C_{1-4}$ alkoxy)-tetrahydropyranyl, hydroxypiperidinyl, hydroxy-N-($C_{1-4}$ alkyl)-piperidinyl, hydroxy-pyridinyl-($C_{1-4}$)alkyl or ($C_{1-4}$ alkoxy)carbonyl($C_{2-6}$)alkenyl. Additional useful values of Ar in this aspect of the invention include 4-amino-3-bromophenyl, 3-(4-hydroxytetrahydropyran-4-yl)-phenyl, 3-(4-hydroxy-1-methylpiperidin-4-yl)-phenyl, 3-(4-methoxytetrahydropyran-4-yl)-phenyl, 3-(hydroxy-pyridin-2-ylmethyl)-phenyl, 3-(1-ethoxycarbonyl-propen-2-yl)-phenyl, 3-chloro-4-fluorophenyl and 3-iodophenyl.

Another group of compounds falling within the scope of the present invention include compounds of Formula I wherein Ar is pyridyl, imidazolyl, furanyl, thienyl, thiazolyl, benzothiazolyl, benzofuranyl, benzothiophenyl, indolyl, benzimidazolyl or benzo[c]chromenyl, any of which is optionally substituted by one or two of $C_{1-6}$ alkyl, $C_{1-6}$ alkoxy, $C_{2-6}$ alkenyl, halo, hydroxy, amino, phenyl, phenoxy or tolyl. Useful values of Ar in this aspect of the invention include pyrid-2-yl, pyrid-3-yl, imidazol-2-yl, 1-methylimidazol-2-yl, 2-methylfuran-2-yl, thien-2-yl, thiazol-2-yl, 4-phenylthiazol-2-yl, 5-ethoxybenzothiazol-2-yl, benzimidazol-2-yl, 7-bromo-1-methyl-1H-benzoimidazolyl, 4-bromo-1-methyl-1H-benzoimidazolyl, 4-bromo-2-methyl-1H-benzoimidazolyl, 4-bromo-1H-benzoimidazolyl, 6-bromo-benzimidazolyl, pyrrol-2-yl, and piperdin-2-yl. An additional useful value of Ar in this aspect of the invention is 6H-benzo[c]chromen-2-yl.

Useful values of Ar in this aspect of the invention also include those of Formula IA:

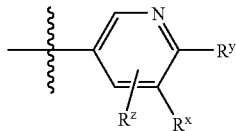

wherein:
R$^x$ is halo, or phenyl substituted by one or two Of C$_{1-6}$ alkyl or (C$_{1-4}$ alkyl)oxy(C$_{1-4}$)alkyl wherein one of the C$_{1-4}$ alkyl portions is optionally substituted by carboxy;
R$^y$ is hydrogen, amino, halo, phenoxy or C$_{1-6}$ alkylamino wherein the alkyl portion is optionally substituted by one of phenyl, pyridyl, tetrahydrofuranyl, imidazolyl, morpholinyl, (C$_{1-4}$ haloalkyl)-pyridyl, sulfonamidophenyl, hydroxy, (C$_{1-4}$ alkyl)-thienyl or aminopyrimidinyl; and
R$^z$ is hydrogen, halo or C$_{1-4}$ alkyl.

Useful values of R$^x$ include 2-methylphenyl, 2-carboxymethoxymethyl-6-methylphenyl and bromo.

Useful values of R$^y$ include hydrogen, chloro, amino, phenoxy, benzylamino, isopropylamino, pyrid-3-ylmethylamino, pyrid-4-ylmethylamino, pyrid-2-ylmethylamino, tetrahydrofuran-2-ylmethylamino, 3-(imidazol-1-yl)-propylamino, 2-methyl-2-(morpholin-4-yl)-propylamino, 6-trifluoromethyl-pyrid-3-ylmethylamino, 2-(3H-imidazol-1-yl)-ethylamino, 4-sulfamoylbenzylamino, 2,2-dimethyl-3-hydroxypropylamino, 3-methylthien-2-ylmethylamino and 4-aminopyrimidin-5-ylmethylamino.

Useful values of R$^z$ include hydrogen, methyl or ethyl.

Preferred values of R$^x$ include bromo. Preferred values of R$^y$ include optionally-substituted C$_{1-6}$ alkylamino. Preferred values of R$^z$ include hydrogen.

Useful values of Ar in this aspect of the invention also include those of Formula IB:

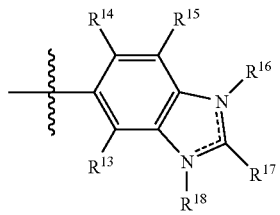

wherein:
R$^{13}$ and R$^{14}$ are independently hydrogen, halo or C$_{1-4}$ alkyl;
R$^{15}$ is hydrogen, halo or tolyl;
R$^{17}$ is hydrogen or C$_{1-4}$ alkyl; and
one of R$^{16}$ and R$^{18}$ is an electron pair and the other is hydrogen, C$_{1-6}$ alkyl, C$_{2-6}$ alkenyl, cyclopropylmethyl, phenyl, benzyl, 1-phenylethyl, pyridylmethyl or isoxazolylmethyl optionally substituted with one or two methyl groups, wherein said benzyl is unsubstituted or is substituted with one or two of halo, nitro, amino or (2-carboxyethyl)-sulfanylacetylamino.

Useful values of R$^{13}$ and R$^{14}$ include hydrogen, methyl and ethyl.

Useful values of R$^{15}$ include hydrogen, bromo, chloro and o-tolyl.

Useful values of R$^{17}$ include hydrogen, methyl and ethyl.

Useful values of R$^{16}$ and R$^{18}$, other than an electron pair, include hydrogen, methyl, cyclopropylmethyl, allyl, 3-methylbut-2-enyl, pyrid-2-ylmethyl, 3,5-dimethylisoxazol-4-ylmethyl, phenyl, 1-phenylethyl, benzyl, 2,6-dichlorobenzyl, 2,5-difluorobenzyl, 2,6-difluorobenzyl, 2-fluoro5-nitrobenzyl, 2-fluoro-4-nitrobenzyl, 2-fluoro-5-aminobenzyl and 5-[(2-carboxyethyl)-sulfanylacetylamino]-2-fluorobenzyl.

Preferred R$^{13}$ include hydrogen. Preferred R$^{14}$ include hydrogen. Preferred R$^{15}$ include bromo and chloro. More preferred is bromo. Preferred R$^{17}$ include hydrogen. Preferred R$^{16}$ and R$^{18}$, other than an electron pair, include hydrogen, phenyl, 1-phenylethyl, benzyl and benzyl substituted with one or two, preferably two, of halo, amino or nitro. More preferred are benzyl and benzyl substituted with two of fluoro, chloro, amino or nitro.

In yet another aspect of the invention, Ar is a substituted phenyl group having a required substituent in the 3-position of the phenyl ring and an optional substituent on one of the remaining positions of the phenyl ring. Thus, this aspect of the invention is directed to compounds of the overall Formula II:

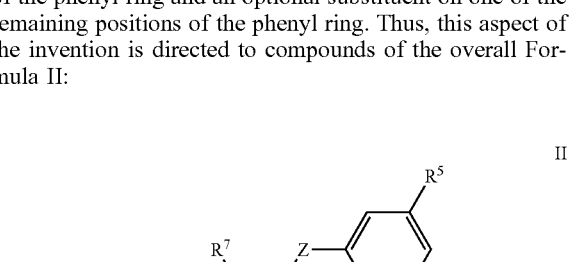

or a solvate, hydrate or pharmaceutically acceptable salt thereof; wherein:
R$^1$, R$^2$, R$^3$, R$^4$, R$^7$ and Z are defined as above, and
R$^5$ is phenyl, naphthyl, thienyl, furanyl, imidazolyl, oxazolyl, isoxazolyl, pyridyl, pyrimidinyl, benzothienyl, benzofuranyl, benzimidazolyl, quinolinyl, isoquinolinyl, pyrazinyl, piperidinyl or piperazinyl, any of which is optionally substituted; and
R$^6$ is hydrogen, C$_{1-4}$ alkyl, hydroxy, C$_{1-4}$ alkoxy, C$_{2-4}$ alkenyloxy, phenoxy, benzyloxy, halo, amino or nitro.

In one embodiment R$^5$ is naphthyl, phenyl or phenyl substituted by one to five, preferably one or two groups independently selected from the group consisting of C$_{1-4}$ alkyl, C$_{1-4}$ alkoxy, C$_{1-4}$ hydroxyalkyl, C$_{1-4}$ haloalkyl, C$_{2-4}$ alkenyl, (C$_{1-4}$ alkyl)carbonyl, cyano, amino, mono(C$_{1-4}$) alkylamino, di(C$_{1-4}$)alkylamino, formyl, (C$_{1-4}$ alkoxy)carbonyl, halo(C$_{1-4}$ alkoxy)carbonyl, phenyl, phenoxy, phenoxyphenyl, biphenyl, halo, C$_{1-4}$ haloalkoxy, carboxy, nitro, methylenedioxo (—O—CH$_2$—O—), ethylenedioxo, C$_{1-4}$ alkylsulfonyl, C$_{1-4}$ alkylsulfinyl, C$_{1-4}$ alkylthio, hydroxy, aminocarbonyl, mono(C$_{1-4}$alkyl)aminocarbonyl, di(C$_{1-4}$ alkyl)aminocarbonyl and halogenated C$_{1-4}$ hydroxyalkyl.

Useful values of R$^5$ in this embodiment include phenyl, 2-methoxyphenyl, 2-methylphenyl, 2-vinylphenyl, 2-hydroxymethylphenyl, 2-(1-hydroxyethyl)phenyl, 2-trifluoromethylphenyl, 2-formylphenyl, 2-hydroxyphenyl, 2-chloromethylphenyl, 2-amino, 2-chlorophenyl, 3-methoxyphenyl, 3-methylphenyl, 3-formylphenyl, 3-hydroxymethylphenyl, 3-aminophenyl, 3-isopropylphenyl, 3-ethoxyphenyl, 3-ethoxycarbonylphenyl, 3-methylcarbonylphenyl, 3-carboxyphenyl, 3-hydroxyphenyl, 3-nitrophenyl, 3-dimethylaminocarbonylphenyl, 3-trifluoromethylphenyl, 3-trifluoromethoxycarbonylphenyl, 4-vinylphenyl, 4-trifluoromethoxyphenyl, 4-methoxycarbonylphenyl, 4-methylphenyl, 4-hydroxymethylphenyl, 4-trifluoromethylphenyl, 4-cyanophenyl, 4-ethoxyphenyl, 4-dimethylaminophenyl, biphenyl, 4-phenoxyphenyl, 4-chloromethyl, 4-methylsulfonyl)phenyl, 4-hydroxyphenyl, 4-fluorophenyl, 2,5-dimethylphenyl, 2,3-dichlorophenyl, 2,3-dimethylphenyl, 2,5-dichlorophenyl, 3,5-dichlorophenyl, 3-hydroxy-4-phenylphenyl, 3,5-bistrifluoromethylphenyl, 2-hydroxy-5-phenylphenyl, 4-methyl-3-nitrophenyl, 3,4-methylenedioxophenyl, 3,5-dimethylphenyl, 2,4-dimethoxyphenyl, 2-ethoxy-6-methylphenyl, 3-isopropoxycarbonyl-2-methylphenyl, 3-fluoro-4-phenylphenyl, 4-formylphenyl, 2-carboxy-6-methylphenyl, 3-formyl-2-methylphenyl, 3-hydroxy-6-methylphenyl, 3-formyl-6-methylphenyl, 3-formyl-6-hydroxyphenyl, 3-formyl-6-methoxyphenyl, 2-amino-6-methylphenyl, 3,4-dimethoxyphenyl, 3-[(2,2,2-trifluoro-1-hydroxy)ethyl]phenyl, 4-nitrophenyl, 2-fluoro-4-phenylphenyl, 2,4-dimethoxyphenyl, 4-hydroxy-3-formylphenyl, 2-tolyl-5-morpholinephenyl, 4-methoxyphenyl, 3-hydroxyaminomethyl phenyl, 4-phenyl-acetamide, 4-benzamide, 2,6-dimethylphenyl, phenoxyphenyl, 2-methyl-6-hydroxymethyl phenyl, 2-methyl-5-hydroxymethyl phenyl, 2-hydroxy-3-phenylphenyl, naphthyl and 4-ethoxycarbonylphenyl. An additional useful value of $R^5$ is 6-methyl-3,4-methylenedioxophenyl.

In another embodiment $R^5$ is phenyl substituted by one to three groups independently selected from the group consisting of $C_{1-4}$ alkyl, $C_{1-4}$ alkoxy, $C_{1-4}$ hydroxyalkyl, $C_{1-4}$ haloalkyl, $C_{2-4}$ alkenyl, ($C_{1-4}$ alkyl)carbonyl, cyano, amino, mono($C_{1-4}$)alkylamino, di($C_{1-4}$)alkylamino, formyl, ($C_{1-4}$ alkoxy)carbonyl, halo($C_{1-4}$ alkoxy)carbonyl, phenyl, phenoxy, phenoxyphenyl, biphenyl, halo, $C_{1-4}$ haloalkoxy, carboxy, nitro, methylenedioxo (—O—$CH_2$—O—), ethylenedioxo, $C_{1-4}$ alkylsulfonyl, $C_{1-4}$ alkylsulfinyl, $C_{1-4}$ alkylthio, hydroxy, aminocarbonyl, mono($C_{1-4}$alkyl)aminocarbonyl, di($C_{1-4}$alkyl)aminocarbonyl, halogenated $C_{1-4}$ hydroxyalkyl, carboxy($C_{1-4}$)alkoxy($C_{1-4}$)alkyl, carboxy($C_{1-4}$)alkoxy, $C_{1-4}$ alkylthio($C_{1-4}$)alkyl wherein the alkyl portion of $C_{1-4}$ alkylthio is optionally substituted with one or two carboxy groups, phosphono($C_{2-4}$)alkenyl, phosphono($C_{1-4}$)alkylamino, $C_{1-4}$ haloalkylsulfonylamino, phosphono($C_{1-4}$)alkoxy, $C_{1-4}$ alkylsulfonylamino, carboxy($C_{1-4}$)alkylamino, morpholinyl($C_{1-4}$)alkyl, morpholinyl, morpholinyl($C_{1-4}$)alkylaminocarbonyl, piperazinyl($C_{1-4}$)alkyl or piperazinyl wherein either of said piperazinyl($C_{1-4}$)alkyl or piperazinyl is optionally N-substituted with methyl or ethyl, formylamino, morpholinyl($C_{1-4}$)alkylamino, optionally-substituted alkylcarbonylamino, optionally-substituted ureido and optionally-substituted guanidino.

Useful optionally-substituted alkylcarbonylamino groups have the formula —N(H)—C(O)—C(H)($W^1$)—$Y^{1a}$—$X^1$—$Y^{1b}$—$Z^1$, wherein:
$W^1$ is hydrogen or amino;
$Y^{1a}$ is a direct covalent bond or an α,ω-diradical of a $C_{1-10}$ straight or branched alkane;
$X^1$ is O or S, or a direct covalent bond;
$Y^{1b}$ is an α,ω-diradical of a $C_{1-10}$ straight or branched alkane, optionally substituted with a carboxy group or an amino group; and
$Z^1$ is carbamoyl, carboxy, $C_{1-6}$ alkylsulfonyl, ($C_{1-6}$ alkoxy)carbonyl, $C_{2-6}$ alkanoylamino, sulfo, phosphono, phenyl, aminosulfonyl, amino, $C_{1-6}$ haloalkylsulfonylamino, formylamino, $C_{1-6}$ alkylamino, $C_{1-6}$ alkylaminosulfonyl, $C_{1-6}$ alkylsulfonylamino or 2-oxo-hexahydro-thieno[3,4-d]imidazol-6-yl-($C_{1-6}$ alkyl)carbonylamino;
or, $W^1$ is hydrogen and $Y^{1a}$—$X^1$—$Y^{1b}$—$Z^1$ represents hydrogen, halo, amino or tri-($C_{1-4}$ alkyl)ammonio;
provided that, if $Y^{1a}$ is a direct covalent bond and X is O or S, then $W^1$ is hydrogen.
Useful optionally-substituted ureido groups have the formula —N($L^1$)—C(O)—N($L^2$)—$Y^{2a}$—$X^2$—$Y^{2b}$—$Z^2$, wherein:
$L^1$ and $L^2$ are both hydrogen, or $L^1$ and $L^2$ together represent ethylene or trimethylene;
$Y^{2a}$ is a direct covalent bond or an α,ω-diradical of a $C_{1-10}$ straight or branched alkane;
$X^2$ is O or S, or a direct covalent bond;
$Y^{2b}$ is an α,ω-diradical of a $C_{1-10}$ straight or branched alkane, optionally substituted with a carboxy group; and
$Z^2$ is carboxy, ($C_{1-6}$ alkoxy)carbonyl, phenoxy, carboxyphenoxy, $C_{1-6}$ alkylsulfonyl, phenyl, benzyloxycarbonylamino, amino, $C_{1-4}$ alkylamino, halophenyl, indolyl, diphenylmethyl, phenylsulfonylamino, N'-(carboxy ($C_{1-4}$)alkyl)ureido, tetrazolyl, phosphono or phenylamino;
or, $Y^{2a}$—$X^2$—$Y^{2b}$—$Z^2$ represents $C_{1-4}$ alkylsulfonyl or —($CH_2CH_2$—O—)$_m$—($CH_2$)$_n$—C(O)OR wherein m is an integer from 2 to 6, n is an integer from 2 to 4, and R is hydrogen or $C_{1-4}$ alkyl.
Useful optionally-substituted guanidino groups have the formula —N($L^3$)—C(=N$L^4$)—N($L^5$)—$Z^3$, wherein:
$L^3$ is hydrogen or $C_{1-4}$ alkyl;
$L^4$ and $L^5$ are both hydrogen, or $L^4$ and $L^5$ together represent ethylene; and
$Z^3$ is hydrogen, $C_{1-6}$ alkyl, phenyl($C_{1-6}$)alkyl, carboxy ($C_{1-6}$)alkyl, $C_{1-4}$ alkoxy, ($C_{1-4}$ alkyl)carbonyl or $C_{1-4}$ alkylsulfonyl($C_{1-6}$)alkyl.
One group of preferred compounds in this embodiment includes those wherein $R^5$ is phenyl substituted at the 2'-position by methyl and at the 4'-position by optionally-substituted guanidino. A more preferred group of compounds in this embodiment includes those wherein $R^5$ is phenyl substituted at the 2'-position by methyl, at the 4'-position by optionally-substituted guanidino, and at the 6'-position by optionally-substituted alkylcarbonylamino or optionally-substituted ureido. Another group of preferred compounds in this embodiment includes those wherein $R^5$ is phenyl substituted at the 2'-position by methyl and at the 6'-position by optionally-substituted alkylcarbonylamino or optionally-substituted ureido. Within these preferred groups, $R^1$ is preferably methylthio, $R^2$, $R^3$, $R^4$, $R^6$ and $R^7$ are preferably hydrogen, and Z is preferably —$SO_2$—.

Useful values of $R^5$ in this embodiment also include those of Formula IIA:

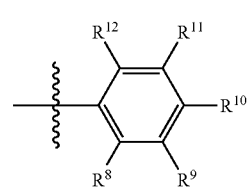

IIA wherein:

$R^8$ is hydrogen or methyl;

$R^9$ is hydrogen, formylamino or carbamoyl;

$R^{10}$ is methoxy, hydroxy, carboxymethoxy, phosphonomethylamino, trifluoromethanesulfonylamino, phosphonomethoxy, carboxymethylamino, amino, chloro, fluoro, 2-(morpholin-4-yl)-ethylamino, carboxy, carbamoyl, (1,2-dicarboxyethyl)-sulfanylacetylamino, carboxymethoxyacetylamino, 4-amino-4-carboxybutyrylamino, 6-[5-(2-oxo-hexahydro-thieno[3,4-d]imidazol-6-yl)-pentanoylamino]-hexanoylamino, bromoacetylamino, 2-amino-4-carboxybutyrylamino, triethylammonioacetylamino, 2-amino-4-methanesulfonylbutyrylamino, aminoacetylamino, carbamoylmethylsulfanylacetylamino, 3-phosphonopropionylamino, ureido, N'-(5-carboxypentyl)-ureido, N'-(5-ethoxycarbonylpentyl)-ureido, N'-(3-methanesulfonylpropyl)-ureido, guanidino, N'-(3-phenylpropyl)-guanidino, N'-(2-phenylethyl)-guanidino, N'-(3-methylbutyl)-guanidino, N'-acetylguanidino, N'-(4-methanesulfonylbutyl)-guanidino, N'-(3-methanesulfonylpropyl)-guanidino, N'-(6-methanesulfonylhexyl)-guanidino, N'-(5-methanesulfonylpentyl)-guanidino, N'-methoxyguanidino, N-methylguanidino, N'-hexylguanidino, N'-(5-carboxypentyl)-guanidino or 4,5-dihydro-1H-imidazol-2-ylamino;

$R^{11}$ is hydrogen, 3-(morpholin-4-yl)-propylaminocarbonyl or carboxymethoxymethyl; and $R^{12}$ is carboxymethoxymethyl, 2-carboxyethoxymethyl, nitro, amino, methyl, (1,2-dicarboxyethyl)-sulfanylmethyl, 2-phosphonovinyl, morpholin-4-ylmethyl, 4-methylpiperazin-1-ylmethyl, morpholin-4-yl, formylamino, methanesulfonylamino, carboxymethylamino, 3-(morpholin-4-yl)-propylaminocarbonyl, chloro, acetylamino, carbamoylmethylsulfanylacetylamino, (2-carboxyethyl)-sulfanylacetylamino, 4-methanesulfonylbutyrylamino, (1,2-dicarboxyethyl)-sulfanylacetylamino, methoxycarbonylmethoxyacetylamino, carboxymethoxyacetylamino, bromoacetylamino, 4-carboxybutyrylamino, carbamoylmethoxyacetylamino, (2-acetylamino-2-carboxy-1,1-dimethylethyl)-sulfanylacetylamino, (2-sulfoethyl)-sulfanylacetylamino, (2-methoxycarbonylethyl)-sulfanylacetylamino, (2-acetylamino-2-carboxyethyl)-sulfanylacetylamino, methanesulfonylacetylamino, 6-methanesulfonylhexanoylamino, 3-methanesulfonylpropionylamino, 2-methanesulfonylpropionylamino, benzylsulfanylacetylamino, 4-aminosulfonylbutyrylamino, 11-aminoundecanoylamino, 4-trifluoromethanesulfonylaminobutyrylamino, 5-carboxyvalerylamino, carboxyacetylamino, 3-carboxypropionylamino, 11-carboxyundecanoylamino, 5-methoxycarbonylvalerylamino, N'-ethoxycarbonylmethylureido, N'-carboxymethylureido, N'-[5-(4-carboxyphenoxy)-pentyl]-ureido, N'-(2-methanesulfonylethyl)-ureido, N'-(5-carboxypentyl)-ureido, N'-(2-[2-{2-(2-carboxyethoxy)-ethoxy}-ethoxy]-ethoxyethyl)-ureido, N'-methanesulfonylureido, N'-(4-methanesulfonylbutyl)-ureido, N'-(3-phenylpropyl)-ureido, N'-benzylureido, N'-(1-carboxy-2-phenylethyl)-ureido, N'-(5-benzyloxycarbonylamino-5-carboxypentyl)-ureido, N'-(2-phenylethyl)-ureido, N'-(5-amino-5-carboxypentyl)-ureido, N'-[2-(4-bromophenyl)-ethyl]-ureido, N'-[2-(indol-3-yl)-ethyl]-ureido, N'-(3,3-diphenylpropyl)-ureido, N'-(2-phenylsulfonylaminoethyl)-ureido, N'-(2-methanesulfonylaminoethyl)-ureido, N'-[2-(N'-carboxymethylureido)-ethyl]-ureido, N'-[2-(2H-tetrazol-5-yl)-ethyl]-ureido, N'-[4-(2H-tetrazol-5-yl)-butyl]-ureido, N'-[5-(2H-tetrazol-5-yl)-pentyl]-ureido, N'-(5-phosphonopentyl)-ureido, N'-(5-ethoxycarbonylpentyl)-ureido, N'-(3-methanesulfonylpropyl)-ureido, N'-(2-phenylaminoethyl)-ureido or 2-oxo-imidazolidin-1-yl.

One preferred group of compounds in this embodiment includes those wherein $R^8$ is methyl, and $R^9$ and $R^{11}$ are both hydrogen. Another preferred group of compounds in this embodiment includes those wherein $R^8$ is methyl, and $R^9$, $R^{11}$ and $R^{12}$ are all hydrogen. Another preferred group of compounds in this embodiment includes those wherein $R^8$ is methyl, and $R^9$, $R^{10}$ and $R^{11}$ are all hydrogen.

In an additional embodiment, $R^5$ is thienyl, furanyl, imidazolyl, oxazolyl, isoxazolyl, pyridyl, pyrimidinyl, benzothienyl, benzofuranyl, dibenzofuranyl, benzimidazolyl, quinolinyl, isoquinolinyl, indolyl or pyrazinyl, optionally substituted by one or two groups independently selected from the group consisting of $C_{1-4}$ alkyl, $C_{1-4}$ alkoxy, $C_{1-4}$ hydroxyalkyl, $C_{1-4}$ haloalkyl, $C_{2-4}$ alkenyl, formyl, $(C_{1-4}$ alkoxy)carbonyl, phenyl, $C_{1-4}$ alkylphenyl, phenoxy, halo, $C_{1-4}$ haloalkoxy, carboxy, hydroxy, nitro, amino, $C_{1-4}$ alkylsulfonyl($C_{1-4}$ alkyl)ureido, sulfo($C_{1-4}$)alkyl, trimethylsilanyl $(C_{1-4})$alkoxy$(C_{1-4})$alkyl and $C_{1-4}$ alkoxy$(C_{1-4})$alkyl.

Where $R^5$ is a heteroaryl group, useful values include thien-3-yl, quinolin-7-yl, 3,5-dimethylisoxazol-4-yl, 5-chlorothien-2-yl, pyrid-3-yl, pyrimidin-4-yl, quinolin-3-yl, benzothien-2-yl, benzofuran-2-yl, furan-2-yl, furan-3-yl, 4-methylpyrid-3-yl, 3-methyl-pyrid-2-yl, 6-methylbenzimidazol-5-yl, benzimidazol-6-yl, 1-methyl-4-(2'-methylphenyl)benzimidazol-6-yl, 2-methyl-4-(2'-methylphenyl)benzimidazol-6-yl, dibenzofuran-2-yl, 2-methylimidazolyl, 6-ethoxy-benzothiazolyl, 6-methyl-pyrid-3-yl, 6-chloro-pyrid-3-yl, and 3-chloro-pyrid-2-yl.

Where $R^5$ is a heteroaryl group, useful values also include 3-methyl-5-nitropyrid-2-yl, 5-amino-3-methylpyrid-2-yl, 4-methylpyrimidin-5-yl, 3-methylpyrid-2-yl, 2-chloropyrid-3-yl, 6-formylpyrid-2-yl, 3-methyl-5-[N'-(3-methanesulfonylprop-1-yl)]-ureidopyrid-2-yl, 3-methyl-pyrid-4-yl, 3-amino-5-methyl-pyrid-4-yl, 3-chloro-5-trifluoromethylpyrid-2-yl, 1H-benzimidazol-2-yl, 1-methyl-1H-benzimidazol-2-yl, 3-methyl-3H-imidazol-4-yl, 1H-imidazol-2-yl, 1-methyl-1H-imidazol-2-yl, 1-ethyl-1H-benzimidazol-2-yl, 2,5-dimethyl-1H-imidazol-4-yl, 1-(3-sulfoprop-1-yl)-1H-benzimidazol-2-yl, 3-methylpyrazin-2-yl, 5-methyl-1-(2-trimethylsilanyl-ethoxymethyl)-1H-benzimidazol-4-yl, 5-methyl-1H-benzimidazol-4-yl, 1-methyl-1H-benzimidazol-5-yl, 2-methoxymethyl-6-methyl-1H-benzimidazol-5-yl, 2,6-dimethyl-1H-benzimidazol-5-yl and 1,6-dimethyl-1H-benzimidazol-5-yl.

In an additional embodiment, $R^5$ is —$NR^aR^b$, wherein $R^a$ and $R^b$ are independently $C_{1-6}$ alkyl, or $R^a$ and $R^b$ together with the nitrogen atom to which they are attached form a ring selected from the group consisting of piperidinyl, pyrroldinyl, piperazinyl, imidazolidinyl, pyrazolidinyl and morpholinyl, wherein said ring is optionally substituted by one or two $C_{1-4}$ alkyl groups. In this embodiment, useful values of $R^5$ include piperidin-1-yl and 4-methylpiperazin-1-yl.

Useful values of $R^6$ include hydrogen, methyl, halo, amino, methoxy, ethoxy, vinyloxy, hydroxy and benzyloxy.

For each embodiment above, preferred values of $R^1$ include bromo, methylthio, ethylthio or prop-2-en-1-ylthio, more preferably bromo or methylthio, most preferably methylthio.

One useful value of Z is $SO_2$. An additional value of Z is SO.

Preferred values of $R^2$, $R^3$ and $R^4$ are independently hydrogen, $C_{1-6}$ alkyl, amino, cyano, $C_{1-4}$ alkoxy or hydroxy, and are preferably all hydrogen. Useful values of $R^2$, $R^3$ and $R^4$ include hydrogen, methyl, ethyl, propyl, n-butyl, hydroxy, methoxy, and ethoxy.

Additional preferred values of $R^2$, $R^3$ and $R^4$ in Formula I also include prodrugs such as —$CO_2R^w$, where $R^w$, in each instance, is preferably one of $C_{1-4}$alkyl, $C_{4-7}$cycloalkyl or benzyl. Suitable values of $R^2$, $R^3$ and $R^4$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$.

Also suitable at $R^2$, $R^3$ and $R^4$ is the group —$CO_2R^w$, where $R^w$ is one of

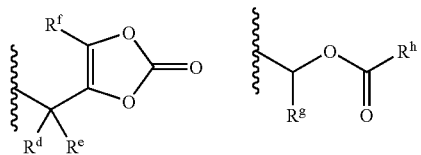

where $R^d$–$R^h$ are defined as above. When $R^2$, $R^3$ and $R^4$ are —$CO_2R^w$, where $R^w$ is one of these moieties, the resulting compounds are prodrugs that possess desirable formulation and bioavailability characteristics. A preferred value for each of $R^d$, $R^e$ and $R^g$ is hydrogen, preferred $R^f$ is methyl, and preferred values for $R^h$ include benzyl and tert-butyl.

Specific compounds for use in the method of the invention include the compounds described in the Examples, such as the following:

- 4-(4'-hydroxy-[1,1';3',1"]terphenyl-3"-sulfonyl)-5-methylsulfanyl-thiophene-2-carboxamidine trifluoroacetate,
- 4-(2'-methoxymethoxy-[1,1';3',1"]terphenyl-3-sulfonyl)-5-methylsulfanyl-thiophene-2-carboxamidine trifluoroacetate,
- 3'-(5-carbamimidoyl-2-methylsulfanyl-thiophene-3-sulfonyl)-2-methyl-biphenyl-3-carboxylic acid isopropyl ester trifluoroacetate,
- 3'-(5-carbamimidoyl-2-methylsulfanyl-thiophene-3-sulfonyl)-6-methyl-biphenyl-2-carboxylic acid trifluoroacetate,
- 4-(6'-hydroxymethyl-2'-methyl-biphenyl-3-sulfonyl)-5-methylsulfanyl-thiophene-2-carboxamidine trifluoroacetate,
- 4-(3'-formyl-2'-methyl-biphenyl-3-sulfonyl)-5-methylsulfanyl-thiophene-2-carboxamidine trifluoroacetate,
- 4-(5'-hydroxymethyl-2'-methyl-biphenyl-3-sulfonyl)-5-methylsulfanyl-thiophene-2-carboxamidine trifluoroacetate,
- 4-(5'-formyl-2'-methyl-biphenyl-3-sulfonyl)-5-methylsulfanyl-thiophene-2-carboxamidine trifluoroacetate,
- 4-[3-(4-methyl-pyridin-3-yl)-benzenesulfonyl]-5-methylsulfanyl-thiophene-2-carboxamidine trifluoroacetate,
- 4-[3-(2-chloro-pyridin-3-yl)-benzenesulfonyl]-5-methylsulfanyl-thiophene-2-carboxamidine trifluoroacetate,
- 4-[3-(3-methyl-pyridin-2-yl)-benzenesulfonyl]-5-methylsulfanyl-thiophene-2-carboxamidine bis-trifluoroacetate,
- 4-(3-allyloxy-5-bromo-benzenesulfonyl)-5-methylsulfanyl-thiophene-2-carboxamidine trifluoroacetate,
- 4-(3-bromo-5-methoxy-benzenesulfonyl)-5-methylsulfanyl-thyophene-2-carboxamidine trifluoroacetate,
- 4-(5-hydroxy-biphenyl-3-sulfonyl)-5-methylsulfanyl-thiophene-2-carboxamidine trifluoroacetate,
- 4-(5-methoxy-biphenyl-3-sulfonyl)-5-methylsulfanyl-thiophene-2-carboxamidine hydrochloride,
- 4-(5-allyloxy-biphenyl-3-sulfonyl)-5-methylsulfanyl-thiophene-2-carboxamidine trifluoroacetate,
- 4-(5-benzyloxy-biphenyl-3-sulfonyl)-5-methylsulfanyl-thiophene-2-carboxamidine hydrochloride,
- 4-(2'-chloro-5-hydroxy-biphenyl-3-sulfonyl)-5-methylsulfanyl-thiophene-2-carboxamidine trifluoroacetate,
- 4-(2'-chloro-5-methoxy-biphenyl-3-sulfonyl)-5-methylsulfanyl-thiophene-2-carboxamidine trifluoroacetate,
- 5-bromo-4-(3'-formyl-biphenyl-3-sulfonyl)-thiophene-2-carboxamidine trifluoroacetate,
- 5-amino-4-(2'-methyl-biphenyl-3-sulfonyl)-thiophene-2-carboxamidine trifluoroacetate,
- 5-chloro-4-(2'-methyl-biphenyl-3-sulfonyl)-thiophene-2-carboxamidine trifluoroacetate,
- 4-(2'-methyl-biphenyl-3-sulfonyl)-thiophene-2-carboxamidine trifluoroacetate,
- 5-bromo-4-(2'-methyl-biphenyl-3-sulfonyl)-thiophene-2-carboxamidine trifluoroacetate, 4-(2'-amino-6'-methyl-biphenyl-3-sulfonyl)-5-methylsulfanyl-thiophene-2-carboxamidine trifluoroacetate,
- 4-(3'-formyl-4'-hydroxy-biphenyl-3-sulfonyl)-5-methylsulfanyl-thiophene-2-carboxamidine trifluoroacetate,
- {[4-(3-bromo-benzenesulfonyl)-5-methylsulfanyl-thiophen-2-yl]-imino-methyl}-carbamic acid tert-butyl ester,
- 5-methylsulfanyl-4-[3'-(2,2,2-trifluoro-1-hydroxy-ethyl)-biphenyl-3-sulfonyl]-thiophene-2-carboxamidine trifluoroacetate,
- 5-methylsulfanyl-4-[3'-(2,2,2-trifluoro-acetyl)-biphenyl-3-sulfonyl]-thiophene-2-carboxamidine trifluoroacetate,
- 4-[3-(6-methyl-3H-benzoimidazol-5-yl)-benzenesulfonyl]-5-methylsulfanyl-thiophene-2-carboxamidine bis-trifluoroacetate,
- N-hydroxy-4-[3-(6-methyl-3H-benzoimidazol-5-yl)-benzenesulfonyl]-5-methylsulfanyl-thiophene-2-carboxamidine trifluoroacetate,
- 4-[2'-(1-hydroxy-ethyl)-biphenyl-3-sulfonyl]-5-methylsulfanyl-thiophene-2-carboxamidine trifluoroacetate,
- 4-[4'-(1-hydroxy-ethyl)-biphenyl-3-sulfonyl]-5-methylsulfanyl-thiophene-2-carboxamidine trifluoroacetate,
- 4-(2'-hydroxy-biphenyl-3-sulfonyl)-5-methylsulfanyl-thiophene-2-carboxamidine trifluoroacetate,
- 4-(3'-hydroxy-biphenyl-3-sulfonyl)-5-methylsulfanyl-thiophene-2-carboxamidine trifluoroacetate,
- 3'-(5-carbamimidoyl-2-methylsulfanyl-thiophene-3-sulfonyl)-biphenyl-3-carboxylic acid trifluoroacetate,
- 4-(5'-formyl-2'-methoxy-biphenyl-3-sulfonyl)-5-methylsulfanyl-thiophene-2-carboxamidine trifluoroacetate,
- 4-(5'-formyl-2'-hydroxy-biphenyl-3-sulfonyl)-5-methylsulfanyl-thiophene-2-carboxamidine trifluoroacetate,
- N-[3'-(5-carbamimidoyl-2-methylsulfanyl-thiophene-3-sulfonyl)-biphenyl-3-yl]-formimidic acid trifluoroacetate,
- 4-(3'-formylamino-biphenyl-3-sulfonyl)-5-methyl-sulfanyl-thiophene-2-carboxamidine trifluoroacetate,
- 4-(4-tert-butyl-benzenesulfonyl)-5-methylsulfanyl-thiophene-2-carboxamidine trifluoroacetate,
- 4-(1-methyl-1H-imidazole-2-sulfonyl)-5-methylsulfanyl-thiophene-2-carboxamidine trifluoroacetate,
- 4-(3,5-dichloro-benzenesulfonyl)-5-methylsulfanyl-thiophene-2-carboxamidine trifluoroacetate, 5-bromo-4-(2-methoxy-benzenesulfonyl)-thiophene-2-carboxamidine trifluoroacetate,
5-methylsulfanyl-4-(naphthalene-2-sulfonyl)-thiophene-2-carboxamidine trifluoroacetate,
4-(2',4'-dimethoxy-biphenyl-3-sulfonyl)-5-methylsulfanyl-thiophene-2-carboxamidine trifluoroacetate,
4-(4'-methoxy-biphenyl-3-sulfonyl)-5-methylsulfanyl-thiophene-2-carboxamidine trifluoroacetate,
4-(3',4'-dimethoxy-biphenyl-3-sulfonyl)-5-methylsulfanyl-thiophene-2-carboxamidine trifluoroacetate,
4-(3'-methoxy-biphenyl-3-sulfonyl)-5-methylsulfanyl-thiophene-2-carboxamidine trifluoroacetate,
4-(2'-methoxy-biphenyl-3-sulfonyl)-5-methylsulfanyl-thiophene-2-carboxamidine trifluoroacetate,
4-(3',5'-dichloro-biphenyl-3-sulfonyl)-5-methylsulfanyl-thiophene-2-carboxamidine trifluoroacetate,
4-(2',5'-dichloro-biphenyl-3-sulfonyl)-5-methylsulfanyl-thiophene-2-carboxamidine trifluoroacetate,
4-(3',5'-bis-trifluoromethyl-biphenyl-3-sulfonyl)-5-methylsulfanyl-thiophene-2-carboxamidine trifluoroacetate,
4-(3-benzofuran-2-yl-benzenesulfonyl)-5-methylsulfanyl-thiophene-2-carboxamidine trifluoroacetate,
4-(3-benzo[b]thiophen-2-yl-benzenesulfonyl)-5-methylsulfanyl-thiophene-2-carboxamidine trifluoroacetate,
4-(4'-methyl-3'-nitro-biphenyl-3-sulfonyl)-5-methylsulfanyl-thiophene-2-carboxamidine trifluoroacetate,
4-(4'-methyl-biphenyl-3-sulfonyl)-5-methylsulfanyl-thiophene-2-carboxamidine trifluoroacetate,
4-(4'-chloro-biphenyl-3-sulfonyl)-5-methylsulfanyl-thiophene-2-carboxamidine trifluoroacetate,
5-methylsulfanyl-4-(4'-trifluoromethyl-biphenyl-3-sulfonyl)-thiophene-2-carboxamidine trifluoroacetate,
5-methylsulfanyl-4-(4'-trifluoromethoxy-biphenyl-3-sulfonyl)-thiophene-2-carboxamidine trifluoroacetate,
5-methylsulfanyl-4-(4'-phenoxy-biphenyl-3-sulfonyl)-thiophene-2-carboxamidine trifluoroacetate,
5-methylsulfanyl-{imino-[4-(4'-methanesulfonyl-biphenyl-3-sulfonyl)-thiophen-2-yl]-methyl}-carbamic acid tert-butyl ester,
4-(3-benzo[1,3]dioxol-5-yl-benzenesulfonyl)-5-methylsulfanyl-thiophene-2-carboxamidine trifluoroacetate,
5-methylsulfanyl-4-(3-quinolin-7-yl-benzenesulfonyl)-thiophene-2-carboxamidine trifluoroacetate,
4-(3'-methyl-biphenyl-3-sulfonyl)-5-methylsulfanyl-thiophene-2-carboxamidine trifluoroacetate,
4-(3'-formyl-biphenyl-3-sulfonyl)-5-methylsulfanyl-thiophene-2-carboxamidine trifluoroacetate,
4-(3'-amino-biphenyl-3-sulfonyl)-5-methylsulfanyl-thiophene-2-carboxamidine trifluoroacetate,
5-methylsulfanyl-4-(3'-trifluoromethyl-biphenyl-3-sulfonyl)-thiophene-2-carboxamidine trifluoroacetate,
4-(3'-hydroxymethyl-biphenyl-3-sulfonyl)-5-methylsulfanyl-thiophene-2-carboxamidine trifluoroacetate,
5-methylsulfanyl-4-([1,1';3',1"]terphenyl-3-sulfonyl)-thiophene-2-carboxamidine trifluoroacetate,
4-(3-dibenzofuran-4-yl-benzenesulfonyl)-5-methylsulfanyl-thiophene-2-carboxamidine trifluoroacetate,
5-methylsulfanyl-4-(2'-trifluoromethyl-biphenyl-3-sulfonyl)-thiophene-2-carboxamidine trifluoroacetate,
4-(2'-hydroxymethyl-biphenyl-3-sulfonyl)-5-methylsulfanyl-thiophene-2-carboxamidine trifluoroacetate,
4-(2'-chloro-biphenyl-3-sulfonyl)-5-methylsulfanyl-thiophene-2-carboxamidine trifluoroacetate,
5-methylsulfanyl-4-(3-pyridin-3-yl-benzenesulfonyl)-thiophene-2-carboxamidine trifluoroacetate,
5-methylsulfanyl-4-(3-pyrimidin-5-yl-benzenesulfonyl)-thiophene-2-carboxamidine trifluoroacetate,
4-(3-furan-3-yl-benzenesulfonyl)-5-methylsulfanyl-thiophene-2-carboxamidine trifluoroacetate,
5-methylsulfanyl-4-(3-quinolin-3-yl-benzenesulfonyl)-thiophene-2-carboxamidine trifluoroacetate,
3'-(5-carbamimidoyl-2-methylsulfanyl-thiophene-3-sulfonyl)-biphenyl-4-carboxylic acid methyl ester,
4-(3',5'-dimethyl-biphenyl-3-sulfonyl)-5-methylsulfanyl-thiophene-2-carboxamidine trifluoroacetate,
4-(3-furan-2-yl-benzenesulfonyl)-5-methylsulfanyl-thiophene-2-carboxamidine trifluoroacetate,
5-methylsulfanyl-4-(3-thiophen-3-yl-benzenesulfonyl)-thiophene-2-carboxamidine trifluoroacetate,
5-methylsulfanyl-4-(3'-nitro-biphenyl-3-sulfonyl)-thiophene-2-carboxamidine trifluoroacetate,
4-(4'-hydroxy-biphenyl-3-sulfonyl)-5-methylsulfanyl-thiophene-2-carboxamidine trifluoroacetate,
4-(4'-formyl-biphenyl-3-sulfonyl)-5-methylsulfanyl-thiophene-2-carboxamidine trifluoroacetate,
4-(4'-fluoro-biphenyl-3-sulfonyl)-5-methylsulfanyl-thiophene-2-carboxamidine trifluoroacetate,
4-(2'-fluoro-[1,1';4',1"]terphenyl-3"-sulfonyl)-5-methylsulfanyl-thiophene-2-carboxamidine trifluoroacetate,
4-(4'-hydroxymethyl-biphenyl-3-sulfonyl)-5-methylsulfanyl-thiophene-2-carboxamidine trifluoroacetate,
4-(4'-cyano-biphenyl-3-sulfonyl)-5-methylsulfanyl-thiophene-2-carboxamidine trifluoroacetate,
4-(4'-acetyl-biphenyl-3-sulfonyl)-5-methylsulfanyl-thiophene-2-carboxamidine trifluoroacetate,
4-(4'-dimethylamino-biphenyl-3-sulfonyl)-5-methylsulfanyl-thiophene-2-carboxamidine trifluoroacetate,
5-methylsulfanyl-4-(2'-vinyl-biphenyl-3-sulfonyl)-thiophene-2-carboxamidine trifluoroacetate,
4-(4'-ethoxy-biphenyl-3-sulfonyl)-5-methylsulfanyl-thiophene-2-carboxamidine trifluoroacetate,
4-[3-(3,5-dimethyl-isoxazol-4-yl)-benzenesulfonyl]-5-methylsulfanyl-thiophene-2-carboxamidine trifluoroacetate,
4-(2'-methyl-biphenyl-3-sulfonyl)-5-methylsulfanyl-thiophene-2-carboxamidine trifluoroacetate,
5-methylsulfanyl-4-(3-naphthalen-1-yl-benzenesulfonyl)-thiophene-2-carboxamidine trifluoroacetate,
4-[3-(5-chloro-thiophen-2-yl)-benzenesulfonyl]-5-methylsulfanyl-thiophene-2-carboxamidine trifluoroacetate,
4-(2'-formyl-biphenyl-3-sulfonyl)-5-methylsulfanyl-thiophene-2-carboxamidine trifluoroacetate,
5-methylsulfanyl-4-(4'-vinyl-biphenyl-3-sulfonyl)-thiophene-2-carboxamidine trifluoroacetate,
4-(3'-ethoxy-biphenyl-3-sulfonyl)-5-methylsulfanyl-thiophene-2-carboxamidine trifluoroacetate,
4-(2',6'-dimethyl-biphenyl-3-sulfonyl)-5-methylsulfanyl-thiophene-2-carboxamidine trifluoroacetate,
4-(3'-methyl-biphenyl-3-sulfonyl)-5-methylsulfanyl-thiophene-2-carboxamidine trifluoroacetate,
4-(3'-isopropyl-biphenyl-3-sulfonyl)-5-methylsulfanyl-thiophene-2-carboxamidine trifluoroacetate,
4-(2',3'-dimethyl-biphenyl-3-sulfonyl)-5-methylsulfanyl-thiophene-2-carboxamidine trifluoroacetate,
4-(2',3'-dichloro-biphenyl-3-sulfonyl)-5-methylsulfanyl-thiophene-2-carboxamidine trifluoroacetate,
4-(3'-acetyl-biphenyl-3-sulfonyl)-5-methylsulfanyl-thiophene-2-carboxamidine trifluoroacetate,
3'-(5-carbamimidoyl-2-methylsulfanyl-thiophene-3-sulfonyl)-biphenyl-3-carboxylic acid ethyl ester,
3'-(5-carbamimidoyl-2-methylsulfanyl-thiophene-3-sulfonyl)-biphenyl-3-carboxylic acid dimethylamide, 3'-(5-carbamimidoyl-2-methylsulfanyl-thiophene-3-sulfonyl)-biphenyl-3-carboxylic acid amide, N-[3'-(5-carbamimidoyl-2-methylsulfanyl-thiophene-3-sulfonyl)-biphenyl-3-yl]-acetamide,
4-(2'-amino-biphenyl-3-sulfonyl)-5-methylsulfanyl-thiophene-2-carboxamidine trifluoroacetate,
4-[3-(1H-benzoimidazol-5-yl)-benzenesulfonyl]-5-methylsulfanyl-thiophene-2-carboxamidine trifluoroacetate,
4-(7-bromo-3-methyl-3H-benzoimidazole-5-sulfonyl)-5-methylsulfanyl-thiophene-2-carboxamidine trifluoroacetate,
4-(7-bromo-1-methyl-1H-benzoimidazole-5-sulfonyl)-5-methylsulfanyl-thiophene-2-carboxamidine trifluoroacetate,
5-methylsulfanyl-4-(3-methyl-7-o-tolyl-3H-benzoimidazole-5-sulfonyl)-thiophene-2-carboxamidine trifluoroacetate,
5-methylsulfanyl-4-(2-methyl-7-o-tolyl-3H-benzoimidazole-5-sulfonyl)-thiophene-2-carboxamidine trifluoroacetate,
5-methylsulfanyl-4-(7-o-tolyl-3H-benzoimidazole-5-sulfonyl)-thiophene-2-carboxamidine trifluoroacetate,
4-(7-bromo-3H-benzoimidazole-5-sulfonyl)-5-methylsulfanyl-thiophene-2-carboxamidine trifluoroacetate,
4-(6-methyl-biphenyl-3-sulfonyl)-5-methylsulfanyl-thiophene-2-carboxamidine trifluoroacetate,
4-(2-methyl-furan-3-sulfonyl)-5-methylsulfanyl-thiophene-2-carboxamidine trifluoroacetate,
5-methylsulfanyl-4-(4-phenyl-thiazole-2-sulfonyl)-thiophene-2-carboxamidine hydrochloride,
4-(6-ethoxy-benzothiazole-2-sulfonyl)-5-methylsulfanyl-thiophene-2-carboxamidine hydrochloride,
4-(6-methyl-biphenyl-3-sulfonyl)-5-methylsulfanyl-thiophene-2-carboxamidine trifluoroacetate,
4-(3-methoxy-benzenesulfonyl)-5-methylsulfanyl-thiophene-2-carboxamidine hydrochloride,
5-methylsulfanyl-4-(3-phenoxy-benzenesulfonyl)-thiophene-2-carboxamidine hydrochloride, and
4-(Biphenyl-3-sulfonyl)-5-methylsulfanyl-thiophene-2-carboxamidine trifluoroacetate,
as well as pharmaceutically acceptable salts thereof, or a prodrug thereof.

DEFINITIONS

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably 2 to 8 carbon atoms in length, most preferably 2 to 4 carbon atoms in length.

In all instances herein where there is an alkenyl moiety as a substituent group, the unsaturated linkage, i.e., the vinylene linkage, is preferably not directly attached to a nitrogen, oxygen or sulfur moiety.

The term "alkylthio" as employed herein by itself or as part of another group refers to a straight or branched chain radical of 1 to 20 carbon atoms, unless the chain length is limited thereto, bonded to a sulfur atom, including, but not limited to, methylthio, ethylthio, n-propylthio, isopropylthio, and the like. Preferably the alkylthio chain is 1 to 10 carbon atoms in length, more preferably 1 to 8 carbon atoms in length.

The term "alkoxy" as employed herein by itself or as part of another group refers to a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "halogen" or "halo" as employed herein by itself or as part of another group refers to chlorine, bromine, fluorine or iodine, with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl or tetrahydronaphthyl.

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The terms "heterocyclic," "heterocyclo" or "heterocycle" as employed herein by themselves or as part of larger groups refer to a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, benzofuranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an NR$^y$R$^z$ moiety, wherein R$^y$ and R$^z$ are, independently from one another, hydrogen or C$_1$ to C$_8$ alkyl, or together with the nitrogen to which they are bound, form a saturated or unsaturated 5-, 6-, or 7-membered ring.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, benzofuranyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where R$^2$, R$^3$ and/or R$^4$ are —CO$_2$R$^w$, where R$^w$ is defined above. See U.S. Pat. No. 5,466,811 and Saulnier et al., *Bioorg. Med. Chem. Lett.* 4:1985–1990 (1994).

The term "substituted," as used herein, means that one or more hydrogens of the designated moiety are replaced with a selection from the indicated group, provided that no atom's normal valency is exceeded, and that the substitution results in a stable compound. When a substituent is keto (i.e., ═O), then 2 hydrogens attached to an atom of the moiety are replaced.

By "stable compound" or "stable formula" is meant herein a compound that is sufficiently robust to survive isolation to a useful degree of purity from a reaction mixture and formulation into an efficacious therapeutic agent.

When any variable occurs more than one time in any constituent or in any Formula, its definition on each occurrence is independent of its definition at every other occurrence. Also, combinations of substituents and/or variables are permissible only if such combinations result in stable compounds.

METHODS OF USE

The present invention provides a method for treating acute and chronic disorders associated with activation of the classical pathway of the complement system by administering to a mammal in need of such treatment a therapeutically effective amount of a compound of Formula I.

These acute and chronic conditions include inflammation and tissue damage that arise as a result of rapid and aggressive enzyme activity of the complement cascade. Complement-mediated inflammation and the resultant tissue damage has been implicated in a number of disease states including: 1) ischaemia reperfusion damage, such as occurs post myocardial infarction, post transplant, post surgery and in hemorrhagic shock; 2) antibody-mediated conditions, such as hyperacute allograft and xenograft rejection, organ transplant rejection and auto-immune diseases; and 3) other disease states, such as thermal injury, trauma, adult respiratory distress syndrome (ARDS), sepsis and prion disease.

The compounds of the present invention are believed to inhibit the functioning of the protease activity of C1s. This protease-inhibition activity results in the inhibition or blocking of a variety of complement-mediated immunological functions. Therefore, compounds of Formula I can be used to ameliorate a number of disease states induced by complement-mediated inflammation and tissue damage.

The term "treatment of inflammation" or "treating inflammation" is intended to include the administration of compounds of the present invention to a subject for purposes which can include prophylaxis, amelioration, prevention or cure of an inflammatory response. Such treatment need not necessarily completely ameliorate the inflammatory response. Further, such treatment can be used in conjunction with other traditional treatments for reducing the inflammatory condition known to those of skill in the art.

By an "efficacious level" of a composition of the invention is meant a level at which some relief is afforded to the patient who is the recipient of the treatment. By an "abnormal" host inflammatory condition is meant a level of inflammation in the subject at a site which exceeds the norm for the healthy medical state of the subject, or exceeds a desired level. By "secondary" tissue damage or toxic effects is meant the tissue damage or toxic effects which occur to otherwise healthy tissues, organs, and the cells therein, due to the presence of an inflammatory response, including as a result of a "primary" inflammatory response elsewhere in the body.

The "animals" referred to herein are preferably mammals and most preferably humans, although the invention is not intended to be limited to such.

In one embodiment, compounds of Formula I can be administered to a mammal to treat complement-mediated inflammation and tissue damage that is a consequence of ischaemia/reperfusion injury. Thus, the C1s inhibitors of the present invention can be employed to prevent, or at least ameliorate, inflammation and tissue damage arising from a stroke, myocardial infarction, hemorrhagic shock, and surgery. In particular, compounds of Formula I can be employed to prevent inflammation of transplanted tissue and organs.

The compounds of Formula I can also be provided as a "preventive" treatment before detection of an inflammatory state, so as to prevent the same from developing in patients at high risk for the same, such as, for example, transplant patients.

The compounds of Formula I can be used to treat chronic or acute inflammation that is the result of an antibody-mediated reaction, such as hyperacute allograft and xenograft rejection, organ transplant rejection and auto-immune diseases, which include arthritis, rheumatoid arthritis, multiple sclerosis (MS), type I diabetes, intestinal inflammation of Crohn's disease, systemic lupus erythematosus (lupus), immune-complex-induced vasculitis, restenosis and psoriasis.

The complement system is activated in hyperacute allograft and hyperacute xenograft rejection, and in acute humoral rejection mediated by donor-specific antibodies. In another embodiment, compounds of Formula I can be administered to a mammal before, during or after the transplant of an organ or a graft to ameliorate the rejection of such organ or graft by the mammal.

Organ transplant and graft patients undergo concurrent immunotherapy. Complement activation during immunotherapy with recombinant IL-2 appears to cause acute vascular leak syndrome that results in the severe toxicity and side effects observed from IL-2 treatment and other conditions such as bone marrow transplantation and acute pancreatitis. Thus, in a further embodiment of the present invention, a compound of Formula I is administered to a mammal before, during or after treatment of said mammal with IL-2, bone marrow transplantation, or onset of pancreatitis, in an amount effective to reduce the vascular leak syndrome that causes toxicity and side-effects associated with the treatment or disorders.

Another embodiment of the present invention is directed to administering a therapeutically effective compound of Formula I to a mammal that has been diagnosed with an autoimmune disease. Autoimmune diseases that are treatable according to the present invention include Addison's disease, Type I diabetes mellitus, Hashimoto's thyroiditis, glomerulonephritis and cutaneous lesions of systemic lupus erythematosus, other glomerulonephritides, bullous pemphigoid, dermatitis herpetiformis, Goodpasture's syndrome, Graves' disease, myasthenia gravis, insulin resistance, autoimmune hemolytic anemia, autoimmune thrombocytopenic purpura, immune-complex-induced vasculitis glomerulonephritis, type II collagen-induced arthritis, rheumatoid arthritis, and allergic neuritis. Autoimmune diseases preferred for treatment by inhibitors of the present invention include myasthenia gravis (MG), rheumatoid arthritis, and systemic lupus erythematosus.

Another embodiment of the present invention is directed to administering a therapeutically effective amount of a compound of Formula I to a mammal that has been diagnosed with a neurodegenerative disease. Neurodegenerative diseases in which inhibitors of the complement cascade system will be therapeutically useful include the demyelinating disorder multiple sclerosis (MS), the neuropathies Guillain-Barré syndrome (GBS) and Miller-Fisher syndrome (MFS), Alzheimer's disease (AD) and variant Creutzfeldt-Jakob disease (vCJD).

In another embodiment, efficacious levels of the C1s inhibitors of the invention are administered so as to provide therapeutic benefits against the secondary harmful inflammatory effects of inflammation.

In an additional embodiment, compounds of the present invention can be administered to a mammal suffering from the symptoms of ARDS. ARDS is a complex pulmonary disorder affecting 150,000 people in the U.S. yearly with a 50% mortality rate. Leukocytes, platelets and the proteolytic pathways of coagulation and complement mediate ARDS. ARDS involves activation of the contact activation pathway and depletion of C1 inhibitor and may be induced by either sepsis or trauma. Sepsis-induced ARDS results in more severe Disseminated intravascular coagulation (DIC) and fibrinolysis, more fibrin degradation products and reduced ATIII levels compared to trauma-induced ARDS (Carvalho et al., *J. Lab. Clin. Med*. 112:270–277 (1988)).

In a further embodiment, compounds of Formula I can be administered to a person in septic shock. Septic shock is the most common cause of death of humans in intensive care units in the United States (Parillo et al., *Ann. Int. Med*. 113:227–242 (1990); Schmeichel C. J. & McCormick D., *BioTechnol*. 10:264–267 (1992)). In recent years aggressive fluid infusion therapy has been accepted as a primary means of treatment for septic shock.

The increase in cardiac output and vasodilation in septic shock is attributed to the action of inflammatory mediators. In septic shock, components of the kallikrein-kinin system are depleted, suggesting activation of this system. This is not the case in cardiogenic shock, suggesting that the kallikrein-kinin system is a key player in septic shock (Martinez-Brotons F. et al., *Thromb. Haemostas*. 58:709–713 (1987)). While the actual events leading to septic shock, DIC and hypotension have not been established, the known interactions among various components of the many physiological systems suggest that activation of the contact pathway may lead to a state of septic shock, multi-organ failure, and death (Bone, R. C., *Arch. Intern. Med*. 152:1381–1389 (1992); Colman, R. W., *New Engl. J. Med*. 320:1207–1209 (1989)). The contact activation pathway is also involved in both fibrin deposition and lysis, as well as triggering neutrophil activation, activation of complement and modulation of blood pressure.

Inhibition of the complement cascade is expected to lead to downstream utilities associated with the contact system of coagulation and the complement system. This interaction between components of the complement and coagulation systems at the surface of blood platelets and endothelium can generate inflammatory and chemotactic peptides at sites of vascular thrombus formation and may contribute to the altered hemostasis associated with immune disease states. In addition, immune reactions affecting blood platelets and endothelium can lead to platelet aggregation, the secretion of proteolytic enzymes and vasoactive amines from platelet storage granules, and increase adherence of platelets and leukocytes to the endothelial lining of blood vessels.

Other diseases and conditions that can be treated with compounds of Formula I include hereditary angioedema, paroxysmal nocturnal hemoglobinuria, wound healing, brain trauma, asthma, hemodialysis, infection, dermatosis, inflammatory bowel disease, osteoporosis, osteoarthritis, thermal injury (burns and frostbite), hemolytic anemia and post pump syndrome in cardiopulmonary bypass.

It has been demonstrated that membrane-uptake of C3b and C5b-9 proteins can occur spontaneously during incubation of platelets in citrated plasma. Complement activation can also occur during blood collection as a result of exposure to plastic surfaces supporting the C3-convertase reaction. While the implications of complement activation during blood collection and in vitro storage for transfusion have not been directly addressed, it is nevertheless known that plasma levels of coagulation factors V and VIII rapidly decline in stored platelet concentrates at a rate considerably faster than their decay in cell-free plasma, suggesting consumptive loss. Further, platelet collection and storage is associated with an increase in vesicular plasma membrane microparticles, a product of C5b-9 initiated platelet secretion. These physiological and enzymatic changes greatly reduce the potential shelf life of stored platelets, particularly platelet-rich plasma concentrates used for transfusions, which is generally only 72 hours at best. Furthermore, this interaction of activated C5b-9, platelets, and coagulation factors in stored platelet concentrates will adversely affect the hemostatic effectiveness of these units when infused.

In vitro human organ and tissue storage and survival of the transplanted graft is also adversely affected by the spontaneous activation of the complement system, resulting in membrane insertion of the C5b-9 proteins into vascular endothelium. Activation of C5 to C5a and C5b can be catalyzed by plastics and other synthetic membranes required to maintain perfusion of vascular beds during in vitro tissue and organ storage. In addition, membrane deposition of C5b-9 in vivo has been implicated in the acute rejection of transplanted tissue due to immune activation of the recipient's plasma complement system against the endothelial cells within the donor's organ.

Platelet and endothelial cell activation by C5b-9 also has ramifications in autoimmune disorders and other disease states. The importance of spontaneous complement activation and the resulting exposure of platelets and endothelium to activated C5b-9 to the evolution of vaso-occlusive disease is underscored by consideration that a) leukocyte infiltration of the subendothelium, which is known to occur in regions of atheromatous degeneration and suggests localized generation of C5a at the vessel wall, is potentially catalyzed by adherent platelets; and b) local intravascular complement activation resulting in membrane deposition of C5b-9 complexes accompanies coronary vessel occlusion and may affect the ultimate extent of myocardial damage associated with infarction.

It is therefore an aspect of the present invention to provide a means and method for the modulation and inhibition of complement-mediated platelet and endothelial cell activation in vivo and in vitro.

It is a further aspect of the present invention to provide a means and method for increasing the survival and therapeutic efficacy of platelets and tissues or organs collected and stored in vitro.

Preferably, the treatment methods of the invention deliver the C1s inhibitor either by contacting cells of the animal with a C1s inhibitor described above or by administering to the animal a C1s inhibitor described above.

The inhibitors can be used in vitro or in vivo. They can be administered by any number of known routes, including orally, intravenously, intramuscularly, subcutaneously, intrathecally, topically, transdermally, and by infusion (Platt et al., U.S. Pat. No. 4,510,130; Badalamente et al., *Proc. Natl. Acad. Sci. U.S.A.* 86:5983–5987 (1989); Staubli et al., *Brain Research* 444:153–158 (1988)) and will generally be administered in combination with a physiologically acceptable carrier (e.g., physiological saline) or diluent. The effective quantity of inhibitor given will be determined empirically and will be based on such considerations as the particular inhibitor used, the condition of the individual, and the size and weight of the individual. It is to be expected that the general end-use application dose range will be about 0.01 to 100 mg per kg per day, preferably 0.1 to 75 mg per kg per day for an effective therapeutic effect.

Amounts and regimens for the administration of C1s inhibitors and compositions of the invention can be determined readily by those with ordinary skill in the clinical art of treating inflammation-related disorders such as arthritis, tissue injury and tissue rejection. Generally, the dosage of the composition of the invention will vary depending upon considerations such as: type of pharmaceutical composition employed; age; health; medical conditions being treated; kind of concurrent treatment, if any; frequency of treatment and the nature of the effect desired; extent of tissue damage; gender; duration of the symptoms; and contraindications, if any, and other variables to be adjusted by the individual physician. A desired dosage can be administered in one or more applications to obtain the desired results. Pharmaceutical compositions containing the C1s inhibitors of the invention can be provided in unit dosage forms.

In one embodiment, dosing will be by intravenous injection or short-term infusion. In a further embodiment, the C1s inhibitors of the present invention will be administered orally, in the form of a tablet, pill, lozenge, troche or capsule. To achieve optimal therapeutic effect, maintenance dosing may be required. Such maintenance dosing may be given repeatedly during the course of a day by, for instance, repeated individual injections, repeated oral dosing, or by introduction of a continuous drip infusion. Effective dosages can be readily determined by one of ordinary skill in the art through routine trials establishing dose response curves.

PHARMACEUTICAL COMPOSITIONS

Pharmaceutical compositions for treating a complement-mediated disease state, comprising a compound of Formula I in an amount effective to inhibit C1s protease function in a mammal and a pharmaceutically acceptable carrier or diluent, are within the scope of the present invention.

Pharmaceutical compositions comprising an effective amount of the C1s inhibitors of the invention, in combination with any conventional pharmaceutically acceptable carrier or diluent, are included in the present invention.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, and HI; sulfuric acid; phosphoric acid and the like. Preferred acids for forming acid addition salts include HCl and acetic acid.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

When employed as thrombin inhibitors, the compounds of the present invention may be administered in an effective amount within the dosage range of about 0.1 to about 500 mg/kg, preferably between about 0.1 and about 10 mg/kg body weight, on a regimen in single or 2–4 divided daily doses.

METHODS OF MAKING

Many synthetic methods used to form compounds of the present invention generally involve the formation of an amidine from a carboxylic acid derivative, such as an ester. In the process a Lewis acid, such as trimethylaluminum, is added to a source of ammonia, such as ammonium chloride, in an aprotic solvent, such as a toluene, under an inert atmosphere (e.g., under an atmosphere of nitrogen or argon gas) at a temperature between −15° C. and 5° C., preferably at 0° C. An appropriate carboxylic acid derivative is added to the mixture and the mixture is heated at reflux for a predetermined period of time, preferably between 1 hr. and 24 hrs., and most preferably between 1 hr. and 4 hrs. The resulting solution is allowed to cool to room temperature and the amidine product is isolated by known methods.

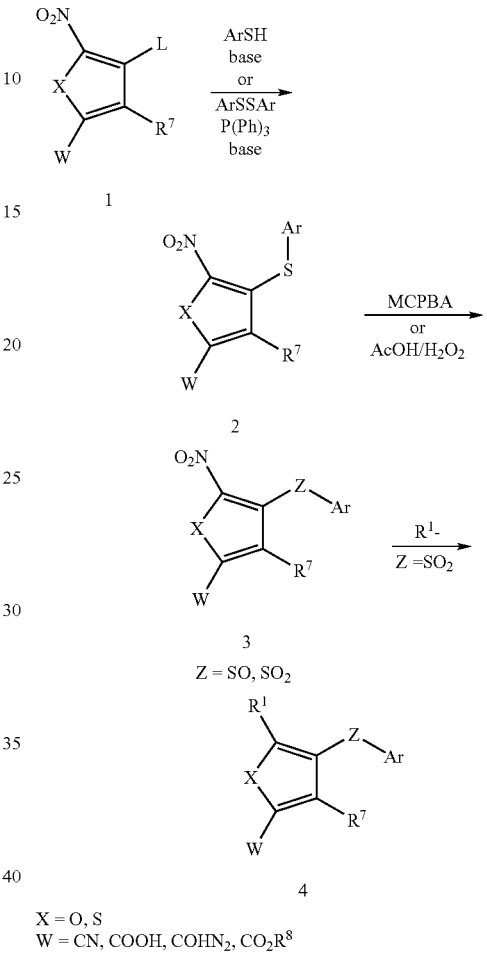

SCHEME 1

X = O, S
W = CN, COOH, COHN$_2$, CO$_2$R$^8$
L = Br

Scheme 1 illustrates a general approach to compounds of Formula I where X=O or S, and R$^1$=alkylthio, aralkylthio, arylthio, alkyloxy, aralkyloxy or aryloxy. Starting with the heterocycle where X=O or S appropriately substituted by a leaving group, the leaving groups can be sequentially displaced by an appropriate thiol to produce the 4-substituted heterocycles. In some cases a disulfide and a reducing agent such as triphenylphosphine can be used for the in situ generation of the thiol. Examples of leaving groups include chlorine, bromine or iodine. The resulting sulfide is oxidized, either to the sulfoxide or the sulfone with an appropriate oxidizing agent such as meta-chloroperoxybenzoic acid or hydrogen peroxide in acetic acid. When the 4-substituent is a sulfone, the nitro group can then be displaced by an appropriate nucleophile (preferably the anion of the group R$^1$ to be substituted) to produce a 5-substituted heterocycle. Preferable nucleophiles include anions of thiols or alcohols having as the counter ion an alkali or alkali earth metal such as sodium, lithium, potassium, magnesium or cesium.

SCHEME 2

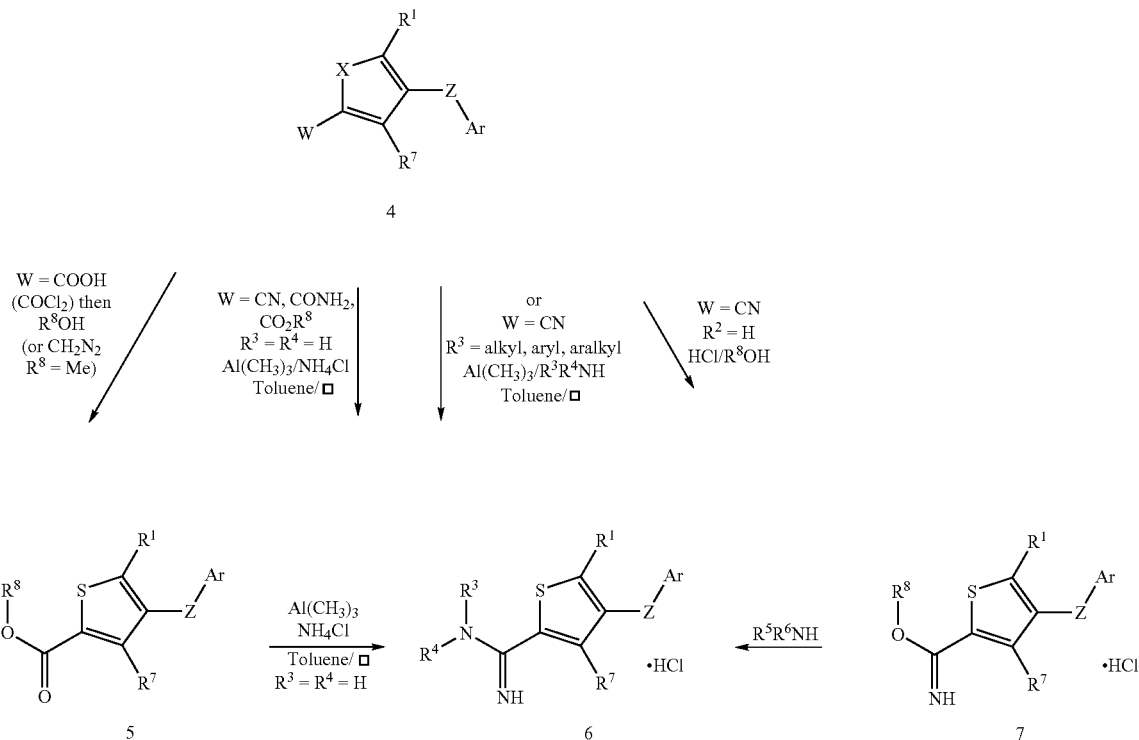

Scheme 2 illustrates approaches to providing the amidine ((R₃R₄N)CNR₂) functionality of compounds of Formula I where X=O or S, and R¹=halo, alkyl, alkylthio, aralkylthio, arylthio, alkyloxy, aralkyloxy or aryloxy. Depending on the nature of the group W in 4, several methods may be employed in the transformation of W to $(R_3R_4N)CNR_2$.

When W in 4 is a cyano group (CN), primary amide ($CONH_2$) or ester ($CO_2R^9$), direct conversion to an unsubstituted amidine 6 (i.e., Formula I where $R^2$, $R^3$, $R^4$=H) can be effected by treatment with a reagent consisting of a Lewis acid complexed to ammonia. This complex is produced by treatment of ammonia or an ammonium salt, preferably an ammonium halide and most preferably ammonium chloride or bromide, with an appropriate Lewis acid, preferably a trialkylaluminum and most preferably trimethyl- or triethylaluminum in a solvent inert to the Lewis acid employed. For example, when a trialkylaluminum Lewis acid is employed with an ammonium halide, reaction occurs with loss of one equivalent of alkane to produce the dialkylhaloaluminum complex of ammonia (see, for example, Sidler, D. R., et al., *J. Org. Chem.*, 59:1231 (1994)). Examples of suitable solvents include unsaturated hydrocarbons such as benzene, toluene, xylenes, or mesitylene, preferably toluene, or halogenated hydrocarbons such as dichloroethane, chlorobenzene or dichlorobenzene. The amidination reaction is generally carried out at elevated temperatures, preferably 40–200° C., more preferably 80–140° C., and most preferably at the reflux temperature of a solvent in the range of 80–120° C. When W is a cyano group (CN), direct conversion to a mono- or disubstituted amidine 6 is also possible by treatment with a reagent consisting of a Lewis acid, preferably a trialkylaluminum, complexed to a mono- or disubstituted amine $H_2NR^3$ or $HNR^3R^4$ (Garigipati, R., *Tetrahedron Lett.* 31: 1969 (1990)). Alternatively the same addition of a mono- or disubstituted amine may be catalyzed by a copper salt such as Cu(I) chloride (Rousselet, G., et al., *Tetrahedron Lett.* 34: 6395 (1993)).

When W in 4 is a carboxyl group ($CO_2H$), indirect conversion to an unsubstituted amidine 6 can be carried out by initial esterification to 5 by any of a number of well-known dehydrating agents (for example, dicyclohexylcarbodiimide) with an alcohol ($R^8OH$). More preferably 5 can be made by initial formation of an acid chloride by treatment of 4 with any of a number of anhydrides of HCl and another acid, such as thionyl chloride, $POCl_3$, $PCl_3$, $PCl_5$, or more preferably oxalyl chloride, with or without an added catalyst such as N,N-dimethylformamide (DMF), followed by the alcohol $R^8OH$. Conversion to the unsubstituted amidine 6 ($R^2$, $R^3$, $R^4$=H) can be carried out by treatment with a Lewis acid complexed to ammonia.

Amidines 6 can also be produced indirectly by conversion of 4 (W=CN) to iminoethers 7 by exposure to a strong acid such as a hydrogen halide, $HBF_4$ or other non-nucleophilic acid, preferably gaseous HCl in the presence of an alcohol $R^8OH$ ($R^8$=alkyl, branched alkyl or cycloalkyl, preferably Me or Et) and most preferably with the alcohol as solvent. Alternatively when W=$CONH_2$, conversion to an iminoether can be carried out by treatment with a trialkyloxonium salt (Meerwein's salts). In either case, treatment of the iminoether with ammonia ($R^3$, $R^4$=H) or a mono- or disubstituted amine (HNR$^3$R$^4$) provides the corresponding unsubstituted or substituted amidines 6 (i.e., via classical Pinner synthesis: Pinner, A., Die Iminoaether und ihre Derivate, Verlag R. Oppenheim, Berlin (1892)).

Conversion to substituted amidine 6 (R$^2$, R$^3$=H and, R$^4$=OH) can be achieved by refluxing in ethanol the unsubstituted amidine 6 (R$^2$, R$^3$, R$^4$=H), hydroxylamine, and a base, preferably triethylamine.

SCHEME 3

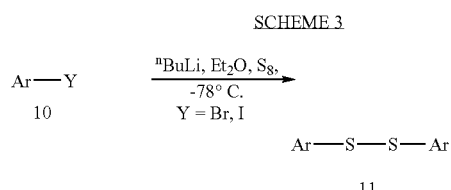

Scheme 3 illustrates one approach to aryl thiols, which can be used in Scheme 1 when such aryl thiols are not commercially available. Starting with an aryl halide with sufficient stability to strong nucleophiles, the aryl halide can be reacted with an alkali earth metal in an inert ethereal solvent such as diethyl ether under reflux, yielding a reactive organometallic species. Preferred metals include lithium, magnesium, and sodium, while the halide can be an aryl iodide or bromide. Alternatively, the aryl-metal species can be generated through a metal-halogen exchange with another organometallic reagent at low temperature in an ethereal solvent. Useful organometallic reagents include any of the isomeric butyllithiums and isopropylmagnesium bromide or chloride. In this instance, the aryl halide must be an aryl bromide or iodide and stable to strong nucleophiles.

The aryl-metal reagent may then be reacted with elemental sulfur to provide a mixture of the aryl thiol (12) and the disulfide oxidation products (11). The disulfide can be reacted with a reducing agent such as sodium borohydride, dithiothreitol, or triphenylphosphine, to give the aryl thiol (12).

SCHEME 4

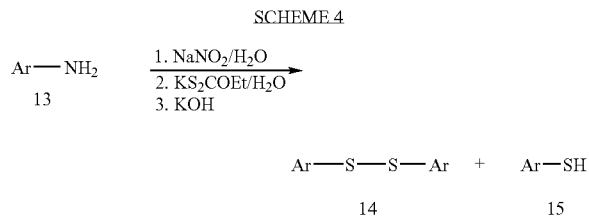

Scheme 4 illustrates another approach to aryl thiols, which can be used in Scheme 1 when such aryl thiols are not commercially available. An arylamine 13 can be converted to the diazonium salt and reacted with O-ethylxanthic acid potassium salt (Aldrich Chemical Company) to give an O-ethyl-S-aryl dithiocarbonate, which can subsequently be hydrolyzed to the aryl thiol 15. In some cases hydrolysis can provide a mixture of the aryl thiol (15) and the disulfide oxidation products (14). The disulfide can be reacted with a reducing agent such as sodium borohydride, dithiothreitol, or triphenylphosphine, to give the aryl thiol (15).

SCHEME 5

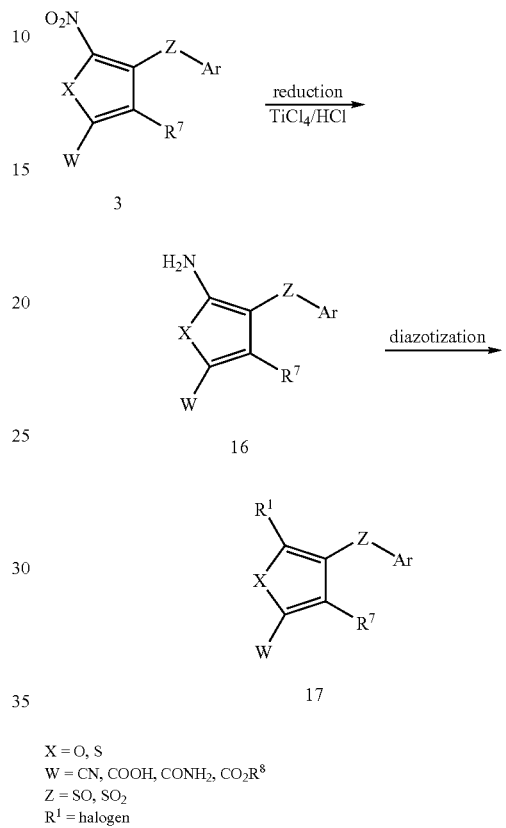

X = O, S
W = CN, COOH, CONH$_2$, CO$_2$R$^8$
Z = SO, SO$_2$
R$^1$ = halogen

Scheme 5 illustrates a general approach to compounds of Formula I where X=O or S, and R$^1$=halo. The nitroheterocycle 3 obtained in the manner described in Scheme 1 is reduced to the aminoheterocycle 16. Appropriate reagents to effect reduction of the nitro functionality include hydrogen gas in the presence of a catalyst such as palladium or platinum metal deposited on carbon or barium sulfate in any number of solvents such as methanol, ethanol, ethyl acetate, DMF, or THF. Tin (II) chloride may be employed as a reductant in a solvent such as methanol or ethanol. Alternatively, metals such as zinc or iron (Stanetty, P. and Kremslehner, M., *Heterocycles* 48: 259 (1998)) may also be used. More preferably, titanium (III) chloride in HCl (see Ho, Wong, *Synthesis*, 45 (1974)) can be used as the reducing reagent. The aminoheterocycle 16 can then be converted to the halide 17 by diazotization. When X=Cl or Br, this reaction is carried out by treating the aminoheterocycle 16 with t-butyl nitrite and copper (II) chloride or bromide as described in the Sandmeyer reaction (see Doyle; Siegfried; Dellaria, *J. Org. Chem.* 42: 2426 (1977)).

SCHEME 6a

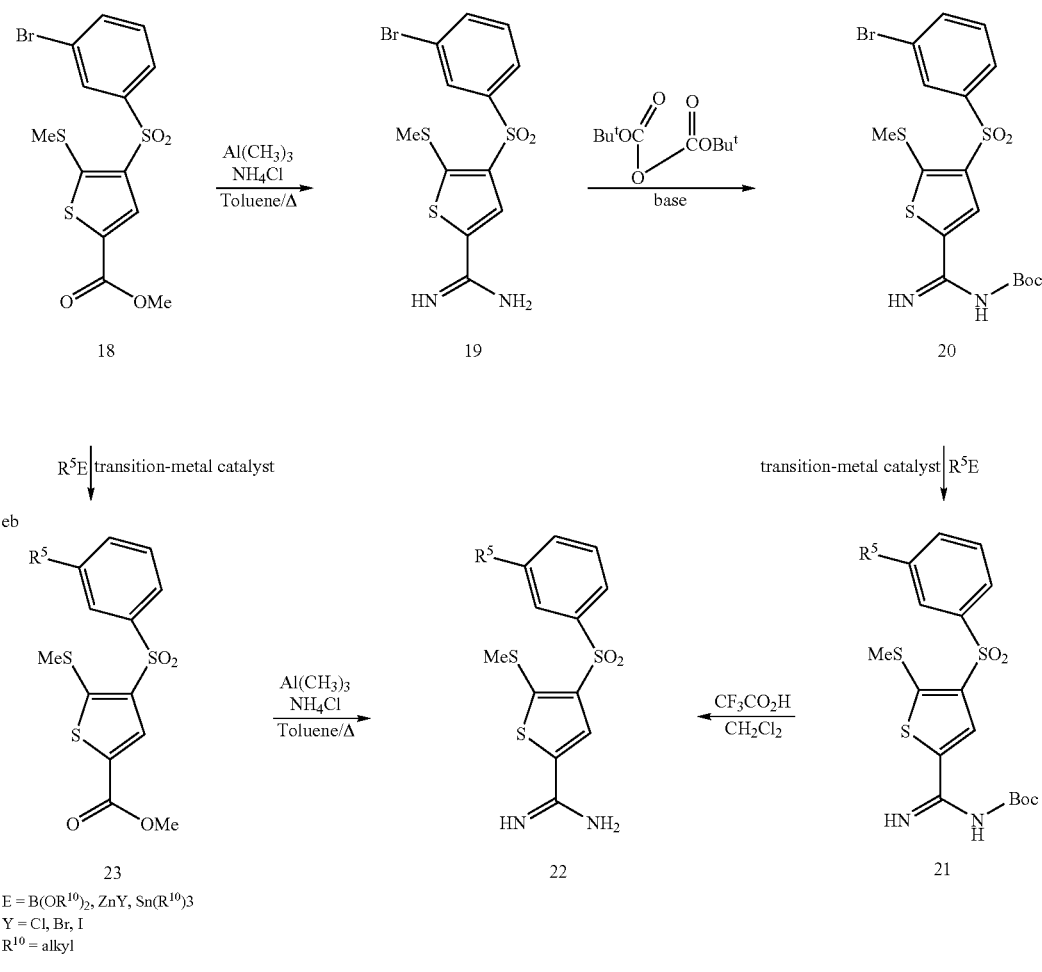

E = B(OR$^{10}$)$_2$, ZnY, Sn(R$^{10}$)$_3$
Y = Cl, Br, I
R$^{10}$ = alkyl

Scheme 6a illustrates approaches to providing the biaryl functionality present in compounds of Formula II, where R$^5$ can be a substituted aromatic or heteroaromatic ring (aryl or heteroaryl). Starting with either of two aryl bromides, the methyl carboxylate 18 or the Boc-amidine 20, a transition-metal catalyzed cross-coupling reaction can take place using an appropriately substituted arylboronic acid, arylzincate, or arylstannane under Suzuki (Miyaura, N.; Suzuki, A., Chem. Rev. 95:2457 (1995)), Negishi (Negishi, E. et al., J. Org. Chem. 42:1821 (1977)), or Stille conditions (Stille, J. K. Angew. Chem., Int. Ed. Engl. 25: 508 (1986), and references contained therein), respectively.

The Stille-type cross-coupling reaction takes place under inert atmosphere between an arylstannane and an aryl halide mediated by a catalyst such as palladium tetrakis-triphenylphosphine. The reaction is usually performed at temperatures ranging from room temperature to 150° C. in an aprotic solvent of appropriate boiling point such as tetrahydrofuran, toluene, or dimethylformamide. In some cases, additives such as lithium chloride (Curran, D. P. et al., J. Org. Chem. 61:6480 (1996)) or copper iodide (Liebeskind, L. S.; Fengl, R. W., J. Org. Chem. 55:5359 (1990)) can facilitate the cross-coupling reaction.

A more preferable cross-coupling reaction of aryl bromides 18 and 20 takes place under Negishi conditions, utilizing an aryl zinc reagent. The aryl zinc reagent can be prepared by transmetalation of an aryl grignard or aryl lithium reagent with a zinc halide salt, or more preferably, directly prepared from an aryl halide and activated zinc (Reike, R. D., Tetrahedron 53:1925 (1997). The cross-coupling reaction generally takes place at temperatures between 60 and 100° C. in THF or THF/polar aprotic co-solvent mixtures. Palladium tetrakis(triphenylphosphine) is the most widely used catalyst, although new catalysts such as palladium di-tert-butylphosphine (Dai, C.; Fu, G. C., J. Am. Chem. Soc. 123:2719 (2001)) can offer enhanced reactivities.

The most preferable and widely applicable biaryl-forming reaction conditions for aryl bromides 18 and 20 take place under Suzuki conditions. Many sets of reaction conditions can be employed to promote the Suzuki-type cross-coupling reactions. These include appropriate combinations of anhydrous or water-containing solvents, appropriate bases such as metal carbonates, phosphates, and fluorides, and the transition-metal catalyst. For the synthesis of biarylsulfones 21 and 23, the most universal reaction conditions consisted of reacting aryl bromide 18 or 20 with an arylboronic acid or an aryboronate ester (e.g. pinacolboronate) in a biphasic toluene/ethanol/aqueous sodium carbonate solvent system. Palladium tetrakis-triphenylphosphine is used as the catalyst under these aqueous conditions. Under anhydrous conditions, new catalysts such as palladium di-tert-butylphosphine (Littke, A. F. et al., *J. Am. Chem. Soc.* 122:4020 (2000)) and bis (o-(dicyclohexylphosphino)biphenyl) palladium (Wolfe, J. P. et al., *J. Am. Chem. Soc.* 121: 9550 (1999)) can offer enhanced reactivity at lower catalyst loadings.

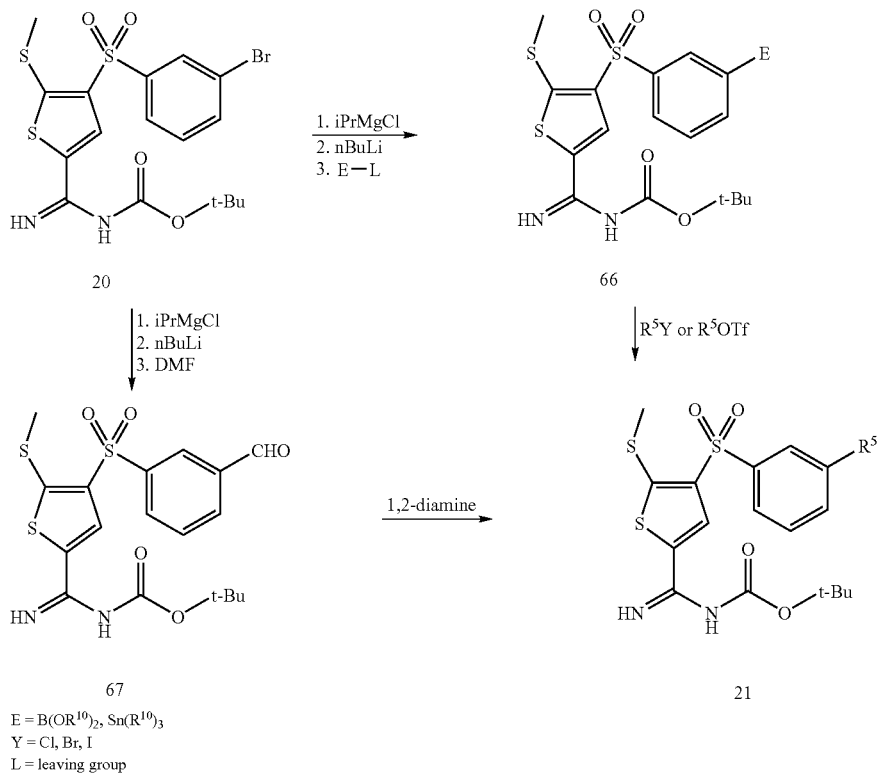

Scheme 6b describes an alternate route to compounds of Formula II where $R^5$ is an aryl, or heteroaryl. Boc-protected amidine 20 is converted to an organoboron or organostannane 66, which is then reacted with a suitable halide or triflate in the presence of a palladium catalyst to give 21, which is converted to the amidine 22 as described in scheme 6a. The preferred method for the synthesis of 66 when E is a boron or tin species is to first treat 20 with a base such isopropylmagnesium chloride, followed by lithiation with a suitable reagent such as n-butyllithium, followed by reaction with an electrophile such as trimethyl borate or tributyltin chloride.

Another approach to introduce heteroaromatics is to prepare 67. This is accomplished by treatment of the organolithium species, prepared as outlined above, with a suitable electrophile such as N,N-dimethylformamide. Conversion of 67 to 21 can then be accomplished using diamine reagents such as 1,2-phenyldiamine to give 2-substituted benzimidazoles or ammonium acetate and glyoxal to give 2-substituted imidazoles, which is converted to the amidine 22 as described in scheme 6a.

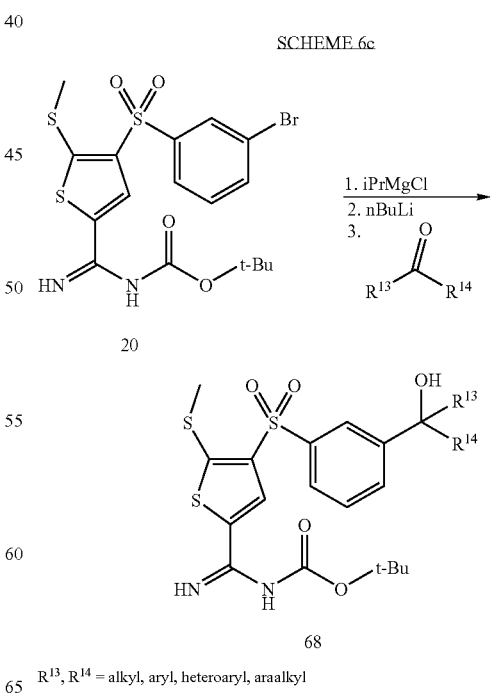

$R^{13}, R^{14}$ = alkyl, aryl, heteroaryl, araalkyl

Scheme 6c describes methods for the introduction of alkyl groups to the phenyl ring of Formula I. Compound 20 is treated with a base such as isopropylmagnesium chloride, followed by lithiation with a suitable reagent such as n-butyllithium, followed by reaction with electrophiles such as aldehydes and ketones to give 68 (Wakefield, B. J. *The Chemistry of Organolithium Compounds*; Pergamon: Oxford, 1974; Wakefield, B. J. *Organolithium Methods*; Academic: San Diego, 1990), which is converted to the amidine 22 as described in scheme 6a.

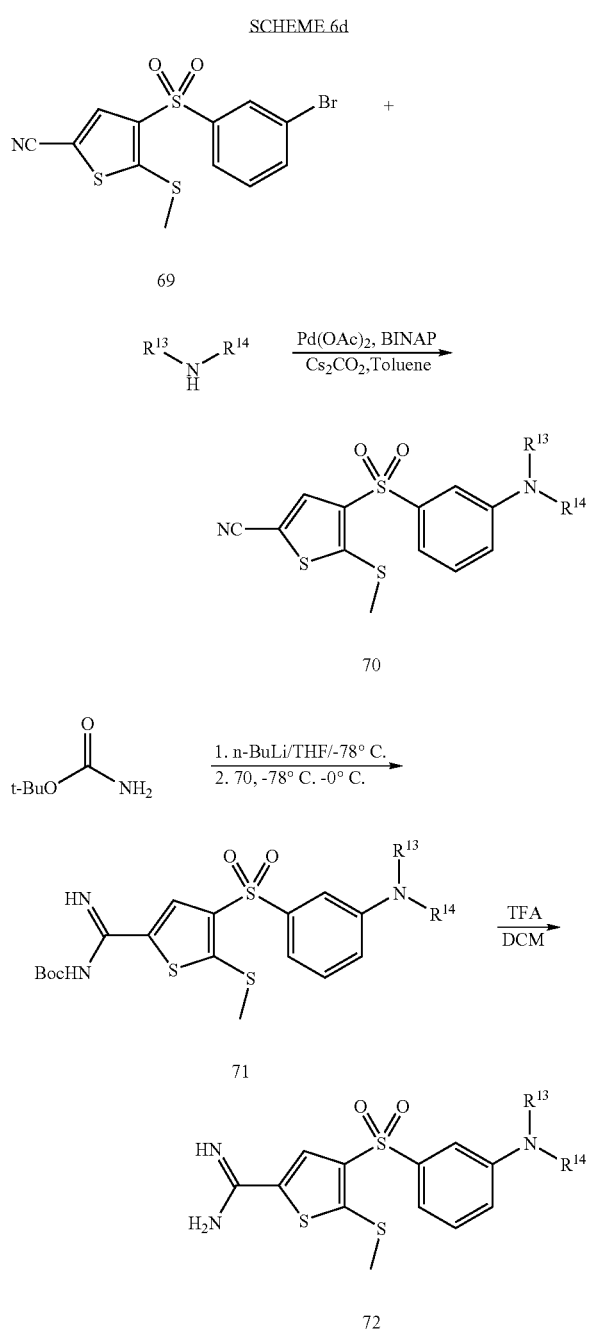

Scheme 6d describes an approach to compounds of formula I, where the Ar residue is substituted with amines at the meta-position. Transition metal catalyzed coupling of the bromide 69 with amines is used to synthesize arylamine 70. Examples of suitable transition metal catalyst include palladium(0) or palladium(II) compounds such as Pd(II) acetate (Pd(OAc)$_2$), dipalladium tris(dibenzylidineacetone) (Pd$_2$(dba)$_3$), tetrakis(triphenylphosphine) palladium(0) (Ph$_3$P)$_3$Pd), nickel(II) bis(1,5-cyclooctadiene) (Ni(COD)$_2$), or (1,1'-bis(diphenylphosphino)ferrocenyl nickel dichloride, in the presence or absence of coordinating ligand and in the presence of a suitable base and solvent. Preferred catalyst include Pd(OAc)$_2$ and Pd$_2$(dba)$_3$. Examples of coordinating ligands include tri-t-butylphosphine, 2,2'-bis(diphenylphosphino)-1,1'-binaphthyl (BINAP), 2,2'-bis(ditolylphosphino)-1,1'binaphthyl (tol-BINAP), 1,1'-bis(diphenylphosphino)ferrocene (DPPF), bis(2-diphenylphosphinophenyl) ether (DPEphos), 2-(di-t-butylphosphino)biphenyl (DBPB), 2-(di-cyclohexylphosphino)biphenyl (DCPB), 2-dicyclohexylphosphino-2,-(N,N-dimethylamino)biphenyl (DCDMB). Preferred ligands for palladium-catalyzed reactions include BINAP, DBPB, DCPB, and DCDMB. Preferred ligands for nickel-catalyzed reactions include DPPF or 1,10-phenanthroline. Examples of suitable bases include sodium t-butoxiode, potassium t-butoxide, cesium carbonate, potassium carbonate, potassium phosphate or cesium fluoride, with sodium t-butoxide, potassium phosphate or cesium carbonate preferred depending on the other functionality present in 70 and the amine being coupled. Suitable solvents include aromatic hydrocarbons such as benzene, toluene, or xylenes; ethers such as dimethoxyethane (DME) or 1,4-dioxane; or amides such as N,N-dimethylformamide, N,N-dimethylacetamide or N-methylpyrrolidinone. Preferred solvents include toluene, DME and 1,4-dioxane. The coupling reaction may be carried out at a temperature of 20–160 C., preferably 20–100 C., and most preferably at the lowest possible temperature that provides reaction times of less than 24 hours. For representative methodologies, catalysts, examples of conditions and reviews of these types of palladium-catalyzed coupling reactions see: J. P. Wolfe, et al., Acc. Chem. Res., 31:805–18(1998), C. G. Frost, et al., J. Chem. Soc., Perkin Trans 1, 2615–23 (1998) and J. P. Wolfe, J. Org. Chem., 65:1158–74 (1998). For examples of nickel-catalyzed reactions see J. P. Wolfe and S. L. Buchwald, J. Am. Chem. Soc., 119:6054–58 (1997). The nitrile 70 can be converted to the BOC-protected amidine by treating with lithiated tert-butylcarbamate (Aldrich Chemical Company, WI, USA). The amidine 72 is obtained by treating 71 with TFA.

After completion of the biaryl species, amidine 22 is completed either through amidination of the methyl carboxylate 23 (Scheme 2), or by deprotection of Boc-amidine 21 with trifluoroacetic acid or hydrochloric acid in an organic solvent such as dioxane.

SCHEME 7

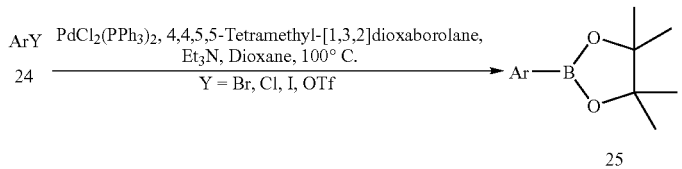

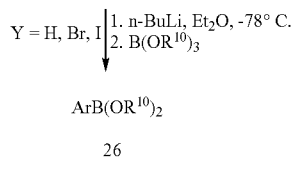

When not commercially available, arylboronic acids of formulas 25 and 26, where Ar is phenyl, naphthyl, or heterocycle, any of which are optionally substituted, can be synthesized by the methods illustrated in Scheme 7. When Y is Br, I, or Cl and Ar is tolerant to strong basic and/or nucleophilic conditions, the preferred method involves lithium/halogen exchange with n-BuLi followed by treatment with trimethyl borate, triisopropyl borate, or triethyl borate to give compounds of formula 26 where $R^{10}$ is Me, Et, iPr, or H. Alternatively, regioselective metalation of 24 can be directly achieved with n-BuLi or t-BuLi when Y is H and an ortho directing group is present in Ar. In such cases, treatment of the metalated species with trimethyl borate, triisopropyl borate, or triethyl borate gives rise to compounds of formula 26 where $R^{10}$ is Me, Et, iPr or H. Examples of ortho directing groups suitable for this transformation include but are not limited to $OCH_2OCH_3$, $SO_2NR_2$, $CONR_2$, CONHR, NHCOR, $NHCO_2R$, and CSNHR (Mark, R., et al, *J. Org. Chem.* 47: 2101 (1982); Townsend, C., et al., *Tetrahedron Lett.* 3923 (1981)). When Ar contains functional groups that are sensitive to base and/or nucleophiles, conversion of 24, where Y is Br, I, Cl, or OTf to arylboronic acids of formula 25 can be effected using one of several methods involving palladium(0)-mediated boronation of arylhalides (Ishiyama, T., et al., *J. Org. Chem.* 60: 7508 (1995)). Examples of this transformation include but are not limited to treatment of 24 with: 1) Pd(PPh_3)_4, (PPh_3)_2PdCl_2, or PdCl_2(dppf), pinacolborane, and Et_3N in dioxane at 100° C. (Murata, M., et al., *J. Org. Chem.* 65:164 (2000)); 2) Pd(OAc)_2, (2'-Dicyclohexylphosphanyl-biphenyl-2-yl)-dimethyl-amine, bis(pinacolato)diboron, and K_3PO_4 in toluene at 95° C. (Old, D. W., et al., *J. Am. Chem. Soc.* 120:9722 (1998)); 3) PdCl_2(dppf), bis(pinacolato)diboron, and KOAc in DMSO (Ishiyama, T., et al., *J. Org. Chem.* 60:7508 (1995)). Suitable reaction times for this transformation are 12–24 hr.

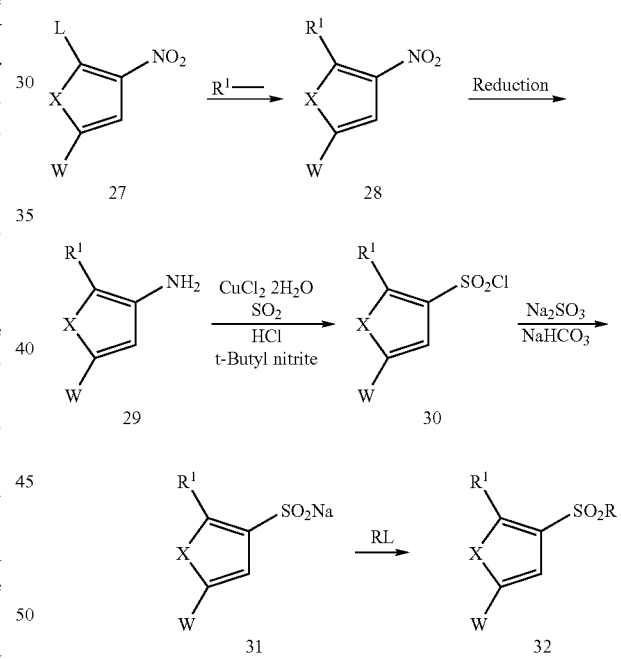

SCHEME 8

X = O, S
W = CN, COOH, $CONH_2$, $CO_2R^8$
L = Br

Scheme 8 illustrates an alternate approach to compounds of Formula I where X=O or S, and $R^1$=halo, alkylthio, aralkylthio, arylthio, alkyloxy, aralkyloxy or aryloxy. A heterocycle 27 appropriately substituted with a leaving group L may be substituted with an anion of $R^1$ to give intermediate 28. When L=halo, the halide can be left alone to give $R^1$=halo. The amine 29 is then derived from reduction of the nitro group. Appropriate reagents to effect reduction of the nitro functionality include hydrogen gas in the presence of a catalyst such as palladium or platinum metal deposited on carbon or barium sulfate in any number of solvents such as methanol, ethanol, ethyl acetate, DMF, or THF. More preferably, tin (II) chloride may be employed as a reductant in a solvent such as methanol or ethanol. Alternatively, metals such as zinc or iron (Stanetty, P. and Kremslehner, M., *Heterocycles* 48: 259 (1998)) may also be used. When $R^1$ is halo, titanium (III) chloride in HCl (see Ho, Wong, *Synthesis* 45 (1974)) is the preferred reducing reagent. The amine 29 can then be converted to the sulfonyl chloride 30 by diazotization in the presence of sulfur dioxide and copper (II) chloride (Ramsay, G. C. et al, *J. Am. Chem. Soc.* 93:1166–1171 (1971), European Patent EP 983982). The sulfonyl chloride 30 can then be treated with sodium sulfite and sodium bicarbonate to afford the sodium sulfinate 31 (Field L. and Clark. R. D., Organic Synthesis Collective Vol. IV, 674–677, John Wiley and Sons, Inc. 1963). The sulfinate 31 can be converted to sulfone 32 by reacting the sulfinate 31 with an alkyl or aryl group appropriately substituted with a leaving group in a solvent such as ethanol (Field L. and Clark. R. D., Organic Synthesis Collective Vol. IV, 674–677, John Wiley and Sons, Inc. 1963).

Scheme 9 illustrates a specific example of the method shown in Scheme 8. The sulfinate 33 can be obtained by treating 4-nitro-5-bromo-thiophene-2-carboxylic acid methyl ester (Dell'Erba, C. and Spinelli, D., *Tetrahedron* 21: 1061 (1965); Dell'Erba, C. et al., *J. Chem. Soc., Perkin Trans* 2, 1779 (1989)) according to scheme 8. The sulfinate 33, can be treated with 34 (Hazelton, C. J. et al., *Tetrahedron*, 51:5597 (1995)) in a solvent such as aqueous ethanol with acetic acid as catalyst to give the sulfone 35. Sulfone 35 is treated with sodium dithionite in aqueous ethanol to afford 36 (Hazelton, C. J. et al., *Tetrahedron*, 51:5597 (1995)), which can be cross-coupled to an aryl residue using the methods described in Scheme 6 to give compounds of formula 37. Both compound 36 and 37 can be treated with hot formic acid to give compounds 42 and 38 respectively. Benzimidazoles 38 and 42 can then be alkylated to give 39–41 and 43–44 respectively. These esters can be converted to their amidines by the methods described in Scheme 2.

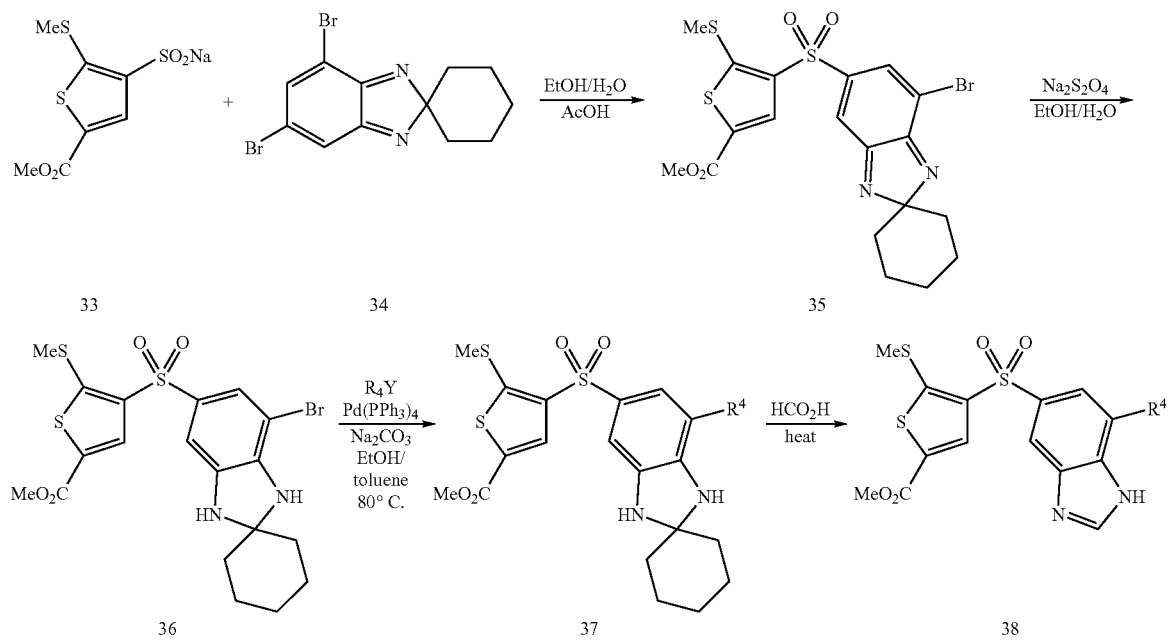

SCHEME 9

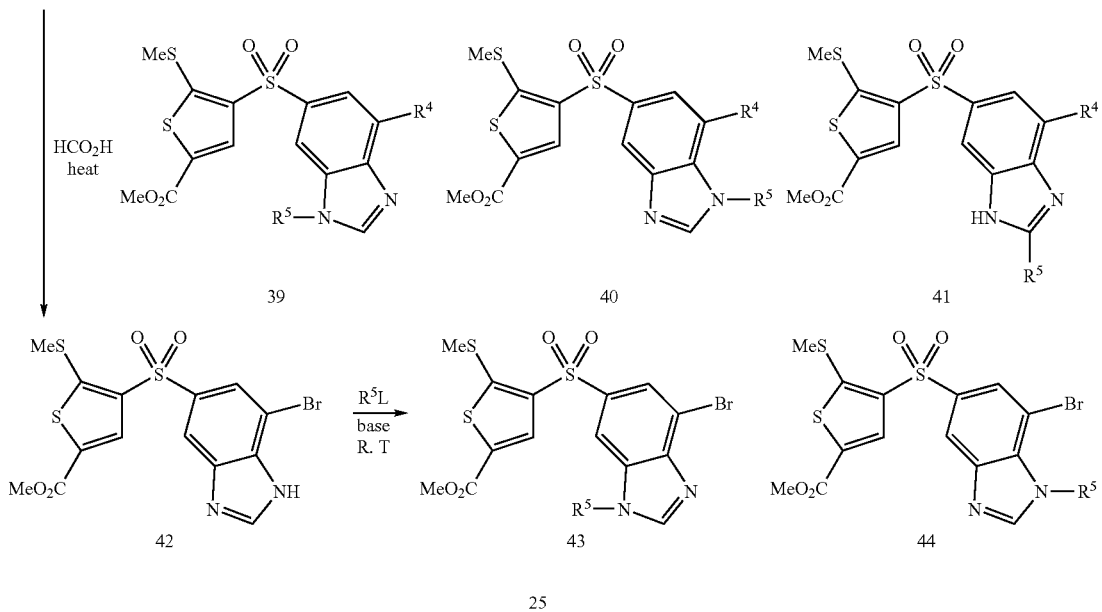
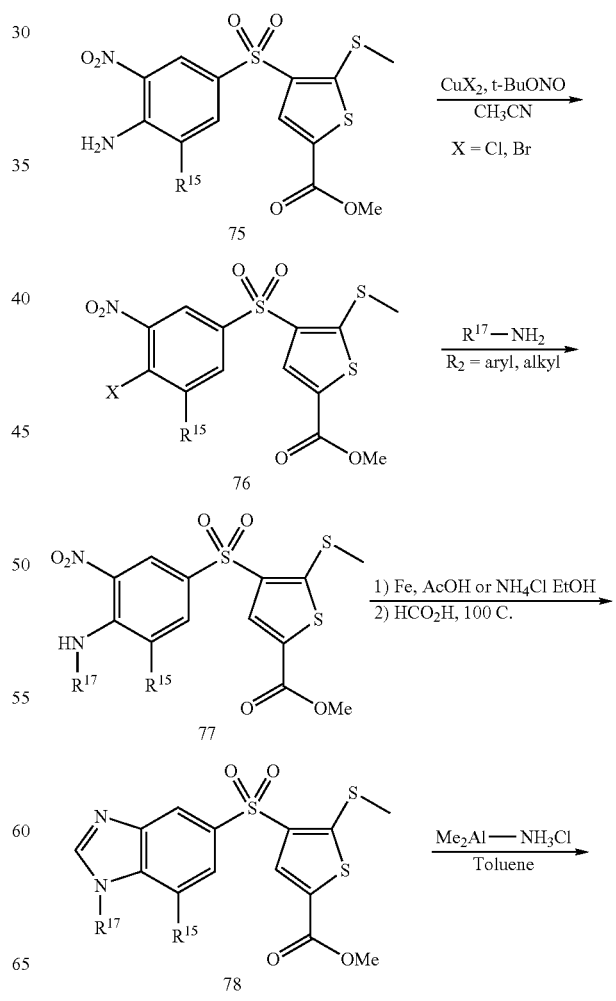
SCHEME 9B

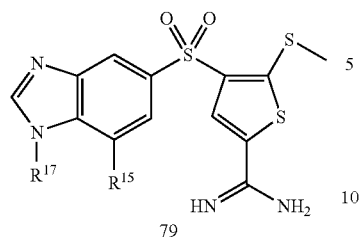

Scheme 9b illustrates approaches to 1-alkyl-5-sulfonyl-benzimidazoles of compounds of Formula X, where R=H, halo, alkyl, alkyloxy, and $R_1$=alkyl or aryl. Appropriately substituted sulfinate can be prepared from the corresponding sulfonyl chloride in a manner similar to that described in scheme 11. Reaction of the appropriately substituted arylsulfinate 74 with the bromo-nitro-thiophene, 1 yields a mixture of mono- and bis-sulfone adducts. Thiomethoxide addition at −78° C. chemoselectively occurs at the 5-position of the thiophene for both adducts, giving the intermediate 75. The aniline 75 is converted to the arylhalide 76 under Sandmeyer diazotization conditions (Doyle, M. P. et al. J. Org. Chem. 42, 2426 (1977)). Heating this halo-nitroarene with an amine or arylamine at 60–80° C. in the presence of a base (NaOAc or DIEA) yields the substituted aniline 77. Reduction of the nitro group (e.g. Fe/AcOH in ethanol) followed by heating in formic acid gives the benzimidazole 78, which can be converted to the amidine 79 as described in Scheme 2.

Scheme 10

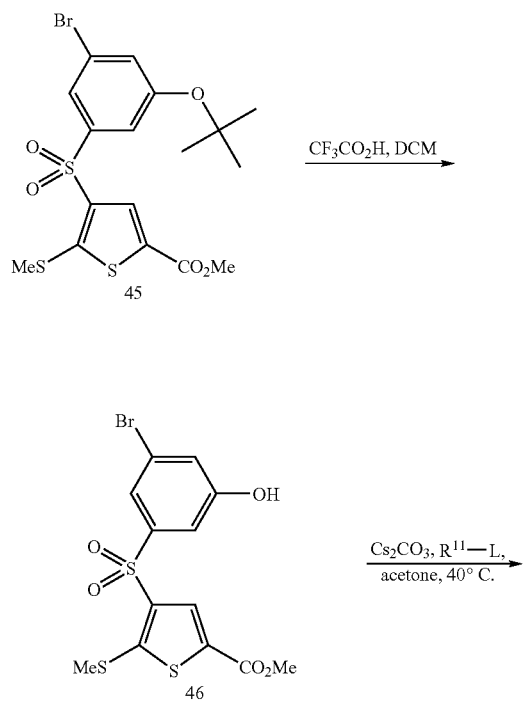

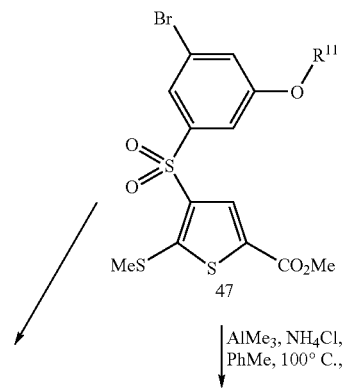

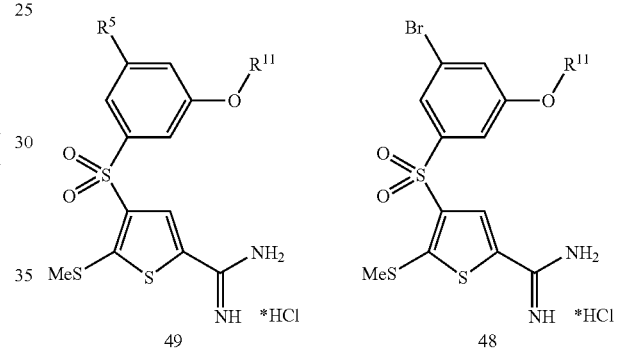

The synthesis of compounds of formulas 48 and 49, having two meta-substitutions on the phenyl ring with respect to the sulfone are described in Scheme 10. The tert-butyl phenol ether in compound 45 can be deprotected using a strong acid treatment such as TFA or HCl in DCM or dioxane, respectively. The free phenol as in compound 46 can be alkylated under standard conditions with alkyl halide and a base, preferably $Cs_2CO_3$ in acetone, to furnish compounds described by formula 47. Examples of alkylating agents ($R^{11}$) include but are not limited to allyl bromide, benzyl bromide, methyl iodide, 2-bromoacetate, and 2-bromoacetamide. The carboxylic acid ester in formula 47 can be directly converted to the amidine or a masked amidine as described in Scheme 2 to give compounds of formula 48. Alternatively, 47 can be cross-coupled with a variety of arylboronic acids and heterocyclic boronic acids as shown in Scheme 6, followed by amidination as previously described to afford compounds contained in formula 49.

SCHEME 11

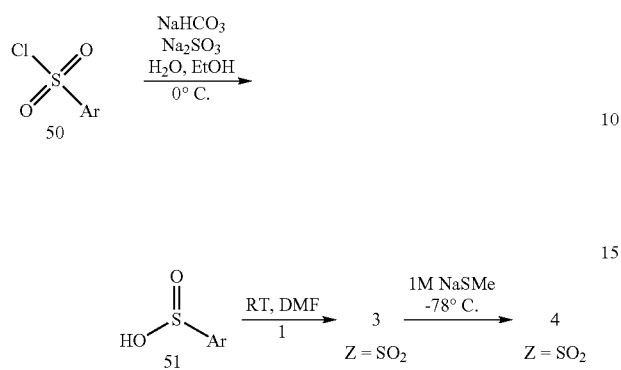

X = O, S
W = CN, CONH$_2$, CO$_2$R$^8$
L = Br

Scheme 11 illustrates yet another approach to compounds of Formula I where X=O or S, R$^1$=halo, alkylthio, aralkylthio, arylthio, alkyloxy, aralkyloxy or aryloxy. A sulfonyl chloride 50, where Ar is aryl or heteroaryl, is treated with sodium sulfite and sodium bicarbonate to afford the sodium sulfinate 51 (Field L. and Clark. R. D., Organic Synthesis Collective Vol. IV, pp. 674–677, John Wiley and Sons, Inc. (1963)). The sulfinate 51 can be converted to sulfone 3 by reacting the sulfinate 51 with 1. The sulfone 3 can then be treated as described in scheme 1 to give intermediate 4, which can be converted to an amidine by the methods described in scheme 2.

SCHEME 12

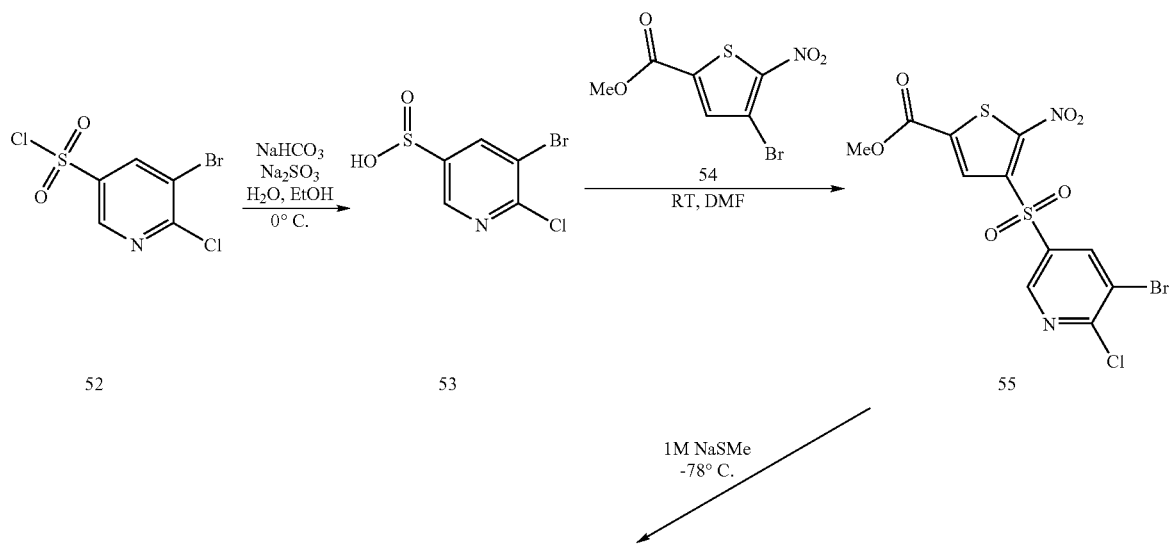

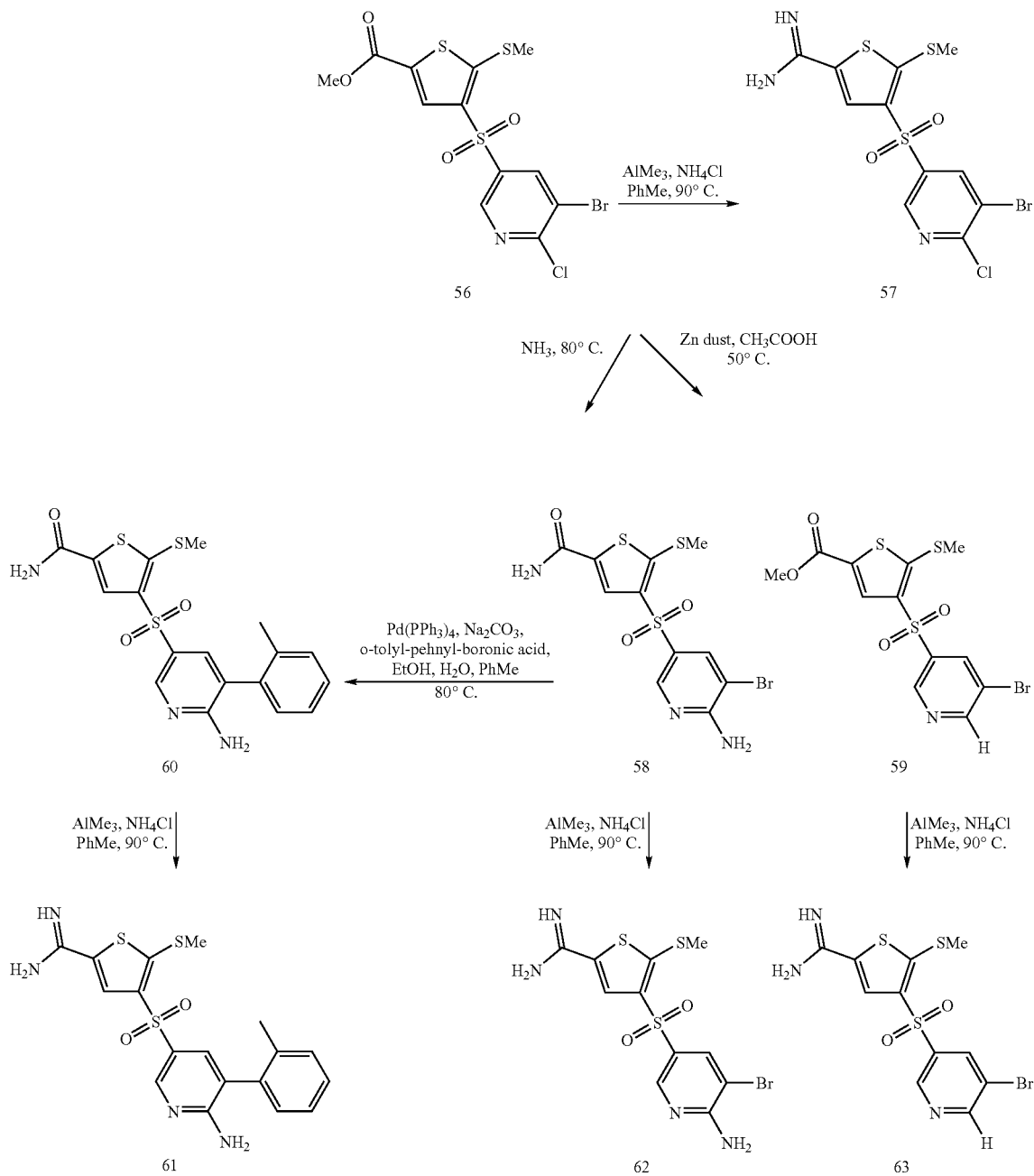

Scheme 12 illustrates a specific example of the method shown in scheme 11. Pyridylsulfonylchloride (Aldrich), 52 is converted to the sulfinic acid and reacted with thiophene ester 54 to give the sulfone, 55. The sulfone (55) is then treated as described in scheme 1 to give the intermediate 56. Intermediate 56 can be treated with ammonia or zinc dust in acetic acid (Krutosikova, A.; Sleziak, R. *Collect. Czech. Chem. Commun.* (1996) 61, 1627–1636) to give compounds 58 or 59 respectively. The amide 58 can be converted to the biaryl compound 60 using methods described in scheme 6. Compounds 56, 58, 59, and 60 can be converted to the corresponding amidines 57, 61, 62, and 63 respectively, as described in scheme 2.

SCHEME 13
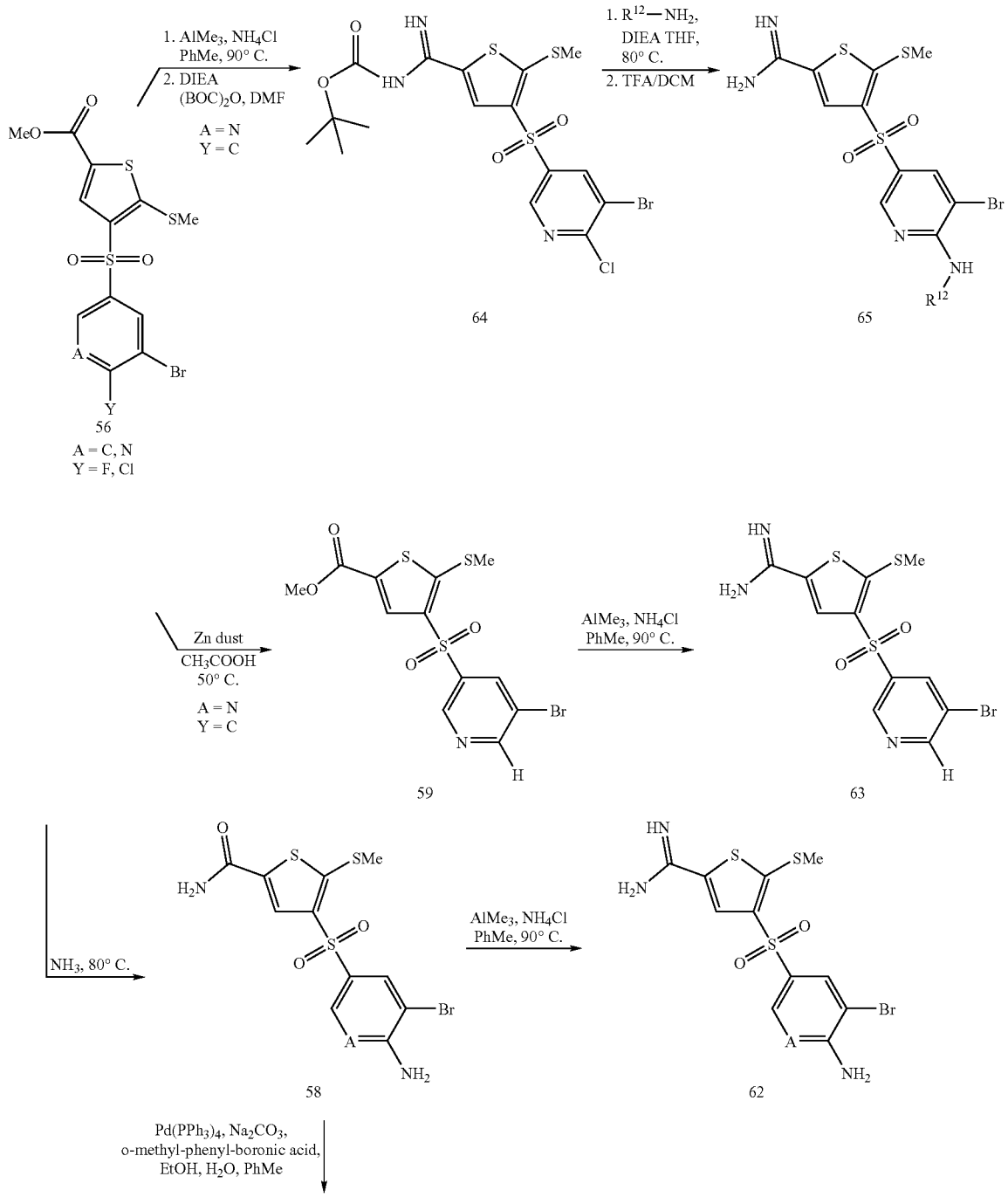

-continued

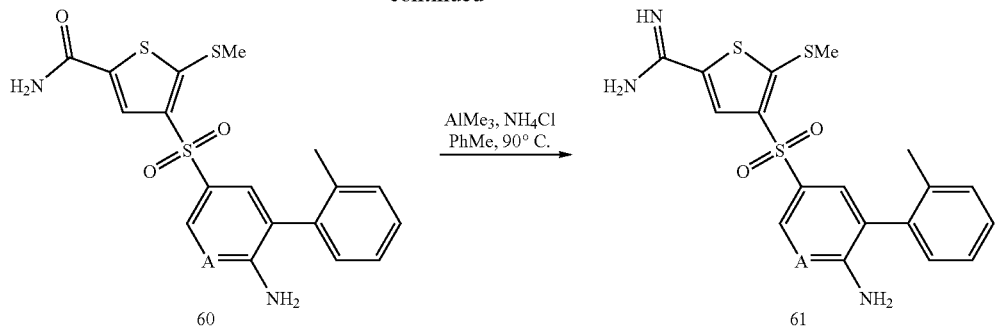

Scheme 13 illustrates a general route to compounds of formula I where Ar is substituted 3-pyridyl (when A=N) and compounds of formula II where the phenylsulfone moiety has an amino group at the 4-position (A=N, C). The sulfone 56 is prepared as described in scheme 12 and then treated as described in scheme 1 to give the corresponding amidine, which is BOC-protected to give intermediate 64. The C1 group in intermediate 64 can be displaced with an amine to give a substituted aminopyridine, which upon treatment with trifluoroacetic acid gives compound 65. Intermediate 56 can be treated with Zn dust (Krutosikova, A.; Sleziak, R. Collect. Czech. Chem. Commun. (1996) 61, 1627–1636) to give the dehalogentaed product 59, which can also be converted to the amidine 63. The halogen Y in intermediate 56 (when A=N or C) can also be substituted with ammonia to give 58, which can be converted to the amidine 62. Alternatively, 58 can be converted to the biaryl compound 60 using methods described in scheme 6.

SCHEME 14

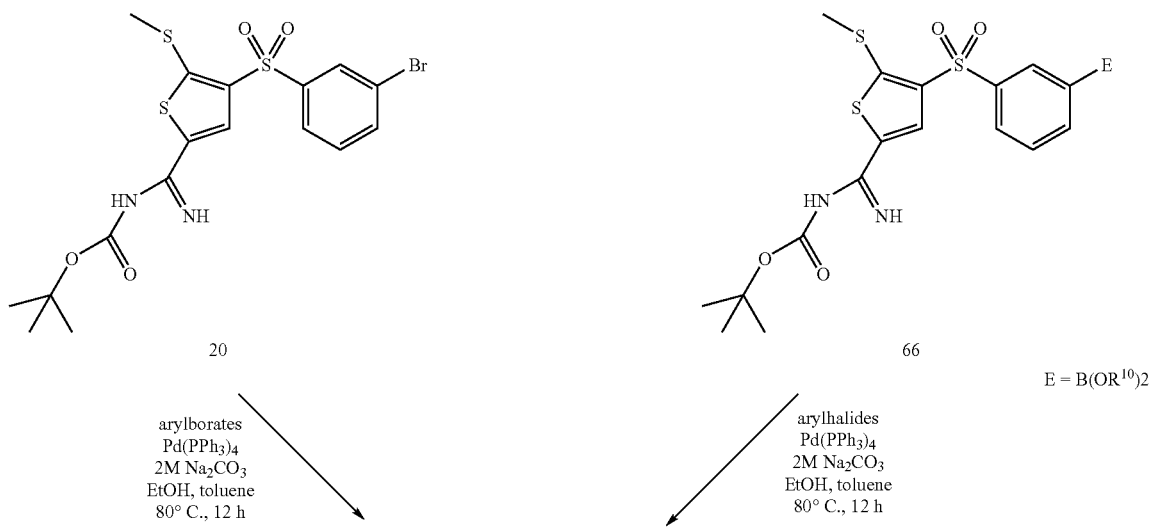

$E = B(OR^{10})_2$

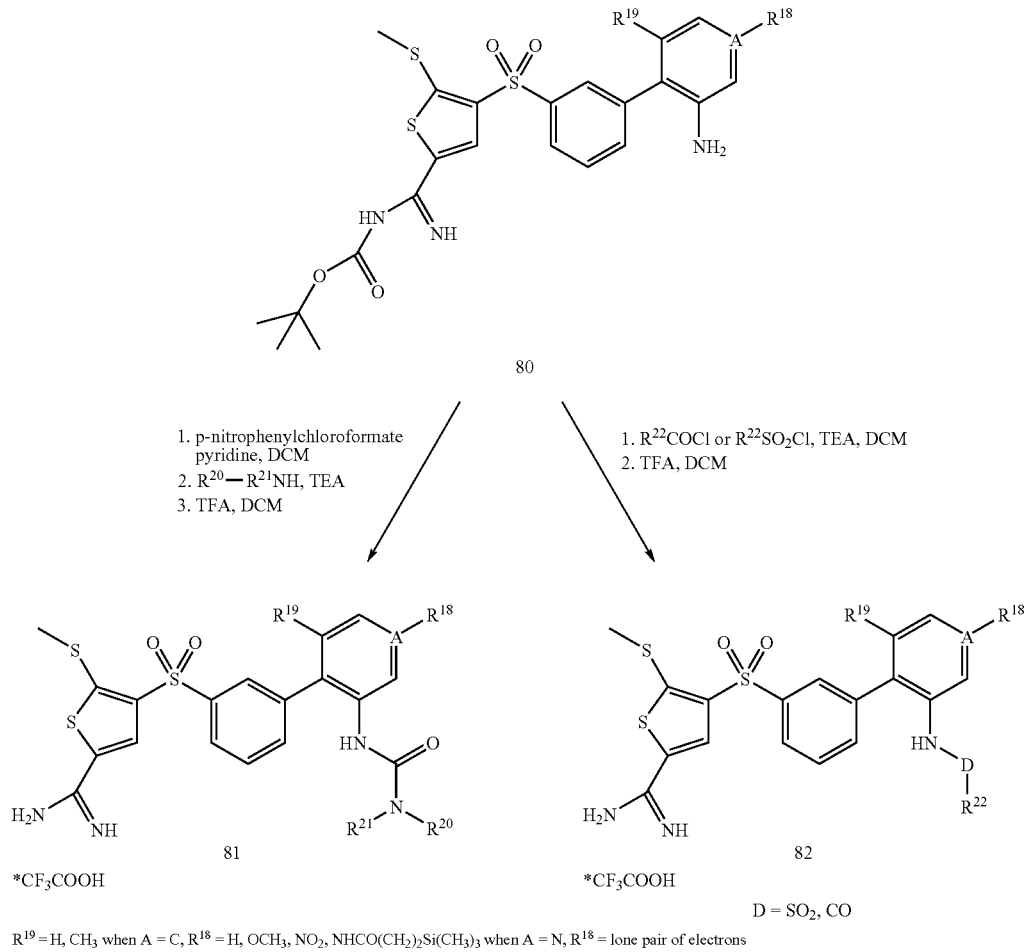

$R^{19}$ = H, CH$_3$ when A = C, $R^{18}$ = H, OCH$_3$, NO$_2$, NHCO(CH$_2$)$_2$Si(CH$_3$)$_3$ when A = N, $R^{18}$ = lone pair of electrons Scheme 14 illustrates the general approach to the synthesis of compounds of formula II, where $R^5$ is 2-aminophenyl or 2-amino-4-pyridyl and the amino groups are further substituted. The Biaryl-intermediate 80 can be prepared either by treating 20 with an appropriately substituted arylboronate or boronic acid using conditions similar that described in scheme 6a or by treating 66 with an appropriately substituted arylhalide or triflate using conditions similar to that described in scheme 6b. Intermediate 2 can be converted to the corresponding substituted ureas 81 using conditions such as p-nitrophenylchloroformate in the presence of a base such as pyridine, followed by addition of a substituted amine, followed by treatment with an acid such as trifluoroacetic acid. In an alternative approach intermediate 80 can be treated with reagents such as substituted isocyanates in the presence of a base such as triethylamine, followed by treatment with an acid such as trifluoroacetic acid to give the corresponding substituted ureas 81. The intermediate 2 can also be converted to the corresponding amides 82 using reagents such as substituted acids in the presence of coupling reagents such as EDCI and HOBt, followed by treatment with an acid such as trifluoroacetic acid. The intermediate 80 can also be converted to the corresponding amides or sulfonamides 82 by treating with acid chlorides, sulfonyl chlorides, anhydrides, or activated esters in the presence of a base such as triethylamine, followed by treatment with an acid such as trifluoroacetic acid.

SCHEME 15

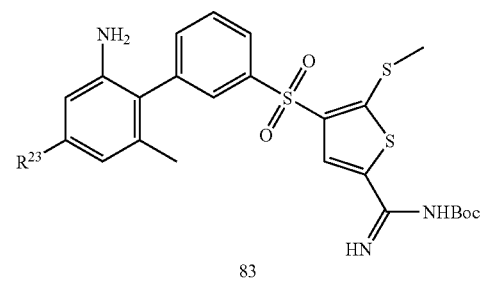

83
$R^{23}$ = $NO_2$, $NHCO_2CH_2CH_2SiMe_3$

↓

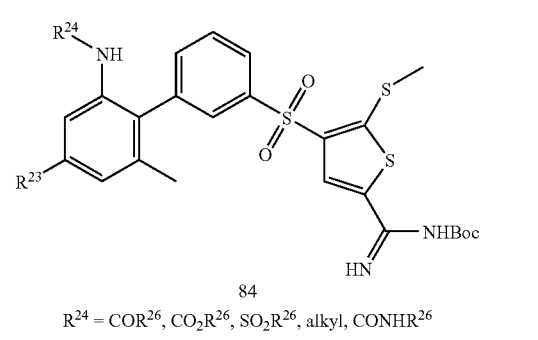

84
$R^{24}$ = $COR^{26}$, $CO_2R^{26}$, $SO_2R^{26}$, alkyl, $CONHR^{26}$

When $R^{23}$ = $NO_2$ | When $R^{23}$ = $NHCO_2CH_2CH_2SiMe_3$
Fe, $NH_4Cl$ | TBAF

↓

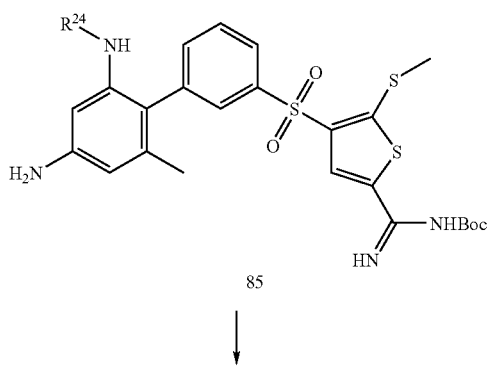

85

↓

-continued

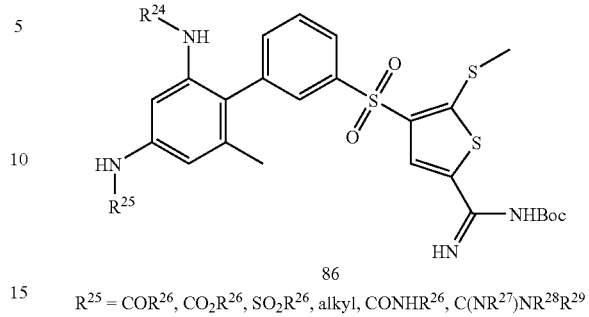

86
$R^{25}$ = $COR^{26}$, $CO_2R^{26}$, $SO_2R^{26}$, alkyl, $CONHR^{26}$, $C(NR^{27})NR^{28}R^{29}$ Scheme 15 illustrates a general approach to the synthesis of compounds of formula II, where $R^5$ is 2,4-diaminophenyl and the amino groups are further substituted. Intermediate 83 can be synthesized in a manner similar to that described in scheme 14. When $R^{23}$ is a masked amine such as nitro, or trimethylsilylethyl carbamate (Teoc), the ortho-aniline may be functionalized with a variety of reagents such as acid chlorides, sulfonyl chlorides, activated carboxylic esters, and isocyanates to give compound 84. When $R^{23}$ of compound 84 is a nitro-group it can be reduced to an amino-group under mild conditions using iron powder in ethanolic aqueous ammonium chloride ($R^1$=$NO_2$) and further reacted with reagents such as acid chlorides, sulfonyl chlorides, activated carboxylic esters, isocyanates, guanidinylating reagents, alkyl halides, and aldehydes (reductive amination) to give compound 86. When $R^{23}$ is a protected aniline it can be deprotected. For example a Teoc group is removed by treatment with a fluoride anion source such as tetrabutylammonium fluoride in THF to give compound 85. This can be further functionalized in the manner described above.

SCHEME 16
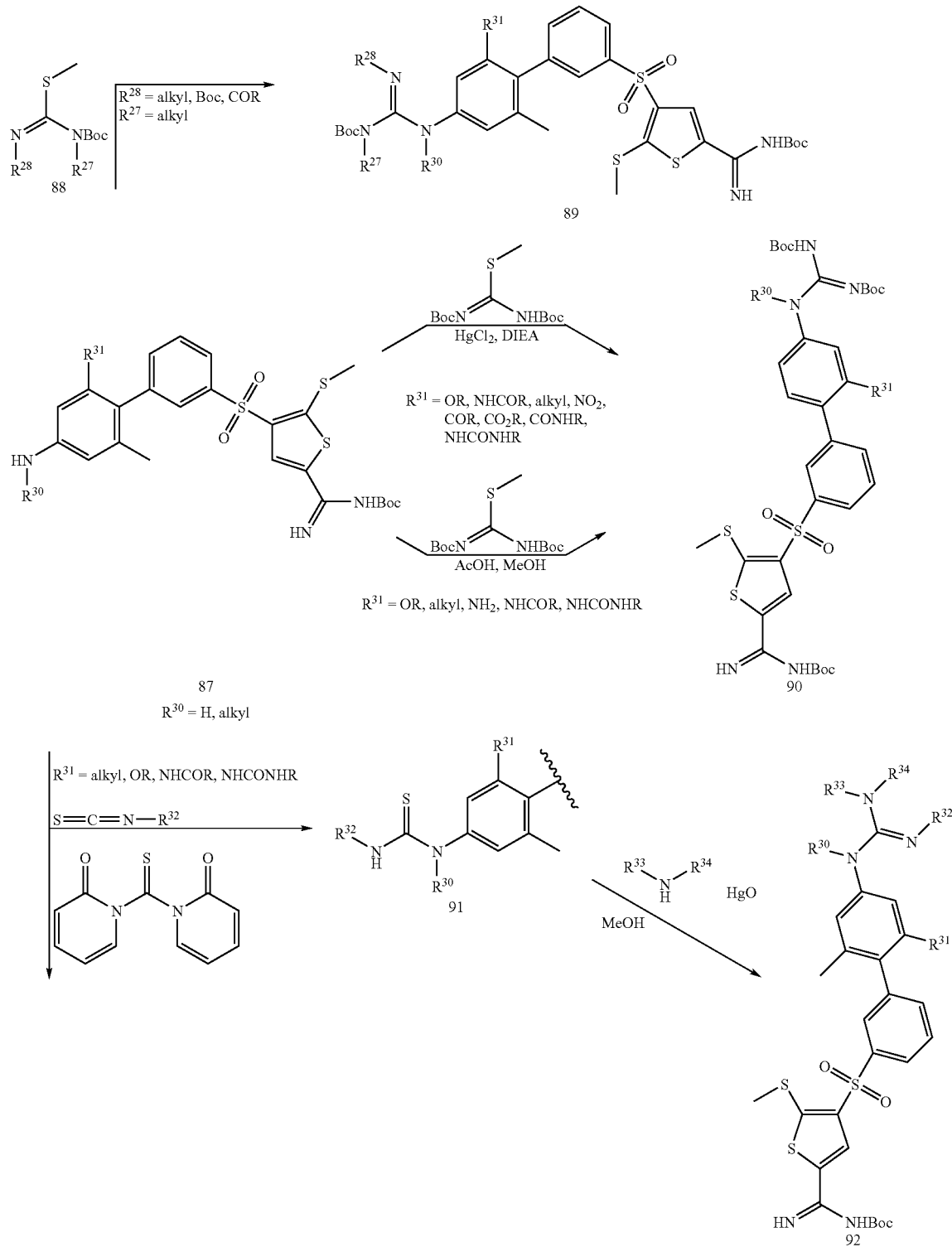

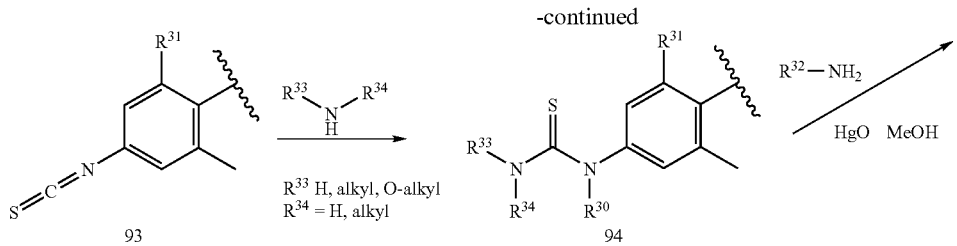

Scheme 16 illustrates approaches to providing the arylguanidine functionality of compounds of Formula II where $R^5$ is a substituted phenyl group with a 4-amino functionality. Depending on the nature of the group R, several methods may be employed in the guandinylation of the aniline 87 to compounds 89, 90 or 92. When $R^1$ is H or alkyl, unsubstituted or N,N'-bis-substituted arylguanidines 90, can be synthesized by the reaction of the aniline with a diprotected S-alkyl isothiourea (e.g. bis-Boc-SMe-isothiourea). This reaction can generally be promoted by either of two reaction conditions; 1) a mercury salt (e.g. $HgCl_2$) with triethylamine at 50° C. [WO-99/206208] or 2) acetic acid in methanol at 40° C. [Tetrahedron Lett., 43, 6563–6566 (2000)]. When $R^1$ is a strong electron-withdrawing group (e.g. nitro), or contains other acid-sensitive functionality, the mercury reagent is preferred. When R is, or, contains an amino-group, selective guanidinylation at the 4-amino group can be achieved using the acetic acid/methanol conditions. Monosubstituted N'-arylguanidines 89 can be synthesized by reaction of the aniline ($R^1$=H, alkyl) with a substituted diprotected S-alkyl isothiourea (e.g. alkylN(Boc)-C(SMe)=NBoc). The acetic acid in methanol reaction condition is the method of choice for this transformation. The monoalkyl isothiourea starting materials can be synthesized via alkylation of the bis-Boc-SMe-isothiourea with a hydride base/alkyl halide [J. Med. Chem., 36, 2956–2963 (1993)] or Mitsunobu reaction [J. Med. Chem., 43, 2362–2370 (2000)].

Alternatively, arylguanidines can be prepared from corresponding thiourea intermediates 91 and 94. Preparation of 91 is achieved by reacting the aniline scaffold with an isothiocyanate. Alternatively, the aniline scaffold may be converted to the isothiocyanate [J. Org. Chem., 51, 2613–2615 (1986)] followed by reaction with an alkylamine, aniline, hydrazide, or alkoxylamine to give 94. The thiourea may then be converted to the guanidine using mercuric oxide in the presence of excess amine (e.g. ammonia, methylamine, etc.) [J. Chem. Soc, 475, 479 (1949)].

SCHEME 17

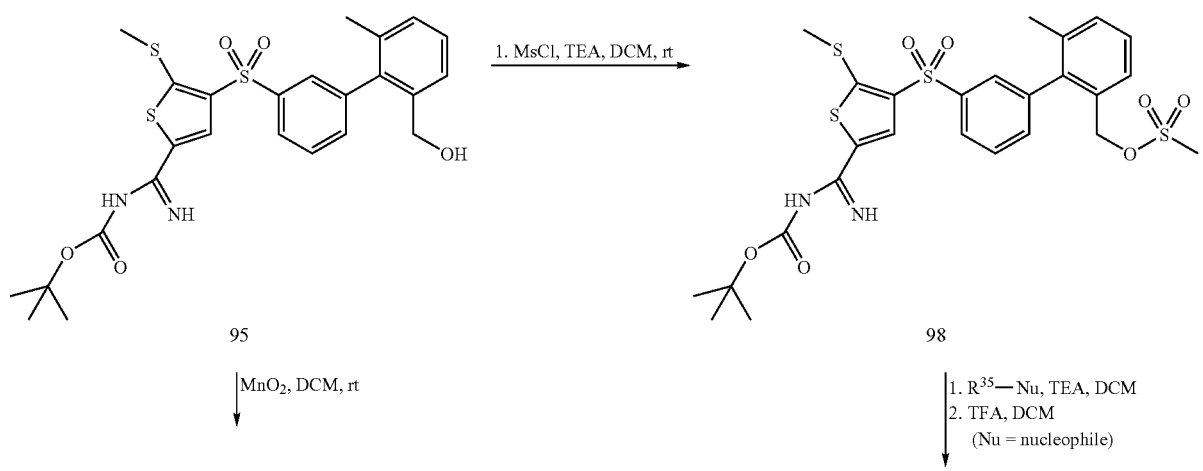

-continued

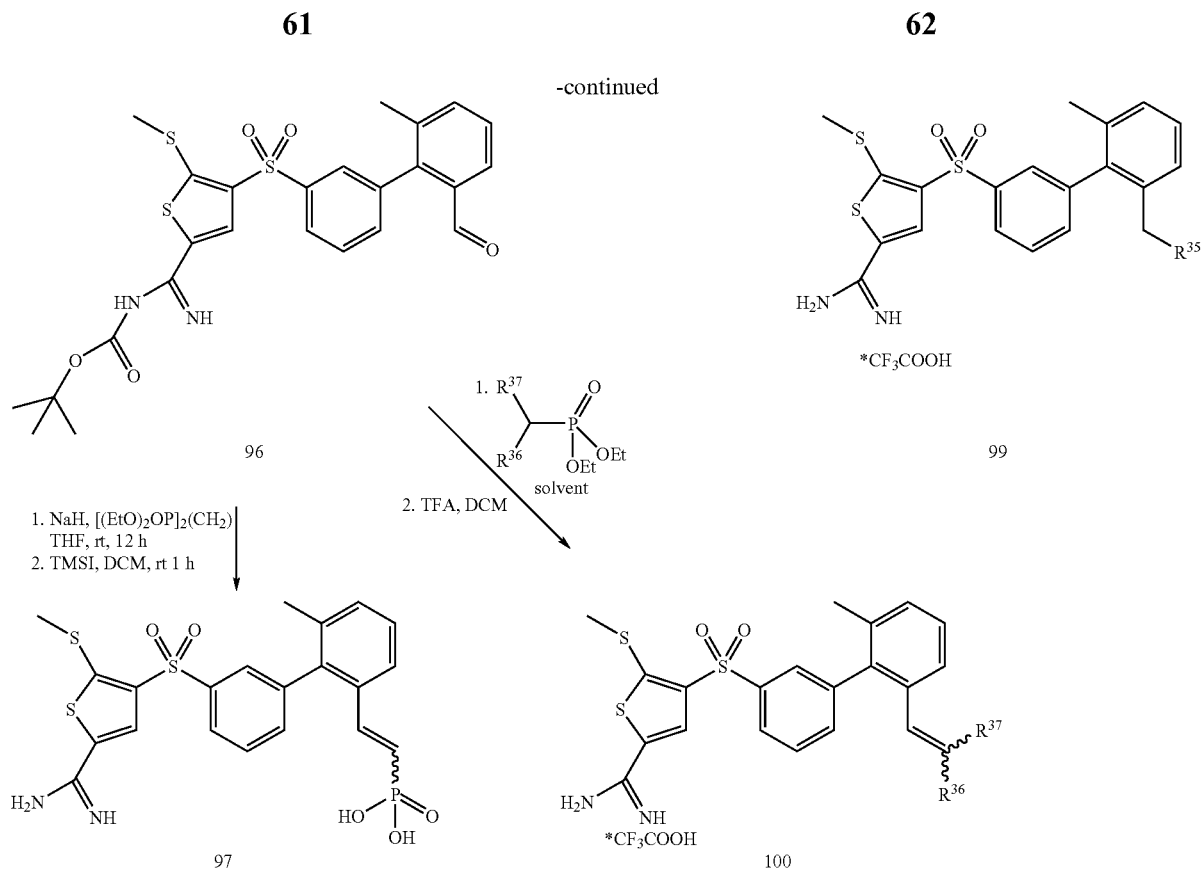

Scheme 17 illustrates the general approach to the synthesis of compounds of formula II, represented by examples 213–214. The alcohol 95 can be converted to the corresponding mesylate 98 in the presence of a methanesulfonyl chloride and a base such as triethylamine, in a solvent such as dichloromethane. Mesylate 98 can be treated with a variety of substituted nucleophiles in the presence of a base such as triethylamine in a solvent such as dichloromethane, followed by treatment with an acid such as trifluoroacetic acid to give the corresponding product 99. Alternatively, compound 95 can be converted to the corresponding aldehyde 96 in the presence of an oxidizing agent such as manganese dioxide. Aldehyde 96 can then be treated with a variety of phosphorus ylides to give the corresponding olefin, (see Paterson, I., et al., Org. Lett. 5(1):35–38 (2003)), followed by treatment with an acid such as trifluoroacetic acid to give compound 100. For example, aldehyde 96 is treated with (diethoxy-phosphorylmethyl)-phosphonic acid diethyl ester in the presence of a base such as sodium hydride in a solvent such as tetrahydrofuran, followed by treatment with trimethylsilyl iodide and a solvent such as dichloromethane to give compound 97 (see Ruzziconi, R. et al., J. Org. Chem. 68(3):736–742 (2003)).

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Example 1

4-(4'-Hydroxy-[1,1';3',1']terphenyl-3'-sulfonyl)-5-methylsulfanyl-thiophene-2-carboxamidine trifluoroacetate

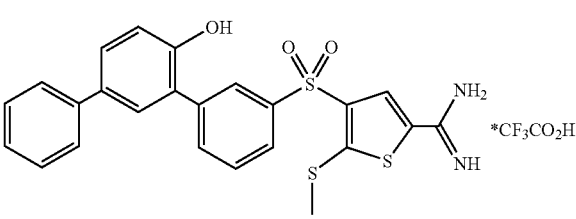

a) 4-Methoxymethoxy-biphenyl

To an oven-dried flask containing a stirbar was added 4-hydroxybiphenyl (1.70 g, 10 mmol), toluenesulfonic acid (190 mg, 1.1 mmol), dichloromethane (DCM, 5 mL), and dimethoxypropane (5 mL). The solution was heated and stirred at 40° C. for 48 h. Solid NaHCO$_3$ (200 mg) was added, followed by EtOAc (100 mL) and NaOH (1N, 20 mL). The layers were separated and the organic layer was further extracted with NaOH (1N, 12×20 mL), brine (30 mL), and was dried over sodium sulfate. Removal of the solvents in vacuo yielded the title compound (385 mg, 18%) which was used without further purification. $^1$H-NMR (CDCl$_3$); δ 7.56 (m, 4H), 7.44 (m, 2H), 7.34 (m, 1H), 7.14 (m, 2H), 5.24 (s, 2H), 3.54 (s, 3H).

b) 4-Methoxymethoxy-biphenyl-3-yl-boronic acid

Butyllithium (2.5M, 1.44 mL, 3.6 mmol) was added over 5 min to a stirred solution of 4-methoxymethoxy-biphenyl (from the previous step 385 mg, 1.8 mmol) in Et$_2$O (18 mL) at 0° C. The reaction was allowed to warm to rt and stirred for 2 h. The solution was cooled to −78° C. and trimethylborate (1.23 mL, 10.8 mmol) in THF (10 mL) was quickly added. The reaction warmed to rt over 1 h and was stirred 1 h at rt, during which it became cloudy and a gelatin-like residue appeared. EtOAc (70 mL) and water (30 mL) were added along with HCl (1N, 1 mL). The biphasic solution was stirred for 10 min and the layers were separated. The organic layer was further extracted with HCl (0.1N, 3×20 mL), brine (60 mL), and was dried over sodium sulfate. Removal of the solvents in vacuo followed by chromatography of the residue (20–40% EtOAc in hexanes) yielded the title compound (135 mg, 29%) as a light-brown solid. The title compound exists as a mixture of boronic acids and anhydrides in CDCl$_3$, therefore the reported NMR signals represent pairs or groups of related signals. $^1$H-NMR (CDCl$_3$): δ 8.07 (d, 1H, J=2.6 Hz), 7.60 (m, 3H), 7.42 (m, 2H), 7.31 (m, 1H), 7.19 (d, 1H, J=8.6 Hz), 6.20 (s, 1H), 5.32 (s, 2H), 3.77 (s, 1H), 3.53 (s, 3H).

c) {Imino-[4-(4'-methoxymethoxy-[1,1';3',1']terphenyl-3-sulfonyl)-5-methylsulfanyl-thiophen-2-yl]-methyl}-carbamic acid tert-butyl ester A 2-dram vial with a septa-containing screwcap was charged with {[4-(3-bromo-benzenesulfonyl)-5-methylsulfanyl-thiophen-2-yl]-imino-methyl}-carbamic acid tert-butyl ester (Example 27 (50 mg, 0.1 mmol)), 4-methoxymethoxy-biphenyl-3-yl-boronic acid (from the previous step 103 mg, 0.4 mmol), aqueous Na$_2$CO$_3$ (2M, 0.8 mL, 1.6 mmol), ethanol (0.8 mL) and toluene (1.6 mL). A stirbar was added, the vial was capped, the solution was sparged with argon for 10 min, and Pd(PPh$_3$)$_4$ (29.4 mg, 0.025 mmol) was added. The biphasic solution was vigorously stirred under inert atmosphere at 80° C. for 16 h, then was cooled to rt. EtOAc (20 mL) and water (10 mL) were added and the layers were separated. The organic layer was washed with saturated NaHCO$_3$ (2×10 mL), brine (10 mL) and was dried over sodium sulfate. Removal of the solvents in vacuo followed by preparative TLC (25% EtOAc in hexanes) of the residue yielded the title compound (15 mg, 24%) as a light-yellow glass. $^1$H-NMR (CDCl$_3$): δ 8.27 (t, 1H, J=1.9), 7.99 (ddd, 1H, J=1.2, 1.6, 7.9 Hz), 7.96 (s, 1H), 7.84 (dt, 1H, J=1.4, 7.9 Hz), 7.57 (m, 5H), 7.45 (m, 2H), 7.36 (m, 1H), 7.30 (m, 1H), 5.18 (s, 2H), 3.41 (s, 3H), 2.59 (s, 3H), 1.52 (s, 9H). ESI-MS (m/z): Calcd. for C$_{31}$H$_{32}$N$_2$O$_6$S$_3$: 624.8; found: 624.9.

d) 4-(4'-Hydroxy-[1,1';3',1']terphenyl-3'-sulfonyl)-5-methylsulfanyl-thiophene-2-carboxamidine trifluoroacetate The {imino-[4-(4'-methoxymethoxy-[1,1';3',1']terphenyl-3-sulfonyl)-5-methylsulfanyl-thiophen-2-yl]-methyl}-carbamic acid tert-butyl ester ((Example 1: step c) 15 mg, 0.024 mmol) was dissolved in DCM (5 mL), water (3 drops) was added, followed by trifluoroacetic acid (5 mL). The solution was stirred for 2 h at rt and the solvents were removed in vacuo. The residue was purified via HPLC (C$_{18}$-column, 10–70% CH$_3$CN over 30 min) which yielded the title compound as a white solid (11 mg, 73%). $^1$H-NMR (CD$_3$OD): δ 8.34 (t, 1H, J=1.6 Hz), 8.32 (s, 1H), 7.98 (m, 2H), 7.66 (t, 1H, J=7.9 Hz), 7.58 (m, 2H), 7.53 (d, 1H, J=2.1 Hz), 7.50 (dd, 1H, J=2.3, 8.4 Hz), 7.41 (m, 2H), 7.29 (m, 1H), 7.02 (d, 1H, J=8.4 Hz), 2.71 (s, 3H). ESI-MS (m/z): Calcd. for C$_{24}$H$_{20}$N$_2$O$_3$S$_3$: 481.6 (M+H); found: 481.3.

Example 2

4-(2'-Methoxymethoxy-[1,1';3',1'']terphenyl-3-sulfonyl)-5-methylsulfanyl-thiophene-2-carboxamidine trifluoroacetate

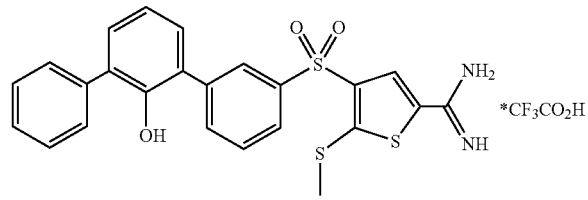

a) 2-Methoxymethoxy-biphenyl

The procedure as in Example 1: step a was followed using 2-hydroxybiphenyl (1.70 g, 10 mmol), p-toluenesulfonic acid (190 mg, 1.1 mmol), DCM (5 mL), and dimethoxypropane (5 mL). Analogous aqueous workup yielded the title compound (225 mg, 11%) which was used without further purification. $^1$H-NMR (CDCl$_3$): δ 7.58 (m, 2H), 7.44 (m, 2H), 7.36 (m, 2H), 7.32 (m, 1H), 7.25 (dd, 1H, J=1.2, 8.1 Hz), 7.12 (dt, 1H, J=1.2, 7.4 Hz), 5.14 (s, 2H), 3.42 (s, 3H).

b) 4-Methoxymethoxy-biphenyl-3-yl-boronic acid

The procedure used in Example 1: step b was followed using 2-methoxymethoxy-biphenyl ((Example 2: step a) 225 mg, 1.05 mmol), butyllithium (2.5M, 1.44 mL, 3.6 mmol), and trimethylborate (1.23 mL, 10.8 mmol). Analogous aqueous workup and SiO$_2$ flash chromatography yielded the title compound (123 mg, 45%) as a light brown solid. The title compound exists as a mixture of boronic acids and anhydrides in CDCl$_3$; therefore the reported NMR signals represent pairs or groups of related signals. $^1$H-NMR (CDCl$_3$): δ 7.53 (m, 1H), 7.23 (m, 2H), 7.12 (m, 3H), 7.05 (m, 1H), 6.94 (m, 1H), 4.28 (s, 2H), 3.51 (s, 1H), 2.96 (s, 3H).

c) {Imino-[4-(2'-methoxymethoxy-[1,1';3',1'']terphenyl-3-sulfonyl)-5-methylsulfanyl-thiophen-2-yl]-methyl}-carbamic acid tert-butyl ester The procedure used in Example 1: step c was followed using {[4-(3-bromo-benzenesulfonyl)-5-methylsulfanyl-thiophen-2-yl]-imino-methyl}-carbamic acid tert-butyl ester (Example 27 (50 mg, 0.1 mmol)), 2-methoxymethoxy-biphenyl-3-yl-boronic acid ((Example 2: step b) 103 mg, 0.4 mmol), Na$_2$CO$_3$ (2M, 0.8 mL, 1.6 mmol), Pd(PPh$_3$)$_4$ (29.4 mg, 0.025 mmol), ethanol (0.8 mL), and toluene (1.6 mL). Analogous aqueous workup and purification of the crude material by preparative TLC (25% EtOAc in hexanes) yielded the title compound (18 mg, 29%) as a light-yellow glass. $^1$H-NMR (CDCl$_3$): δ 8.24 (t, 1H, J=1.7 Hz), 8.06 (s, 1H), 7.95 (ddd, 1H, J=1.2, 1.9, 7.9 Hz), 7.86 (dt, 1H, J=1.4, 7.7 Hz), 7.60 (t, 1H, J=7.9 Hz), 7.56 (m, 2H), 7.2–7.45 (m, 6H), 4.22 (s, 2H), 2.60 (s, 3H), 2.47 (s, 3H), 1.48 (s, 9H). ESI-MS (m/z): Calcd. for C$_{31}$H$_{32}$N$_2$O$_6$S$_3$: 624.8; found: 624.9.

d) 4-(2'-Methoxymethoxy-[1,1';3',1'']terphenyl-3-sulfonyl)-5-methylsulfanyl-thiophene-2-carboxamidine trifluoroacetate The procedure used in Example 1: step d was followed using {imino-[4-(2'-methoxymethoxy-[1,1';3',1'']terphenyl-3-sulfonyl)-5-methylsulfanyl-thiophen-2-yl]-methyl}-carbamic acid tert-butyl ester ((Example 2: step c) 18 mg, 0.029 mmol). Analogous purification by HPLC yielded the title compound as a white solid (17 mg, 94%). $^1$H-NMR (CD$_3$OD): δ 8.32 (s, 1H), 8.27 (t, 1H, J=1.7 Hz), 7.99 (ddd, 1H, J=1.2, 1.9, 7.9 Hz), 7.92 (ddd, 1H, J=1.2, 1.6, 7.9 Hz), 7.66 (dt, 1H, J=0.5, 7.9 Hz), 7.52 (m, 2H), 7.45 (m, 2H), 7.36 (m, 2H), 7.26 (ddd, 2H, J=1.7, 3.5, 7.2 Hz), 7.07 (t, 1H, J=7.9 Hz), 2.71 (s, 3H). ESI-MS (m/z): Calcd. for C$_{24}$H$_{20}$N$_2$O$_3$S$_3$ (M+H): 481.6; found: 481.2.

Example 3

3'-(5-Carbamimidoyl-2-methylsulfanyl-thiophene-3-sulfonyl)-2-methyl-biphenyl-3-carboxylic acid isopropyl ester trifluoroacetate

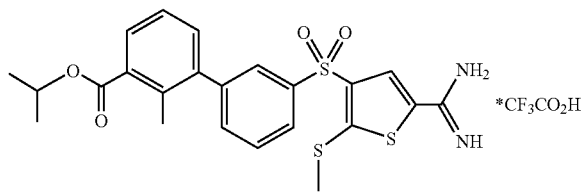

a) 3-Bromo-2-methyl-benzoic acid isopropyl ester

Thionyl chloride (6 mL) was added over 1 min to a 0° C. suspension of 3-bromo-2-methyl benzoic acid (2.15 g, 10 mmol) in DCM (10 mL). After 30 min of stirring, THF (5 mL) was added to induce dissolution. The now homogeneous solution was stirred for 24 h at rt and the volatile component were removed in vacuo. A portion of the crude acid chloride was dissolved in dry isopropyl alcohol (10 mL) and pyridine (2 mL) was added. After stirring for 4 h at rt, the volatile components were removed in vacuo. The residue was partitioned between EtOAc (70 mL) and HCl (1M, 30 mL) and the layers were separated. The organic layer was washed with HCl (1M, 10 mL), NaHCO$_3$ (3×20 mL), water (30 mL), brine (30 mL), and was dried over sodium sulfate. Removal of solvent in vacuo yielded the title compound as a light-yellow oil which was used without further purification. $^1$H-NMR (CDCl$_3$): δ 7.69 (d, 2H, J=7.7 Hz), 7.11 (t, 1H, J=7.9 Hz), 5.26 (heptet, 1H, J=6.3 Hz), 2.63 (s, 3H), 1.39 (d, 6H, J=6.3 Hz).

b) 2-Methyl-3-(4,4,5,5-tetramethyl-[1,3,2]dioxaborolan-2-yl)-benzoic acid isopropyl ester A 2-dram vial with a septa-containing screwcap was charged with a stirbar, 3-bromo-2-methyl-benzoic acid isopropyl ester ((Example 3: step a) 257 mg, 1 mmol), PdCl$_2$(PPh$_3$)$_2$ (42 mg, 0.06 mmol), dioxane (4 mL), and triethylamine (420 µL, 3 mmol). Upon dissolution, 4,4,5,5-tetramethyl-[1,3,2]dioxaborolane (220 µL, 1.5 mmol) was added and the solution was vigorously stirred for 16 h at 100° C. After cooling to rt, EtOAc (30 mL) and water (10 mL) were added (gas evolution!) and the layers were separated. The organic layer was washed with NaHCO₃ (2×10 mL), brine (10 mL), and was dried over sodium sulfate. Removal of the solvents in vacuo followed by SiO₂ flash chromatography of the residue yielded the title compound (130 mg, 43%) as a light-yellow glass. $^1$H-NMR (CDCl₃): δ 7.86 (dd, 1H, J=1.4, 7.4 Hz), 7.80 (dd, 1H, J=1.6, 7.7 Hz), 7.23 (t, 1H, J=7.7 Hz), 5.26 (heptet, 1H, J=6.3 Hz), 2.75 (s, 3H), 1.37 (m, 18H).

c) 3'-[5-(tert-Butoxycarbonylamino-imino-methyl)-2-methylsulfanyl-thiophene-3-sulfonyl]-2-methyl-biphenyl-3-carboxylic acid isopropyl ester The procedure used in Example 1: step c was followed using {[4-(3-bromo-benzenesulfonyl)-5-methylsulfanyl-thiophen-2-yl]-imino-methyl}-carbamic acid tert-butyl ester (Example 27 (50 mg, 0.1 mmol)), 2-methyl-3-(4,4,5,5-tetramethyl-[1,3,2]dioxaborolan-2-yl)-benzoic acid isopropyl ester ((Example 3: step b) 92 mg, 0.3 mmol), Na₂CO₃ (2M, 0.4 mL, 0.8 mmol), Pd(PPh₃)₄ (29.4 mg, 0.025 mmol), ethanol (0.4 mL) and toluene (0.8 mL). Analogous aqueous workup and purification of the crude material by preparative TLC (25% EtOAc in hexanes) yielded the title compound (29 mg, 49%) as a colorless glass. $^1$H-NMR (CDCl₃): δ 7.98 (dt, 1H, J=1.6, 7.6 Hz), 7.93 (m, 2H), 7.79 (t, 1H, J=1.7 Hz), 7.58 (t, 1H, J=7.6 Hz), 7.53 (dt, 1H, J=1.6, 7.6 Hz), 7.36 (s, 1H), 7.30 (d, 1H, J=4.5 Hz), 5.27 (heptet, 1H, J=6.2 Hz), 2.58 (s, 3H), 2.35 (s, 3H), 1.51 (s, 9H), 1.39 (d, 1H, J=6.2 Hz). ESI-MS (m/z): Calcd. for $C_{28}H_{32}N_2O_6S_3$: 588.8; found: 588.9.

d) 3'-(5-Carbamimidoyl-2-methylsulfanyl-thiophene-3-sulfonyl)-2-methyl-biphenyl-3-carboxylic acid isopropyl ester trifluoroacetate The procedure used in Example 1: step d was followed using 3'-[5-(tert-butoxycarbonylamino-imino-methyl)-2-methylsulfanyl-thiophene-3-sulfonyl]-2-methyl-biphenyl-3-carboxylic acid isopropyl ester ((Example 3: step c) 29 mg, 0.049 mmol). Analogous purification by HPLC yielded the title compound (25 mg, 83%) as a white solid. $^1$H-NMR (CD₃OD): δ 8.32 (s, 1H), 8.05 (dt, 1H, J=1.7, 7.7 Hz), 7.95 (t, 1H, J=1.7 Hz), 7.78 (m, 1H), 7.70 (t, 1H, J=7.7 Hz), 7.66 (dt, 1H, J=1.4, 7.7 Hz), 7.36 (s, 1H), 7.35 (d, 1H, J=1.2 Hz), 5.22 (heptet, 1H, J=6.3 Hz), 2.71 (s, 3H), 2.31 (s, 3H), 1.38 (d, 1H, J=6.3 Hz). ESI-MS (m/z): Calcd. for $C_{23}H_{24}N_2O_4S_3$: 489.7 (M+H); found: 489.2.

Example 4

3'-(5-Carbamimidoyl-2-methylsulfanyl-thiophene-3-sulfonyl)-6-methyl-biphenyl-2-carboxylic acid trifluoroacetate

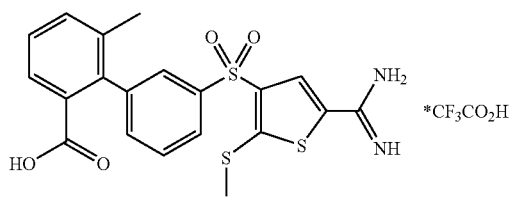

a) 2-Iodo-3-methyl-benzoic acid tert-butyl ester

A 100-mL RB flask was charged with 2-iodo-3-methyl-benzoic acid (1.1 g, 4.2 mmol), a stirbar, Et₂O (15 mL) and DCM (35 mL) and was cooled to −78° C. under an argon atmosphere. Trifluoromethanesulfonic acid (250 μL) was added over 30 sec and isobutylene was bubbled into the solution (until the solution became cloudy) using a 8"/20 gauge steel needle. The reaction was stirred for 6 h between −78 and −20° C. Solid NaHCO₃ (250 mg) was added and the solution was allowed to warm to rt with stirring. After 20 min, the solution was poured into an extraction funnel containing DCM (50 mL) and Na₂CO₃ (2M, 20 mL). The layers were separated and the organic layer was washed with Na₂CO₃ (2M, 2×10 mL), water (20 mL), brine (30 mL) and dried over sodium sulfate. Removal of the solvent in vacuo yielded the title compound (1.05 g, 78%) which was used without further purification. $^1$H-NMR (CDCl₃): δ 7.25 (m, 3H), 2.50 (s, 3H), 1.62 (m, 9H).

b) 4-Methyl-2-(4,4,5,5-tetramethyl-[1,3,2]dioxaborolan-2-yl)-benzoic acid tert-butyl ester The procedure used in Example 3: step b was followed using 2-iodo-3-methyl-benzoic acid tert-butyl ester ((Example 4: step a) 960 mg, 3 mmol), PdCl₂(PPh₃)₂ (126 mg, 0.18 mmol), triethylamine (1.25 mL, 9 mmol), and 4,4,5,5-tetramethyl-[1,3,2]dioxaborolane (660 μL, 4.5 mmol) in dioxane (12 mL) at a reaction temperature of 80° C. Analogous aqueous workup and purification by SiO₂ flash chromatography yielded the title compound (618 mg, 64%). $^1$H-NMR (CDCl₃): δ 7.67 (m, 1H), 7.25 (m, 2H), 2.43 (s, 3H), 1.57 (m, 9H), 1.44 (m, 12H).

c) 3'-[5-(tert-Butoxycarbonylamino-imino-methyl)-2-methylsulfanyl-thiophene-3-sulfonyl]-6-methyl-biphenyl-2-carboxylic acid tert-butyl ester The procedure used in Example 1: step c was followed using {[4-(3-bromo-benzenesulfonyl)-5-methylsulfanyl-thiophen-2-yl]-imino-methyl}-carbamic acid tert-butyl ester (Example 27 (50 mg, 0.1 mmol)), 4-methyl-2-(4,4,5,5-tetramethyl-[1,3,2]dioxaborolan-2-yl)-benzoic acid tert-butyl ester ((Example 4: step b) 127 mg, 0.4 mmol), Na₂CO₃ (2M, 0.8 mL, 1.6 mmol), Pd(PPh₃)₄ (29.4 mg, 0.025 mmol), ethanol (0.8 mL) and toluene (1.6 mL). Analogous aqueous workup and purification of the crude material by preparative TLC (25% EtOAc in hexanes) yielded the title compound (35 mg, 58%) as a light-yellow glass. $^1$H-NMR (CDCl₃): δ 8.01 (ddd, 1H, J=1.2, 1.9, 7.9 Hz), 7.92 (s, 1H), 7.83 (t, 1H, J=1.7 Hz), 7.65 (m, 1H), 7.56 (t, 1H, J=7.8 Hz), 7.43 (dt, 1H, J=1.4, 7.7 Hz), 7.36 (m, 2H), 2.58 (s, 3H), 2.00 (s, 3H), 1.51 (s, 9H). ESI-MS (m/z): Calcd. for $C_{29}H_{34}N_2O_6S_3$: 602.8; found: 602.9.

d) 3'-(5-Carbamimidoyl-2-methylsulfanyl-thiophene-3-sulfonyl)-6-methyl-biphenyl-2-carboxylic acid trifluoroacetate The procedure used in Example 1: step d was followed using 3'-[5-(tert-butoxycarbonylamino-imino-methyl)-2-methylsulfanyl-thiophene-3-sulfonyl]-6-methyl-biphenyl-2-carboxylic acid tert-butyl ester ((Example 4, step c) 29 mg, 0.048 mmol). Analogous purification by HPLC yielded the title compound (23 mg, 70%) as a white solid. $^1$H-NMR (CD₃OD): δ 8.28 (s, 1H), 7.99 (ddd, 1H, J=1.2, 1.9, 7.9 Hz), 7.83 (m, 1H, J=0.5, 1.9 Hz), 7.76 (ddd, 1H, J=0.5, 1.4, 7.7

Hz), 7.63 (dt, 1H, J=0.5, 7.7 Hz), 7.50 (ddd, 1H, J=1.2, 1.6, 4.9 Hz), 7.49 (ddd, 1H, J=0.7, 1.4, 7.7 Hz), 7.40 (t, 1H, J=7.7 Hz), 2.72 (s, 3H), 2.02 (s, 3H). ESI-MS (m/z): Calcd. for $C_{20}H_{18}N_2O_4S_3$ (M+H): 447.6; found: 447.1.

Example 5

4-(6'-Hydroxymethyl-2'-methyl-biphenyl-3-sulfonyl)-5-methylsulfanyl-thiophene-2-carboxamidine

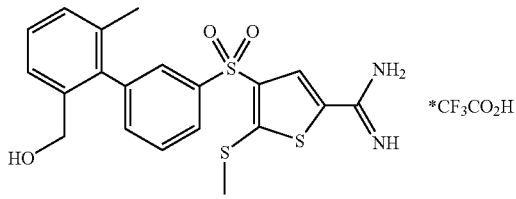

a) (2-Iodo-3-methyl-phenyl)-methanol

Thionyl chloride (6 mL) was added over 1 min to a 0° C. solution of 2-iodo-3-methyl benzoic acid (3.0 g, 11.4 mmol) in DCM (10 mL). The solution was stirred for 24 h at rt and the volatile components were removed in vacuo. A portion of the crude acid chloride (955 mg) was dissolved in THF (15 mL) and NaBH$_4$ (380 mg, 10 mmol) was added. After stirring for 90 min, multiple spots were evident by TLC analysis. The reaction mixture was cooled to −78° C. and solid LiAlH$_4$ (300 mg, 7.91 mmol) was added. The reaction was stirred for 30 min, after which TLC analysis showed one major spot. The reaction was quenched by addition of EtOAc (10 mL) and was slowly poured into a vigorously stirred solution of HCl (1M, 30 mL). EtOAc (70 mL) was added, the layers were separated, and the organic layer was washed with NaHCO$_3$ (3×15 mL), water (15 mL), brine (40 mL), and was dried over sodium sulfate. Removal of the solvent in vacuo yielded the title compound (752 mg, 89%) as a thick oil which was used without further purification. $^1$H-NMR (CDCl$_3$): δ 7.27 (m, 2H), 7.20 (m, 2H), 4.74 (m, 2H), 2.50 (s, 3H), 2.0 (br s, 1H).

b) 7-Methyl-3H-benzo[c][1,2]oxaborol-1-ol

Butyllithium (2.5 M, 2.91 mL, 7.3 mmol) was added dropwise to a −78° C. solution of aryl halide ((Example 5: step a) 723 mg, 2.91 mmol) in Et$_2$O (12 mL). The solution was stirred at −78° C. for 2 h and trimethylborate (3.3 mL, 29.1 mmol) was added in one portion. The solution was warmed to rt over 15 min and stirred for 1 h at rt (appearance of gelatin-like ppt). EtOAc (80 mL) and HCl (0.1 N, 30 mL) were added and the biphasic solution was stirred for 15 min. The layers were separated and the organic layer was washed with HCl (0.1N, 2×10 mL), water (10 mL), brine (30 mL), and was dried over sodium sulfate. Concentration of the solution in vacuo yielded an oily solid which further solidified upon trituration with hexanes. The crude title compound (contaminated with butylboronate products) was used without further purification, existing as a mixture of the cyclic half-ester and the free boronic acid. $^1$H-NMR (CDCl$_3$): δ 7.1–7.4 (m, 3H), 5.23 (m, 2H), 2.57 (s, 3H).

c) {[4-(6'-Hydroxymethyl-2'-methyl-biphenyl-3-sulfonyl)-5-methylsulfanyl-thiophen-2-yl]-imino-methyl}-carbamic acid tert-butyl ester The procedure used in Example 1: step c was followed using {[4-(3-bromo-benzenesulfonyl)-5-methylsulfanyl-thiophen-2-yl]-imino-methyl}-carbamic acid tert-butyl ester (Example 27 (50 mg, 0.1 mmol)), 7-methyl-3H-benzo[c][1,2]oxaborol-1-ol ((Example 5: step b) 59 mg, 0.4 mmol), Na$_2$CO$_3$ (2M, 0.8 mL, 1.6 mmol), Pd(PPh$_3$)$_4$ (29.4 mg, 0.025 mmol), ethanol (0.8 mL) and toluene (1.6 mL). Analogous aqueous workup and purification of the crude material by preparative TLC (40% EtOAc in hexanes) yielded the title compound (21 mg, 40%) as a light-yellow glass. $^1$H-NMR (CDCl$_3$): δ 7.96 (m, 2H), 7.86 (m, 1H), 7.54 (m, 1H), 7.43 (m, 1H), 7.18–7.38 (m, 3H), 4.53 (d, 1H, J=13.3 Hz), 4.45 (d, 1H, J=13.3 Hz), 2.54 (s, 3H), 1.96 (s, 3H), 1.49 (s, 9H). ESI-MS (m/z): Calcd. for $C_{25}H_{28}N_2O_5S_3$: 532.7; found: 532.9.

d) 4-(6'-Hydroxymethyl-2'-methyl-biphenyl-3-sulfonyl)-5-methylsulfanyl-thiophene-2-carboxamidine The procedure used in Example 1: step d was followed using {[4-(6'-hydroxymethyl-2'-methyl-biphenyl-3-sulfonyl)-5-methylsulfanyl-thiophen-2-yl]-imino-methyl}-carbamic acid tert-butyl ester ((Example 5, step c) 21 mg, 0.039 mmol). Analogous purification by C$_{18}$-HPLC yielded the title compound (19 mg, 86%) as a white solid. $^1$H-NMR (CD$_3$OD): δ 8.33 (s, 1H), 8.04 (ddd, 1H, J=1.2, 1.9, 7.9 Hz), 7.88 (m, 1H), 7.71 (dt, 1H, J=0.5, 7.7 Hz), 7.57 (ddd, 1H, J=1.2, 1.6, 7.7 Hz), 7.42 (m, 1H), 7.34 (t, 1H, J=7.7 Hz), 7.26 (m, 1H), 4.20 (s, 2H), 2.72 (s, 3H), 1.99 (s, 3H). ESI-MS (m/z): Calcd. for $C_{20}H_{20}N_2O_3S_3$ (M+H): 433.6; found: 433.1.

Example 6

4-(3'-formyl-2'-methyl-biphenyl-3-sulfonyl)-5-methylsulfanyl-thiophene-2-carboxamidine trifluoroacetate

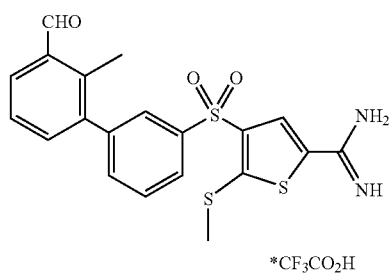

a) 3-Bromo-N-methoxy-2,N-dimethyl-benzamide

Thionyl chloride (6 mL) was added over 1 min to a 0° C. solution of 2-iodo-3-methyl benzoic acid (3.0 g, 11.4 mmol) in DCM (10 mL). The solution was stirred for 24 h at rt and the volatile components were removed in vacuo. A portion of the crude acid chloride (1.56 g, 6.7 mmol) was dissolved in dry DCM (15 mL). N,O-dimethylhydroxylamine (814 mg, 8.35 mmol) was added followed by triethylamine (2.80 mL, 20.1 mmol). After stirring for 18 h at rt the solvents were removed in vacuo. After partitioning the residue between EtOAc (60 mL) and aqueous HCl (1N, 20 mL), the organic layer was further extracted with HCl (1N, 10 mL), NaOH (1N, 3×10 mL), water (10 mL), brine (20 mL), and was dried over sodium sulfate. Removal of the solvent in vacuo yielded the title compound (1.58 g, 92%) which was used in subsequent reactions without further purification. $^1$H-NMR (CDCl$_3$): δ 7.57 (dd, 1H, J=1.2, 7.9 Hz), 7.21 (d, 1H, J=7.4 Hz), 7.08 (t, 1H, J=7.7 Hz), 3.39 (br s, 3H), 3.35 (br s, 3H), 2.36 (s, 3H).

b) 3-Bromo-2-methyl-benzaldehyde

Lithium aluminum hydride (201 mg, 5.31 mmol) was added in one portion to a −78° C. solution of 3-bromo-N-methoxy-2,N-dimethyl-benzamide ((Example 6: step b) 1.1 g, 4.24 mmol) in THF (25 mL). After stirring for 1 h at −78° C., the hydride reagent was quenched with EtOAc (10 mL), and the solution was slowly poured into a vigorously stirred mixture of citric acid (10%, 30 mL) and EtOAc (50 mL). After separating the layers, the organic layer was washed with NaHCO$_3$ (3×20 mL), water (20 mL), and brine (30 mL). The solution was dried (sodium sulfate) and the solvent was removed in vacuo, giving the title compound (813 mg, 96%) as a colorless oil which was used without further purification. $^1$H-NMR (CDCl$_3$): δ 10.28 (s, 1H), 7.80 (m, 2H), 7.25 (m, 1H), 2.78 (s, 3H).

c) 1-Bromo-3-dimethoxymethyl-2-methyl-benzene

The 3-bromo-2-methyl-benzaldehyde ((Example 6: step c) 813 mg, 4.08 mmol) was dissolved in dry MeOH (50 mL) and trimethyl orthoformate (8 mL). Toluenesulfonic acid (100 mg) was added and the solution was stirred for 6 h at rt. Solid NaHCO$_3$ (200 mg) was added, the solution was stirred for 30 min, and the volatile components were removed in vacuo. The residue was dissolved in dry EtOAc (10 mL), the solution was filtered (45 micron filter), and the solvent was removed in vacuo. $^1$H NMR analysis of the crude material (918 mg, 92%) revealed approximately a 90% conversion of the starting material to the title compound, which was used without further purification. $^1$H-NMR (CDCl$_3$): δ 7.47 (dd, 1H, J=1.2, 8.1 Hz), 7.44 (dd, 1H, J=0.9, 7.9 Hz), 6.99 (t, 1H, J=7.9 Hz), 5.37 (s, 1H), 3.25 (s, 6H), 2.37 (s, 3H).

d) 2-Formyl-1-methyl-phenylboronic acid

The 1-bromo-3-dimethoxymethyl-2-methyl-benzene ((Example 6: step c) 500 mg, 2 mmol), butyllithium (2.5 M, 1 mL, 2.5 mmol), and trimethylborate (2.3 mL, 20 mmol) were reacted as in Example 5: step b. After aqueous workup, the residue was dissolved in acetone (18 mL) and HCl (1N, 2 mL). After standing for 18 h at rt, the volatile components were removed in vacuo and the residue was purified by SiO$_2$ flash chromatography (25–40% EtOAc in hexanes) to give the title compound (126 mg, 38%). The title compound exists as a mixture of boronic acids and anhydrides in CDCl$_3$, therefore the reported NMR signals represent pairs or groups of related signals. $^1$H-NMR (CDCl$_3$): δ 10.44 (s, 1H), 8.38 (dd, 1H, J=1.4, 7.4 Hz), 7.49 (t, 1H, J=7.5 Hz), 3.12 (s, 3H).

e) [4-(3'-Formyl-2'-methyl-biphenyl-3-sulfonyl)-5-methylsulfanyl-thiophen-2-yl]-imino-methyl}-carbamic acid tert-butyl ester The procedure used in Example 1: step c was followed using {[4-(3-bromo-benzenesulfonyl)-5-methylsulfanyl-thiophen-2-yl]-imino-methyl}-carbamic acid tert-butyl ester ((Example 27) 50 mg, 0.1 mmol), Pd(PPh$_3$)$_4$ (29.4 mg, 0.025 mmol), 2-formyl-1-methyl-phenylboronic acid ((Example 6: step d) 65 mg, 0.4 mmol), Na$_2$CO$_3$ (2M, 0.8 mL, 1.6 mmol), ethanol (0.8 mL) and toluene (1.6 mL). Analogous aqueous workup and purification of the crude material by preparative TLC (25% EtOAc in hexanes) yielded the title compound (30 mg, 56%) as a light-yellow glass. $^1$H-NMR (CDCl$_3$): δ 10.36 (s, 1H), 8.02 (s, 1H), 7.99 (ddd, 1H, J=1.4, 1.9, 7.7 Hz), 7.93 (t, 1H, J=1.6 Hz), 7.87 (dd, 1H, J=3.0, 6.3 Hz), 7.60 (dt, 1H, J=0.5, 7.7 Hz), 7.54 (dt, 1H, J=1.5, 7.7 Hz), 7.43 (m, 2H), 2.57 (s, 3H), 2.49 (s, 3H), 1.51 (s, 9H). ESI-MS (m/z): Calcd. for C$_{25}$H$_{26}$N$_2$O$_5$S$_3$: 530.7; found: 530.9.

f) 4-(3'-Formyl-2'-methyl-biphenyl-3-sulfonyl)-5-methylsulfanyl-thiophene-2-carboxamidine trifluoroacetate The procedure used in Example 1: step d was followed using {[4-(3'-formyl-2'-methyl-biphenyl-3-sulfonyl)-5-methylsulfanyl-thiophen-2-yl]-imino-methyl}-carbamic acid tert-butyl ester ((Example 6: step e) 30 mg, 0.056 mmol). Analogous purification by HPLC yielded the title compound (22 mg, 73%) as a white solid. The aldehyde is hydrated according to proton NMR analysis. $^1$H-NMR (CD$_3$OD): δ 8.36 (s, 1H), 8.07 (ddd, 1H, J=1.4, 1.9, 7.7 Hz), 7.98 (t, 1H, J=1.5 Hz), 7.72 (dt, 1H, J=0.5, 7.7 Hz), 7.67 (dt, 1H, J=1.5, 7.9 Hz), 7.63 (dd, 1H, J=1.4, 7.7 Hz), 7.33 (t, 1H, J=7.7 Hz), 7.22 (dd, 1H, J=1.4, 7.4 Hz), 5.56 (s, 1H), 2.76 (s, 3H), 2.22 (s, 3H). ESI-MS (m/z): Calcd. for C$_{20}$H$_{18}$N$_2$O$_3$S$_3$: 431.6 (M+H); found: 431.3, 448.2 (M+H$_2$O).

Example 7

4-(5'-Hydroxymethyl-2'-methyl-biphenyl-3-sulfonyl)-5-methylsulfanyl-thiophene-2-carboxamidine trifluoroacetate

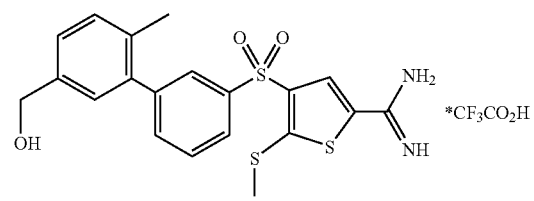

a) 3-Hydroxymethyl-2-methyl-phenylboronic acid

Butyllithium (2.5 M, 4 mL, 10 mmol), 3-iodo-4-methyl-benzyl alcohol (1 g, 4 mmol), and trimethylborate (6 mL, 53 mmol) were reacted as in Example 5: step b. Aqueous workup and purification by SiO$_2$ flash chromatography (40–50% EtOAc in hexanes) yielded the title compound (180 mg, 27%). The title compound exists as a mixture of boronic acids and anhydrides in CDCl$_3$, therefore the reported NMR signals represent pairs or groups of related signals. ¹H-NMR (CDCl₃): δ 7.06–7.30 (m, 3H), 4.56 (s, 3H), 4.16 (br s, 1H), 2.32 (s, 3H).

b) {[4-(5'-Hydroxymethyl-2'-methyl-biphenyl-3-sulfonyl)-5-methylsulfanyl-thiophen-2-yl]-imino-methyl}-carbamic acid tert-butyl ester The procedure used in Example 1: step c was followed using {[4-(3-bromo-benzenesulfonyl)-5-methylsulfanyl-thiophen-2-yl]-imino-methyl}-carbamic acid tert-butyl ester (Example 27 (100 mg, 0.2 mmol)), Pd(PPh₃)₄ (59 mg, 0.05 mmol), 3-hydroxymethyl-2-methyl-phenylboronic acid ((Example 7: step a) 105 mg, 0.63 mmol), Na₂CO₃ (2M, 0.8 mL, 1.6 mmol), ethanol (0.8 mL) and toluene (1.6 mL). Analogous aqueous workup and purification of the crude material by SiO₂ flash chromatography (25–50% EtOAc in hexanes) yielded the title compound (72 mg, 67%) as a light-yellow glass. ¹H-NMR (CDCl₃): δ 8.00 (s, 1H), 7.96 (dt, 1H, J=2.1, 4.4 Hz), 7.93 (m, 1H), 7.54 (m, 2H), 7.27 (m, 2H), 7.18 (d, 1H, J=1.4 Hz), 4.68 (s, 2H), 2.54 (s, 3H), 2.20 (s, 3H), 1.51 (s, 9H).

c) 4-(5'-Hydroxymethyl-2'-methyl-biphenyl-3-sulfonyl)-5-methylsulfanyl-thiophene-2-carboxamidine trifluoroacetate The procedure used in Example 1: step d was followed using {[4-(3'-formyl-2'-methyl-biphenyl-3-sulfonyl)-5-methyl sulfanyl-thiophen-2-yl]-imino-methyl}-carbamic acid tert-butyl ester ((Example 7: step b) 15 mg, 0.028 mmol). Analogous purification by HPLC yielded. the title compound (12 mg, 80%) as a white solid. ¹H-NMR (CD₃OD): δ 8.32 (s, 1H), 8.02 (m, 1H), 7.99 (m, 1H), 7.68 (m, 2H), 7.29 (d, 2H, J=1.8 Hz), 7.21 (br s, 1H), 4.61 (s, 2H), 2.72 (s, 3H), 2.22 (s, 3H). ESI-MS (m/z): Calcd. for C₂₀H₂₀N₂O₃S₃ (M+H): 433.6; found: 433.1.

Example 8

4-(5'-Formyl-2'-methyl-biphenyl-3-sulfonyl)-5-methylsulfanyl-thiophene-2-carboxamidine trifluoroacetate

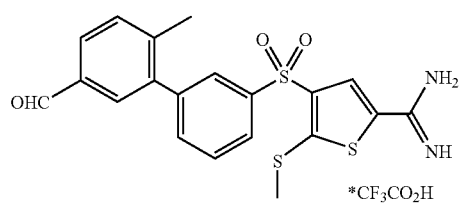

a) {[4-(5'-formyl-2'-methyl-biphenyl-3-sulfonyl)-5-methylsulfanyl-thiophen-2-yl]-imino-methyl}-carbamic acid tert-butyl ester The {[4-(5'-hydroxymethyl-2'-methyl-biphenyl-3-sulfonyl)-5-methylsulfanyl-thiophen-2-yl]-imino-methyl}-carbamic acid tert-butyl ester ((Example 7: step b) 30 mg, 0.056 mmol) was dissolved in a mixture of DMSO (1 mL) and DCM (1 mL) and cooled to 0° C. Triethylamine (12 μL, 0.084 mmol) and sulfur trioxide-pyridine complex (11 mg, 0.068 mmol) were added and the solution was stirred for 1 h at 0° C. Partial conversion was evident by TLC. Additional triethylamine (20 μL, 0.14 μL) and sulfur trioxide-pyridine complex (18 mg, 0.11 mmol) were added and the solution was stirred for 3 h at rt. Isopropanol (250 μL) was added, the reaction was stirred for 15 min, and EtOAc (40 mL) was added. The EtOAc solution was extracted with citric acid (2×10 mL), NaHCO₃ (2×10 mL), water (5×10 mL), and brine (20 mL), and was dried over sodium sulfate. Removal of the solvent in vacuo yielded the title compound (26 mg, 87%) which was used without further purification. 1H-NMR (CD₃OD): δ 10.00 (s, 1H), 7.99 (m, 3H), 7.81 (dd, 1H, J=1.6 7.7 Hz), 7.72 (d, 1H, J=7.7 Hz), 7.59 (m, 2H), 7.46 (d, 1H, J=7.7 Hz), 2.58 (s, 3H), 2.30 (s, 3H), 1.51 (s, 9H).

b) 4-(5'-Formyl-2'-methyl-biphenyl-3-sulfonyl)-5-methylsulfanyl-thiophene-2-carboxamidine trifluoroacetate The procedure used in Example 1: step d was followed using {[4-(5'-formyl-2'-methyl-biphenyl-3-sulfonyl)-5-methylsulfanyl-thiophen-2-yl]-imino-methyl}-carbamic acid tert-butyl ester ((Example 8: step b) 15 mg). Analogous purification by HPLC yielded the title compound (12 mg, 80%) as a white solid. The aldehyde is apparently 80% hydrated according to proton NMR analysis. 1H-NMR (CD₃OD): δ 8.33 (s, 1H), 8.03 (m, 1H), 7.98 (m, 1H), 7.68 (m, 2H), 7.35 (m, 2H), 7.26 (d, 1H, J=1.6 Hz), 5.39 (s, 1H), 2.73 (s, 3H), 2.24 (s, 3H). ESI-MS (m/z): Calcd. for C₂₀H₁₈N₂O₃S₃ (M+H): 431.6; found: 431.2.

Example 9

4-[3-(4-Methyl-pyridin-3-yl)-benzenesulfonyl]-5-methylsulfanyl-thiophene-2-carboxamidine trifluoroacetate

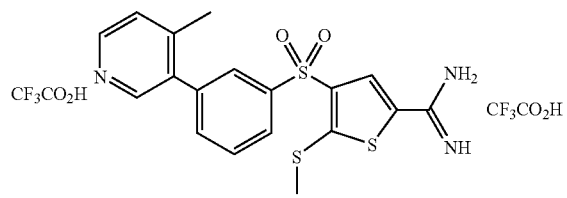

a) (Imino-{4-[3-(4-methyl-pyridin-3-yl)-benzenesulfonyl]-5-methylsulfanyl-thiophen-2-yl}-methyl)-carbamic acid tert-butyl ester Butyllithium (2.5 M, 1.88 mL, 4.5 mmol) was added dropwise to a −78° C. solution of 3-bromo-4-methylpyridine (645 mg, 3.75 mmol) in Et₂O (15 mL). The solution was stirred at −78° C. for 1 h and trimethylborate (5 mL, 44 mmol) was added in one portion. The solution was warmed to rt over 15 min and stirred for 2 h at rt . The volatile components were removed in vacuo and the solid residue was dried under high vacuum for 2 h. A portion of the crude solid (81 mg, 0.4 mmol) was reacted with {[4-(3-bromo-benzenesulfonyl)-5-methylsulfanyl-thiophen-2-yl]-imino-methyl}-carbamic acid tert-butyl ester (Example 27 (50 mg, 0.1 mmol)), Pd(PPh₃)₄ (29 mg, 0.025 mmol), Na₂CO₃ (2M, 0.8 mL, 1.6 mmol), ethanol (0.8 mL) and toluene (1.6 mL) according to the procedure used in Example 1: step c. Analogous aqueous workup and purification of the crude material by preparative TLC (50% EtOAc in hexanes)

yielded the title compound (36 mg, 71%) as a light-yellow glass. $^1$H-NMR (CDCl$_3$): δ 8.50 (d 1H, J=5.1 Hz), 8.42 (s, 1H), 8.07 (s, 1H), 7.99 (m, 2H), 7.45–7.70 (m, 5H), 7.24 (d, 1H, J=5.1 Hz), 2.59 (s, 3H), 2.27 (s, 3H), 1.52 (s, 9H). ESI-MS (m/z): Calcd. for C$_{23}$H$_{25}$N$_3$O$_4$S$_3$: 503.7; found: 503.8.

b) 4-[3-(4-Methyl-pyridin-3-yl)-benzenesulfonyl]-5-methylsulfanyl-thiophene-2-carboxamidine bis-trifluoroacetate The procedure used in Example 1: step d was followed using (imino-{4-[3-(4-methyl-pyridin-3-yl)-benzenesulfonyl]-5-methylsulfanyl-thiophen-2-yl}-methyl)-carbamic acid tert-butyl ester ((Example 9: step a) 36 mg, 0.071 mmol). Analogous purification by C$_{18}$-HPLC (10–40% CH$_3$CN over 30 min) yielded the title compound (22 mg, 49%) as a white solid. $^1$H-NMR (CD$_3$OD): δ 8.74 (br s, 2H), 8.37 (s, 1H), 8.19 (m, 2H), 8.01 (d, 1H, J=5.6 Hz), 7.85 (m, 2H), 2.74 (s, 3H), 2.55 (s, 3H). ESI-MS (m/z): Calcd. for C$_{18}$H$_{17}$N$_3$O$_2$S$_3$ (M+H): 404.5; found: 404.1.

Example 10

4-[3-(2-Chloro-pyridin-3-yl)-benzenesulfonyl]-5-methylsulfanyl-thiophene-2-carboxamidine; bis-trifluoroacetate

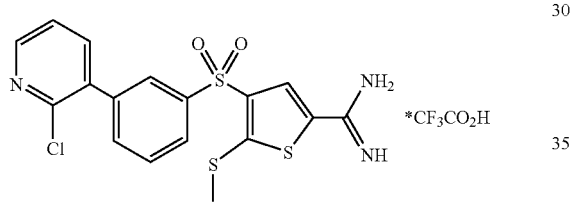

a) ({4-[3-(2-Chloro-pyridin-3-yl)-benzenesulfonyl]-5-methylsulfanyl-thiophen-2-yl}-imino-methyl)-carbamic acid tert-butyl ester Butyllithium (2.5 M, 1.0 mL, 2.5 mmol) was added dropwise to a −78° C. solution of 3-bromo-2-chloropyridine (384 mg, 2.0 mmol) in Et$_2$O (10 mL). The solution was stirred at −78° C. for 1 h and trimethylborate (2.3 mL, 20 mmol) was added in one portion. The solution was warmed to rt over 15 min and stirred for 2 h at rt. The volatile components were removed and the solid material was dried under high vacuum for 2 h. A portion of the crude solid (105 mg, 0.63 mmol) was reacted with {[4-(3-bromo-benzenesulfonyl)-5-methylsulfanyl-thiophen-2-yl]-imino-methyl}-carbamic acid tert-butyl ester (Example 27 (50 mg, 0.1 mmol)), Pd(PPh$_3$)$_4$ (29 mg, 0.025 mmol), Na$_2$CO$_3$ (2M, 0.8 mL, 1.6 mmol), ethanol (0.8 mL) and toluene (1.6 mL) according to the procedure used in Example 1: step c. Analogous aqueous workup and purification of the crude material by preparative TLC (50% EtOAc in hexanes) yielded the title compound (31 mg, 58%) as a light-yellow glass.

b) 4-[3-(2-Chloro-pyridin-3-yl)-benzenesulfonyl]-5-methylsulfanyl-thiophene-2-carboxamidine; bis-trifluoroacetate The procedure used in Example 1: step d was followed using ({4-[3-(2-chloro-pyridin-3-yl)-benzenesulfonyl]-5-methylsulfanyl-thiophen-2-yl}-imino-methyl)-carbamic acid tert-butyl ester ((Example 10: step b) 31 mg, 0.059 mmol). Analogous purification by $C_{18}$-HPLC (10–40% $CH_3CN$ over 30 min) yielded the title compound (29 mg, 74%) as a white solid. $^1$H-NMR ($CD_3OD$): δ 8.45 (dd, 1H, J=1.9, 4.9 Hz), 8.36 (s, 1H), 8.16 (t, 1H, J=1.5 Hz), 8.12 (ddd, 1H, J=1.2, 1.9, 7.7 Hz), 7.90 (dd, 1H, J=1.9, 7.7 Hz), 7.83 (dt, 1H, J=1.5, 7.7 Hz), 7.75 (dt, 1H, J=0.5, 7.7 Hz), 7.53 (dd, 1H, J=4.9, 7.7 Hz), 2.73 (s, 3H). ESI-MS (m/z): Calcd. for $C_{17}H_{14}ClN_3O_2S_3$ (M+H): 424.0; found: 424.1.

Example 11

4-[3-(3-Methyl-pyridin-2-yl)-benzenesulfonyl]-5-methylsulfanyl-thiophene-2-carboxamidine bis-trifluoroacetate

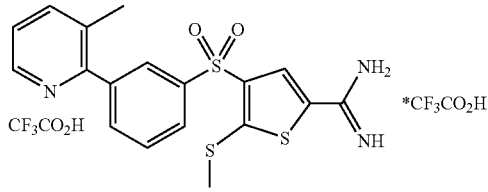

A 2-dram vial with a septa-containing screwcap was charged with {[4-(3-bromo-benzenesulfonyl)-5-methylsulfanyl-thiophen-2-yl]-imino-methyl}-carbamic acid tert-butyl ester (Example 27 (100 mg, 0.2 mmol)) and $Pd(PPh_3)_4$ (59 mg, 0.025 mmol). Tetrahydrofuran was added followed by 3-methyl-2-pyridylzinc bromide (Aldrich Chemical Company) (0.5 M in THF, 800 μL, 0.4 mmol). The reaction was heated to 80° C. for 1 h and was worked up as in Example 1: step c. Flash chromatography ($SiO_2$) of the crude material (25–50% EtOAc in hexanes) yielded a light-yellow glass (74 mg, 73%) which was treated with trifluoroacetic acid and purified by $C_{18}$-HPLC (10–40% $CH_3CN$ over 30 min) as in Example 1: step d, giving the title compound (46 mg, 61%) as a white solid. $^1$H-NMR ($CD_3OD$): δ 8.59 (dd, 1H, J=0.9, 5.1 Hz), 8.34 (s, 1H), 8.22 (m, 2H), 8.16 (ddd, 1H, J=0.7, 1.4, 7.9 Hz), 7.92 (ddd, 1H, J=0.5, 1.1, 7.7 Hz), 7.82 (dt, 1H, J=0.7, 7.7 Hz), 7.68 (dd, 1H, J=5.4, 7.9 Hz), 2.73 (s, 3H), 2.39 (s, 3H). ESI-MS (m/z): Calcd. for $C_{18}H_{17}N_3O_2S_3$ (M+H): 404.5; found: 404.1.

Example 12

4-(3-Allyloxy-5-bromo-benzenesulfonyl)-5-methylsulfanyl-thiophene-2-carboxamidine hydrochloride

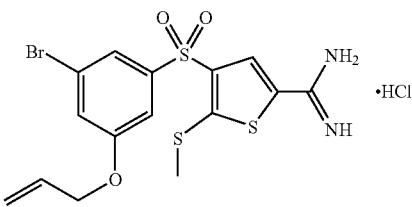

a) 1,3-Dibromo-5-tert-butoxy-benzene

To a vigorously stirred solution of 1,3-dibromophenylboronic acid (4.5 g, 16.1 mmol) in MeOH (50 mL) and THF (50 mL) was alternately added (dropwise) aqueous hydrogen peroxide (30%, 10 mL) and NaOH (1M, 20 mL) (dropwise), maintaining pH~10. The solution became cloudy and was stirred for 30 min (pH maintained at ~10 using 10 N NaOH). EtOAc (200 mL) and sat'd NaHCO$_3$ (50 mL) were added and the layers were separated. The organic layer was extracted with NaHCO$_3$ (50 mL), water (20 mL), brine (50 mL), and was dried over sodium sulfate. The solvent was removed in vacuo and the residue was dissolved in DCM (80 mL). After cooling to −78° C., isobutylene was added (~20 mL) followed by trifluoromethanesulfonic acid (300 μL). The cloudy solution was stirred for 15 min at −78° C. and for 1 h at −20 to −10° C. Additional amounts of isobutylene (~10 mL) and trifluoromethanesulfonic acid (200 μL) were added and the solution was stirred for 1 h. Solid K$_2$CO$_3$ (1 g) was carefully added, the solution was stirred for 10 min at rt, and NaOH (1N, 30 mL) was added. The layers were separated and the organic layer was further extracted with NaOH (1N, 5×10 mL), water (10 mL), and brine (30 mL). After drying and removal of the solvent in vacuo, the residue was purified by SiO$_2$ flash chromatography (2–5% EtOAc in hexanes) to yield the title compound (3.80 g, 77%). $^1$H-NMR (CDCl$_3$): δ 7.38 (t, 1H, J=1.6 Hz), 7.09 (d, 2H, J=1.6 Hz), 1.36 (s, 9H).

b) 4-(3-Bromo-5-tert-butoxy-benzenesulfonyl)-5-nitro-thiophene-2-carboxylic acid methyl ester Butyllithium (2.5 M, 3.25 mL, 8.13 mmol) was added dropwise to a −78° C. solution of 1,3-dibromo-5-tert-butoxy-benzene ((Example 12: step a) 2.4 g, 7.71 mmol) in Et$_2$O (80 mL). The solution was stirred at −78° C. for 2 h and sulfur (310 mg, 9.69 mmol) was added in one portion. The solution was warmed to rt over 30 min and stirred for 2 h at rt. EtOAc (50 mL) and citric acid (5%, 30 mL) were added and the layers were separated. The organic layer was washed with NaHCO$_3$ (2×30 mL), water (10 mL) and brine (30 mL), and was dried over sodium sulfate. The solvent was removed in vacuo and the residue was redissolved in THF (40 mL). Triphenylphosphine (2.03 g, 7.74 mmol), 4-bromo-5-nitro-thiophene-2-carboxylic acid methyl ester ((Example 114, step c) 2.13 g, 8.0 mmol), water (1 mL), and DMAP-resin (7.0 g, 10 mmol) were added and the mixture was stirred for 18 h at rt. The solution was filtered, the solids were washed with DCM, and the solvent was removed in vacuo. The residue was partially purified by SiO$_2$ flash chromatography (25% EtOAc in hexanes) to yield a mixture of the title compound and 4-bromo-5-nitro-thiophene-2-carboxylic acid methyl ester starting material. The crude material was redissolved in DCM (60 mL), mCPBA (77%, 6.04 g, 27.1 mmol) was added, and the solution was stirred for 5 h at 40° C. DCM (50 mL) and aqeous sodium thiosulfate were added (exothermic), and the layers were separated. The organic layer was extracted with Na$_2$CO$_3$ (2M, 6×30 mL), brine (50 mL), and was dried over sodium sulfate. Concentration of the solvent in vacuo followed by SiO$_2$ flash chromatography (25–75% DCM in hexanes) yielded the title compound as a colorless glass (2.85 g, 77%). $^1$H-NMR (CDCl$_3$): δ 8.28 (d, 1H, J=0.5 Hz), 7.71 (t, 1H, J=1.6 Hz), 7.68 (m, 1H), 7.39 (m, 1H), 4.00 (s, 3H), 1.42 (s, 9H).

c) 4-(3-Bromo-5-tert-butoxy-benzenesulfonyl)-5-methylsulfanyl-thiophene-2-carboxylic acid methyl ester Sodium thiomethoxide (1M in EtOH, 4.4 mL, 4.4 mmol) was added dropwise to a −78° C. solution of 4-(3-bromo-5-tert-butoxy-benzenesulfonyl)-5-nitro-thiophene-2-carboxylic acid methyl ester (1.91 g, 4.0 mmol) in THF (40 mL). The solution was stirred for 30 min at −78° C. and glacial acetic acid (1 mL) was added. The solution was diluted with EtOAc (60 mL), extracted with NaHCO$_3$ (2×30 mL), water (2×20 mL), brine (30 mL), and was dried over sodium sulfate. Concentration of the solution in vacuo followed by SiO$_2$ flash chromatography of the residue yielded the title compound (1.48 g, 76%). $^1$H-NMR (CDCl$_3$): δ 8.01 (d, 1H, J=0.5 Hz), 7.74 (m, 1H), 7.66 (m, 1H), 7.37 (m, 1H), 3.99 (s, 3H), 2.48 (s, 3H), 1.41 (s, 9H).

d) 4-(3-Bromo-5-hydroxy-benzenesulfonyl)-5-methylsulfanyl-thiophene-2-carboxylic acid methyl ester Trifluoroacetic acid (5 mL) was added to a solution of 4-(3-bromo-5-tert-butoxy-benzenesulfonyl)-5-methylsulfanyl-thiophene-2-carboxylic acid methyl ester ((Example 12: step c) 240 mg, 0.5 mmol) in DCM (5 mL). The solution was stirred at rt for 2 h and the solvents were removed in vacuo, yielding 214 mg of an oil (quantitative) which was used without further purification.

e) 4-(3-Allyloxy-5-bromo-benzenesulfonyl)-5-methylsulfanyl-thiophene-2-carboxylic acid methyl ester Cesium carbonate (33 mg, 0.1 mmol) and allylbromide (30 μL, 0.35 mmol) were added to a solution of 4-(3-bromo-5-hydroxy-benzenesulfonyl)-5-methylsulfanyl-thiophene-2-carboxylic acid methyl ester ((Example 12: step d) 30 mg, 0.71 mmol) dissolved in dry DMF (3 mL). After stirring for 16 h at rt, the solution was poured into a mixture of water (20 mL) and EtOAc (30 mL). The layers were separated and the organic layer was extracted with water (5×5 mL), brine (20 mL), and was dried over sodium sulfate. The solvent was removed in vacuo to yield the title compound, which was used without further purification.

f) 4-(3-Allyloxy-5-bromo-benzenesulfonyl)-5-methylsulfanyl-thiophene-2-carboxamidine hydrochloride A 1M stock solution of dimethylaluminum amide was freshly prepared by careful addition of trimethylaluminum (2M in toluene, 10 mL) to a suspension of NH$_4$Cl (1.08 g, 11 mmol) in toluene (10 mL). 4-(3-Allyloxy-5-bromo-benzenesulfonyl)-5-methylsulfanyl-thiophene-2-carboxylic acid methyl ester (33 mg, 0.07 mmol) was treated with the dimethylaluminum amide solution (2 mL, 20 mmol) and was heated to 100° C. for 2 h, during which a precipitate formed. The solution was poured into a vigorously stirred mixture of SiO$_2$ (20 g) in CHCl$_3$ (70 mL). The flask was rinsed with methanol (10 mL) and the SiO$_2$ mixture was stirred for 10 min. The solution was filtered through a fritted column and the SiO$_2$ was eluted with 15% MeOH in DCM (150 mL). Concentration of the eluent and purification of the residue by preparative TLC (10% MeOH in DCM) yielded the title compound (15 mg, 44%) as a white solid. $^1$H-NMR (CD$_3$OD): δ 8.27 (s, 1H), 7.69 (t, 1H, J=1.6 Hz), 7.52 (dd, 1H, J=1.6, 2.3 Hz), 7.44 (dd, 1H, J=1.6, 2.3 Hz), 6.03 (m, 1H), 5.41 (ddd, 1H, J=1.6, 3.3, 17.2 Hz), 5.29 (ddd, 1H, J=1.4, 2.8, 10.5 Hz), 4.64 (dt, 2H, J=1.6, 5.4 Hz), 2.74 (s, 3H). ESI-MS (m/z): Calcd. for C$_{15}$H$_{15}$BrN$_2$O$_3$S$_3$: 447.4; found: 447.1.

Example 13

4-(3-Bromo-5-methoxy-benzenesulfonyl)-5-methyl-sulfanyl-thiophene-2-carboxamidine hydrochloride

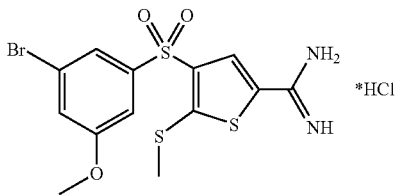

Following the procedure for Example 12: step e, 4-(3-bromo-5-hydroxy-benzenesulfonyl)-5-methylsulfanyl-thiophene-2-carboxylic acid ethyl ester ((Example 12: step d) 30 mg, 0.71 mmol) was alkylated using cesium carbonate (33 mg, 0.1 mmol) and methyl iodide (44 μL, 0.71 mmol). After analogous workup, the residue was subjected to amidination conditions as Example 12: step f. Analogous purification procedures yielded the title compound (17 mg, 53%) as a white solid. $^1$H-NMR (CD$_3$OD): δ 8.27 (s, 1H), 7.69 (t, 1H, J=1.6 Hz), 7.52 (dd, 1H, J=1.6, 2.3 Hz), 7.37 (dd, 1H, J=1.6, 2.3 Hz), 3.87 (s, 3H), 2.72 (s, 3H). ESI-MS (m/z): Calcd. for C$_{13}$H$_{13}$BrN$_2$O$_3$S$_3$: 421.4; found: 421.1.

Example 14

4-(5-Hydroxy-biphenyl-3-sulfonyl)-5-methylsulfanyl-thiophene-2-carboxamidine hydrochloride

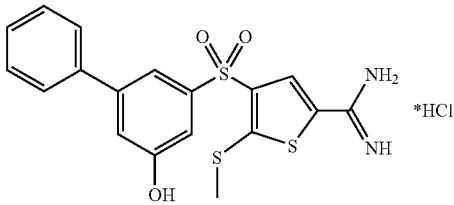

a) 4-(5-tert-Butoxy-biphenyl-3-sulfonyl)-5-methyl-sulfanyl-thiophene-2-carboxylic acid ethyl ester The procedure used in Example 1: step d was followed using benzeneboronic acid (42 mg, 0.35 mmol), 4-(3-bromo-5-tert-butoxy-benzenesulfonyl)-5-methylsulfanyl-thiophene-2-carboxylic acid methyl ester ((Example 12: step c) (83 mg, 0.17 mmol)), Na$_2$CO$_3$ (2M, 1.4 mL, 2.8 mmol), Pd(PPh$_3$)$_4$ (48 mg, 0.04 mmol), toluene (5.6 mL), and ethanol (2.8 mL). Analogous aqueous workup and SiO$_2$ flash chromatography (20% EtOAc in hexanes) yielded the title compound (55 mg, 65%). $^1$H-NMR (CDCl$_3$): δ 8.03 (s, 1H), 7.91 (t, 1H, J=1.6 Hz), 7.63 (t, 1H, J=2.0 Hz), 7.57 (m, 2H), 7.47 (m, 2H), 7.41 (m, 2H), 4.33 (q, 2H, J=7.2 Hz), 2.60 (s, 3H), 1.42 (s, 9H), 1.36 (t, 3H, J=7.2 Hz).

b) 4-(5-Hydroxy-biphenyl-3-sulfonyl)-5-methylsul-fanyl-thiophene-2-carboxylic acid ethyl ester 4-(5-tert-butoxy-biphenyl-3-sulfonyl)-5-methylsulfanyl-thiophene-2-carboxylic acid ethyl ester (55 mg, 0.11 mmol) was dissolved in 1:1 TFA/DCM (10 mL) and stirring for 1 h. Removal of the solvent in vacuo yielded the title compound (48 mg, 98%), which was used without further purification.

c) 4-(5-Hydroxy-biphenyl-3-sulfonyl)-5-methylsul-fanyl-thiophene-2-carboxamidine hydrochloride 4-(5-Hydroxy-biphenyl-3-sulfonyl)-5-methylsulfanyl-thiophene-2-carboxylic acid ethyl ester ((Example 14: step b) 12 mg, 0.028 mmol) was treated with dimethylaluminum amide reagent (2 mL, 2 mmol) as in Example 12: step f. Analogous quench, workup, and purification procedures yielded the title compound (10 mg, 89%) as a white solid. $^1$H-NMR (CD$_3$OD): δ 8.30 (s, 1H), 7.69 (t, 1H, J=1.6 Hz), 7.59 (m, 2H), 7.47 (m, 2H), 7.40 (m, 2H), 7.32 (m, 1H), 2.74 (s, 3H). ESI-MS (m/z): Calcd. for C$_{13}$H$_{13}$BrN$_2$O$_3$S$_3$: 421.36; found: 421.1.

Example 15

4-(5-Methoxy-biphenyl-3-sulfonyl)-5-methylsulfa-nyl-thiophene-2-carboxamidine hydrochloride

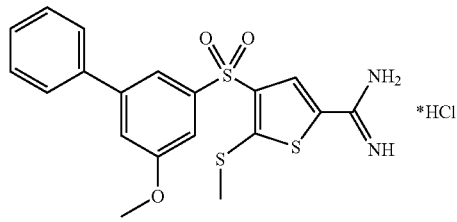

Following the procedure in Example 12: step e, 4-(5-hydroxy-biphenyl-3-sulfonyl)-5-methylsulfanyl-thiophene-2-carboxylic acid ethyl ester ((Example 14: step b) 12 mg, 0.028 mmol) was alkylated using cesium carbonate (13.5 mg, 0.041 mmol) and iodomethane (9 μL, 0.138 mmol) in DMF (1.2 mL). After analogous workup, the residue was treated with dimethylaluminum amide reagent (2 mL) following the procedure in Example 12: step f. The title compound was isolated as a white solid (10 mg, 86%) after preparative TLC purification (15% MeOH in DCM). $^1$H-NMR (CD$_3$OD): δ 8.32 (s, 1H), 7.82 (t, 1H, J=1.6 Hz), 7.65 (m, 1H), 7.63 (m, 1H), 7.53 (dd, 1H, J=1.6, 2.3 Hz), 7.46–7.50 (m, 3H), 7.41 (m, 1H), 3.93 (s, 3H), 2.74 (s, 3H). ESI-MS (m/z): Calcd. for C$_{13}$H$_{13}$BrN$_2$O$_3$S$_3$: 421.4; found: 421.1.

Example 16

4-(5-Allyloxy-biphenyl-3-sulfonyl)-5-methylsulfa-nyl-thiophene-2-carboxamidine

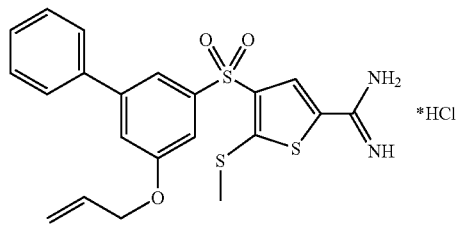

Following the procedure in Example 12: step e, 4-(5-hydroxy-biphenyl-3-sulfonyl)-5-methylsulfanyl-thiophene-2-carboxylic acid ethyl ester ((Example 14: step b) 12 mg, 0.028 mmol) was alkylated using cesium carbonate (13.5 mg, 0.041 mmol) and allyl bromide (12 μL, 0.138 mmol) in DMF (1.2 mL). After analogous workup, the residue was treated with dimethylaluminum amide reagent (2 mL) following the procedure in Example 12: step f. The title compound was isolated as a white solid (10 mg, 81%) after preparative TLC purification (15% MeOH in DCM). $^1$H-NMR (CD$_3$OD): δ 8.32 (s, 1H), 7.82 (t, 1H, J=1.6 Hz), 7.63 (m, 2H), (dd, 1H, J=1.6, 2.3 Hz), 7.48 (m, 3H), 7.42 (m, 1H), 6.08 (m, 1H), 5.45 (ddd, 1H, J=1.6, 3.3, 17.2 Hz), 5.31 (ddd, 1H, J=1.4, 2.8, 10.5 Hz), 4.64 (dt, 2H, J=1.6, 5.1 Hz), 2.75 (s, 3H).

Example 17

4-(5-Benzyloxy-biphenyl-3-sulfonyl)-5-methylsulfanyl-thiophene-2-carboxamidine hydrochloride

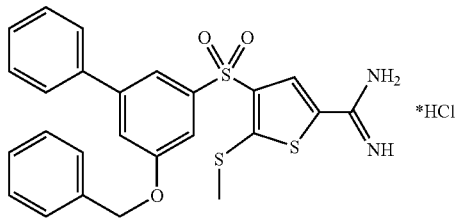

Following the procedure in Example 12: step e, 4-(5-hydroxy-biphenyl-3-sulfonyl)-5-methylsulfanyl-thiophene-2-carboxylic acid ethyl ester ((Example 14: step b) 12 mg, 0.028 mmol) was alkylated using cesium carbonate (13.5 mg, 0.041 mmol) and benzyl bromide (17 μL, 0.138 mmol) in DMF (2 mL). After analogous workup, the residue was treated with dimethylaluminum amide reagent (2 mL) following the procedure in Example 12: step f. The title compound was isolated as a white solid (9 mg, 66%) after preparative TLC purification (15% MeOH in DCM). $^1$H-NMR (CD$_3$OD): δ 8.26 (s, 1H), 7.82 (t, 1H, J=1.6 Hz), 7.62 (m, 2H), 7.54 (m, 2H), 7.30–7.50 (m, 8H), 5.26 (s, 2H), 2.70 (s, 3H). ESI-MS (m/z): Calcd. for C$_{13}$H$_{13}$BrN$_2$O$_3$S$_3$: 421.4; found: 421.1.

Example 18

4-(2'-Chloro-5-hydroxy-biphenyl-3-sulfonyl)-5-methylsulfanyl-thiophene-2-carboxamidine trifluoroacetate

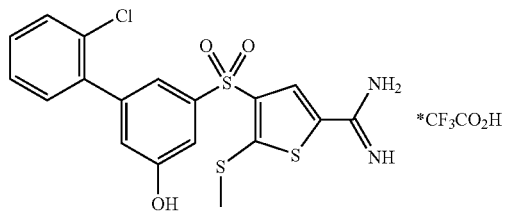

a) {[4-(3-Bromo-5-hydroxy-benzenesulfonyl)-5-methylsulfanyl-thiophen-2-yl]-imino-methyl}-carbamic acid tert-butyl ester Following the procedure and workup in Example 14: step f, the 4-(3-bromo-5-tert-butoxy-benzenesulfonyl)-5-methylsulfanyl-thiophene-2-carboxylic acid methyl ester ((Example 12: step c) 1.48 g, 3.1 mmol) was converted to the amidine (40 mL of dimethylaluminum amide reagent) with concomitant removal of the tert-butyl ether. A portion of the crude amidine (800 mg) was dissolved in DMF and di-tert-butyl dicarbonate (436 mg, 2 mmol), diisopropylethylamine (350 μL, 2 mmol), and DMAP (50 mg) were added. After stirring for 16 h, the solution was poured into EtOAc (60 mL) and citric acid (20 mL). The layers were separated and the organic layer was further extracted with citric acid (10 mL), NaHCO$_3$ (2×20 mL), water (5×10 mL), and brine (30 mL). After drying over sodium sulfate and removal of solvent in vacuo, the residue was dissolved in MeOH and solid K$_2$CO$_3$ was added. The mixture was stirred overnight, the solution was filtered, and the solvent was removed in vacuo. Purification of the residue by SiO$_2$ flash chromatography yielded the title compound (80 mg, 0.158 mmol).

b) {[4-(2'-Chloro-5-hydroxy-biphenyl-3-sulfonyl)-5-methylsulfanyl-thiophen-2-yl]-imino-methyl}-carbamic acid tert-butyl ester Following the procedure outlined in Example 1: step c, {[4-(3-bromo-5-hydroxy-benzenesulfonyl)-5-methylsulfanyl-thiophen-2-yl]-imino-methyl}-carbamic acid tert-butyl ester (80 mg, 0.158 mmol) was reacted with 2-chlorophenylboronic acid (98.6 mg, 0.631 mmol), Na$_2$CO$_3$ (134 mg, 1.26 mmol), and Pd(PPh$_3$)$_4$ (45.5 mg, 0.039 mmol). Aqueous workup followed by SiO$_2$ flash chromatography yielded the title compound (20 mg, 24%).

c) 4-(2'-Chloro-5-hydroxy-biphenyl-3-sulfonyl)-5-methylsulfanyl-thiophene-2-carboxamidine trifluoroacetate The procedure used in Example 1: step d was followed using {[4-(2'-chloro-5-methoxy-biphenyl-3-sulfonyl)-5-methylsulfanyl-thiophen-2-yl]-imino-methyl}-carbamic acid tert-butyl ester (10 mg, 0.0185 mmol). Analogous purification by C$_{18}$-HPLC yielded the title compound (4 mg, 50%) as a white solid. $^1$H-NMR (CD$_3$OD): δ 8.28 (s, 1H), 7.51 (m, 2H), 7.44 (dd, 1H, J=1.6, 2.3 Hz), 7.40 (m, 2H), 7.38 (m, 3H), 7.13 (dd, 1H, J=1.6, 2.3 Hz), 2.73 (s, 3H). ESI-MS (m/z): Calcd. for C$_{13}$H$_{13}$BrN$_2$O$_3$S$_3$: 421.4; found: 421.1.

Example 19

4-(2'-Chloro-5-methoxy-biphenyl-3-sulfonyl)-5-methylsulfanyl-thiophene-2-carboxamidine trifluoroacetate

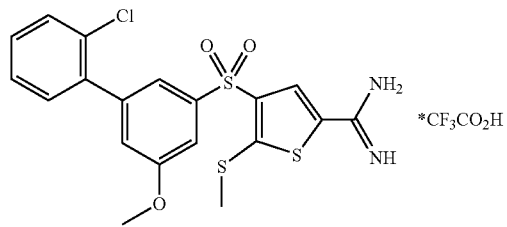

a) {[4-(2'-Chloro-5-methoxy-biphenyl-3-sulfonyl)-5-methylsulfanyl-thiophen-2-yl]-imino-methyl}-carbamic acid tert-butyl ester Iodomethane (3 μL, 0.045 mmol) and tetrabutylammonium fluoride (1M in THF, 14 μL, 0.014 mmol) was added to a solution of {[4-(2'-chloro-5-hydroxy-biphenyl-3-sulfonyl)-5-methylsulfanyl-thiophen-2-yl]-imino-methyl}-carbamic acid tert-butyl ester ((Example 19: step b) 5 mg, 0.009 mmol) in THF. After stirring for 2 hours, the solution was diluted with EtOAc (20 mL). The organic layer was washed with water (2×4 mL) and brine (5 mL), and was dried over MgSO$_4$. Removal of the solvent in vacuo followed by purification of the residue (preparative TLC; 30% EtOAc in hexanes) afforded the title compound (3.1 mg, 62%). $^1$H-NMR (CDCl$_3$): δ 7.84 (s, 1H), 7.64 (t, 1H, J=1.6 Hz), 7.53 (dd, 1H, J=1.6, 2.6 Hz), 7.47 (m, 1H), 7.33 (m, 3H), 7.21 (dd, 1H, J=1.6, 2.6 Hz), 3.89 (s, 3H), 2.60 (s, 3H), 1.52 (s, 9H). ESI-MS (m/z): Calcd. for $C_{13}H_{13}BrN_2O_3S_3$: 421.4; found: 421.1.

b) 4-(2'-Chloro-5-methoxy-biphenyl-3-sulfonyl)-5-methylsulfanyl-thiophene-2-carboxamidine trifluoroacetate The procedure used in Example 1: step d was followed using {[4-(2'-chloro-5-methoxy-biphenyl-3-sulfonyl)-5-methylsulfanyl-thiophen-2-yl]-imino-methyl}-carbamic acid tert-butyl ester (3.1 mg, 0.008 mmol). Analogous purification by C$_{18}$-HPLC yielded the title compound (1.8 mg, 50%) as a white solid. $^1$H-NMR (CD$_3$OD): δ 8.32 (s, 1H), 7.64 (t, 1H, J=1.6 Hz), 7.59 (dd, 1H, J=1.4, 2.6 Hz), 7.55 (m, 1H), 7.42 (m, 3H), 7.13 (dd, 1H, J=1.4, 2.6 Hz), 3.93 (s, 3H), 2.75 (s, 3H). ESI-MS (m/z): Calcd. for $C_{13}H_{13}BrN_2O_3S_3$: 421.4; found: 421.1.

Example 20

5-Bromo-4-(3'-formyl-biphenyl-3-sulfonyl)-thiophene-2-carboxamidine trifluoroacetate

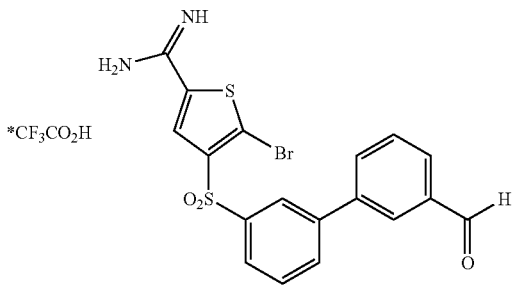

a) 4-(3-Bromo-phenylsulfanyl)-5-nitro-thiophene-2-carboxylic acid methyl ester 4-Bromo-5-nitro-thiophene-2-carboxylic acid methyl ester ((Example 114, step c) 1 g, 3.75 mmol) and Et$_3$N (523 μL, 3.75 mmol) were dissolved with THF (10 mL) into a round bottom flask with stir bar. To this 3-bromothiophenol (467 μL, 4.51 mmol) was added with stirring. The reaction became turbid therefore additional THF (12 mL) was added. The reaction was stirred at rt for 12 hours. The reaction mixture was concentrated in vacuo and then dissolved into EtOAc. The organic layer was washed several times with saturated NaHCO$_3$ and brine. The combined organic layers were dried over sodium sulfate. Removal of the solvents in vacuo yielded the title compound (1.40 g, quantitative yield), which was used without further purification. $^1$H-NMR (CDCl$_3$): δ 7.79 (t, 1H, J=1.8 Hz), 7.67–7.70 (m, 1H), 7.54–7.85 (m, 1H), 7.37–7.41 (t, 1H, J=7.9 Hz), 6.87 (s, 1H), 3.88 (s, 1H).

b) 4-(3-Bromo-benzenesulfonyl)-5-nitro-thiophene-2-carboxylic acid methyl ester 4-(3-Bromo-phenylsulfanyl)-5-nitro-thiophene-2-carboxylic acid methyl ester (1.40 g, 4 mmol) and m-CPBA (6.1 g, 20 mmol) were dissolved into DCM (25 mL) with heating at 40° C. for 2 hours. The reaction mixture was quenched by the addition of saturated sodium thiosulfate followed by aqueous workup with brine and saturated NaHCO$_3$. The combined organic layers were dried over sodium sulfate. Removal of the solvents in vacuo yielded the title compound (1.60 g, quantitative yield) which was used without further purification. $^1$H-NMR (CDCl$_3$): δ 8.31 (s, 1H), 8.12–8.14 (t, 1H, J=1.9 Hz), 8.02–8.05 (m, 1H), 7.78–7.82 (m, 1H), 7.44–7.50 (t, 1H, J=7.9 Hz), 4.01 (s, 3H).

c) 5-Amino-4-(3-bromo-benzenesulfonyl)-thiophene-2-carboxylic acid methyl ester 4-(3-Bromo-benzenesulfonyl)-5-nitro-thiophene-2-carboxylic acid methyl ester (407 mg, 1.0 mmol, Example 20: step b) was dissolved into EtOH (6 mL). To this was added ammonium chloride (535 mg, 10 mmol) dissolved into water (3 mL). This mixture was heated to 50° C. with stirring and then iron (277 mg, 5 mmol) was added. The reaction was then heated to 80° C. with stirring for 12 hours. The reaction mixture was then filtered through Celite® and washed with 10% DCM/MeOH. Removal of the solvents in vacuo yielded the title compound (598 mg, quantitative yield) which was used without further purification. $^1$H-NMR (CDCl$_3$): δ 8.05 (s, 1H), 7.84–7.86 (m, 1H), 7.70–7.75 (m, 1H), 7.56 (s, 1H), 7.40 (m, 1H), 6.02 (br s, 2H), 3.85 (s, 3H). ESI-MS (m/z): Calcd. for $C_{12}H_{10}BrNO_4S_2$: 375.9 (M+H); found: 376.1.

d) 5-Amino-4-(3'-formyl-biphenyl-3-sulfonyl)-thiophene-2-carboxylic acid methyl ester The procedure as in Example 1: step c was followed using 5-amino-4-(3-bromo-benzenesulfonyl)-thiophene-2-carboxylic acid methyl ester (754.2 mg, 2 mmol, Example 20: step e), 3-formyl phenyl boronic acid (599.7 mg, 4 mmol), Pd(PPh$_3$)$_4$ (462.2 mg, 0.4 mmol), aqueous Na$_2$CO$_3$ (2M, 8 mL, 16 mmol), ethanol (8 mL) and toluene (16 mL). Purification by flash column chromatography (Biotage Flash™ System—40 M SiO$_2$ column) (25% EtOAc in hexanes) of the residue yielded the title compound (317 mg, 40%) as a brown solid. $^1$H-NMR (CDCl$_3$): δ 10.10 (s, 1H), 8.10–8.17 (m, 2H), 7.92–7.95 (m, 2H), 7.82–7.89 (t, 2H, J=8.1 Hz), 7.58–7.70 (m, 3H), 6.05 (br s, 2H), 3.80 (s, 3H).

e) 5-Bromo-4-(3'-formyl-biphenyl-3-sulfonyl)-thiophene-2-carboxylic acid methyl ester A dry 3-neck flask fitted with addition funnel, condenser and septa cap was purged with argon. To this flask t-butylnitrite (121 μL, 1.58 mmol) and copper (II) bromide (36.8 mg, 1.58 mmol) were dissolved with acetonitrile (2 mL) and heated to 60° C. A solution of 5-amino-4-(3'-formyl-biphenyl-3-sulfonyl)-thiophene-2-carboxylic acid methyl ester (317.2 mg, 0.79 mmol, Example 20: step d) in acetonitrile (2 mL) was added dropwise with continued stirring and heat for 1.5 hours. The reaction mixture was dissolved into EtOAc and washed with brine. The organic layer was dried over sodium sulfate. Removal of the solvents in vacuo followed by flash column chromatography (Biotage Flash™ System—40 M SiO$_2$ column) (25% EtOAc in hexanes) of the residue yielded the title compound (128 mg, 34%) as a brown solid. $^1$H-NMR (CDCl$_3$): δ 10.10 (s, 1H), 8.26–8.28 (m, 1H), 8.08–8.16 (m, 2H) 8.01–8.06 (m, 1H), 7.86–7.89 (m, 3H), 7.64–7.70 (t, 2H, J=8.1 Hz), 3.90 (s, 3H).

f) 5-Bromo-4-(3'-formyl-biphenyl-3-sulfonyl)-thiophene-2-carboxamidine trifluoroacetate A 1M solution of dimethylaluminum amide was prepared by combining NH$_4$Cl (426 mg, 8 mmol), AlMe$_3$ (2M solution in toluene, 4 mL, 8 mmol) and toluene (4 mL). This solution was then heated to 80° C. for 15 minutes and then allowed to cool to rt. The 1M solution of dimethyl aluminum amide was then added to a dry flask containing 5-bromo-4-(3'-formyl-biphenyl-3-sulfonyl)-thiophene-2-carboxylic acid methyl ester (128 mg, 0.28 mmol) and the reaction was heated 90° C. for 2 hours. The reaction was quenched by adding silica (1 g) to the solution with stirring followed by filtration and elution with 10% MeOH in DCM. Concentration of the filtrate in vacuo followed by purification by C$_{18}$-HPLC (10–80% CH$_3$CN over 25 min) yielded the title compound (49 mg, 38%) as an off-white solid. $^1$H-NMR (CD$_3$OD and CD$_3$Cl): δ: 10.10 (s, 1H), 8.35 (s, 1H), 8.31–8.33 (m, 1H), 8.17–8.18 (t, 1H, J=1.39 Hz), 8.04–8.10 (m, 2H), 7.96–7.99 (m, 2H), 7.75–7.77 (m, 2H). ESI-MS (m/z): Calcd. for C$_{18}$H$_{13}$BrN$_2$O$_3$S$_2$: 448.9 (M+H); found: 449.2.

Example 21

5-Amino-4-(2'-methyl-biphenyl-3-sulfonyl)-thiophene-2-carboxamidine trifluoroacetate

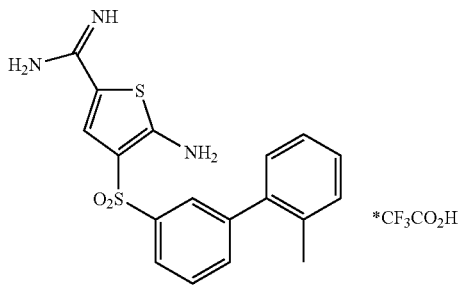

5-Amino-4-(2'-methyl-biphenyl-3-sulfonyl)-thiophene-2-carboxylic acid methyl ester was prepared following the procedure as in Example 1: step c using 5-amino-4-(3-bromo-benzenesulfonyl)-thiophene-2-carboxylic acid methyl ester (598.9 mg, 1.6 mmol) (Example 20: steps a-c), o-tolyl-phenyl boronic acid (435.6 mg, 3.2 mmol), Pd(PPh$_3$)$_4$ (366.6 mg, 0.32 mmol), aqueous Na$_2$CO$_3$ (2M, 6.4 mL, 12.8 mmol), ethanol (6.4 mL) and toluene (12.8 mL). Purification by flash column chromatography (Biotage Flash™ System—40 M SiO$_2$ column) (25% EtOAc in hexanes) of the residue yielded the adduct (137 mg, 23%) as a light brown solid. ESI-MS (m/z): Calcd. for C$_{19}$H$_{17}$NO$_4$S$_2$: 387.02; found: 388.3. 5-Amino-4-(2'-methyl-biphenyl-3-sulfonyl)-thiophene-2-carboxylic acid methyl ester (61 mg, 16 mmol) was then converted to the amidine and purified as described in Example 20: step f to isolate the title compound (6 mg, 10%) as a light brown solid. $^1$H-NMR (CD$_3$OD): δ: 7.96–7.99 (m, 1H), 7.95 (s, 1H), 7.93–7.94 (m, 1H), 7.63–7.69 (m, 3H), 7.18–7.32 (m, 3H), 2.22 (s, 3H). ESI-MS (m/z): Calcd. for C$_{18}$H$_{17}$N3O$_2$S$_2$: 372.0 (M+H); found: 372.2.

Example 22

5-Chloro-4-(2'-methyl-biphenyl-3-sulfonyl)-thiophene-2-carboxamidine trifluoroacetate

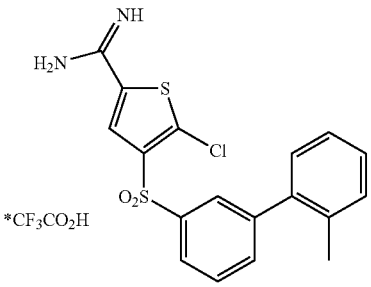

a) 5-Chloro-4-(2'-methyl-biphenyl-3-sulfonyl)-thiophene-2-carboxylic acid methyl ester The procedure as in Example 20: step e was followed using t-butylnitrite (104 μL, 88 mmol) and copper (II) chloride (118.5 mg, 0.88 mmol), acetonitrile (2 mL) and 5-amino-4-(2'-methyl-biphenyl-3-sulfonyl)-thiophene-2-carboxylic acid methyl ester (170.2 mg, 0.43 mmol, Example 21) in acetonitrile (2 mL). Purification by flash column chromatography (Biotage Flash™ System—12 M SiO$_2$ column) (25% EtOAc in hexanes) of the residue yielded the title compound (128 mg, 34%) as a brown solid. $^1$H-NMR (CDCl$_3$): δ 8.26 (1H, s), 7.92–7.98 (3H, m), 7.56–7.60 (2H, m) 7.28–7.32 (3H, m), 3.90 (3H, s), 2.24 (3H, s).

b) 5-Chloro-4-(2'-methyl-biphenyl-3-sulfonyl)-thiophene-2-carboxamidine trifluoroacetate 5-Chloro-4-(2'-methyl-biphenyl-3-sulfonyl)-thiophene-2-carboxylic acid methyl ester (36 mg, 0.09 mmol) was then converted to the amidine and purified as described in Example 20: step f to isolate the title compound (7.1 mg, 20%) as a white solid. $^1$H-NMR (CD$_3$OD): δ: 8.35 (s, 1H), 8.03–8.06 (m, 1H), 7.95–7.97 (m, 1H), 7.71–7.74 (m, 2H), 7.30–7.33 (m, 2H), 7.25–7.30 (m, 1H), 7.19–7.21 (d, 1H, J=6.74 Hz), 2.24 (s, 3H). ESI-MS (m/z): Calcd. for C$_{18}$H$_{15}$ClN$_2$O$_2$S$_2$: 391.0 (M+H); found: 391.2.

Example 23

4-(2'-Methyl-biphenyl-3-sulfonyl)-thiophene-2-carboxamidine trifluoroacetate

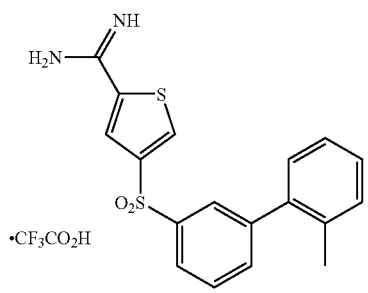

4-(2'-methyl-biphenyl-3-sulfonyl)-thiophene-2-carboxylic acid methyl ester (4.0 mg, 0.01 mmol) was isolated as a byproduct from Example 22: step a. The molecule was then converted to the amidine and purified as described in Example 20: step f to isolate the title compound (0.9 mg, 25%). $^1$H-NMR (CD$_3$OD): δ: 8.80 (s, 1H), 8.25–8.26 (d, 1H, J=1.6 Hz), 8.02–8.05 (m, 1H), 7.95–7.96 (m, 2H), 7.68–7.71 (m, 2H), 7.17–7.21 (m, 1H), 2.24 (s, 3H). ESI-MS (m/z): Calcd. for C$_{18}$H$_{16}$N$_2$O$_2$S$_2$: 357.0 (M+H); found: 357.3.

Example 24

5-Bromo-4-(2'-methyl-biphenyl-3-sulfonyl)-thiophene-2-carboxamidine trifluoroacetate

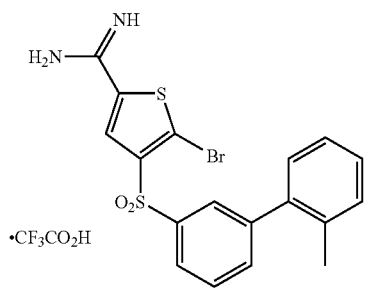

a) 5-Chloro-4-(2'-methyl-biphenyl-3-sulfonyl)-thiophene-2-carboxylic acid methyl ester The procedure as in Example 20: step e was followed using t-butylnitrite (10 μL, 0.05 mmol) and copper (II) bromide (11 mg, 0.05 mmol) and 5-amino-4-(2'-methyl-biphenyl-3-sulfonyl)-thiophene-2-carboxylic acid methyl ester (9.1 mg, 0.03 mmol, Example 21) in acetonitrile (1 mL). Purification by flash column chromatography (Biotage Flash™ System—12 M SiO$_2$ column) (25% EtOAc in hexanes) of the residue yielded the title compound (5.1 mg, 42%) as an off-white solid. $^1$H-NMR (CDCl$_3$): δ 8.08 (s, 1H), 7.92–7.98 (m, 2H), 7.59–7.61 (m, 2H) 7.29–7.30 (m, 3H), 7.19–7.21 (m, 1H), 3.90 (s, 3H), 2.24 (s, 3H).

b) 5-Bromo-4-(2'-methyl-biphenyl-3-sulfonyl)-thiophene-2-carboxamidine trifluoroacetate 5-Bromo-4-(2'-methyl-biphenyl-3-sulfonyl)-thiophene-2-carboxylic acid methyl ester (5.1 mg, 0.01 mmol, Example 24: step a) was then converted to the amidine and purified as described in Example 20: step f to isolate the title compound (1.1 mg, 21%). $^1$H-NMR (CD$_3$OD): δ: 8.33 (s, 1H), 8.04–8.07 (m, 1H), 7.98–7.99 (m, 1H) 7.71–7.73 (m, 2H), 7.30–7.32 (m, 3H), 7.25–7.30 (m, 1H), 7.19–7.21 (m, 1H), 2.24 (s, 3H). ESI-MS (m/z): Calcd. for C$_{18}$H$_{13}$BrN$_2$O$_2$S$_2$: 434.0 found: 437.1.

Example 25

4-(2'-Amino-6'-methyl-biphenyl-3-sulfonyl)-5-methylsulfanyl-thiophene-2-carboxamidine trifluoroacetate

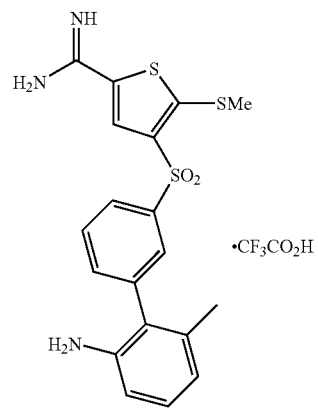

a) 2-Bromo-3-methyl-phenylamine

The procedure as in Example 20: step c was followed using 2-bromo-1-methyl-3-nitro-benzene (1 g, 4.6 mmol dissolved in 12 mL EtOH, Aldrich Chemical Company), ammonium chloride (2.5 g, 46 mmol dissolved in 6 mL H$_2$O) and iron (1.3 g, 23 mmol). The title compound was obtained (1.0 g, quantitative yield) which was used without further purification. $^1$H-NMR (CDCl$_3$): δ 6.95–7.00 (t, 1H, J=7.6 Hz), 6.60–6.65 (dd, 2H, J=8.1, 4.4 Hz), 4.10 (br s, 2H), 2.35 (s, 3H).

b) 3-Methyl-2-(4,4,5,5-tetramethyl-[1,3,2]dioxaborolan-2-yl)-phenylamine

The procedure described in Example 3: step b was followed using 2-bromo-3-methyl-phenylamine (185 mg, 1.0 mmol, Example 25: step a), PdCl$_2$(PPh$_3$)$_2$ (70.2 mg, 0.1 mmol), dioxane (3 mL), and Et$_3$N (729 μL, 6 mmol), 4,4,5,5,-tetramethyl-[1,3,2]-dioxaborolane (453 μL, 3 mmol). Purification by preparative SiO$_2$ TLC (25% EtOAc in hexanes) of the residue yielded the title compound (94 mg, 40%) as a yellow solid. ESI-MS (m/z): Calcd. for C$_{13}$H$_{20}$BNO$_2$:234.1 (M+H) found: 234.1.

c) {[4-(2'-Amino-6'-methyl-biphenyl-3-sulfonyl)-5-methylsulfanyl-thiophen-2-yl]-imino-methyl}-carbamic acid tert-butyl ester The procedure described in Example 1: step c was followed using 3-methyl-2-(4,4,5,5-tetramethyl-[1,3,2]dioxaborolan-2-yl)-phenylamine (95 mg. 0.41 mmol, Example 25: step b), {[4-(3-bromo-benzenesulfonyl)-5-methylsulfanyl-thiophen-2-yl]-imino-methyl}-carbamic acid tert-butyl ester (100.7 mg, 0.21 mmol, Example 27: step c), Pd(PPh$_3$)$_4$ (47 mg, 0.04 mmol), aqueous Na$_2$CO$_3$ (2M, 0.8 mL, 1.6 mmol), ethanol (0.8 mL) and toluene (1.6 mL). Purification by preparative SiO$_2$ TLC (33% EtOAc in hexanes) of the residue yielded the title compound (30 mg, 28%) as an off-white solid. ESI-MS (m/z): Calcd. For C$_{24}$H$_{27}$N$_3$O$_4$S$_3$: 517.2; found: 517.8.

d) 4-(2'-Amino-6'-methyl-biphenyl-3-sulfonyl)-5-methylsulfanyl-thiophene-2-carboxamidine trifluoroacetate {[4-(2'-Amino-6'-methyl-biphenyl-3-sulfonyl)-5-methylsulfanyl-thiophen-2-yl]-imino-methyl}-carbamic acid tert-butyl ester (30 mg, 0.058 mmol, Example 25: step c) was deprotected and purified as in Example 1: step d, yielding the title compound as an off-white solid (28.1 mg, 94%). $^1$H-NMR (CD$_3$OD): δ 8.36 (s, 1H), 8.08–8.12 (m, 1H), 7.96 (t, 1H, J=1.6 Hz), 7.76–7.80 (t, 1H, J=7.6 Hz), 7.60–7.64 (dd, 1H, J=1.6, 7.6 Hz), 7.22–7.25 (t, 1H, J=7.9 Hz), 6.98–7.03 (m, 2H), 2.73 (s, 3H), 1.97 (s, 3H). ESI-MS (m/z): Calcd. for C$_{19}$H$_{19}$N$_3$O$_2$S$_3$: 418.1 (M+1); found: 418.1.

Example 26

4-(3'-Formyl-4'-hydroxy-biphenyl-3-sulfonyl)-5-methylsulfanyl-thiophene-2-carboxamidine trifluoroacetate

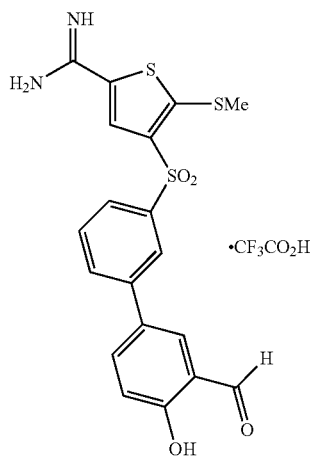

a) 4-Bromo-2-dimethoxymethyl-phenol

To a solution of 5-bromo-2-hydroxy-benzaldehyde (1 g, 4.9 mmol, Aldrich Chemical Company) in MeOH (25 mL) at 0° C., sodium borohydride (226 mg, 5.9 mmol) was added slowly with stirring. After the addition, the reaction was allowed to warm to rt and stir for an additional hour. Reaction mixture was dissolved into EtOAc and washed with brine (20 mL×2). The organic layer was dried over sodium sulfate. Removal of the solvents in vacuo gave the title compound (1.2 g, quantitative) a yellow oil which was used with out further purification. $^1$H-NMR (CD$_3$OD): δ 7.35 (m, 2H), 6.75–6.77 (d, 1H, J=7.2 Hz), 5.55 (s, 1H), 3.33 (s, 6H).

b) {[4-(3'-Dimethoxymethyl-4'-hydroxy-biphenyl-3-sulfonyl)-5-methylsulfanyl-thiophen-2-yl]-imino-methyl}-carbamic acid tert-butyl ester 2-Dimethoxymethyl-4-hydroxyl phenylboronic acid (212 mg. 1.0 mmol) was prepared using the procedure described in Example 1: step b using butyllithium (2.5M, 2.8 mL, 7 mmol), trimethylborate (0.812 mL, 5.6 mmol), 4-bromo-2-dimethoxymethyl-phenol (685 mg, 2.8 mmol, Example 26: step a) in THF (5 mL) and was used in the next step without purification. The procedure described in Example 1: step c was followed using {[4-(3-bromo-benzenesulfonyl)-5-methylsulfanyl-thiophen-2-yl]-imino-methyl}-carbamic acid tert-butyl ester (100 mg, 0.21 mmol, Example 27: step c), Pd(PPh$_3$)$_4$ (47 mg, 0.04 mmol), aqueous Na$_2$CO$_3$ (2M, 0.8 mL, 1.6 mmol), ethanol (0.8 mL), toluene (1.6 mL) and 2-dimethoxymethyl-4-hydroxy-phenylboronic acid (212 mg, 1.0 mmol). Purification by preparative SiO$_2$ TLC (33% EtOAc in hexanes) of the residue yielded the title compound (37 mg, 28%) as a white solid. ESI-MS (m/z): Calcd. for C$_{26}$H$_{30}$N$_2$O$_7$S$_3$: 579.1 (M+1); found: 579.9.

c) 4-(3'-Formyl-4'-hydroxy-biphenyl-3-sulfonyl)-5-methylsulfanyl-thiophene-2-carboxamidine trifluoroacetate {[4-(3'-Dimethoxymethyl-4'-hydroxy-biphenyl-3-sulfonyl)-5-methylsulfanyl-thiophen-2-yl]-imino-methyl}-carbamic acid tert-butyl ester (37 mg) (Example 26: step b) was deprotected and purified as in Example 1: step d, yielding the title compound as an off-white solid (5 mg, 14%). $^1$H-NMR (CD$_3$OD): δ 10.34 (s, 1H), 8.46 (m, 1H), 8.25–8.27 (m, 1H), 7.89–7.94 (m, 3H), 7.72–7.75 (m, 1H), 7.13–7.16 (m, 1H), 2.49 (s, 3H). ESI-MS (m/z): Calcd. for C$_{19}$H$_{16}$N$_2$O$_4$S$_3$: 433.0 (M+1); found: 433.2.

Example 27

{[4-(3-Bromo-benzenesulfonyl)-5-methylsulfanyl-thiophen-2-yl]-imino-methyl}-carbamic acid tert-butyl ester

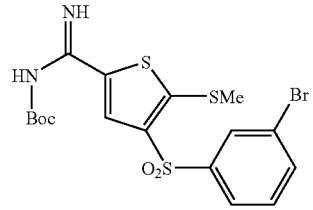

a) 4-(3-Bromo-benzenesulfonyl)-5-methylsulfanyl-thiophene-2-carboxylic acid methyl ester 4-(3-Bromo-benzenesulfonyl)-5-nitro-thiophene-2-carboxylic acid methyl ester (5.9 g, 0.015 mol, Example 20: step b) was dissolved into 40 mL THF and cooled to −78° C. To this was added sodium thiomethoxide (1M, 15 mL, 0.015 mmol, in EtOH) dropwise for an hour. The reaction was quenched with acetic acid (878 μL, 0.015 mol) and the reaction mixture was concentrated in vacuo. The residue was then dissolved into EtOAc and washed with saturated NaHCO₃ and brine solutions. The organic layer was dried over sodium sulfate. Removal of the solvents in vacuo followed by flash column chromatography SiO₂ (25% EtOAc in hexanes) of the residue yielded the title compound (3.0 g, 50%) as a yellow solid. ¹H-NMR (CDCl₃): δ 8.14 (t, 1H, J=1.8 Hz), 8.02 (s 1H), 7.94–7.96 (m, 1H), 7.72–7.74 (m, 1H), 7.38–7.42 (t, 1H, J=7.9 Hz), 7.26 (s 1H), 3.88 (s 1H), 2.62 (s 1H).

b) 4-(3-Bromo-benzenesulfonyl)-5-methylsulfanyl-thiophene-2-carboxamidine trifluoroacetate 4-(3-Bromo-benzenesulfonyl)-5-methylsulfanyl-thiophene-2-carboxylic acid methyl ester (1.9 g, 0.004 mol) was converted to the amidine and purified as described in Example 20: step f to isolate the title compound (1.9 g, quantitative yield). ¹H-NMR (CD₃OD): δ: 8.31 (s, 1H), 8.16 (t, 1H, J=1.8 Hz), 8.01–8.04 (m, 1H), 7.86–7.90 (m, 1H), 7.52–7.57 (t, 1H, J=7.9 Hz), 2.74 (s, 3H).

c) {[4-(3-Bromo-benzenesulfonyl)-5-methylsulfanyl-thiophen-2-yl]-imino-methyl}-carbamic acid tert-butyl ester 4-(3-Bromo-benzenesulfonyl)-5-methylsulfanyl-thiophene-2-carboxamidine (1.9 g, 0.0048 mol, Example 27: step b) was dissolved into DMF (35 mL) with sonication. To this was added DIEA (1.67 mL, 0.0096 mol) and di-tert-butyl-dicarbonate (1.27 g, 0.0058 mol) and reaction stirred at rt for 16 hours. The reaction mixture was dissolved into EtOAc and washed with 20% citric acid and then brine. The organic layer was dried over Na₂SO₄ and concentrated in vacuo. The remaining residue was triturated with hexane to isolate the title compound (1.84 g, 76%). ¹H-NMR (CDCl₃): δ: 8.15 (s, 1H), 8.13–8.14 (t, 1H, J=1.6 Hz), 7.95–7.99 (m, 1H), 7.79–7.84 (m, 1H), 7.72 (s, 1H), 7.48–7.52 (t, 1H, J=7.9 Hz), 7.19–7.21 (m, 1H), 2.66 (s, 3H), 1.51 (s, 9H). ESI-MS (m/z): Calcd. for C₁₇H₁₉BrN₂O₄S₃: 492.4 (M+1); found: 492.6.

Example 28

5-Methylsulfanyl-4-[3'-(2,2,2-trifluoro-1-hydroxy-ethyl)-biphenyl-3-sulfonyl]-thiophene-2-carboxamidine trifluoroacetate

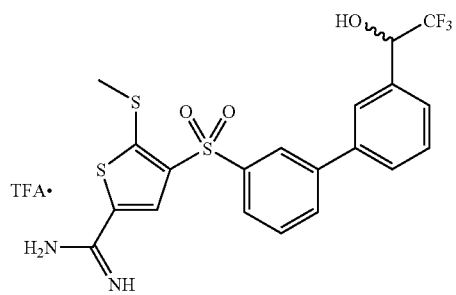

a) 1-(3-Bromo-phenyl)-2,2,2-trifluoro-ethanone

In a dry round bottom flask, 3-bromo-benzoic acid methyl ester (2 g, 9.3 mmol, Aldrich Chemical Company) and trimethyl(trifluoromethyl)silane (1.72 mL, 11.6 mmol, Aldrich Chemical Company) were dissolved in dry toluene (50 mL). Upon cooling the solution to −78° C., TBAF (232 μL, 0.23 mmol) was added and the reaction was allowed to warm up slowly to rt overnight. After stirring for 20 hr, 2N HCl (50 mL) and EtOAc (100 mL) were added, the layers were separated, and the aqueous layer was extracted with another portion of EtOAc. The combined organic fractions were dried (MgSO₄), concentrated in vacuo, and resulting crude oil was purified using SiO₂ flash chromatography (elution: 5–20% EtOAc in hexanes) to give 1.5 g (65%) the title compound as a light yellow oil. ¹H-NMR (CDCl₃; 400 MHz) δ 8.18 (br s, 1H), 7.98–8.00 (m, 1H), 7.82–7.85 (m, 1H), 7.42–7.46 (m, 1H). ¹⁹F-NMR (CDCl₃; 400 MHz) δ −72.06 (s).

b) 2,2,2-Trifluoro-1-[3-(4,4,5,5-tetramethyl-[1,3,2]dioxaborolan-2-yl)-phenyl]-ethanol To an oven-dried round bottom flask fitted with a stir bar and a rubber septum was added 1-(3-bromo-phenyl)-2,2,2-trifluoro-ethanone (560 mg, 2.2 mmol, as prepared in Example 28, step a), 4,4,5,5-tetramethyl-[1,3,2]dioxaborolane (0.96 mL, 6.6 mmol, Aldrich Chemical Company), (PPh₃)₂PdCl₂ (93 mg, 0.132 mmol, Strem Chemicals, Inc., Newburyport, Mass.), and Et₃N (1.8 mL, 13.2 mmol). The reaction mixture was evacuated, purged with argon, and then suspended in dioxane (16 mL). After stirring for 18 hr at 95° C., the reaction was allowed to cool and then filtered through Celite.® The filtrate was concentrated in vacuo and the residue was purified by chromatography (SiO₂, flash elution: 5% EtOAc in hexanes) to give 350 mg (53%) of an oil that was used without further purification.

c) (Imino-{5-methylsulfanyl-4-[3'-(2,2,2-trifluoro-1-hydroxy-ethyl)-biphenyl-3-sulfonyl]-thiophen-2-yl}-methyl)-carbamic acid tert-butyl ester Following the same procedure in Example 1, step c, reaction of 2,2,2-trifluoro-1-[3-(4,4,5,5-tetramethyl-[1,3,2]dioxaborolan-2-yl)-phenyl]-ethanol (123 mg, 416 mmol, as prepared in Example 28, step b), {[4-(3-bromo-benzenesulfonyl)-5-methylsulfanyl-thiophen-2-yl]-imino-methyl}-carbamic acid tert-butyl ester (100 mg, 0.2 mmol, as prepared in Example 27, step c), tetrakis(triphenylphosphine) palladium(0) (59 mg, 0.05 mmol, Strem Chemicals Inc, Newburyport, Mass.), Na₂CO₃ (800 μL, 2M aqueous), and toluene/EtOH mixture (2:1, 2.4 mL) afforded 100 mg (85%) after purification (SiO₂, flash elution: 30% EtOAc in hexanes) of the title compound as a white foam. ¹H-NMR (CDCl₃; 400 MHz) δ 8.20 (t, 1H, J=1.7 Hz), 7.94–7.99 (m, 2H), 7.77–7.81 (m, 1H), 7.67 (br s, 1H), 7.57 (m, 1H), 7.27–7.34 (m, 1H), 7.15–7.21 (m, 2H), 5.11 (q, 1H, J=6.8 Hz), 2.51 (s, 3H), 1.49 (s, 9H). ¹⁹F-NMR (CDCl₃; 400 MHz) δ −78.51 (d, J=6.9 Hz). ESI-MS (m/z): Calcd. for C₂₅H₂₅F₃N₂O₅S₃: 586.7; found: 586.7.

d) 5-Methylsulfanyl-4-[3'-(2,2,2-trifluoro-1-hydroxy-ethyl)-biphenyl-3-sulfonyl]-thiophene-2-carboxamidine trifluoroacetate (Imino-{5-methylsulfanyl-4-[3'-(2,2,2-trifluoro-1-hydroxy-ethyl)-biphenyl-3-sulfonyl]-thiophen-2-yl}-methyl)-carbamic acid tert-butyl ester (25 mg, 0.043 mmol, as prepared in Example 28, step c) was treated with trifluoroacetic acid (50% in DCM) for 1 hr at rt. The reaction mixture was concentrated in vacuo and the residue obtained was purified using C$_{18}$-HPLC (10–80% CH$_3$CN in H$_2$O (0.1% TFA) over 25 min) to give 18 mg (86%) of the title compound as a white solid. $^1$H-NMR (CD$_3$OD; 400 MHz) δ 8.33 (s, 1H), 8.30 (t, 1H, J=1.7), 7.97–8.05 (m, 2H), 7.91 (br s, 1H), 7.68–7.74 (m, 2H), 7.53–7.56 (m, 2H), 5.15 (q, 1H, J=7.0 Hz), 2.74 (s, 3H). $^{19}$F-NMR (CD$_3$OD; 400 MHz) δ −80.09 (d, J=6.9 Hz). ESI-MS (m/z): Calcd. for C$_{20}$H$_{17}$F$_3$N$_2$O$_3$S$_3$: 487.6 (M+H); found: 487.3.

Example 29

5-Methylsulfanyl-4-[3'-(2,2,2-trifluoro-acetyl)-biphenyl-3-sulfonyl]-thiophene-2-carboxamidine trifluoroacetate

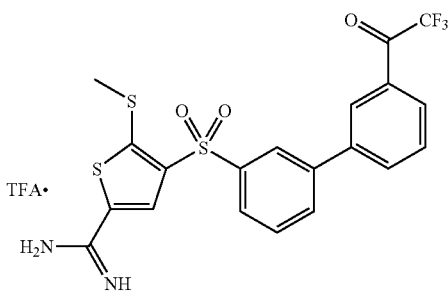

a) (Imino-{5-methylsulfanyl-4-[3'-(2,2,2-trifluoro-acetyl)-biphenyl-3-sulfonyl]-thiophen-2-yl}-methyl)-carbamic acid tert-butyl ester In a reaction vial, (imino-{5-methylsulfanyl-4-[3'-(2,2,2-trifluoro-1-hydroxy-ethyl)-biphenyl-3-sulfonyl]-thiophen-2-yl}-methyl)-carbamic acid tert-butyl ester (30 mg, 0.051 mmol, as prepared in Example 28, step c) and 1,1,1-triacetoxy-1,1-dihydro-1,2-benziodoxol-3(1H)-one (31 mg, 0.072 mmol, Lancaster Synthesis, Windham, N.H.) were dissolved in DCM (2 mL). To that solution, wet DCM (1 mL, 4 μL H$_2$O) was added slowly via a syringe. After 1 hr of stirring at rt, the reaction was evaporated and the residue was partitioned between Et$_2$O (30 mL) and 10% Na$_2$S$_2$O$_3$-saturated NaHCO$_3$ (1:1, 15 mL). The aqueous layer was washed with an additional portion of Et$_2$O. The combined organic washes were dried with MgSO$_4$ and concentrated in vacuo to give 30 mg (quantitative yield) of the title compound that was used without purification. $^1$H-NMR (CDCl$_3$; 400 MHz) δ 8.28 (br s, 1H), 8.26 (t, 1H, J=1.7 Hz), 8.08–8.13 (m, 1H), 7.99–8.04 (m, 1H), 7.96 (s, 1H), 7.91–7.95 (m, 1H), 7.82–7.86 (m, 1H), 7.62–7.71 (m, 2H), 2.59 (s, 3H), 1.51 (s, 9H). $^{19}$F-NMR (CDCl$_3$; 400 MHz) δ −84.93 (s). ESI-MS (m/z): Calcd. for C$_{25}$H$_{23}$F$_3$N$_2$O$_5$S$_3$: 487.6 (M+H); found: 487.2.

b) 5-Methylsulfanyl-4-[3'-(2,2,2-trifluoro-acetyl)-biphenyl-3-sulfonyl]-thiophene-2-carboxamidine trifluoroacetate (Imino-{5-methylsulfanyl-4-[3'-(2,2,2-trifluoro-acetyl)-biphenyl-3-sulfonyl]-thiophen-2-yl}-methyl)-carbamic acid tert-butyl ester (30 mg, 0.051 mmol, as prepared in Example 29, step a) was treated with trifluoroacetic acid (50% in DCM) for 1 hr at rt. The reaction mixture was concentrated in vacuo and the residue obtained was purified using C$_{18}$-HPLC (20–60% CH$_3$CN in H$_2$O (0.1% TFA) over 25 min) to give 20 mg (80%) of the title compound as a white solid. $^1$H-NMR (CD$_3$OD; 400 MHz) δ 8.35 (s, 1H), 8.33 (t, 1H, J=1.7 Hz), 7.98–8.07 (m, 2H), 7.90–7.93 (m, 1H), 7.68–7.78 (m, 3H), 7.60 (t, 1H, J=7.8 Hz), 2.77 (s, 3H). $^{19}$F-NMR (CDCl$_3$; 400 MHz) δ −84.99 (s). ESI-MS (m/z): Calcd. for C$_{20}$H$_{15}$F$_3$N$_2$O$_3$S$_3$: 485.5 (M+H); found: 485.3, 503.3 (M+H$_2$O), 517.3 (M+CH$_3$OH).

Example 30

4-[3-(6-Methyl-3H-benzoimidazol-5-yl)-benzenesulfonyl]-5-methylsulfanyl-thiophene-2-carboxamidine bis-trifluoroacetate

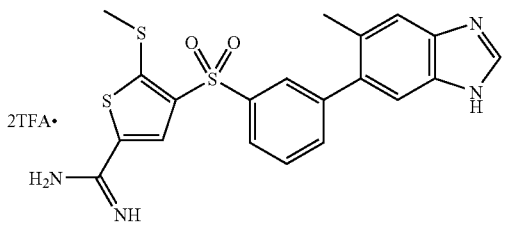

a) 5-Chloro-6-methyl-benzoimidazole-1-carboxylic acid tert-butyl ester and 5-Chloro-6-methyl-benzoimidazole-3-carboxylic acid tert-butyl ester 4-Chloro-5-methyl-benzene-1,2-diamine (560 mg, 3.6 mmol, Maybridge Chemical Co. Ltd., Cornwall, UK) was dissolved in formic acid (10 mL) and the solution was refluxed at 100° C. for 18 hr. The reaction was allowed to cool and then evaporated to dryness in vacuo to give 5-chloro-6-methyl-1H-benzoimidazole as a tan solid (quantitative yield) that was used without further purification. The solid obtained above (410 mg, 2.4 mmol), di-tert-butyl dicarbonate (1.6 g, 7.4 mmol), and DMAP (29 mg, 0.24 mmol) were dissolved in CH$_3$CN (20 mL). To the mixture, DIEA (1.3 mL, 7.4 mmol) was added and the reaction was stirred for 18 hr at rt. The solvents were evaporated in vacuo and the residue partitioned between EtOAc (100 mL) and saturated aqueous NaHCO$_3$ (75 mL). The aqueous layer was separated and washed with EtOAc (100 mL). The combined organic layers were dried with MgSO$_4$ and concentrated in vacuo. The crude residue was purified using flash SiO$_2$ chromatography (20% EtOAc in hexanes) to give 620 mg (97%) of the title compound as a 1:1 mixture of regioisomers that were used without separation. $^1$H-NMR (CDCl$_3$; 400 MHz, 1:1 mixture of isomers) δ 8.35 and 8.36 (s, 1H), 7.89 and 7.99 (s, 1H), 7.62 and 7.75 (s, 1H), 2.48 and 2.50 (s, 3H), 1.698 and 1.700 (s, 9H). ESI-MS (m/z): Calcd. for C$_{13}$H$_{15}$ClN$_2$O$_2$: 266.7; found: 266.9, 167.2 (M−Boc).

b) 5-Methyl-6-(4,4,5,5-tetramethyl-[1,3,2]dioxaborolan-2-yl)-benzoimidazole-1-carboxylic acid tert-butyl ester and 5-Methyl-6-(4,4,5,5-tetramethyl-[1,3,2]dioxaborolan-2-yl)-benzoimidazole-1-carboxylic acid tert-butyl ester To a dry reaction vial fitted with a stir bar and a Teflon®-lined screw cap, a mixture of 5-chloro-6-methyl-benzoimidazole-1-carboxylic acid tert-butyl ester and 5-chloro-6-methyl-benzoimidazole-3-carboxylic acid tert-butyl ester (150 mg, 0.56 mmol, as prepared in Example 30, step a), 4,4,5,5,4',4',5',5'-octamethyl-[2,2']bi[[1,3,2]dioxaborolanyl] (284 mg, 1.12 mmol, Aldrich Chemical Company), (2'-dicyclohexylphosphanyl-biphenyl-2-yl)-dimethyl-amine (17.7 mg, 0.045 mmol, Strem Chemicals Inc, Newburyport, Mass.), Pd(OAc)$_2$ (6.7 mg, 0.03 mmol. Strem Chemicals Inc, Newburyport, Mass.), and K$_3$PO$_4$ (238 mg, 1.12, mmol) were added. The vial was capped, purged with argon, and then suspended in toluene (3 mL). After stirring for 18 hr at 95° C., the reaction was allowed to cool and then filtered through Celite.® The filtrate was concentrated in vacuo and the residue was purified using preparative thin layer chromatography (1:3 EtOAc/hexanes, 2000μ SiO$_2$ plate) to afford 100 mg (50%) of the title compound (1:1 mixture of regioisomers) as a yellow oil. ESI-MS (m/z): Calcd. for C$_{19}$H$_{27}$BN$_2$O$_4$: 358.2; found: 303.2 (M–$^t$Bu), 259.3 (M–Boc).

c) 4-[3-(6-Methyl-3H-benzoimidazol-5-yl)-benzene-sulfonyl]-5-methylsulfanyl-thiophene-2-carboxami-dine bis-trifluoroacetate Following the same procedure in Example 1, step c, 5-methyl-6-(4,4,5,5-tetramethyl-[1,3,2]dioxaborolan-2-yl)-benzoimidazole-1-carboxylic acid tert-butyl ester and 5-methyl-6-(4,4,5,5-tetramethyl-[1,3,2]dioxaborolan-2-yl)-benzoimidazole-1-carboxylic acid tert-butyl ester (90 mg, 0.25 mmol, as prepared in Example 30, step b), {[4-(3-bromo-benzenesulfonyl)-5-methylsulfanyl-thiophen-2-yl]-imino-methyl}-carbamic acid tert-butyl ester (62 mg, 0.126 mmol, as prepared in Example 27, step c), tetrakis(triphenylphosphine)palladium(0) (37 mg, 0.032 mmol, Strem Chemicals, Inc., Newburyport, Mass.), Na$_2$CO$_3$ (400 μL, 2M aqueous), and toluene/EtOH mixture (2:1, 1.2 mL) were reacted to give 170 mg of a tan foam. This crude material was separated using preparative thin layer chromatography (1:2 EtOAc/hexanes, 2000μ SiO$_2$ plate). From several bands that were isolated and analyzed by ESI-MS, two bands exhibited an observed mass consistent with the di-Boc (7 mg) and mono-Boc (47 mg) products, respectively. Both of these compounds were combined and then treated with trifluoroacetic acid (50% in DCM) for 1 hr at rt. The reaction mixture was concentrated in vacuo and the residue obtained was purified using C$_{18}$-HPLC (15–35% CH$_3$CN in H$_2$O (0.1% TFA) over 25 min) to give 8 mg (15%) of the title compound as a white solid. $^1$H-NMR (CD$_3$OD): δ 9.34 (s, 1H), 8.34 (s, 1H), 8.04–8.10 (m, 2H), 7.79 (br s, 1H), 7.74–7.75 (m, 2H), 7.67 (br s, 1H), 2.72 (s, 3H), 2.37 (s, 3H). ESI-MS (m/z): Calcd. for C$_{20}$H$_{18}$N$_4$O$_2$S$_3$: 443.6 (M+H); found: 443.1, 222.3 (M$^{++}$).

Example 31

N-Hydroxy-4-[3-(6-methyl-3H-benzoimidazol-5-yl)-benzenesulfonyl]-5-methylsulfanyl-thiophene-2-carboxamidine trifluoroacetate

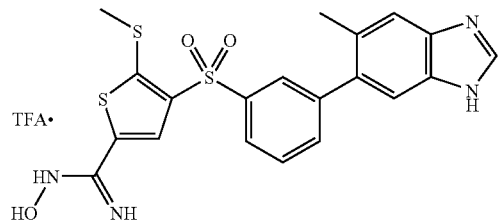

a) N-Hydroxy-4-[3-(6-methyl-3H-benzoimidazol-5-yl)-benzenesulfonyl]-5-methylsulfanyl-thiophene-2-carboxamidine trifluoroacetate 4-[3-(6-Methyl-3H-benzoimidazol-5-yl)-benzenesulfonyl]-5-methylsulfanyl-thiophene-2-carboxamidine bis-trifluoroacetate (5 mg, 7.5 μmol, as prepared in Example 30, step c), hydroxylamine hydrochloride (50 mg, 720 μmol), and Et$_3$N (139 μL, 1 mmol)) were suspended in EtOH (3 mL). The reaction mixture was refluxed for 2 hr at which time thin layer chromatography showed complete disappearance of the starting material. The reaction mixture was concentrated in vacuo and the residue was purified using C$_{18}$-HPLC (10–50% CH$_3$CN in H$_2$O (0.1% TFA) over 20 min) to give 4.9 mg (quantitative yield) of the title compound as a hygroscopic white solid. $^1$H-NMR (CD$_3$OD): δ 9.38 (s, 1H), 8.08–8.12 (m, 2H), 8.05–8.07 (m, 1H), 7.82 (br s, 1H), 7.73–7.77 (m, 2H), 7.70 (br s, 1H), 2.70 (s, 3H), 2.38 (s, 3H). ESI-MS (m/z): Calcd. for C$_{20}$H$_{18}$N$_4$O$_3$S$_3$: 459.6 (M+H); found: 459.2.

Example 32

4-[2'-(1-Hydroxy-ethyl)-biphenyl-3-sulfonyl]-5-methylsulfanyl-thiophene-2-carboxamidine trifluoroacetate

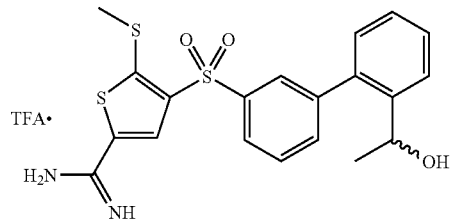

a) {Imino-[5-methylsulfanyl-4-(2'-vinyl-biphenyl-3-sulfonyl)-thiophen-2-yl]-methyl}-carbamic acid tert-butyl ester Following the procedure outlined for Examples 41–107, reaction of 2-vinyl-phenylboronic acid (30 mg, 0.20 mmol, Aldrich Chemical Company), {[4-(3-bromo-benzenesulfonyl)-5-methylsulfanyl-thiophen-2-yl]-imino-methyl}-carbamic acid tert-butyl ester (50 mg, 0.1 mmol, as prepared in Example 27, step c), tetrakis(triphenylphosphine)palladium (0) (29 mg, 0.025 mmol, Strem Chemicals, Inc., Newburyport, Mass.), Na$_2$CO$_3$ (400 μL, 2M aqueous), and toluene/EtOH mixture (2:1, 1.2 mL) afforded 25 mg (50%) after purification (1:3 EtOAc/hexanes, 2000μ SiO$_2$ plate) of the title compound as a white foam.

b) 4-[2'-(1-Hydroxy-ethyl)-biphenyl-3-sulfonyl]-5-methylsulfanyl-thiophene-2-carboxamidine trifluoroacetate {Imino-[5-methylsulfanyl-4-(2'-vinyl-biphenyl-3-sulfonyl)-thiophen-2-yl]-methyl}-carbamic acid tert-butyl ester (25 mg, 0.05 mmol) was treated with trifluoroacetic acid (50% in DCM) for 1 hr at rt. The reaction mixture was concentrated in vacuo and then basified with 1 M NaOH to pH 8 and allowed to stand for 10 min. The solution was then re-acidified with TFA and purified using C$_{18}$-HPLC (10–80% CH$_3$CN in H$_2$O (0.1% TFA) over 30 min) to give 7 mg (33%) of the title compound as a white solid (R$_t$: 12.3 min). $^1$H-NMR (CD$_3$OD): δ 8.32 (s, 1H), 8.01–8.05 (m, 1H), 7.98–8.00 (m, 1H), 7.64–7.71 (m, 3H), 7.44–7.49 (m, 1H), 7.32–7.36 (m, 1H), 7.16–7.18 (m, 1H), 4.75 (q, 1H, J=6.5 Hz), 2.72 (s, 3H), 1.28 (d, 3H, J=6.5 Hz). ESI-MS (m/z): Calcd. for C$_{20}$H$_{20}$N$_2$O$_3$S$_3$: 433.6 (M+H); found: 433.1.

Example 33

4-[4'-(1-Hydroxy-ethyl)-biphenyl-3-sulfonyl]-5-methylsulfanyl-thiophene-2-carboxamidine Trifluoroacetate

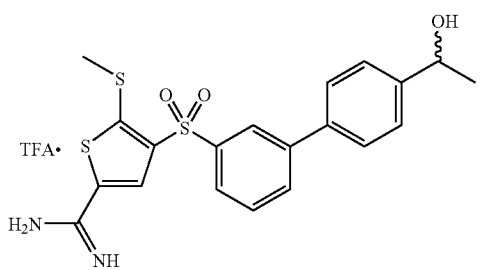

a) {Imino-[5-methylsulfanyl-4-(4'-vinyl-biphenyl-3-sulfonyl)-thiophen-2-yl]-methyl}-carbamic acid tert-butyl ester Following the procedure outlined in Example 1, step c, reaction of 4-vinyl-phenyl-boronic acid (181 mg, 1.22 mmol), {[4-(3-bromo-benzenesulfonyl)-5-methylsulfanyl-thiophen-2-yl]-imino-methyl}-carbamic acid tert-butyl ester (300 mg, 0.61 mmol, as prepared in Example 27, step c), tetrakis(triphenylphosphine)palladium(0) (141 mg, 0.122 mmol, Strem Chemicals, Inc., Newburyport, Mass.), Na$_2$CO$_3$ (2.4 mL, 2M aqueous), and toluene/EtOH mixture (2:1, 7.2 mL) afforded 138 mg (45%) of the title compound as a white glassy solid after SiO$_2$ flash chromatography (1:3 EtOAc/hexanes). $^1$H-NMR (CDCl$_3$): δ 8.21 (t, 1H, 1.7 Hz), 8.00 (brs, 1H), 7.92–7.95 (m, 1H), 7.79–7.81 (m, 1H), 7.48–7.58 (m, 5H), 6.75 (dd, 1H, J=17.7, 10.9 Hz), 5.82 (d, 1H, J=17.5), 5.31 (d, 1H, J=10.9 Hz), 2.54 (s, 3H), 1.50 (s, 9H).

b) 4-[4'-(1-Hydroxy-ethyl)-biphenyl-3-sulfonyl]-5-methylsulfanyl-thiophene-2-carboxamidine Trifluoroacetate {Imino-[5-methylsulfanyl-4-(4'-vinyl-biphenyl-3-sulfonyl)-thiophen-2-yl]-methyl}-carbamic acid tert-butyl ester (14 mg, 0.027 mmol, as prepared in Example 33, step a) was treated with trifluoroacetic acid (50% in DCM) for 1 hr at rt. The reaction mixture was concentrated in vacuo and then brought to pH 8 with 1 M NaOH and allowed to stand for 10 min. The solution was then re-acidified with TFA and purified using C$_{18}$-HPLC (10–80% CH$_3$CN in H$_2$O (0.1% TFA) over 30 min) to give 9 mg (81%) of the title compound as a white solid (R$_t$: 11.8 min). $^1$H-NMR (CD$_3$OD): δ 8.33 (s, 1H), 8.25 (t, 1H, 1.7 Hz), 7.95–8.01 (m, 2H), 7.61–7.71 (m, 3H), 7.49–7.53 (m, 2H), 4.89 (q, 1H, J=6.5 Hz), 2.73 (s, 3H), 1.47 (d, 3H, J=6.5 Hz). ESI-MS (m/z): Calcd. for C$_{20}$H$_{20}$N$_2$O$_3$S$_3$: 433.6 (M+H); found: 433.2.

Example 34

4-(2'-Hydroxy-biphenyl-3-sulfonyl)-5-methylsulfanyl-thiophene-2-carboxamidine trifluoroacetate

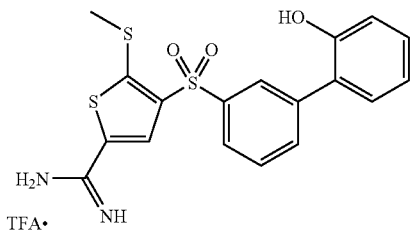

a) 4-(2'-Methoxy-biphenyl-3-sulfonyl)-5-methylsulfanyl-thiophene-2-carboxamidine trifluoracetate Following the procedure outlined in Example 1, step c, reaction of 2-methoxy-phenyl-boronic acid (181 mg, 1.22 mmol), {[4-(3-bromo-benzenesulfonyl)-5-methylsulfanyl-thiophen-2-yl]-imino-methyl}-carbamic acid tert-butyl ester (100 mg, 0.2 mmol, as prepared in Example 27, step c), tetrakis(triphenylphosphine)palladium(0) (141 mg, 0.122 mmol, Strem Chemicals, Inc., Newburyport, Mass.), Na$_2$CO$_3$ (800 μL, 2M aqueous), and toluene/EtOH mixture (2:1, 2.4 mL) afforded 100 mg (96%) of a white glassy solid after SiO$_2$ flash chromatography (1:3 EtOAc/hexanes). This material was treated with trifluoroacetic acid (50% in DCM) for 1 hr at rt and the crude product was purified using C$_{18}$-HPLC to give 65 mg (80%) of the title compound as a white solid. $^1$H-NMR (CD$_3$OD): δ 8.29 (s, 1H), 8.12 (brs, 1H), 8.02 (brd, 1H, J=7.9 Hz), 7.86–7.90 (m, 1H), 7.54 (t, 1H, J=8.0 Hz), 6.88–7.36 (m, 4H), 3.30 (s, 3H), 2.73 (s, 3H). ESI-MS (m/z): Calcd. for C$_{19}$H$_{18}$N$_2$O$_3$S$_3$: 419.5 (M+H); found: 419.3.

b) 4-(2'-Hydroxy-biphenyl-3-sulfonyl)-5-methylsulfanyl-thiophene-2-carboxamidine trifluoroacetate 4-(2'-Methoxy-biphenyl-3-sulfonyl)-5-methylsulfanyl-thiophene-2-carboxamidine trifluoroacetate (46 mg, 0.086 mmol, as prepared in Example 34, step a) was treated with BBr$_3$ (1 M in DCM) for 18 hr at rt. The reaction was quenched with MeOH at 0° C. and then concentrated in vacuo to a solid. Purification of this solid using C$_{18}$-HPLC (10–80% CH$_3$CN in H$_2$O (0.1% TFA) over 25 min) afforded 34 mg (77%) of the title compound as a white solid. $^1$H-NMR (CD$_3$OD): δ 8.30 (s, 1H), 8.27 (t, 1H, J=1.9 Hz), 7.89–7.96 (m, 2H), 7.61 (t, 1H, J=7.9 Hz), 7.26–7.30 (m, 1H), 7.19–7.24 (m, 1H), 6.90–6.95 (m, 2H), 2.70 (s, 3H). ESI-MS (m/z): Calcd. for C$_{18}$H$_{16}$N$_2$O$_3$S$_3$: 405.5 (M+H); found: 405.2.

Example 35

4-(3'-Hydroxy-biphenyl-3-sulfonyl)-5-methylsulfanyl-thiophene-2-carboxamidine trifluoroacetate

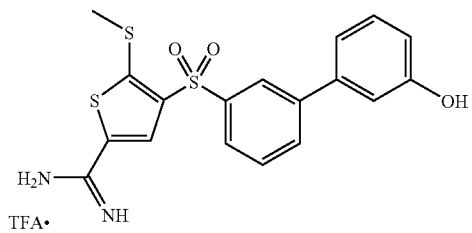

4-(3'-Methoxy-biphenyl-3-sulfonyl)-5-methylsulfanyl-thiophene-2-carboxamidine trifluoroacetate (1.4 mg, 3.3 μmol, as prepared in Example 44) was treated with BBr$_3$ (1 M in DCM) for 18 hr at rt. The reaction was quenched with MeOH at 0° C. and then concentrated in vacuo to a solid. Purification of this solid using C$_{18}$-HPLC (10–80% CH$_3$CN in H$_2$O (0.1% TFA) over 25 min) afforded 1.0 mg (77%) of the title compound as a white solid. $^1$H-NMR (CD$_3$OD): δ 8.33 (s, 1H), 8.23 (t, 1H, J=1.6 Hz), 7.98–8.01 (m, 1H), 7.92–7.95 (m, 1H), 7.68 (t, 1H, J=7.8 Hz), 7.31 (t, 1H, J=7.8 Hz), 7.05–7.12 (m, 2H), 6.84–6.87 (m, 1H), 2.74 (s, 3H). ESI-MS (m/z): Calcd. for C$_{18}$H$_{16}$N$_2$O$_3$S$_3$: 405.5 (M+H); found: 405.2.

Example 36

5-Bromo-4-(2-methoxy-benzenesulfonyl)-thiophene-2-carboxamidine triflouroacetate

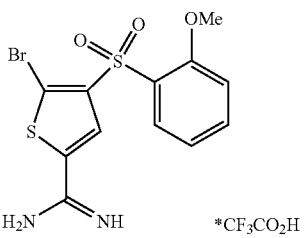

The procedure as in Example 20: step a was followed using 4-bromo-5-nitro-thiophene-2-carboxylic acid methyl ester ((Example 114, step c) 200 mg, 0.75 mmol) and 2-methoxy-benzenethiol (109 μL, 1.25 mmol, Aldrich Chemical Company) to isolate 4-(2-methoxy-phenylsulfanyl)-5-nitro-thiophene-2-carboxylic acid methyl ester. 4-(2-Methoxy-phenylsulfanyl)-5-nitro-thiophene-2-carboxylic acid methyl ester (200 mg, 0.61 mmol) was then treated with TiCl$_3$ (20% aq. HCl solution, 5 mL, 6.1 mmol) in THF (6 mL). The reaction was stirred for 20 minutes at rt. The reaction mixture was concentrated in vacuo and then dissolved into EtOAc. The organic layer was washed several times with saturated NaHCO$_3$. The combined organic layers were dried over sodium sulfate. Removal of the solvents in vacuo yielded 5-amino-4-(2-methoxy-phenylsulfanyl)-thiophene-2-carboxylic acid methyl ester. The procedure as in Example 20: step e was followed using 5-amino-4-(2-methoxy-phenylsulfanyl)-thiophene-2-carboxylic acid methyl ester (160 mg, 0.54 mmol), t-butylnitrite (96 μL, 0.81 mmol), and copper (II) bromide (112.6 mg, 0.65 mmol) resulting in 5-bromo-4-(2-methoxy-phenylsulfanyl)-thiophene-2-carboxylic acid methyl ester. The procedure as in Example 20: step b was followed using 5-bromo-4-(2-methoxy-phenylsulfanyl)-thiophene-2-carboxylic acid methyl ester (18 mg, 0.05 mmol) and m-CPBA (32 mg, 0.25 mmol) resulting in 5-bromo-4-(2-methoxy-benzenesulfonyl)-thiophene-2-carboxylic acid methyl ester. The procedure as in Example 20: step f was followed using 5-bromo-4-(2-methoxy-benzenesulfonyl)-thiophene-2-carboxylic acid methyl ester (45 mg, 11 mmol) and dimethyl aluminum amide (1M, 0.57 mL, 0.55 mmol) resulting in the title compound 5-bromo-4-(2-methoxy-benzenesulfonyl)-thiophene-2-carboxamidine (4 mg, 13%). $^1$H-NMR (CD$_3$OD): δ: 8.30 (s, 1H), 8.12–8.14 (d of d, J=6.1, 1.8 Hz, 1H), 7.70–7.74 (m, 1H), 7.16–7.24 (m, 2H), 3.79 (s, 3H).

Example 37

5-Methylsulfanyl-4-(naphthalene-2-sulfonyl)-thiophene-2-carboxamidine triflouroacetate

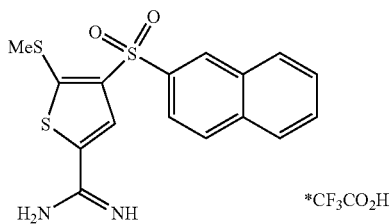

To a suspension of NaH (30 mg, 1.24 mmol) in DMF was slowly added dropwise naphthalene-2-thiol (199 mg, 1.24 mmol, Aldrich Chemical Company) in DMF at rt. This clear solution was then added dropwise to a solution of 4-bromo-5-nitro-thiophene-2-carboxylic acid methyl ester ((Example 114, step c) 300 mg, 1.27 mmol) in DMF at rt. Aqueous workup resulted in isolation of 4-(naphthalen-2-ylsulfanyl)-5-nitro-thiophene-2-carboxylic acid methyl ester. The procedure as in Example 20: step b was followed using 4-(naphthalen-2-ylsulfanyl)-5-nitro-thiophene-2-carboxylic acid methyl ester (194 mg, 0.56 mmol) and m-CPBA (354.4 mg, 1.2 mmol) resulting in 4-(naphthalene-2-sulfonyl)-5-nitro-thiophene-2-carboxylic acid methyl ester. The procedure as in Example 27: step a was followed using 4-(naphthalene-2-sulfonyl)-5-nitro-thiophene-2-carboxylic acid methyl ester (32 mg, 0.085 mmol) sodium thiomethoxide (7.55 mg, 0.94 mmol) resulting in 5-methylsulfanyl-4-(naphthalene-2-sulfonyl)-thiophene-2-carboxylic acid methyl ester. The procedure as in Example 20: step f was followed using 5-methylsulfanyl-4-(naphthalene-2-sulfonyl)-thiophene-2-carboxylic acid methyl ester (29 mg, 0.77 mmol) and dimethyl aluminum amide (0.39 mL, 0.39 mmol) resulting in the title compound 5-methylsulfanyl-4-(naphthalene-2-sulfonyl)-thiophene-2-carboxamidine triflouroacetate (19 mg, 70%). $^1$H-NMR (CD$_3$OD): δ: 8.67 (m, 1H), 8.37 (s, 1H), 8.05–8.15 (m, 2H), 7.95–8.01 (d, J=7.21 Hz, 1H), 7.90–7.95 (d of d, J=6.7, 2.0 Hz), 7.65–7.75 (m, 2H), 2.70 (s, 3H).

Example 38

4-(7-Bromo-3H-benzoimidazole-5-sulfonyl)-5-methylsulfanyl-thiophene-2-carboxamidine trifluoroacetate

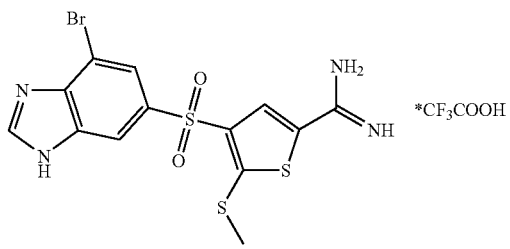

a) 4-Chlorosulfonyl-5-methylsulfanyl-thiophene-2-carboxylic acid methyl ester

To a −5° C. solution of 4-amino-5-methylsulfanyl-thiophene-2-carboxylic acid methyl ester (Illig et al. U.S. Pat. No. 6,291,514, 24 g, 0.12 mol) in methylene chloride: methanol (2:1, 40 mL), CuCl$_2$.2H$_2$O (6.04 g, 0.035 mol), and concentrated HCl (19.7 mL, 0.24 mol) was added. Excess SO$_2$ was condensed into the reaction mixture. To this mixture, was added t-butyl nitrite (27.6 mL, 0.24 mol) dropwise at −5° C. and then stirred at same temperature for 2 hours. The reaction mixture was allowed to warm up to room temperature, and the solvents were removed in vacuo. The residue was diluted in methylene chloride (500 mL), washed with water (100 mL) and brine (50 mL), and dried over Na$_2$SO$_4$. The solvent was removed in vacuo and the residue was purified by flash chromatography in 30–50% ethyl acetate in hexanes to afford 4-chlorosulfonyl-5-methylsulfanyl-thiophene-2-carboxylic acid methyl ester as a solid (12 g, 35%).

b) Sodium salt of 5-methylsulfanyl-4-sulfino-thiophene-2-carboxylic acid methyl ester To a solution of Na$_2$SO$_3$ (7.51 g, 0.06 mol) and NaHCO$_3$ (5.22 g, 0.06 mol) in water (27 mL) at 75° C. was added 4-chlorosulfonyl-5-methylsulfanyl-thiophene-2-carboxylic acid methyl ester ((Example 38, step a) 12 g, 0.05 mol) portion-wise over 3 hours and then stirred for an additional hour. Water was removed in vacuo, and the residue was dissolved in hot water (10 mL). This solution was cooled in a refrigerator for 1 week at which time the product precipitated out. This solid was filtered, washed with cold water and dried to give 12 g (87%) of the sodium salt of 5-methylsulfanyl-4-sulfino-thiophene-2-carboxylic acid methyl ester. $^1$H-NMR (DMSO-d$_6$): δ 7.64 (s, 1H), 3.78 (s, 3H), 2.57 (s, 3H).

c) 4-(7-Bromo-spiro[benzoimidazole-2,1'-cyclohex]e-5-sulfonyl)-5-methylsulfanyl-thiophene-2-carboxylic acid methyl ester To a solution of 4,6-dibromo-spiro[benzoimidazole-2,1'-cyclohexane] (200 mg, 0.58 mmol, prepared according to Hazelton et al., Tetrahedron:51:5597 (1995)) in ethanol (15 mL) was added an aqueous solution of the sodium salt of 5-methylsulfanyl-4-sulfino-thiophene-2-carboxylic acid methyl ester ((Example 38, step b) 175 mg, 0.64 mmol, 15 mL H$_2$O) and acetic acid (40 μL, 0.70 mmol). This mixture was stirred for 2.5 hours at room temperature and poured into an ice-water slurry. The resulting aqueous solution was extracted with methylene chloride (100 mL, 3×). The organic layer was separated, washed with brine (25 mL), and dried over MgSO$_4$. The solvents were removed in vacuo to afford 4-(7-bromo-spiro[benzoimidazole-2,1'-cyclohex]e-5-sulfonyl)-5-methylsulfanyl-thiophene-2-carboxylic acid methyl ester as a brown solid (200 mg, 67%). $^1$H-NMR (CDCl$_3$): δ 8.08 (m, 1H), 8.04 (s, 1H), 7.60 (m, 1H), 3.91 (s, 3H), 2.66 (s, 3H), 2.00–1.24 (m, 10H).

d) 4-(3,4-Diamino-5-bromo-benzenesulfonyl)-5-methylsulfanyl-thiophene-2-carboxylic acid methyl ester To a solution of 4-(7-bromo-spiro[benzoimidazole-2,1'-cyclohex]e-5-sulfonyl)-5-methylsulfanyl-thiophene-2-carboxylic acid methyl ester ((Example 38, step c) 200 mg, 0.39 mmol) in 1:1 ethanol:water (30 mL) was added sodium dithionite (159 mg, 0.78 mmol) and heated to 80° C. for 45 minutes. The solution was cooled to room temperature and poured into an ice-water slurry. This aqueous mixture was extracted with methylene chloride (50 mL, 3×). The organic layer was separated, washed with brine (25 mL), and dried over MgSO$_4$. The solvents were removed in vacuo to afford 170 mg of 4-(3,4-diamino-5-bromo-benzenesulfonyl)-5-methylsulfanyl-thiophene-2-carboxylic acid methyl ester as a brown oil. This was used in the next step without further purification.

e) 4-(7-Bromo-3H-benzoimidazole-5-sulfonyl)-5-methylsulfanyl-thiophene-2-carboxylic acid methyl ester 4-(3,4-Diamino-5-bromo-benzenesulfonyl)-5-methylsulfanyl-thiophene-2-carboxylic acid methyl ester ((Example 38, step d) 170 mg, 0.39 mmol) was dissolved in formic acid (2.5 mL) and heated to 100° C. for 2 hours. The resulting solution was cooled to room temperature, poured over ice-water slurry, and basified to pH 8 with NaHCO$_3$. This aqueous solution was extracted with ethyl acetate (75 mL, 3×). The organic layer was separated and washed with water, brine, and dried over MgSO$_4$. Solvents were removed in vacuo to afford 100 mg (57%) of 4-(7-bromo-3H-benzoimidazole-5-sulfonyl)-5-methylsulfanyl-thiophene-2-carboxylic acid methyl ester as a brown oil. ESI-MS (m/z): Calcd. for C$_{14}$H$_{11}$BrN$_2$O$_4$S$_3$: 447 (M+H); found: 447.1 and 449.1.

f) 4-(7-Bromo-3H-benzoimidazole-5-sulfonyl)-5-methylsulfanyl-thiophene-2-carboxamidine trifluoroacetate 1M stock solution of dimethylaluminum amide reagent was made by the addition of AlMe$_3$ solution (2M in toluene, 5 mL, 10 mmol) to a suspension of NH$_4$Cl (0.54 g, 10 mmol) in toluene (5 mL) under inert conditions, and then heated to 80° C. for 5 minutes. This solution (2.5 mL, 2.5 mmol) was added to 4-(7-bromo-3H-benzoimidazole-5-sulfonyl)-5-methylsulfanyl-thiophene-2-carboxylic acid methyl ester ((Example 38, step e) 15 mg, 0.034 mmol) and then heated to 100° C. for 2 hrs. The resulting solution was cooled to room temperature and added to a slurry of silica gel in methylene chloride (15 g silica gel in methylene chloride 120 mL), and stirred for 30 minutes. The slurry was filtered and the silica was washed with methanol. The filtrate and methanol fractions were combined and evaporated under vacuum. The residue was purified by HPLC (C$_{18}$-column, 10–70% CH$_3$CN over 30 min) to afford 3.0 mg (21%) of 4-(7-bromo-3H-benzoimidazole-5-sulfonyl)-5-methylsulfanyl-thiophene-2-carboxamidine trifluoroacetate as a white solid. $^1$H-NMR (CD$_3$OD): δ 8.51 (s, 1H), 8.36 (d, 1H, J=1.6), 8.33 (s, 1H), 8.05 (d, 1H, J=1.6), 2.72 (s, 3H). ESI-MS (m/z): Calcd. for C$_{13}$H$_{11}$BrN$_4$O$_2$S$_3$: 430.92 (M+H); found 431.2 and 433.1.

Examples 39–40

4-(7-Bromo-3-methyl-3H-benzoimidazole-5-sulfonyl)-5-methylsulfanyl-thiophene-2-carboxamidine trifluoroacetate and 4-(7-Bromo-1-methyl-1H-benzoimidazole-5-sulfonyl)-5-methylsulfanyl-thiophene-2-carboxamidine trifluoroacetate

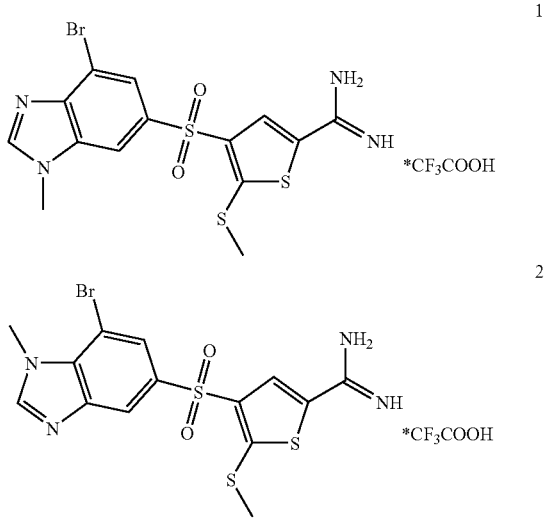

a) 4-(7-Bromo-3-methyl-3H-benzoimidazole-5-sulfonyl)-5-methylsulfanyl-thiophene-2-carboxylic acid methyl ester and 4-(7-Bromo-1-methyl-1H-benzoimidazole-5-sulfonyl)-5-methylsulfanyl-thiophene-2-carboxylic acid methyl ester To a solution of 4-(7-bromo-3H-benzoimidazole-5-sulfonyl)-5-methylsulfanyl-thiophene-2-carboxylic acid methyl ester (as prepared in Example 38, step e) (100 mg, 0.22 mmol) in dimethylformamide (2 mL) was added MeI (13.9 μL, 0.22 mmol) and K$_2$CO$_3$ (61.8 mg, 0.45 mmol), then stirred overnight at room temperature. The solvents were removed in vacuo and the residue was diluted with ethyl acetate (100 mL). The ethyl acetate layer was washed with water (15 mL) and brine (25 mL), and dried over MgSO$_4$. The solvent was removed in vacuo to afford 20 mg (19%) of 4-(7-bromo-3-methyl-3H-benzoimidazole-5-sulfonyl)-5-methylsulfanyl-thiophene-2-carboxylic acid methyl ester and 4-(7-bromo-1-methyl-1H-benzoimidazole-5-sulfonyl)-5-methylsulfanyl-thiophene-2-carboxylic acid methyl ester as a mixture. This mixture was used directly in the following step.

b) 4-(7-Bromo-3-methyl-3H-benzoimidazole-5-sulfonyl)-5-methylsulfanyl-thiophene-2-carboxamidine trifluoroacetate and 4-(7-Bromo-1-methyl-1H-benzoimidazole-5-sulfonyl)-5-methylsulfanyl-thiophene-2-carboxamidine trifluoroacetate 1M stock solution of dimethylaluminum amide reagent was made by the addition of AlMe₃ solution (2M in toluene, 5 mL, 10 mmol) to a suspension of NH₄Cl (0.54 g, 10 mmol) in toluene (5 mL) under inert conditions, and then heated to 80° C. for 5 minutes. To the mixture from above ((Examples 39–40, step a) 20 mg, 0.043 mmol) was added dimethylaluminum amide reagent (2.5 mL, 2.5 mmol), and then heated to 100° C. for 2 hrs. This solution was cooled to room temperature, added to 15 g silica gel and methylene chloride (120 mL) slurry, and stirred for 30 minutes. The slurry was filtered and washed with methanol. The solvents were removed in vacuo, and the crude material was purified by HPLC ($C_{18}$-column, 10–70% $CH_3CN$ over 30 min) to afford 4-(7-bromo-3-methyl-3H-benzoimidazole-5-sulfonyl)-5-methylsulfanyl-thiophene-2-carboxamidine trifluoroacetate, 39 (4.5 mg) and 4-(7-bromo-1-methyl-1H-benzoimidazole-5-sulfonyl)-5-methylsulfanyl-thiophene-2-carboxamidine trifluoroacetate, 40 (2.5 mg).

Example 39: ¹H-NMR (CD₃OD): δ 8.48 (s, 1H), 8.34 (s, 1H), 8.33 d, 1H, J=1.6), 8.06 (d, 1H, J=1.6), 4.01 (s, 3H), 2.72 (s, 3H). ESI-MS (m/z): Calcd. for $C_{14}H_{13}BrN_4O_2S_3$: 445 (M+H); found 445.1 and 447.1.

Example 40: ¹H-NMR (CD₃OD): δ 8.39 (s, 1H), 8.34 (d, 1H, J=1.4), 8.33 (s, 1H), 8.07 (d, 1H, J=1.2), 4.21 (s, 3H), 2.72 (s, 3H). ESI-MS (m/z): Calcd. for $C_{14}H_{13}BrN_4O_2S_3$: 445 (M+H); found 445.1 and 447.1.

Examples 41–107

The compounds in examples 41 to 107 (see table 1) were synthesized in a parallel fashion as follows: To dry 2-dram vials, each fitted with a stir bar and a Teflon®-lined screw cap was added {[4-(3-bromo-benzenesulfonyl)-5-methylsulfanyl-thiophen-2-yl]-imino-methyl}-carbamic acid tert-butyl ester (0.1 mmol, as prepared in Example 27, step c), the appropriate boronic acid (0.2 mmol), and tetrakis(triphenylphosine)palladium(0) (0.025 mmol). Each vial was twice treated with an argon purge/evacuation cycle and then charged with a mixture of toluene/EtOH (2:1, 1.2 mL) and 2 M $Na_2CO_3$ (0.4 mL) via a syringe. The vials were placed in an oil bath at 80° C. and stirred overnight. To the cooled reaction mixtures was added EtOAc (4 mL), the organic layer was filtered (1-g silica SPE column), and the filtrate was evaporated in vacuo. The resulting residue was purified using preparative TLC ($SiO_2$) to afford the Boc-protected amidine product. After treatment of this material with trifluoroacetic acid (50% in DCM) for 1 hr at rt, the solvents were removed in vacuo and the residue was purified using $C_{18}$-HPLC (typical HPLC method: 10% to 80% $CH_3CN$ in $H_2O$ (0.1% TFA) over 25 min) to afford the desired compound. Example 94 was prepared in an identical fashion except for removal of the Boc protecting group which was achieved by treatment with 4 N HCl in dioxane for 1 hr at rt. This was found to minimize side reactions involving the vinylic group (see Example 32).

| Ex. No. | Reagent | Compound | Formula | Calcd. (M + H) | Found |
|---|---|---|---|---|---|
| 41 | 2,4-dimethoxy phenyl boronic acid | 4-(2',4'-Dimethoxy-biphenyl-3-sulfonyl)-5-methylsulfanyl-thiophene-2-carboxamidine | $C_{20}H_{20}N_2O_4S_3$ | 449.5 | 449.2 |
| 42 | 4-methoxy phenyl boronic acid | 4-(4'-Methoxy-biphenyl-3-sulfonyl)-5-methylsulfanyl-thiophene-2-carboxamidine | $C_{19}H_{18}N_2O_3S_3$ | 419.5 | 419.2 |
| 43 | 3,4-dimethoxy phenyl boronic acid | 4-(3',4'-Dimethoxy-biphenyl-3-sulfonyl)-5-methylsulfanyl-thiophene-2-carboxamidine | $C_{20}H_{20}N_2O_4S_3$ | 449.5 | 449.3 |
| 44 | 3-methoxy phenyl boronic acid | 4-(3'-Methoxy-biphenyl-3-sulfonyl)-5-methylsulfanyl-thiophene-2-carboxamidine | $C_{19}H_{18}N_2O_3S_3$ | 419.5 | 419.3 |
| 45 | 2-methoxy phenyl boronic acid | 4-(2'-Methoxy-biphenyl-3-sulfonyl)-5-methylsulfanyl-thiophene-2-carboxamidine | $C_{19}H_{18}N_2O_3S_3$ | 419.5 | 419.3 |
| 46 | 3,5-dichloro phenyl boronic acid | 4-(3',5'-Dichloro-biphenyl-3-sulfonyl)-5-methylsulfanyl-thiophene-2-carboxamidine | $C_{18}H_{14}Cl_2N_2O_2S_3$ | 457.4 | 457.2 |
| 47 | 2,5-dichloro phenyl boronic acid | 4-(2',5'-Dichloro-biphenyl-3-sulfonyl)-5-methylsulfanyl-thiophene-2-carboxamidine | $C_{18}H_{14}Cl_2N_2O_2S_3$ | 457.4 | 457.2 |
| 48 | 3,5-di(trifluouoromethyl) phenyl boronic acid | 4-(3',5'-Bis-trifluoromethyl-biphenyl-3-sulfonyl)-5-methylsulfanyl-thiophene-2-carboxamidine | $C_{20}H_{14}F_6N_2O_2S_3$ | 525.5 | 525.2 |
| 49 | 2-Benzofuran boronic acid | 4-(3-Benzofuran-2-yl-benzenesulfonyl)-5-methylsulfanyl-thiophene-2-carboxamidine | $C_{20}H_{16}N_2O_3S_3$ | 429.5 | 429.3 |
| 50 | 2-Benzothiophene boronic acid | 4-(3-Benzo[b]thiophen-2-yl-benzenesulfonyl)-5-methylsulfanyl-thiophene-2-carboxamidine | $C_{20}H_{16}N_2O_2S_4$ | 445.6 | 445.2 |
| 51 | 4-methyl-3-nitro-phenylboronic acid | 4-(4'-Methyl-3'-nitro-biphenyl-3-sulfonyl)-5-methylsulfanyl-thiophene-2-carboxamidine | $C_{19}H_{17}N_3O_4S_3$ | 448.5 | 448.3 |

-continued

| Ex. No. | Reagent | Compound | Formula | Calcd. (M + H) | Found |
|---|---|---|---|---|---|
| 52 | 4-methyl-phenylboronic acid | 4-(4'-Methyl-biphenyl-3-sulfonyl)-5-methylsulfanyl-thiophene-2-carboxamidine | $C_{19}H_{18}N_2O_2S_3$ | 403.5 | 403.3 |
| 53 | 4-Chloro-phenylboronic acid | 4-(4'-Chloro-biphenyl-3-sulfonyl)-5-methylsulfanyl-thiophene-2-carboxamidine | $C_{18}H_{15}ClN_2O_2S_3$ | 423.98 | 423.3 |
| 54 | 4-Trifluoromethyl-phenylbornic acid | 5-Methylsulfanyl-4-(4'-trifluoromethyl-biphenyl-3-sulfonyl)-thiophene-2-carboxamidine | $C_{19}H_{15}F_3N_2O_2S_3$ | 457.5 | 457.2 |
| 55 | 4-trifluoromethoxy-phenylbornic acid | 5-Methylsulfanyl-4-(4'-trifluoromethoxy-biphenyl-3-sulfonyl)-thiophene-2-carboxamidine | $C_{19}H_{15}F_3N_2O_3S_3$ | 473.5 | 473.2 |
| 56 | 4-phenoxy-phenyl-boronic acid | 5-Methylsulfanyl-4-(4'-phenoxy-biphenyl-3-sulfonyl)-thiophene-2-carboxamidine | $C_{24}H_{20}N_2O_3S_3$ | 481.6 | 481.3 |
| 57 | 4-methanesulfonyl phenylboronic acid | {Imino-[4-(4'-methanesulfonyl-biphenyl-3-sulfonyl)-5-methylsulfanyl-thiophen-2-yl]-methyl}-carbamic acid tert-butyl ester | $C_{24}H_{26}N_2O_6S_4$ | 467.6 | 467.3 |
| 58 | Benzo[1,3]dioxole-5-boronic acid | 4-(3-Benzo[1,3]dioxol-5-yl-benzenesulfonyl)-5-methylsulfanyl-thiophene-2-carboxamidine | $C_{19}H_{16}N_2O_4S_3$ | 433.5 | 433.3 |
| 59 | Quinoline-7-boronic acid | 5-Methylsulfanyl-4-(3-quinolin-7-yl-benzenesulfonyl)-thiophene-2-carboxamidine | $C_{21}H_{17}N_3O_2S_3$ | 440.5 | 440.1 |
| 60 | 3-tolyl phenylboronic acid | 4-(3'-methyl-biphenyl-3-sulfonyl)-5-methylsulfanyl-thiophene-2-carboxamidine | $C_{19}H_{18}N_2O_2S_3$ | 403.5 | 403.2 |
| 61 | 3-formyl phenylboronic acid | 4-(3'-Formyl-biphenyl-3-sulfonyl)-5-methylsulfanyl-thiophene-2-carboxamidine | $C_{19}H_{16}N_2O_3S_3$ | 417.5 | 417.2 |
| 62 | 3-amino phenylboronic acid | 4-(3'-Amino-biphenyl-3-sulfonyl)-5-methylsulfanyl-thiophene-2-carboxamidine | $C_{18}H_{17}N_3O_2S_3$ | 404.5 | 404.2 |
| 63 | 3-trifluoromethyl phenyl boronic acid | 5-Methylsulfanyl-4-(3'-trifluoromethyl-biphenyl-3-sulfonyl)-thiophene-2-carboxamidine | $C_{19}H_{15}F_3N_2O_2S_3$ | 457.5 | 457.2 |
| 64 | 3-hydroxymethyl phenyl boronic acid | 4-(3'-Hydroxymethyl-biphenyl-3-sulfonyl)-5-methylsulfanyl-thiophene-2-carboxamidine | $C_{19}H_{18}N_2O_3S_3$ | 419.5 | 419.2 |
| 65 | Biphenyl-3-boronic acid | 5-Methylsulfanyl-4-([1,1';3',1'']terphenyl-3-sulfonyl)-thiopbene-2-carboxamidine | $C_{24}H_{20}N_2O_2S_3$ | 465.6 | 465.3 |
| 66 | 4-dibenzofuran boronic acid | 4-(3-Dibenzofuran-4-yl-benzenesulfonyl)-5-methylsulfanyl-thiophene-2-carboxamidine | $C_{24}H_{18}N_2O_3S_3$ | 479.6 | 479.3 |
| 67 | 2-trifluoromethyl phenyl boronic acid | 5-Methylsulfanyl-4-(2'-trifluoromethyl-biphenyl-3-sulfonyl)-thiophene-2-carboxamidine | $C_{19}H_{15}F_3N_2O_2S_3$ | 457.5 | 457.2 |
| 68 | 2-hydroxymethyl phenyl boronic acid | 4-(2'-Hydroxymethyl-biphenyl-3-sulfonyl)-5-methylsulfanyl-thiophene-2-carboxamidine | $C_{19}H_{18}N_2O_3S_3$ | 419.5 | 419.1 |
| 69 | 2-chloro phenylboronic acid | 4-(2'-Chloro-biphenyl-3-sulfonyl)-5-methylsulfanyl-thiophene-2-carboxamidine | $C_{18}H_{15}ClN_2O_2S_3$ | 423.9 | 423.2 |
| 70 | 3-pyridine boronic acid | 5-Methylsulfanyt-4-(3-pyridin-3-yl-benzenesulfonyl)-thiophene-2-carboxamidine | $C_{17}H_{15}N_3O_2S_3$ | 390.5 | 390.1 |
| 71 | Pyrimidine-5-boronic acid | 5-Methylsulfanyl-4-(3-pyrimidin-5-yl-benzenesulfonyl)-thiophene-2-carboxamidine | $C_{16}H_{14}N_4O_2S_3$ | 391.5 | 391.2 |
| 72 | Furan 3-boronic acid | 4-(3-Furan-3-yl-benzenesulfonyl)-5-methylsulfanyl-thiophene-2-carboxamidine | $C_{16}H_{14}N_2O_3S_3$ | 379.5 | 379.2 |
| 73 | 3-quinolone boronic acid | 5-Methylsulfanyl-4-(3-quinolin-3-yl-benzenesulfonyl)- | $C_{21}H_{17}N_3O_2S_3$ | 440.5 | 440.2 |

-continued

| Ex. No. | Reagent | Compound | Formula | Calcd. (M + H) | Found |
|---|---|---|---|---|---|
| 74 | 4-methoxycarbonyl phenyl boronic acid | thiophene-2-carboxamidine 3'-(5-Carbamimidoyl-2-methylsulfanyl-thiophene-3-sulfonyl)-biphenyl-4-carboxylic acid methyl ester | $C_{20}H_{18}N_2O_4S_3$ | 447.5 | 447.2 |
| 75 | 3,5-dimethyl phenyl boronic acid | 4-(3',5'-Dimethyl-biphenyl-3-sulfonyl)-5-methylsulfanyl-thiophene-2-carboxamidine | $C_{20}H_{20}N_2O_2S_3$ | 417.5 | 417.3 |
| 76 | 2-Furan-2-yl-4,4,5,5-tetramethyl-[1,3,2]dioxaborolane | 4-(3-Furan-2-yl-benzenesulfonyl)-5-methylsulfanyl-thiophene-2-carboxamidine | $C_{16}H_{14}N_2O_3S_3$ | 379.5 | 379.2 |
| 77 | 3-thiophene boronic acid | 5-Methylsulfonyl-4-(3-thiophen-3-yl-benzenesulfonyl)-thiophene-2-carboxamidine | $C_{16}H_{14}N_2O_2S_4$ | 395.5 | 395.2 |
| 78 | 3-nitro phenyl boronic acid | 5-Methylsulfanyl-4-(3'-nitro-biphenyl-3-sulfonyl)-thiophene-2-carboxamidine | $C_{18}H_{15}N_3O_4S_3$ | 434.5 | 434.2 |
| 79 | 4-hydroxy phenyl boronic acid | 4-(4'-Hydroxy-biphenyl-3-sulfonyl)-5-methylsulfanyl-thiophene-2-carboxamidine | $C_{18}H_{16}N_2O_3S_3$ | 405.5 | 405.2 |
| 80 | 4-formyl phenyl boronic acid | 4-(4'-Formyl-biphenyl-3-sulfonyl)-5-methylsulfanyl-thiophene-2-carboxamidine | $C_{19}H_{16}N_2O_3S_3$ | 417.5 | 417.3 |
| 81 | 4-flouro phenyl boronic acid | 4-(4'-Fluoro-biphenyl-3-sulfonyl)-5-methylsulfanyl-thiophene-2-carboxamidine | $C_{18}H_{15}FN_2O_2S_3$ | 407.5 | 407.3 |
| 82 | (2-Fluoro-biphenyl-4-yl)-dimethyl-boronic acid | 4-(2'-Fluoro-[1,1';4',1'']terphenyl-3''-sulfonyl)-5-methylsulfanyl-thiophene-2-carboxamidine | $C_{24}H_{19}FN_2O_2S_3$ | 483.6 | 483.0 |
| 83 | 4-hydroxymethyl-phenyl-boronic acid | 4-(4'-hydroxymethyl-biphenyl-3-sulfonyl)-5-methylsulfanyl-thiophene-2-carboxamidine | $C_{19}H_{18}N_2O_3S_3$ | 419.6 | 419.3 |
| 84 | 4-cyano-phenyl-boronic acid | 4-(4'-cyano-biphenyl-3-sulfonyl)-5-methylsulfanyl-thiophene-2-carboxamidine | $C_{19}H_{15}N_3O_2S_3$ | 414.5 | 414.2 |
| 85 | 4-acetyl-phenyl-boronic acid | 4-(4'-acetyl-biphenyl-3-sulfonyl)-5-methylsulfanyl-thiophene-2-carboxamidine | $C_{20}H_{18}N_2O_3S_3$ | 431.6 | 431.2 |
| 86 | 4-dimethylamino-phenyl-boronic acid | 4-(4'-dimethylamino-biphenyl-3-sulfonyl)-5-methylsulfanyl-thiophene-2-carboxamidine | $C_{20}H_{21}N_3O_2S_3$ | 432.6 | 432.2 |
| 87 | 2-vinyl-phenyl-boronic acid | 5-methylsulfanyl-4-(2'-vinyl-biphenyl-3-sulfonyl)-thiophene-2-carboxamidine | $C_{20}H_{18}N_2O_2S_3$ | 415.6 | 415.2 |
| 88 | 4-ethoxy-phenyl-boronic acid | 4-(4'-ethoxy-biphenyl-3-sulfonyl)-5-methylsulfanyl-thiophene-2-carboxamidine | $C_{20}H_{20}N_2O_3S_3$ | 433.6 | 433.2 |
| 89 | 3,5-dimethyl-isoxazole-4-boronic acid | 4-[3-(3,5-dimethyl-isoxazol-4-yl)-benzenesulfonyl]-5-methylsulfanyl-thiophene-2-carboxamidine | $C_{17}H_{17}N_3O_3S_3$ | 408.5 | 408.2 |
| 90 | 2-methyl-phenyl-boronic acid | 4-(2'-methyl-biphenyl-3-sulfonyl)-5-methylsulfanyl-thiophene-2-carboxamidine | $C_{19}H_{18}N_2O_2S_3$ | 403.6 | 403.3 |
| 91 | 1-naphthyl-boronic acid | 5-methylsulfanyl-4-(3-naphthalen-1-yl-benzenesulfonyl)-thiophene-2-carboxamidine | $C_{22}H_{18}N_2O_2S_3$ | 439.6 | 439.3 |
| 92 | 5-chloro-thiophene-2-boronic acid | 4-[3-(5-Chloro-thiophen-2-yl)-benzenesulfonyl]-5-methylsulfanyl-thiophene-2-carboxamidine | $C_{16}H_{13}ClN_2O_2S_4$ | 430.0 | 429.2, 431.1. |
| 93 | 2-formyl-phenyl-boronic acid | 4-(2'-formyl-biphenyl-3-sulfonyl)-5-methylsulfanyl-thiophene-2-carboxamidine | $C_{19}H_{16}N_2O_3S_3$ | 417.5 | 417.2 |
| 94 | 4-vinyl-phenyl-boronic acid | 5-methylsulfanyl-4-(4'-vinyl-biphenyl-3-sulfonyl)-thiophene-2-carboxamidine | $C_{20}H_{18}N_2O_2S_3$ | 415.6 | 415.2 |
| 95 | 3-ethoxy-phenyl-boronic acid | 4-(3'-ethoxy-biphenyl-3-sulfonyl)-5-methylsulfanyl-thiophene-2-carboxamidine | $C_{20}H_{20}N_2O_3S_3$ | 433.6 | 433.3 |
| 96 | 2,6-dimethyl-phenyl-boronic acid | 4-(2',6'-dimethyl-biphenyl-3-sulfonyl)-5-methylsulfanyl-thiophene-2-carboxamidine | $C_{20}H_{20}N_2O_2S_3$ | 417.6 | 417.2 |

-continued

| Ex. No. | Reagent | Compound | Formula | Calcd. (M + H) | Found |
|---|---|---|---|---|---|
| 97 | 3-methyl-phenyl-boronic acid | 4-(3'-methyl-biphenyl-3-sulfonyl)-5-methylsulfanyl-thiophene-2-carboxamidine | $C_{19}H_{18}N_2O_2S_3$ | 403.6 | 403.2 |
| 98 | 3-isopropyl-phenyl-boronic acid | 4-(3'-isopropyl-biphenyl-3-sulfonyl)-5-methylsulfanyl-thiophene-2-carboxamidine | $C_{21}H_{22}N_2O_2S_3$ | 431.6 | 431.3 |
| 99 | 2,3-dimethyl-phenyl-boronic acid | 4-(2',3'-dimethyl-biphenyl-3-sulfonyl)-5-methylsulfanyl-thiophene-2-carboxamidine | $C_{20}H_{20}N_2O_2S_3$ | 417.6 | 417.2 |
| 100 | 2,3-dichloro-phenyl-boronic acid | 4-(2',3'-dichloro-biphenyl-3-sulfonyl)-5-methylsulfanyl-thiophene-2-carboxamidine | $C_{18}H_{14}Cl_2N_2O_2S_3$ | 458.4 | 457.2, 459.2, 461.2. |
| 101 | 3-acetyl-phenyl-boronic acid | 4-(3'-acetyl-biphenyl-3-sulfonyl)-5-methylsulfanyl-thiophene-2-carboxamidine | $C_{20}H_{18}N_2O_3S_3$ | 431.6 | 431.2 |
| 102 | 3-ethoxycarbonyl-phenyl-boronic acid | 3'-(5-carbamimidoyl-2-methylsulfanyl-thiophene-3-sulfonyl)-biphenyl-3-carboxylic acid ethyl ester | $C_{21}H_{20}N_2O_4S_3$ | 461.6 | 461.2 |
| 103 | 3-N,N-dimethyl-acetamido-phenyl-boronic acid | 3'-(5-carbamimidoyl-2-methylsulfanyl-thiophene-3-sulfonyl)-biphenyl-3-carboxylic acid dimethylamide | $C_{21}H_{21}N_3O_3S_3$ | 460.6 | 460.3 |
| 104 | 3-carbamoyl-phenyl-boronic acid | 3'-(5-carbamimidoyl-2-methylsulfanyl-thiophene-3-sulfonyl)-biphenyl-3-carboxylic acid amide | $C_{19}H_{17}N_3O_3S_3$ | 432.6 | 432.3 |
| 105 | 3-acetamido-phenyl-N-boronic acid | [3'-(5-carbamimidoyl-2-methylsulfanyl-thiophene-3-sulfonyl)-biphenyl-3-yl]-acetamide | $C_{19}H_{17}N_3O_3S_3$ | 432.6 | 432.3 |
| 106 | 5-(4,4,5,5-Tetramethyl-[1,3,2]dioxaborolan-2-yl)-benzoimidazole-1-carboxylic acid tert-butyl ester | 4-[3-(1H-benzoimidazol-5-yl)-benzenesulfonyl]-5-methylsulfanyl-thiophene-2-carboxamidine | $C_{19}H_{16}N_4O_2S_3$ | 429.6 | 429.3 |
| 107 | 2-tert-butoxycarbonylamino-phenyl-boronic acid | 4-(2'-amino-biphenyl-3-sulfonyl)-5-methylsulfanyl-thiophene-2-carboxamidine | $C_{18}H_{17}N_3O_2S_3$ | 404.5 | 404.2 |

Examples 108–110

5-Methylsulfanyl-4-(3-methyl-7-o-tolyl-3H-benzoimidazole-5-sulfonyl)-thiophene-2-carboxamidine trifluoroacetate, 5-Methylsulfanyl-4-(2-methyl-7-o-tolyl-3H-benzoimidazole-5-sulfonyl)-thiophene-2-carboxamidine and 5-Methylsulfanyl-4-(7-o-tolyl-3H-benzoimidazole-5-sulfonyl)-thiophene-2-carboxamidine

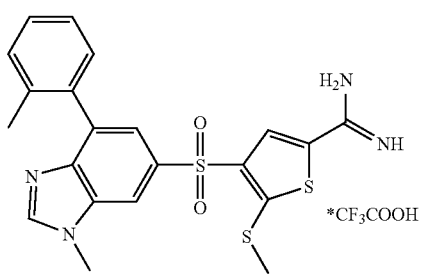

A

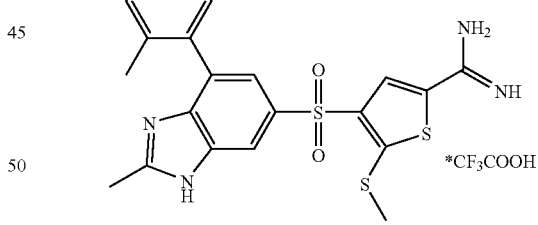

B

-continued

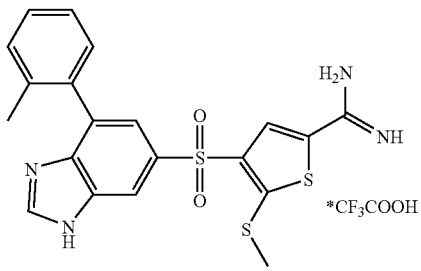

C a) 4-(7-Bromo-1,3-dihydro-spiro[benzoimidazole-2,1'-cyclohex]e-5-sulfonyl)-5-methylsulfanyl-thiophene-2-carboxylic acid methyl ester 4-(7-Bromo-spiro[benzoimidazole-2,1'-cyclohex]e-5-sulfonyl)-5-methylsulfanyl-thiophene-2-carboxylic acid methyl ester ((Example 38, step c) 300 mg, 0.58 mmol) in ethanol:water solution (1:1, 60 mL) was treated with sodium dithionite (203 mg, 1.16 mmol) as in Example 38, step d. A brown precipitate formed upon addition of sodium dithionite. This precipitate was filtered and dried under vacuum to give 163.6 mg of 4-(7-bromo-1,3-dihydro-spiro[benzoimidazole-2,1'-cyclohex]e-5-sulfonyl)-5-methylsulfanyl-thiophene-2-carboxylic acid methyl ester as a brown solid. This solid was used in the next step without further purification.

b) 5-Methylsulfanyl-4-(7-o-tolyl-1,3-dihydro-spiro[benzoimidazole-2,1'-cyclohex]e-5-sulfonyl)-thiophene-2-carboxylic acid methyl ester and 5-Methylsulfanyl-4-(7-o-tolyl-1,3-dihydro-spiro[benzoimidazole-2,1'-cyclohex]e-5-sulfonyl)-thiophene-2-carboxylic acid ethyl ester To a dried flask was added 4-(7-bromo-1,3-dihydro-spiro[benzoimidazole-2,1'-cyclohex]e-5-sulfonyl)-5-methylsulfanyl-thiophene-2-carboxylic acid methyl ester (129 mg, 0.249 mmol) from above step a, o-tolyl boronic acid (136 mg, 0.779 mmol), aqueous $Na_2CO_3$ (2M, 1 mL, 43 mmol), ethanol (1 mL), and toluene (2 mL). The flask was sparged with argon, and $Pd(PPh_3)_4$ (72 mg, 0.062 mmol) was added. The reaction mixture was stirred and heated at 80° for 18 hrs, and then cooled to room temperature. The solvents were removed in vacuo. The residue was dissolved in ethyl acetate (150 mL), washed with water (20 mL) and brine (20 mL), and then dried over $MgSO_4$. Ethyl acetate was removed in vacuo and the residue was purified via preparative TLC (20–30% ethyl acetates/hexanes) to afford a mixture of 5-methylsulfanyl-4-(7-o-tolyl-1,3-dihydro-spiro[benzoimidazole-2,1'-cyclohex]e-5-sulfonyl)-thiophene-2-carboxylic acid methyl ester and 5-methylsulfanyl-4-(7-o-tolyl-1,3-dihydro-spiro[benzoimidazole-2,1'-cyclohex]e-5-sulfonyl)-thiophene-2-carboxylic acid ethyl ester as a brown oil (130 mg). ESI-MS (m/z): Calcd. for $C_{26}H_{28}N_2O_4S_3$ and $C_{27}H_{30}N_2O_4S_3$: 529.12 (M+H); found 529.3 and 543.3.

c) 5-Methylsulfanyl-4-(7-o-tolyl-3H-benzoimidazole-5-sulfonyl)-thiophene-2-carboxylic acid methyl and ethyl esters A mixture of 5-methylsulfanyl-4-(7-o-tolyl-1,3-dihydro-spiro[benzoimidazole-2,1'-cyclohex]e-5-sulfonyl)-thiophene-2-carboxylic acid methyl and ethyl esters (130 mg) from above step b was treated with formic acid as in Example 38: step e followed by analogous work up to afford a crude mixture of 5-methylsulfanyl-4-(7-o-tolyl-3H-benzoimidazole-5-sulfonyl)-thiophene-2-carboxylic acid methyl and ethyl esters as a brown oil (100 mg). This mixture was used in the following step without further purification. MS (m/z): Calcd. for $C_{21}H_{18}N_2O_4S_3$: 459.04 (M+1); found 459.2 and 473.2.

d) 5-Methylsulfanyl-4-(3-methyl-7-o-tolyl-3H-benzoimidazole-5-sulfonyl)-thiophene-2-carboxamidine trifluoroacetate, 5-Methylsulfanyl-4-(2-methyl-7-o-tolyl-3H-benzoimidazole-5-sulfonyl)-thiophene-2-carboxamidine trifluoroacetate and 5-Methylsulfanyl-4-(7-o-tolyl-3H-benzoimidazole-5-sulfonyl)-thiophene-2-carboxamidine trifluoroacetate A mixture of 5-methylsulfanyl-4-(7-o-tolyl-3H-benzoimidazole-5-sulfonyl)-thiophene-2-carboxylic acid methyl and ethyl esters (100 mg, 0.22 mmol) from above step c was treated with methyl iodide (13.6 μL, 0.22 mmol) and $K_2CO_3$ (60.2 mg, 0.44 mmol) in dimethylformamide (2 mL) as in Example 39: step a, followed by analogous work up to afford 40 mg of a crude mixture. This mixture was treated with the dimethylaluminum amide reagent (5 mL, 5 mmol) as in Example 39: step b. After 1 hour, additional dimethylaluminum amide reagent (5 mL, 5 mmol) was added. After 1.5 hours, the reaction was quenched as in Example 39: step b followed by HPLC (C18-column, 10–70% $CH_3CN$ over 30 min) purification to afford 5-methylsulfanyl-4-(3-methyl-7-o-tolyl-3H-benzoimidazole-5-sulfonyl)-thiophene-2-carboxamidine trifluoroacetate (108), 5-methylsulfanyl-4-(2-methyl-7-o-tolyl-3H-benzoimidazole-5-sulfonyl)-thiophene-2-carboxamidine trifluoroacetate (109) and 5-methylsulfanyl-4-(7-o-tolyl-3H-benzoimidazole-5-sulfonyl)-thiophene-2-carboxamidine trifluoroacetate (110). 108: $^1$H-NMR (CD$_3$OD): δ 8.63 (s, 1H), 8.41 (m, 1H), 8.36 (m, 1H), 7.82 (m, 1H), 7.38–7.26 (m, 4H), 4.08 (s, 3H), 2.72 (s, 3H), 2.09 (s, 3H). 109: $^1$H-NMR (CD$_3$OD): δ 8.41 (m, 1H), 8.35 (s, 1H), 7.73 (m, 1H), 7.46–7.28 (m, 4H), 3.32 (s, 3H), 2.70 (s, 3H), 2.02 (s, 3H). 110: $^1$H-NMR (CD$_3$OD) C: δ 8.56 (s, 1H), 8.41 (m, 1H), 8.36 (m, 1H), 7.78 (m, 1H), 7.44–7.27 (m, 4H), 2.71 (s, 3H), 2.10 (s, 3H).

Example 111

4-(2-Methyl-furan-3-sulfonyl)-5-methylsulfanyl-thiophene-2-carboxamidine hydrochloride

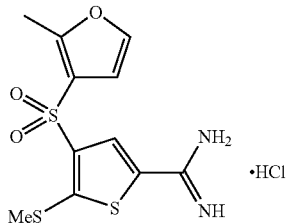

a) 4-(2-Methyl-furan-3-ylsulfanyl)-5-nitro-thiophene-2-carboxylic acid methyl ester 4-Bromo-5-nitro-thiophene-2-carboxylic acid methyl ester ((Example 114, step c) 532 mg, 2 mmol), 2-methyl-furan-3-thiol (600 mg, 5.26 mmol), and DMAP-polystyrene resin (2 g, 2.86 mmol) were stirred in THF (10 mL) for 12 h at rt. The resin was filtered and washed with several portions of DCM (100 mL total volume). The filtrate was concentrated in vacuo and the yellow residue (480 mg, 80%) was used without further purification. $^1$H-NMR (CDCl$_3$): δ 7.46 (d, 1H, J=1.9 Hz), 7.05 (s, 1H), 6.43 (d, 1H, J=1.9 Hz), 3.90 (s, 3H), 2.38 (s, 3H).

b) 4-(2-Methyl-furan-3-sulfonyl)-5-methylsulfanyl-thiophene-2-carboxylic acid methyl ester m-Chloroperbenzoic acid (276 mg, 4 mmol) and 4-(2-methyl-furan-3-ylsulfanyl)-5-nitro-thiophene-2-carboxylic acid methyl ester (117 mg, 0.39 mmol) were dissolved in DCM (15 mL) and stirred for 6 h at 40° C. DCM (50 mL) and aqueous sodium thiosulfate were added (exothermic), and the layers were separated. The organic layer was extracted with Na$_2$CO$_3$ (2M, 6×30 mL), brine (50 mL), and was dried over sodium sulfate. Concentration of the solvent in vacuo followed by SiO$_2$ flash chromatography (25–75% DCM in hexanes) yielded the sulfone compound (85 mg, 66%) which was redissolved THF (5 mL). The procedure in Example 12: step c was followed, using 275 μL (0.275 mmol) of sodium thiomethoxide. Analogous aqueous workup and purification by SiO$_2$ flash chromatography yielded the title compound (72 mg, 85%) as a colorless solid.

c) 4-(2-Methyl-furan-3-sulfonyl)-5-methylsulfanyl-thiophene-2-carboxamidine hydrochloride Following the procedure used in Example 12: step f, 4-(2-methyl-furan-3-sulfonyl)-5-methylsulfanyl-thiophene-2-carboxylic acid methyl ester (26 mg, 0.078 mmol) was converted to the amidine using 3 mL of dimethylaluminum amide reagent. The title compound was isolated as a white solid (16 mg, 58%) after preparative TLC purification (15% MeOH in DCM). $^1$H-NMR (CD$_3$OD): δ 8.26 (s, 1H), 7.49 (d, 1H, J=2.1 Hz), 6.69 (d, 1H, J=2.1 Hz), 2.74 (s, 3H), 2.63 (s, 3H). ESI-MS (m/z): Calcd. for C$_{11}$H$_{12}$N$_2$O$_3$S$_3$ (M+H): 317.4; found: 317.2.

Example 112

5-Methylsulfanyl-4-(4-phenyl-thiazole-2-sulfonyl)-thiophene-2-carboxamidine hydrochloride

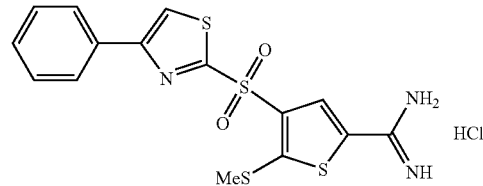

a) 5-Nitro-4-(4-phenyl-thiazole-2-sulfonyl)-thiophene-2-carboxylic acid methyl ester The procedure in Example 111: step a was followed, using 4-bromo-5-nitro-thiophene-2-carboxylic acid methyl ester ((Example 114, step c) 532 mg, 2 mmol), 4-phenyl-thiazole-2-thiol (483 mg, 2.5 mmol), and DMAP-polystyrene resin (2 g, 2.86 mmol) in THF (10 mL). Analogous workup yielded the crude sulfide which was treated with m-chloroperoxybenzoic acid (1.38 g, 8 mmol) in DCM (30 mL) as in Example 111: step b. Analogous workup and purification by SiO$_2$ flash chromatography (25–50% EtOAc in hexanes) yielded the title compound (245 mg, 30%) as a white solid. $^1$H-NMR (CDCl$_3$): δ 8.25 (s, 1H), 7.80 (m, 2H), 7.75 (s, 1H), 7.34–7.44 (m, 3H), 7.05 (s, 1H), 6.43 (d, 1H, J=1.9 Hz), 3.98 (s, 3H).

b) 5-Methylsulfanyl-4-(4-phenyl-thiazole-2-sulfonyl)-thiophene-2-carboxamidine hydrochloride Following the procedure in Example 12: step c, 5-nitro-4-(4-phenyl-thiazole-2-sulfonyl)-thiophene-2-carboxylic acid methyl ester (110 mg, 0.27 mmol) was reacted with sodium thiomethoxide (1M in EtOH, 325 μL, 0.325 mmol) in THF (5 mL). Analogous aqueous workup and purification by SiO$_2$ flash chromatography yielded the thiomethylated intermediate (82 mg, 75%) as a white solid. A portion of the solid (52 mg, 0.126 mmol) was treated with dimethylaluminum amide reagent (5 mL) as in Example 12: step f. Analogous workup and purification by preparative TLC (15% MeOH in DCM) resulted in the title compound (21 mg, 38%) as a white solid. $^1$H-NMR (CD$_3$OD): δ 8.38 (s, 1H), 8.31 (s, 1H), 7.90 (m, 2H), 7.36–7.46 (m, 3H), 2.76 (s, 3H). ESI-MS (m/z): Calcd. for C$_{15}$H$_{13}$N$_3$O$_2$S$_4$ (M+H): 396.6; found: 396.1.

Example 113

4-(6-Ethoxy-benzothiazole-2-sulfonyl)-5-methylsulfanyl-thiophene-2-carboxamidine hydrochloride

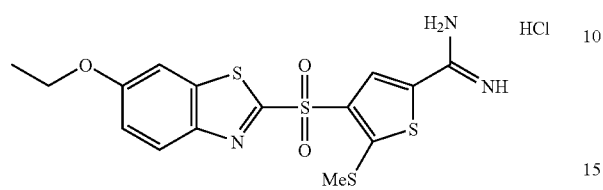

a) 4-(6-Ethoxy-benzothiazole-2-sulfonyl)-5-nitro-thiophene-2-carboxylic acid methyl ester The procedure in Example 111: step a was followed, using 4-bromo-5-nitro-thiophene-2-carboxylic acid methyl ester ((Example 114, step c) 266 mg, 1 mmol), 6-ethoxy-benzothiazole-2-thiol (264 mg, 1.25 mmol), and DMAP-polystyrene resin (0.75 g, 1.05 mmol) in THF (6 mL). Analogous workup yielded the crude sulfide, which was treated with m-chloroperoxybenzoic acid (692 mg, 4 mmol) in DCM (30 mL) as in Example 111: step b. Analogous workup and purification by $SiO_2$ flash chromatography (25–50% EtOAc in hexanes) yielded the title compound (250 mg, 58%) as a colorless glass. $^1$H-NMR (CDCl$_3$): δ 8.40 (s, 1H), 7.94 (d, 1H, J=9.1 Hz), 7.38 (d, 1H, J=2.6 Hz), 7.17 (dd, 1H, J=2.6, 9.1 Hz), 4.13 (q, 2H, J=7.0 Hz), 4.00 (s, 3H), 1.47 (t, 3H, J=7.0 Hz). ESI-MS (m/z): Calcd. for $C_{15}H_{12}N_2O_7S_3$ (M+H): 429.5; found: 429.1.

b) 4-(6-Ethoxy-benzothiazole-2-sulfonyl)-5-methylsulfanyl-thiophene-2-carboxamidine hydrochloride Following the procedure in Example 12: step c, 4-(6-ethoxy-benzothiazole-2-sulfonyl)-5-nitro-thiophene-2-carboxylic acid methyl ester (65 mg, 0.15 mmol) was reacted with sodium thiomethoxide (1M in EtOH, 175 μL 0.175 μmol) in THF (5 mL). Analogous aqueous workup and purification by $SiO_2$ flash chromatography yielded the thiomethyl intermediate (53 mg, 82%) as a colorless glass. A portion of the material (41 mg, 0.10 mmol) was treated with dimethylaluminum amide reagent (3 mL) as in Example 12: step f. Analogous workup and purification by preparative TLC (15% MeOH in DCM) yielded the title compound (18 mg, 42%) as a white solid. $^1$H-NMR (CD$_3$OD): δ 8.37 (s, 1H), 7.96 (d, 1H, J=9.1 Hz), 7.62 (d, 1H, J=2.6 Hz), 7.22 (dd, 1H, J=2.6, 9.1 Hz), 4.14 (q, 2H, J=7.0 Hz), 2.74 (s, 3H), 1.44 (t, 3H, J=7.0 Hz). ESI-MS (m/z): Calcd. for $C_{15}H_{15}N_3O_3S_4$ (M+H): 414.6; found: 414.1.

Example 114

4-(3-Methoxy-benzenesulfonyl)-5-methylsulfanyl-thiophene-2-carboxamidine hydrochloride HCl

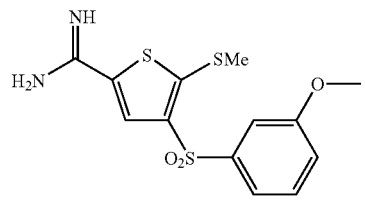

a) 4-Bromothiophene-2-carboxylic acid

To a flask equipped with a mechanical stirrer was added 25 g (130 mmol) 4-bromothiophene-2-carbaldehyde (Aldrich Chemical Company), acetonitrile (200 mL), and 4.5 g (37.5 mmol) of sodium dihydrogen phosphate dissolved in 35 mL of water. After cooling this mixture on an ice-salt bath, 15 mL (169 mmol) of 35% hydrogen peroxide and 15.3 g (169 mmol) of sodium chlorite were added, and the mixture was stirred for 1 h. The reaction mixture was then stirred at room temperature for 3 h. The solvent was removed in vacuo, and the solid was suspended in a mixture of water (175 mL) and 1 N hydrochloric acid (4 mL) and stirred for 10 min at rt. The solid was collected on a Büchner funnel and washed with water (2×150 mL) to afford 26 g (97%) of 4-bromothiophene-2-carboxylic acid, which was used in the next step without further purification.

b) 4-Bromothiophene-2-carboxylic acid Methyl Ester

To a dry flask under $N_2$ with a stirbar was added 6 g (29.1 mmol) of 4-bromothiophene-2-carboxylic acid (as prepared in the previous step) and dry methanol (100 mL). The solution was cooled in an ice-salt bath for 15 min and 2.55 mL (34.9 mmol) of thionyl chloride was added over 15 min, keeping the temperature <−5° C. The reaction mixture was stirred on the ice-salt bath for an additional 15 min, then for 1 h at rt, and finally refluxed for 8 h under $N_2$. The resulting solution was cooled and concentrated to 6.7 g of pale amber oil. This oil was passed through 150 g of silica with ~600 mL $CH_2Cl_2$ (discarded the first 120 mL which contained minor impurities and no ester). The solvent was removed in vacuo to afford 6.11 g (95% yield) of the title compound as a colorless solid, which was used in the next step without further purification.

c) 4-Bromo-5-nitrothiophene-2-carboxylic acid Methyl Ester

The nitrating mixture (HNO$_3$ d=1.42, 2 mL; concentrated H$_2$SO$_4$, 6 mL) was slowly added with stirring, at −5 to −10° C., to 4-Bromothiophene-2-carboxylic acid methyl ester (3 g, 13.57 mmol) dissolved in concentrated H$_2$SO$_4$ (10 mL). After being kept at −5 to −10° C. for 30 min. the mixture was poured over crushed ice. The solid precipitate was separated by filtration and washed with water and dried over P$_2$O$_5$ to give 3.7 g of 4-bromo-5-nitrothiophene-2-carboxylic acid methyl ester as a tan solid, which was used in the next step without further purification.

d) 4-(3-Methoxy-benzenesulfonyl)-5-methylsulfanyl-thiophene-2-carboxylic acid methyl ester To a cooled (ice bath) solution of 4-bromo-5-nitrothiophene-2-carboxylic acid methyl ester (0.5 g, 1.88 mmol) from above step c, in dimethylformamide (DMF) was added 3-methoxybenzenethiol (0.29 g, 2.1 mmol) and $Cs_2CO_3$ (0.67 g, 2.1 mmol). The resulting mixture was heated at 50° C. for 3 h. DMF was removed under vacuum and the residue was partitioned between EtOAc and 10% HCl. The EtOAc layer was washed with brine, dried over $Na_2SO_4$ and concentrated in vacuo to give an oil. This oil was purified by silica gel column chromatography (EtOAc:hexane) to give 0.56 g (91%) of 4-(3-Methoxy-phenylsulfanyl)-5-nitro-thiophene-2-carboxylic acid methyl ester. This ester was dissolved in $CH_2Cl_2$ (6 mL) and treated with m-chloroperoxybenzoic acid (MCPBA, 1.1 g) and heated at reflux for 6 h. The resulting mixture was diluted with $CH_2Cl_2$ (10 mL) and washed with sat. sodium thiosulfate, 1N NaOH and brine. The organic layer was dried over $Na_2SO_4$ and concentrated in vacuo. The residue was purified by silica gel column chromatography (EtOAc:hexane) to give an oil. This oil was dissolved in DMF (5 mL) and cooled in an ice bath. To this solution sodium thiomethoxide (126 mg, Aldrich Chemical Company) was added and the mixture was stirred for 5 h. The reaction was quenched with 10% HCl and the solvents were removed in vacuo. The residue was dissolved in EtOAc, washed with brine and dried over $Na_2SO_4$. The solvent was removed in vacuo and the residue was purified by preparative thin-layer chromatography to give 171 mg of 4-(3-methoxy-benzenesulfonyl)-5-methylsulfanyl-thiophene-2-carboxylic acid methyl ester, which was directly used in the next step.

e) 4-(3-Methoxy-benzenesulfonyl)-5-methylsulfanyl-thiophene-2-carboxamidine 4-(3-methoxy-benzenesulfonyl)-5-methylsulfanyl-thiophene-2-carboxylic acid methyl ester from above step d (171 mg, 0.48 mmol) was treated with dimethylaluminum amide reagent (2 mL) as in Example 12: step f. Analogous workup and purification by preparative TLC (15% MeOH in DCM) gave the title compound (50 mg, 30%) as a white solid. $^1$H-NMR (DMSO-$d_6$): δ 9.24 (broad s, 4H), 8.43 (s, 1H), 7.64–7.51 (m, 2H), 7.44 (s, 1H), 7.31 (d, 1H, J=9.3 Hz), 3.83 (s, 3H), 2.70 (s, 3H). ESI-MS (m/z): Calcd. for $C_{13}H_{14}N_2O_3S_3$ (M+H): 343.0; found: 343.2.

Example 115

4-(6-Methyl-biphenyl-3-sulfonyl)-5-methylsulfanyl-thiophene-2-carboxamidine trifluoroacetate

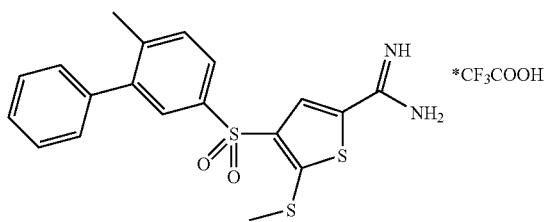

a) 6-Methyl-biphenyl-3-ylamine

To a dried flask was added 3-bromo-4-methyl-phenylamine (1 g, 5.37 mmol), phenyl boronic acid (2.62 g, 21.5 mmol), aqueous $Na_2CO_3$ (2M, 21.5 mL, 43 mmol), ethanol (21.5 mL), and toluene (43 mL). The flask was sparged with Ar, and $Pd(PPh_3)_4$ (1.55 g, 1.34 mmol) was added. The reaction mixture was stirred and heated at 80° for 18 hrs, then cooled to room temperature. The solvent was removed in vacuo and the residue was dissolved in ethyl acetate. The organic layer was washed with water and brine, then dried over $MgSO_4$. The solvent was removed in vacuo and the residue was purified via column chromatography ($SiO_2$, 5% DCM/hexane) to afford a yellow oil (463 mg, 47%). This was directly used in the next step.

b) 6-Methyl-biphenyl-3-thiol

To a cooled solution of 6-methyl-biphenyl-3-ylamine (463 mg, 2.53 mmol) from above step a, in hydrochloride solution (0.42 mL conc. HCl in 0.5 mL $H_2O$, 5 mmol) was added dropwise a solution of $NaNO_2$ (Aldrich, 0.18 g in 0.3 mL $H_2O$, 2.6 mmol) at −2° C. The resulting diazonium ion solution was stirred for 20 min and added to a solution of $KS_2COEt$ in $H_2O$ (0.61 g in 0.8 mL of $H_2O$, 3.81 mmol) with stirring. The resultant mixture was heated to 80° C. for a few minutes, then cooled to room temperature and extracted with diethyl ether. Ether was removed in vacuo and the residue was treated with a potassium hydroxide solution (0.5 g in 1.5 mL in ethanol, 8.91 mmol, 3.56 eq) and heated at reflux for 8 h. The reaction mixture was cooled to room temperature, diluted with $H_2O$, and acidified with HCl to pH~3. This solution was extracted with $Et_2O$ and the organic layer was washed with $H_2O$ and brine, then dried over $MgSO_4$. The solvent was removed in vacuo to afford a yellow oil (510 mg, 100%). This was directly used in the next step.

c) 4-(6-Methyl-biphenyl-3-ylsulfanyl)-5-nitro-thiophene-2-carboxylic acid methyl ester To a solution of triphenylphosphine (0.67 g, 2.55 mmol), 4-bromo-5-nitro-thiophene-2-carboxylic acid methyl ester ((Example 114, step c) 1 g, 3.76 mmol) and 4-(dimethyl)aminopyridine resin (1 eq) in THF was added 6-methyl-biphenyl-3-thiol from above step b. This mixture was stirred for 3 hrs. The reaction mixture was filtered and the solvents were removed in vacuo. The residue was purified via column chromatography ($SiO_2$, 15% ethyl acetate/hexane) to afford a yellow glass (600 mg, 61%), which was used in the following step.

d) 4-(6-Methyl-biphenyl-3-sulfonyl)-5-nitro-thiophene-2-carboxylic acid methyl ester To a solution of 4-(6-Methyl-biphenyl-3-ylsulfanyl)-5-nitro-thiophene-2-carboxylic acid methyl ester (0.6 g, 1.56 mmol, 1 eq) from above step c, in DCM was added 3-chloroperoxybenzoic acid (1.04 g, 3.42 mmol, 2.2 eq). The reaction mixture was heated to reflux for 2 hrs, then cooled to room temperature. The reaction mixture was quenched with saturated $Na_2S_2O_3$ solution, then washed with saturated $Na_2CO_3$ solution, water, brine, and was dried over $MgSO_4$. The solvent was removed in vacuo to afford a yellow solid (170 mg, 26%), which was taken on to the next step.

e) 4-(6-Methyl-biphenyl-3-sulfonyl)-5-methylsulfanyl-thiophene-2-carboxylic acid methyl ester To a solution of 4-(6-methyl-biphenyl-3-sulfonyl)-5-nitro-thiophene-2-carboxylic acid methyl ester (170 mg, 0.41 mmol) from above step d, in anhydrous THF at −78° C. was added dropwise a 1M solution of NaSMe in ethanol (0.4 mL, 0.41 mmol). The reaction mixture was stirred for 2 hrs. at −78° C., quenched with acetic acid (23 μl, 0.41 mmol), and warmed to room temperature. The reaction mixture was diluted with ethyl acetate, washed with saturated NaHCO$_3$ solution (2×), water, and brine. The organic layer was dried over MgSO$_4$ and removed in vacuo. The residue was purified via column chromatography (SiO$_2$, 15% DCM/hexane) to afford a yellow glass (130 mg, 76%).

f) 4-(6-Methyl-biphenyl-3-sulfonyl)-5-methylsulfanyl-thiophene-2-carboxamidine trifluoroacetate In a dried flask was suspended NH$_4$Cl (Aldrich, 1.08 g, 20 mmol) in anhydrous toluene (10 mL) under argon. To this suspension was added 2M solution of AlMe$_3$ in toluene (10 mL, 20 mmol). This mixture was heated to 100° C. for a few minutes. This dimethylaluminum amide reagent (5 mL, 5 mmol) was added to 4-(6-methyl-biphenyl-3-sulfonyl)-5-methylsulfanyl-thiophene-2-carboxylic acid methyl ester (130 mg, 0.31 mmol) from above step e, under Ar. This reaction mixture was heated to reflux for 1.5 h then cooled to room temperature. The reaction mixture was quenched by pouring it into a slurry of silica gel in CHCl$_3$. The slurry was stirred for 30 minutes, and then filtered with 10% MeOH/DCM and MeOH. The solvents were removed in vacuo and the residue was dissolved in 10% MeOH/DCM, and filtered through a syringe filter. The solvent was removed in vacuo and the residue was purified via preparatory HPLC to afford a beige solid (5 mg, 4%). $^1$H-NMR (DMSO-d$_6$): δ 9.39 (bs, 1H), 8.96 (bs, 2H), 8.41 (s, 1H), 7.88 (dd, 1H), 7.74 (m, 1H), 7.61 (m, 1H), 7.52–7.35 (m, 5H). Calcd. for C$_{19}$H$_{18}$N$_2$O$_2$S$_3$: 402.05; found: 403.2.

Example 116

5-Metylsulfanyl-4-(3-phenoxy-benzenesulfonyl)-thiophene-2-carboxamidine hydrochloride salt

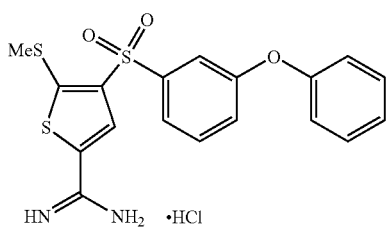

a) 3-Phenoxy-benzenethiol

To a cooled solution of 3-phenoxyaniline (2 g, 0.01 mol) in hydrochloride solution (1.69 mL conc. HCl in 2 mL H$_2$O, 0.02 mol) was added dropwise a solution of NaNO$_2$ (Aldrich, 0. 8 g in 2 mL H$_2$O, 0.01 mol) at 0–2° C. The resulting diazonium ion solution was stirred for 20 min and then added to a solution of KS$_2$COEt in H$_2$O (2.6 g in 4 mL of H$_2$O, 0.02 mol) with stirring. This mixture was heated to 80° C. for a 20 minutes, then cooled to room temperature, and extracted with diethyl ether. The ether layer was washed with water, brine and dried over Na$_2$SO$_4$. Ether was removed in vacuo and the residue was taken in ethanol and treated with a sodium hydroxide solution (12 N, 0.04 mol, 3.56 eq) and heated at reflux for 8 h. The reaction mixture was cooled to room temperature, diluted with H$_2$O, and acidified with H$_2$SO$_4$ to pH~3. This solution was extracted with Et$_2$O and the organic layer was washed with H$_2$O and brine, and then dried over MgSO$_4$. The solvent was removed in vacuo to afford a yellow oil which was purified by silica gel column chromatography to give a mixture of 3-Phenoxy-benzenethiol and the corresponding disulfide (1.2 g). This was directly used in the next step.

b) 5-Nitro-4-(3-phenoxy-phenylsulfanyl)-thiophene-2-carboxylic acid methyl ester The mixture from above step a (171 mg, 0.48 mmol) was treated with triphenylphosphine (1.98 g, 7.52 mmol), 4-bromo-5-nitro-thiophene-2-carboxylic acid methyl ester ((Example 114, step c) 0.5 g, 1.88 mmol) and 4-(dimethyl) aminopyridine resin (1 eq) in THF (25 mL). This mixture was stirred for 18 h. The reaction mixture was filtered and the solvents were removed in vacuo. The residue was purified via silica gel column chromatography to afford a yellow glass (420 mg), which was used in the following step.

c) 5-Nitro-4-(3-phenoxy-benzenesulfonyl)-thiophene-2-carboxylic acid methyl ester To a solution of 5-nitro-4-(3-phenoxy-phenylsulfanyl)-thiophene-2-carboxylic acid methyl ester (420 mg, 1.1 mmol) from above step b, in DCM was added 3-chloroperoxybenzoic acid (1.31 g, 4.34 mmol, 4 eq). The reaction mixture was heated to reflux for 18 h, then cooled to room temperature. The reaction mixture was quenched with saturated Na$_2$S$_2$O$_3$ solution, then washed with 1N NaOH solution, brine, and dried over MgSO$_4$. The solvent was removed in vacuo and the residue was taken on to the next step.

d) 5-Methylsulfanyl-4-(3-phenoxy-benzenesulfonyl)-thiophene-2-carboxylic acid methyl ester To a solution of 5-Nitro-4-(3-phenoxy-benzenesulfonyl)-thiophene-2-carboxylic acid methyl ester from above step c, in anhydrous THF at −78° C. was added dropwise a 1M solution of NaSMe in ethanol (1.06 mL, 1.08 mmol). The reaction mixture was stirred for 5 h at −78° C., quenched with acetic acid (61 μL, 1.08 mmol), and warmed to room temperature. The reaction mixture was diluted with ethyl acetate, washed with 10% HCl, saturated NaHCO$_3$ solution (2×), water, and brine. The organic layer was dried over Na$_2$SO$_4$ and removed in vacuo. The residue was purified via silica gel column chromatography to afford 250 mg (55%) of 5-methylsulfanyl-4-(3-phenoxy-benzenesulfonyl)-thiophene-2-carboxylic acid methyl ester.

e) 5-Methylsulfanyl-4-(3-phenoxy-benzenesulfonyl)-thiophene-2-carboxamidine hydrochloride salt 5-Methylsulfanyl-4-(3-phenoxy-benzenesulfonyl)-thiophene-2-carboxylic acid methyl ester from above step d (200 mg, 0.48 mmol) was treated with dimethylaluminum amide reagent (2 mL) as in Example 12: step f. Analogous workup and purification by preparative TLC (10% MeOH in DCM) gave the title compound (120 mg, 62%) as a white solid: ¹H-NMR (DMSO-d₆): δ 9.46 (bs, 2H), 9.20 (bs, 2H), 8.43 (s, 1H), 7.71–7.63 (m, 2H), 7.49–7.43 (m, 3H), 7.35 (d, 1H, J=7.9 Hz), 7.24 (t, 1H, J=7.2 and 7.4 Hz), 7.1 (d, 2H, J=7.7 Hz), 2.68 (s, 3H). Calcd. for $C_{18}H_{16}N_2O_3S_3$: 405.03 (M+H); found: 405.2.

Example 117

4-(Biphenyl-3-sulfonyl)-5-methylsulfanyl-thiophene-2-carboxamidine trifluoroacetate

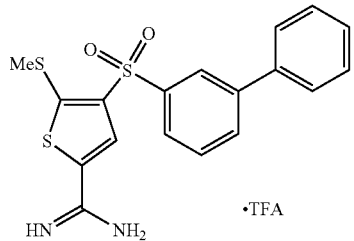

To a dry 2-dram vial, fitted with a stir bar and a Teflon®-lined screw cap was added {[4-(3-bromo-benzenesulfonyl)-5-methylsulfanyl-thiophen-2-yl]-imino-methyl}-carbamic acid tert-butyl ester (100 mg, 0.2 mmol, as prepared in Example 27, step c), phenylboronic acid (0.3 mmol), and tetrakis(triphenylphosine)palladium(0) (0.025 mmol). Each vial was twice treated with an argon purge/evacuation cycle and then charged with a mixture of toluene/EtOH (2:1, 2.4 mL) and 2 M $Na_2CO_3$ (0.8 mL) via a syringe. The vials were placed in an oil bath at 80° C. and stirred overnight. To the cooled reaction mixtures was added EtOAc (4 mL), the organic layer was filtered (1-g silica SPE column), and the filtrate was evaporated in vacuo. The resulting residue was purified using preparative TLC ($SiO_2$) to afford the Boc-protected amidine product. After treatment of this material with trifluoroacetic acid (50% in DCM) for 1 hr at rt, the solvents were removed in vacuo and the residue was purified using $C_{18}$-HPLC (20% to 100% $CH_3CN$ in $H_2O$ (0.1% TFA) over 15 min) to afford 10 mg (13%) 4-(biphenyl-3-sulfonyl)-5-methylsulfanyl-thiophene-2-carboxamidine trifluoroacetate: ¹H-NMR (DMSO-d₆): δ 8.32 (s, 1H), 8.25 (m, 2H), 8.02–7.95 (m, 2H), 7.72–7.63 (m, 3H), 7.52–7.47 (m, 2H), 7.44–7.39 (m, 1H), 2.72 (s, 3H). Calcd. for $C_{18}H_{16}N_2O_2S_3$: 389.04 (M+H); found: 389.2.

Example 118

4-(5-Bromo-6-chloro-pyridine-3-sulfonyl)-5-methylsulfanyl-thiophene-2-carboxamidine

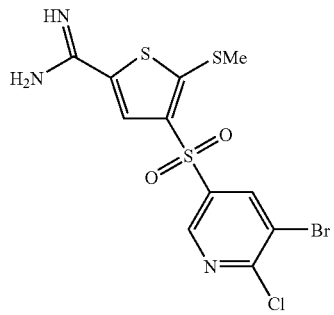

a) 5-Bromo-6-chloro-pyridine-3-sulphenic acid

5-Bromo-6-chloro-pyridine-3-sulfonyl chloride (2.5 g, 8.6 mmol), sodium sulfite (2.0 g, 16.1 mmol), and sodium bicarbonate (1.4 g, 16.9 mmol) were dissolved into water (8 mL) and EtOH (3 mL). The reaction mixture was allowed to stir at RT for 12 hours. TLC analysis showed loss of SM and formation of a very polar new spot. Reaction mixture was concentrated in vacuo resulting in a white solid and was used without further purification. ESI-MS (m/z): Calcd. for $C_5H_3BrClNO_2S$: 255.8 (M+H); found: 256.0. ¹H-NMR ($CD_3OD$): δ 8.55 (m, 1H), 8.29 (m, 1H).

b) 4-(5-Bromo-6-chloro-pyridine-3-sulfonyl)-5-nitro-thiophene-2-carboxylic acid methyl ester 4-Bromo-5-nitro-thiophene-2-carboxylic acid methyl ester (5.0 g, 19.9 mmol) was dissolved into DMF (20 mL) and cooled to 0° C. To this was added a solution of 5-bromo-6-chloro-pyridine-3-sulphenic acid (Example 118, step a) (1.8 g, 6.6 mmol) in DMF (20 mL) dropwise for 2 hours. The reaction was then warmed to RT and allowed to continue to stir for an additional 2 hours. The reaction was concentrated in vacuo and purified by $SiO_2$ flash column chromatography (Biotage—40 M, 25% EtOAc in hexanes). The product was isolated as a white solid (2.5 g, 48%). ESI-MS (m/z): Calcd. for $C_{11}H_6BrClN_2O_6S_2$: 440.8 (M+H); found: 441.0.

c) 4-(5-Bromo-6-chloro-pyridine-3-sulfonyl)-5-methylsulfanyl-thiophene-2-carboxylic acid methyl ester The procedure as in Example 27, a was followed using 4-(5-bromo-6-chloro-pyridine-3-sulfonyl)-5-nitro-thiophene-2-carboxylic acid methyl ester (3.5 g, 8.10 mmol, Example 118, step b) and sodium thiomethoxide (560 mg, 8.10 mmol as 1M solution in EtOH). The reaction was allowed to stir for 2.5 hours and was quenched with acetic acid. The resulting mixture was dissolved into EtOAc, and aqueous work up with brine and saturated $NaHCO_3$ resulted in isolation of a mixture. This mixture was purified by $SiO_2$ flash column chromatography (Biotage—40 M, 100% hexanes to 25% EtOAc in hexanes). The product was isolated as a yellow solid (750 mg, 21%). ESI-MS (m/z): Calcd. for $C_{12}H_{10}BrClNO_4S_3$: 441.8 (M+H); found: 442.1. ¹H-NMR ($CD_3OD+CDCl_3$): δ 8.93 (m, 1H), 8.50 (m, 1H), 8.06 (s, 1H), 3.91 (m, 3H), 2.67 (m, 3H).

d) 4-(5-Bromo-6-chloro-pyridine-3-sulfonyl)-5-methylsulfanyl-thiophene-2-carboxamidine The procedure as in Example 20, f was followed using 4-(5-bromo-6-chloro-pyridine-3-sulfonyl)-5-methylsulfanyl-thiophene-2-carboxylic acid methyl ester (14 mg, 0.03 mmol, Example 118 step c) dimethylaluminum amide (1M, 5 mL). The reaction was stirred for 3 hours at 90° C. and TLC analysis indicated that the reaction was complete. The reaction was quenched with $SiO_2$ and filtered. The resulting filtrate was concentrated in vacuo followed by purification by $C_{18}$-HPLC (10–70% $CH_3CN$ over 30 minutes). The title compound was isolated as a white solid (6.4 mg, 46%). ESI-MS (m/z): Calcd. for $C_{11}H_9BrClN_3O_2S_3$: 425.9 (M+H); found: 426.1. ¹H-NMR ($CD_3OD$): δ 8.96 (s, 1H), 8.65 (s, 1H), 8.33 (s, 1H), 2.76 (s, 3H).

Example 119

4-(6-Amino-5-bromo-pyridine-3-sulfonyl)-5-methyl-sulfanyl-thiophene-2-carboxamidine

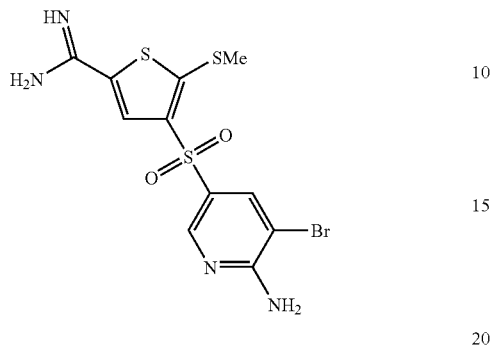

a) 4-(6-Amino-5-bromo-pyridine-3-sulfonyl)-5-methylsulfanyl-thiophene-2-carboxylic acid amide An ammonia bomb was used to prepare the title compound. Ammonia gas (5 mL) was condensed into the Teflon® core of a metal bomb with a stir bar and 4-(5-bromo-6-chloro-pyridine-3-sulfonyl)-5-methylsulfanyl-thiophene-2-carboxylic acid methyl ester (321 mg, 0.73 mmol, Example 118, step c). The Teflon® core was kept at −78° C. during the addition of reagents. Following the addition of reagents, the bomb was assembled and then sealed tight by hand and then tightened by wrench action. The sealed bomb was checked for leaks by use of pH paper. The bomb was then added to an oil bath and heated to 80° C. overnight with a shield in place. The following day the bomb was allowed to cool to rt and then was cooled further to −78° C. in an dry ice/acetone bath. The cooled vessel was then opened and remaining ammonia was allowed to evaporate. The resulting red solid obtained was used without further purification (306 mg, 95%). ESI-MS (m/z): Calcd. for $C_{11}H_{10}BrN_3O_3S_3$: 407.9 (M+H); found: 408.1. $^1$H-NMR (CD$_3$OD): δ 8.56 (m, 1H), 8.18 (m, 1H), 8.07 (s, 1H), 2.72 (s, 3H).

b) 4-(6-Amino-5-bromo-pyridine-3-sulfonyl)-5-methylsulfanyl-thiophene-2-carboxamidine The procedure as in Example 20, f was followed using 4-(6-amino-5-bromo-pyridine-3-sulfonyl)-5-methylsulfanyl-thiophene-2-carboxylic acid amide (14 mg, 0.03 mmol, Example 119, step a) dimethylaluminuim amide (1M, 5 mL). The reaction was stirred for 3 hours at 90° C. and TLC analysis indicated that the reaction was complete. The reaction was quenched with SiO$_2$ and filtered. The resulting filtrate was concentrated in vacuo followed by purification by C$_{18}$-HPLC (10–70% CH$_3$CN over 30 minutes). The title compound was isolated as a white solid (4.9 mg, 39%). ESI-MS (m/z): Calcd. for $C_{11}H_{11}BrN_4O_2S_3$: 406.9 (M+H); found: 407.1. $^1$H-NMR (CD$_3$OD): δ 8.54 (m, 1H), 8.26 (m, 1H), 8.15 (m, 1H), 2.74 (s, 3H).

Example 120

4-(5-Bromo-pyridine-3-sulfonyl)-5-methylsulfanyl-thiophene-2-carboxamidine

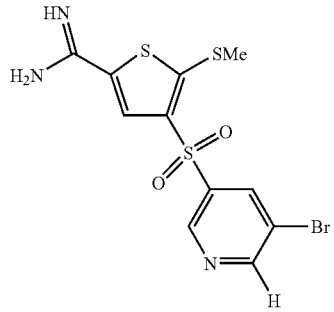

a) 4-(5-Bromo-pyridine-3-sulfonyl)-5-methylsulfanyl-thiophene-2-carboxylic acid methyl ester A flask with 4-(5-bromo-6-chloro-pyridine-3-sulfonyl)-5-methylsulfanyl-thiophene-2-carboxylic acid methyl ester (25 mg, 0.06 mmol, Example 118, step c) and zinc dust (4 mg, 0.06 mmol) was dissolved with 1 mL acetic acid and heated to 50° C. for 4 hours. TLC analysis indicated the formation of a new spot. The reaction mixture was concentrated in vacuo and purified by elution through Celite® using 10% MeOH in DCM. The crude product was carried on without further purification. ESI-MS (m/z): Calcd. for $C_{12}H_{10}BrNO_4S_3$: 407.9 (M+H); found: 408.1.

b) 4-(5-Bromo-pyridine-3-sulfonyl)-5-methylsulfanyl-thiophene-2-carboxamidine The procedure as in Example 20, f was followed using 4-(5-bromo-pyridine-3-sulfonyl)-5-methylsulfanyl-thiophene-2-carboxylic acid methyl ester (5 mg, 0.01 mmol, Example 120, step a) dimethylaluminuim amide (1M, 5 mL). The reaction was stirred for 3 hours at 90° C. and TLC analysis indicated that the reaction was complete. The reaction was quenched with $SiO_2$ and filtered. The resulting filtrate was concentrated in vacuo followed by purification by $C_{18}$-HPLC (10–70% $CH_3CN$ over 30 minutes). The title compound was isolated as a white solid (4.6 mg, 92%). ESI-MS (m/z): Calcd. for $C_{11}H_{10}BrN_3O_2S_3$: 391.9 (M+H); found: 392.1. $^1$H-NMR (CD$_3$OD): δ 9.14 (m, 1H), 8.97 (m, 1H), 8.55 (m, 1H), 8.34 (s, 1H), 2.76 (m, 3H).

Example 121

4-(6-Amino-5-o-tolyl-pyridine-3-sulfonyl)-5-methylsulfanyl-thiophene-2-carboxamidine

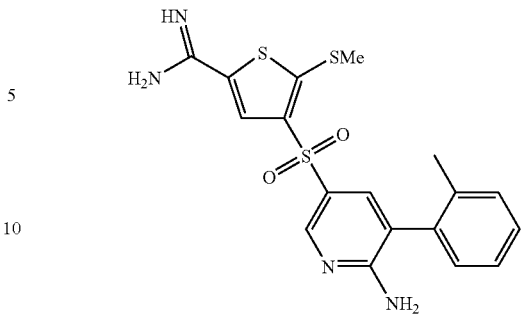

a) 4-(6-Amino-5-o-tolyl-pyridine-3-sulfonyl)-5-methylsulfanyl-thiophene-2-carboxylic acid amide The procedure as in Example 1: step c was followed using 4-(6-amino-5-bromo-pyridine-3-sulfonyl)-5-methylsulfanyl-thiophene-2-carboxylic acid amide (25 mg, 0.06 mmol, Example 120: step a), o-tolyl phenyl boronic acid (33 mg, 0.25 mmol), Pd(PPh$_3$)$_4$ (14 mg, 0.01 mmol), aqueous Na$_2$CO$_3$ (2M, 0.4 mL), ethanol (0.4 mL) and toluene (0.8 mL). Purification by preparative $SiO_2$ chromatography (25% EtOAc in hexanes) of the residue yielded the title compound (7.4 mg, 32%) as a brown solid. ESI-MS (m/z): Calcd. for $C_{18}H_{17}N_3O_3S_3$: 420.0 (M+H); found: 420.2.

b) 4-(6-Amino-5-o-tolyl-pyridine-3-sulfonyl)-5-methylsulfanyl-thiophene-2-carboxamidine The procedure as in Example 20, f was followed using 4-(6-amino-5-o-tolyl-pyridine-3-sulfonyl)-5-methylsulfanyl-thiophene-2-carboxylic acid amide (7.4 mg, 0.02 mmol, Example 121, step a) dimethylaluminuim amide (1M, 5 mL). The reaction was stirred for 3 hours at 90° C. and TLC analysis indicated that the reaction was complete. The reaction was quenched with $SiO_2$ and filtered. The resulting filtrate was concentrated in vacuo followed by purification by $C_{18}$-HPLC (10–70% $CH_3CN$ over 30 minutes). The title compound was isolated as a white solid (2.6 mg, 35%). ESI-MS (m/z): Calcd. for $C_{18}H_{18}N_4O_2S_3$: 419.0 (M+H); found: 419.1. $^1$H-NMR (CD$_3$OD): δ 8.6 (m, 1H), 8.28 (s, 1H), 7.74 (m, 1H), 7.36 (m, 3H), 7.16 (m, 1H), 2.74 (m, 3H), 2.13 (m, 3H).

Example 122

4-(6'-Methyl-2'-morpholin-4-yl-biphenyl-3-sulfonyl)-5-methylsulfanyl-thiophene-2-carboxamidine trifluoroacetate

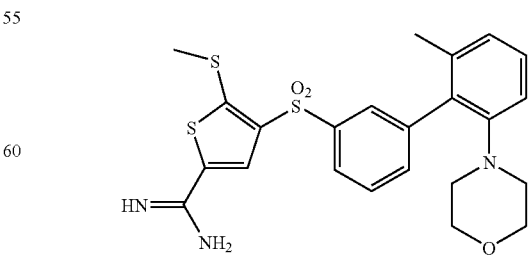

a) {Imino-[4-(6'-methyl-2'-morpholin-4-yl-biphenyl-3-sulfonyl)-5-methylsulfanyl-thiophen-2-yl]-methyl}-carbamic acid tert-butyl ester {[4-(2'-Amino-6'-methyl-biphenyl-3-sulfonyl)-5-methylsulfanyl-thiophen-2-yl]-imino-methyl}-carbamic acid tert-butyl ester (20 mg, 0.04 mmol, Example 25: step c). $K_2CO_3$ (8 mg, 0.06 mmol), 2,6-lutidine (8 mg, 0.08 mmol) and 2-bromoethyl ether (18 mg, 0.08 mmol) were dissolved in acetonitrile (1 mL) and heated to 80° C. with stirring under argon. After 6 hours, $Et_3N$ (8 μL, 0.06 mmol) was added and the reaction continued stirring for 20 hours. Purification of the residue by preparative $SiO_2$ TLC (50% EtOAc in hexanes) yielded the title compound (7.5 mg, 32%) as a yellow solid. ESI-MS (m/z): Calcd. for $C_{28}H_{33}N_3O_5S_3$: 588.2 (M+1); found: 588.0.

b) 4-(6'-Methyl-2'-morpholin-4-yl-biphenyl-3-sulfonyl)-5-methylsulfanyl-thiophene-2-carboxamidine trifluoroacetate {Imino-[4-(6'-methyl-2'-morpholin-4-yl-biphenyl-3-sulfonyl)-5-methylsulfanyl-thiophen-2-yl]-methyl}-carbamic acid tert-butyl ester (7.5 mg, 0.013 mmol, Example 122: step a) was deprotected and purified as in Example 1: step d, yielding the title compound as a clear glass (2.2 mg, 35%). $^1$H-NMR (CD$_3$OD): δ 8.34(s, 1H), 8.02–8.05 (m, 1H), 7.94–7.92 (t, 1H, J=1.6 Hz), 7.66–7.70 (t, 1H, J=7.2 Hz), 7.61–7.64 (m, 1H, J=7.9 Hz), 7.23–7.28 (t, 1H, J=7.67 Hz), 6.98–7.05 (m, 2H), 3.13–3.27 (m, 4H), 2.71 (s, 3H), 2.63–2.67 (m, 4H), 2.05 (s, 3H). ESI-MS (m/z): Calcd. for $C_{23}H_{25}N_3O_3S_3$: 488.1 (M+1); found: 488.3.

Example 123

4-(6-Bromo-5-chloro-pyridine-3-sulfonyl)-5-methylsulfanyl-thiophene-2-carboxamidine trifluoroacetate

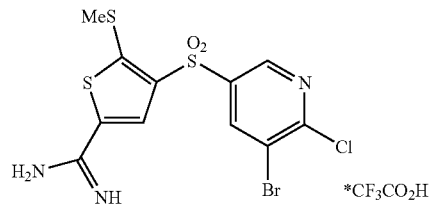

a) 6-Bromo-5-chloro-pyridine-3-sodium sulphonate

Sodium sulfite (794 mg, 6.3 mmol) and sodium bicarbonate (554 mg, 6.6 mmol) were dissolved into water (4 mL) with heat (70° C.). 6-Bromo-5-chloro-pyridine-3-sulfonyl chloride (1000 mg, 3.4 mmol) was added slowly as a solid over one hour. The reaction was heated at 70° C. for two additional hours followed by standing at RT overnight. The solvents were removed in vacuo resulting in the title compound that was used without further purification or characterization.

b) 4-(6-Bromo-5-chloro-pyridine-3-sulfonyl)-5-nitro-thiophene-2-carboxylic acid methyl ester 4-Bromo-5-nitro-thiophene-2-carboxylic acid methyl ester (2.6 g, 10.2 mmol, Example 27: step c) was dissolved into DMF (15 mL) and 6-Bromo-5-chloro-pyridine-3-sodium sulphonate (946 mg, 3.4 mmol, Example 123: step a) was partially dissolved into DMF (15 mL). The solution of 4-Bromo-5-nitro-thiophene-2-carboxylic acid methyl ester was cooled to −20° C. and to this was added the solution of 6-Bromo-5-chloro-pyridine-3-sodium sulphonate, dropwise over one hour. The reaction mixture was maintained at −20° C. with stirring for 3 hours. The solvents were removed in vacuo followed by purification by flash column chromatography (Biotage Flash System—40 M $SiO_2$ column) (30% EtOAc in hexanes) that yielded the title compound (430 mg, 29%) as a white solid. ESI-MS (m/z): Calcd. for $C_{11}H_6BrClN_2O_2S_2$: 440.9 (M+1); found: 441.1.

c) 4-(6-Bromo-5-chloro-pyridine-3-sulfonyl)-5-methylsulfanyl-thiophene-2-carboxylic acid methyl ester The procedure described in Example 27: step a was followed using 4-(6-Bromo-5-chloro-pyridine-3-sulfonyl)-5-nitro-thiophene-2-carboxylic acid methyl ester (63 mg, 0.14 mmol, Example 123: step b) and sodium thiomethoxide (0.5 M in EtOH, 0.18 mmol, 360 μL). The reaction was quenched with acetic acid (10 uL, 0.18 mol) followed by concentration in vacuo. The residue was then dissolved into EtOAc and washed with saturated NaHCO$_3$ and brine solutions. The organic layers were dried (Na$_2$SO$_4$) and removal of the solvents in vacuo was followed by purification by preparative SiO$_2$ TLC (30% EtOAc in hexanes) that yielded the title compound (14.2 mg, 23%) as a yellow solid. ESI-MS (m/z): Calcd. for $C_{12}H_9BrClNO_4S_3$: 441.9 (M+1) found: 442.0.

d) 4-(6-Bromo-5-chloro-pyridine-3-sulfonyl)-5-methylsulfanyl-thiophene-2-carboxamidine trifluoroacetate 4-(6-Bromo-5-chloro-pyridine-3-sulfonyl)-5-methylsulfanyl-thiophene-2-carboxylic acid methyl ester (Example 123: step c) was then converted to the amidine and purified as described in Example 20: step f to isolate the title compound (6.4 mg, 50%). $^1$H-NMR (CD$_3$OD): δ: 8.97 (s, 1H), 8.66 (s, 1H), 8.33 (s, 1H), 2.76 (s, 3H). ESI-MS (m/z): Calcd. for $C_{11}H_9BrClN_3O_2S_3$: 425.9 (M+1) found: 426.1.

Example 124

4-(6-Amino-5-bromo-pyridine-3-sulfonyl)-5-methylsulfanyl-thiophene-2-carboxamidine trifluoroacetate

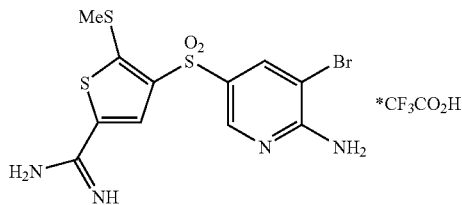

a) 4-(6-Amino-5-bromo-pyridine-3-sulfonyl)-5-methylsulfanyl-thiophene-2-carboxylic acid methyl ester Ammonia gas was condensed with a cold finger into the Teflon core of a stainless steel bomb. Approximately 5 mL of liquid ammonia was collected and maintained at −78° C. To this was added 4-(6-Bromo-5-chloro-pyridine-3-sulfonyl)-5-methylsulfanyl-thiophene-2-carboxylic acid methyl ester (15 mg, 0.034 mmol, Example 123: step c). The reaction vessel was capped, sealed and heated to 80° C. overnight protected by shield. The reaction bomb was cooled to RT then to −78° C. before opening. The remaining ammonia mixture was allowed to evaporate to dryness in hood resulting in title compound and 4-(6-Amino-5-bromo-pyridine-3-sulfonyl)-5-methylsulfanyl-thiophene-2-carboxylic acid amide (14 mg, 98%). ESI-MS (m/z): Calcd. for $C_{12}H_{11}BrN_2O_4S_3$: 422.9 (M+1) found: 423.0.

b) 4-(6-Amino-5-bromo-pyridine-3-sulfonyl)-5-methylsulfanyl-thiophene-2-carboxamidine trifluoroacetate The mixture of 4-(6-Amino-5-bromo-pyridine-3-sulfonyl)-5-methylsulfanyl-thiophene-2-carboxylic acid methyl ester and 4-(6-Amino-5-bromo-pyridine-3-sulfonyl)-5-methylsulfanyl-thiophene-2-carboxylic acid amide (Example 124: step a) was then converted to the amidine and purified as described in Example 20: step f to isolate the title compound (4.9 mg, 36%). $^1$H-NMR (CD$_3$OD): δ: 8.55 (s, 1H), 8.27 (s, 1H), 8.14 (s, 1H), 2.74 (s, 3H). ESI-MS (m/z): Calcd. for $C_{11}H_{11}BrClN_4O_2S_3$: 406.9 (M+1) found: 407.1.

Example 125

4-(6-Amino-5-o-tolyl-pyridine-3-sulfonyl)-5-methylsulfanyl-thiophene-2-carboxamidine trifluoroacetate

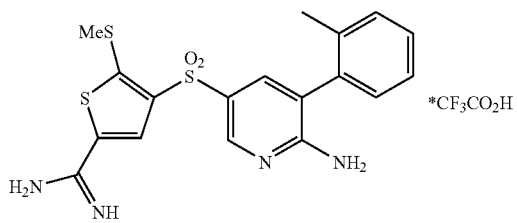

a) 4-(6-Amino-5-o-tolyl-pyridine-3-sulfonyl)-5-methylsulfanyl-thiophene-2-carboxylic acid methyl ester The procedure as in Example 1: step c was followed using 4-(6-Amino-5-bromo-pyridine-3-sulfonyl)-5-methylsulfanyl-thiophene-2-carboxylic acid methyl ester (25 mg, 0.06 mmol, Example 124: step a), 2-methyl phenyl boronic acid (33 mg, 0.25 mmol), Pd(PPh$_3$)$_4$ (14 mg, 0.01 mmol), aqueous Na$_2$CO$_3$ (2M, 400 μL, 0.5 mmol), ethanol (400 μL) and toluene (800 μL). The reaction was heated to 80° C. for 12 hours. The residue was dissolved into EtOAc and washed with brine. The organic layers were dried (MgSO$_4$) and removal of the solvents in vacuo was followed by preparative SiO$_2$ TLC purification (20% MeOH in DCM) that yielded the title compound (7.4 mg, 29%) as a white solid. ESI-MS (m/z): Calcd. for $C_{19}H_{18}N_2O_4S_3$: 420.0 (M+1) found: 420.2.

b) 4-(6-Amino-5-o-tolyl-pyridine-3-sulfonyl)-5-methylsulfanyl-thiophene-2-carboxamidine trifluoroacetate 4-(6-Amino-5-o-tolyl-pyridine-3-sulfonyl)-5-methylsulfanyl-thiophene-2-carboxylic acid methyl ester (Example 125: step a) was then converted to the amidine and purified as described in Example 20: step f to isolate the title compound (2.6 mg, 35%). $^1$H-NMR (CD$_3$OD): δ: 8.60 (s, 1H), 8.28 (s, 1H), 8.14 (s, 1H), 7.74–7.73(d, 1H, J=2.74 Hz) 7.36 (s, 1H), 7.32–7.28 (m, 1H), 7.16–7.14 (d, 1H, J=8.14 Hz), 2.74 (s, 3H), 2.13 (s, 3H). ESI-MS (m/z): Calcd. for $C_{18}H_{18}N_4O_2S_3$: 419.1 (M+1) found: 419.1.

Example 126

4-(5-Bromo-6-phenoxy-pyridine-3-sulfonyl)-5-methylsulfanyl-thiophene-2-carboxamidine trifluoroacetate

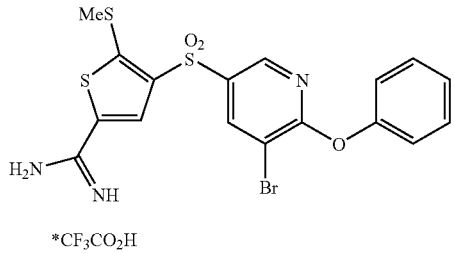

*CF$_3$CO$_2$H a) 4-(5-Bromo-6-phenoxy-pyridine-3-sulfonyl)-5-methylsulfanyl-thiophene-2-carboxylic acid methyl ester 4-(6-Bromo-5-chloro-pyridine-3-sulfonyl)-5-methylsulfanyl-thiophene-2-carboxylic acid methyl ester (110 mg, 0.24 mmol, Example 123, step c), cesium carbonate (156 mg, 0.48 mmol), phenol (180 mg, 1.92 mmol), copper (II) trifluoromethanesulfonate benzene complex (4 mg, 0.006 mmol) and EtOAc (1.0 mg, 0.02 mmol) were all dissolved into toluene (10 mL) and heated to 110° C. for 12 hours. The reaction mixture was dissolved into EtOAc and washed with brine. The organic layers were dried (MgSO$_4$) and removal of the solvents in vacuo was followed by purification by flash column SiO$_2$ (30% EtOAc in hexanes) that yielded the title compound. ESI-MS (m/z): Calcd. for C$_{18}$H$_{14}$BrNO$_5$S$_3$: 599.9 (M+1) found: 500.1.

b) 4-(5-Bromo-6-phenoxy-pyridine-3-sulfonyl)-5-methylsulfanyl-thiophene-2-carboxamidine trifluoroacetate 4-(5-Bromo-6-phenoxy-pyridine-3-sulfonyl)-5-methylsulfanyl-thiophene-2-carboxylic acid methyl ester (Example 126: step a) was then converted to the amidine and purified as described in Example 20: step f to isolate the title compound (1.0 mg). $^1$H-NMR (CD$_3$OD): δ: 8.66–8.65 (m, 1H), 8.59–8.58 (m, 1H), 8.33 (s, 1H), 7.48–7.44(m, 2H), 7.33–7.29 (m, 1H), 7.18–7.15 (m, 2H), 2.76 (s, 3H). ESI-MS (m/z): Calcd. for C$_{17}$H$_{14}$BrN$_3$O$_3$S$_3$: 483.9 (M+1) found: 484.1.

Example 127

4-(5-Bromo-pyridine-3-sulfonyl)-5-methylsulfanyl-thiophene-2-carboxamidine trifluoroacetate

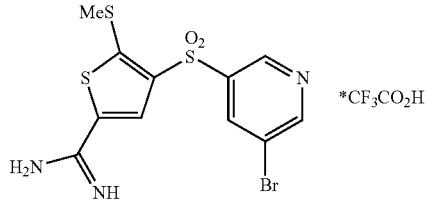

*CF$_3$CO$_2$H a) Di-5-bromo-3-pyridyl disulfide 2,4-dibromopyridine (2000 mg, 8.4 mmol) was dissolved into ether (10 mL) at RT. The reaction mixture was cooled to −78° C. and n-butyllithium (2.5M, 3.4 mL, 8.4 mmol) was added dropwise. The reaction was stirred at −78° C. for an hour followed by quenching with sulfur (269 mg, 8.4 mmol). The reaction was allowed to warm to RT over 2 hours. Removal of the solvents in vacuo was followed by purification by flash column SiO$_2$ (30% EtOAc in hexanes). The product was used without further characterization or purification.

b) 4-(5-Bromo-pyridin-3-ylsulfanyl)-5-nitro-thiophene-2-carboxylic acid methyl ester Di-5-bromo-3-pyridyl disulfide (600 mg, 1.6 mmol, Example 127: step a), Et$_3$N (223 μL, 1.6 mmol), triphenylphosphine (419 mg, 1.6 mmol) and 4-Bromo-5-nitro-thiophene-2-carboxylic acid methyl ester (427 mg, 1.6 mmol, Example 114: step c) were dissolved into THF (5 mL) and stirred at RT for 3 days. Removal of the solvents in vacuo was followed by flash column SiO$_2$ purification (25% EtOAc in hexanes) to isolate the title compound (200 mg, 33%). ESI-MS (m/z): Calcd. for C$_{11}$H$_7$BrN$_2$O$_4$S$_2$: 374.9 (M+1) found: 377.1.

c) 4-(5-Bromo-pyridine-3-sulfonyl)-5-nitro-thiophene-2-carboxylic acid methyl ester 4-(5-Bromo-pyridin-3-ylsulfanyl)-5-nitro-thiophene-2-carboxylic acid methyl ester (126 mg, 0.33 mmol, Example 127: step b) and m-CPBA (438 mg, 1.67 mmol, 77%) were dissolved into DCM (10 mL) and heated to 38° C. with stirring for 2 hours. The reaction was quenched with Na$_2$S$_2$O$_3$, dissolved into DCM and washed with NaHCO$_3$. The organic layers were dried (MgSO$_4$) and the solvents were removed in vacuo followed by flash column SiO$_2$ purification (25% EtOAc in hexanes) to isolate the title compound (151 mg, 99%) as a yellow solid. ESI-MS (m/z): Calcd. for C$_{11}$H$_7$BrN$_2$O$_6$S$_2$: 406.9 (M+1) found: 407.1 d) 4-(5-Bromo-pyridine-3-sulfonyl)-5-methylsulfanyl-thiophene-2-carboxylic acid methyl ester The procedure described in Example 27: step a was followed using 4-(5-Bromo-pyridine-3-sulfonyl)-5-nitro-thiophene-2-carboxylic acid methyl ester (151 mg, 0.37 mmol, Example 127: step c) and sodium thiomethoxide (1.0 M in EtOH, 26.3 mg, 0.37 mmol). The reaction was quenched with acetic acid (21 uL, 0.37 mol) and the solvents were removed in vacuo. The residue was then dissolved into EtOAc and washed with saturated NaHCO$_3$ and brine solutions. The organic layer was dried (Na$_2$SO$_4$) and removal of the solvents in vacuo was followed by purification by flash column chromatography SiO$_2$ (30% EtOAc in hexanes) to yield the title compound. ESI-MS (m/z): Calcd. for C$_{12}$H$_{10}$BrNO$_4$S$_3$: 407.9 (M+1) found: 408.1.

e) 4-(5-Bromo-pyridine-3-sulfonyl)-5-methylsulfanyl-thiophene-2-carboxamidine trifluoroacetate 4-(5-Bromo-pyridine-3-sulfonyl)-5-methylsulfanyl-thiophene-2-carboxylic acid methyl ester (Example 127: step d) was then converted to the amidine and purified as described in Example 20: step f to isolate the title compound (2.7 mg). $^1$H-NMR (CD$_3$OD): δ: 9.15 (m, 1H), 9.00 (m, 1H), 8.58 (m, 1H), 8.35(s, 1H), 2.77 (s, 3H). ESI-MS (m/z): Calcd. for $C_{11}H_{10}BrN_3O_2S_3$: 391.9 (M+1) found: 392.2.

Example 128

5-Methylsulfanyl-4-(5-o-tolyl-pyridine-3-sulfonyl)-thiophene-2-carboxamidine trifluoroacetate

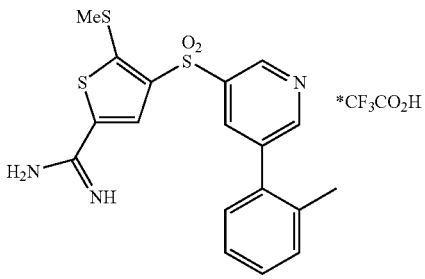

a) {[4-(5-Bromo-pyridine-3-sulfonyl)-5-methylsulfanyl-thiophen-2-yl]-imino-methyl}-carbamic acid tert-butyl ester 4-(5-Bromo-pyridine-3-sulfonyl)-5-methylsulfanyl-thiophene-2-carboxamidine (300 mg, 0.77 mmol, Example 127: step e) was dissolved into DMF (10 mL). To this was added DIEA (267 µL mg, 1.53 mmol) and (Boc)$_2$O (201.6, 0.92 mmol). The reaction was stirred at RT for 12 hours. The solvents were removed in vacuo and the residue was dissolved into DCM and washed with 20% citric acid and brine. The organic layers were dried (MgSO$_4$) and the solvents were removed in vacuo followed by purification by flash column chromatography SiO$_2$ (50% EtOAc in hexanes) that resulted in the title compound. ESI-MS (m/z): Calcd. for $C_{16}H_{18}BrN_3O_4S_3$: 491.9 (M+1) found: 491.1.

b) {Imino-[5-methylsulfanyl-4-(5-o-tolyl-pyridine-3-sulfonyl)-thiophen-2-yl]-methyl}-carbamic acid tert-butyl ester The procedure described in Example 1: step c was followed using {[4-(5-Bromo-pyridine-3-sulfonyl)-5-methyl-sulfanyl-thiophen-2-yl]-imino-methyl}-carbamic acid tert-butyl ester (50 mg, 0.08 mmol), 2-methyl phenyl boronic acid (23 mg, 0.17 mmol), Pd(PPh$_3$)$_4$ (19 Mg, 0.02 mmol), aqueous Na$_2$CO$_3$ (2M, 800 µL, 0.4 mmol), ethanol (800 µL) and toluene (1600 µL). The reaction was heated to 80° C. for 12 hours. The residue was dissolved into EtOAc and washed with brine. The organic layers were dried (MgSO$_4$) and removal of the solvents in vacuo resulted in a crude mixture of the product that was used without further purification or characterization.

c) 5-Methylsulfanyl-4-(5-o-tolyl-pyridine-3-sulfonyl)-thiophene-2-carboxamidine trifluoroacetate {Imino-[5-methylsulfanyl-4-(5-o-tolyl-pyridine-3-sulfonyl)-thiophen-2-yl]-methyl}-carbamic acid tert-butyl ester (127 mg, Example 128: step b) was deprotected and purified as in Example 1: step d, yielding the title compound as an off-white solid (8 mg, 8%). $^1$H-NMR (CD$_3$OD): δ 9.15 (s, 1H), 8.84 (s, 1H), 8.37 (m, 2H), 8.36 (m, 4H), 2.75 (s, 3H), 2.56 (s, 3H). ESI-MS (m/z): Calcd. for $C_{18}H_{17}N_3O_2S_3$: 404.1 (M+1); found: 404.1

Example 129

4-(2'-Formylamino-6'-methyl-biphenyl-3-sulfonyl)-5-methylsulfanyl-thiophene-2-carboxamidine trifluoroacetate

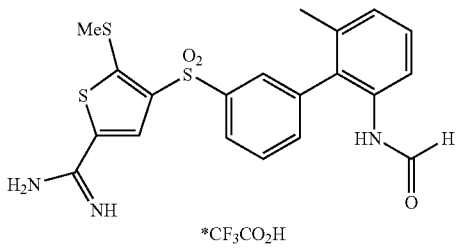

{[4-(2'-Amino-6'-methyl-biphenyl-3-sulfonyl)-5-methyl-sulfanyl-thiophen-2-yl]-imino-methyl}-carbamic acid tert-butyl ester (58 mg, 0.11 mmol, Example 25: step c) was dissolved into formic acid (3 mL, 96%) and heated to 100° C. for 24 hours. The solvents were removed in vacuo resulting in the desired product with removal of the tert-butyl protection group. The resulting compound was purified as in Example 1: step d, yielding the title compound as an off-white solid (11 mg, 22%). ESI-MS (m/z): Calcd. for $C_{20}H_{19}N_3O_3S_3$: 446.1 (M+1); found: 446.1.

Example 130

[3'-(5-Carbamimidoyl-2-methylsulfanyl-thiophene-3-sulfonyl)-6-methyl-biphenyl-2-ylamino]-acetic acid

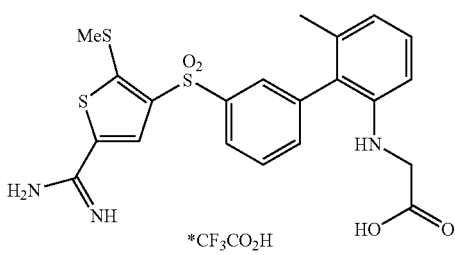

{[4-(2'-Amino-6'-methyl-biphenyl-3-sulfonyl)-5-methyl-sulfanyl-thiophen-2-yl]-imino-methyl}-carbamic acid tert-butyl ester (75 mg, 0.15 mmol, Example 25: step c), tert-butyl bromoacetate (43 µL, 0.29 mmol), potassium carbonate (29 mg, 0.21 mmol) and 2,6-lutidine (33 µL, 0.29 mmol) were dissolved into toluene (2 mL). The reaction was stirred and heated to 80° C. for 12 hours. Et$_3$N (41 µL, 0.3 mmol) was added to reaction and heated to 80° C. for another 12 hours. The reaction mixture was dissolved into EtOAc and washed with brine. The organic layers were dried (MgSO$_4$), the solvents were removed in vacuo followed purified by preparative SiO$_2$ TLC purification (20% MeOH in DCM) resulting in {3'-[5-(tert-Butoxycarbonylamino-imino-methyl)-2-methylsulfanyl-thiophene-3-sulfonyl]-6-methyl-biphenyl-2-ylamino}-acetic acid tert-butyl ester. ESI-MS (m/z): Calcd. for $C_{30}H_{37}N_3O_6S_3$: 632.2 (M+1) found: 631.9. {3'-[5-(tert-Butoxycarbonylamino-imino-methyl)-2-methylsulfanyl-thiophene-3-sulfonyl]-6-methyl-biphenyl-2-ylamino}-acetic acid tert-butyl ester was deprotected and purified as Example 1: step d, yielding the title compound as brown solid (1.7 mg). ¹H-NMR (CD₃OD): δ 8.35 (s, 1H), 8.08–8.06 (d, 1H, J=8.83 Hz), 7.77 (t, 1H, J=7.44 Hz, J=7.67 Hz), 7.63–7.61 (d, 1H, J=7.67 Hz), 7.16 (t, 1H, J=7.91 Hz, J=7.91 Hz), 7.05–6.68 (d, 2H, J=7.67 Hz), 6.52–6.50 (d, 1H, J=8.14 Hz), 3.81 (s, 1H), 2.72 (s, 3H), 2.17 (s, 3H). ESI-MS (m/z): Calcd. for C₂₁H₂₁N₃O₄S₃: 476.1 (M+1); found: 476.1.

Example 131

{2-[5-(5-Carbamimidoyl-2-methylsulfanyl-thiophene-3-sulfonyl)-pyridin-3-yl]-3-methyl-benzyloxy}-acetic acid

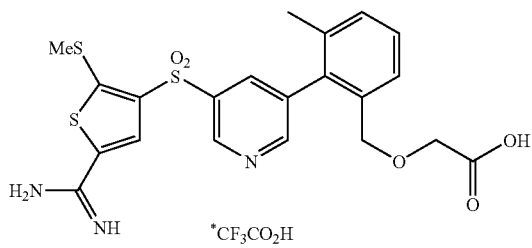

a) 2-Iodo-3-methyl-benzoyl chloride 2-iodo-3-methyl benzoic acid (1310 mg, 5 mmol) and thionyl chloride (730 μL, 10 mmol) were dissolved into THF (10 mL) and stirred at RT for 4 days. The solvents were removed in vacuo and the resulting residue was dissolved into EtOAc, washed with brine. The combined organic layers were dried (MgSO₄) and the solvents were removed in vacuo resulting in an oil that was used without further purification or characterization.

b) (2-Iodo-3-methyl-phenyl)-methanol

2-Iodo-3-methyl-benzoyl chloride (1360 mg, 4.86 mmol, Example 131: a) was dissolved into THF (2 mL) and cooled to −78° C. To this was slowly added a slurry of lithium aluminum hydride (184.3 mg, 4.86 mmol) that was carefully weighed into a dry flask and cooled to 78° C., before THF (2 mL) was added. The reaction was warmed to RT slowly and stirred for an hour. The reaction was quenched by cooling back to −78° C. and adding 200 μL water, 200 μL 15% NaOH, 600 μL water and then poured over celite and filtered with THF. The title compound was obtained as a yellow solid. ¹H-NMR (CDCl₃): δ 7.21–7.19 (m, 2H), 7.14–7.11 (m, 1H,), 4.61 (s, 2H), 2.43 (s, 3H).

c) (2-Iodo-3-methyl-benzyloxy)-acetic acid tert-butyl ester (2-Iodo-3-methyl-phenyl)-methanol (1608 mg, 6.8 mmol, Example 131: step b) was dissolved into DMF (10 mL). The solution was cooled to 0° C. To this was added sodium hydride in one portion and the reaction continued to stir at 0° C. for 30 minutes. To the cooled solution was added t-butylbromoacetate (1.3 mL, 8.9 mmol) and then the reaction was warmed to RT and then heated to 50° C. for 4 hours. The solvents were removed in vacuo and the resulting residue was dissolved into EtOAc and washed with brine. The combined organic layers were dried (MgSO₄) and the solvent was removed in vacuo resulting in the title compound (1.29 g, 53%) that was used with out further purification. ¹H-NMR (CDCl₃): δ 7.28–7.13 (m, 3H), 4.63 (s, 2H), 4.07 (s, 2H), 2.44 (s, 3H), 1.47 (s, 9H).

d) [3-Methyl-2-(4,4,5,5-tetramethyl-[1,3,2]dioxaborolan-2-yl)-benzyloxy]-acetic acid tert-butyl ester (2-Iodo-3-methyl-benzyloxy)-acetic acid tert-butyl ester (360 mg, 1.46 mmol, Example 131: step c), trans-Dichlorobis(triphenylphosphine)palladium(II) (102 mg, 0.15 mmol) and Et₃N (1.2 mL, 8.76 mmol) were dissolved into dioxane (10 mL). To this was slowly added 4,4,4,5,5,5-tetramethyldioxaborolane (423 μL, 2.91 mmol) and reaction was heated to 80° C. for 2 hours. Catalytic amounts of 4,4,4,5,5,5-tetramethyldioxaborolane and dichlorobis(triphenylphosphine)palladium(II) were added and the reaction continued heating at 50° C. overnight. The solvents were removed in vacuo and the residue was dissolved into EtOAc followed by washing with brine. The combined organic layers were dried (MgSO₄) and the solvents were removed in vacuo. The crude reaction mixture was purified by flash column chromatography (30% EtOAc/hexanes) yielding the title compound (335 mg, 63%) as a brown oil. ¹H-NMR (CDCl₃): δ 7.23–7.06 (m, 3H), 4.72 (s, 2H), 4.09 (s, 2H), 2.42 (s, 3H), 1.45 (m, 12H), 1.38 (s, 9H).

e) (2-{5-[5-(tert-Butoxycarbonylamino-imino-methyl)-2-methylsulfanyl-thiophene-3-sulfonyl]-pyridin-3-yl}-3-methyl-benzyloxy)-acetic acid tert-butyl ester The procedure as in Example 1: step c was followed using [3-Methyl-2-(4,4,5,5-tetramethyl-[1,3,2]dioxaborolan-2-yl)-benzyloxy]-acetic acid tert-butyl ester (252.2 mg, 0.62 mmol, Example 131: step d), {[4-(5-Bromo-pyridine-3-sulfonyl)-5-methylsulfanyl-thiophen-2-yl]-imino-methyl}-carbamic acid tert-butyl ester (75.9 mg, 0.15 mmol, Example 128: step a), Pd(PPh₃)₄ (35 mg, 0.03 mmol), aqueous Na₂CO₃ (2M, 1 mL), ethanol (1 mL) and toluene (2 mL). The reaction was heated to 80° C. for 24 hours. The reaction mixture was dissolved into EtOAc and washed with brine. The organic layers were dried (MgSO₄) and removal of the solvents in vacuo was followed by purification by flash column chromatography (SiO₂) (30% EtOAc in hexanes) of the residue yielded the title compound (460 mg) as a brown oil. ESI-MS (m/z): Calcd. for C₃₀H₃₇N₃O₇S₃: 648.2 (M+1) found: 647.9.

f) {2-[5-(5-Carbamimidoyl-2-methylsulfanyl-thiophene-3-sulfonyl)-pyridin-3-yl]-3-methyl-benzyloxy}-acetic acid (2-{5-[5-(tert-Butoxycarbonylamino-imino-methyl)-2-methylsulfanyl-thiophene-3-sulfonyl]-pyridin-3-yl}-3-methyl-benzyloxy)-acetic acid tert-butyl ester (127 mg) (Example 11: step e) was deprotected and purified as in Example 1: step d, yielding the title compound as an off-white solid. ¹H-NMR (CD₃OD): δ 9.05 (s, 1H), 8.65 (s, 1H), 8.26 (m, 1H), 8.19 (s, 1H), 7.28–7.24 (m, 3H), 4.12 (s, 2H), 3.67 (s, 2H ), 2.63 (s, 3H), 1.92 (s, 3H). ESI-MS (m/z): Calcd. for C₂₁H₂₁N₃O₅S₃: 492.1 (M+1); found: 492.1.

Example 132

N-[3'-(5-Carbamimidoyl-2-methylsulfanyl-thiophene-3-sulfonyl)-6-methyl-biphenyl-2-yl]-malonamic acid

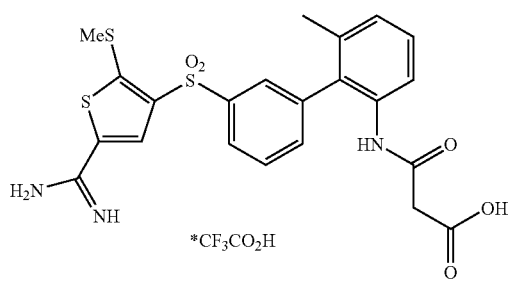

*CF$_3$CO$_2$H a) N-{3'-[5-(tert-Butoxycarbonylamino-imino-methyl)-2-methylsulfanyl-thiophene-3-sulfonyl]-6-methyl-biphenyl-2-yl}-malonamic acid methyl ester {[4-(2'-Amino-6'-methyl-biphenyl-3-sulfonyl)-5-methyl-sulfanyl-thiophen-2-yl]-imino-methyl}-carbamic acid tert-butyl ester (22 mg, 0.04 mmol, Example 25: step c) was dissolved into THF (1 mL) and to this was added chlorocarbonyl-acetic acid methyl ester (9 µL, 0.085 mmol). The reaction was heated to 50° C. for 5 hours and then allowed to stir at RT for 48 hours. The reaction mixture was dissolved into EtOAc and washed with brine. The organic layers were dried (MgSO$_4$) and removal of the solvents in vacuo was followed by purification by preparative TLC (SiO$_2$) (30% EtOAc in hexanes) that yielded the title compound. ESI-MS (m/z): Calcd. for C$_{28}$H$_{31}$N$_3$O$_7$S$_3$: 618.1 (M+1) found: 617.9.

b) N-{3'-[5-(tert-Butoxycarbonylamino-imino-methyl)-2-methylsulfanyl-thiophene-3-sulfonyl]-6-methyl-biphenyl-2-yl}-malonamic acid N-{3'-[5-(tert-Butoxycarbonylamino-imino-methyl)-2-methylsulfanyl-thiophene-3-sulfonyl]-6-methyl-biphenyl-2-yl}-malonamic acid methyl ester (20 mg, 0.03 mmol, Example 132: step a) and NaOH (1M, 90 µL, 0.09 mmol) were dissolved into MeOH (1.5 mL). The reaction was stirred for 2 hours. LiOH (1.0 mg, 0.05 mmol) was added and the reaction was stirred at RT overnight. The solvents were removed in vacuo and used with out further purification in the next step. ESI-MS (m/z): Calcd. for C$_{27}$H$_{29}$N$_3$O$_7$S$_3$: 604.1 (M+1); found: 504.0 (loss of boc).

c) N-[3'-(5-Carbamimidoyl-2-methylsulfanyl-thiophene-3-sulfonyl)-6-methyl-biphenyl-2-yl]-malonamic acid N-{3'-[5-(tert-Butoxycarbonylamino-imino-methyl)-2-methylsulfanyl-thiophene-3-sulfonyl]-6-methyl-biphenyl-2-yl}-malonamic acid (Example 132: step b) was deprotected and purified as in Example 1: step d, yielding the title compound as a glassy solid. $^1$H-NMR (CD$_3$OD): δ 8.28 (s, 1H), 8.07–8.05 (m, 1H), 7.85 (s, 1H), 7.72–7.68 (t, 1H, J=7.67 Hz, J=7.90 Hz), 7.57–7.55 (m, 1H), 7.43–7.26 (m, 3H), 2.74 (s, 3H), 2.07 (s, 3H), 2.05 (s, 2H). ESI-MS (m/z): Calcd. for C$_{22}$H$_{21}$N$_3$O$_5$S$_3$: 504.1 (M+1); found: 503.9.

Example 133

N-[3'-(5-Carbamimidoyl-2-methylsulfanyl-thiophene-3-sulfonyl)-6-methyl-biphenyl-2-yl]-succinamic acid trifluoroacetate

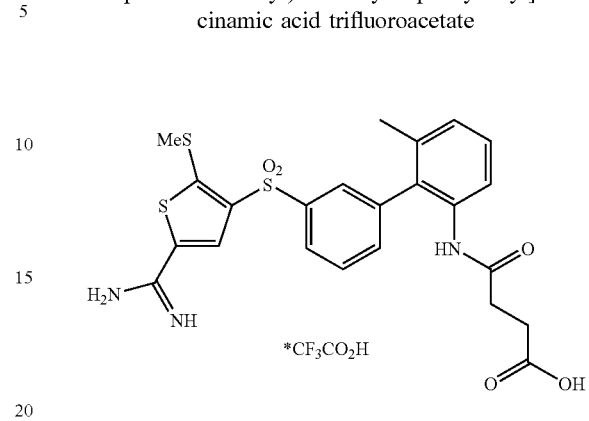

*CF$_3$CO$_2$H a) N-{3'-[5-(tert-Butoxycarbonylamino-imino-methyl)-2-methylsulfanyl-thiophene-3-sulfonyl]-6-methyl-biphenyl-2-yl}-succinamic acid ethyl ester {[4-(2'-Amino-6'-methyl-biphenyl-3-sulfonyl)-5-methyl-sulfanyl-thiophen-2-yl]-imino-methyl}-carbamic acid tert-butyl ester (38.5 mg, 0.07 mmol, Example 25: step c) and 3-chlorocarbonyl-propionic acid ethyl ester (13 µL, 0.09 mmol) were dissolved into THF (1 mL) and heated to 50° C. for one hour. The reaction was dissolved into EtOAc and washed with brine. The combined organic layers were dried, (MgSO$_4$) and the solvents were removed in vacuo. Purification by preparative TLC (30% EtOAc/hexanes) yielded the title compound. ESI-MS (m/z): Calcd. for C$_{30}$H$_{35}$N$_3$O$_7$S$_3$: 646.2 (M+1); found: 645.8.

b) N-{3'-[5-(tert-Butoxycarbonylamino-imino-methyl)-2-methylsulfanyl-thiophene-3-sulfonyl]-6-methyl-biphenyl-2-yl}-succinamic acid N-{3'-[5-(tert-Butoxycarbonylamino-imino-methyl)-2-methylsulfanyl-thiophene-3-sulfonyl]-6-methyl-biphenyl-2-yl}-succinamic acid ethyl ester (Example 133: step a) and LiOH were dissolved into MeOH and stirred at RT for 2 hours. The solvents were removed in vacuo yielding the title compound that was used with out further purification or characterization.

c) N-[3'-(5-Carbamimidoyl-2-methylsulfanyl-thiophene-3-sulfonyl)-6-methyl-biphenyl-2-yl]-malonamic acid trifluoroacetate N-{3'-[5-(tert-Butoxycarbonylamino-imino-methyl)-2-methylsulfanyl-thiophene-3-sulfonyl]-6-methyl-biphenyl-2-yl}-succinamic acid (Example 133: step c) was deprotected and purified as in Example 1: step d, yielding the title compound as a white solid. $^1$H-NMR (CD$_3$OD): δ 8.31 (s, 1H), 8.07–8.05 (m, 1H), 7.85 (s, 1H), 7.72–7.68 (t, 1H, J=7.67 Hz, J=7.90 Hz), 7.56–7.53 (m, 1H), 7.37–7.35 (t, 1H, J=7.67 Hz, J=7.67 Hz), 7.29–7.21 (m, 1H), 3.36 (s, 4H), 2.74 (s, 3H), 2.09 (s, 3H). ESI-MS (m/z): Calcd. for C$_{23}$H$_{23}$N$_3$O$_5$S$_3$: 518.1 (M+1); found: 518.1.

Example 134

4-(4'-Amino-2'-chloro-6'-methyl-biphenyl-3-sulfonyl)-5-methylsulfanyl-thiophene-2-carboxamidine trifluoroacetate

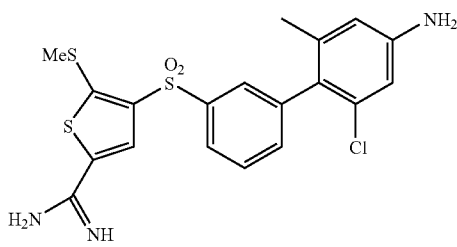

a) {[4-(2'-Chloro-6'-methyl-4'-nitro-biphenyl-3-sulfonyl)-5-methylsulfanyl-thiophen-2-yl]-imino-methyl}-carbamic acid tert-butyl ester 2-Bromo-1-chloro-3-methyl-5-nitro-benzene (45 mg, 0.219 mmol), {[4-(3-Boranyl-dihydroxy-benzenesulfonyl)-5-methylsulfanyl-thiophen-2-yl]-imino-methyl}-carbamic acid tert-butyl ester (50 mg, 0.11 mmol, Example 140: step a) and $Pd(PPh_3)_4$ (25 mg, 0.02 mmol) were combined in aqueous $Na_2CO_3$ (2M, 500 µL), ethanol (500 µL) and toluene (1 mL). The reaction was heated to 80° C. overnight. The resulting residue was dissolved into EtOAc and washed with brine. The organic layers were dried ($MgSO_4$) and the solvent was removed in vacuo followed by preparative TLC purification (30% EtOAc/hexanes) that yielded the title compound (20 mg, 29%). ESI-MS (m/z): Calcd. for $C_{24}H_{24}ClN_3O_6S_3$: 582.1 (M+1); found: 582.1.

b) {[4-(4'-Amino-2'-chloro-6'-methyl-biphenyl-3-sulfonyl)-5-methylsulfanyl-thiophen-2-yl]-imino-methyl}-carbamic acid tert-butyl ester {[4-(2'-Chloro-6'-methyl-4'-nitro-biphenyl-3-sulfonyl)-5-methylsulfanyl-thiophen-2-yl]-imino-methyl}-carbamic acid tert-butyl ester (20 mg, 0.034 mmol, Example 134: step a) was dissolved into EtOH (2 mL). To this was added ammonium chloride (18 mg, 0.34 mmol) dissolved into water (4 mL). The reaction was heated to 50° C. and iron (9.6 mg, 0.34 mmol) was added. The reaction was then heated to 80° C. for 12 hours followed by filtration through celite with methanol and EtOAc. The solvents were removed in vacuo resulting in desired product that was used with out further purification or characterization.

c) 4-(4'-Amino-2'-chloro-6'-methyl-biphenyl-3-sulfonyl)-5-methylsulfanyl-thiophene-2-carboxamidine trifluoroacetate {[4-(4'-Amino-2'-chloro-6'-methyl-biphenyl-3-sulfonyl)-5-methylsulfanyl-thiophen-2-yl]-imino-methyl}-carbamic acid tert-butyl ester (Example 134: step b) was deprotected and purified as in Example 1: step d, yielding the title compound as a dark yellow solid. $^1$H-NMR ($CD_3OD$): δ 8.33 (s, 1H), 8.03–8.00 (m, 1H), 7.85–7.84 (m, 1H), 7.70–7.66 (t, 1H, J=7.67 Hz, J=7.67 Hz), 7.54–7.52 (m, 1H), 6.94 (s, 1H), 6.84 (m, 1H), 2.70 (s, 3H), 1.99 (s, 3H). ESI-MS (m/z): Calcd. for $C_{19}H_{18}N_3O_2S_3$: 452.0 (M+1); found: 452.1.

Example 135

N-[3'-(5-Carbamimidoyl-2-methylsulfanyl-thiophene-3-sulfonyl)-4-chloro-6-methyl-biphenyl-2-yl]-4-methanesulfonyl-butyramide trifluoroacetate

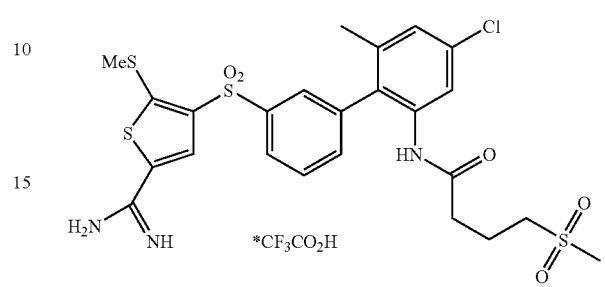

a) 4-Bromo-3-methyl-5-nitro-phenylamine (4-Bromo-3-methyl-5-nitro-phenyl)-carbamic acid tert-butyl ester (1000 mg, 2.9 mmol) was dissolved into DCM (10 mL). To this was added TFA (10 mL) and the reaction was stirred at RT for 1 hour. The pH was adjusted to 8 with 1 N NaOH and the solvents were removed in vacuo. The reaction mixture was dissolved into EtOAc and the layers were separated. The organic layers were dried ($MgSO_4$) and the solvents were removed in vacuo resulting in title compound (756 mg, quantitative) as a brown oil. $^1$H-NMR ($CDCl_3$): δ 8.44 (s, 1H), 8.02 (s, 1H), 7.61 (s, 1H), 3.05 (s, 3H).

b) 2-Bromo-5-chloro-1-methyl-3-nitro-benzene

A 3-neck flask fitted with septa, addition funnel and condenser was charged with t-butylnitrite (966µ, 8.12 mmol) and copper (II) chloride (1090 mg, 8.12 mmol) in acetonitrile (10 mL). 4-Bromo-3-methyl-5-nitro-phenylamine (756 mg, 4.06 mmol, Example 135: step a) was dissolved in acetonitrile (6 mL) and added slowly through the addition funnel while heating to 60° C. The reaction was quenched with EtOAc and washed with water. The organic layers were dried ($MgSO_4$) and the solvents were removed in vacuo resulting in the title compound as a brown solid (721 mg, 72%). $^1$H-NMR ($CDCl_3$): δ 7.54 (d, 1H, J=2.33), 7.44 (d, 1H, J=2.56 Hz), 2.55 (s, 3H).

c) 2-Bromo-5-chloro-3-methyl-phenylamine

2-Bromo-5-chloro-1-methyl-3-nitro-benzene (721 mg, 3.5 mmol, Example 135: step b) was dissolved into EtOH (6 mL). To this was added ammonium chloride (1.9 g, 35 mmol) dissolved into water (10 mL). The reaction was heated to 50° C., iron (9.6 mg, 0.34 mmol) was added and the reaction was then heated to 80° C. for 12 hours. The reaction mixture was filtered through celite, washed with methanol and EtOAc and the solvents were removed in vacuo. The residue was dissolved into EtOAc and washed with brine to remove salts. The organic layers were dried ($MgSO_4$) and the solvents were removed in vacuo resulting in the title compound (595 mg, 78%) as a brown solid. $^1$H-NMR ($CDCl_3$): δ 6.63–6.61 (m, 2H), 2.33 (s, 3H).

d) 5-Chloro-3-methyl-2-(4,4,5,5-tetramethyl-[1,3,2] dioxaborolan-2-yl)-phenylamine 2-Bromo-5-chloro-3-methyl-phenylamine (595 mg, 2.7 mmol, Example 135: step c), Pd(OAc)$_2$ (30.3 mg, 0.14 mmol), 2-(dicyclohexylphosphino)biphenyl (189.2 mg, 0.54 mmol) and Et$_3$N (1.5 mL, 10.8 mmol) were dissolved into dioxane (10 mL). To this was added 4,4,5,5-Tetramethyl-[1,3,2]dioxaborolane (1.2 mL, 8.1 mmol) slowly. The reaction was heated to 80° C. overnight. The solvents were removed in vacuo and the resulting residue was dissolved into EtOAc and washed with brine. The combined organic layers were dried (MgSO$_4$) and removal of the solvents in vacuo resulted in a mixture of the title compound and 3-Methyl-2,5-bis-(4,4,5,5-tetramethyl-[1,3,2]dioxaborolan-2-yl)-phenylamine were obtained and used with out further purification.

e) {[4-(2'-Amino-4'-chloro-6'-methyl-biphenyl-3-sulfonyl)-5-methylsulfanyl-thiophen-2-yl]-imino-methyl}-carbamic acid tert-butyl ester The procedure as in Example 1: step c was followed 5-Chloro-3-methyl-2-(4,4,5,5-tetramethyl-[1,3,2]dioxaborolan-2-yl)-phenylamine (663 mg, 2.5 mmol, Example 135, step d), {[4-(3-Bromo-benzenesulfonyl)-5-methylsulfanyl-thiophen-2-yl]-imino-methyl}-carbamic acid tert-butyl ester (1.2 g, 2.5 mmol, Example 27: step c), Pd(PPh$_3$)$_4$ (577 mg, 0.5 mmol), aqueous Na$_2$CO$_3$ (2M, 10 mL), ethanol (10 mL) and toluene (20 mL). The reaction was heated to 80° C. for 24 hours. The reaction mixture was dissolved into EtOAc and washed with brine. The organic layers were dried (MgSO$_4$) and removal of the solvents in vacuo was followed by purification by flash column chromatography (SiO$_2$) (30% EtOAc in hexanes) that yielded the title compound as a brown oil. ESI-MS (m/z): Calcd. for C$_{24}$H$_{26}$ClN$_3$O$_4$S$_3$: 552.1 (M+1) found: 551.7.

f) ({4-[4'-Chloro-2'-(4-methanesulfonyl-butyrylamino)-6'-methyl-biphenyl-3-sulfonyl]-5-methylsulfanyl-thiophen-2-yl}-imino-methyl)-carbamic acid tert-butyl ester {[4-(2'-Amino-4'-chloro-6'-methyl-biphenyl-3-sulfonyl)-5-methylsulfanyl-thiophen-2-yl]-imino-methyl}-carbamic acid tert-butyl ester (120 mg, 0.22 mmol, Example 135, e) and Et$_3$N (0.91 µL, 0.65 mmol) were dissolved into DCM (4 mL). To this was added (4-Methanesulfonyl-butyryl chloride (0.144 M, 3.1 mL, 0.44 mmol, Example 209: a) and the reaction was stirred at RT overnight. The solvents were removed in vacuo followed by purification by flash column chromatography (20% EtOAc/hexanes) that yielded the title compound as an orange solid (124 mg, 81%). ESI-MS (m/z): Calcd. for C$_{29}$H$_{34}$ClN$_3$O$_7$S$_4$: 700.1 (M+1) found: 700.1.

g) N-[3'-(5-Carbamimidoyl-2-methylsulfanyl-thiophene-3-sulfonyl)-4-chloro-6-methyl-biphenyl-2-yl]-4-methanesulfonyl-butyramide trifluoroacetate ({4-[4'-Chloro-2'-(4-methanesulfonyl-butyrylamino)-6'-methyl-biphenyl-3-sulfonyl]-5-methylsulfanyl-thiophen-2-yl}-imino-methyl)-carbamic acid tert-butyl ester (124 mg, 0.18 mmol, Example 135: step f) was deprotected and purified as in Example 1: step d, yielding the title compound as a clear glass (70 mg, 65%). $^1$H-NMR (CD$_3$OD): δ 8.32 (s, 1H), 8.08–8.06 (d, 1H, J=10.00 Hz), 7.87 (m, 1H), 7.71 (t, 1H, J=7.91 Hz, J=8.61 Hz), 7.56–7.54 (d, 1H, J=9.07), 7.33 (m, 2H), 2.92 (s, 3H), 2.85 (t, 2H, J=7.91 Hz, J=7.67 Hz), 2.73 (s, 3H), 2.21 (t, 2H, J=5.35 Hz, J=7.91 Hz), 2.07 (s, 3H), 1.82–1.73 (m, 2H). ESI-MS (m/z): Calcd. for C$_{24}$H$_{26}$ClN$_3$O$_5$S$_4$: 600.1 (M+1); found: 600.1.

Example 136

4-[4'-(N'-Hexyl-guanidino)-2'-methyl-biphenyl-3-sulfonyl]-5-methylsulfanyl-thiophene-2-carboxamidine trifluoroacetate

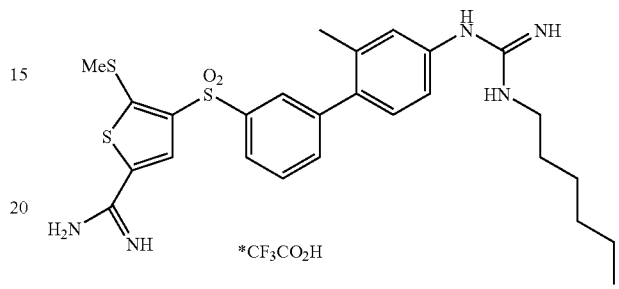

a) ({4-[4'-(3-Hexyl-thioureido)-2'-methyl-biphenyl-3-sulfonyl]-5-methylsulfanyl-thiophen-2-yl}-imino-methyl)-carbamic acid tert-butyl ester 4-(4'-Amino-2'-methyl-biphenyl-3-sulfonyl)-5-methylsulfanyl-thiophene-2-carboxamidine (26 mg, 0.05 mmol, Example 220: step b) was dissolved into EtOH. To this was added hexylisothiocyanate (30 µL) and the reaction was heated for 4 hour at 80° C. The solvent was removed in vacuo and the reaction was purified by preparative TLC resulting in the title compound that was used without further purification or characterization.

b) ({4-[4'-(N'-Hexyl-guanidino)-2'-methyl-biphenyl-3-sulfonyl]-5-methylsulfanyl-thiophen-2-yl}-imino-methyl)-carbamic acid tert-butyl ester ({4-[4'-(3-Hexyl-thioureido)-2'-methyl-biphenyl-3-sulfonyl]-5-methylsulfanyl-thiophen-2-yl}-imino-methyl)-carbamic acid tert-butyl ester (33 mg, 0.14 mmol. Example 136: step a) was dissolved into ammonia in methanol (2.0 M, 4 mL). To this was added mercury (II) oxide (33.9 mg, 0.16 mmol) and the reaction stirred at RT for 2 hours. Additional mercury (II) oxide (154 mg, 0.08 mmol) was added and the reaction was heated to 40° C. overnight. The reaction was filtered with 0.2 µM disk and washed with EtOAc followed by removal of solvents in vacuo that yielded the title compound which was used without further purification (30 mg). ESI-MS (m/z): Calcd. for C$_{31}$H$_{41}$N$_5$O$_4$S$_3$: 644.2 (M+1); found: 644.1.

c) 4-[4'-(N'-Hexyl-guanidino)-2'-methyl-biphenyl-3-sulfonyl]-5-methylsulfanyl-thiophene-2-carboxamidine trifluoroacetate ({4-[4'-(N'-Hexyl-guanidino)-2'-methyl-biphenyl-3-sulfonyl]-5-methylsulfanyl-thiophen-2-yl}-imino-methyl)-carbamic acid tert-butyl ester (30 mg, Example 136: step b) was deprotected and purified as in Example 1: step d, yielding the title compound as a yellow glass (11.5 mg, 43%). $^1$H-NMR (CD$_3$OD): δ 8.34 (s, 1H), 8.03–8.00 (m, 2H), 7.73–7.67 (m, 2H), 7.33–7.31 (m, 1H), 7.24–7.18 (m, 2H), 3.63 (m, 2H), 2.72 (s, 3H), 2.27 (s, 3H), 1.69–1.62 (m, 2H), 1.44–1.33 (m, 6H). ESI-MS (m/z): Calcd. for $C_{26}H_{33}N_5O_2S_3$: 544.2 (M+1); found: 544.1.

Example 137

5-[3'-(5-Carbamimidoyl-2-methylsulfanyl-thiophene-3-sulfonyl)-6-methyl-biphenyl-2-ylcarbamoyl]-pentanoic acid trifluoroacetate

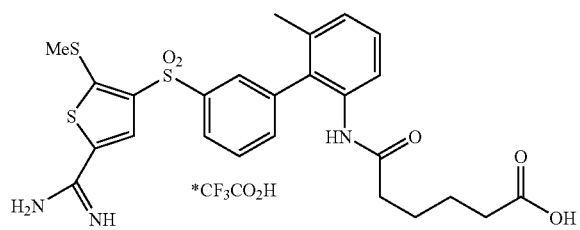

a) 5-{3'-[5-(tert-Butoxycarbonylamino-imino-methyl)-2-methylsulfanyl-thiophene-3-sulfonyl]-6-methyl-biphenyl-2-ylcarbamoyl}-pentanoic acid methyl ester {[4-(2'-Amino-6'-methyl-biphenyl-3-sulfonyl)-5-methyl-sulfanyl-thiophen-2-yl]-imino-methyl}-carbamic acid tert-butyl ester (100 mg, 0.19 mmol, Example 25: step c) was dissolved into THF (3 mL). To this was added 5-Chlorocarbonyl-pentanoic acid methyl ester (41.5 mg, 0.23 mmol) and the reaction was stirred at RT for 2 hours. The reaction was dissolved into EtOAc and washed with brine. The combined organic layers were dried (MgSO$_4$) followed by removal of solvents in vacuo resulted in the title compound that was used without further purification. ESI-MS (m/z): Calcd. for $C_{31}H_{37}N_3O_7S_3$: 660.2 (M+1); found: 660.8.

b) 5-{3'-[5-(tert-Butoxycarbonylamino-imino-methyl)-2-methylsulfanyl-thiophene-3-sulfonyl]-6-methyl-biphenyl-2-ylcarbamoyl}-pentanoic acid 5-{3'-[5-(tert-Butoxycarbonylamino-imino-methyl)-2-methylsulfanyl-thiophene-3-sulfonyl]-6-methyl-biphenyl-2-ylcarbamoyl}-pentanoic acid methyl ester (125 mg, 0.19 mmol, Example 137: step a) and LiOH (12.5 mg, 0.54 mmol) were dissolved into MeOH (3 mL) and heated to 60° C. for 12 hours. The reaction was dissolved into EtOAc and washed with 20% citric acid. The aqueous layers were acidified with acetic acid (pH 3) and extracted with EtOAc. The organic layers were combined and dried (MgSO$_4$) followed by removal of solvents in vacuo. The resulting material was purified by preparative RP-HPLC (0–100% water/acetonitrile—both solvents were free of TFA, 45 minutes, λ=245 nm). $^1$H-NMR (CDCl$_3$): δ 7.95–7.93 (d, 1H, J=9.3 Hz), 7.81–7.78 (d, 1H, J=7.91 Hz), 7.63–7.59 (m, 1H), 7.55–7.53 (t, 1H, J=8.35, Hz, J=7.59 Hz), 7.38–7.36 (d, 1H, J=9.35 Hz), 7.25–7.21 (m, 1H), 7.07–7.05 (d, 1H, J=7.07 Hz), 6.78 (s, 1H), 3.55 (s, 2H), 2.51 (s, 3H), 2.15–2.12 (m, 2H), 1.96–1.95 (m, 2H), 1.93 (s, 3H).

c) 5-[3'-(5-Carbamimidoyl-2-methylsulfanyl-thiophene-3-sulfonyl)-6-methyl-biphenyl-2-ylcarbamoyl]-pentanoic acid trifluoroacetate 5-{3'-[5-(tert-Butoxycarbonylamino-imino-methyl)-2-methylsulfanyl-thiophene-3-sulfonyl]-6-methyl-biphenyl-2-ylcarbamoyl}-pentanoic acid (Example 137: step b) was deprotected and purified as in Example 1: step d, yielding the title compound as a white glass. $^1$H-NMR (CD$_3$OD): δ 8.29 (s, 1H), 8.06–8.04 (m, 1H), 7.89 (s, 1H), 7.68 (t, 1H, J=7.67 Hz, J=8.84 Hz), 7.54–7.52 (d, 1H, J=7.91 Hz), 7.38–7.29 (m, 2H), 7.18–7.16 (d, 1H, J=7.67 Hz), 2.75 (s, 3H), 2.11–2.09 (m, 2H), 2.08 (s, 3H), 2.03–1.91 (m, 2H), 1.27–1.08 (m, 4H). ESI-MS (m/z): Calcd. for $C_{25}H_{27}N_3O_5S_3$: 546.1 (M+1); found: 546.1.

Example 138

4-[3-(3-Methyl-pyridin-4-yl)-benzenesulfonyl]-5-methylsulfanyl-thiophene-2-carboxamidine trifluoroacetate

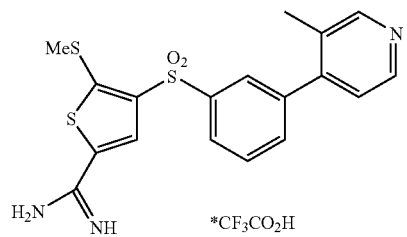

a) 4-Bromo-3-methyl-pyridin-1-ol

Acetyl bromide (5 mL) was cooled to 0° C. To this was added 4-Nitro-3-methyl-pyridin-1-ol (1000 mg, 6.48 mmol) portionwise while maintaining temperature. After the addition was complete, the reaction was heated to 50° C. and stirred for 2 hours. The reaction was then cooled to 0° C., quenched with ice and neutralized with solid Na$_2$CO$_3$ (pH=8). The neutral aqueous reaction mixture was extracted into DCM. The organic layer was dried (MgSO$_4$), the solvents were removed in vacuo resulting in the title compound as a yellow solid (1.05 mg, 86%). ESI-MS (m/z): Calcd. for $C_6H_6BrNO$: 188.0 (M+1); found: 188.0.

b) 4-Bromo-3-methyl-pyridine

4-Bromo-3-methyl-pyridin-1-ol (1050 mg, 5.6 mmol, Example 138: step a) was dissolved into DCM (10 mL) and cooled to −20° C. To this was slowly added PCl$_3$ and the reaction was stirred at −20° C. for 15 minutes. The reaction was then warmed to RT for 15 minutes. The reaction was then quenched with water (5 mL) after cooling back to −20° C. The reaction was then warmed to RT and quenched with NaOH (246 mg, 1.1 mmol) in water (5 mL). The reaction mixture was separated and the organic layers were washed with brine. The water layer was adjusted with 10N NaOH to pH=10. The aqueous layer was then extracted with DCM and EtOAc, all organic layers were combined and dried with (MgSO$_4$) and the solvents were removed in vacuo. $^1$H-NMR (CDCl$_3$): δ 8.26 (s, 1H), 8.08–8.06 (d, 1H, J=5.14 Hz), 7.30–7.29 (d, 1H, J=5.35 Hz), 2.21 (s, 3H).

c) (Imino-{4-[3-(3-methyl-pyridin-4-yl)-benzene-sulfonyl]-5-methylsulfanyl-thiophen-2-yl}-methyl)-carbamic acid tert-butyl ester 4-Bromo-3-methyl-pyridine (100 mg, 0.219 mmol, Example 138: step b), {[4-(3-Boranyl-dihydroxy-benzene-sulfonyl)-5-methylsulfanyl-thiophen-2-yl]-imino-methyl}-carbamic acid tert-butyl ester (266 mg, 0.58 mmol, Example 140: step a) and Pd(PPh$_3$)$_4$ (134 mg, 0.12 mmol) were combined in aqueous Na$_2$CO$_3$ (2M, 2 mL), ethanol (2 mL) and toluene (4 mL) and heated to 80° C. overnight. The reaction mixture was dissolved into EtOAc and washed with brine. The organic layers were dried (MgSO$_4$) and the solvent was removed in vacuo. Purification by flash column chromatography (10% DCM/MeOH) afforded the title compound (120 mg, 41%). ESI-MS (m/z): Calcd. for C$_{23}$H$_{25}$N$_3$O$_4$S$_3$: 504.1 (M+1); found: 503.7.

d) 4-[3-(3-Methyl-pyridin-4-yl)-benzenesulfonyl]-5-methylsulfanyl-thiophene-2-carboxamidine trifluoroacetate (Imino-{4-[3-(3-methyl-pyridin-4-yl)-benzenesulfonyl]-5-methylsulfanyl-thiophen-2-yl}-methyl)-carbamic acid tert-butyl ester (Example 138: step c) was deprotected and purified as in Example 1: step d, yielding the title compound as a white glass. $^1$H-NMR (CD$_3$OD): δ 8.85 (s, 1H), 8.78–8.76 (d, 1H, J=5.78 Hz), 8.38 (s, 1H), 8.24–8.21 (m, 2H), 7.92–7.84 (m, 3H), 2.75 (s, 3H), 2.47 (s, 3H). ESI-MS (m/z): Calcd. for C$_{18}$H$_{17}$N$_3$O$_2$S$_3$: 404.1 (M+1); found: 404.1.

Example 139

4-[3-(3-Amino-5-methyl-pyridin-4-yl)-benzenesulfonyl]-5-methylsulfanyl-thiophene-2-carboxamidine trifluoroacetate

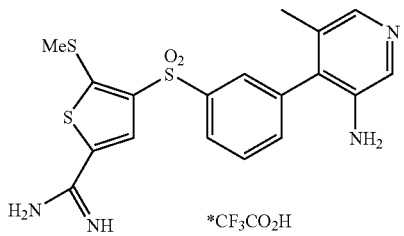

a) (5-Methyl-pyridin-3-yl)-carbamic acid tert-butyl ester

5-Methyl-nicotinic acid (2 g, 14.6 mmol) was dissolved into t-Butanol (59 mL). To this was added N,N-Diisopropylethylamine (7.6 mL, 43.8 mmol) and diphenylphosphoryl azide (3.8 mL, 17.5 mmol). The reaction was heated to 80° C. overnight in a flask fitted with septa and argon gas line. The solvents were evaporated in vacuo and the resulting residue was dissolved into EtOAc, washed with saturated NaHCO$_3$ and water. The combined organic layers were dried (MgSO$_4$) and the solvents were removed in vacuo. The residue was purified by flash column chromatography (SiO$_2$) (50% EtOAc in hexanes) that yielded the title compound as a white solid (2.03 g, 67%). $^1$H-NMR (CDCl$_3$): δ 8.22 (m, 1H), 8.14 (m, 1H), 7.88 (br s, 1H), 6.58 (br s, 1H), 2.34 (s, 3H), 1.55 (s, 9H).

b) (4-Iodo-5-methyl-pyridin-3-yl)-carbamic acid tert-butyl ester (5-Methyl-pyridin-3-yl)-carbamic acid tert-butyl ester (255 mg, 1.2 mmol, Example 139: step a) and trimethylethylenediamine (905 µL, 6.0 mmol) were dissolved into THF (4 mL) and cooled to −78° C. To this was added n-Butyllithium (2.5M, 2.4 mL, 6.0 mmol). The reaction was stirred at −78° C. for 30 minutes and then warmed to RT for 30 minutes. Iodine (1.5 g, 6.0 mmol) was dissolved into THF (4 mL) and added to the reaction mixture at −78° C. slowly. The reaction was warmed to RT for 1 hour and the solvents were removed in vacuo. The residue was dissolved into EtOAc and washed with brine and water. The combined organic layers were dried (MgSO$_4$) and solvents were removed in vacuo followed by purification by flash column chromatography (SiO$_2$) (50% EtOAc in hexanes) that yielded the title compound as a yellow solid (55 mg, 14%). $^1$H-NMR (CDCl$_3$): δ 8.91 (s, 1H), 8.07 (s, 1H), 6.81 (br s, 1H), 2.44 (s, 3H), 1.56 (s, 9H). ESI-MS (m/z): Calcd. for C$_{11}$H$_{15}$IN$_2$O$_2$: 335.0 (M+1); found: 334.9.

c) ({4-[3-(3-Amino-5-methyl-pyridin-4-yl)-benzene-sulfonyl]-5-methylsulfanyl-thiophen-2-yl}-imino-methyl)-carbamic acid tert-butyl ester (4-Iodo-5-methyl-pyridin-3-yl)-carbamic acid tert-butyl ester (106 mg, 0.32 mmol, Example 139: step b), {[4-(3-Boranyl-dihydroxy-benzenesulfonyl)-5-methylsulfanyl-thiophen-2-yl]-imino-methyl}-carbamic acid tert-butyl ester (145 mg, 0.32 mmol, Example 140: step a) and Pd(PPh$_3$)$_4$ (74 mg, 0.06 mmol) were combined in aqueous Na$_2$CO$_3$ (2M, 1.2 mL), ethanol (1.2 mL) and toluene (2.4 mL) and was heated to 80° C. overnight. The reaction mixture was dissolved into EtOAc and washed with brine. The organic layers were dried (MgSO$_4$) and solvents were removed in vacuo. Purification by flash column chromatography (40% EtOAc/hexanes) afforded the title compound. ESI-MS (m/z): Calcd. for C$_{28}$H$_{34}$N$_4$O$_6$S$_3$: 619.2 (M+1); found: 618.8.

d) 4-[3-(3-Amino-5-methyl-pyridin-4-yl)-benzene-sulfonyl]-5-methylsulfanyl-thiophene-2-carboxamidine trifluoroacetate ({4-[3-(3-Amino-5-methyl-pyridin-4-yl)-benzenesulfonyl]-5-methylsulfanyl-thiophen-2-yl}-imino-methyl)-carbamic acid tert-butyl ester (Example 139: step c) was deprotected and purified as in Example 1: step d, yielding the title compound as a white solid. $^1$H-NMR (CD$_3$OD): δ 8.37 (s, 1H), 8.18–8.16 (d, 1H, J=8.84 Hz), 8.06–8.05(m, 2H), 7.99 (s, 1H), 7.87 (t, 1H, J=7.67 Hz, J=7.44 Hz), 7.71–7.68 (d, 1H, J=7.67 Hz), 2.73 (s, 3H), 2.09 (s, 3H). ESI-MS (m/z): Calcd. for C$_{18}$H$_{18}$N$_4$O$_2$S$_3$: 419.1 (M+1); found: 419.1

Example 140

4-[3-(2,5-Dimethyl-1H-imidazol-4-yl)-benzenesulfonyl]-5-methylsulfanyl-thiophene-2-carboxamidine trifluoroacetate a) {[4-(3-Dihydroxyboranyl-benzenesulfonyl)-5-methylsulfanyl-thiophen-2-yl]-imino-methyl}-carbamic acid tert-butyl ester.

A solution of 2M i-PrMgCl in THF (1.1 mL, 2.2 mmol) was added dropwise at 0° C. to {[4-(3-bromo-benzenesulfonyl)-5-methylsulfanyl-thiophen-2-yl]-imino-methyl}-carbamic acid tert-butyl ester (0.5 g, 1.0 mmol) (Example 27c) in 5.0 mL THF. The solution was stirred for 20 mins at 0° C., then cooled to −78° C. and a solution of 2.5 M n-BuLi in hexanes (0.6 mL, 1.5 mmol) was added. The mixture was stirred for 5 mins then trimethylborate (0.35 mL, 3.3 mmol) was added at −78 C° C. and the mixture allowed to attain RT. The reaction was quenched with sat. NH$_4$Cl (10 mL) and extracted with EtOAc (3×20 mL), dried over Na$_2$SO$_4$ and evaporated. The crude solid was purified by elution from a 5 g SPE with 10% MeOH/DCM to give 0.45 g (95%) of the title compound as a yellow solid: $^1$H NMR (400 MHz, CD$_3$OD) δ 8.28 (m, 1H), 8.05 (m, 1H), 7.95 (m, 1H), 7.60 (m, 2H), 2.66 (s, 3H), 1.51 (s, 9H). Mass spectrum (ESI, m/z) calcd. for C$_{17}$H$_{21}$BN$_2$O$_6$S$_3$ 456.1, found 456.7 (M+H).

General Procedure for Suzuki Coupling:

To a flask charged with 0.50 g (1.1 mmol) of {[4-(3-dihydroxyboranyl-benzenesulfonyl)-5-methylsulfanyl-thiophen-2-yl]-imino-methyl}-carbamic acid tert-butyl ester, 0.22 g (1 mmol) of 5-iodo-2,4-dimethyl-1H-imidazole and 0.006 g of Pd(PPh$_3$)$_4$ (5 mol %) is added 8 mL of toluene, 4 mL of EtOH, and 4 mL of 2 M Na$_2$CO$_3$. The mixture is backfilled with argon and then heated at 80° C. for 4 hrs. The mixture is diluted with water (10 mL) and the product extracted with EtOAc (3×10 mL), dried (Na$_2$SO$_4$), filtered and evaporated. The crude product is purified by flash chromatography to give the title compound as a BOC-protected amidine. The BOC-protected amidine is stirred at 25° C. for 1 hr in 2 mL of 50% TFA/DCM, and then the solvents are evaporated and the crude product purified by RP-HPLC, eluting with a linear gradient of 10% CH$_3$CN to 50% CH$_3$CN in 0.1% TFA/H$_2$O over 30 mins to give 0.39 g (75%) of the title compound as a yellow solid: $^1$H NMR (400 MHz, CD$_3$OD) δ 8.37 (s, 1H), 8.25 (m, 1H), 8.14 (m, 2H), 7.88 (m, 1H), 7.63 (s, 1H), 2.74 (s, 3H), 2.68 (s, 3H), 2.49 (s, 3H). Mass spectrum (ESI, m/z) calcd. for C$_{17}$H$_{18}$N$_4$O$_2$S$_3$ 406.1, found 407.1 (M+H).

Example 141

4-[3-(3-Methyl-3H-imidazol-4-yl)-benzenesulfonyl]-5-methylsulfanyl-thiophene-2-carboxamidine trifluoroacetate

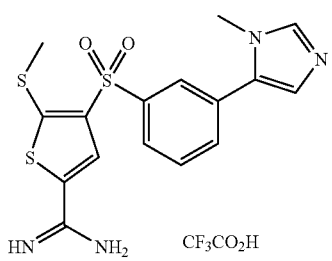

Prepared according to the general procedure in Example 140. $^1$H NMR (400 MHz, CD$_3$OD) δ 9.08 (s, 1H), 8.38 (s, 1H), 8.29 (m, 1H), 8.24 (m, 1H), 7.96 (m, 1H), 7.85 (m, 1H), 7.81 (s, 1H), 3.92 (s, 3H), 2.75 (s, 3H). Mass spectrum (ESI, m/z) calcd. for C$_{16}$H$_{16}$N$_4$O$_2$S$_3$ 392.1, found 393.1 (M+H).

Example 142

4-[3-(1-Methyl-1H-imidazol-2-yl)-benzenesulfonyl]-5-methylsulfanyl-thiophene-2-carboxamidine trifluoroacetate

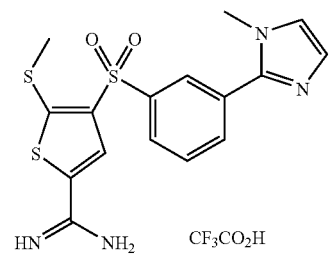

Prepared according to the general procedure in Example 140. $^1$H NMR (400 MHz, CD$_3$OD) δ 8.37 (s, 1H), 8.25 (m, 1H), 8.14 (m, 1H), 7.91 (m, 1H), 7.81 (m, 1H), 2.74 (s, 3H), 2.68 (s, 3H), 2.49 (s, 3H). Mass spectrum (ESI, m/z) calcd. for C$_{16}$H$_{16}$N$_4$O$_2$S$_3$ 392.1, found 393.1 (M+H).

Example 143

4-[3-(1-Methyl-1H-benzoimidazol-2-yl)-benzenesulfonyl]-5-methylsulfanyl-thiophene-2-carboxamidine trifluoroacetate

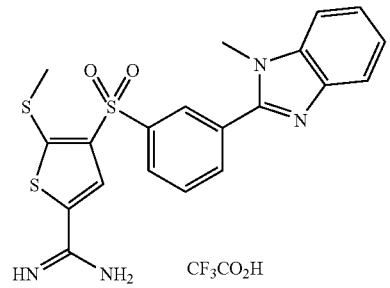

a) {[4-(3-Formyl-benzenesulfonyl)-5-methylsulfanyl-thiophen-2-yl]-imino-methyl}-carbamic acid tert-butyl ester A solution of 2 M i-PrMgCl in THF (1.1 mL, 2.2 mmol) was added dropwise at 0° C. to {[4-(3-bromo-benzenesulfonyl)-5-methylsulfanyl-thiophen-2-yl]-imino-methyl}-carbamic acid tert-butyl ester (0.5 g, 1.0 mmol) (Example 27c) in 5.0 mL THF. The solution was stirred for 20 mins at 0° C., then cooled to −78° C. and a solution of 2.5 M n-BuLi in hexanes (0.6 mL, 1.5 mmol) was added. The mixture was stirred for 5 mins then N,N-dimethylformamide (0.30 mL, 3.8 mmol) was added at −78° C. and the mixture allowed to attain RT. The reaction was quenched with sat. NH$_4$Cl (10 mL) and extracted with EtOAc (3×20 mL), dried over Na$_2$SO$_4$ and evaporated. The crude solid was purified by elution from a 20 g SPE with 50% EtOAc/hex to give 0.33 g (75%) of the title compound as a yellow solid: $^1$H NMR (400 MHz, CDCl$_3$) δ 10.06 (s, 1H), 8.48 (s, 1H), 8.26 (m, 1H), 8.10 (m, 1H), 8.06 (m, 1H), 7.71 (s, 1H), 2.50 (s, 3H), 1.51 (s, 9H). Mass spectrum (ESI, m/z) calcd. for C$_{18}$H$_{20}$N$_2$O$_5$S$_3$ 440.1, found 440.8 (M+H).

The above aldehyde (0.026 g, 0.06 mmol) and N-methyl-1,2-phenylenediamine (0.014 g, 0.12 mmol) in 0.2 mL of ethanol was heated at 80° C. for 12 hours. The solvent was evaporated and the residue taken up in 1 mL of 50% TFA/DCM and stirred for 30 mins at 25° C. The solvent was evaporated and the crude product purified by RP-HPLC, eluting with a linear gradient of 10% CH$_3$CN in 0.1% TFA/H$_2$O to 50% CH$_3$CN over 30 mins, to give 0.028 g (87%) of the title compound as red solid: $^1$H NMR (400 MHz, CD$_3$OD) δ 8.62 (m, 1H), 8.45 (m, 1H), 8.41 (s, 1H), 8.28 (m, 1H), 8.03 (m, 1H), 8.00 (m, 1H), 7.90 (m, 1H), 7.75 (m, 2H), 4.13 (s, 3H), 2.76 (s, 3H). Mass spectrum (ESI, m/z) calcd. for C$_{20}$H$_{18}$N$_4$O$_2$S$_3$ 442.1, found 443.1 (M+H).

Example 144

4-[3-(1H-Benzoimidazol-2-yl)-benzenesulfonyl]-5-methylsulfanyl-thiophene-2-carboxamidine trifluoroacetate

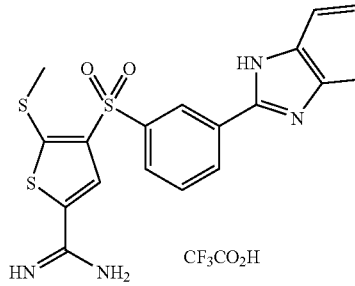

This compound was prepared according to Example 143 using 1,2-phenylenediamine. $^1$H NMR (400 MHz, CD$_3$OD) δ 8.85 (m, 1H), 8.44 (m, 1H), 8.42 (s, 1H), 8.33 (m, 1H), 7.95 (m, 1H), 7.82 (m, 2H), 7.56 (m, 2H), 2.74 (s, 3H). Mass spectrum (ESI, m/z) calcd. for C$_{19}$H$_{16}$N$_4$O$_2$S$_3$ 428.0, found 429.1 (M+H).

Example 145

4-[3-(1-Ethyl-1H-benzoimidazol-2-yl)-benzenesulfonyl]-5-methylsulfanyl-thiophene-2-carboxamidine trifluoroacetate

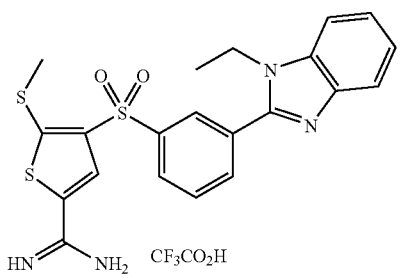

A mixture containing ({4-[3-(1H-benzoimidazol-2-yl)-benzenesulfonyl]-5-methylsulfanyl-thiophen-2-yl}-imino-methyl)-carbamic acid tert-butyl ester (prepared in Example 144) (25 mg, 0.05 mmol), K$_2$CO$_3$ (13 mg, 0.10 mmol), and iodoethane (12 mg, 0.08 mmol) in 0.5 mL acetone was heated to 60° C. for 2 hrs. The mixture was filtered then concentrated, and the residue dissolved in 0.5 mL of 50% TFA/DCM and stirred at 25° C. for 30 mins. The solvent was evaporated and the crude product purified by RP-HPLC, eluting with a linear gradient of 10% CH$_3$CN in 0.1% TFA/H$_2$O to 50% CH$_3$CN over 30 mins, to give 26 mg (93%) of the title compound as yellow solid: $^1$H NMR (400 MHz, CD$_3$OD) δ 8.58 (m, 1H), 8.44 (m, 1H), 8.41 (s, 1H), 8.20 (m, 1H), 8.02 (m, 2H), 7.90 (m, 1H), 7.71 (m, 2H), 4.55 (q, 2H), 2.75 (s, 3H), 1.59 (t, 3H). Mass spectrum (ESI, m/z) calcd. for C$_{21}$H$_{20}$N$_4$O$_2$S$_3$ 456.1, found 457.1 (M+H).

Example 146

3-{2-[3-(5-Carbamimidoyl-2-methylsulfanyl-thiophene-3-sulfonyl)-phenyl]-benzoimidazol-1-yl}-propane-1-sulfonic acid trifluoroacetate

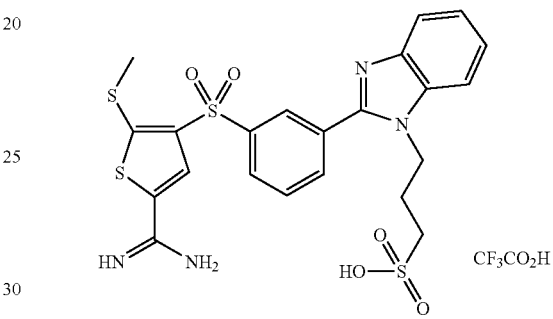

This compound was prepared in a similar manner to Example 145 using 1,3-propane sultone in DMF. $^1$H NMR (400 MHz, CD$_3$OD) δ 8.58 (m, 1H), 8.43 (m, 1H), 8.36 (s, 1H), 8.25 (m, 1H), 8.10 (m, 1H), 8.00 (m, 1H), 7.88 (m, 1H), 7.71 (m, 2H), 4.72 (t, 2H), 2.79 (t, cH), 2.77 (s, 3H), 2.32 (m, 2H). Mass spectrum (ESI, m/z) calcd. for C$_{22}$H$_{22}$N$_4$O$_5$S$_4$ 550.1, found 550.1 (M+H).

Example 147

4-[3-(Hydroxy-pyridin-2-yl-methyl)-benzenesulfonyl]-5-methylsulfanyl-thiophene-2-carboxamidine trifluoroacetate

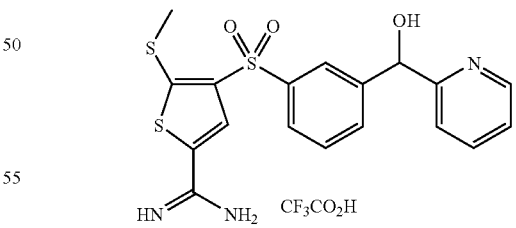

A solution of 2 M i-PrMgCl in THF (0.16 mL, 0.36 mmol) was added dropwise at 0° C. to {[4-(3-bromo-benzenesulfonyl)-5-methylsulfanyl-thiophen-2-yl]-imino-methyl}-carbamic acid tert-butyl ester (0.08 g, 0.16 mmol) (Example 27c) in 0.75 mL THF. The solution was stirred for 20 mins at 0° C., then cooled to −78° C. and a solution of 2.5 M n-BuLi in hexanes (0.084 mL, 0.21 mmol) was added. The mixture was stirred for 5 mins then 2-pyridinecarboxaldehyde (0.023 mL, 0.24 mmol) was added at −78° C. and the

Example 148

4-[3-(4-Hydroxy-1-methyl-piperidin-4-yl)-benzene-sulfonyl]-5-methylsulfanyl-thiophene-2-carboxami-dine trifluoroacetate

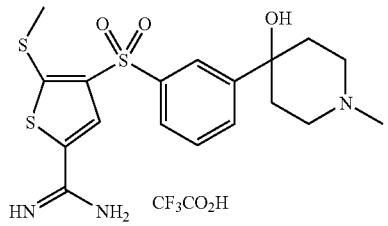

Prepared in a similar manner to Example 147 using 1-methyl-4-piperdone. $^1$H NMR (400 MHz, CD$_3$OD) δ 8.34 (s, 1H), 8.28 (m, 1H), 7.96 (m, 1H), 7.84 (m, 1H), 7.66 (m, 1H), 3.48 (m, 4H), 2.96 (s, 3H), 2.73 (s, 3H), 2.38 (m, 2H), 1.98 (m, 2H). Mass spectrum (ESI, m/z) calcd. for C$_{18}$H$_{23}$N$_3$O$_3$S$_3$ 425.1, found 426.1 (M+H).

Example 149

4-[3-(4-Hydroxy-tetrahydro-pyran-4-yl)-benzene-sulfonyl]-5-methylsulfanyl-thiophene-2-carboxami-dine trifluoroacetate

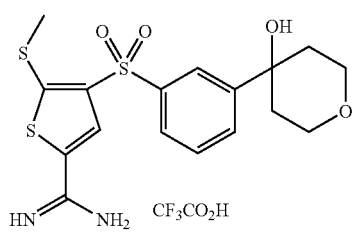

Prepared in a similar manner to Example 147 using tetrahydro-4H-pyran-4-one. $^1$H NMR (400 MHz, CD$_3$OD) δ 8.30 (s, 1H), 8.24 (m, 1H), 7.92 (m, 1H), 7.83 (m, 1H), 7.60 (m, 1H), 3.88 (m, 4H), 2.71 (s, 3H), 2.12 (m, 2H), 1.63 (m, 2H). Mass spectrum (ESI, m/z) calcd. for C$_{17}$H$_{20}$N$_2$O$_4$S$_3$ 412.1, found 413.0 (M+H).

Example 150

4-[3-(4-Methoxy-tetrahydro-pyran-4-yl)-benzene-sulfonyl]-5-methylsulfanyl-thiophene-2-carboxami-dine trifluoroacetate

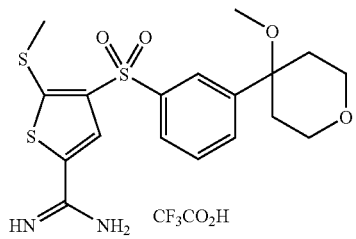

To a solution of the BOC-protected amidine (46 mg, 0.09 mmol) (prepared in example 149) in 0.2 mL of DMF at 25° C. was added NaH (60% oil dispersion, 5.7 mg, 0.14 mmol). The reaction was allowed to stir for 20 mins then iodomethane (6 uL, 0.09 mmol) was added and the reaction stirred for additional 12 hrs. The solvent was evaporated and the crude material purified by flash chromatography to give the title compound as a BOC protected amidine, which was deprotected in 2 mL of 50% TFA/DCM (25° C., 1 hr) to give the title compound (11.5 mg, 20%) as a yellow solid: $^1$H NMR (400 MHz, CD$_3$OD) δ 8.34 (s, 1H), 8.14 (m, 1H), 7.92 (m, 1H), 7.80 (m, 1H), 7.66 (m, 1H), 3.89 (m, 4H), 3.00 (s, 3H), 2.74 (s, 3H), 2.02 (m, 4H). Mass spectrum (ESI, m/z) calcd. for C$_{18}$H$_{22}$N$_2$O$_4$S$_3$ 426.1, found 427.1 (M+H).

Example 151

4-(3-Furan-2-yl-benzenesulfonyl)-5-methylsulfanyl-thiophene-2-carboxamidine trifluoroacetate

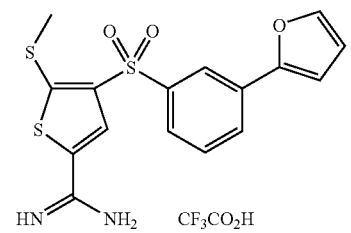

A solution containing 50 mg (0.10 mmol) of {[4-(3-bromo-benzenesulfonyl)-5-methylsulfanyl-thiophen-2-yl]-imino-methyl}-carbamic acid tert-butyl ester (prepared in Example 27c), 54 mg (0.15 mmol) of 2-tributylstannylfuran, and 12 mg (10 mol %) of Pd(PPh$_3$)$_4$ in 0.5 mL of THF was heated at 80° C. under Argon for 10 hrs. The reaction was quenched with NH$_4$Ac (5 mL), extracted with EtOAc (3×5 mL), dried over Na$_2$SO$_4$ and concentrated under reduced pressure. The crude material was stirred in 1 mL of 50% TFA/DCM for 1 hr at 25° C. and then concentrated and purified by RP-HPLC to give 19 mg (50%) of the title compound as a yellow solid: $^1$H NMR (400 MHz, CD$_3$OD) δ 8.35 (s, 1H), 8.32 (m, 1H), 8.01 (m, 1H), 7.90 (m, 1H), 7.66 (m, 1H), 7.65 (m, 1H), 6.98 (m, 1H), 6.60 (m, 1H), 2.75 (s, 3H). Mass spectrum (ESI, m/z) calcd. for C$_{16}$H$_{14}$N$_2$O$_3$S$_3$ 378.0, found 379.1 (M+H).

Example 152

3-[3-(5-Carbamimidoyl-2-methylsulfanyl-thiophene-3-sulfonyl)-phenyl]-but-2-enoic acid ethyl ester trifluoroacetate

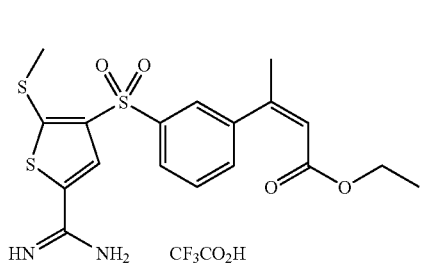

a) Imino-[5-methylsulfanyl-4-(3-tributylstannanyl-benzenesulfonyl)-thiophen-2-yl]-methyl}-carbamic acid tert-butyl ester A solution of 2 M i-PrMgCl in THF (1.1 mL, 2.2 mmol) was added dropwise at 0° C. to {[4-(3-bromo-benzenesulfonyl)-5-methylsulfanyl-thiophen-2-yl]-imino-methyl}-carbamic acid tert-butyl ester (0.5 g, 1.0 mmol) (Example 27c) in 5.0 mL THF. The solution was stirred for 20 mins at 0° C., then cooled to –78° C. and a solution of 2.5 M n-BuLi in hexanes (0.6 mL, 1.5 mmol) was added. The mixture was stirred for 5 mins then tributyltin chloride (0.65 g, 2.0 mmol) was added at –78° C. and the mixture allowed to attain RT. The reaction was quenched with sat. NH$_4$Cl (10 mL) and extracted with EtOAc (3×20 mL), dried over Na$_2$SO$_4$ and evaporated. The crude solid was purified by flash chromatography to give 0.35 g (50%) of the title compound as a yellow solid: $^1$H NMR (400 MHz, CDCl$_3$) δ 8.14 (m, 1H), 8.00 (s, 1H), 7.87 (m, 1H), 7.71 (m, 1H), 7.46 (m, 1H), 2.59 (s, 3H), 1.53 (s, 9H), 1.51 (m, 6H), 1.34 (m, 6H), 1.11 (m, 6H), 0.89 (m, 9H). Mass spectrum (ESI, m/z) calcd. for C$_{29}$H$_{46}$N$_2$O$_4$S$_3$Sn 702.2, found 702.7 (M+H).

A mixture containing 42 mg (0.06 mmol) of {imino-[5-methylsulfanyl-4-(3-tributylstannanyl-benzenesulfonyl)-thiophen-2-yl]-methyl}-carbamic acid tert-butyl ester, 21 mg (0.09 mmol) of ethyl cis-3-iodocrotonate, 3 mg (5 mol %) of Pd(PPh$_3$)$_4$ and 1 mg (10 mol %) of CuI in 0.3 mL of DMF was heated under argon at 100° C. for 12 hrs. The DMF was evaporated and the crude material stirred in 1 mL of 50% TFA/DCM for 1 hr at 25° C. The solvents were evaporated and the crude product was purified by RP-HPLC to give 7 mg (23%) of the title compound as a yellow solid: $^1$H NMR (400 MHz, CD$_3$OD) δ 8.30 (s, 1H), 8.02 (m, 1H), 7.88 (m, 1H), 7.61 (m, 2H), 6.05 (s, 1H), 3.90 (q, 3H), 2.78 (s, 3H), 2.22 (s, 3H), 1.02 (t, 3H). Mass spectrum (ESI, m/z) calcd. for C$_{18}$H$_{20}$N$_2$O$_4$S$_3$ 424.1, found 425.1 (M+H).

Example 153

4-[3-(1H-Imidazol-2-yl)-benzenesulfonyl]-5-methylsulfanyl-thiophene-2-carboxamidine trifluoroacetate

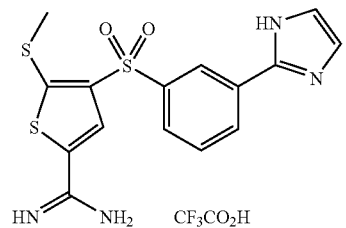

A mixture containing 20 mg (0.04 mmol) of {[4-(3-formyl-benzenesulfonyl)-5-methylsulfanyl-thiophen-2-yl]-imino-methyl}-carbamic acid tert-butyl ester (Example 143a), 10 uL (0.06 mmol) of 40% aqueous glyoxal, and 65 mg (0.84 mmol) of NH$_4$Ac was heated at 80° C. for 12 hrs in methanol. The solvents were evaporated and the residue stirred in 1 mL of 50% TFA/DCM for 1 hr at 25° C. The solvents were again evaporated and the crude material purified by RP-HPLC to give 4 mg (18%) of the title compound as a yellow solid: $^1$H NMR (400 MHz, CD$_3$OD) δ 8.64 (m, 1H), 8.39 (s, 1H), 8.24 (m, 2H), 7.88 (m, 1H), 7.63 (s, 1H), 2.73 (s, 3H). Mass spectrum (ESI, m/z) calcd. for C$_{15}$H$_{14}$N$_4$O$_2$S$_3$ 378.0, found 379.1 (M+H).

Example 154

N-[3'-(5-Carbamimidoyl-2-methylsulfanyl-thiophene-3-sulfonyl)-biphenyl-2-yl]-acetamide trifluoroacetate

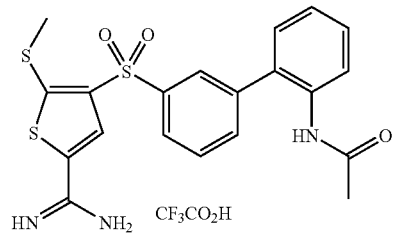

A solution containing 30 mg (0.06 mmol) of {[4-(2'-amino-biphenyl-3-sulfonyl)-5-methylsulfanyl-thiophen-2-yl]-imino-methyl}-carbamic acid tert-butyl ester (prepared according to the general procedure for Suzuki coupling in Example 140 using 2-aminophenyl boronic acid), 10 mg (0.09 mmol) of 2,6-lutidine, and 7 mg (0.07 mmol) of acetic anhydride was stirred in 2 mL of DCM at 25° C. for 12 hrs. The crude material was purified by flash chromatograpy to give the title compound as a BOC protected amidine which was deprotected by stirring at 25° C. for 1 hr in 1 mL of 50% TFA/DCM. The solvent was evaporated and the crude material purified by RP-HPLC to give 20 mg (60%) of the title compound as a yellow solid: $^1$H NMR (400 MHz, CD$_3$OD) δ 8.31 (s, 1H), 8.18 (m, 1H), 8.07 (m, 1H), 7.76 (m, 1H), 7.71 (s, 1H), 7.47 (m, 4H), 2.82 (s, 3H), 2.74 (s, 3H). Mass spectrum (ESI, m/z) calcd. for C$_{20}$H$_{19}$N$_3$O$_3$S$_3$ 445.1, found 446.1 (M+H).

Example 155

4-(2'-Methanesulfonylamino-biphenyl-3-sulfonyl)-5-methylsulfanyl-thiophene-2-carboxamidine trifluoroacetate

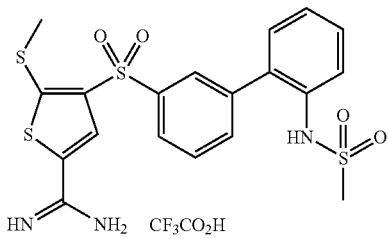

A solution containing 30 mg (0.06 mmol) of {[4-(2'-amino-biphenyl-3-sulfonyl)-5-methylsulfanyl-thiophen-2-yl]-imino-methyl}-carbamic acid tert-butyl ester (prepared according to the general procedure for Suzuki coupling in Example 140 using 2-aminophenyl boronic acid), 10 mg (0.09 mmol) of 2,6-lutidine, and 8 mg (0.07 mmol) of methanesulfonyl chloride was stirred in 2 mL of DCM at 25° C. for 12 hrs. The crude material was purified by flash chromatograpy to give the title compound as a BOC protected amidine which was deprotected by stirring at 25° C. for 1 hr in 1 mL of 50% TFA/DCM. The solvent was evaporated and the crude material purified by RP-HPLC to give 25 mg (70%) of the title compound as a yellow solid: $^1$H NMR (400 MHz, CD$_3$OD) δ 8.29 (s, 1H), 8.06 (m, 1H), 8.03 (m, 1H), 7.73 (m, 2H), 7.42 (m, 4H), 2.73 (s, 3H), 1.96 (s, 3H). Mass spectrum (ESI, m/z) calcd. for C$_{19}$H$_{19}$N$_3$O$_4$S$_4$ 481.0, found 482.1 (M+H).

Example 156

4-[5-Bromo-6-(3-imidazol-1-yl-propylamino)-pyridine-3-sulfonyl]-5-methylsulfanyl-thiophene-2-carboxamidine trifluoroacetate

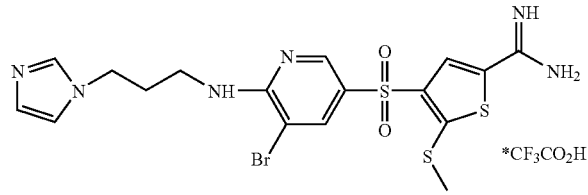

a) 4-[5-Bromo-6-(3-imidazol-1-yl-propylamino)-pyridine-3-sulfonyl]-5-methylsulfanyl-thiophene-2-carboxylic acid methyl ester To a vial containing a stirbar was added 4-(5-bromo-6-chloro-pyridine-3-sulfonyl)-5-methylsulfanyl-thiophene-2-carboxylic acid methyl ester (0.050 g, 0.113 mmol), (Example 2: step c), 3-imidazol-1-yl-propylamine (0.018 g, 0.146 mmol), diisopropylethylamine (0.073 g, 0.565 mmol), THF [0.50 mL], DMF [0.50 mL]. The reaction vessel was sealed and the solution was heated to 80° C. for 18 hours. Removal of the solvents in vacuo followed by chromatography (5% MeOH/DCM) yielded the title compound. $^1$H-NMR (CDCl$_3$): δ 8.69 (d, 1H, J=2.1 Hz), 8.10 (d, 1H J=2.1 Hz), 8.03 (s, 1H), 8.02 (s, 1H), 7.57 (s, 1H), 7.10 (s, 1H), 6.97 (s 1H), 5.70 (t, 1H, J=5.8 Hz), 4.06 (t, 2H, J=6.8 Hz), 3.89 (s, 3H), 3.57 (m, 2H), 2.97 (s, 2H), 2.90 (s, 2H), 2.64 (s, 3H), 2.17 (m, 2H). ESI-MS (m/z): Calcd. For C$_{18}$H$_{19}$BrN$_4$O$_4$S$_3$: 532.5 (M+H); found 530.9, 532.9.

b) 4-[5-Bromo-6-(3-imidazol-1-yl-propylamino)-pyridine-3-sulfonyl]-5-methylsulfanyl-thiophene-2-carboxamidine trifluoroacetate Trimethyl aluminum [2M in toluene], (1.12 mL, 2.26 mmol) was added slowly to a flask containing a stirbar and ammonium chloride (0.120 g, 2.26 mmol). This solution was placed in a 90° C. oil bath for 5 minutes under argon. Solution was allowed to cool to room temperature. This solution was then added to 4-[5-Bromo-6-(3-imidazol-1-yl-propylamino)-pyridine-3-sulfonyl]-5-methylsulfanyl-thiophene-2-carboxylic acid methyl ester (100 mg, 0.22 mmol) which was dissolved in toluene [2 mL]. Reaction was heated at 80° C. for two hours. Reaction was added to a slurry of silica gel in DCM. The slurry was filtered using 15% MeOH/DCM. Removal of the solvents in vacuo followed by reverse-phase HPLC of the residue [acetonitrile/water (0.01% TFA)] yielded the title compound. $^1$H-NMR (MeOH): δ 8.96 (s, 1H), 8.62 (d, 1H, J=2.0 Hz), 8.26 (s, 1H), 8.12 (d, 1H, J=2.3 Hz), 7.68 (t, 1H, J=1.7 Hz), 7.56 (t, 1H, J=1.6 Hz), 4.32 (t, 2H, J=7.2 Hz), 3.60 (t, 2H, J=6.7 Hz), 2.72(s, 3H), 2.24 (m, 2H). ESI-MS (m/z): Calcd. For C$_{17}$H$_{19}$BrN$_6$O$_2$S$_3$: 515.47 (M+H); found 515.1, 517.0.

Example 157

4-[5-Bromo-6-(2-methyl-2-morpholin-4-yl-propylamino)-pyridine-3-sulfonyl]-5-methylsulfanyl-thiophene-2-carboxamidine trifluoroacetate

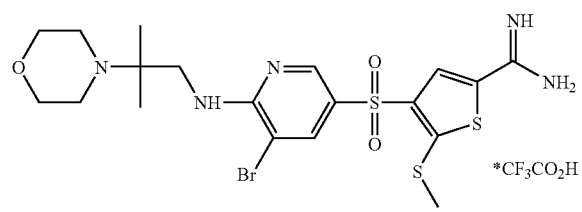

a) 4-[5-Bromo-6-(2-methyl-2-morpholin-4-yl-propylamino)-pyridine-3-sulfonyl]-5-methylsulfanyl-thiophene-2-carboxylic acid methyl ester The reaction was conducted following the procedure for Example 156: step a, using 4-(5-bromo-6-chloro-pyridine-3-sulfonyl)-5-methylsulfanyl-thiophene-2-carboxylic acid methyl ester (0.050 g, 0.113 mmol), (Example 2: step c), 2-methyl-2-morpholin-4-yl-propylamine (0.023 g, 0.146 mmol), diisopropylethylamine (0.073 g, 0.565 mmol), THF [0.5 mL], DMF [0.5 mL]. Chromatography of the residue (25%–50%EtOAc/Hx) yielded the title compound. $^1$H-NMR (CDCl$_3$): δ 8.70(d, 1H, J=2.1 Hz), 8.08(d, 1H, J=2.1 Hz), 8.02 (s, 1H), 6.82 (t, 1H, J=4.1), 3.90 (s, 3H), 3.76 (t, 4H, J=4.1), 3.37 (d, 2H, J=4.1), 2.64 (s, 3H), 2.57 (t, 4H, J=4.5),1.59 (s, 3H), 1.13 (s, 6H). ESI-MS (m/z): Calcd. For C$_{20}$H$_{26}$BrN$_3$O$_5$S$_3$: 565.54 (M+H); found 564.0, 565.9.

b) 4-[5-Bromo-6-(2-methyl-2-morpholin-4-yl-propylamino)-pyridine-3-sulfonyl]-5-methylsulfanyl-thiophene-2-carboxamidine trifluoroacetate The reaction was conducted following the procedure for Example 156: step b, using trimethyl aluminum [2M in toluene], (0.194 mL, 0.389 mmol), ammonium chloride (0.021 g, 0.389 mmol), 4-[5-bromo-6-(2-methyl-2-morpholin-4-yl-propylamino)-pyridine-3-sulfonyl]-5-methylsulfanyl-thiophene-2-carboxylic acid methyl ester (0.022 g, 0.039 mmol), toluene [1 mL]. Reverse-phase HPLC yielded title compound. ESI-MS (m/z): Calcd. for $C_{19}H_{26}BrN_5O_3S_3$: 549.54 (M+H); found 547.9, 549.9.

Example 158

4-{5-Bromo-6-[(6-trifluoromethyl-pyridin-3-ylmethyl)-amino]-pyridine-3-sulfonyl}-5-methylsulfanyl-thiophene-2-carboxamidine trifluoroacetate

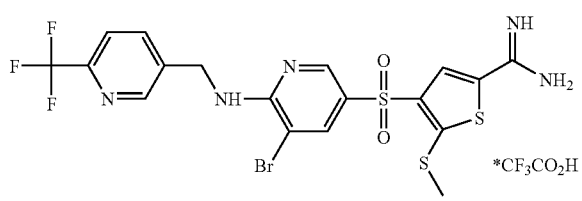

a) 4-{5-Bromo-6-[(6-trifluoromethyl-pyridin-3-ylmethyl)-amino]-pyridine-3-sulfonyl}-5-methylsulfanyl-thiophene-2-carboxylic acid methyl ester The reaction was conducted following the procedure for Example 156: step a, using 4-(5-bromo-6-chloro-pyridine-3-sulfonyl-5-methylsulfanyl-thiophene-2-carboxylic acid methyl ester (0.050 g, 0.113 mmol), (Example 2: step c), 3-aminomethyl-6-trifluoromethyl pyridine (0.026 g, 0.146 mmol), diisopropylethylamine (0.073 g, 0.565 mmol), THF [0.5 mL], DMF [0.5 mL]. Chromatography of the residue (25%–50%EtOAc/Hx) yielded the title compound. ESI-MS (m/z): Calcd. For $C_{19}H_{15}BrN_3O_4S_3$: 583.44 (M+H); found 582.0, 583.9.

b.) 4-{5-Bromo-6-[(6-trifluoromethyl-pyridin-3-ylmethyl)-amino]-pyridine-3-sulfonyl}-5-methylsulfanyl-thiophene-2-carboxamidine trifluoroacetate The reaction was conducted following the procedure for Example 156: step b, using trimethyl aluminum [2M in toluene], (0.463 mL, 0.927 mmol), ammonium chloride (0.049 g, 0.927 mmol), 4-{5-bromo-6-[(6-trifluoromethyl-pyridin-3-ylmethyl)-amino]-pyridine-3-sulfonyl}-5-methylsulfanyl-thiophene-2-carboxylic acid methyl ester (0.054 g, 0.093 mmol), toluene [1 mL]. Reverse-phase HPLC yielded title compound. ESI-MS (m/z): Calcd. For $C_{18}H_{15}BrF_3N_5O_2S_3$: 567.44 (M+H); found 566.0, 567.9.

Example 159

4-{5-Bromo-6-[2-(3H-imidazol-4-yl)-ethylamino]-pyridine-3-sulfonyl}-5-methylsulfanyl-thiophene-2-carboxamidine trifluoroacetate

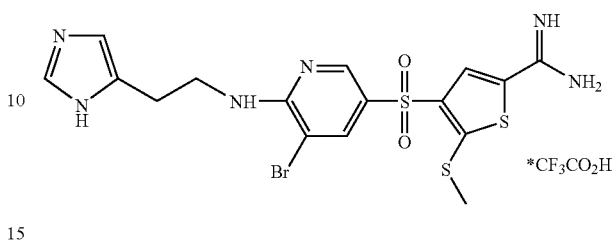

a) 4-{5-Bromo-6-[2-(3H-imidazol-4-yl)-ethylamino]-pyridine-3-sulfonyl}-5-methylsulfanyl-thiophene-2-carboxylic acid methyl ester The reaction was conducted following the procedure for Example 156: step a, using. 4-(5-bromo-6-chloro-pyridine-3-sulfonyl)-5-methylsulfanyl-thiophene-2-carboxylic acid methyl ester (0.050 g, 0.113 mmol), (Example 2: step c), 2-(3H-imidazol-4-yl)-ethylamine (0.027 g, 0.146 mmol), diisopropylethylamine (0.073 g, 0.565 mmol), THF [0.5 mL], DMF [0.5 mL]. Chromatography of the residue (0%–6% MeOH/DCM) yielded the title compound. ESI-MS (m/z): Calcd. for $C_{17}H_{17}BrN_4O_4S_3$: 518.44 (M+H); found 517.0, 519.

b) 4-{5-Bromo-6-[2-(3H-imidazol-4-yl)-ethylamino]-pyridine-3-sulfonyl}-5-methylsulfanyl-thiophene-2-carboxamidine trifluoroacetate The reaction was conducted following the procedure for Example 156: step b, using trimethyl aluminum [2M in toluene], (0.773 mL, 1.546 mmol), ammonium chloride (0.082 g, 1.546 mmol), 4-{5-bromo-6-[2-(3H-imidazol-4-yl)-ethylamino]-pyridine-3-sulfonyl}-5-methylsulfanyl-thiophene-2-carboxylic acid methyl ester (0.080 g, 0.155 mmol), toluene [2 mL]. HPLC yielded title compound. ESI-MS (m/z): Calcd. for $C_{17}H_{17}BrN_4O_4S_3$: 501.45 (M+H); found 502.2, 504.2.

Example 160

4-[5-Bromo-6-(4-sulfamoyl-benzylamino)-pyridine-3-sulfonyl]-5-methylsulfanyl-thiophene-2-carboxamidine trifluoroacetate

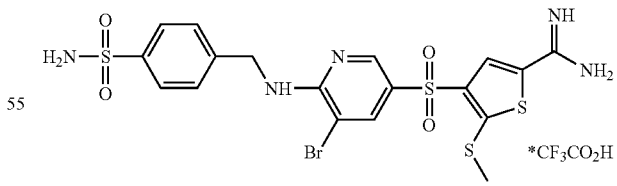

a) 4-[5-Bromo-6-(4-sulfamoyl-benzylamino)-pyridine-3-sulfonyl]-5-methylsulfanyl-thiophene-2-carboxylic acid methyl ester The reaction was conducted following the procedure for Example 156: step a, using. 4-(5-bromo-6-chloro-pyridine-3-sulfonyl)-5-methylsulfanyl-thiophene-2-carboxylic acid methyl ester (0.050 g, 0.113 mmol), (Example 2: step c), 4-aminomethyl-benzenesulfonamide (0.033 g, 0.146 mmol), diisopropylethylamine (0.073 g, 0.565 mmol), THF [0.5 mL], DMF [0.5 mL]. Chromatography of the residue (0%–5% MeOH/DCM) yielded the title compound. ESI-MS (m/z): Calcd. for $C_{19}H_{18}BrN_3O_6S_4$: 592.53 (M+H); found 592.0, 593.9.

b) 4-[5-Bromo-6-(4-sulfamoyl-benzylamino)-pyridine-3-sulfonyl]-5-methylsulfanyl-thiophene-2-carboxamidine trifluoroacetate The reaction was conducted following the procedure for Example 156: step b, using trimethyl aluminum [2M in toluene], (0.773 mL, 1.546 mmol), ammonium chloride (0.082 g, 1.546 mmol), 4-{5-bromo-6-[2-(3H-imidazol-4-yl)-ethylamino]-pyridine-3-sulfonyl}-5-methylsulfanyl-thiophene-2-carboxylic acid methyl ester (0.080 g, 0.155 mmol), toluene [2 mL]. Reverse-phase HPLC yielded the title compound. ESI-MS (m/z): Calcd. for $C_{17}H_{17}BrN_4O_4S_3$: 501.45 (M+H); found 502.2, 504.2.

Example 161

4-(6-Benzylamino-5-bromo-pyridine-3-sulfonyl)-5-methylsulfanyl-thiophene-2-carboxamidine trifluoroacetate

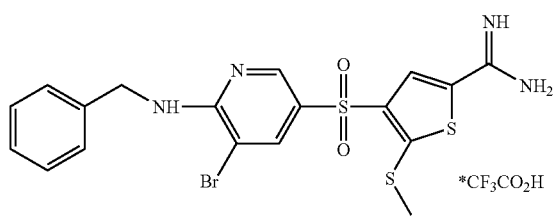

a) 4-(6-Benzylamino-5-bromo-pyridine-3-sulfonyl)-5-methylsulfanyl-thiophene-2-carboxylic acid methyl ester To a vial containing a stirbar was added 4-(5-bromo-6-chloro-pyridine-3-sulfonyl)-5-methylsulfanyl-thiophene-2-carboxylic acid methyl ester (0.020 g, 0.045 mmol), (Example 2: step c), benzylamine (0.005 g, 0.407 mmol), MeOH [2.0 mL]. Reaction vessel was sealed and heated to 50° C. for 72 hours. Removal of the solvents in vacuo followed by chromatography of the residue (10%–20% EtOAc/Hx) yielded the title compound. ESI-MS (m/z): Calcd. for $C_{19}H_{17}BrN_2O_4S_3$: 514.45 (M+H); found 513.2, 515.1.

b) 4-(6-Benzylamino-5-bromo-pyridine-3-sulfonyl)-5-methylsulfanyl-thiophene-2-carboxamidine trifluoroacetate The reaction was conducted following the procedure for Example 156: step b, using trimethyl aluminum [2M in toluene], (0.120 mL, 0.253 mmol), ammonium chloride (0.014 g, 0.253 mmol), 4-(6-Benzylamino-5-bromo-pyridine-3-sulfonyl)-5-methylsulfanyl-thiophene-2-carboxylic acid methyl ester (0.013 g, 0.0253 mmol), toluene [2 mL]. Reverse-phase HPLC yielded title compound. ESI-MS (m/z): Calcd. for $C_{19}H_{18}BrN_3O_2S_3$: 497.47 (M+H); found 497.3, 499.1.

Example 162

4-(5-Bromo-6-isobutylamino-pyridine-3-sulfonyl)-5-methylsulfanyl-thiophene-2-carboxamidine trifluoroacetate

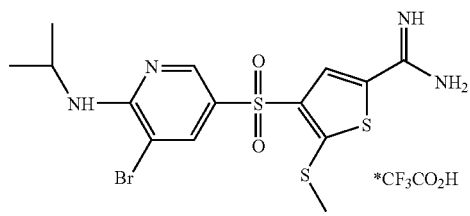

a) 4-(5-Bromo-6-isopropylamino-pyridine-3-sulfonyl)-5-methylsulfanyl-thiophene-2-carboxylic acid methyl ester To a vial containing a stirbar was added 4-(5-bromo-6-chloro-pyridine-3-sulfonyl)-5-methylsulfanyl-thiophene-2-carboxylic acid methyl ester (0.100 g, 0.226 mmol), (Example 2: step c), isopropylamine (0.012 g, 0.204 mmol), THF [2.0 mL]. Reaction vessel was sealed and heated to 70° C. for 72 hours. Removal of the solvents in vacuo followed by chromatography (0%–15% EtOAc/Hx) yielded the title compound. ESI-MS (m/z): Calcd. for $C_{15}H_{17}BrN_2O_4S_3$: 466.41 (M+H); found 466.9.

b) 4-(5-Bromo-6-isobutylamino-pyridine-3-sulfonyl)-5-methylsulfanyl-thiophene-2-carboxamidine trifluoroacetate The reaction was conducted following the procedure for Example 156: step b, using trimethyl aluminum [2M in toluene], (0.620 mL, 1.247 mmol), ammonium chloride (0.067 g, 1.247 mmol), 4-(5-bromo-6-isopropylamino-pyridine-3-sulfonyl)-5-methylsulfanyl-thiophene-2-carboxylic acid methyl ester (0.058 g, 0.125 mmol), toluene [2 mL]. Reverse-phase HPLC yielded title compound. ESI-MS (m/z): Calcd. for $C_{14}H_{17}BrN_4O_2S_3$: 450.41 (M+H); found 449.1, 451.0.

Example 163

4-{5-Bromo-6-[(pyridin-3-ylmethyl)-amino]-pyridine-3-sulfonyl}-5-methylsulfanyl-thiophene-2-carboxamidine trifluoroacetate

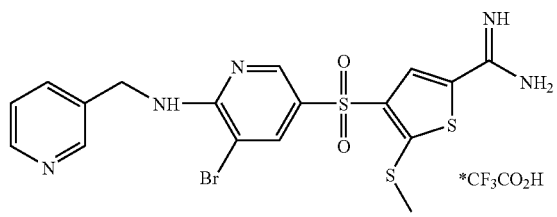

a) 4-{5-Bromo-6-[(pyridin-3-ylmethyl)-amino]-pyridine-3-sulfonyl}-5-methylsulfanyl-thiophene-2-carboxylic acid methyl ester The reaction was conducted following the procedure for Example 162: step a, using 4-(5-bromo-6-chloro-pyridine-3-sulfonyl)-5-methylsulfanyl-thiophene-2-carboxylic acid methyl ester (0.100 g, 0.226 mmol), (Example 2: step c), 3-aminomethyl pyridine (0.046 g, 0.430 mmol), THF [4.0 mL]. Chromatography of the residue (25%–50% EtOAc/Hx) yielded the title compound. ESI-MS (m/z): Calcd. for $C_{18}H_{16}BrN_3O_4S_3$: 515.44 (M+H); found 514.1, 516.0.

b) 4-{5-Bromo-6-[(pyridin-3-ylmethyl)-amino]-pyridine-3-sulfonyl}-5-methylsulfanyl-thiophene-2-carboxamidine trifluoroacetate The reaction was conducted following the procedure for Example 156: step b, using trimethyl aluminum [2M in toluene], (0.710 mL, 1.439 mmol), ammonium chloride (0.077 g, 1.439 mmol) 4-{5-Bromo-6-[(pyridin-3-ylmethyl)-amino]-pyridine-3-sulfonyl}-5-methylsulfanyl-thiophene-2-carboxylic acid methyl ester (0.074 g, 0.1439 mmol), toluene [2 mL]. Reverse-phase HPLC yielded title compound. ESI-MS (m/z): Calcd. for $C_{17}H_{16}BrN_5O_2S_3$: 499.44 (M+H); found 499.1, 501.0.

Example 164

4-{5-Bromo-6-[(pyridin-4-ylmethyl)-amino]-pyridine-3-sulfonyl}-5-methylsulfanyl-thiophene-2-carboxamidine trifluoroacetate

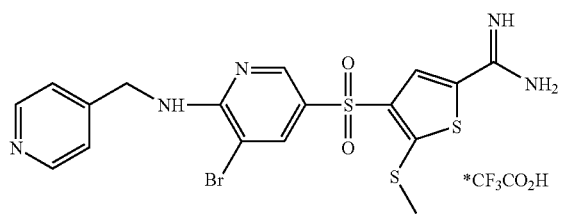

a) 4-(5-Bromo-6-chloro-pyridine-3-sulfonyl)-5-methylsulfanyl-thiophene-2-carboxamidine Trimethyl aluminum [2M in toluene], (0.850 mL, 1.694 mmol) was added slowly to a flask containing ammonium chloride (0.091 g, 1.694 mmol) and a stir bar. This solution was placed in a 90° C. oil bath for 5 minutes under argon. Solution was then allowed to cool to room temperature. This solution was then added 4-(5-bromo-6-chloro-pyridine-3-sulfonyl)-5-methylsulfanyl-thiophene-2-carboxylic acid methyl ester (0.075 g, 0.1694 mmol), (Example 2: step c), which was dissolved in toluene [1 mL]. Reaction was heated at 80° C. for two hours. Reaction was added to a slurry of silica gel in DCM. The slurry was filtered using 15% MeOH/DCM. Used crude material in next step. ESI-MS (m/z): Calcd. for $C_{11}H_9BrClN_3O_2S_3$: 427.76 (M+H); found 426.0, 428.0.

b) {[4-(5-Bromo-6-chloro-pyridine-3-sulfonyl)-5-methylsulfanyl-thiophen-2-yl]-imino-methyl}-carbamic acid tert-butyl ester To a flask containing a stir bar was added 4-(5-bromo-6-chloro-pyridine-3-sulfonyl)-ethylsulfanyl-thiophene-2-carboxamidine (0.96 g, 2.25 mmol), di-tert-butyl dicarbonate (0.74 g, 3.39 mmol), diisopropylamine (1.16 g, 9.03 mmol), DMF (60.0 mL). Solution was stirred at room temperature for 18 hours. Removal of the solvents in vacuo followed by chromatography (10%–15% EtOAc/Hx). Compound contained residual di-tert-butyl dicarbonate. Compound was dissolved in hexane, heated to 40° C. for 1 hour. Solution was filtered to yield title compound. ESI-MS (m/z): Calcd. for $C_{11}H_9BrClN_3O_2S_3$: 527.76 (M+H); found 426.0, 428.0.

c) [(4-{5-Bromo-6-[(pyridin-4-ylmethyl)-amino]-pyridine-3-sulfonyl}-5-methylsulfanyl-thiophen-2-yl)-imino-methyl]-carbamic acid tert-butyl ester To a vessel containing a stir bar was added {[4-(5-bromo-6-chloro-pyridine-3-sulfonyl)-5-methylsulfanyl-thiophen-2-yl]-imino-methyl}-carbamic acid tert-butyl ester (0.035 g, 0.066 mmol), 4-aminomethylpyridine (0.015 g, 0.133 mmol), THF [3 mL]. The reaction vessel was sealed and heated to 70° C. for 18 hours, cooled to room temperature and concentrated in vacuo. The crude residue was dissolved in a solution of chloroform/trifluoroacetic acid (1/1) [2 mL] and was allowed to stir at room temperature for 2 hours. The reaction was concentrated in vacuo followed by reverse-phase HPLC [acetonitrile/water (0.01% TFA)] to give the title compound. ESI-MS (m/z): Calcd. for $C_{17}H_{16}BrN_5O_2S_3$: 499.44 (M+H); found 498.0, 500.0.

Example 165

4-{5-Bromo-6-[(pyridin-2-ylmethyl)-amino]-pyridine-3-sulfonyl}-5-methylsulfanyl-thiophene-2-carboxamidine trifluoroacetate

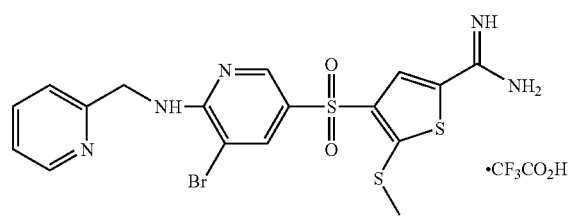

a) 4-{5-Bromo-6-[(pyridin-2-ylmethyl)-amino]-pyridine-3-sulfonyl}-5-methylsulfanyl-thiophene-2-carboxamidine trifluoroacetate The reaction was conducted following the procedure for Example 164: step c, using {[4-(5-bromo-6-chloro-pyridine-3-sulfonyl)-5-methylsulfanyl-thiophen-2-yl]-imino-methyl}-carbamic acid tert-butyl ester (0.035 g, 0.066 mmol), (example 164: step b), 2-aminomethylpyridine (0.014 g, 0.133 mmol), THF [3 mL], followed by chloroform/TFA (1:1) to yield the title compound. ESI-MS (m/z): Calcd. for $C_{17}H_{16}BrN_5O_2S_3$: 499.44 (M+H); found 499.1, 501.0.

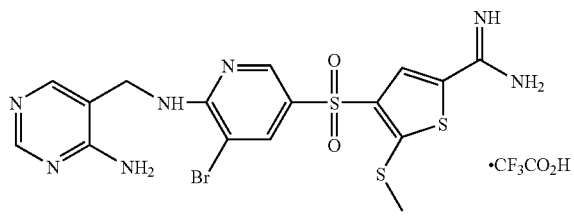

The reaction was conducted following the procedure for Example 164: step c, using {[4-(5-bromo-6-chloro-pyridine-3-sulfonyl)-5-methylsulfanyl-thiophen-2-yl]-imino-methyl}-carbamic acid tert-butyl ester (0.035 g, 0.067 mmol), 4-amino-5-aminomethyl-2-methylpyrimidine (0.018 g, 0.135 mmol), THF [2 mL], followed by DCM/TFA (1:1) and reverse-phase HPLC to yield the title compound. ESI-MS (m/z): Calcd. for $C_{18}H_{19}BrN_6O_2S_3$: 528.48 (M+H); found 528.0, 529.9.

Example 167

4-[5-Bromo-6-(3-hydroxy-2,2-dimethyl-propylamino)-pyridine-3-sulfonyl]-5-methylsulfanyl-thiophene-2-carboxamidine trifluoroacetate

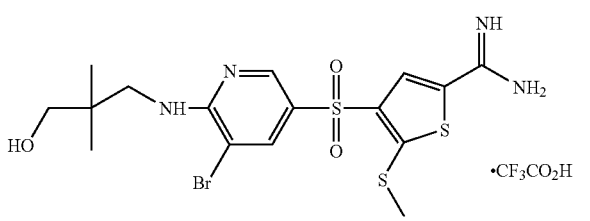

The reaction was conducted following the procedure for Example 164: step c, using {[4-(5-bromo-6-chloro-pyridine-3-sulfonyl)-5-methylsulfanyl-thiophen-2-yl]-imino-methyl}-carbamic acid tert-butyl ester (0.035 g, 0.066 mmol), 3-amino-2,2-dimethylpropanol (0.013 g, 0.133 mmol), THF [2 mL], followed by DCM/TFA (1:1) and reverse-phase HPLC to yield the title compound. ESI-MS (m/z): Calcd. for $C_{17}H_{22}BrN_3O_3S_3$: 493.48 (M+H); found 493.1, 495.0.

Example 168

4-{5-Bromo-6-[(3-methyl-thiophen-2-ylmethyl)-amino]-pyridine-3-sulfonyl}-5-methylsulfanyl-thiophene-2-carboxamidine trifluoroacetate

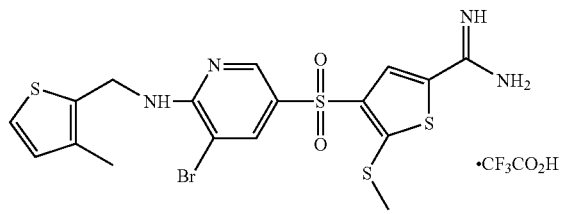

To a vessel containing a stir bar was added {[4-(5-bromo-6-chloro-pyridine-3-sulfonyl)-5-methylsulfanyl-thiophen-2-yl]-imino-methyl}-carbamic acid tert-butyl ester (0.035 g, 0.066 mmol), 3-methylthiophene-2-methylamine (0.016 g, 0.133 mmol), THF [2 mL]. The reaction vessel was sealed and heated to 70° C. for 18 hours, cooled to room temperature and concentrated in vacuo. Chromatography of crude material (10%–25% EtOAC/Hx) yielded the intermediate which was dissolved in a solution of chloroform/trifluoroacetic acid (1/1) [2 mL] and was allowed to stir at room temperature for 2 hours. The reaction was concentrated in vacuo followed by reverse-phase HPLC [acetonitrile/water (0.01% TFA)] to give the title compound. ESI-MS (m/z): Calcd. for $C_{18}H_{18}BrN_3O_2S_4$: 517.52 (M+H); found 516.9, 518.9.

Example 169

4-{5-Bromo-6-[(tetrahydro-furan-2-ylmethyl)-amino]-pyridine-3-sulfonyl}-5-methylsulfanyl-thiophene-2-carboxamidine trifluoroacetate

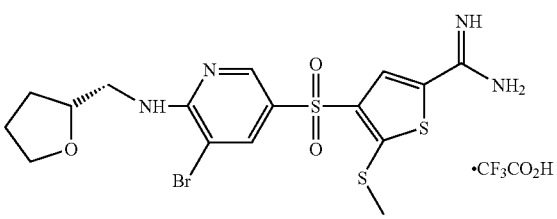

a) 4-{5-Bromo-6-[(tetrahydro-furan-2-ylmethyl)-amino]-pyridine-3-sulfonyl}-5-methylsulfanyl-thiophene-2-carboxylic acid methyl ester The reaction was conducted following the procedure for Example 156: step a, using. 4-(5-bromo-6-chloro-pyridine-3-sulfonyl)-5-methylsulfanyl-thiophene-2-carboxylic acid methyl ester (0.050 g, 0.113 mmol), (Example 2: step c), c-(tetrahydro-furan-2-yl)-methylamine (0.015 g, 0.146 mmol), diisopropylethylamine (0.073 g, 0.565 mmol), THF [0.5 mL], DMF [0.5 mL]. Chromatography of the residue (10%–35% EtOAc/Hx) yielded the title compound. ESI-MS (m/z): Calcd. for $C_{17}H_{19}BrN_2O_5S_4$: 508.45 (M+H); found 507.1, 509.0 b) 4-{5-Bromo-6-[(tetrahydro-furan-2-ylmethyl)-amino]-pyridine-3-sulfonyl}-5-methylsulfanyl-thiophene-2-carboxamidine trifluoroacetate The reaction was conducted following the procedure for Example 156: step b, using trimethyl aluminum [2M in toluene], (0.443 mL, 0.867 mmol), ammonium chloride (0.046 g, 0.867 mmol), 4-{5-bromo-6-[(tetrahydro-furan-2-ylmethyl)-amino]-pyridine-3-sulfonyl}-5-methylsulfanyl-thiophene-2-carboxylic acid methyl ester (0.044 g, 0.087 mmol), toluene [1 mL]. Reverse-phase HPLC yielded title compound. ESI-MS (m/z): Calcd. For $C_{16}H_{19}BrN_4O_3S_3$: 492.45 (M+H); found 491.1, 493.0.

Example 170

4-{4'-[N'-(4-Methanesulfonyl-butyl)-guanidino]-2'-methyl-biphenyl-3-sulfonyl}-5-methylsulfanyl-thiophene-2-carboxamidine trifluoroacetate

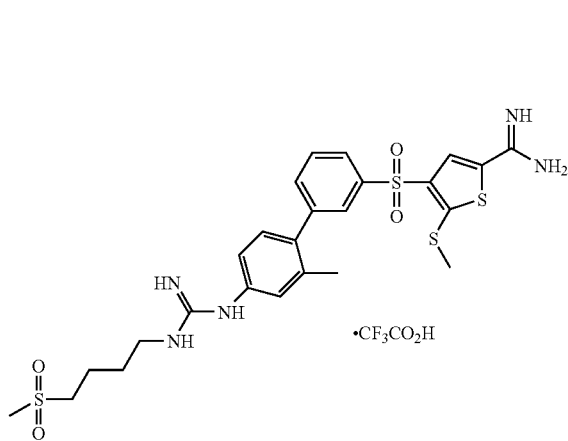

a) 2-methyl-1-(4-methanesulfonyl-butyl)-1,3-bis (carbamic acid-tert-butyl ester)-isothiourea The reaction was conducted following the procedure for Example 171: step b, using 4-methanesulfonyl-butylamine (0.058 g, 0.378 mmol), 2-methyl-1-(3-methanesulfonyl-propyl)-1,3-bis (carbamic acid-tert-butyl ester)-isothiourea (0.100 g, 0.344 mmol), Triphenylphosphine (0.098 g, 0.378 mmol), THF[6 mL]. To this was added Diisopropyl azodicarboxylate (0.076 g, 0.378 mmol). Chromatography of the residue (50% EtOAc/Hx) yielded the title compound.

b) [Imino-(4-{4'-[N'-(4-methanesulfonyl-butyl)-N', N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester The reaction was conducted following the procedure for Example 171: step c, using {[4-(4'-amino-2'-methyl-biphenyl-3-sulfonyl)-5-methylsulfanyl-thiophen-2-yl]-imino-methyl)-carbamic acid tert-butyl ester (0.025 g, 0.480 mmol), (Example 120: step b), 2-methyl-1-(4-methanesulfonyl-butyl)-1,3-bis (carbamic acid-tert-butyl ester)-isothiourea (0.101 g, 0.240 mmol), MeOH [2 mL], acetic acid (0.029 g, 0.480 mmol). Chromatography (10%–20% EtOAc/Hx). The compound was dissolved in trifluoroacetic acid/dichloromethane (1:1). [4 mL]. Solvent was removed in vacuo followed by reverse-phase HPLC to yield the title compound. ESI-MS (m/z): Calcd. for $C_{25}H_{31}N_5O_4S_4$: 594.81 (M+H); found 594.1.

Example 171

4-{4'-[N'-(3-Methanesulfonyl-propyl)-guanidino]-2'-methyl-biphenyl-3-sulfonyl}-5-methylsulfanyl-thiophene-2-carboxamidine trifluoroacetate

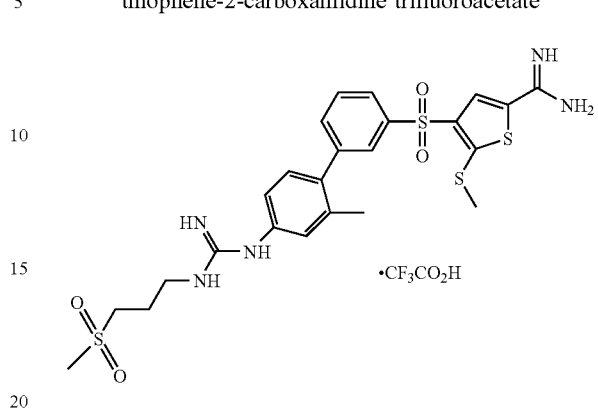

a) 3-Methanesulfonyl-propan-1-ol 3-bromo-propan-1-ol was dissolved in EtOH [2 mL], methane sulfinic acid was dissolved in H$_2$O [2 mL]. The two solutions were added together and heated to 50° C. for 18 hours. Reaction was cooled to room temperature and the compound was extracted with EtOAc, dried using sodium sulfate, and the solvent was removed in vacuo. Chromatography of the residue (1%–7% MeOH/DCM) yielded the title compound. $^1$H-NMR (CDCl$_3$): δ 3.69 (m, 2H), 3.14 (m, 2H), 2.91 (s, 3H), 2.02 (m, 2H).

b) 2-methyl-1-(3-methanesulfonyl-propyl)-1,3-bis (carbamic acid-tert-butyl ester)-isothiourea Under argon, 3-methanesulfonyl-propan-1-ol (0.059 g, 0.362 mmol), 2-methyl-1-(3-methanesulfonyl-propyl)-1,3-bis (carbamic acid-tert-butyl ester)-isothiourea (0.123 g, 0.329 mmol), Triphenylphosphine (0.112 g, 0.362 mmol), THF [8 mL] was charged to a flask containing a stirbar. To this was added diisopropyl azodicarboxylate (0.095 g, 0.362 mmol). Reaction stirred at room temperature for 18 hours. Solvent was removed in vacuo followed by chromatography (0%–25% EtOAc/Hx) to yield title compound (0.089 g). $^1$H-NMR (CDCl$_3$): δ 3.75 (t, 2H, J=6.7 Hz), 3.14 (m, 2H), 2.94 (s, 3H), 2.42 (s, 3H), 2.20 (m, 2H), 1.52 (s, 9H), 1.50 (s, 9H).

c) [Imino-(4-{4'-[N'-(3-methanesulfonyl-propyl)-N', N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester 2-methyl-1-(3-methanesulfonyl-propyl)-1,3-bis (carbamic acid-tert-butyl ester)-isothiourea (0.089 g, 0.217 mmol), {[4-(4'-Amino-2'-methyl-biphenyl-3-sulfonyl)-5-methylsulfanyl-thiophen-2-yl]-imino-methyl}-carbamic acid tert-butyl ester (0.022 g, 0.043 mmol), (Example 120: step b), MeOH [2 mL] was added to a flask containing a stirbar. To this was added acetic acid (0.026 g, 0.434 mmol) and the solution was heated to 40° C. for 18 hours. Reaction was cooled to room temperature, solvent was removed in vacuo, and residue was chromatographed (10%–20% EtOAc/DCM) giving the title compound (0.026 g, 68%). ESI-MS (m/z): Calcd. for $C_{39}H_{53}N_5O_{10}S_4$: 881.13 (M+H);

found 879.8, 880.8.

d) 4-{4'-[N'-(3-Methanesulfonyl-propyl)-guanidino]-2'-methyl-biphenyl-3-sulfonyl}-5-methylsulfanyl-thiophene-2-carboxamidine trifluoroacetate

[Imino-(4-{4'-[N'-(3-methanesulfonyl-propyl)-N',N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester (0.026 g, 0.029 mmol) was dissolved in 1:1 solution of trifluoroacetic acid:dichloromethane [1.5 mL:1.5 mL]. Solution was allowed to stir at room temperature for 2 hours. The reaction was concentrated in vacuo followed by reverse-phase HPLC [acetonitrile/water (0.01% TFA)] to give the title compound (0.017 g). ESI-MS (m/z): Calcd. for $C_{24}H_{29}N_5O_4S_4$: 580.78 (M+H); found 580.1.

Example 172

4-{4'-[N'-(6-Methanesulfonyl-hexyl)-guanidino]-2'-methyl-biphenyl-3-sulfonyl}-5-methylsulfanyl-thiophene-2-carboxamidine trifluoroacetate

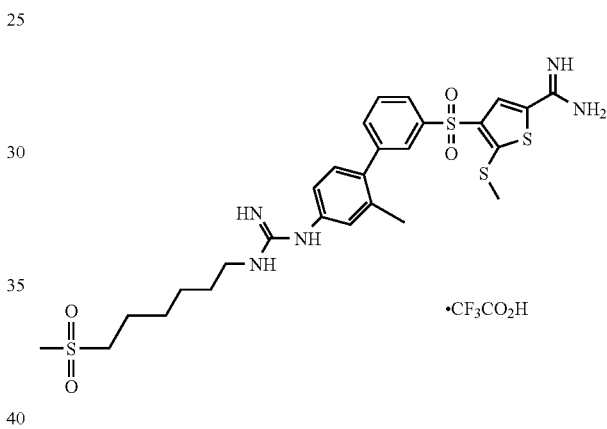

a) 6-Methanesulfonyl-hexan-1-ol

The reaction was conducted following the procedure for Example 171: step a, using 6-bromo-hexan-1-ol (0.300 g, 1.660 mmol), methane sulfinic acid, (0.844 g, 8.280 mmol), EtOH [2 mL], H$_2$O, [2 mL]. Chromatography of the residue (1%–5% MeOH/DCM) yielded the title compound (0.141 g 48%). $^1$H-NMR (CDCl$_3$): δ 3.67 (t, 2H, J=6.2 Hz), 3.03 (t, 2H, J=8.0 Hz), 2.92 (s, 3H), 1.89 (m, 2H), 1.60 (m, 2H), 1.46 (m, 4H).

b) 2-methyl-1-(6-methanesulfonyl-hexyl)-1,3-bis (carbamic acid-tert-butyl ester)-isothiourea The reaction was conducted following the procedure for Example 171: step b, using 6-methanesulfonyl-hexan-1-ol (0.141 g, 0.782 mmol), 2-methyl-1-(3-methanesulfonyl-propyl)-1,3-bis (carbamic acid-tert-butyl ester)-isothiourea (0.206 g, 0.711 mmol), Triphenylphosphine (0.205 g, 0.782 mmol), THF [5 mL]. To this was added Diisopropyl azodicarboxylate (0.158 g, 0.782 mmol). Chromatography of the residue (0%–100% EtOAc/Hx) yielded the title compound (0.213 g, 66%) ESI-MS (m/z): Calcd. for $C_{19}H_{36}N_2O_6S_2$: 453.63 (M+H); found 253.1.

c) [Imino-(4-{4'-[N'-(6-methanesulfonyl-hexyl)-N',N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester The reaction was conducted following the procedure for Example 171: step c, using 2-methyl-1-(6-methanesulfonyl-hexyl)-1,3-bis (carbamic acid-tert-butyl ester)-isothiourea (0.213 g, 0.471 mmol), {[4-(4'-amino-2'-methyl-biphenyl-3-sulfonyl)-5-methylsulfanyl-thiophen-2-yl]-imino-methyl}-carbamic acid tert-butyl ester (0.081 g, 0.157 mmol), (Example 120: step b), MeOH [4 mL], acetic acid (0.094 g, 1.570 mmol). Chromatography (0%–20% EtOAc/Hx) yielded the title compound. (0.086 g 60%) ESI-MS (m/z): Calcd. for $C_{42}H_{59}N_5O_{10}S_4$: 923.21 (M+H); found 921.8.

d) 4-{4'-[N'-(6-Methanesulfonyl-hexyl)-guanidino]-2'-methyl-biphenyl-3-sulfonyl}-5-methylsulfanyl-thiophene-2-carboxamidine trifluoroacetate The reaction was conducted following the procedure for Example 171: step d, using imino-(4-{4'-[N'-(6-methanesulfonyl-hexyl)-N',N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester (0.086 g, 0.093 mmol), trifluoroacetic acid [2 mL], DCM [2 mL]. Reverse-phase HPLC yielded the title compound (0.021 g, 38%). ESI-MS (m/z): Calcd. for $C_{27}H_{35}N_5O_4S_4$: 622.86 (M+H); found 622.2.

Example 173

4-{4'-[N'-(5-Methanesulfonyl-pentyl)-guanidino]-2'-methyl-biphenyl-3-sulfonyl}-5-methylsulfanyl-thiophene-2-carboxamidine trifluoroacetate

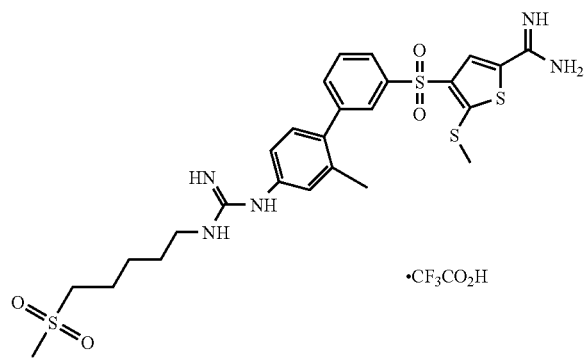

a) 1-Chloro-5-methanesulfonyl-pentane

The reaction was conducted following the procedure for Example 171: step a, using 1-bromo-5-chloro-pentane (0.400 g, 2.150 mmol), methane sulfinic acid, (1.090 g, 10.75 mmol), EtOH [3 mL], H₂O, [3 mL]. Chromatography of the residue (0%–25% MeOH/DCM) yielded the title compound (0.213 g 53%). $^1$H-NMR (CDCl₃): δ 3.55 (t, 2H, J=6.3 Hz), 3.03 (t, 2H, J=8.0 Hz), 2.91 (s, 3H), 1.85 (m, 4H), 1.63 (m, 2H)

b) 2-methyl-1-(5-methanesulfonyl-pentyl)-1,3-bis (carbamic acid-tert-butyl ester)-isothiourea 1-chloro-5-methanesulfonyl-pentane (0.021 g, 1.153 mmol), sodium iodide (0.086 g, 5.765 mmol), acetone [5 mL] were heated to 50° C. for 1 hour. Reaction was cooled to room temperature, extracted EtOAc, and concentrated in vacuo. This solid was then taken up in DMF [1 mL] and added to a solution of sodium hydride (0.020 g, 0.865 mmol) and 2-methyl-1-(3-methanesulfonyl-propyl)-1,3-bis (carbamic acid-tert-butyl ester)-isothiourea (0.016 g, 0.576 mmol) in DMF [3 mL] at 0° C. To this was added sodium iodide (0.864 g, 5.765 mmol) and the reaction was heated at 50° C. for 18 hours. The reaction was cooled to room temperature and filtered to give the title compound (0.124 g, 49%). ESI-MS (m/z): Calcd. for $C_{18}H_{34}N_2O_6S_4$: 439.60 (M+H); found 239.2.

c) [Imino-(4-{4'-[N'-(6-methanesulfonyl-hexyl)-N',N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester The reaction was conducted following the procedure for Example 171: step c, using 2-methyl-1-(5-methanesulfonyl-pentyl)-1,3-bis (carbamic acid-tert-butyl ester)-isothiourea (0.124 g, 0.283 mmol), {[4-(4'-amino-2'-methyl-biphenyl-3-sulfonyl)-5-methylsulfanyl-thiophen-2-yl]-imino-methyl}-carbamic acid tert-butyl ester (0.048 g, 0.094 mmol), (Example 120: step b), MeOH [4 mL], acetic acid (0.057 g, 0.942 mmol). Chromatography (5%–40% EtOAc/Hx) yielded the title compound (0.049 g 18%). ESI-MS (m/z): Calcd. for $C_{41}H_{57}N_5O_{10}S_4$: 909.18 (M+H); found 907.8, 908.9.

d) 4-{4'-[N'-(5-Methanesulfonyl-pentyl)-guanidino]-2'-methyl-biphenyl-3-sulfonyl}-5-methylsulfanyl-thiophene-2-carboxamidine trifluoroacetate

[Imino-(4-{4'-[N'-(6-methanesulfonyl-hexyl)-N',N''-(carbamic acid tert-butyl ester)-guanidino]-2'-methyl-biphenyl-3-sulfonyl}-5-methylsulfanyl-thiophen-2-yl)-methyl]-carbamic acid tert-butyl ester (0.049 g, 0.054 mmol) was dissolved in 1:1 solution of trifluoroacetic acid:dichloromethane [3 mL:3 mL]. Solution was allowed to stir at room temperature for 2 hours. The reaction was concentrated in vacuo followed by reverse-phase HPLC [acetonitrile/water (0.01% TFA)] to give the title compound (0.030 g, 92%). ESI-MS (m/z): Calcd. for $C_{26}H_{33}N_5O_4S_4$: 608.84 (M+H); found 608.2.

Example 174

(5-{3-[3'-(5-Carbamimidoyl-2-methylsulfanyl-thiophene-3-sulfonyl)-6-methyl-biphenyl-2-yl]-ureido}-pentyl)-phosphonic acid trifluoroacetate

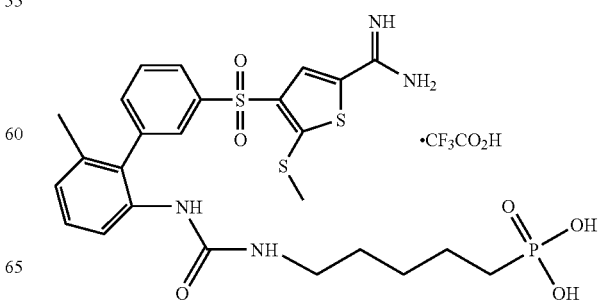

a) [5-(1,3-Dioxo-1,3-dihydro-isoindol-2-yl)-pentyl]-phosphonic acid diethyl ester Added bromophthalamide (0.400 g, 1.351 mmol) and trimethylphosphite (0.900 mL, 5.250 mmol) together in flask containing stirbar. Heat reaction to 80° C. for 18 hours. Reaction was cooled to room temperature followed by chromatography (50%–100% EtOAc/Hx) to yield the title compound (0.300 g, 62%). ESI-MS (m/z): Calcd. for $C_{21}H_{24}NO_5P$: 354.35 (M+H); found 354.1.

b) (5-Amino-pentyl)-phosphonic acid diethyl ester

[5-(1,3-dioxo-1,3-dihydro-isoindol-2-yl)-pentyl]-phosphonic acid diethyl ester (0.300 g, 0.849 mmol) was dissolved in THF [2 mL], IPA [4 mL]. Hydrazine (0.081 g, 2.540 mmol) was added to this solution and stirred at room temperature for 18 hours. The white precipitate was filtered and washed with dichloromethane. Removal of the solvent in vacuo yielded the title compound (0.136 g, 72%) $^1$H-NMR (CDCl$_3$): δ 4.07 (m, 4H), 2.68 (t, 2H, J=6.74 Hz), 1.72 (m, 2H), 1.60 (m, 2H), 1.43 (m, 4H), 1.31 (m, 6H).

c) [5-(3-{3'-[5-(tert-Butoxycarbonylamino-imino-methyl)-2-methylsulfanyl-thiophene-3-sulfonyl]-6-methyl-biphenyl-2-yl}-ureido)-pentyl]-phosphonic acid {[4-(6'-Amino-2'-methyl-biphenyl-3-sulfonyl)-5-methylsulfanyl-thiophen-2-yl]-imino-methyl}-carbamic acid tert-butyl ester (0.100 g, 0.204 mmol), (Example 25: step c), 4-nitrophenyl chloroformate (0.041 g, 0.204 mmol), pyridine (0.018 g, 0.224 mmol), DCM [3 mL] were added to a flask containing a stirbar. This solution was stirred at room temperature for 2.5 hours. To this solution was added (5-Amino-pentyl)-phosphonic acid diethyl ester (0.136 g, 0.611 mmol) and Triethylamine (0.062 g, 0.611 mmol). Solution was stirred at room temperature for 18 hours. Reaction was concentrated in vacuo followed by chromatography (50%–100% EtOAc/Hx) to yield title compound (0.138 g, 88%). ESI-MS (m/z): Calcd. for $C_{34}H_{47}N_4O_8PS_3$: 767.93 (M+H); found 667.1.

d) (5-{3-[3'-(5-Carbamimidoyl-2-methylsulfanyl-thiophene-3-sulfonyl)-6-methyl-biphenyl-2-yl]-ureido}-pentyl)-phosphonic acid

[5-(3-{3'-[5-(tert-Butoxycarbonylamino-imino-methyl)-2-methylsulfanyl-thiophene-3-sulfonyl]-6-methyl-biphenyl-2-yl}-ureido)-pentyl]-phosphonic acid (0.058 g, 0.076 mmol), trimethylsilyl iodide (0.162 g, 0.756 mmol) and DCM [5 mL] were added to a flask and heated to 40° C. for 10 minutes. The reaction was removed from the heat bath and allowed to stir at room temperature for 1 hour. H$_2$O [56 µL] was added to this solution and stirred for 1 hour. The reaction was concentrated in vacuo. MeOH [2 mL] and 20 wt. % HCl (aq.) [84 µL] were added to the concentrate and allowed to stir at room temperature for 18 hours. Reaction was concentrated in vacuo followed by reverse-phase HPLC [acetonitrile/water (0.01% TFA)] to yield the title compound. ESI-MS (m/z): Calcd. for $C_{25}H_{31}N_4O_6PS_3$: 611.71 (M+H); found 611.0.

Example 175

N-[3'-(5-Carbamimidoyl-2-methylsulfanyl-thiophene-3-sulfonyl)-6-methyl-biphenyl-2-yl]-4-methanesulfonyl-butyramide hydrochloride

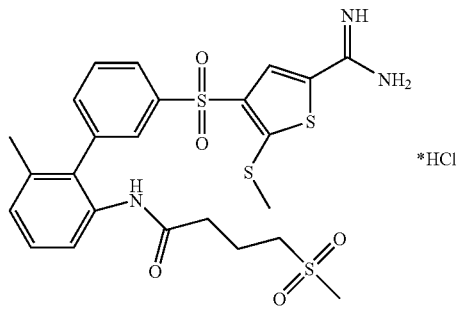

a) (Imino-{4-[6'-(4-methanesulfonyl-butyrylamino)-2'-methyl-biphenyl-3-sulfonyl]-5-methylsulfanyl-thiophen-2-yl}-methyl)-carbamic acid tert-butyl ester {[4-(6'-Amino-2'-methyl-biphenyl-3-sulfonyl)-5-methylsulfanyl-thiophen-2-yl]-imino-methyl}-carbamic acid tert-butyl ester (0.500 g, 2.020 mmol), (Example 25: step c), triethylamine (0.153 g, 3.030 mmol), and DCM [30 mL] were added to a flask containing a stirbar. 4-Methanesulfonyl-butyryl chloride (0.013 g, 0.611 mmol) was added slowly while monitoring reaction. Reaction was concentrated in vacuo followed by chromatography (50%–80% EtOAc/Hx). Material was dissolved in a solution of trifluoroacetic acid/dichloromethane (1:1), [4 mL]. This solution stirred at room temperature for 2 hours. Reaction was concentrated in vacuo followed by reverse-phase HPLC [acetonitrile/water (0.01% TFA)] to yield title compound (0.138 g, 88%). ESI-MS (m/z): Calcd. for $C_{24}H_{27}N_3O_5S_4$: 566.75; found 566.1.

Example 176

{[3'-(5-Carbamimidoyl-2-methylsulfanyl-thiophene-3-sulfonyl)-2-methyl-biphenyl-4-ylamino]-methyl}-phosphonic acid

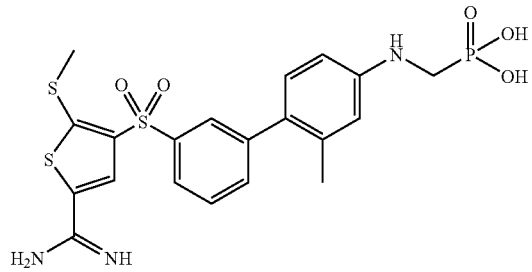

a) ({3'-[5-(tert-Butoxycarbonylamino-imino-methyl)-2-methylsulfanyl-thiophene-3-sulfonyl]-2-methyl-biphenyl-4-ylamino}-methyl)-phosphonic acid diethyl ester To a mixture of {[4-(4'-amino-2'-methyl-biphenyl-3-sulfonyl)-5-methylsulfanyl-thiophen-2-yl]-imino-methyl}-carbamic acid tert-butyl ester (30 mg, 58.0 μmol), as prepared according to the procedure of step b of Example 120, cesium carbonate (19 mg, 58 μmol), and N,N-dimethylacetamide (0.4 mL) was added a solution of trifluoro-methanesulfonic acid diethoxy-phosphorylmethyl ester (18 mg, 58 μmol) (Xu, Y. et al, *J. Org. Chem.* 61, 7697 (1996); Phillion, D. et al, *Tetrahedron Lett.* 27, 1477 (1986)), and heated at 50° C. for 48 h. Additional trifluoro-methanesulfonic acid diethoxy-phosphorylmethyl ester (18 mg, 58 μmol) was added. The mixture was heated at 50° C. for additional 24 h. Solvent was evaporated. The resulting mixture was partitioned between DCM and H$_2$O. Aqueous layer was separated and extracted with DCM. All the DCM layers were combined, washed with H$_2$O and brine, dried over Na$_2$SO$_4$, concentrated, and flash chromatographed on silica gel column, eluting with EtOAc/DCM (20 and 30%) to give the title compound (38 mg, 98% yield) as an orange oil. $^1$H NMR (CDCl$_3$): δ 8.23 (s, 1H), 7.92–7.88 (m, 2H), 7.53–7.46 (m, 2H), 6.98 (d, 1H, J=8.0 Hz), 6.56–6.53 (m, 2H), 4.23–4.15 (m, 4H), 3.56 (d, 2H, J=12.5 Hz), 2.43 (S, 3H), 2.16 (S, 3H), 1.52 (S, 9H), 1.35 (t, 6H, J=7.0 Hz). ESI-MS (m/z): Cald. For C$_{29}$H$_{39}$N$_3$O$_7$PS$_3$: 668.2 (M+H); found: 667.8.

b) {[3'-(5-Carbamimidoyl-2-methylsulfanyl-thiophene-3-sulfonyl)-2-methyl-biphenyl-4-ylamino]-methyl}-phosphonic acid To a solution of ({3'-[5-(tert-butoxycarbonylamino-imino-methyl)-2-methylsulfanyl-thiophene-3-sulfonyl]-2-methyl-biphenyl-4-yl amino}-methyl) phosphonic acid diethyl ester (38 mg, 0.057 mmol) in DCM (1.2 mL) at 0° C. was added iodotrimethylsilane (25 μL) over 3 minutes period. After 1 h at 0° C., H$_2$O was added. The mixture was stirred for 30 minutes, and then concentrated to give a brown solid. The solid was dissolved in MeOH (1.32 mL), 20% HCl was added, and stirred at ambient temperature for 3 h. The mixture was concentrated to give a brown solid. To this solid was added TFA/DCM (1:1, 3 mL) and stirred at ambient temperature for 40 minutes. The reaction mixture was then concentrated and purified by HPLC (C$_{18}$ column, 10–70% CH$_3$CN over 30 minutes) to give the title compound (11 mg, 38% yield) as a white solid.

ESI-MS (m/z): Cald. For C$_{20}$H$_{23}$N$_3$O$_5$PS$_3$: 512.1 (M+H); found: 512.1.

Example 177

5-Methylsulfanyl-4-(2'-methyl-4'-trifluoromethane-sulfonylamino-biphenyl-3-sulfonyl)-thiophene-2-carboxamidine trifluoroacetate

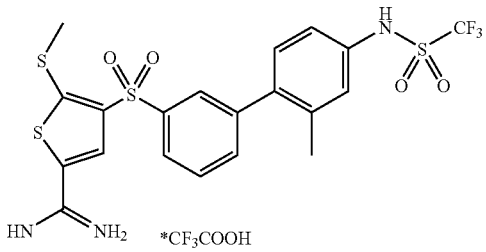

a) {Imino-[5-methylsulfanyl-4-(2'-methyl-4'-trifluoromethanesulfonylamino-biphenyl-3-sulfonyl)-thiophen-2-yl]-methyl}-carbamic acid tert-butyl ester To a solution of {[4-(4'-amino-2'-methyl-biphenyl-3-sulfonyl)-5-methylsulfanyl-thiophen-2-yl]-imino-methyl}-carbamic acid tert-butyl ester (34 mg, 66 μmol), as prepared according to the procedure of step b of Example 120, and DIEA (28 μL, 0.16 mmol) in DCM (1.0 mL) in an ice-H$_2$O bath was added trifluoromethanesulfonic anhydride (12 μL, 72 μmol) with stirring. After the ice bath expired, the mixture was continued to stir at ambient temperature for 16 h, and then poured into saturated NaHCO$_3$, and extracted with EtOAc (2×). The extracts were combined, washed with H$_2$O and brine, dried over Na$_2$SO$_4$, concentrated, and flash chromatographed on silica gel column, eluting with EtOAc/hexane (20 to 40%) to give the title compound (9 mg, 21% yield) as an oil.

ESI-MS (m/z): Cald. For C$_{25}$H$_{27}$F$_3$N$_3$O$_6$S$_4$: 650.1 (M+H); found: 649.6.

b) 5-Methylsulfanyl-4-(2'-methyl-4'-trifluoromethanesulfonylamino-biphenyl-3-sulfonyl)-thiophene-2-carboxamidine trifluoroacetate A mixture of {imino-[5-methylsulfanyl-4-(2'-methyl-4'-trifluoromethanesulfonylamino-biphenyl-3-sulfonyl)-thiophen-2-yl]-methyl}-carbamic acid tert-butyl ester (9 mg, 14 μmol) in TFA/DCM (1:1, 3 mL) was stirred at ambient temperature for 40 min. The mixture was concentrated, and flashed chromatographed on silica gel column, eluting with MeOH/DCM (5 to 8%) to give the title compound (5 mg, 54% yield) as a pale yellow solid.

$^1$H NMR (CDCl$_3$): δ 8.32 (s, 1H), 8.04–8.01 (m, 1H), 7.96–7.95 (m, 1H), 7.68–7.66 (m, 2H), 7.17 (m, 3H), 2.72 (s, 3H), 2.21 (s, 3H), ESI-MS (m/z): Cald. For C$_{20}$H$_{19}$F$_3$N$_3$O$_4$S$_4$: 550.0 (M+H); found: 550.0.

Example 178

3-[3'-(5-Carbamimidoyl-2-methylsulfanyl-thiophene-3-sulfonyl)-6-methyl-biphenyl-2-yl-methoxy]-propionic acid

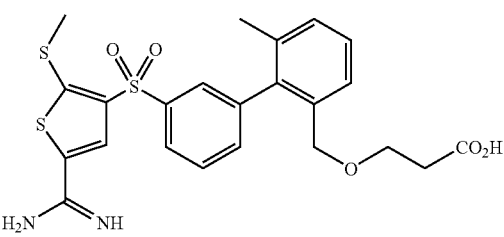

a) 3-{3'-[5-(tert-Butoxycarbonylamino-imino-methyl)-2-methylsulfanyl-thiophene-3-sulfonyl]-6-methyl-biphenyl-2-ylmethoxy}-propionic acid ethyl ester To a suspension of NaH (2.7 mg, 68 μmol, 60% oil dispersion) in DMF (0.1 mL) was added a solution of {[4-(2'-hydroxymethyl-6'-methyl-biphenyl-3-sulfonyl)-5-methylsulfanyl-thiophen-2-yl]-imino-methyl}-carbamic acid tert-butyl ester (30 mg, 56.4 μmol) in DMF (0.1 mL), as prepared according to the procedure of step b of Example 213. The mixture was stirred at ambient temperature for 30 min, and then placed in an ice-water bath. After 20 min, a solution of ethyl 3-bromopropionate (8.6 µL, 67.0 µmol) in DMF (0.05 mL) was added once. Ice-water bath was removed, and the mixture was stirred for 16 h. H$_2$O was added, and the mixture was extracted with EtOAc (3×). The extracts were combined, washed with H$_2$O, dried over Na$_2$SO$_4$, concentrated, and flash chromatographed on silica gel, eluting with EtOAc/DCM (15%) followed by EtOAc/hexane (40%) to give the title compound (9 mg, 25%) yield) as an oil.

$^1$H NMR (CDCl$_3$): δ 7.99 (d, 1H, J=7.7 Hz), 7.88 (s, 1H), 7.68 (s, 1H), 7.60–7.56 (m, 1H), 7.44 (d, 1H, J=7.6 Hz), 7.38 (d, 1H, J=7.4 Hz), 7.34–7.30 (m, 1H), 7.23 (d, 1H, J=7.3 Hz), 4.27–4.09 (m, 4H), 3.78 (bs, 2H), 2.67 (t, 2H, J=5.9 Hz), 2.57 (s, 3H), 2.02 (s, 3H), 1.47 (s, 9H), 1.28 (t, 3H, J=7.1 Hz). ESI-MS (m/z): Cald. For C$_{30}$H$_{37}$N$_2$O$_7$S$_3$: 633.2 (M+H); found: 632.9.

b) 3-{3'-[5-(tert-Butoxycarbonylamino-imino-methyl)-2-methylsulfanyl-thiophene-3-sulfonyl]-6-methyl-biphenyl-2-ylmethoxy}-propionic acid To a solution of 3-{3'-[5-(tert-butoxycarbonylamino-imino-methyl)-2-methylsulfanyl-thiophene-3-sulfonyl]-6-methyl-biphenyl-2-ylmethoxy}-propionic acid ethyl ester (7.0 mg, 11 µmol) in THF (0.5 mL) and MeOH (0.25 mL) was added a solution of lithium hydroxide monohydrate (0.56 mg, 13 µmol) in H$_2$O (50 mL). The mixture was microwaved at 80° C. for 150 seconds, acidified with 0.25 N HCl to ~pH 3, extracted with EtOAc/DCM (1:1, 3×). The extracts were combined, washed with H$_2$O, dried over Na$_2$SO$_4$, concentrated, and flash chromatographed on silica gel column, eluting with MeOH/DCM (2 to 4%) to give the title compound (5.1 mg, 76% yield) as a white solid.

$^1$H NMR (CDCl$_3$): δ 8.03–8.00 (m, 1H), 7.88–7.87 (m, 1H), 7.70 (bs, 1H), 7.57 (t, 1H, J=7.7 Hz), 7.43–7.40 (m, 1H), 7.36–7.28 (m, 2H), 7.23 (d, 1H, J=6.9 Hz), 4.28–4.15 (m, 2H), 3.65–3.75 (m, 2H), 2.65 (t, 2H, J=6.0 Hz), 2.58 (s, 3H), 2.01 (s, 3H). ESI-MS (m/z): Cald. For C$_{28}$H$_{33}$N$_2$O$_7$S$_3$: 605.1 (M+H); found: 604.8.

c) 3-[3'-(5-Carbamimidoyl-2-methylsulfanyl-thiophene-3-sulfonyl)-6-methyl-biphenyl-2-ylmethoxy]-propionic acid A mixture of 3-{3'-[5-(tert-butoxycarbonylamino-imino-methyl)-2-methylsulfanyl-thiophene-3-sulfonyl]-6-methyl-biphenyl-2-ylmethoxy}-propionic acid (5.1 mg, 8.4 µmol) in TFA/DCM (1:1, 1.5 mL) was stirred at ambient temperature for 1 h. The mixture was concentrated and flash chromatographed on silica gel, eluting with MeOH/DCM (5 to 12%) to give the title compound (3.0 mg, 69% yield) as a white solid.

$^1$H NMR (CD$_3$OD): δ 8.18 (s, 1H), 8.03–8.00 (m, 1H), 7.88 (t, 1H, J=1.6 Hz), 7.68 (t, 1H, J=7.8 Hz), 7.54–7.52 (m, 1H), 7.41 (d, 1H, J=7.6 Hz), 7.33 (t, 1H, J=7.6 Hz), 7.24 (d, 1H, J=7.4 Hz), 4.23–4.16 (m, 2H), 3.64 (t, 2H, J=6.1 Hz), 2.69 (s, 3H), 2.54 (t, 2H, J=6.0 Hz), 1.99 (s, 3H). ESI-MS (m/z): Cald. for C$_{23}$H$_{24}$N$_2$O$_5$S$_3$: 505.1 (M+H); found: 505.1.

Example 179

5-Methylsulfanyl-4-(6'-methyl-2'-{3-[4-(2H-tetrazol-5-yl)-butyl]-ureido}-biphenyl-3-sulfonyl)-thiophene-2-carboxamidine trifluoroacetate

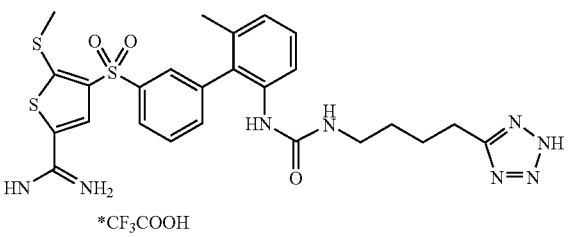

*CF$_3$COOH a) 5-(1,3-Dioxo-1,3-dihydro-isoindol-2-yl)-pentanenitrile

To a solution of 5-bromovaleronitrile (5.12 g, 30.0 mmol) in DMF (40 mL) was added potassium phthalimide (6.00 g, 32.4 mmol). The above suspension was heated at 60° C. for 16 h, concentrated, and partitioned between H$_2$O and DCM. The DCM layer was separated, washed with H$_2$O (3×) and brine, dried over Na$_2$SO$_4$, and concentrated to give the title compound (6.84 g, quantitative yield) as a white solid.

$^1$H NMR (CDCl$_3$): δ 7.87–7.80 (m, 2H), 7.76–7.70 (m, 2H), 3.73 (t, 2H, J=6.1 Hz), 2.43 (t, 2H, J=7.1 Hz), 1.89–1.82 (m, 2H), 1.74–1.67 (m, 2H). ESI-MS (m/z): Cald. For C$_{13}$H$_{13}$N$_2$O$_2$: 229.1 (M+H); found: 229.1.

b) 2-[4-(2H-Tetrazol-5-yl)-butyl]-isoindole-1,3-dione

To a solution of 5-(1,3-dioxo-1,3-dihydro-isoindol-2-yl)-pentanenitrile (6.84 g, 30 mmol) and azidotrimethylsilane (14 mL, 108 mmol) in toluene (40 mL) was added dibutyltin oxide (2.1 g, 6.0 mmol). The mixture was heated at 100° C. for 48 h, concentrated, and flash chromatographed on silica gel column, eluting with EtOAc/DCM (30 and 60%) followed by methanol/DCM (2.5 and 5%) to give the title compound (6.72 g, 83% yield) as a white solid.

$^1$H NMR (DMSO): δ 7.86–7.80 (m, 4H), 3.59 (t, 2H, J=6.8 Hz), 2.90 (t, 2H, J=7.1 Hz), 1.74–1.58 (m, 4H). ESI-MS (m/z): Cald. For C$_{13}$H$_{14}$N$_5$O$_2$: 272.1 (M+H); found: 272.0.

c) 2-[4-(2-Trityl-2H-tetrazol-5-yl)-butyl]-isoindole-1,3-dione

To a solution of 2-[4-(2H-tetrazol-5-yl)-butyl]-isoindole-1,3-dione (4.07 g, 15.0 mmol) and diisopropylethylamine (7.8 mL, 45.0 mmol) in DCM (60 mL) was added trityl chloride (5.86 g, 21.0 mmol). The solution was stirred at ambient temperature for 14 h, and concentrated. The resulting residue was partitioned between EtOAc/DCM (3:1) and H$_2$O. Organic layer was separated, washed with H$_2$O and brine, dried over Na$_2$SO$_4$, concentrated, and flash chromatographed on silica gel, eluting with DCM/hexane (40, 80, and 100%) followed by EtOAc/DCM (1 and 2%) to give the title compound (5.08 g, 66% yield) as a pale yellow solid.

$^1$H NMR (CDCl$_3$): δ 7.87–7.82 (m, 2H), 7.74–7.70 (m, 2H), 7.36–7.31 (m, 9H), 7.12–7.09 (m, 6H), 3.71 (t, 2H, J=7.1 Hz), 2.99 (t, 2H, J=7.2 Hz), 1.89–1.71 (m, 4H).

d) 4-(2-Trityl-2H-tetrazol-5-yl)-butylamine

To a solution of 2-[4-(2-trityl-2H-tetrazol-5-yl)-butyl]-isoindole-1,3-dione (175 mg, 0.313 mmol) in 2-propanol/THF (2:1, 3.0 mL) was added hydrazine (30 mL, 0.939 mmol). The solution was stirred at ambient temperature for 16 h. White solid was filtered off and washed with DCM (5×). The filtrate and the washings were combined, concentrated, dissolved in DCM, washed with $H_2O$ (2×) and brine, dried over $Na_2SO_4$, and concentrated to give the title compound (131 mg, 97% yield) as a pale yellow oil.

$^1$H NMR (CDCl$_3$): δ 7.36–7.28 (m, 9H), 7.12–7.09 (m, 6H), 2.93 (t, 2H, J=7.6 Hz), 2.69 (t, 2H, J=7.0 Hz), 1.84–1.77 (m, 2H), 1.52–1.45 (m, 2H).

e) {Imino-[5-methylsulfanyl-4-(6'-methyl-2'-{3-[4-(2-trityl-2H-tetrazol-5-yl)-butyl]-ureido}-biphenyl-3-sulfonyl)-thiophen-2-yl]-methyl}-carbamic acid tert-butyl ester To a solution of {[4-(2'-amino-6'-methyl-biphenyl-3-sulfonyl)-5-methylsulfanyl-thiophen-2-yl]-imino-methyl}-carbamic acid tert-butyl ester (60 mg, 0.116 mmol), as prepared according to the procedure of step c of Example 25, and pyridine (10 mg, 0.128 mmol) in DCM (1.1 mL) was added 4-nitrophenyl chloroformate (23 mg, 0.116 mmol), and stirred at ambient temperature for 4 h. To the above mixture was added a solution of 4-(2-trityl-2H-tetrazol-5-yl)-butylamine (65 mg, 0.151 mmol) in DCM (0.65 mL), and stirred for 48 h. The mixture was concentrated and purified on a preparative TLC plate (1000 μm), developing with EtOAc/DCM (5 and 20%) to give the title compound (15 mg, 14% yield) as a yellow solid.

$^1$H NMR (CDCl$_3$): δ 7.95 (d, 1H, J=7.93 Hz), 7.88 (t, 1H, J=1.6 Hz), 7.74 (s, 1H), 7.56 (t, 1H, J=7.7 Hz), 7.44–7.42 (m, 1H), 7.35–7.28 (m, 13H), 7.23–7.19 (m, 1H), 7.11–7.08 (m, 7H), 4.94 (t, 1H, J=5.5 Hz), 3.26–3.16 (m, 2H), 2.91 (t, 2H, J=7.3 Hz), 2.62 (s, 3H), 2.10 (s, 3H), 1.80–1.72 (m, 2H), 1.56–1.44 (m, 1H). ESI-MS (m/z): Cald. For $C_{49}H_{51}N_8O_5S_3$: 927.3 (M+H); found: 926.8.

f) 5-Methylsulfanyl-4-(6'-methyl-2'-{3-[4-(2H-tetrazol-5-yl)-butyl]-ureido}-biphenyl-3-sulfonyl)-thiophene-2-carboxamidine trifluoroacetate A solution of {imino-[5-methylsulfanyl-4-(6'-methyl-2'-{3-[4-(2-trityl-2H-tetrazol-5-yl)-butyl]-ureido}-biphenyl-3-sulfonyl)-thiophen-2-yl]-methyl}-carbamic acid tert-butyl ester (15 mg, 16 μmol) in TFA/DCM (1:1, 2.0 mL) was stirred at ambient temperature for 1 h. The mixture was concentrated, and flash chromatographed on silica gel column, eluting with MeOH/DCM (3 to 7.5% containing 0.1% TFA) to give the title compound (5 mg, 45% yield) as a white solid.

$^1$H NMR (CDCl$_3$): δ 8.29 (s, 1H), 8.02–8.00 (m, 1H), 7.88 (t, 1H, J=1.7 Hz), 7.67 (t, 1H, J=7.7 Hz), 7.56–7.53 (m, 1H), 7.42 (d, 1H, J=7.8 Hz), 7.28 (t, 1H, J=7.7 Hz), 7.12 (d, 1H, J=7.5 Hz), 3.05 (t, 2H, J=6.4 Hz), 2.92 (t, 2H, J=7.5 Hz), 2.70 (s, 3H), 2.92 (s, 3H), 1.73–1.65 (m, 2H), 1.44–1.36 (m, 2H) ESI-MS (m/z): Cald. For $C_{25}H_{29}N_8O_5S_3$: 585.1 (M+H); found: 585.0.

Example 180

5-Methylsulfanyl-4-(6'-methyl-2'-{3-[5-(2H-tetrazol-5-yl)-pentyl]-ureido}-biphenyl-3-sulfonyl)-thiophene-2-carboxamidine trifluoroacetate

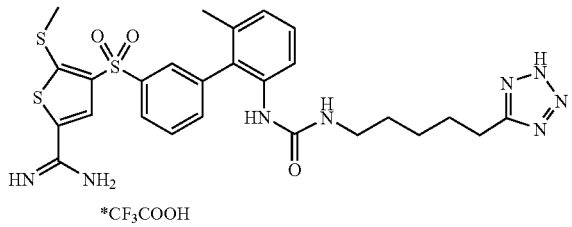

*CF$_3$COOH

The title compound was prepared from 6-bromohexanenitrile according to the procedures in Example 179.

$^1$H NMR (CD$_3$OD): δ 8.30 (s, 1H), 8.05–8.02 (m, 1H), 7.89 (t, 1H, J=1.6 Hz), 7.69 (t, 1H, J=7.8 Hz), 7.56–7.54 (m, 1H), 7.42 (d, 1H, J=7.8 Hz), 7.28 (t, 1H, J=7.8 Hz), 7.11 (d, 1H, J=7.5 Hz), 3.00 (t, 2H, J=6.5 Hz), 2.93 (t, 2H, J=7.5 Hz), 2.70 (s, 3H), 1.99 (s, 3H), 1.78–1.71 (m, 2H), 1.42–1.34 (m, 2H), 1.30–1.25 (m, 2H). ESI-MS (m/z): Cald. For $C_{26}H_{31}N_8O_3S_3$: 599.2 (M+H); found: 599.0.

Example 181

5-Methylsulfanyl-4-(6'-methyl-2'-{3-[2-(2H-tetrazol-5-yl)-ethyl]-ureido}-biphenyl-3-sulfonyl)-thiophene-2-carboxamidine trifluoroacetate

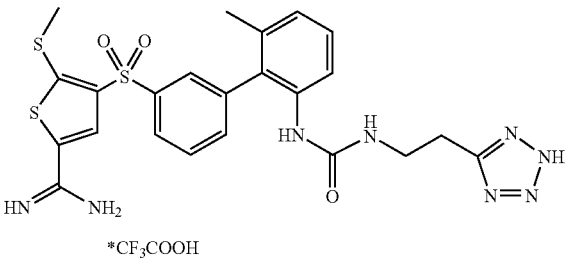

*CF$_3$COOH a) {Imino-[5-methylsulfanyl-4-(6'-methyl-2'-{3-[2-(2H-tetrazol-5-yl)-ethyl]-ureido}-biphenyl-3-sulfonyl)-thiophen-2-yl]-methyl}-carbamic acid tert-butyl ester A mixture of [(4-{2'-[3-(2-cyano-ethyl)-ureido]-6'-methyl-biphenyl-3-sulfonyl}-5-methylsulfanyl-thiophen-2-yl)-imino-methyl]-carbamic acid tert-butyl ester (31 mg, 51 μmol), as prepared from {[4-(2'-amino-6'-methyl-biphenyl-3-sulfonyl)-5-methylsulfanyl-thiophen-2-yl]-imino-methyl}-carbamic acid tert-butyl ester and 3-aminopropionitrile according to the procedure of step e of Example 179, azidotrimethylsilane (40 μL, 0.30 mmol), dibutyltin oxide (3.5 mg, 10 μmol), and toluene (1.5 mL) was heated at 70° C. for 16 h and 80° C. for 4 h. The mixture was concentrated and purified by flash chromatography on silica gel, eluting with EtOAc/DCM (50, 100%) followed by MeOH/DCM (5, 10%) to give the title compound (14 mg, 42% yield) as a colorless oil.

$^1$H NMR (CDCl$_3$): δ 8.00 (s, 1H), 7.75–7.71 (m, 2H), 7.34–7.29 (m, 3H), 7.21 (t, 1H, J=7.8 Hz), 7.10–1.01 (m, 2H), 6.58 (bs, 1H), 6.00 (bs, 1H), 3.60 (bs, 2H), 3.04 (bs,

2H), 2.52 (s, 3H), 1.93 (s, 3H), 1.49 (s, 9H). ESI-MS (m/z): Cald. For $C_{28}H_{33}N_8O_5S_3$: 657.2 (M+H); found: 656.8.

b) 5-Methylsulfanyl-4-(6'-methyl-2'-{3-[2-(2H-tetrazol-5-yl)-ethyl]-ureido}-biphenyl-3-sulfonyl)-thiophene-2-carboxamidine trifluoroacetate A solution of {imino-[5-methylsulfanyl-4-(6'-methyl-2'-{3-[2-(2H-tetrazol-5-yl)-ethyl]-ureido}-biphenyl-3-sulfonyl)-thiophen-2-yl]-methyl}-carbamic acid tert-butyl ester (10 mg, 15.3 µmol) in TFA/DCM (2.0 mL, 1:1) was stirred at ambient temperature for 1.5 h. The reaction mixture was concentrated to dryness, and flash chromatographed on silica gel column, eluting with 10% MeOH/DCM containing 0.1% TFA to give the title compound (4.7 mg, 46% yield) as a white solid.

$^1$H NMR (CD$_3$OD): δ 8.29 (s, 1H), 8.03–8.01 (m, 1H), 7.86 (t, 1H, J=1.6 Hz), 7.68 (t, 1H, J=7.8 Hz), 7.52–7.50 (m, 1H), 7.42 (d, 1H, J=7.9 Hz), 7.28 (t, 1H, J=7.7 Hz), 7.12 (d, 1H, J=7.5 Hz), 3.48–3.41 (m, 2H), 3.00 (t, 2H, J=6.7 Hz), 2.70 (s, 3H), 1.99 (s, 3H). ESI-MS (m/z): Cald. For $C_{23}H_{25}N_8O_3S_3$: 557.1 (M+H); found: 557.0.

Example 182

5-Methylsulfanyl-4-(2'-methyl-4'-{3-[4-(2H-tetrazol-5-yl)-butyl]-ureido}-biphenyl-3-sulfonyl)-thiophene-2-carboxamidine trifluoroacetate

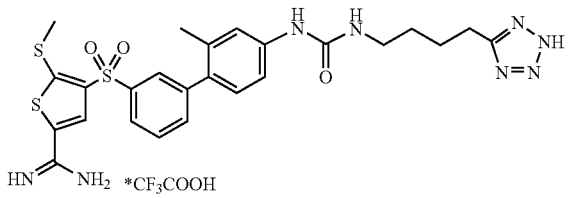

According to the procedures of Example 179, the title compound was synthesized from {[4-(4'-amino-2'-methyl-biphenyl-3-sulfonyl)-5-methylsulfanyl-thiophen-2-yl]-imino-methyl}-carbamic acid tert-butyl ester, which was prepared using the procedure of step b of Example 120.

$^1$H NMR (CD$_3$OD): δ 8.32 (s, 1H), 8.00–7.95 (m, 2H), 7.66–7.65 (m, 2H), 7.31–7.27 (m, 2H), 7.10 (d, 1H, J=8.3 Hz), 3.26 (t, 2H, J=6.8 Hz), 3.00 (t, 2H, J=7.5 Hz), 2.72 (s, 3H), 2.20 (s, 3H), 1.90–1.82 (m, 2H), 1.64–1.57 (m, 2H) ESI-MS (m/z): Cald. For $C_{25}H_{29}N_8O_5S_3$: 585.1 (M+H); found: 585.0.

Example 183

4-[4'-(N'-Acetyl-guanidino)-2'-methyl-biphenyl-3-sulfonyl]-5-methylsulfanyl-thiophene-2-carboxamidine trifluoroacetate

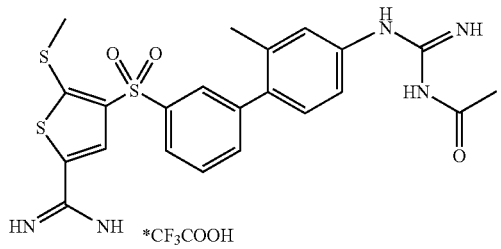

a) 1-Acetyl-1,3-bis-tert-butoxycarbonylimino-2-methyl-isothiourea

To a solution of 1,3-bis-tert-butoxycarbonylimino-2-methyl-isothiourea (2.33 g, 8.0 mmol) in dichloromethane (DCM) (8.0 mL) was added diisopropylethylamine (DIEA) (2.79 mL, 16.0 mmol) and acetyl chloride (0.60 mL, 8.4 mmol) and stirred at ambient temperature for 2 hours. Additional DIEA (2.79 mL, 16.0 mmol) and acetyl chloride (0.60 mL, 8.4 mmol) were added. After 1 hour the mixture was concentrated to dryness, partitioned between dichloromethane and saturated NaHCO$_3$. Organic layer was separated, washed with H$_2$O and brine, dried over Na$_2$SO$_4$, concentrated, and flash chromatographed on silica gel column, eluting with DCM/hexane (40%, 100%) to give the title compound (2.60 g, 97% yield) as a yellow oil. $^1$H NMR (CDCl$_3$): δ 2.48 (s, 3H), 2.46 (s, 3H), 1.52 (s, 9H), 1.47 (s, 9H).

b) 4-[4'-(N'-Acetyl-guanidino)-2'-methyl-biphenyl-3-sulfonyl]-5-methylsulfanyl-thiophene-2-carboxamidine trifluoroacetate To a solution of {[4-(4'-amino-2'-methyl-biphenyl-3-sulfonyl)-5-methylsulfanyl-thiophen-2-yl]-imino-methyl}-carbamic acid tert-butyl ester (60 mg, 0.116 mmol), as synthesized from {[4-(4'-amino-2'-methyl-biphenyl-3-sulfonyl)-5-methylsulfanyl-thiophen-2-yl]-imino-methyl}-carbamic acid tert-butyl ester using the procedure of step b of Example 120, and 1-acetyl-1,3-bis-tert-butoxycarbonylimino-2-methyl-isothiourea (193 mg, 0.58 mmol) in methanol (4.0 mL) was added acetic acid (66 µL, 1.16 mmol) and heated at 40° C. for 16 h. Triethylamine (0.25 mL) was added. The mixture was concentrated to dryness followed by flash chromatography on silica gel column, eluting with ethylacetate/DCM (5, 10 15%) to deliver the guanidinated product (60 mg) as a yellow solid. This solid was treated with trifluoroacetic acid/DCM (6 mL, 1:1) at ambient temperature for 1 h, and concentrated to dryness. The resulting residue was purified via HPLC (C18-column, 20–65% CH$_3$CN over 25 min) to give the title compound (33 mg, 49% yield) as a white solid.

$^1$H NMR (CD$_3$OD): δ 8.32 (s, 1H), 8.02–7.98 (m, 1H), 7.96 (s, 1H), 7.67–7.66 (m, 2H), 7.50–7.48 (m, 2H), 7.15 (d, 1H, J=8.0 Hz), 2.72 (s, 3H), 2.22 (s, 3H), 2.14 (s, 3H).

Example 184

4-{4'-Guanidino-2'-[3-(4-methanesulfonyl-butyl)-ureido]-6'-methyl-biphenyl-3-sulfonyl}-5-methylsulfanyl-thiophene-2-carboxamidine trifluoroacetate

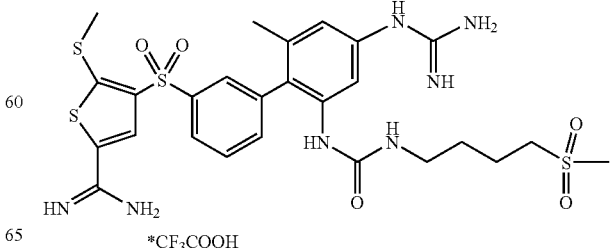

a) [(4-{4'-Amino-2'-[3-(4-methanesulfonyl-butyl)-ureido]-6'-methyl-biphenyl-3-sulfonyl}-5-methylsulfanyl-thiophen-2-yl)-imino-methyl]-carbamic acid tert-butyl ester To a solution of a) {3'-(5-carbamimidoyl-2-methylsulfanyl-thiophene-3-sulfonyl)-2-[3-(4-methanesulfonyl-butyl)-ureido]-6'-methyl-biphenyl-4-yl}-carbamic acid 2-trimethyl silanyl-ethyl ester (148 mg, 0.173 mmol), as prepared from 4-methanesulfonyl-butylamine (step c of Example 202) and [2-amino-3'-(5-carbamoyl-2-methylsulfanyl-thiophene-3-sulfonyl)-6-methyl-biphenyl-4-yl]-carbamic acid 2-trimethylsilanyl-ethyl ester (step c of Example 294) using the procedure of step e of Example 179, in THF (5.0 mL) was added a solution of tetrabutylammonium fluoride in THF (0.87 mL, 0.87 mmol, 1.0 M) over 5 minutes period. The mixture was then heated at 50° C. for 30 minutes, concentrated, and flash chromatographed on silica gel column, eluting with EtOAc followed by methanol/DCM (2.5, 5%) to give the title compound (100 mg, 82% yield) as a yellow solid.

$^1$H NMR (CD$_3$OD): δ 8.16 (s, 1H), 7.98–7.95 (m, 1H), 7.85 (t, 1H, J=1.6 Hz), 7.64 (t, 1H, J=7.8 Hz), 7.50–7.48 (m, 1H), 6.82 (d, 1H, J=2.2 Hz), 6.49–6.48 (m, 1H), 3.11–3.02 (m, 4H), 2.94 (s, 3H), 2.65 (s, 3H), 1.90 (s, 3H), 1.73–1.67 (m, 2H), 1.51–1.46 (m, 1H).

b) [(4-{4'-(N',N''-Di-tert-tert-butoxycarbonyl-guanidino)-2'-[3-(4-methanesulfonyl-butyl)-ureido]-6'-methyl-biphenyl-3-sulfonyl}-5-methylsulfanyl-thiophen-2-yl)-imino-methyl]-carbamic acid tert-butyl ester To a mixture of [(4-{4'-amino-2'-[3-(4-methanesulfonyl-butyl)-ureido]-6'-methyl-biphenyl-3-sulfonyl}-5-methylsulfanyl-thiophen-2-yl)-imino-methyl]-carbamic acid tert-butyl ester (100 mg, 0.141 mmol), 1,3-bis-tert-butoxycarbonylimino-2-methyl-isothiourea (205 mg, 0.705 mmol), and methanol (5.0 mL) was added acetic acid (0.081 mL, 1.41 mmol), and heated at 40° C. for 16 h. Triethylamine (0.3 mL) was added. The mixture was concentrated, and flash chromatographed on silica gel column, eluting with EtOAc/DCM (0 to 40%) to afford the title compound (110 mg, 82% yield) as an off-white solid.

$^1$H NMR (CD$_3$OD): δ 8.19 (s, 1H), 8.04–8.02 (m, 1H), 7.87 (t, 1H, J=1.6 Hz), 7.70 (t, 1H, J=7.9 Hz), 7.63 (bs, 1H), 7.51–7.54 (m, 1H), 7.35 (bs, 1H), 3.11–3.04 (m, 4H), 2.93 (s, 3H), 2.64 (s, 3H), 1.98 (s, 3H), 1.76–1.68 (m, 2H), 1.58 (bs, 9H), 1.54–1.46 (m, 20 H).

c) 4-{4'-Guanidino-2'-[3-(4-methanesulfonyl-butyl)-ureido]-6'-methyl-biphenyl-3-sulfonyl}-5-methylsulfanyl-thiophene-2-carboxamidine trifluoroacetate To a flask charged with [(4-{4'-(N',N''-di-tert-butoxycarbonyl-guanidino)-2'-[3-(4-methanesulfonyl-butyl)-ureido]-6'-methyl-biphenyl-3-sulfonyl}-5-methylsulfanyl-thiophen-2-yl)-imino-methyl]-carbamic acid tert-butyl ester (110 mg, 0.116 mmol) was added a solution of trifluoroacetic acid in DCM (3.0 mL, 50%) and stirred at ambient temperature for 1 h. The mixture was concentrated, and purified by HPLC (C$_{18}$-column, 5–50% CH$_3$CN in H$_2$O over 15 min.) to give the title compound (63 mg, 62% yield) as a white solid.

$^1$H NMR (CD$_3$OD): δ 8.34 (s, 1H), 8.08–8.05 (m, 1H), 7.91 (t, 1H, J=1.7 Hz), 7.76 (t, 1H, J=7.9 Hz), 7.57–7.52 (m, 2H), 7.00 (d, 1H, J=1.7 Hz), 3.13–3.10 (m, 4H), 2.95 (s, 3H), 2.71 (s, 3H), 2.00 (s, 3H), 1.78–1.71 (m, 2H), 1.57–1.50 (m, 2H). ESI-MS (m/z): Cald. For C$_{26}$H$_{34}$N$_7$O$_5$S$_4$: 652.1 (M+H); found: 652.1. (M+H); found: 652.1.

Examples 185–186

4-[7-Chloro-3-(2,6-difluoro-benzyl)-3H-benzoimidazole-5-sulfonyl]-5-methylsulfanyl-thiophene-2-carboxamidine trifluoroacetate

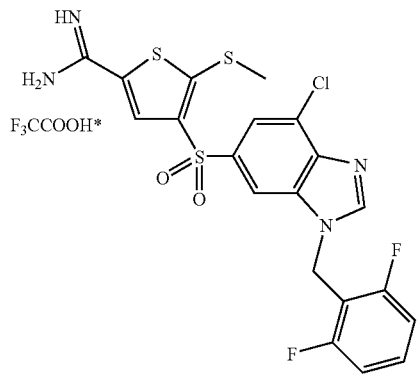

4-[7-Chloro-1-(2,6-difluoro-benzyl)-1H-benzoimidazole-5-sulfonyl]-5-methylsulfanyl-thiophene-2-carboxamidine trifluoroacetate a) Sodium salt of 5-methylsulfanyl-4-sulfino-thiophene-2-carboxylic acid methyl ester

4,6-Dichloro-spiro[benzoimidazole-2,1'-cyclohexane]

4-(7-Chloro-spiro[benzoimidazole-2,1'-cyclohex]e-5-sulfonyl)-5-methylsulfanyl-thiophene-2-carboxylic acid methyl ester A solution of 4,6-dichloro-spiro[benzoimidazole-2,1'-cyclohexane](*made according to literature preparation*: Hazelton, C. J. et al., *Tetrahedron*, 51:5597 (1995)) 0.200 g, 0.729 mmol) in absolute ethanol (5 mL) was treated with the sodium salt of 5-methylsulfanyl-4-sulfino-thiophene-2-carboxylic acid methyl ester ((Example 38: step b) 0.200 g, 0.729 mmol) as a solution in water:ethanol (2:1, 3.3 mL). Acetic acid was added and the reaction stirred at room temperature 21.5 h. The reaction mixture was poured over ice water and the ethanol was removed in vacuo. The resulting aqueous mixture was extracted with CH$_2$Cl$_2$ (4×25 mL). The combined organic layers were washed with brine and dried over Na$_2$SO$_4$. The solvents were removed in vacuo to afford the product 4-(7-chloro-spiro[benzoimidazole-2,1'-cyclohex]e-5-sulfonyl)-5-methylsulfanyl-thiophene-2-carboxylic acid methyl ester (0.307 g, 89%) as a brown oil. $^1$H NMR (CDCl$_3$): δ 8.051 (d, 1H, J=1.2 Hz), 8.038 (s, 1H), 7.381 (d, 1H, J=1.2 Hz), 3.908 (s, 3H), 2.662 (s, 3H), 1.964 (m, 10H).

b) 4-(3,4-Diamino-5-chloro-benzenesulfonyl)-5-methylsulfanyl-thiophene-2-carboxylic acid methyl ester A solution of 4-(7-chloro-spiro[benzoimidazole-2,1'-cyclohex]e-5-sulfonyl)-5-methylsulfanyl-thiophene-2-carboxylic acid methyl ester (from above step a, 0.307 g, 0.652 mmol) in ethanol:water (1:1, 6.4 mL) was treated with Na₂S₂O₄ and heated to 80° C. 1.5 h. The mixture was cooled, poured over ice water, and extracted with CH$_2$Cl$_2$ (4×25 mL). The combined organic layers were washed with brine and dried over Na$_2$SO$_4$. The solvents were removed in vacuo to afford the product 4-(3,4-diamino-5-chloro-benzenesulfonyl)-5-methylsulfanyl-thiophene-2-carboxylic acid methyl ester (0.224 g, 87%) as a brown oil. Formic acid (4.5 mL) was added and the resulting solution was refrigerated for storage overnight due to the instability of the free diamine.

c) 4-(7-Chloro-1H-benzoimidazole-5-sulfonyl)-5-methylsulfanyl-thiophene-2-carboxylic acid methyl ester The refrigerated solution of 4-(3,4-diamino-5-chloro-benzenesulfonyl)-5-methylsulfanyl-thiophene-2-carboxylic acid methyl ester ((from above step b) 0.224 g, 0.570 mmol) in formic acid (4.5 mL) from above was allowed to slowly warm to room temperature and then heated to reflux (110° C.) 3 h. The mixture was cooled to room temperature and poured over ice. The pH was adjusted to pH 8 by carefully adding solid NaHCO$_3$ portionwise with stirring. The aqueous solution was extracted with EtOAc (2×150 mL). The combined organic layers were washed with brine and dried over Na$_2$SO$_4$. The solvent was removed in vacuo to afford the product 4-(7-chloro-1H-benzoimidazole-5-sulfonyl)-5-methylsulfanyl-thiophene-2-carboxylic acid methyl ester (0.201 g, 87%) as a brown foamy solid. The crude material was used directly in the next reaction.

d) 4-[7-Chloro-3-(2,6-difluoro-benzyl)-3H-benzoimidazole-5-sulfonyl]-5-methylsulfanyl-thiophene-2-carboxylic acid methyl ester 4-[7-Chloro-1-(2,6-difluoro-benzyl)-1H-benzoimidazole-5-sulfonyl]-5-methylsulfanyl-thiophene-2-carboxylic acid methyl ester
A solution of 4-(7-chloro-1H-benzoimidazole-5-sulfonyl)-5-methylsulfanyl-thiophene-2-carboxylic acid methyl ester ((from above step c) 0.201 g, 0.499 mmol) in DMF (4 mL) was treated with α-bromo-2,6-difluorotoluene (0.114 g, 0.549 mmol) and solid K$_2$CO$_3$ (0.152 g, 1.10 mmol). The reaction was stirred at room temperature 17 h, diluted with EtOAc and washed well with water (5×150 mL). The organic layer was dried over MgSO$_4$ and concentrated in vacuo. Silica gel chromatography (2% MeOH with 2 M NH$_3$ in CH$_2$Cl$_2$) afforded the products 4-[7-chloro-3-(2,6-difluoro-benzyl)-3H-benzoimidazole-5-sulfonyl]-5-methylsulfanyl-thiophene-2-carboxylic acid methyl ester and 4-[7-chloro-1-(2,6-difluoro-benzyl)-1H-benzoimidazole-5-sulfonyl]-5-methylsulfanyl-thiophene-2-carboxylic acid methyl ester (0.102 g, 38%). These isomers were not separable by silica gel chromatography, but they were carried on together into the next reaction.

e) 4-[7-Chloro-3-(2,6-difluoro-benzyl)-3H-benzoimidazole-5-sulfonyl]-5-methylsulfanyl-thiophene-2-carboxamidine trifluoroacetate 4-[7-Chloro-1-(2,6-difluoro-benzyl)-1H-benzoimidazole-5-sulfonyl]-5-methylsulfanyl-thiophene-2-carboxamidine trifluoroacetate
A solution of 4-[7-chloro-3-(2,6-difluoro-benzyl)-3H-benzoimidazole-5-sulfonyl]-5-methylsulfanyl-thiophene-2-carboxylic acid methyl ester and 4-[7-chloro-1-(2,6-difluoro-benzyl)-1H-benzoimidazole-5-sulfonyl]-5-methylsulfanyl-thiophene-2-carboxylic acid methyl ester ((from above step d) 0.101 g, 0.191 mmol) in dry toluene (5 mL) was treated with preformed dimethylaluminum amide and heated to 100° C. 2.5 h. The reaction mixture was cooled to room temperature and added portionwise to silica suspended in CH$_2$Cl$_2$. The suspension was stirred 20 min. then was filtered through a fine porosity fritted funnel. The silica was rinsed with 10% MeOH in CH$_2$Cl$_2$ (1000 mL), and the filtrate was concentrated in vacuo. Preparatory HPLC (10–55% acetonitrile in 1% TFA/water over 30 min.) afforded products 4-[7-chloro-3-(2,6-difluoro-benzyl)-3H-benzoimidazole-5-sulfonyl]-5-methylsulfanyl-thiophene-2-carboxamidine trifluoroacetate (0.006 g, 6%) and 4-[7-chloro-1-(2,6-difluoro-benzyl)-1H-benzoimidazole-5-sulfonyl]-5-methylsulfanyl-thiophene-2-carboxamidine trifluoroacetate (0.007 g, 7%) as white solids.

Example 185

4-[7-chloro-3-(2,6-difluoro-benzyl)-3H-benzoimidazole-5-sulfonyl]-5-methylsulfanyl-thiophene-2-carboxamidine trifluoroacetate ¹H NMR (MeOD): δ 8.479 (s, 1H), 8.348 (d, 1H, J=1.6 Hz), 8.341 (s, 1H), 7.931 (d, 1H, J=1.6 Hz), 7.460 (m, 1H), 7.049 (t, 2H, J=8.4 Hz), 6.004 (s, 2H), 2.736 (s, 3H). C$_{20}$H$_{15}$ClF$_2$N$_4$O$_2$S$_3$: 513.00 (M+1) found: 513.10.

Example 186

4-[7-chloro-1-(2,6-difluoro-benzyl)-1H-benzoimidazole-5-sulfonyl]-5-methylsulfanyl-thiophene-2-carboxamidine trifluoroacetate ¹H NMR (MeOD): δ 9.001 (s, 1H), 8.384 (d, 1H, J=2.0 Hz), 8.372 (s, 1H), 7.984 (d, 1H, J=1.6 Hz), 7.532 (m, 1H), 7.141 (t, 2H, J=8.0 Hz), 5.825 (s, 2H), 2.674 (s, 3H). C$_{20}$H$_{15}$ClF$_2$N$_4$O$_2$S$_3$: 513.00 (M+1) found: 513.10

Example 187–188

4-[7-Bromo-3-(2-fluoro-5-nitro-benzyl)-3H-benzoimidazole-5-sulfonyl]-5-methylsulfanyl-thiophene-2-carboxamidine trifluoroacetate

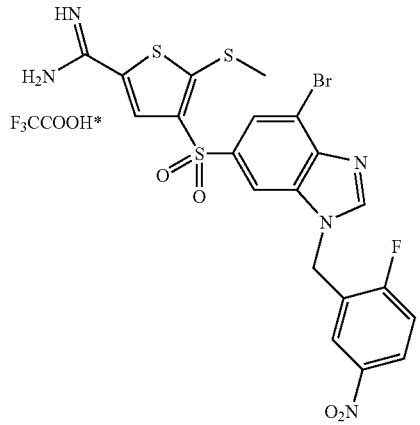

4-[7-Bromo-1-(2-fluoro-5-nitro-benzyl)-1H-benzoimidazole-5-sulfonyl]-5-methylsulfanyl-thiophene-2-carboxamidine trifluoroacetate

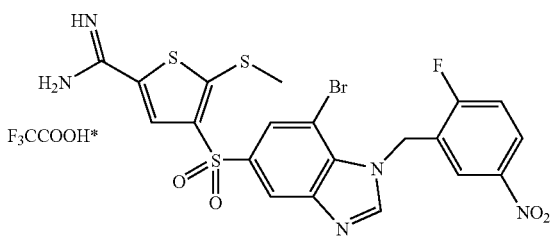

a) 4-(7-Bromo-3H-benzoimidazole-5-sulfonyl)-5-methylsulfanyl-thiophene-2-carboxylic acid methyl ester 4-(7-Bromo-3H-benzoimidazole-5-sulfonyl)-5-methylsulfanyl-thiophene-2-carboxamidine A solution of 4-(7-bromo-3H-benzoimidazole-5-sulfonyl)-5-methylsulfanyl-thiophene-2-carboxylic acid methyl ester ((Example 38: step e) 2.19 g, 4.90 mmol) in dry toluene (20 mL) was treated with a solution of 2 M $AlMe_3$ (39.0 mL, 78.0 mmol) and $NH_4Cl$ (4.21 g, 78.7 mmol) in dry toluene (39 mL) as described in Example 20: step f. The crude material (2.11 g, 100%) was used directly in the next reaction.

b) 4-Bromo-6-[5-(tert-butoxycarbonylamino-imino-methyl)-2-methylsulfanyl-thiophene-3-sulfonyl]-benzoimidazole-1-carboxylic acid tert-butyl ester A solution of 4-(7-bromo-3H-benzoimidazole-5-sulfonyl)-5-methylsulfanyl-thiophene-2-carboxamidine ((from above step a) 2.11 g, 4.89 mmol) in dry DMF (30 mL) was treated with di-tert-butyl dicarbonate (4.27 g, 19.6 mmol) and N,N-diisopropylethylamine (3.40 mL, 19.5 mmol). The reaction mixture was stirred at room temperature 2 days, and the solvents were removed in vacuo. Silica gel chromatography (30–50% EtOAc in hexanes raised in 5% increments) afforded the product 4-bromo-6-[5-(tert-butoxycarbonylamino-imino-methyl)-2-methylsulfanyl-thiophene-3-sulfonyl]-benzoimidazole-1-carboxylic acid tert-butyl ester (1.30 g, 42%) as a brown oil. $^1$H NMR ($CDCl_3$): δ 8.675 (m, 1H), 8.62 (s, 1H), 8.16 (d, 1H, J=1.6 Hz), 7.89 (s, 1H), 2.56 (s, 3H), 1.73 (s, 9H), 1.52 (s, 9H).

c) {[4-(7-Bromo-3H-benzoimidazole-5-sulfonyl)-5-methylsulfanyl-thiophen-2-yl]-imino-methyl}-carbamic acid tert-butyl ester A solution of 4-bromo-6-[5-(tert-butoxycarbonylamino-imino-methyl)-2-methylsulfanyl-thiophene-3-sulfonyl]-benzoimidazole-1-carboxylic acid tert-butyl ester ((from above step b) 1.00 g, 1.58 mmol) in MeOH (10 mL) was treated with aqueous $Na_2CO_3$ (0.340 g, 3.17 mmol in 2 mL water). The reaction mixture was stirred at room temperature 30 min., and solvents were removed in vacuo. The residue was taken up in EtOAc and washed with water (1×50 mL) and brine (1×50 mL). The organic layer was dried over $MgSO_4$ and concentrated in vacuo to afford the product {[4-(7-bromo-3H-benzoimidazole-5-sulfonyl)-5-methylsulfanyl-thiophen-2-yl]-imino-methyl}-carbamic acid tert-butyl ester (0.755 g, 90%) as a brown solid. $^1$H NMR (MeOD): δ 8.48 (s, 1H), 8.32 (m, 1H), 8.20 (s, 1H), 8.03 (d, 1H, J=1.6 Hz), 2.63 (s, 3H), 1.48 (s, 9H).

d) ({4-[7-Bromo-1-(2-fluoro-5-nitro-benzyl)-1H-benzoimidazole-5-sulfonyl]-5-methylsulfanyl-thiophen-2-yl}-imino-methyl)-carbamic acid tert-butyl ester {4-[7-Bromo-3-(2-fluoro-5-nitro-benzyl)-3H-benzoimidazole-5-sulfonyl]-5-methylsulfanyl-thiophen-2-yl}-imino-methyl)-carbamic acid tert-butyl ester A solution of {[4-(7-bromo-3H-benzoimidazole-5-sulfonyl)-5-methylsulfanyl-thiophen-2-yl]-imino-methyl}-carbamic acid tert-butyl ester ((from above step c) 0.132 g, 0.248 mmol) in dry DMF (3 mL) was treated with 2-fluoro-5-nitrobenzylbromide (0.087 g, 0.373 mmol) and diisopropylamine (0.070 mL, 0.497 mmol) and heated to 40° C. 24 h. The solution was diluted with EtOAc and washed well with water (4×35 mL). The organic layer was dried over $MgSO_4$ and concentrated in vacuo to afford the products ({4-[7-bromo-1-(2-fluoro-5-nitro-benzyl)-1H-benzoimidazole-5-sulfonyl]-5-methylsulfanyl-thiophen-2-yl}-imino-methyl)-carbamic acid tert-butyl ester and ({4-[7-bromo-3-(2-fluoro-5-nitro-benzyl)-3H-benzoimidazole-5-sulfonyl]-5-methylsulfanyl-thiophen-2-yl}-imino-methyl)-carbamic acid tert-butyl ester (0.015 g, 9%) as a brown solid. $C_{25}H_{23}BrFN_5O_6S_3$: 684.00 (M+1) found 684.60.

e) 4-[7-Bromo-3-(2-fluoro-5-nitro-benzyl)-3H-benzoimidazole-5-sulfonyl]-5-methylsulfanyl-thiophene-2-carboxamidine trifluoroacetate 4-[7-Bromo-1-(2-fluoro-5-nitro-benzyl)-1H-benzoimidazole-5-sulfonyl]-5-methylsulfanyl-thiophene-2-carboxamidine trifluoroacetate A solution of ({4-[7-bromo-1-(2-fluoro-5-nitro-benzyl)-1H-benzoimidazole-5-sulfonyl]-5-methylsulfanyl-thiophen-2-yl}-imino-methyl)-carbamic acid tert-butyl ester and ({4-[7-bromo-3-(2-fluoro-5-nitro-benzyl)-3H-benzoimidazole-5-sulfonyl]-5-methylsulfanyl-thiophen-2-yl}-imino-methyl)-carbamic acid tert-butyl ester ((from above step d) 0.015 g, 0.022 mmol) in $CH_2Cl_2$ (1 mL) was cooled to 0° C. and treated with 25% trifluoroacetic acid in $CH_2Cl_2$ (1.00 mL). The mixture was allowed to warm to room temperature and was stirred 3.2 h. The solvents were removed in vacuo. Preparatory HPLC (10–80% acetonitrile in 1% TFA/water over 30 min.) afforded the products 4-[7-bromo-3-(2-fluoro-5-nitro-benzyl)-3H-benzoimidazole-5-sulfonyl]-5-methylsulfanyl-thiophene-2-carboxamidine trifluoroacetate (0.002 g, 47%) and 4-[7-bromo-1-(2-fluoro-5-nitro-benzyl)-1H-benzoimidazole-5-sulfonyl]-5-methylsulfanyl-thiophene-2-carboxamidine trifluoroacetate (0.002 g, 47%) as white solids.

Example 187

4-[7-bromo-3-(2-fluoro-5-nitro-benzyl)-3H-benzoimidazole-5-sulfonyl]-5-methylsulfanyl-thiophene-2-carboxamidine trifluoroacetate $^1$H NMR (MeOD): δ 8.728 (s, 1H), 8.355 (m, 2H), 8.309 (s 1H), 8.286 (d, 1H, J=1.6 Hz), 8.060 (d, 1H, J=1.6 Hz), 7.468 (t, 1H, J=9.6 Hz), 5.832 (s, 2H), 2.623 (s, 3H). $C_{20}H_{15}BrFN_5O_4S_3$: 583.95 (M+1) found 585.0.

Example 188

4-[7-bromo-1-(2-fluoro-5-nitro-benzyl)-1H-benzoimidazole-5-sulfonyl]-5-methylsulfanyl-thiophene-2-carboxamidine trifluoroacetate $^1$H NMR (MeOD): δ 8.636 (s, 1H), 8.455 (d, 1H, J=1.6 Hz), 8.337 (s, 1H), 8.295 (m, 1H), 8.098 (d, 1H, J=2.0 Hz), 7.610 (dd, 1H, J=6.4 Hz, J=2.8 Hz), 7.468

(t, 1H, J=8.8 Hz), 6.054 (s, 2H), 2.722 (s, 3H). $C_{20}H_{15}BrFN_5O_4S_3$: 583.95 (M+1) found 585.0.

Example 189

4-[7-Bromo-3-(2-fluoro-4-nitro-benzyl)-3H-benzoimidazole-5-sulfonyl]-5-methylsulfanyl-thiophene-2-carboxamidine trifluoroacetate

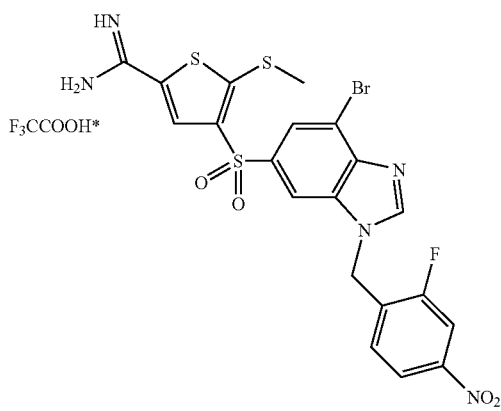

a) ({4-[7-Bromo-1-(2-fluoro-4-nitro-benzyl)-1H-benzoimidazole-5-sulfonyl]-5-methylsulfanyl-thiophen-2-yl)-imino0methyl)-carbamic acid tert-butyl ester {4-[7-Bromo-3-(2-fluoro-4-nitro-benzyl)-3H-benzoimidazole-5-sulfonyl]-5-methylsulfanyl-thiophen-2-yl)-iminomethyl)-carbamic acid tert-butyl ester A solution of {[4-(7-bromo-3H-benzoimidazole-5-sulfonyl)-5-methylsulfanyl-thiophen-2-yl]-imino-methyl}-carbamic acid tert-butyl ester ((Example 187–188: step c) 0.097 g, 0.183 mmol) in DMF (3 mL) was treated with 2-fluoro-4-nitrobenzylbromide (0.064 g, 0.274 mmol) and diisopropylamine (0.051 mL, 0.365 mmol) and heated to 40° C. 24 h. The solution was diluted with EtOAc and washed well with water (4×35 mL). The organic layer was dried over MgSO$_4$ and concentrated in vacuo to afford the products ({4-[7-bromo-1-(2-fluoro-4-nitro-benzyl)-1H-benzoimidazole-5-sulfonyl]-5-methylsulfanyl-thiophen-2-yl)-iminomethyl)-carbamic acid tert-butyl ester and ({4-[7-bromo-3-(2-fluoro-4-nitro-benzyl)-3H-benzoimidazole-5-sulfonyl]-5-methylsulfanyl-thiophen-2-yl)-imino-methyl)-carbamic acid tert-butyl ester (0.012 g, 10%) as a brown solid. $C_{25}H_{23}BrFN_5O_6S_3$: 684.00 (M+1) found 684.50.

b) 4-[7-Bromo-3-(2-fluoro-4-nitro-benzyl)-3H-benzoimidazole-5-sulfonyl]-5-methylsulfanyl-thiophene-2-carboxamidine trifluoroacetate A solution of ({4-[7-bromo-1-(2-fluoro-4-nitro-benzyl)-1H-benzoimidazole-5-sulfonyl]-5-methylsulfanyl-thiophen-2-yl)-imino-methyl)-carbamic acid tert-butyl ester and ({4-[7-bromo-3-(2-fluoro-4-nitro-benzyl)-3H-benzoimidazole-5-sulfonyl]-5-methylsulfanyl-thiophen-2-yl)-iminomethyl)-carbamic acid tert-butyl ester ((from above step a) 0.005 g, 0.007 mmol) in $CH_2Cl_2$ (1 mL) was cooled to 0° C. and treated with 25% trifluoroacetic acid in $CH_2Cl_2$ (1.00 mL). The mixture was allowed to warm to room temperature and was stirred 3 h. Solvents were removed in vacuo. Preparatory HPLC (10–80% acetonitrile in 1% TFA/water over 30 min.) afforded the product 4-[7-bromo-3-(2-fluoro-4-nitro-benzyl)-3H-benzoimidazole-5-sulfonyl]-5-methylsulfanyl-thiophene-2-carboxamidine trifluoroacetate (0.002 g, 47%) as a white solid. $^1$H NMR (MeOD): δ 8.714 (s, 1H), 8.308 (s, 1H), 8.231 (d, 1H, J=1.6 Hz), 8.106 (m, 2H), 8.047 (d, 1H, J=0.8 Hz), 7.556 (t, 1H, J=8.4 Hz), 5.854 (s, 2H), 2.630 (s, 3H). $C_{20}H_{15}BrFN_5O_4S_3$: 583.95 (M+1) found 585.05.

Example 190

4-[1-(5-Amino-2-fluoro-benzyl)-7-bromo-1H-benzoimidazole-5-sulfonyl]-5-methylsulfanyl-thiophene-2-carboxamidine trifluoroacetate

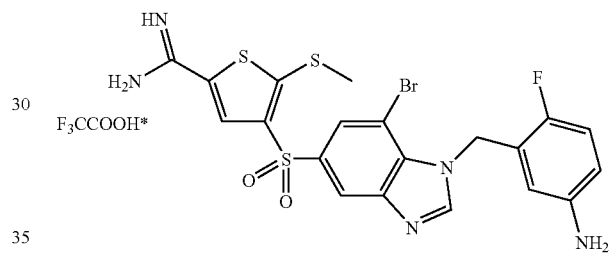

A solution of ({4-[7-bromo-1-(2-fluoro-5-nitro-benzyl)-1H-benzoimidazole-5-sulfonyl]-5-methylsulfanyl-thiophen-2-yl}-imino-methyl)-carbamic acid tert-butyl ester ((Example 187–188: step d) 0.030 g, 0.044 mmol) in EtOH (3 mL) was treated with NH$_4$Cl (0.023 g, 0.438 mmol) as an aqueous solution and heated to 50° C. Iron powder (0.012 g, 0.219 mmol) was added and the reaction heated to 80° C. for 4 h. The mixture was cooled and filtered through Celite. The filter cake was rinsed with EtOH, and the EtOH was removed in vacuo. The remaining aqueous solution was basified to pH 10 with saturated aqueous NaHCO$_3$ and extracted with EtOAc (2×25 mL). The combined organic layers were dried over MgSO$_4$ and concentrated in vacuo. The residue was taken up in $CH_2Cl_2$ (3 mL) and treated with trifluoroacetic acid (0.75 mL). The mixture was stirred at room temperature 1.5 h, and solvents were removed in vacuo. Preparatory HPLC (10–50% acetonitrile in 1% TFA/water over 30 min.) afforded the product 4-[3-(5-amino-2-fluoro-benzyl)-7-bromo-3H-benzoimidazole-5-sulfonyl]-5-methylsulfanyl-thiophene-2-carboxamidine trifluoroacetate (0.014 g, 49%) as a white solid. $^1$H NMR (MeOD): δ 8.714 (s, 1H), 8.308 (s, 1H), 8.231 (d, 1H, J=1.6 Hz), 8.106 (m, 2H), 8.047 (d, 1H, J=0.8 Hz), 7.556 (t, 1H, J=8.4 Hz), 5.854 (s, 2H), 2.630 (s, 3H).

Example 191

3-({3-[4-Bromo-6-(5-carbamimidoyl-2-methylsulfa-nyl-thiophene-3-sulfonyl)-benzoimidazol-1-ylm-ethyl]-4-fluoro-phenylcarbamoyl}-methylsulfanyl)-propionic acid trifluoroacetate

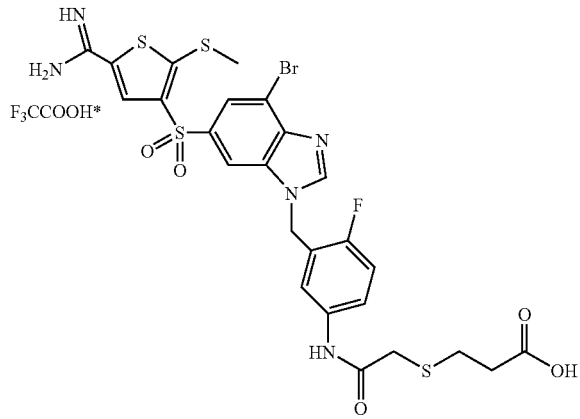

a) [(4-{7-Bromo-3-[5-(2-bromo-acetylamino)-2-fluoro-benzyl]-3H-benzoimidazole-5-sulfonyl}-5-methylsulfanyl-thiophen-2-yl)-imino-methyl]-carbamic acid tert-butyl ester A solution of ({4-[3-(5-amino-2-fluoro-benzyl)-7-bromo-3H-benzoimidazole-5-sulfonyl]-5-methylsulfanyl-thiophen-2-yl}-imino-methyl)-carbamic acid tert-butyl ester ((Example 190) 0.012 g, 0.018 mmol) in CH$_2$Cl$_2$ (3 mL) was treated with bromoacetylbromide (0.007 g, 0.037 mmol) and triethylamine (0.006 mL, 0.046 mmol) and stirred at room temperature 3 h. The reaction mixture was diluted with CH$_2$Cl$_2$ and washed with water (2×10 mL). The organic layer was dried over MgSO$_4$ and concentrated in vacuo to afford the product [(4-{7-bromo-3-[5-(2-bromo-acety-lamino)-2-fluoro-benzyl]-3H-benzoimidazole-5-sulfonyl}-5-methylsulfanyl-thiophen-2-yl)-imino-methyl]-carbamic acid tert-butyl ester (0.014 g, 92%) as a tan solid. C$_{27}$H$_{26}$Br$_2$FN$_5$O$_5$S$_3$: 773.94 (M+1) found 774.10.

b) 3-[(3-{4-Bromo-6-[5-(tert-butoxycarbonylamino-imino-methyl)-2-methylsulfanyl-thiophene-3-sulfo-nyl]-benzoimidazol-1-ylmethyl}-4-fluoro-phenylcar-bamoyl)-methylsulfanyl]-propionic acid methyl ester A solution of [(4-{7-bromo-3-[5-(2-bromo-acetylamino)-2-fluoro-benzyl]-3H-benzoimidazole-5-sulfonyl}-5-methylsulfanyl-thiophen-2-yl)-imino-methyl]-carbamic acid tert-butyl ester ((Example 191: step a) 0.014 g, 0.017 mmol) in CH$_2$Cl$_2$ (2 mL) was treated with methyl 3-mercaptopropionoate (2.50 µL, 0.025 mmol) and stirred at room temperature 30 min. The reaction was diluted with CH$_2$Cl$_2$ and washed with water (1×10 mL). The organic layer was dried over MgSO$_4$ and concentrated in vacuo to afford the product 3-[(3-{4-bromo-6-[5-(tert-butoxycarbonylamino-imino-methyl)-2-methylsulfanyl-thiophene-3-sulfonyl]-benzoimida-zol-1-ylmethyl}-4-fluoro-phenylcarbamoyl)-methylsulfanyl]-propionic acid methyl ester (0.011, 85%) as a tan solid. C$_{31}$H$_{33}$BrFN$_5$O$_8$S$_4$: 814.04 (M+1) found 814.70.

c) 3-({3-[4-Bromo-6-(5-carbamimidoyl-2-methyl-sulfanyl-thiophene-3-sulfonyl)-benzoimidazol-1-ylmethyl]-4-fluoro-phenylcarbamoyl}-methylsulfa-nyl)-propionic acid trifluoroacetate A solution of 3-[(3-{4-bromo-6-[5-(tert-butoxycarbony-lamino-imino-methyl)-2-methylsulfanyl-thiophene-3-sulfo-nyl]-benzoimidazol-1-ylmethyl}-4-fluoro-phenylcarbam-oyl)-methylsulfanyl]-propionic acid methyl ester ((Example 191: step b) 0.011 g, 0.014 mmol) in MeOH:H$_2$O (2:1, 3 mL) was treated with LiOH (1.61 mg, 0.070 mmol) and the reaction stirred at room temperature 2 h. The solvents were evaporated in vacuo and the residue taken up in CH$_2$Cl$_2$ (3 mL). Trifluoroacetic acid (0.750 mL) was added and the reaction stirred at room temperature 45 min. Solvents were evaporated in vacuo. Preparatory HPLC (10–50% acetoni-trile in 1% TFA/water over 30 min.) afforded the product 3-({3-[4-bromo-6-(5-carbamimidoyl-2-methylsulfanyl-thiophene-3-sulfonyl)-benzoimidazol-1-ylmethyl]-4-fluoro-phenylcarbamoyl}-methylsulfanyl)-propionic acid trifluoro-acetate (0.004 g, 43%) as a white solid. $^1$H NMR (MeOD): δ 8.691 (s, 1H), 8.140 (s, 1H), 8.068 (s, 1H), 8.018 (s, 1H), 7.647 (m, 1H), 7.547 (dd, 1H, J=6.4 Hz, J=2.4 Hz), 7.176 (t, 1H, J=9.6 Hz), 5.692 (s, 2H), 3.498 (quint, 1H, J=1.6 Hz), 3.148 (quint, 1H, J=1.6 Hz), 2.875 (d, 2H, J=7.2 Hz), 2.651 (d, 2H, J=7.2 Hz), 2.529 (s, 3H). C$_{25}$H$_{23}$BrFN$_5$O$_5$S$_4$: 699.97 (M+1) found 700.90.

Example 192

[3'-(5-Carbamimidoyl-2-methylsulfanyl-thiophene-3-sulfonyl)-4-methoxy-6-methyl-biphenyl-2-yl-methoxy]-acetic acid trifluoroacetate

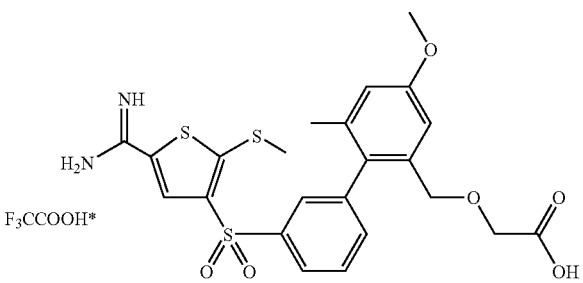

a) 2-Bromo-5-methoxy-1,3-dimethyl-benzene

A solution of 4-bromo-3,5-dimethylphenol (1.00 g, 4.97 mmol) in acetone (40 mL) was treated with solid CsCO$_3$ (1.17 g, 4.97 mmol) and methyl iodide (0.310 mL, 4.97 mmol) and heated to 40° C. for 3 h. Additional methyl iodide (0.310 mL, 4.97 mmol) was added over the course of the reaction to replace that lost to evaporation. The acetone was removed in vacuo. The resulting white solid residue was partitioned between water and CH$_2$Cl$_2$. The layers were separated and the aqueous layer was further extracted with CH$_2$Cl$_2$ (2×25 mL). The combined organic layers were washed with water (1×25 mL) and dried over MgSO$_4$. The solvent was removed in vacuo to afford the product 2-bromo-5-methoxy-1,3-dimethyl-benzene (1.01 g, 94%) as a colorless oil, which slowly solidified upon standing. $^1$H NMR (CDCl$_3$): δ 6.644 (s, 2H), 3.762 (s, 3H), 2.382 (s, 6H).

b) 2-Bromo-1-bromomethyl-5-methoxy-3-methyl-benzene

A solution of 2-bromo-5-methoxy-1,3-dimethyl-benzene ((Example 192: step a) 1.01 g, 4.70 mmol) in $CCl_4$ (50 mL) was treated with N-bromosuccinamide and AIBN (catalytic amount) and heated to 75° C. 3.5 h. The reaction was diluted with $CH_2Cl_2$ and washed with saturated aqueous $NaHCO_3$. The organic layer was dried over $MgSO_4$ and concentrated in vacuo to afford the product 2-bromo-1-bromomethyl-5-methoxy-3-methyl-benzene (1.27 g, 92%) as a pale orange solid. $^1H$ NMR ($CDCl_3$): δ 6.641 (s, 2H), 4.601 (s, 2H), 3.760 (s, 3H), 2.380 (s, 3H).

c) (2-Bromo-5-methoxy-3-methyl-phenyl)-methanol

A solution of 2-bromo-1-bromomethyl-5-methoxy-3-methyl-benzene ((Example 192: step b) 10.8 g, 36.7 mmol) in dioxane:water (1:1, 200 mL) was treated with $CaCO_3$ and heated to reflux (110° C.)18 h. The reaction mixture was cooled to room temperature and filtered by gravity to remove solid salts. The dioxane was removed in vacuo. Dilute HCl (10 mL) was added, and the mixture was extracted with $CH_2Cl_2$ (2×150 mL). The combined organic layers were dried over $MgSO_4$. The solvents were removed in vacuo to afford a pale orange oil, which slowly solidified upon standing. Silica gel chromatography (25% EtOAc in hexanes) yielded the product (2-bromo-5-methoxy-3-methyl-phenyl)-methanol (1.03 g, 12%) as a yellow oil. $^1H$ NMR ($CDCl_3$): δ 6.905 (d, 1H, J=3.2 Hz), 6.746 (d, 1H, J=3.2 Hz), 4.720 (d, 2H, J=3.6 Hz), 3.798 (s, 3H), 2.390 (s, 3H).

d) (2-Bromo-5-methoxy-3-methyl-benzyloxy)-acetic acid tert-butyl ester

A solution of (2-bromo-5-methoxy-3-methyl-phenyl)-methanol ((Example 192: step c) 0.800 g, 3.46 mmol) in DMF (10 mL) was cooled to 0° C. and treated with NaH (0.100 g of 95% dispersion, 4.15 mmol) and allowed to warm to room temperature 30 min. The mixture was then treated with tert-butyl bromoacetate (0.614 mL, 4.15 mmol) and stirred at room temperature 1 h. The reaction was diluted with water and extracted with EtOAc (2×125 mL). The combined organic layers were washed well with water (3×300 mL), dried over $MgSO_4$, and concentrated in vacuo to afford the product (2-bromo-5-methoxy-3-methyl-benzyloxy)-acetic acid tert-butyl ester (1.19 g, 98%) as a yellow oil. $^1H$ NMR ($CDCl_3$): δ 6.967 (d, 1H, J=2.8 Hz), 6.745 (d, 1H, J=3.2 Hz), 4.683 (s, 2H), 4.086 (s, 2H), 3.794 (s, 3H), 2.380 (s, 3H), 1.496 (s, 9H).

e) [5-Methoxy-3-methyl-2-(4,4,5,5-tetramethyl-[1,3,2]dioxaborolan-2-yl)-benzyloxy]-acetic acid tert-butyl ester A solution of (2-bromo-5-methoxy-3-methyl-benzyloxy)-acetic acid tert-butyl ester ((Example 192: step d) 1.19 g, 3.45 mmol) in dioxane (10 mL) was treated with $PdCl_2(PPh_3)_2$ (0.242 g, 0.345 mmol) and triethylamine (2.88 mL, 20.7 mmol). 4,4,5,5-Tetramethyl-1,3,2-dioxaborolane (1.00 mL, 6.89 mmol) was added slowly and the mixture heated to 80° C. 15 h. The reaction was diluted with EtOAc and washed with brine (2×50 mL). The organic layer was dried over $MgSO_4$ and concentrated in vacuo. Silica gel chromatography (25% EtOAc in hexanes) afforded the product [5-methoxy-3-methyl-2-(4,4,5,5-tetramethyl-[1,3,2]dioxaborolan-2-yl)-benzyloxy]-acetic acid tert-butyl ester (0.793 g, 58%) as a brown oil. The crude material was used directly in the next reaction.

f) 3'-[5-(tert-Butoxycarbonylamino-imino-methyl)-2-methylsulfanyl-thiophene-3-sulfonyl]-4-methoxy-6-methyl-biphenyl-2-ylmethoxy}-acetic acid tert-butyl ester A solution of [5-methoxy-3-methyl-2-(4,4,5,5-tetramethyl-[1,3,2]dioxaborolan-2-yl)-benzyloxy]-acetic acid tert-butyl ester ((Example 192: step e) 0.790 g, 2.01 mmol) in tolutene:EtOH (2:1, 15 mL) was treated with {[4-(3-bromo-benzenesulfonyl)-5-methylsulfanyl-thiophen-2-yl]-imino-methyl}-carbamic acid tert-butyl ester ((Example27: step c) 0.247 g, 0.503 mmol), aqueous $Na_2CO_3$ (2 M, 2.01 mL, 4.03 mmol), and $Pd(PPh_3)_4$ (0.116 g, 0.101 mmol). The mixture was heated to 80° C. 16.3 h. The reaction was diluted with EtOAc and washed with brine (2×25 mL). The organic layer was dried over $MgSO_4$ and concentrated in vacuo. Silica gel chromatography (5%–60% EtOAc in hexanes raised in 5% increments) afforded the product 3'-[5-(tert-butoxycarbonylamino-imino-methyl)-2-methylsulfanyl-thiophene-3-sulfonyl]-4-methoxy-6-methyl-biphenyl-2-ylmethoxy}-acetic acid tert-butyl ester (0.107 g, 31%) as an off-white solid. $^1H$ NMR ($CDCl_3$): δ 8.013 (d, 1H, J=7.6 Hz), 7.961 (s, 1H), 7.934 (t, 1H, J=1.6 Hz), 7.570 (t, 1H, J=7.6 Hz), 7.440 (d, 1H, J=2.0 Hz), 6.896 (d, 1H, J=2.4 Hz), 6.832 (d, 1H, J=2.4 Hz) 4.200 (s, 2H), 3.876 (s, 3H), 3.868 (s, 2H), 2.630 (s, 3H), 2.036 (s, 3H), 1.585 (s, 9H), 1.540 (s, 9H). $C_{32}H_{40}N_2O_8S_3$: 677.19 (M+1) found 676.90.

g) [3'-(5-Carbamimidoyl-2-methylsulfanyl-thiophene-3-sulfonyl)-4-methoxy-6-methyl-biphenyl-2-ylmethoxy]-acetic acid trifluoroacetate A solution of 3'-[5-(tert-butoxycarbonylamino-imino-methyl)-2-methylsulfanyl-thiophene-3-sulfonyl]-4-methoxy-6-methyl-biphenyl-2-ylmethoxy}-acetic acid tert-butyl ester ((Example 192: step f) 0.107 g, 0.158 mmol) in $CH_2Cl_2$ (10 mL) was treated with 50% trifluoroacetic acid in $CH_2Cl_2$ (10 mL) and stirred at room temperature 4 h. Solvents were evaporated in vacuo. Preparatory HPLC (5–50% acetonitrile in 1% TFA/water over 30 min.) afforded the product [3'-(5-carbamimidoyl-2-methylsulfanyl-thiophene-3-sulfonyl)-4-methoxy-6-methyl-biphenyl-2-ylmethoxy]-acetic acid trifluoroacetate (0.080 g, 97%) as a white glassy solid. $^1H$ NMR (MeOD): δ 8.345 (s, 1H), 8.047 (d, 1H, J=8.8 Hz), 7.848 (t, 1H, J=1.6 Hz), 7.692 (t, 1H, J=7.6 Hz), 7.554 (d, 1H, J=7.6 Hz), 6.992 (d, 1H, J=2.0 Hz), 6.871 (d, 1H, J=2.0 Hz), 4.202 (d, 2H, J=5.6 Hz), 3.852 (s, 3H), 3.818 (d, 2H, J=2.4 Hz), 2.736 (s, 3H), 1.999 (s, 3H). $C_{23}H_{24}N_2O_6S_3$: 521.08 (M+1) found 521.00.

Example 193 a) [3'-(5-Carbamimidoyl-2-methylsulfanyl-thiophene-3-sulfonyl)-4-hydroxy-6-methyl-biphenyl-2-ylmethoxy]-acetic acid trifluoroacetate A solution of [3'-(5-carbamimidoyl-2-methylsulfanyl-thiophene-3-sulfonyl)-4-methoxy-6-methyl-biphenyl-2-ylmethoxy]-acetic acid ((Example 192: step g) 0.077 g, 0.0148 mmol) in dry $CH_2Cl_2$ (10 mL) was cooled to 0° C. and treated with $BBr_3$ (0.592 mL, 0.592 mmol) dropwise. The reaction stirred at 0° C. for 30 min. then was allowed to warm to room temperature and stir 27 h. The reaction mixture was cooled to 0° C. and quenched with MeOH. Some HBr evolution was seen. All solvents were evaporated in vacuo, and the residue was taken up in EtOAc (100 mL) and washed with water (1×75 mL) and brine (2×50 mL). The organic layer was dried over MgSO₄ and concentrated in vacuo. Preparatory HPLC (5–50% acetonitrile in 1% TFA/water over 30 min.) afforded the product [3'-(5-carbamimidoyl-2-methylsulfanyl-thiophene-3-sulfonyl)-4-hydroxy-6-methyl-biphenyl-2-ylmethoxy]-acetic acid trifloroacetate (0.039, 52%) as a white glassy solid. ¹H NMR (MeOD): δ 8.344 (s, 1H), 8.090 (d, 1H, J=8.0 Hz), 7.877 (t, 1H, J=2.0 Hz), 7.721 (t, 1H, J=7.6 Hz), 7.572 (d, 1H, J=7.6 Hz), 6.778 (d, 1H, J=2.8 Hz), 6.735 (d, 1H, J=2.0 Hz), 2.710 (s, 3H), 2.028 (s, 2H), 1.935 (s, 3H), 1.254 (t, 2H, J=7.6 Hz).

Example 194

4-{2'-[3-(2-Benzenesulfonylamino-ethyl)-ureido]-6'-methyl-biphenyl-3-sulfonyl}-5-methylsulfanyl-thiophene-2-carboxamidine trifluoroacetate

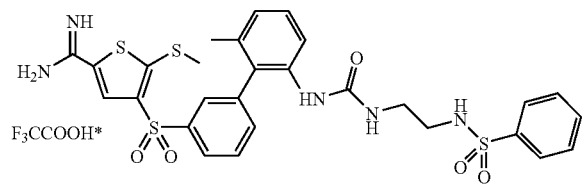

a) (4-{2'-[3-(2-Amino-ethyl)-ureido]-6'-methyl-biphenyl-3-sulfonyl}-5-methylsulfanyl-thiophen-2-yl)-imino-methyl]-carbamic acid tert-butyl ester A solution of [4-(2'-amino-6'-methyl-biphenyl-3-sulfonyl)-5-methylsulfanyl-thiophen-2-yl]-imino-methyl}-carbamic acid tert-butyl ester ((Example 25: step c) 0.150 g, 0.290 mmol) in dry CH₂Cl₂ (10 mL) was treated with pyridine (0.026 mL, 0.319 mol) and p-nitrophenyl chloroformate (0.064 g, 0.319 mmol) and stirred 1.7 h. The reaction mixture was treated with ethylene diamine (0.194 mL, 2.90 mmol) and triethylamine (0.485 mL, 3.48 mmol) and stirred at room temperature 16 h. The reaction was diluted with CH₂Cl₂ and washed with water (3×50 mL). The combined organic layers were dried over MgSO₄ and concentrated in vacuo to afford the product [(4-{2'-[3-(2-amino-ethyl)-ureido]-6'-methyl-biphenyl-3-sulfonyl}-5-methylsulfanyl-thiophen-2-yl)-imino-methyl]-carbamic acid tert-butyl ester (0.145 g, 82%) as a tan solid. ¹H NMR (MeOD): δ 8.195 (s, 1H), 8.057 (d, 1H, J=8.0 Hz), 7.902 (t, 1H, J=1.6 Hz), 7.718 (t, 1H, J=8.0 Hz), 7.554 (d, 1H, J=8.0 Hz), 7.511 (d, 1H, J=8.0 Hz), 7.289 (t, 1H, J=7.6 Hz), 7.119 (d, 1H, J=7.2 Hz), 3.099 (m, 2H), 2.676 (s, 3H), 2.621 (m, 2H), 2.007 (s, 3H), 1.511 (s, 9H). C₂₇H₃₃N₅O₅S₃: 604.16 (M+1) found 603.90.

b) 4-{2'-[3-(2-Benzenesulfonylamino-ethyl)-ureido]-6'-methyl-biphenyl-3-sulfonyl}-5-methylsulfanyl-thiophene-2-carboxamidine trifluoroacetate A solution of [(4-{2'-[3-(2-amino-ethyl)-ureido]-6'-methyl-biphenyl-3-sulfonyl}-5-methylsulfanyl-thiophen-2-yl)-imino-methyl]-carbamic acid tert-butyl ester ((Example 194: step a) 0.060 g, 0.099 mmol) in CH₂Cl₂ (10 mL) was treated with phenylsulfonyl chloride (0.015 mL, 0.119 mmol) and triethylamine (0.033 mL, 0.238 mmol) and stirred 16 h. The reaction mixture was diluted with CH₂Cl₂ and washed with water (2×25 mL). The organic layer was dried over MgSO₄ and concentrated in vacuo. The residue was taken up in CH₂Cl₂ (10 mL), treated with trifluoroacetic acid (2 mL), and stirred at room temperature 1.5 h. The solvents were evaporated in vacuo. Preparatory HPLC (10–80% acetonitrile in 1% TFA/water over 30 min.) afforded the product 4-{2'-[3-(2-benzenesulfonylamino-ethyl)-ureido]-6'-methyl-biphenyl-3-sulfonyl}-5-methylsulfanyl-thiophene-2-carboxamidine trifluoroacetate (0.026 g, 41%) as a white glassy solid. ¹H NMR (MeOD): δ 8.292 (s, 1H), 8.036 (d, 1H, J=8.0 Hz), 7.878 (t, 1H, J=1.6 Hz), 7.820 (d, 2H, J=6.8 Hz), 7.534 (t, 1H, J=1.6 Hz), 7.694 (t, 1H, J=8.0 Hz), 7.616 (m, 1H), 7.562 (d, 2H, J=7.6 Hz), 7.438 (d, 1H, J=7.6 Hz), 7.276 (t, 1H, J=7.6 Hz), 7.212 (d, 1H, J=7.2 Hz), 3.075 (q, 2H, J=4.8 Hz), 2.448 (dt, 2H, J=6.0 Hz, J=2.4 Hz), 2.710 (s, 3H), 2.003 (s, 3H).

Example 195 a) 4-{2'-[3-(2-Methanesulfonylamino-ethyl)-ureido]-6'-methyl-biphenyl-3-sulfonyl}-5-methylsulfanyl-thiophene-2-carboxamidine trifluoroacetate A solution of [(4-{2'-[3-(2-amino-ethyl)-ureido]-6'-methyl-biphenyl-3-sulfonyl}-5-methylsulfanyl-thiophen-2-yl)-imino-methyl]-carbamic acid tert-butyl ester ((Example 194: step a) 0.050 g, 0.083 mmol) in CH₂Cl₂ (10 mL) was treated with methylsulfonylchloride (9.50 μL, 0.099 mmol) and triethylamine (27.7 μL, 0.199 mmol) and stirred at room temperature 7 h. The reaction was diluted with CH₂Cl₂ and washed with water (1×50 mL). The organic layer was dried over MgSO₄, concentrated in vacuo, taken up in CH₂Cl₂ (8 mL), treated with trifluoroacetic acid (0.4 mL) and stirred at room temperature 2 h. Solvents were evaporated in vacuo. Preparatory HPLC (10–50% acetonitrile in 1% TFA/water over 30 min.) afforded the product 4-{2'-[3-(2-methanesulfonylamino-ethyl)-ureido]-6'-methyl-biphenyl-3-sulfonyl}-5-methylsulfanyl-thiophene-2-carboxamidine trifluoroacetate (0.023 g, 48%) as a white glassy solid. ¹H NMR (MeOD): δ 8.305 (s, 1H), 8.052 (d, 1H, J=9.2 Hz), 7.887 (t, 1H, J=1.6 Hz), 7.719 (t, 1H, J=7.6 Hz), 7.571 (d, 1H, J=7.2 Hz), 7.450 (d, 1H, J=7.2 Hz), 7.284 (t, 1H, J=8.0 Hz), 7.131 (d, 1H, J=7.6 Hz), 3.140 (m, 2H), 3.040 (m, 2H), 2.898 (s, 3H), 2.718 (s, 3H), 2.005 (s, 3H). C₂₃H₂₇N₅O₅S₄: 582.09 (M+1) found 582.00.

Example 196

[3-(2-{3-[3'-(5-Carbamimidoyl-2-methylsulfanyl-thiophene-3-sulfonyl)-6-methyl-biphenyl-2-yl]-ureido}-ethyl)-ureido]-acetic acid trifluoroacetate

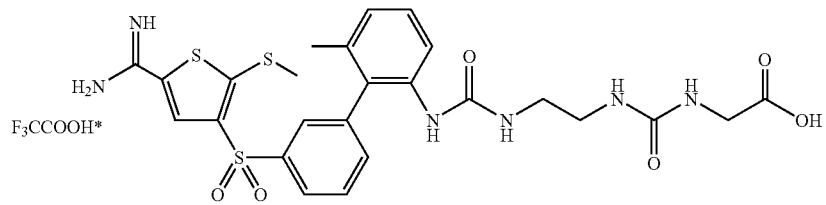

a) {3-[2-(3-{3'-[5-(tert-Butoxycarbonylamino-imino-methyl)-2-methylsulfanyl-thiophene-3-sulfonyl]-6-methyl-biphenyl-2-yl}-ureido)-ethyl]-ureido}-acetic acid methyl ester A solution of [(4-{2'-[3-(2-amino-ethyl)-ureido]-6'-methyl-biphenyl-3-sulfonyl}-5-methylsulfanyl-thiophen-2-yl)-imino-methyl]-carbamic acid tert-butyl ester ((Example 194: step a) 0.030 g, 0.050 mmol) in CH$_2$Cl$_2$ (10 mL) was treated with ethyl isocyanatoacetate (6.70 μL, 0.060 mmol) and stirred at room temperature 35 min. The reaction was diluted with CH$_2$Cl$_2$ and washed with water (1×15 mL). The organic layer was dried over MgSO$_4$ and concentrated in vacuo to afford the product {3-[2-(3-{3'-[5-(tert-butoxycarbonylamino-imino-methyl)-2-methylsulfanyl-thiophene-3-sulfonyl]-6-methyl-biphenyl-2-yl}-ureido)-ethyl]-ureido}-acetic acid methyl ester (0.031 g, 86%) as an off-white solid. C$_{32}$H$_{40}$N$_6$O$_8$S$_3$: 733.21 (M+1) found 732.90.

b) {3-[2-(3-{3'-[5-(tert-Butoxycarbonylamino-imino-methyl)-2-methylsulfanyl-thiophene-3-sulfonyl]-6-methyl-biphenyl-2-yl}-ureido)-ethyl]-ureido}-acetic acid A solution of {3-[2-(3-{3'-[5-(tert-butoxycarbonylamino-imino-methyl)-2-methylsulfanyl-thiophene-3-sulfonyl]-6-methyl-biphenyl-2-yl}-ureido)-ethyl]-ureido}-acetic acid methyl ester ((Example 197: step a) 0.031 g, 0.042 mmol) in MeOH:water (2:1, 15 mL) was treated with NaOH (10 N, 0.042 mL, 0.420 mmol) and stirred at room temperature 18 h. MeOH was evaporated in vacuo and the remaining aqueous solution was acidified to pH 5 with glacial acetic acid. The solution was extracted with CH$_2$Cl$_2$ (3×50 mL). The combined organic layers were dried over MgSO$_4$ and evaporated in vacuo to afford the product {3-[2-(3-{3'-[5-(tert-butoxycarbonylamino-imino-methyl)-2-methylsulfanyl-thiophene-3-sulfonyl]-6-methyl-biphenyl-2-yl}-ureido)-ethyl]-ureido}-acetic acid (0.025 g, 83%) as an off-white solid. The crude material was used directly in the next reaction.

c) [3-(2-{3-[3'-(5-Carbamimidoyl-2-methylsulfanyl-thiophene-3-sulfonyl)-6-methyl-biphenyl-2-yl]-ureido}-ethyl)-ureido]-acetic acid trifluoroacetate A suspension of {3-[2-(3-{3'-[5-(tert-butoxycarbonylamino-imino-methyl)-2-methylsulfanyl-thiophene-3-sulfonyl]-6-methyl-biphenyl-2-yl}-ureido)-ethyl]-ureido}-acetic acid ((Example 196: step b) 0.025 g, 0.035 mmol) in CH$_2$Cl$_2$ (10 mL) was treated with trifluoroacetic acid (1.00 mL) and stirred at room temperature 1.2 h. Solvents were removed in vacuo. Preparatory HPLC (10–80% acetonitrile in 1% TFA/water over 30 min.) afforded the product [3-(2-{3-[3'-(5-carbamimidoyl-2-methylsulfanyl-thiophene-3-sulfonyl)-6-methyl-biphenyl-2-yl]-ureido}-ethyl)-ureido]-acetic trifluoroacetate (0.013 g, 60%) as a white glassy solid. $^1$H NMR (CD$_3$CN): δ 8.099 (s, 1H), 8.048 (d, 1H, J=9.6 Hz), 7.815 (t, 1H, J=1.6 Hz), 7.709 (t, 1H, J=8.0 Hz), 7.575 (d, 1H, J=7.6 Hz), 7.498 (d, 1H, J=8.0 Hz), 7.295 (t, 1H, J=7.6 Hz), 7.161 (d, 1H, J=8.0 Hz), 3.756 (s, 2H), 2.979 (s br, 4H), 2.681 (s, 3H), 2.079 (s, 3H).

Example 197 a) 5-methylsulfanyl-4-[6'-methyl-2'-(N'-methanesulfonylureido)-biphenyl-3-sulfonyl]-thiophene-2-carboxamidine A solution of [4-(2'-amino-6'-methyl-biphenyl-3-sulfonyl)-5-methylsulfanyl-thiophen-2-yl]-imino-methyl}-carbamic acid tert-butyl ester ((Example 25: step c) 0.050 g, 0.097 mmol) in CH$_2$Cl$_2$ (5 mL) was treated with pyridine (8.6 μL, 0.106 mmol) and p-nitrophenylchloroformate (0.021 g, 0.106 mmol) and stirred 2 h. The mixture was treated with methane sulfonamide (0.018 g, 0.193 mmol) and triethylamine (0.108 mL, 0.773 mmol) and stirred 2 h. The reaction mixture was diluted with CH$_2$Cl$_2$ and washed with water (2×25 mL). The organic layer was dried over MgSO$_4$ and concentrated in vacuo. The residue was taken up in CH$_2$Cl$_2$ (5 mL), treated with trifluoroacetic acid (1.00 mL), and stirred 1 h. Solvents were evaporated in vacuo. Preparatory HPLC (10–80% acetonitrile in 1% TFA/water over 30 min.) afforded the title compound (0.015 g, 57%) as a white glassy solid. $^1$H NMR (MeOD): δ 8.359 (s, 1H), 8.123 (d, 1H, J=9.6 Hz), 7.993 (t, 1H J=1.6 Hz), 7.790 (t, 1H, J=8.4 Hz), 7.625 (d, 1H, J=7.6 Hz), 7.370 (t, 1H, J=8.0 Hz), 7.244 (d, 1H, J=7.2 Hz), 7.170 (d, 1H, J=7.2 Hz), 3.008 (s, 3H), 2.722 (s, 3H), 2.003 (s, 3H). C$_{21}$H$_{22}$N$_4$O$_5$S$_4$: 539.05 (M+1) found 538.90.

Example 198

4-[4'-Methoxy-6'-methyl-2'-(2-oxo-imidazolidin-1-yl)-biphenyl-3-sulfonyl]-5-methylsulfanyl-thiophene-2-carboxamidine trifluoroacetate

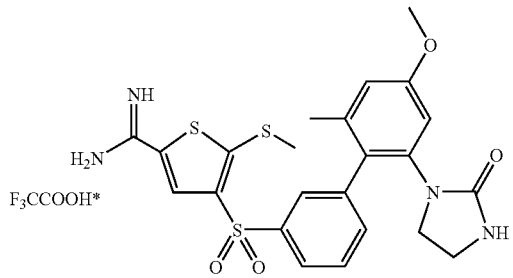

a) 2-Bromo-5-methoxy-3-methyl-benzoic acid

A solution of (2-bromo-5-methoxy-3-methyl-phenyl)-methanol ((Example 192: step c) 7.85 g, 34.0 mmol) in acetone (300 mL) was heated to 60° C. and treated over 25 min. with KMnO₄ (12.6 g, 79.8 mmol) as an aqueous solution (175 mL). The mixture was heated to 60° C. for an additional 35 min. A saturated aqueous solution of NaHSO₃ was added until the solution turned beige in color. Concentrated NH₄OH was added to pH 10 and the solids were filtered through a medium porosity fritted funnel. The filtrate was acidified to pH 4 with concentrated HCl, and the solution was extracted with ether (2×200 mL). The combined organic layers were dried over MgSO₄ and concentrated in vacuo to afford the product 2-bromo-5-methoxy-3-methyl-benzoic acid (4.15 g, 50%) as a white solid. $^1$H NMR (MeOD): δ 6.968 (d, 1H, J=2.8 Hz), 6.775 (d, 1H, J=3.2 Hz), 3.776 (s, 3H), 2.352 (s, 3H).

b) (2-Bromo-5-methoxy-3-methyl-phenyl)-carbamic acid tert-butyl ester

A solution of 2-bromo-5-methoxy-3-methyl-benzoic acid ((Example 198: step a) 3.39 g, 13.8 mmol) in dry tert-butanol was treated with DPPA (3.58 mL, 16.6 mmol) dropwise and stirred 5 min. The solution was treated with diisopropylethylamine (2.89 mL, 16.6 mmol) and heated to 80° C. 17.5 h. Tert-butanol was removed in vacuo. The residue was taken up in EtOAc and washed with saturated aqueous NaHCO₃ (2×60 mL) and water (1×60 mL). The combined organic layers were dried over MgSO₄ and concentrated in vacuo. Silica gel chromatography (10% EtOAc in hexanes) afforded the product (2-bromo-5-methoxy-3-methyl-phenyl)-carbamic acid tert-butyl ester (3.05 g, 70%) as a colorless oil. $^1$H NMR (CDCl₃): δ 7.701 (d, 1H, J=1.6 Hz), 7.146 (s, NH), 6.517 (d, 1H, J=3.2 Hz), 3.797 (s, 3H), 2.360 (s, 3H), 1.534 (s, 9H).

c) 2-Bromo-5-methoxy-3-methyl-phenylamine

A solution of (2-bromo-5-methoxy-3-methyl-phenyl)-carbamic acid tert-butyl ester ((Example 198: step b) 3.00 g, 9.49 mmol) in CH₂Cl₂ (50 mL) was treated with trifluoroacetic acid (7.00 mL) dropwise. The solution was stirred at room temperature 1.3 h. The solvents were evaporated in vacuo to yield the product 2-bromo-5-methoxy-3-methyl-phenylamine (2.04 g, 65%) as a yellow solid trifluoroacetate salt. The crude mixture was used directly in the next reaction.

d) 5-Methoxy-3-methyl-2-(4,4,5,5-tetramethyl-[1,3,2]dioxaborolan-2-yl)-phenylamine A solution of 2-bromo-5-methoxy-3-methyl-phenylamine ((Example 198: step c) 2.04 g, 6.18 mmol) in dry dioxane (100 mL) was treated with triethylamine (5.26 mL, 37.7 mmol), 2-(dicyclohexylphosphino)biphenyl (0.662 g, 1.89 mmol), and Pd(OAc)₂ (0.106 g, 0.472 mmol). 4,4,5,5-Tetramethyl-1,3,2-dioxaborolane (4.09 mL, 28.3 mmol) was added slowly and the mixture heated to reflux for 1 h. The dioxane was evaporated in vacuo. The residue was taken up in EtOAc and washed with water (2×75 mL). The organic layer was filtered by gravity to remove the palladium residue, dried over MgSO₄ and concentrated in vacuo. Silica gel chromatography (10–25% EtOAc in hexanes raised in 5% increments) afforded the product 5-methoxy-3-methyl-2-(4,4,5,5-tetramethyl-[1,3,2]dioxaborolan-2-yl)-phenylamine (1.61 g, 98%) as a light brown solid. $^1$H NMR (CDCl₃): δ 7.361 (d, 1H, J=7.6 Hz), 7.279 (d, 1H, J=8.0 Hz), 3.815 (s, 3H), 2.46 (s, 3H), 1.356 (s, 12H).

e) {[4-(2'-Amino-4'-methoxy-6'-methyl-biphenyl-3-sulfonyl)-5-methylsulfanyl-thiophen-2-yl]-imino-methyl}-carbamic acid tert-butyl ester A solution of {[4-(3-bromo-benzenesulfonyl)-5-methylsulfanyl-thiophen-2-yl]-imino-methyl}-carbamic acid tert-butyl ester ((Example 27: step c) 1.50 g, 3.05 mmol) in toluene:EtOH (2:1, 45 mL) was treated with 5-methoxy-3-methyl-2-(4,4,5,5-tetramethyl-[1,3,2]dioxaborolan-2-yl)-phenylamine (((Example 198: step d) 1.61 g, 6.11 mmol), aqueous Na₂CO₃ (2 M, 12.2 mL, 24.4 mmol) and Pd (PPh₃)₄ (0.706 g, 0.611 mmol). The mixture was heated to 80° C. 4 h. The reaction was cooled to room temperature, diluted with EtOAc, washed with brine (1×75 mL) and water (2×75 mL), dried over MgSO₄ and concentrated in vacuo. Silica gel chromatography (25% then 35% then 50% EtOAc in hexanes) afforded the product {[4-(2'-amino-4'-methoxy-6'-methyl-biphenyl-3-sulfonyl)-5-methylsulfanyl-thiophen-2-yl]-imino-methyl}-carbamic acid tert-butyl ester (0.680 g, 40%) as a yellow-brown solid. $^1$H NMR (MeOD): δ 8.223 (s, 1H), 8.001 (d, 1H, J=7.2 Hz), 7.879 (t, 1H, J=1.6 Hz), 7.698 (t, 1H, J=8.0 Hz), 7.549 (d, 1H, J=8.0 Hz), 6.287 (dd, 2H, J=7.2 Hz, J=2.4 Hz), 3.770 (s, 3H), 2.669 (s, 3H), 1.900 (s, 3H), 1.510 (s, 9H). $C_{25}H_{29}N_3O_5S_3$: 548.13 (M+1) found 547.70.

f) 4-[4'-Methoxy-6'-methyl-2'-(2-oxo-imidazolidin-1-yl)-biphenyl-3-sulfonyl]-5-methylsulfanyl-thiophene-2-carboxamidine trifluoroacetate A solution of {[4-(2'-amino-4'-methoxy-6'-methyl-biphenyl-3-sulfonyl)-5-methylsulfanyl-thiophen-2-yl]-imino-methyl}-carbamic acid tert-butyl ester ((Example 198: step e) 0.050 g, 0.091 mmol) in dry CH₂Cl₂ (10 mL) was treated with bromoethylisocyanate (0.010 mL, 0.110 mmol) and stirred at room temperature 4 h. Additional bromoethylisocyanate (0.010 mL, 0.110 mmol) was added and the reaction stirred at room temperature 15 h. The reaction mixture was washed with water (1×15 mL), dried over MgSO₄, and concentrated in vacuo. The residue was taken up in CH₂Cl₂ (10 mL), treated with trifluoroacetic acid (1.00 mL), and stirred at room temperature 1 h. The solvents were evaporated in vacuo. Preparatory HPLC (10–80% acetonitrile in 1% TFA/water over 30 min.) afforded the product 4-[4'-methoxy-6'-methyl-2'-(2-oxo-imidazolidin-1-yl)-biphenyl-3-sulfonyl]-5-methylsulfanyl-thiophene-2-carboxamidine trifluoroacetate (0.010 g, 21%) as a white glassy solid. $^1$H NMR (MeOD): δ 8.354 (s, 1H), 8.032 (d, 1H, J=7.6 Hz), 7.946 (s, 1H), 7.733 (t, 1H, J=7.6 Hz), 7.574 (d, 1H, J=8.0 Hz), 7.059 (s, 1H), 6.967 (s, 1H), 3.877 (s, 3H), 2.730 (s, 3H), 2.101 (s, 3H), 3.841 (dt, 4H, J=8.8 Hz, J=2.4 Hz). $C_{23}H_{24}N_4O_4S_3$: 517.10 (M+1) found 517.10.

Example 199

N-[3'-(5-Carbamimidoyl-2-methylsulfanyl-thiophene-3-sulfonyl)-4-methoxy-6-methyl-biphenyl-2-yl]-4-methanesulfonyl-butyramide trifluoroacetate

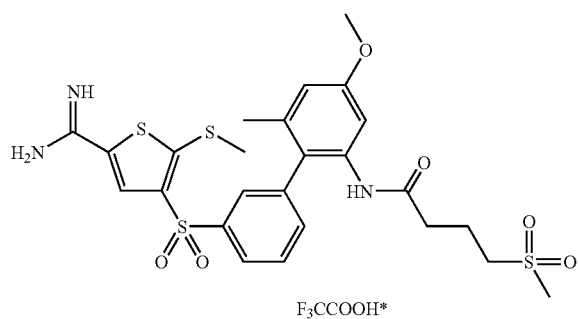

A solution of {[4-(2'-amino-4'-methoxy-6'-methyl-biphenyl-3-sulfonyl)-5-methylsulfanyl-thiophen-2-yl]-imino-methyl}-carbamic acid tert-butyl ester ((Example 198: step e) 0.050 g, 0.091 mmol) in CH$_2$Cl$_2$ (10 mL) was treated with triethylamine (38.0 μL, 0.274 mmol) and 4-methanesulfonyl-butyryl chloride (0.025 g, 0.137 mmol) as a solution in CH$_2$Cl$_2$ (3 mL) and stirred at room temperature 3 h. The reaction mixture was washed with saturated aqueous NaHCO$_3$ (1×15 mL). The organic layer was dried over MgSO$_4$ and trifluoroacetic acid (0.5 mL) was added. The solution stirred at room temperature 1 h and solvents were removed in vacuo. Preparatory HPLC (10–50% acetonitrile in 1% TFA/water over 30 min.) afforded the product N-[3'-(5-carbamimidoyl-2-methylsulfanyl-thiophene-3-sulfonyl)-4-methoxy-6-methyl-biphenyl-2-yl]-4-methanesulfonyl-butyramide trifluoroacetate (0.013 g, 24%) as a white glassy solid. $^1$H NMR (MeOD): δ 8.309 (s, 1H), 8.032 (d, 1H, J=8.8 Hz), 7.868 (t, 1H, J=1.6 Hz), 7.684 (t, 1H, J=8.0 Hz), 7.543 (d, 1H, J=8.0 Hz), 6.871 (s, 1H), 6.817 (d, 1H, J=2.4 Hz), 3.841 (s, 3H), 2.922 (s, 3H), 2.822 (t, 2H, J=7.6 Hz), 2.742 (s, 3H), 2.202 (t, 2H, J=6.8 Hz), 2.063 (s, 3H), 1.765 (m, 2H). C$_{25}$H$_{29}$N$_3$O$_6$S$_4$: 596.09 (M+1) found 596.10.

Example 200 a) 4-{2'-[3-(2-Methanesulfonyl-ethyl)-ureido]-4'-methoxy-6'-methyl-biphenyl-3-sulfonyl}-5-methyl-sulfanyl-thiophene-2-carboxamidine trifluoroacetate A solution of {[4-(2'-amino-4'-methoxy-6'-methyl-biphenyl-3-sulfonyl)-5-methylsulfanyl-thiophen-2-yl]-imino-methyl}-carbamic acid tert-butyl ester ((Example 198: step e) 0.070 g, 0.128 mmol) in dry CH$_2$Cl$_2$ (3 mL) was treated with 1-isocyanato-2-methanesulfonyl-ethane (0.019 g, 0.128 mmol) as a solution in CH$_2$Cl$_2$ (2 mL) and stirred 20 min. The reaction mixture was washed with saturated aqueous NaHCO$_3$ (1×25 mL). The organic layer was dried over MgSO$_4$ and concentrated in vacuo. The residue was taken up in CH$_2$Cl$_2$ (10 mL) and treated with trifluoroacetic acid (2.00 mL), stirring at room temperature 30 min. The solvents were removed in vacuo. Preparatory HPLC (10–80% acetonitrile in 1% TFA/water over 30 min.) afforded the product 4-{2'-[3-(2-methanesulfonyl-ethyl)-ureido]-4'-methoxy-6'-methyl-biphenyl-3-sulfonyl}-5-methylsulfanyl-thiophene-2-carboxamidine trifluoroacetate (0.040 g, 53%) as a white glassy solid. $^1$H NMR (MeOD): δ 8.300 (s, 1H), 8.031 (d, 1H, J=8.0 Hz), 7.865 (t, 1H, J=1.6 Hz), 7.688 (t, 1H, J=7.6 Hz), 7.568 (d, 1H, J=8.0 Hz), 7.063 (d, 1H, J=1.6 Hz), 6.730 (d, 1H, J=1.6 Hz), 3.818 (s, 3H), 3.507 (t, 2H, J=6.4 Hz), 3.171 (t, 2H, J=6.0 Hz), 2.928 (s, 3H), 2.725 (s, 3H), 2.315 (s, 3H). C$_{24}$H$_{28}$N$_4$O$_6$S$_4$: 597.09 (M+1) found 597.00.

Example 201

4-{2'-[3-(4-Methanesulfonyl-butyl)-ureido]-6'-methyl-biphenyl-3-sulfonyl}-5-methylsulfanyl-thiophene-2-carboxamidine trifluoroacetate

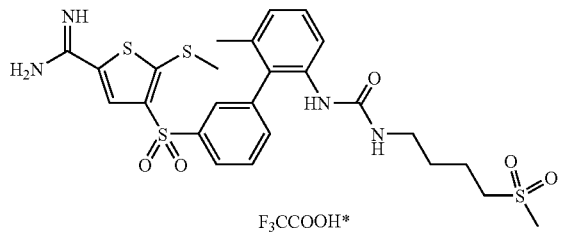

F₃CCOOH* a) 2-(4-Methylsulfanyl-butyl)-isoindole-1,3-dione

A solution of 2-(4-bromo-butyl)-isoindole-1,3-dione (1.00 g, 3.54 mmol) in MeOH (60 mL) was treated with sodium thiomethoxide (0.298 g, 4.25 mmol) and heated to reflux 18 h. The solvent was evaporated in vacuo and the residue partitioned between EtOAc and water. The aqueous layer was further extracted with EtOAc (1×75 mL). The organic layers were dried over MgSO₄ and concentrated in vacuo to afford the product 2-(4-methylsulfanyl-butyl)-isoindole-1,3-dione (0.803 g, 91%). $^1$H NMR (MeOD) 7.844 (m, 4H), 3.704 (t, 2H, J=7.2 Hz), 2.549 (t, 2H, J=7.2 Hz), 2.063 (s, 3H), 1.792 (quint, 2H, J=7.2 Hz), 1.731 (quint, 2H, J=7.2 Hz).

b) 2-(4-Methanesulfonyl-butyl)-isoindole-1,3-dione

A solution of 2-(4-methylsulfanyl-butyl)-isoindole-1,3-dione ((Example 201: step a) 1.35 g, 5.42 mmol) in CH₂Cl₂ (50 mL) was treated with 3-chloroperbenzoic acid (mCPBA, 3.03 g, 13.5 mmol) and stirred at room temperature 17 h. The solution was washed with aqueous Na₂S₂O₃ (2×40 mL) and water (1×40 mL). The organic layer was dried over MgSO₄ and concentrated in vacuo to afford the product 2-(4-methanesulfonyl-butyl)-isoindole-1,3-dione (0.866 g, 57%). $^1$H NMR (MeOD): δ 7.827 (m, 4H), 3.732 (t, 2H, J=6.4 Hz), 3.193 (t, 2H, J=7.2 Hz), 2.939 (s, 3H), 1.843 (m, 4H).

c) 4-Methanesulfonyl-butylamine

A solution of 2-(4-methanesulfonyl-butyl)-isoindole-1,3-dione ((Example 201: step b) 0.866 g, 3.08 mmol) in EtOH (30 mL) was treated with hydrazine and stirred at room temperature 18 h. The solid precipitate was removed by filtration and the filtrate was concentrated in vacuo. To remove any excess hydrazine, the resulting waxy solid was titrated with toluene and with THF and placed under high vacuum overnight to afford the product (0.400 g, 86%) as a waxy, off-white solid. $^1$NMR (MeOD): δ 3.153 (dd, 2H, J=8.8 Hz, J=0.0 Hz), 2.962 (s, 3H), 2.582 (dd, 2H, J=7.6 Hz, J=0.0 Hz), 1.811 (m, 2H) 1.747 (m, 2H).

d) 4-{2'-[3-(4-Methanesulfonyl-butyl)-ureido]-6'-methyl-biphenyl-3-sulfonyl}-5-methylsulfanyl-thiophene-2-carboxamidine trifluoroacetate A solution of [4-(2'-amino-6'-methyl-biphenyl-3-sulfonyl)-5-methylsulfanyl-thiophen-2-yl]-imino-methyl}-carbamic acid tert-butyl ester ((Example 25: step c) 0.100 g, 0.193 mmol) in CH₂Cl₂ (10 mL) was treated with pyridine (0.017 mL, 0.213 mmol) and p-nitrophenylchloroformate (0.043 g, 0.213 mmol) and stirred 2 h. The solution was treated with 4-methanesulfonylbutylamine (Example 201: step c, 0.035 g, 0.232 mmol) and triethylamine (0.215 mL, 1.54 mmol) and stirred 2 h. The mixture was diluted with CH₂Cl₂ and washed with water (1×50 mL). The organic layer was dried over MgSO₄ and filtered. The remaining CH₂Cl₂ solution was treated with trifluoroacetic acid (1.00 mL) and stirred 1.5 h. The solvents were evaporated in vacuo. Preparatory HPLC (10–50% acetonitrile in 1% TFA/water over 30 min.) afforded the product 4-{2'-[3-(4-methanesulfonyl-butyl)-ureido]-6'-methyl-biphenyl-3-sulfonyl}-5-methylsulfanyl-thiophene-2-carboxamidine trifluoroacetate (0.022 g, 19%) as a white glassy solid. $^1$H NMR (MeOD): δ 8.326 (s, 1H), 8.069 (d, 1H, J=8.0 Hz), 7.917 (t, 1H, J=1.6 Hz), 7.740 (t, 1H, J=8.0 Hz), 7.586 (d, 1H, J=7.6 Hz), 7.441 (d, 1H, J=7.2 Hz), 7.305 (t, 1H, J=8.0 Hz), 7.151 (d, 1H, J=8.0 Hz), 3.116 (dd, 2H, J=8.8 Hz, J=6.4 Hz), 3.069 (t, 2H, J=6.8 Hz), 2.962 (s, 3H), 2.739 (s, 3H), 2.025 (s, 3H) 1.732 (quint, 2H, J=7.6 Hz), 1.506 (quint, 2H, J=7.6 Hz). $C_{25}H_{30}N_4O_5S_4$: 595.11 (M+1) found 595.10.

Examples 202–208

A solution of [4-(2'-amino-6'-methyl-biphenyl-3-sulfonyl)-5-methylsulfanyl-thiophen-2-yl]-imino-methyl}-carbamic acid tert-butyl ester ((Example 25: step c) 1.00 g, 1.93 mmol) in dry CH₂Cl₂ (20 mL) was treated with pyridine (0.172 mL, 2.13 mmol) and p-nitrophenylchloroformate (0.428 g, 2.13 mmol). The mixture was stirred at room temperature 2 h. The solution of the resulting carbamate, {3'-[5-(tert-butoxycarbonylamino-imino-methyl)-2-methylsulfanyl-thiophene-3-sulfonyl]-6-methyl-biphenyl-2-yl}-carbamic acid 4-nitro-phenyl ester, was divided into vials and treated with the following amines (1.1 equivalents) and triethylamine (8.0 equivalents).

Example 202

2-((4-Bromo-phenyl)-ethylamine)

Example 203

3-Phenyl-propylamine

Example 204

Benzylamine

Example 205

2-Amino-3-phenyl-propionic acid

Example 206

6-Amino-2-tert-butoxycarbonylamino-hexanoic acid

Example 207

2-(1H-Indol-3-yl)-ethylamine

Example 208

3,3-Diphenyl-propylamine

The reaction mixtures stirred at room temperature 4 h. The solutions were washed with water and the organic layers

Example 202

4-(2'-{3-[2-(4-Bromo-phenyl)-ethyl]-ureido}-6'-methyl-biphenyl-3-sulfonyl)-5-methylsulfanyl-thiophene-2-carboxamidine trifluoroacetate

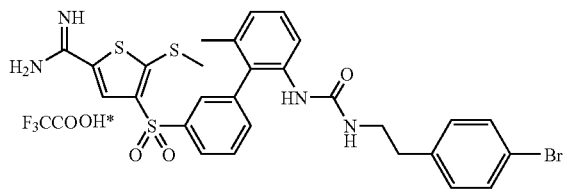

¹H NMR (MeOD): δ 8.299 (s, 1H), 8.075 (d, 1H, J=8.4 Hz), 7.894 t, 1H, J=1.6 Hz), 7.708 (t, 1H, J=8.0 Hz), 7.529 (d, 1H, J=8.4 Hz), 7.376 (d, 2H, J=8.4 Hz), 7.834 (t, 1H, J=8.4 Hz), 7.279 (t, 1H, J=7.6 Hz), 7.134 (d, 1H, J=7.6 Hz), 6.957 (d, 2H, J=7.6 Hz), 3.20 (m, 2H), 2.656 (s, 3H), 2.555 (m, 2H), 1.995 (s, 3H). $C_{28}H_{27}BrN_4O_3S_3$: 643.04 (M+1) found 643.00.

Example 203

4-{6'-Methyl-2'-[3-(3-phenyl-propyl)-ureido]-biphenyl-3-sulfonyl}-5-methylsulfanyl-thiophene-2-carboxamidine trifluoroacetate

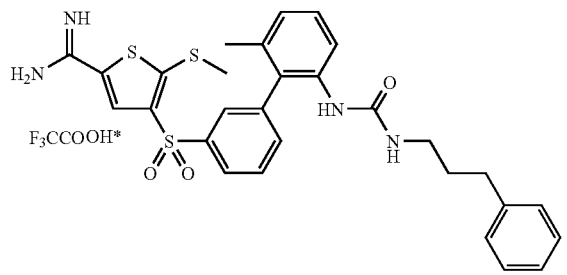

¹H NMR (MeOD): δ 8.293 (s, 1H), 8.056 (d, 1H, J=8.0 Hz), 7.916 (t, 1H, J=1.6 Hz), 7.715 (t, 1H, J=7.6 Hz), 7.592 (d, 1H, J=7.6 Hz), 7.449 (d, 1H, J=7.6 Hz), 7.308 (t, 1H, J=7.6 Hz), 7.255 (d, 2H, J=7.2 Hz), 7.166 (t, 2H, J=7.2 Hz), 7.147 (d, 2H, J=8.0 Hz), 3.021 (t, 2H, J=6.4 Hz), 2.697 (s, 3H), 2.515 (t, 2H, J=7.6 Hz), 2.026 (s, 3H), 1.638 (quint, 2H, J=7.6 Hz). $C_{29}H_{30}N_4O_3S_3$: 579.15 (M+1) found 579.10.

Example 204

4-[2'-(3-Benzyl-ureido)-6'-methyl-biphenyl-3-sulfonyl]-5-methylsulfanyl-thiophene-2-carboxamidine trifluoroacetate

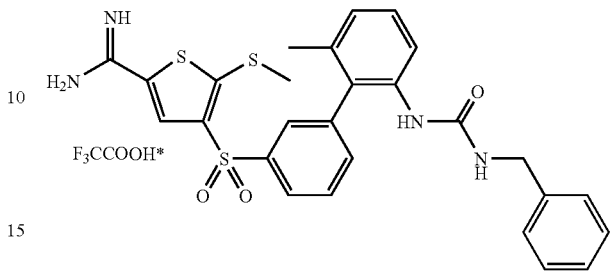

¹H NMR (MeOD): δ 8.243 (s, 1H), 8.073 (d, 1H, J=9.2 Hz), 7.951 (t, 1H, J=1.6 Hz), 7.685 (t, 1H, J=8.0 Hz), 7.558 (d, 1H, J=7.6 Hz), 7.406 (d, 1H, J=8.8 Hz), 7.301 (t, 1H, J=8.0 Hz), 7.232 (m, 4H), 6.977 (d, 2H, J=8.4 Hz), 4.137 (q, 2H, J=16 Hz), 2.649 (s, 3H), 2.029 (s, 3H). $C_{27}H_{26}N_4O_3S_3$: 55.12 (M+1) found 551.10.

Example 205

2-{3-[3'-(5-Carbamimidoyl-2-methylsulfanyl-thiophene-3-sulfonyl)-6-methyl-biphenyl-2-yl]-ureido}-3-phenyl-propionic acid trifluoroacetate

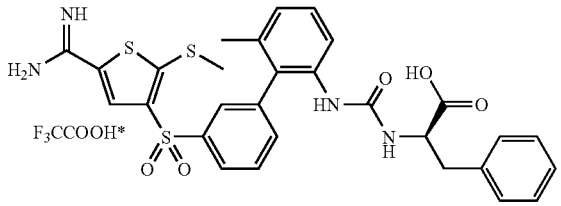

¹H NMR (CD₃CN): δ 10.027 (s br, 1H), 8.083 (s, 1H), 7.875 (s, 1H), 7.807 (s, 1H), 7.729 (t, 1H, J=7.525 Hz), 7.525 (d, 1H, J=6.8 Hz), 7.429 (m, 1H), 7.272 (m, 5H), 7.101 (m, 2H), 5.446 (t, 1H, J=10.4 Hz), 3.077 (m, 2H), 2.674 (s, 3H), 2.018 (s, 3H). $C_{29}H_{28}N_4O_5S_3$: 609.12 (M+1) found 609.10.

Example 206

2-Amino-6-{3-[3'-(5-carbamimidoyl-2-methylsulfanyl-thiophene-3-sulfonyl)-6-methyl-biphenyl-2-yl]-ureido}-hexanoic acid trifluoroacetate

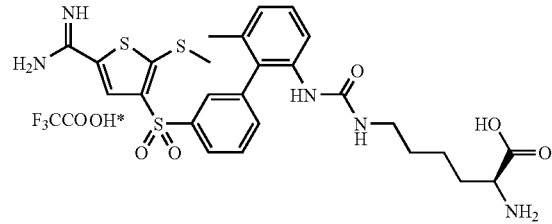

¹H NMR (CD₃CN): δ 8.135 (s, 1H), 8.037 (d, 1H, J=7.6 Hz), 7.839 (s, 1H), 7.702 (t, 1H, J=7.6 Hz), 7.566 (d, 1H, J=8.0 Hz), 7.413 (d, 1H, J=8.0 Hz), 7.297 (t, 1H, J=7.6 Hz), 7.186 (d, 1H, J=7.2 Hz), 3.951 (s br, 1H), 2.939 (t, 2H, J=1.6 Hz), 2.674 (s, 3H), 2.043 (s, 3H), 1.854 (m, 2H), 1.311 (m, 4H). $C_{26}H_{31}N_5O_5S_3$: 590.15 (M+1) found 590.10.

Example 207

4-(2'-{3-[2-(1H-Indol-3-yl)-ethyl]-ureido}-6'-methyl-biphenyl-3-sulfonyl)-5-methylsulfanyl-thiophene-2-carboxamidine trifluoroacetate

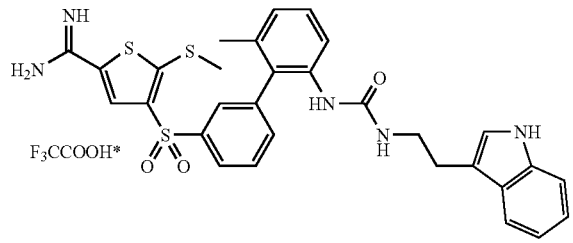

$^1$H NMR (MeOD): δ 8.270 (s, 1H), 8.069 (d, 1H, J=8.0 Hz), 7.901 (t, 1H, J=1.6 Hz), 7.661 (t, 1H, J=7.2 Hz), 7.467 (t, 2H, J=8.8 Hz), 7.351 (t, 2H, J=6.8 Hz), 7.296 (t, 1H, J=7.6 Hz), 7.163 (d, 1H, J=8.0 Hz), 7.103 (t, 1H, J=7.2 Hz), 6.991 (t, 1H, J=6.8), 6.855 (s, 1H), 3.428 (m, 2H), 2.712 (t, 2H, J=8.8 Hz), 2.575 (s, 3H), 2.028 (s, 3H). $C_{30}H_{29}N_5O_3S_3$: 604.14 (M+1) found 604.10.

Example 208

4-{2'-[3-(3,3-Diphenyl-propyl)-ureido]-6'-methyl-biphenyl-3-sulfonyl}-5-methylsulfanyl-thiophene-2-carboxamidine trifluoroacetate

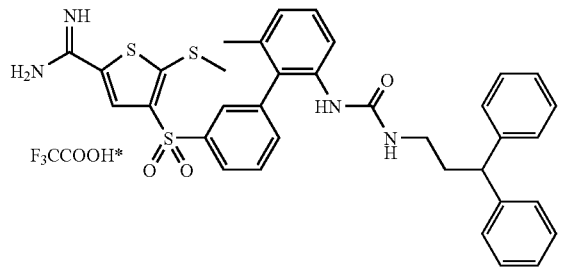

$^1$H NMR (MeOD): δ 8.263 (s, 1H), 8.022 (d, 1H, J=8.8 Hz), 7.913 (t, 1H, J=1.6 Hz), 7.679 (t, 1H, J=7.6 Hz), 7.585 (d, 1H, J=7.6 Hz), 7.416 (d, 1H, J=7.416 Hz), 7.253 (m, 9H), 7.163 (t, 3H, J=6.8 Hz), 3.878 (t, 1H, J=7.6 Hz), 2.944 (dt, 2H, J=6.8 Hz, J=2.4 Hz), 2.689 (s, 3H), 2.081 (q, 2H, J=7.6 Hz), 2.032 (s, 3H). $C_{35}H_{34}N_4O_3S_3$: 655.18 (M+1) found 655.10.

Example 209

N-[3'-(5-Carbamimidoyl-2-methylsulfanyl-thiophene-3-sulfonyl)-6-methyl-biphenyl-2-yl]-4-methanesulfonyl-butyramide trifluoroacetate

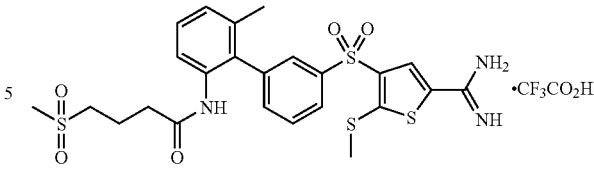

a) 4-Methanesulfonyl-butyryl chloride

4-Methylsulfanyl-butyric acid methyl ester (0.50 g, 3.37 mmol) in dichloromethane [5 mL] was added dropwise to a solution of mCPBA (1.57 g, 9.10 mmol) in dichloromethane [15 mL] at room temperature and then refluxed for 1 hour. The solution was then cooled to room temperature and solid sodium sulfite was added. The reaction was filtered, washed with 1N NaOH, brine and dried with magnesium sulfate and evaporated. The crude residue was then dissolved in THF/methanol/water [2/1/0.1 mL] and lithium hydroxide (0.18 g, 4.38 mmol) was added. The reaction was heated to 50° C. for 24 hours. The reaction was cooled to room temperature and 1N HCl was added and the product was extracted with ethyl acetate, dried with magnesium sulfate to give the product (0.12 g, 21%). $^1$H-NMR (CDCl$_3$): δ 3.20 (t, 2H, J=7.6 Hz), 2.98 (s, 3H), 2.52 (t, 2H, J=7.2 Hz), 2.09 (m, 2H). The acid was dissolved in dichloromethane [5 mL] and thionyl chloride [5 mL] was added. The reaction was stirred at room temperature for 3 hours, evaporated and used directly in the next step.

b) (Imino-{4-[2'-(4-methanesulfonyl-butyrylamino)-6'-methyl-biphenyl-3-sulfonyl]-5-methylsulfanyl-thiophen-2-yl}-methyl)-carbamic acid tert-butyl ester 4-Methanesulfonyl-butyryl chloride (0.333 g, 1.81 mmol) [example 209, step a] was added to a solution of {[4-(2'-amino-6'-methyl-biphenyl-3-sulfonyl)-5-methylsulfanyl-thiophen-2-yl]-imino-methyl}-carbamic acid tert-butyl ester (0.468 g, 0.905 mmol) [example 25, step c] and triethylamine (1.83 g, 18.1 mmol) in dichloromethane at room temperature. The reaction was stirred for 24 hours and then evaporated. Column chromatography (25% EtOAc in hexanes) of the residue yielded the title compound (0.520 g, 78%) as a solid. ESI-MS (m/z): Calcd. for $C_{29}H_{35}N_3O_7S_4$: 665.14; found: 665.8.

c) N-[3'-(5-Carbamimidoyl-2-methylsulfanyl-thiophene-3-sulfonyl)-6-methyl-biphenyl-2-yl]-4-methanesulfonyl-butyramide trifluoroacetate A solution of dichloromethane/trifluoroacetic acid (1/1) [1 mL] was added to (imino-{4-[2'-(4-methanesulfonyl-butyrylamino)-6'-methyl-biphenyl-3-sulfonyl]-5-methylsulfanyl-thiophen-2-yl}-methyl)-carbamic acid tert-butyl ester (0.011 g, 0.017 mmol) [example 209, step b] at room temperature and stirred for 1 hour. The reaction mixture was evaporated and purified via reverse-phase HPLC [acetonitrile/water (0.01% TFA)] to give the title compound (0.004 g, 36%) as a solid. ¹H-NMR (MeOD): δ 8.29 (s, 1H), 8.04 (md, 1H, J=6.4 Hz), 7.87 (t, 1H, J=2.0 Hz), 7.69 (t, 1H, J=7.6 Hz), 7.54 (md, 1H, J=7.6 Hz), 7.34 (t, 1H, J=7.6 Hz), 7.28 (d, 1H, J=7.2 Hz), 7.18 (d, 1H J=7.2 Hz), 2.91 (s, 3H), 2.78 (t, 2H, J=7.6 Hz), 2.72 (s, 3H), 2.18 (t, 2H, J=7.6 Hz), 2.07 (s, 3H), 1.74 (m, 2H). ESI-MS (m/z): Calcd. for $C_{24}H_{27}N_3O_5S_4$: 566.1; found: 566.8.

Example 210

N-[3'-(5-Carbamimidoyl-2-methylsulfanyl-thiophene-3-sulfonyl)-6-methyl-biphenyl-2-yl]-4-sulfamoyl-butyramide trifluoroacetate a) (Imino-{4-[6'-methyl-2'-(4-sulfamoyl-butyrylamino)-biphenyl-3-sulfonyl]-5-methylsulfanyl-thiophen-2-yl}-methyl)-carbamic acid tert-butyl ester {[4-(2'-Amino-6'-methyl-biphenyl-3-sulfonyl)-5-methylsulfanyl-thiophen-2-yl]-imino-methyl}-carbamic acid tert-butyl ester (0.013 g, 0.025 mmol) [example 25, step c] was added to a solution of 4-sulfamoyl-butyric acid (0.011 g, 0.068 mmol), EDCI (0.013 g, 0.068 mmol) and HOBt (0.009 g, 0.068 mmol) in DMF [0.5 mL] at room temperature. The reaction was stirred for 24 hours and then evaporated. Column chromatography (25% EtOAc in hexanes) of the residue yielded the title compound (0.010 g, 60%) as a solid. ESI-MS (m/z): Calcd. for $C_{28}H_{34}N_4O_7S_4$: 666.13; found: 666.8.

b) N-[3'-(5-Carbamimidoyl-2-methylsulfanyl-thiophene-3-sulfonyl)-6-methyl-biphenyl-2-yl]-4-sulfamoylbutyramide trifluoroacetate A solution of dichloromethane/trifluoroacetic acid (1/1) [1 mL] was added (imino-{4-[6'-methyl-2'-(4-sulfamoyl-butyrylamino)-biphenyl-3-sulfonyl]-5-methylsulfanyl-thiophen-2-yl}-methyl)-carbamic acid tert-butyl ester (0.010 g, 0.015 mmol) [example 210, step a] at room temperature and stirred for 1 hour. The reaction mixture was evaporated and purified via reverse-phase HPLC [acetonitrile/water (0.01% TFA)] to give the title compound (0.005 g, 36%) as a solid. ¹H-NMR (MeOD): δ 8.30 (s, 1H), 8.04 (md, 1H, J=7.6 Hz), 7.88 (t, 1H, J=1.6 Hz), 7.70 (t, 1H, J=7.6 Hz), 7.54 (md, 1H, J=7.6 Hz), 7.36 (t, 1H, J=7.6 Hz), 7.29 (d, 1H, J=6.8 Hz), 7.19 (d, 1H, J=8.0 Hz), 2.77–2.72 (m, 5H), 2.16 (t, 2H, J=7.2 Hz), 2.09 (s, 3H), 1.76 (m, 2H). ESI-MS (m/z): Calcd. for $C_{23}H_{26}N_4O_5S_4$: 566.08; found: 567.1.

Example 211

11-Amino-undecanoic acid [3'-(5-carbamimidoyl-2-methylsulfanyl-thiophene-3-sulfonyl)-6-methyl-biphenyl-2-yl]-amide bistrifluoroacetate

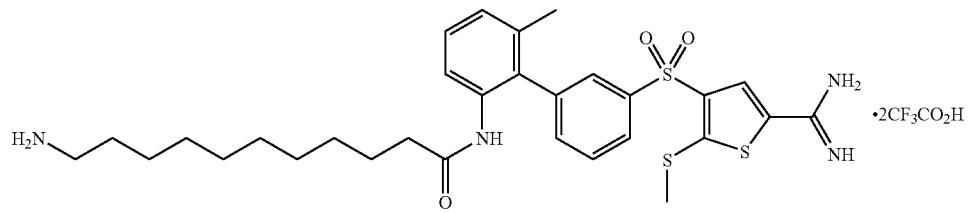

a) (10-{3'-[5-(tert-Butoxycarbonylamino-iminomethyl)-2-methylsulfanyl-thiophene-3-sulfonyl]-6-methyl-biphenyl-2-ylcarbamoyl}-decyl)-carbamic acid 9H-fluoren-9-ylmethyl ester Thionyl chloride (0.86 mL, 2.36 mmol) was added to a solution of 11-(9H-fluoren-9-ylmethoxycarbonylamino)-undecanoic acid (0.086 g, 0.194 mmol) in dichloromethane/DMF [1 mL/1 drop] and stirred at room temperature for 3 hours. The reaction mixture was evaporated, dissolved in dichloromethane [5 mL] was added dropwise to a solution of {[4-(2'-amino-6'-methyl-biphenyl-3-sulfonyl)-5-methylsulfanyl-thiophen-2-yl]-imino-methyl}-carbamic acid tert-butyl ester (0.050 g, 0.097 mmol) [example 25, step c] and triethylamine (0.03 mL, 0.19 mmol) in dichloromethane [3 mL] at room temperature and stirred for several hours. The crude reaction was evaporated and column chromatography (25% EtOAc in hexanes) of the residue yielded the title compound (0.042 g, 47%) as a solid. ESI-MS (m/z): Calcd. for $C_{50}H_{58}N_4O_7S_3$: 922.35; found: 923.0.

b) ({4-[2'-(11-Amino-undecanoylamino)-6'-methyl-biphenyl-3-sulfonyl]-5-methylsulfanyl-thiophen-2-yl}-imino-methyl)-carbamic acid tert-butyl ester A solution of 50% piperidine in DMF [1 mL] was added to (10-{3'-[5-(tert-butoxycarbonylamino-imino-methyl)-2-methylsulfanyl-thiophene-3-sulfonyl]-6-methyl-biphenyl-2-ylcarbamoyl}-decyl)-carbamic acid 9H-fluoren-9-ylmethyl ester (0.040 g, 0.043 mmol) [example 211, step a] and stirred for 0.5 hours, followed by evaporation. Column chromatography (10% MeOH in dichloromethane) of the residue yielded the title compound (0.024 g, 77%) as a solid. ESI-MS (m/z): Calcd. for $C_{35}H_{48}N_4O_5S_3$: 700.28; found: 701.0.

c) 11-Amino-undecanoic acid [3'-(5-carbamimidoyl-2-methylsulfanyl-thiophene-3-sulfonyl)-6-methyl-biphenyl-2-yl]-amide bistrifluoroacetate A solution of dichloromethane/trifluoroacetic acid (1/1) [1 mL] was added to ({4-[2'-(11-amino-undecanoylamino)-6'-methyl-biphenyl-3-sulfonyl]-5-methylsulfanyl-thiophen-2-yl}-imino-methyl)-carbamic acid tert-butyl ester (0.005 g, 0.007 mmol) [example 211, step b] at room temperature and stirred for 1 hour. The reaction mixture was evaporated and purified via reverse-phase HPLC [acetonitrile/water (0.01% TFA)] to give the title compound (0.003 g, 76%) as a solid. $^1$H-NMR (MeOD): δ 8.28 (s, 1H), 8.02 (d, 1H, J=7.2 Hz), 7.87 (m, 1H), 7.66 (t, 1H, J=8.0 Hz), 7.53 (d, 1H, J=8.0 Hz), 7.34 (t, 1H, J=7.6 Hz), 7.27 (d, 1H, J=7.6 Hz), 2.91 (t, 2H, J=8.0 Hz), 2.71 (s, 3H), 2.03 (s, 3H), 1.96 (q, 2H, J=7.2 Hz), 1.65 (m, 2H), 1.41–1.12 (m, 14H). ESI-MS (m/z): Calcd. for $C_{30}H_{40}N_4O_3S_3$: 600.23; found: 601.2.

Example 212

N-[3'-(5-Carbamimidoyl-2-methylsulfanyl-thiophene-3-sulfonyl)-6-methyl-biphenyl-2-yl]-4-trifluoromethanesulfonylamino-butyramide trifluoroacetate

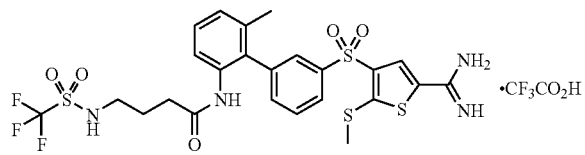

a) 4-Trifluoromethanesulfonylamino-butyric acid methyl ester

Trifluoromethanesulfonyl chloride (0.23 mL, 2.16 mmol) was added dropwise to a solution of 4-amino-butyric acid methyl ester hydrochloride (0.30 g, 1.96 mmol) and triethylamine (0.68 mL, 4.90 mmol) in dichloromethane and stirred at room temperature for 18 hours. 1N HCl was added and the product was extracted with dichloromethane, dried with magnesium sulfate and evaporated to give the title compound (0.42 g, 85%). $^1$H-NMR (CDCl$_3$): δ 4.89 (s, 1H), 3.12 (t, 2H, J=7.2 Hz), 2.94 (s, 3H), 2.41 (t, 2H, J=7.2 Hz), 1.84 (m, 2H, J=7.2 Hz).

b) 4-Trifluoromethanesulfonylamino-butyryl chloride

4-Trifluoromethanesulfonylamino-butyric acid methyl ester (0.42 g, 1.77 mmol) [example 212, step a] was taken up in methanol [2 mL] and 1N NaOH was added [2.66 mL] and stirred for 2 hours. 1N HCl was added and the product was extracted with ethyl acetate, dried with magnesium sulfate and evaporated. The crude product (0.13 g, 0.57 mmol) was dissolved in dichloromethane/DMF [1 mL/1 drop] and thionyl chloride (0.08 mL, 1.14 was added. The reaction was stirred at room temperature for 2 hours and then evaporated and used directly in the next step.

c) (Imino-{5-methylsulfanyl-4-[6'-methyl-2'-(4-trifluoromethanesulfonylaminobutyrylamino)-biphenyl-3-sulfonyl]-thiophen-2-yl}-methyl)-carbamic acid tert-butyl ester A solution of 4-trifluoromethanesulfonylamino-butyryl chloride (0.015 g, 0.058 mmol) [example 212, step b] in dichloromethane [1 mL] was added to a solution of {[4-(2'-amino-6'-methyl-biphenyl-3-sulfonyl)-5-methylsulfanyl-thiophen-2-yl]-imino-methyl}-carbamic acid tert-butyl ester (0.025 g, 0.049 mmol) [example 25, step c] in dichloromethane [1 mL] at room temperature with vigorous stirring for 0.5 hours. The reaction mixture was evaporated and column chromatography (25% EtOAc in hexanes) of the residue yielded the title compound (0.020 g, 57%) as a solid. ESI-MS (m/z): Calcd. for $C_{29}H_{33}F_3N_4O_7S_4$: 734.12; found: 734.7.

d) N-[3'-(5-Carbamimidoyl-2-methylsulfanyl-thiophene-3-sulfonyl)-6-methyl-biphenyl-2-yl]-4-trifluoromethanesulfonylamino-butyramide trifluoroacetate A solution of dichloromethane/trifluoroacetic acid (1/1) [2 mL] was added to (imino-{5-methylsulfanyl-4-[6'-methyl-2'-(4-trifluoromethanesulfonylaminobutyrylamino)-biphenyl-3-sulfonyl]-thiophen-2-yl}-methyl)-carbamic acid tert-butyl ester (0.020 g, 0.027 mmol) [example 212, step c] at room temperature and stirred for 1 hour. The reaction mixture was evaporated and purified via reverse-phase HPLC [acetonitrile/water (0.01% TFA)] to give the title compound (0.009 g, 54%) as a solid. $^1$H-NMR (MeOD): δ 8.29 (s, 1H), 8.03 (md, 1H, J=8.4 Hz), 7.87 (m, 1H), 7.68 (t, 1H, J=7.6 Hz), 7.53 (md, 1H, J=7.6 Hz), 7.34 (t, 1H, J=7.6 Hz), 7.28 (d, 1H, J=7.2 Hz), 7.19 (d, 1H, J=7.2 Hz), 2.98 (m, 2H), 2.72 (s, 3H), 2.06 (s, 3H), 2.05 (t, 2H, J=7.6 Hz), 1.48 (m, 2H). ESI-MS (m/z): Calcd. for $C_{24}H_{25}F_3N_4O_5S_4$: 634.07; found: 635.1.

Example 213

E/Z-{2-[3'-(5-Carbamimidoyl-2-methylsulfanyl-thiophene-3-sulfonyl)-6-methyl-biphenyl-2-yl]-vinyl}-phosphonic acid trifluoroacetate

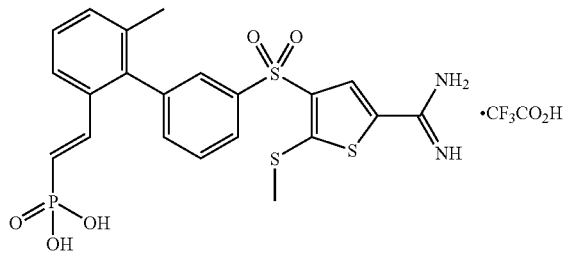

a) (2-Iodo-3-methyl-phenyl)-methanol

Thionyl chloride [5 mL] was added to 2-iodo-3-methyl-benzoic acid (2.00 g, 7.63 mmol) at room temperature and heated to 50° C. for 1 hour. The solution was then cooled and evaporated. The crude residue was dissolved in ethyl acetate, washed with brine and dried with magnesium sulfate. The crude product was then dissolved in THF [5 mL] and a 1M solution of lithium aluminum hydride [10.7 mL] was added at room temperature and stirred for 1 hour. Water [0.1 mL] and 15% NaOH [0.1 mL] were added followed by evaporation. Column chromatography (50% EtOAc in hexanes) of the residue yielded the title compound (0.50 g, 26%) as a solid. $^1$H-NMR (CDCl$_3$): δ 3.20 (t, 2H, J=7.6 Hz), 2.98 (s, 3H), 2.52 (t, 2H, J=7.2 Hz), 2.09 (m, 2H).

b) {[4-(2'-Hydroxymethyl-6'-methyl-biphenyl-3-sulfonyl)-5-methylsulfanyl-thiophen-2-yl]-iminomethyl}-carbamic acid tert-butyl ester n-Butyllithium (2.5M) [4.03 mL] was added to a solution of (2-iodo-3-methyl-phenyl)-methanol (1.00 g, 4.04 mL) [example 213, step a] in ether [20 mL] at −78° C. and stirred for 0.5 hours. Trimethyl borate [1.13 mL, 10.1 mmol] was added and the solution was stirred for 2 hours at room temperature, followed by evaporation. The crude residue was dissolved in ethanol/toluene (1/2) [30 mL] and 2M sodium carbonate [16.2 mL] followed by addition of {[4-(3-bromo-benzenesulfonyl)-5-methylsulfanyl-thiophen-2-yl]-imino-methyl}-carbamic acid tert-butyl ester (0.49 g, 1.01 mmol) [example 27, step c]. The solution was bubbled with argon and then tetrakis (triphenylphosphine) palladium (0) (0.18 g, 0.15 mmol) was added. The reaction was refluxed for 3 hours and then cooled to room temperature. Ethyl acetate was added and the crude reaction was washed with brine, dried over magnesium sulfate and evaporated. Column chromatography (50% EtOAc in hexanes) of the residue yielded the title compound (0.40 g, 74%) as a solid. ESI-MS (m/z): Calcd. for $C_{25}H_{28}N_2O_5S_3$: 532.12; found: 532.7.

c) E/Z-(2-{3'-[5-(tert-Butoxycarbonylamino-iminomethyl)-2-methylsulfanyl-thiophene-3-sulfonyl]-6-methyl-biphenyl-2-yl}-vinyl)-phosphonic acid diethylester Manganese dioxide (0.041 g, 0.470 mmol) was added to a solution of ({[4-(2'-hydroxymethyl-6'-methyl-biphenyl-3-sulfonyl)-5-methylsulfanyl-thiophen-2-yl]-imino-methyl}-carbamic acid tert-butyl ester (0.025 g, 0.047 mmol) [example 213, step b] in dichloromethane [5 mL] and refluxed for 3 hours. The reaction was filtered through Celite and evaporated. The crude residue was dissolved in anhydrous THF [2 mL] and added to a solution of (diethoxy-phosphorylmethyl)-phosphonic acid diethyl ester (0.011 g, 0.061 mmol) and sodium hydride (0.003 g, 0.056 mmol) in THF [2 mL] at room temperature and stirred for 0.5 hours. A solution of 1N NaOH/MeOH (1/1) [10 mL] was added and the crude product was extracted with ether, dried with magnesium sulfate and evaporated. Column chromatography (50% EtOAc in hexanes) of the residue yielded the title compound (0.019 g, 57%) as a solid. ESI-MS (m/z): Calcd. for $C_{30}H_{37}N_2O_7PS_3$: 664.15; found: 664.8.

d) E/Z-{2-[3'-(5-Carbamimidoyl-2-methylsulfanyl-thiophene-3-sulfonyl)-6-methyl-biphenyl-2-yl]-vinyl}-phosphonic acid trifluoroacetate Trimethylsilyl iodide (0.058 g, 0.271 mmol) was added dropwise to a solution of E/Z-(2-{3'-[5-(tert-butoxycarbonylamino-imino-methyl)-2-methylsulfanyl-thiophene-3-sulfonyl]-6-methyl-biphenyl-2-yl}-vinyl)-phosphonic acid diethylester (0.018 g, 0.027 mmol) [example 213, step c] in dichloromethane [3 mL] and heated to 45° C. for 3 hours. The reaction was quenched with water [0.025 mL], stirred for 0.5 hours and evaporated. The crude residue was the dissolved in methanol and 20% HCl was added [0.020 mL], stirred for 1 hour and concentrated. The reaction mixture was purified via reverse-phase HPLC [acetonitrile/water (0.01% TFA)] to give the title compound (0.005 g, 28%) as a solid. $^1$H-NMR (MeOD): δ 8.28 (s, 1H), 8.04 (t, 1H, J=7.6 Hz), 7.83 (s, 1H), 7.71 (t, 1H, J=7.6 Hz), 7.63 (m, 1H), 7.52 (m 1H), 7.38 (m, 1H), 7.26 (m, 1H), 7.18 (t, 1H, J=7.2 Hz), 6.92 (t, 1H, J=17.6 Hz), 6.34 (t, 1H, J=18.0 Hz), 2.74 (s, 3H), 2.02–1.95 (d, 3H). ESI-MS (m/z): Calcd. for $C_{21}H_{21}N_2O_5PS_3$: 508.04; found: 509.1.

Example 214

2-[3'-(5-Carbamimidoyl-2-methylsulfanyl-thiophene-3-sulfonyl)-6-methyl-biphenyl-2-ylmethylsulfanyl]-succinic acid trifluoroacetate

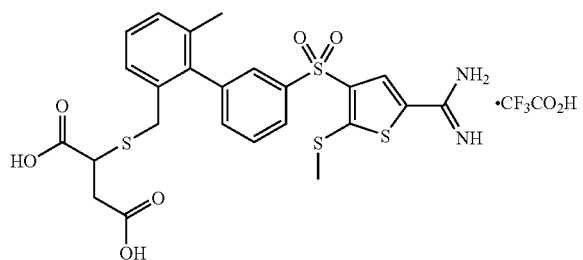

a) Methanesulfonic acid 3'-[5-(tert-butoxycarbonylamino-imino-methyl)-2-methylsulfanyl-thiophene-3-sulfonyl]-6-methyl-biphenyl-2-ylmethyl ester Methanesulfonyl chloride (0.027 g, 0.241 mmol) was added to a solution of {[4-(2'-hydroxymethyl-6'-methyl-biphenyl-3-sulfonyl)-5-methylsulfanyl-thiophen-2-yl]-imino-methyl}-carbamic acid tert-butyl ester (0.100 g, 0.188 mmol) [example 213, step b] and triethylamine (0.048 g, 0.470 mmol) in THF [3 mL] at room temperature and stirred for 18 hours. Column chromatography (25% EtOAc in hexanes) of the residue yielded the title compound (0.017 g, 14%). ESI-MS (m/z): Calcd. for $C_{26}H_{30}N_2O_7S_4$: 610.09; found: 611.8.

b) 2-[3'-(5-Carbamimidoyl-2-methylsulfanyl-thiophene-3-sulfonyl)-6-methyl-biphenyl-2-ylmethylsulfanyl]-succinic acid trifluoracetate 2-Mercapto-succinic acid (0.004 g, 0.028 mmol) was added to a solution of methanesulfonic acid 3'-[5-(tert-butoxycarbonylamino-imino-methyl)-2-methylsulfanyl-thiophene-3-sulfonyl]-6-methyl-biphenyl-2-ylmethyl ester (0.017 g, 0.028 mmol) [example 214, step a] and triethylamine (0.009 g, 0.084 mmol) in dichloromethane [0.5 mL] at 40° C., stirred for 2 hours and then evaporated. The crude reaction was dissolved in a solution of dichloromethane/trifluoroacetic acid (1/1) [2 mL] and stirred for 1 hour. The reaction mixture was evaporated and purified via reverse-phase HPLC [acetonitrile/water (0.01% TFA)] to give the title compound (0.005 g, 42%) as a solid. $^1$H-NMR (MeOD): δ 8.31 (s, 1H), 8.06 (t, 1H, J=8.0 Hz), 7.83 (d, 1H, J=16.8 Hz), 7.70 (q, 1H, J=6.8 Hz), 7.57 (t, 1H, J=7.2 Hz), 7.29–7.21 (m, 3H), 3.60–3.48 (m, 1H), 3.54 (s, 3H), 3.37–3.34 (m, 1H), 2.70 (s, 3H), 2.68–2.57 (m, 1H), 2.31–2.14 (m, 1H), 1.97 (s, 3H). ESI-MS (m/z): Calcd. for $C_{24}H_{24}N_2O_6S_4$: 564.05; found: 565.1.

Example 215

[3'-(5-Carbamimidoyl-2-methylsulfanyl-thiophene-3-sulfonyl)-2,6-dimethyl-biphenyl-4-yloxy]-acetic acid trifluoroacetate

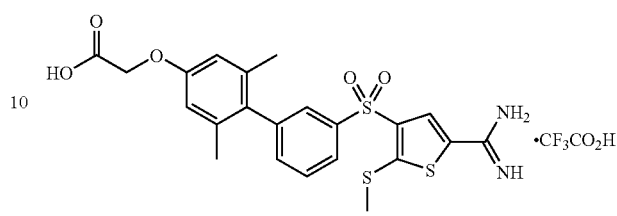

a) {3'-[5-(tert-Butoxycarbonylamino-imino-methyl)-2-methylsulfanyl-thiophene-3-sulfonyl]-2,6-dimethyl-biphenyl-4-yloxy}-acetic acid tert-butyl ester Bromo-acetic acid tert-butyl ester (0.013 mL, 0.085 mmol) was added dropwise to a solution of {[4-(4'-hydroxy-2',6'-dimethyl-biphenyl-3-sulfonyl)-5-methylsulfanyl-thiophen-2-yl]-imino-methyl}-carbamic acid tert-butyl ester (0.050 g, 0.077 mmol) [example 124, step b] and potassium carbonate (0.021 g, 0.154 mmol) in acetone [1 mL] at room temperature and stirred for 18 hours. The reaction was evaporated and column chromatography (25% EtOAc in hexanes) of the residue yielded the title compound (0.011 g, 28%) as a solid. ESI-MS (m/z): Calcd. for $C_{31}H_{38}N_2O_7S_3$: 646.18; found: 646.8.

b) [3'-(5-Carbamimidoyl-2-methylsulfanyl-thiophene-3-sulfonyl)-2,6-dimethyl-biphenyl-4-yloxy]-acetic acid trifluoroacetate A solution of dichloromethane/trifluoroacetic acid (1/1) [2 mL] was added to {3'-[5-(tert-butoxycarbonylamino-imino-methyl)-2-methylsulfanyl-thiophene-3-sulfonyl]-2,6-dimethyl-biphenyl-4-yloxy}-acetic acid tert-butyl ester (0.020 g, 0.030 mmol) [example 215, step a] at room temperature and stirred for 1 hour. The reaction mixture was evaporated and purified via reverse-phase HPLC [acetonitrile/water (0.01% TFA)] to give the title compound (0.011 g, 75%) as a solid. $^1$H-NMR (MeOD): δ 8.36 (s, 1H), 8.01 (md, 1H, J=7.6 Hz), 7.81 (m, 1H), 7.72 (m, 1H), 7.51 (d, 1H, J=7.6 Hz), 7.26 (d, 1H, J=8.0 Hz), 6.74 (s, 2H), 4.67 (s, 2H), 2.73 (s, 3H), 1.96 (s, 6H). ESI-MS (m/z): Calcd. for $C_{22}H_{22}N_2O_5S_3$: 490.07; found: 491.2.

Example 216

4-{4'-Guanidino-6'-methyl-2'-[3-(2-phenylamino-ethyl)-ureido]-biphenyl-3-sulfonyl}-5-methylsulfanyl-thiophene-2-carboxamidine trifluoroacetate

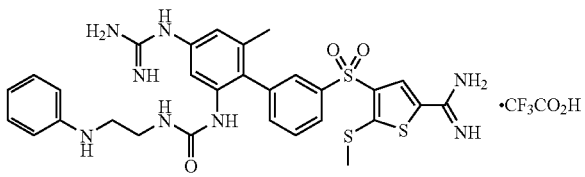

a) [(4-{4'-Amino-6'-methyl-2'-[3-(2-phenylamino-ethyl)-ureido]-biphenyl-3-sulfonyl}-5-methylsulfanyl-thiophen-2-yl)-imino-methyl]-carbamic acid tert-butyl ester 4-Nitrophenylchloroformate (0.047 g, 0.232 mmol) was added to a solution of {2-amino-3'-[5-(tert-butoxycarbonylamino-imino-methyl)-2-methylsulfanyl-thiophene-3-sulfonyl]-6-methyl-biphenyl-4-yl}-carbamic acid 2-trimethylsilanyl-ethyl ester (0.150 g, 0.222 mmol) [example 294, step f] and pyridine (0.018 g, 0.232 mmol) in dichloromethane [5 mL] and stirred at room temperature for 1 hour. N-1-Phenylethane-1,2-diamine (0.060 g, 0.444 mmol) was added and the reaction was stirred for an additional hour. The reaction was evaporated and column chromatography (50% EtOAc in hexanes) of the residue yielded the title compound (0.150 g, 81%) as a solid. This solid was dissolved in THF [1 mL] and tetrabutylammonium fluoride [0.536 mL] was added. The reaction was heated to 50° C. and stirred for 2 hours. The reaction was evaporated and column chromatography (50% EtOAc in hexanes) of the residue yielded the title compound (0.079 g, 64%) as a solid. ESI-MS (m/z): Calcd. for $C_{33}H_{38}N_6O_5S_3$: 694.21; found: 694.9.

b) [(4-{4'-(N', N''-di-tert-butoxycarbonyl-guanidino)-6'-methyl-2'-[3-(2-phenylamino-ethyl)-ureido]-biphenyl-3-sulfonyl}-5-methylsulfanyl-thiophen-2-yl)-imino-methyl]-carbamic acid tert-butylester 1,3-Bis-t-butoxycarbonyl-2-methyl-2-thiopseudourea (0.033 g, 0.114 mmol) was added to a solution of [(4-{4'-amino-6'-methyl-2'-[3-(2-phenylamino-ethyl)-ureido]-biphenyl-3-sulfonyl}-5-methylsulfanyl-thiophen-2-yl)-imino-methyl]-carbamic acid tert-butyl ester [example 216, step a] in methanol [1 mL] and 1 drop of acetic acid. The reaction was stirred at room temperature for 1 hour and evaporated. The reaction was evaporated and column chromatography (25% EtOAc in hexanes) of the residue yielded the title compound (0.072 g, 68%) as a solid. ESI-MS (m/z): Calcd. for $C_{44}H_{56}N_8O_9S_3$: 936.33; found: 936.9.

c) 4-{4'-Guanidino-6'-methyl-2'-[3-(2-phenylamino-ethyl)-ureido]-biphenyl-3-sulfonyl}-5-methylsulfanyl-thiophene-2-carboxamidine bistrifluoroacetate A solution of dichloromethane/trifluoroacetic acid (1/1) [1 mL] was added to [(4-{4'-(N',N''-di-tert-butoxycarbonyl-guanidino)-6'-methyl-2'-[3-(2-phenylamino-ethyl)-ureido]-biphenyl-3-sulfonyl}-5-methylsulfanyl-thiophen-2-yl)-imino-methyl]-carbamic acid tert-butylester (0.007 g, 0.007 mmol) [example 216, step b] at room temperature and stirred for 1 hour. The reaction mixture was evaporated and purified via reverse-phase HPLC [acetonitrile/water (0.01% TFA)] to give the title compound as a solid. ¹H-NMR (MeOD): δ 8.35 (s, 1H), 8.05 (md, 1H, J=8.0 Hz), 7.95 (m, 1H), 7.73 (t, 1H, J=8.0 Hz), 7.57 (m, 1H), 7.39 (m, 2H), 7.14 (m, 3H), 7.05 (m, 1H), 3.37 (m, 4H), 2.71 (s, 3H), 2.03 (s, 3H). ESI-MS (m/z): Calcd. for $C_{29}H_{32}N_8O_3S_3$: 636.18; found: 637.1.

Example 217

4-(3'-Formylamino-biphenyl-3-sulfonyl)-5-methylsulfanyl-thiophene-2-carboxamidine trifluoroacetate

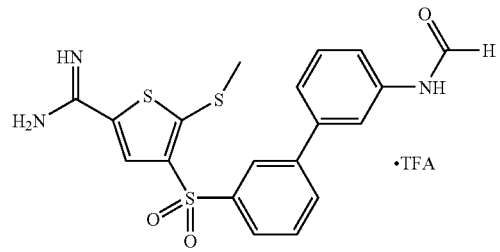

a) {[4-(3'-Amino-biphenyl-3-sulfonyl)-5-methylsulfanyl-thiophen-2-yl]-imino-methyl}-carbamic acid tert-butyl ester Following the same procedure as in Example 1, step c, reaction of 3-amino-phenyl boronic acid (27 mg, 0.2 mmol), {[4-(3-bromo-benzenesulfonyl)-5-methylsulfanyl-thiophen-2-yl]-imino-methyl}-carbamic acid tert-butyl ester (50 mg, 0.1 mmol, as prepared in Example 27, step c), tetrakis(triphenylphosine)palladium(0) (29 mg, 0.025 mmol, Strem Chemicals Inc, Newburyport, Mass.), $Na_2CO_3$ (400 μL, 2M), and toluene/EtOH mixture (2:1, 1.2 mL) afforded 35 mg (70%) after purification (SiO₂, flash elution: 30% EtOAc in hexanes) of the title compound as a white foam. ESI-MS (m/z): Calcd. for $C_{23}H_{25}N_3O_4S_3$: 503.6; found: 503.9, 404.1 (M−Boc).

b) 4-(3'-Formylamino-biphenyl-3-sulfonyl)-5-methylsulfanyl-thiophene-2-carboxamidine trifluoroacetate {[4-(3'-Amino-biphenyl-3-sulfonyl)-5-methylsulfanyl-thiophen-2-yl]-imino-methyl}-carbamic acid tert-butyl ester (30 mg, 0.06 mmol, as prepared in Example 217, step a) was dissolved in formic acid (5 mL) and the reaction mixture was refluxed overnight. The formic acid was removed in vacuo and the residue was treated with trifluoacetic acid (50% in DCM) for 1 h at rt. The mixture was concentrated in vacuo and the residue obtained was purified using $C_{18}$-HPLC (10–80% $CH_3CN$ in $H_2O$ (0.1% TFA) over 25 min) to give the title compound as a white solid. ¹H-NMR (CD₃OD; 400 MHz): δ 8.34 (s, 1H), 8.33 (s, 1H), 8.29 (t, 1H, J=1.6 Hz), 8.11–8.13 (m, 1H), 7.96–8.03 (m, 2H), 7.70 (t, 1H, J=7.7 Hz), 7.42–7.50 (m, 3H), 2.75 (s, 3H). ESI-MS (m/z): Calcd. for $C_{19}H_{17}N_3O_3S_3$: 432.1 (M+H); found: 432.1.

Example 218

3'-(5-Carbamimidoyl-2-methylsulfanyl-thiophene-3-sulfonyl)-biphenyl-3-carboxylic acid amide trifluoracetate

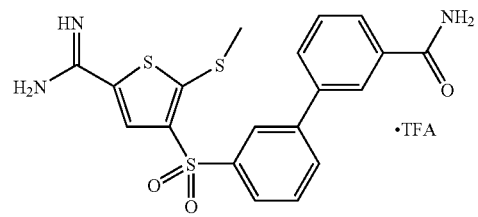

Following the same procedure as in Example 1; step c, reaction of 3-carbamoyl-phenyl boronic acid (33 mg, 0.2 mmol), {[4-(3-bromo-benzenesulfonyl)-5-methylsulfanyl-thiophen-2-yl]-imino-methyl}-carbamic acid tert-butyl ester (50 mg, 0.1 mmol, as prepared in Example 27, step c), tetrakis(triphenylphosine)palladium(0) (29 mg, 0.025 mmol, Strem Chemicals Inc, Newburyport, Mass.), $Na_2CO_3$ (400 μL, 2M), and toluene/EtOH mixture (2:1, 1.2 mL) afforded 38 mg (72%) after purification ($SiO_2$, flash elution: 30% EtOAc in hexanes) of a white foam whose mass was consistent with the Boc protected title intermediate. ESI-MS (m/z): Calcd. for $C_{24}H_{25}N_3O_5S_3$: 531.7; found: 531.9, 432.1 (M–Boc). Treatment of this intermediate with trifluoacetic acid (50% in DCM) for 1 h at rt and purification using $C_{18}$-HPLC (10–65% $CH_3CN$ in $H_2O$ (0.1% TFA) over 30 min) provided the title compound as a white solid (25 mg, 66%). $^1$H-NMR ($CD_3OD$; 400 MHz): δ 8.34 (s, 1H), 8.33 (t, 1H, J=1.9 Hz), 8.19 (t, 1H, J=1.9 Hz), 8.00–8.05 (m, 2H), 7.85–7.88 (m, 2H), 7.73 (t, 1H, J=7.8 Hz), 7.62 (t, 1H, J=7.8 Hz), 2.74 (s, 3H). ESI-MS (m/z): Calcd. for $C_{19}H_{17}N_3O_3S_3$: 432.2 (M+H); found: 432.2.

Example 219

4-(4'-Fluoro-2'-methyl-biphenyl-3-sulfonyl)-5-methylsulfanyl-thiophene-2-carboxamidine trifluoroacetate

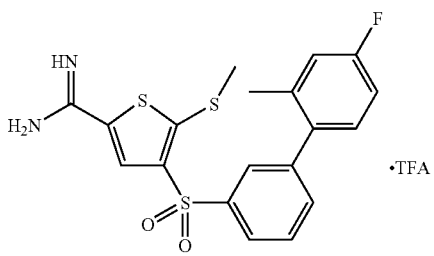

Following the same procedure as in Example 1, step c, reaction of 4-fluoro-2-methyl-phenyl boronic acid (35 mg, 0.2 mmol), {[4-(3-bromo-benzenesulfonyl)-5-methylsulfanyl-thiophen-2-yl]-imino-methyl}-carbamic acid tert-butyl ester (50 mg, 0.1 mmol, as prepared in Example 27, step c), tetrakis(triphenylphosine)palladium(0) (29 mg, 0.025 mmol, Strem Chemicals Inc, Newburyport, Mass.), $Na_2CO_3$ (400 μL, 2M), and toluene/EtOH mixture (2:1, 1.2 mL) afforded after purification (Preparative TLC, 1:3 EtOAc/hexanes, 2000μ $SiO_2$ plate) 62 mg of {[4-(4'-fluoro-2'-methyl-biphenyl-3-sulfonyl)-5-methylsulfanyl-thiophen-2-yl]-imino-methyl}-carbamic acid tert-butyl ester as a tan oil. NMR ($CDCl_3$; 400 MHz) δ 8.02 (s, 1H), 7.91–7.97 (m, 2H), 7.51–7.57 (m, 2H), 7.14 (dd, 1H, J=8.4, 5.8 Hz), 6.92–7.00 (m, 2H), 2.57 (s, 3H), 2.20 (s, 3H), 1.51 (s, 9H). Treatment of this intermediate with trifluoacetic acid (50% in DCM) for 1 h at rt and purification using $C_{18}$-HPLC (20–70% $CH_3CN$ in $H_2O$ (0.1% TFA) over 30 min) provided the title compound as a white solid (30 mg, 60%). $^1$H-NMR ($CD_3OD$; 400 MHz) δ 8.32 (s, 1H), 8.03 (dt, 1H, J=7.0, 1.9 Hz), 7.94–7.96 (m, 1H), 7.64–7.70 (m, 2H), 7.22 (dd, 1H, J=8.6, 5.8 Hz), 6.98–7.09 (m, 2H), 2.72 (s, 3H), 2.22 (s, 3H). ESI-MS (m/z): Calcd. for $C_{19}H_{17}FN_2O_2S_3$: 421.2 (M+H); found: 421.2.

Example 220

4-(4'-Amino-2'-methyl-biphenyl-3-sulfonyl)-5-methylsulfanyl-thiophene-2-carboxamidine bis-trifluoroacetate

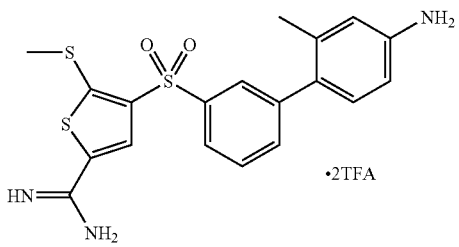

a) 3-Methyl-4-(4,4,5,5-tetramethyl-[1,3,2]dioxaborolan-2-yl)-phenylamine

To an oven-dried round bottom flask fitted with a stir bar was added 4-bromo-3-methylaniline (5.7 gm, 31 mmol), 4,4,5,5-tetramethyl-1,3,2-dioxaborolane (13.3 mL, 92 mmol, Aldrich Chemical Company), and $PdCl_2(PPh_3)_2$ (2.2 gm, 3.1 mmol, Strem Chemicals Inc, Newburyport, Mass.). The flask was sealed with a rubber septum, purged with Argon, and then charged with dry dioxane (100 mL) and triethylamine (26 mL). The reaction mixture was stirred vigorously at 95° C. for 16 h. After cooling to rt, the dioxane was removed in vacuo and the residue was partitioned between EtOAc (200 mL) and water (100 mL). The organic layer was washed with saturated $NaHCO_3$ (2×75 mL), brine (50 mL), and was dried over $MgSO_4$. Removal of the solvents in vacuo followed by flash chromatography of the residue yielded the product (3.3 gm, 46%) as a tan oil. $^1$H-NMR ($CDCl_3$; 400 MHz): δ 7.61–7.64 (m, 1H), 6.48–6.58 (m, 2H), 3.60–3.90, (br s, 2H), 2.49 (s, 3H), 1.34 (s, 12H). ESI-MS (m/z): Calcd. for $C_{13}H_{20}BNO_2$: 234.1 (M+H); found: 234.2 b) {4-(4'-Amino-2'-methyl-biphenyl-3-sulfonyl)-5-methylsulfanyl-thiophene-2-yl]-imino-methyl}-carbamic acid tert-butyl ester Following the same procedure as in Example 1, step c, reaction of 3-methyl-4-(4,4,5,5-tetramethyl-[1,3,2]dioxaborolan-2-yl)-phenylamine (432 mg, 1.86 mmol, as prepared in Example 220, step a), {[4-(3-bromo-benzenesulfonyl)-5-methylsulfanyl-thiophen-2-yl]-imino-methyl}-carbamic acid tert-butyl ester (610 mg, 1.24 mmol, as prepared in Example 27, step c), tetrakis(triphenylphosine) palladium(0) (215 mg, 0.186 mmol, Strem Chemicals Inc, Newburyport, Mass.), $Na_2CO_3$ (5 mL, 2M), and toluene/ EtOH mixture (2:1, 15 mL) afforded 403 mg (63%) after purification ($SiO_2$, flash elution: 30% to 50% EtOAc in hexanes) of the title compound as a white foam. $^1$H-NMR ($CDCl_3$, 400 MHz): δ 8.00 (s, 1H), 7.87–7.92 (m, 2H), 7.47–7.55 (m, 2H), 6.98 (d, 1H, J=7.9 Hz), 6.55–6.61 (m, 2H), 3.65–3.82 (br s, 2H), 2.53 (s, 3H), 2.15 (s, 3H), 1.51 (s, 9H). ESI-MS (m/z): Calcd. for $C_{24}H_{27}N_3O_4S_3$: 517.7; found: 517.7, 418.1 (M–Boc).

c) 4-(4'-Amino-2'-methyl-biphenyl-3-sulfonyl)-5-methylsulfanyl-thiophene-2-carboxamidine bis-trifluoroacetate {4-(4'-Amino-2'-methyl-biphenyl-3-sulfonyl)-5-methylsulfanyl-thiophen-2-yl]-imino-methyl}-carbamic acid tert-butyl ester (32 mg, 0.06 mmol, as prepared in Example 220, step b) was treated with trifluoroacetic (50% in DCM) for 1 h at rt and purified using $C_{18}$-HPLC (20–70% $CH_3CN$ in $H_2O$ (0.1% TFA) over 30 min) affording the title compound as a white solid (20 mg, 55%). $^1$H-NMR ($CD_3OD$; 400 MHz) δ 8.35 (s, 1H), 7.99–8.05 (m, 2H), 7.67–7.73 (m, 2H), 7.28 (d, 1H, J=8.1 Hz), 7.10–7.17 (m, 2H), 2.74 (s, 3H), 2.27 (s, 3H). ESI-MS (m/z): Calcd. for $C_{19}H_{19}N_3O_2S_3$: 418.1 (M+H); found: 418.1.

Example 221

4-[2'-Methyl-4'-(2-morpholin-4-yl-ethylamino)-biphenyl-3-sulfonyl]-5-methylsulfanyl-thiophene-2-carboxamidine bis-trifluoroacetate

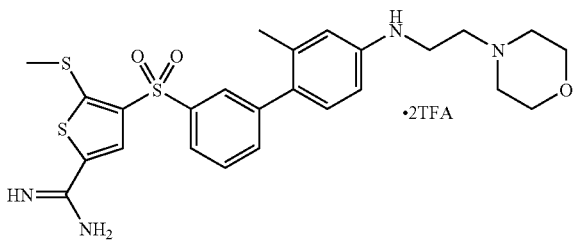

a) (4-Bromo-3-methyl-phenyl)-(2-morpholin-4-yl-ethyl)-amine

4-Bromo-3-methylaniline (0.96 gm, 5.14 mmol), 4-(2-chloro-ethyl)-morpholine (1 gm, 5.4 mmol), $K_2CO_3$ (1.5 gm, 10.8 mmol), and NaI (0.81 gm, 5.4 mmol) were suspended in DMSO (10 mL) and the mixture was stirred vigorously at reflux for 12 h. The mixture was cooled, diluted with EtOAc, and washed with saturated $NaHCO_3$. The organic layer was washed with another portion of $NaHCO_3$, brine (50 mL), and was dried over $MgSO_4$. Removal of the solvents in vacuo followed by flash chromatography of the residue (Biotage Flash System—40 M $SiO_2$ column, 10% EtOAc in hexanes to 100% EtOAc) yielded the product (500 mg, 31%) as a tan oil. $^1$H-NMR ($CDCl_3$; 400 MHz): δ 7.36 (d, 1H, J=8.6 Hz), 6.61 (d, 1H, J=2.8 Hz), 6.43 (dd, 1H, d, 8.6, 2.8 Hz), 4.36 (br s, 1H), 3.80 (t, 4H, J=4.6 Hz), 3.20 (t, 2H, J=5.8 Hz), 2.69 (t, 2H, J=6.0 Hz), 2.54 (t, 4H, J=4.4 Hz), 2.40 (s, 3H). ESI-MS (m/z): Calcd. for $C_{13}H_{19}BrN_2O$: 299.2; found: 299.1, 301.1.

b) 4-[2'-Methyl-4'-(2-morpholin-4-yl-ethylamino)-biphenyl-3-sulfonyl]-5-methylsulfanyl-thiophene-2-carboxamidine Following the same procedure as in Example 220, step a, reaction of (4-bromo-3-methyl-phenyl)-(2-morpholin-4-yl-ethyl)-amine (440 mg, 1.9 mmol, as prepared in Example 221, step a), 4,4,5,5-tetramethyl-1,3,2-dioxaborolane (13.3 mL, 92 mmol, Aldrich Chemical Company), $PdCl_2(PPh_3)_2$ (2.2 gm, 3.1 mmol, Strem Chemicals Inc, Newburyport, Mass.), $Et_3N$ (1.6 mL, 11.4 mmol), and dioxane (5 mL) afforded 520 mg (79%) after purification ($SiO_2$, flash elution: 30% EtOAc in hexanes) of a tan oil. ESI-MS (m/z): Calcd. for $C_{19}H_{31}BN_2O_3$: 347.3 (M+H); found: 347.2. The above boronate ester (520 mg, 1.5 mmol) was reacted according to the procedure used in Example 1, step c, with {[4-(3-bromo-benzenesulfonyl)-5-methylsulfanyl-thiophen-2-yl]-imino-methyl}-carbamic acid tert-butyl ester (368 mg, 0.75 mmol, as prepared in Example 27, step c), tetrakis (triphenylphosine)palladium(0) (217 mg, 0.19 mmol, Strem Chemicals Inc, Newburyport, Mass.), $Na_2CO_3$ (3 mL, 2M), and toluene/EtOH mixture (2:1, 9 mL) to afford 400 mg (85%) of (imino-{4-[2'-methyl-4'-(2-morpholin-4-yl-ethylamino)-biphenyl-3-sulfonyl]-5-methylsulfanyl-thiophen-2-yl}-methyl)-carbamic acid tert-butyl ester after purification ($SiO_2$, flash elution: EtOAc in hexanes). ESI-MS (m/z): Calcd. for $C_{30}H_{38}N_4O_5S_3$: 630.8; found: 630.9, 531.1 (M−Boc). Treatment of this intermediate with trifluoroacetic acid and purification using $C_{18}$-HPLC (as in Example 220, step c) provided 312 mg (78%) of the title compound as a white solid. $^1$H-NMR ($CD_3OD$, 400 MHz): δ 8.31 (s, 1H), 7.90–7.95 (m, 2H), 7.60–7.65 (m, 2H), 7.04 (d, 1H, J=8.1 Hz), 6.61–6.66 (m, 2H), 3.95 (br s, 4H), 3.61 (t, 2H, J=6.3 Hz), 3.41 (m, 6H), 2.71 (s, 3H), 2.19 (s, 3H). ESI-MS (m/z): Calcd. for $C_{25}H_{30}N_4O_3S_3$: 531.2 (M+H); found: 531.1, 266.2 ($M^{2+}$).

Example 222

3'-(5-Carbamimidoyl-2-methylsulfanyl-thiophene-3-sulfonyl)-2-methyl-biphenyl-4-carboxylic acid trifluoroacetate

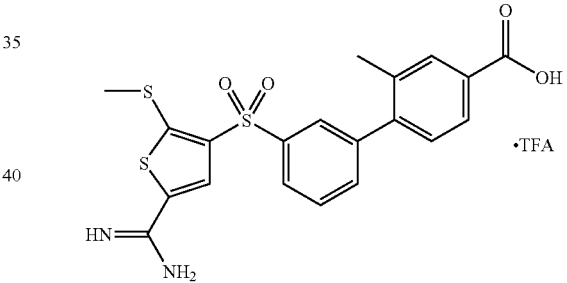

Following the same procedure as in Example 220, step a, reaction of 4-bromo-3-methyl-benzoic acid methyl ester (1.75 gm, 7.6 mmol), 4,4,5,5-tetramethyl-1,3,2-dioxaborolane (3.3 mL, 23 mmol, Aldrich Chemical Company), $PdCl_2(PPh_3)_2$ (530 mg, 0.76 mmol, Strem Chemicals Inc, Newburyport, Mass.), $Et_3N$ (6.3 mL, 46 mmol), and dioxane (30 mL) afforded 1.2 gm of a clear oil (79%) after purification ($SiO_2$, flash elution: 30% EtOAc in hexanes. The above boronate ester (220 mg, 0.8 mmol) was reacted according to the procedure used in Example 1, step c, with {[4-(3-bromo-benzenesulfonyl)-5-methylsulfanyl-thiophen-2-yl]-imino-methyl}-carbamic acid tert-butyl ester (100 mg, 0.8 mmol, as prepared in Example 27, step c), tetrakis(triphenylphosine)palladium(0) (58 mg, 0.05 mmol, Strem Chemicals Inc, Newburyport, Mass.), $Na_2CO_3$ (1.6 mL, 2 M), and toluene/EtOH mixture (2:1, 2.4 mL) to afford 3'-[5-(tert-butoxycarbonylamino-imino-methyl)-2-methyl-sulfanyl-thiophene-3-sulfonyl]-2-methyl-biphenyl-4-carboxylic acid methyl ester after purification (preparative TLC, 1:3 EtOAc/hexanes, 2000μ $SiO_2$ plate). ESI-MS (m/z): Calcd. for $C_{26}H_{28}N_2O_6S_3$: 560.7; found: 461.1 (M−Boc). The above methyl benzoate (45 mg. 0.08 mmol) was treated with 1 N NaOH in MeOH (1:1) and stirred at 50° C.

overnight. The reaction mixture was neutralized with acetic acid, the solvents were removed in vacuo, and the residue was subjected to TFA treatment followed by $C_{18}$-HPLC purification as described in Example 220, step c to afford the title compound as a white solid. $^1$H-NMR (CD$_3$OD; 400 MHz) δ 8.35 (s, 1H), 8.06–8.11 (m, 1H), 8.00–8.03 (m, 2H), 7.95 (m, 1H), 7.72–7.76 (m, 2H), 7.35 (d, 1H, J=7.9 Hz), 2.75 (s, 3H), 2.30 (s, 3H). ESI-MS (m/z): Calcd. for $C_{20}H_{18}N_2O_4S_3$: 447.1 (M+H); found: 447.1.

Example 223

2-Amino-N-[3'-(5-carbamimidoyl-2-methylsulfanyl-thiophene-3-sulfonyl)-2-methyl-biphenyl-4-yl]-acetamide trifluoroacetate

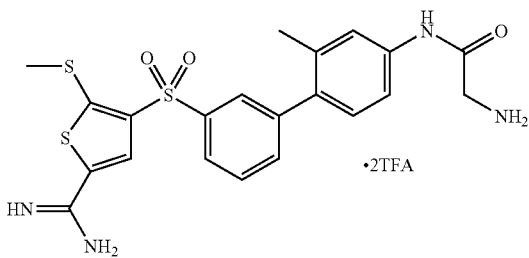

To a solution of {4-(4'-amino-2'-methyl-biphenyl-3-sulfonyl)-5-methylsulfanyl-thiophene-2-yl]-imino-methyl}-carbamic acid tert-butyl ester (80 mg, 0.15 mmol, as prepared in Example 220, step b) in DCM (2.2 mL) was added Boc-gly-N-hydroxysuccinimide ester (126 mg, 0.5 mmol), and triethylamine (69 µL, 0.5 mmol). The reaction mixture was stirred at rt overnight (16 h). The reaction mixture was then diluted with EtOAc and extracted with water and saturated NaHCO$_3$. The separated organic layer was dried with MgSO$_4$, filtered, and concentrated in vacuo to give a residue that was purified using preparative TLC (1:3 EtOAc/hexanes, 1000µ SiO$_2$ plate) to provide 100 mg (99%) of a tan glassy solid. ESI-MS (m/z): Calcd. for $C_{31}H_{38}N_4O_7S_3$: 674.8 (M$^+$); found: 674.8, 575.0, 519.0, 475.1. Treatment of this intermediate with trifluoroacetic acid and purification using $C_{18}$-HPLC (as in Example 220, step c) provided the title compound as a white solid in 78% yield. $^1$H-NMR (CD$_3$OD, 400 MHz): δ 8.34 (s, 1H), 7.99–8.05 (m, 2H), 7.67–7.72 (m, 2H), 7.57 (m, 2H), 7.22 (d, 1H, J=8.1 Hz), 3.90 (s, 2H), 2.74 (s, 3H), 2.25 (s, 3H). ESI-MS (m/z): Calcd. for $C_{21}H_{22}N_4O_3S_3$: 475.1 (M+H); found: 475.1.

Example 224

4-(4'-Hydroxy-2',6'-dimethyl-biphenyl-3-sulfonyl)-5-methylsulfanyl-thiophene-2-carboxamidine trifluoroacetate

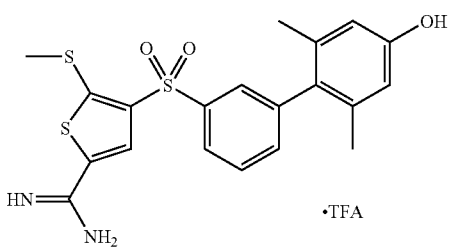

a) 3,5-Dimethyl-4-(4,4,5,5-tetramethyl-[1,3,2]dioxaborolan-2-yl)-phenol

Following the procedure described in Example 220, step a, reaction of 4-bromo-3,5-dimethyl-phenol (1.5 gm, 7.6 mmol), 4,4,5,5-tetramethyl-1,3,2-dioxaborolane (3.3 mL, 23 mmol, Aldrich Chemical Company), PdCl$_2$(PPh$_3$)$_2$ (530 mg, 0.76 mmol, Strem Chemicals Inc, Newburyport, Mass.), Et$_3$N (634 µL, 46 mmol), and dioxane (30 mL) afforded 3.4 gm of a tan glassy solid after chromatography (50 gm, silica SPE column) which was used without further purification. $^1$H-NMR (CDCl$_3$; 400 MHz): δ 6.4 (s, 2H), 2.3 (s, 6H), 1.4 (s, 12H).

b) {[4-(4'-Hydroxy-2',6'-dimethyl-biphenyl-3-sulfonyl)-5-methylsulfanyl-thiophen-2-yl]-imino-methyl}-carbamic acid tert-butyl ester Following the same procedure as in Example 1, step c, reaction of 3,5-dimethyl-4-(4,4,5,5-tetramethyl-[1,3,2]dioxaborolan-2-yl)-phenol (355 mg, 0.8 mmol, assuming quantitative yield from Example 224, step a), {[4-(3-bromo-benzenesulfonyl)-5-methylsulfanyl-thiophen-2-yl]-imino-methyl}-carbamic acid tert-butyl ester (100 mg, 0.2 mmol, as prepared in Example 27, step c), tetrakis(triphenylphosine)palladium(0) (58 mg, 0.05 mmol, Strem Chemicals Inc, Newburyport, Mass.), Na$_2$CO$_3$ (0.8 mL, 2M), and toluene/EtOH mixture (2:1, 2.4 mL) afforded 35 mg (13%) after purification (PTLC) of the title compound as a tan solid. ESI-MS (m/z): Calcd. for $C_{25}H_{28}N_2O_5S_3$: 532.7; found: 532.8, 477.0, 433.1 (M–Boc).

c) 4-(4'-Hydroxy-2',6'-dimethyl-biphenyl-3-sulfonyl)-5-methylsulfanyl-thiophene-2-carboxamidine trifluoroacetate {[4-(4'-Hydroxy-2',6'-dimethyl-biphenyl-3-sulfonyl)-5-methylsulfanyl-thiophen-2-yl]-imino-methyl}-carbamic acid tert-butyl ester (15 mg, 0.03 mmol, as prepared in Example 224, step c) was treated with trifluoroacetic (50% in DCM) for 1 h at rt and purified using $C_{18}$-HPLC (10–60% CH$_3$CN in H$_2$O (0.1% TFA) over 30 min) affording the title compound as a white solid (8 mg, 53%). $^1$H-NMR (CD$_3$OD; 400 MHz) δ 8.35 (s, 1H), 8.00 (m, 1H), 7.80 (t, 1H, J=1.6 Hz), 7.68 (t, 1H, J=7.7 Hz), 7.50 (m, 1H), 6.58 (s, 2H), 0.67–7.73 (m, 2H), 7.28 (d, 1H, J=8.1 Hz), 7.10–7.17 (m, 2H), 2.73 (s, 3H), 1.91 (s, 6H). ESI-MS (m/z): Calcd. for $C_{20}H_{20}N_2O_3S_3$: 433.1 (M+H); found: 433.1.

Example 225

3'-(5-Carbamimidoyl-2-methylsulfanyl-thiophene-3-sulfonyl)-2-methyl-biphenyl-4-carboxylic acid amide trifluoroacetate

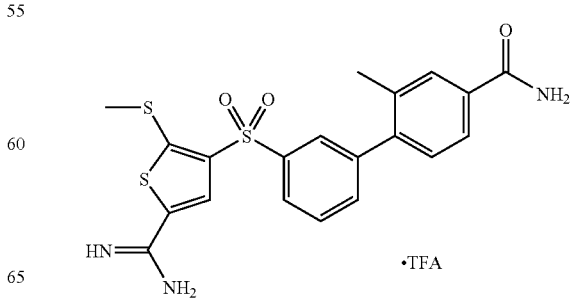

Following the same procedure as in Example 220, step a, reaction of 4-bromo-3-methyl-benzamide (200 mg, 0.93 mmol), 4,4,5,5-tetramethyl-1,3,2-dioxaborolane (0.41 mL, 2.8 mmol, Aldrich Chemical Company), PdCl$_2$(PPh$_3$)$_2$ (65 mg, 0.093 mmol, Strem Chemicals Inc, Newburyport, Mass.), Et$_3$N (700 µL, 46 mmol), and dioxane (5 mL) afforded 140 mg of a brown oil (58%) after purification (SiO$_2$, flash elution: 30% EtOAc in hexanes. The above boronate ester (140 mg, 0.54 mmol) was reacted according to the procedure used in Example 1, step c, with {[4-(3-bromo-benzenesulfonyl)-5-methylsulfanyl-thiophen-2-yl]-imino-methyl}-carbamic acid tert-butyl ester (88 mg, 0.18 mmol, as prepared in Example 27, step c), tetrakis(triphenylphosine)palladium(0) (52 mg, 0.05 mmol, Strem Chemicals Inc, Newburyport, Mass.), Na$_2$CO$_3$ (0.7 mL, 2 M), and toluene/EtOH mixture (2:1, 2.1 mL) to afford {[4-(4'-Carbamoyl-2'-methyl-biphenyl-3-sulfonyl)-5-methylsulfanyl-thiophen-2-yl]-imino-methyl}-carbamic acid tert-butyl ester after purification (preparative TLC, 1:3 EtOAc/hexanes, 3×1000µ SiO$_2$ plate). ESI-MS (m/z): Calcd. for C$_{25}$H$_{27}$N$_3$O$_5$S$_3$: 545.7; found: 446.1 (M−Boc). The above benzamide (44 mg. 0.08 mmol) was subjected to TFA treatment followed by C$_{18}$-HPLC purification as described in Example 220, step c to afford 26 mg (59%) of the title compound as a white solid. $^1$H-NMR (CD$_3$OD; 400 MHz) δ 8.33 (s, 1H), 8.04–8.08 (m, 1H), 7.99–8.01 (m, 1H), 7.85 (m, 1H), 7.78 (m, 1H), 7.70–7.73 (m, 2H), 7.32 (d, 1H, J=7.9 Hz), 2.72 (s, 3H), 2.29 (s, 3H). ESI-MS (m/z): Calcd. for C$_{20}$H$_{19}$N$_3$O$_3$S$_3$: 446.1 (M+H); found: 446.1.

Example 226

{2-[3'-(5-Carbamimidoyl-2-methylsulfanyl-thiophene-3-sulfonyl)-2-methyl-biphenyl-4-ylcarbamoyl]-ethyl}-phosphonic acid trifluoroacetate

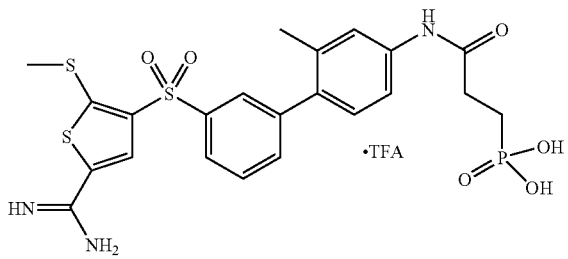

Thionyl chloride (1.7 mL, 23.0 mmol) was added dropwise to a suspension of 3-(diethylphosphono)propanoic acid (0.5 gm, 2.3 mmol, Epsilpon Chimie, Brest, France) in DCM (2 mL) at 0° C. The reaction mixture became clear upon addition of acid chloride. The ice bath was removed and stirring was continued overnight at rt. The solvents were removed in vacuo and the resulting solid was stored under high vacuum before further use. The acid chloride prepared above (53 mg, 0.232 mmol) was transferred to a solution of {4-(4'-amino-2'-methyl-biphenyl-3-sulfonyl)-5-methylsulfanyl-thiophen-2-yl]-imino-methyl}-carbamic acid tert-butyl ester (40 mg, 0.077 mmol, as prepared in Step 220, step b) and Et$_3$N (900 µL, 0.62 mmol) in DCM (2 mL). The mixture was stirred for 4 h at rt and then another 40 mg of the acid chloride was added. After stirring for ~12 h, the volatiles were removed and the residue was partitioned between EtOAc and water. The organic layer was washed with another portion of water and saturated NaHCO$_3$, dried over MgSO$_4$, and filtered. The crude product was chromatographed (PTLC 1000µ plate) to give 33 mg (61%) of the desired (diethylphosphono)propanamide. ESI-MS (m/z): Calcd. for C$_{31}$H$_{40}$N$_3$O$_8$PS$_3$: 709.8 (M$^+$); found: 709.8, 610.1 (M−Boc).

Using a modification of the procedure reported by Zhang, Z.-Y., et al., (J. Med. Chem., 1999, 42:3199–3202), the above (diethylphosphono)propanamide (33 mg, 0.046) in DCM (2 mL) was treated with iodotrimethylsilane (20 µL, 0.14 mmol) at 0° C. for 1 h. Water was added to quench the reaction. After stirring for 20 minutes, 2.0 N HCl (2 mL) and MeOH (2 mL) were added to the reaction mixture. The reaction mixture became clear following the addition. Stirring was continued for 3 h at rt, solvents were removed in vacuo, and the resulting residue was treated with TFA and purified using C$_{18}$-HPLC as described in Example 220, step c to afford 12 mg (50%) of the title compound as a white solid. $^1$H-NMR (CD$_3$OD; 400 MHz): δ 7.61–7.69 (m, 3H), 6.95–7.27 (m, 4H), 6.55 (d, 1H, J=8.6 Hz), 2.41–2.50 (m, 2H), 2.19 (s, 3H), 1.76 (s, 3H), 1.58–1.63 (m, 2H). ESI-MS (m/z): Calcd. for C$_{22}$H$_{24}$N$_3$O$_6$PS$_3$: 554.1 (M+H); found: 554.1.

Example 227

{[3'-(5-Carbamimidoyl-2-methylsulfanyl-thiophene-3-sulfonyl)-2-methyl-biphenyl-4-ylcarbamoyl]-methoxy}-acetic acid trifluoroacetate

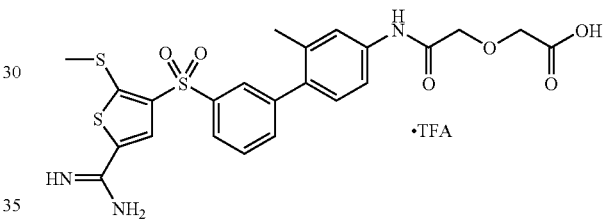

To a solution of {4-(4'-amino-2'-methyl-biphenyl-3-sulfonyl)-5-methylsulfanyl-thiophene-2-yl]-imino-methyl}-carbamic acid tert-butyl ester (25 mg, 0.048 mmol, as prepared in Step 220, step b) and Et$_3$N (33 µL, 0.24 mmol) in DCM (1 mL) was added diglycolic anhydride (17 mg, 0.144 mmol). The reaction was stirred overnight at rt. The solvents were removed in vacuo and the residue was treated with TFA (as in Example 220, step c). Purification using a C$_{18}$-HPLC provided 17 mg (68%) of the title compound as a white solid. $^1$H-NMR (CD$_3$OD, 400 MHz): δ 8.32 (s, 1H), 7.96–8.03 (m, 2H), 7.65–7.70 (m, 2H), 7.57–7.62 (m, 2H), 7.19 (d, 1H, J=8.6 Hz), 4.31 (s, 2H), 4.24 (s, 2H), 2.72 (s, 3H), 2.23 (s, 3H). ESI-MS (m/z): Calcd. for C$_{23}$H$_{23}$N$_3$O$_6$S$_3$: 534.1 (M+H); found: 534.1.

Example 228

5-Methylsulfanyl-4-(2'-methyl-4'-ureido-biphenyl-3-sulfonyl)-thiophene-2-carboxamidine trifluoroacetate

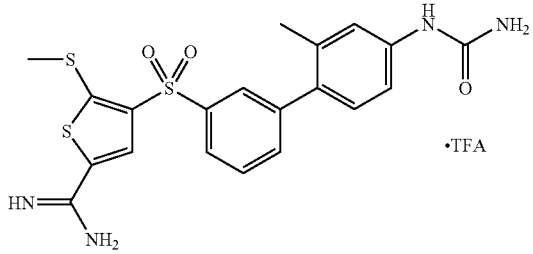

According to the procedure by Rivier et al. (*J. Med. Chem.* 2001, 44, 453–467) trimethylsilyl isocyante (45 µL, 0.29 mmol) was added to a solution of {4-(4'-Amino-2'-methyl-biphenyl-3-sulfonyl)-5-methylsulfanyl-thiophene-2-yl]-imino-methyl}-carbamic acid tert-butyl ester (43 mg, 0.083 mmol, as prepared in Step 220, step b) in DMF (0.2 mL). The reaction was stirred for 3 days at rt. The DMF was removed in vacuo and the residue was treated with TFA (as in Example 220, step c, except 1% m-cresol was added in the deprotection mixture). The crude reaction mixture was concentrated to an oily residue that was triturated with Et$_2$O to remove m-cresol. Purification using C$_8$-HPLC provided 10 mg (25%) of the title compound as a white solid. $^1$H-NMR (CD$_3$OD, 400 MHz): δ 8.34 (s, 1H), 7.96–8.04 (m, 2H), 7.65–7.70 (m, 2H), 7.31.738 (m, 2H), 7.13 (d, 1H, J=7.9 Hz), 2.74 (s, 3H), 2.22 (s, 3H). ESI-MS (m/z): Calcd. for C$_{20}$H$_{20}$N$_4$O$_3$S$_3$: 461.1 (M+H); found: 461.1.

Example 229

2-Amino-4-[3'-(5-carbamimidoyl-2-methylsulfanyl-thiophene-3-sulfonyl)-2-methyl-biphenyl-4-ylcarbamoyl]-butyric acid bis-trifluoroacetate

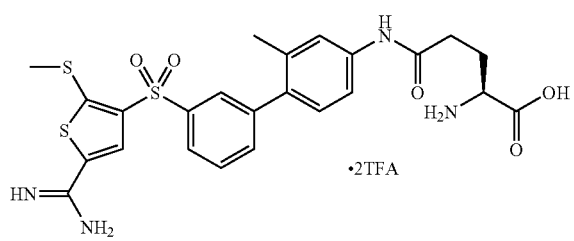

Following the same procedure described for Example 223, but substituting Boc-L-glu(OSu)-OtBu for Boc-gly-N-hydroxysuccinimide ester, provided the title compound as a white solid in 75% yield. $^1$H-NMR (CD$_3$OD, 400 MHz): δ 8.34 (s, 1H), 7.97–8.03 (m, 2H), 7.66–7.71 (m, 2H), 7.52–7.56 (m, 2H), 7.18 (d, 1H, J=8.1 Hz), 4.12 (t, 1H, J=6.5 Hz), 2.73 (s, 3H), 2.71–2.75 (m, 2H), 2.24 (s, 3H), 2.24–2.38 (m, 2H). ESI-MS (m/z): Calcd. for C$_{24}$H$_{26}$N$_4$O$_5$S$_3$: 547.1 (M+H); found: 547.1.

Example 230

6-[5-(2-Oxo-hexahydro-thieno[3,4-d]imidazol-6-yl)-pentanoylamino]-hexanoic acid[3'-(5-carbamimidoyl-2-methylsulfanyl-thiophene-3-sulfonyl)-2-methyl-biphenyl-4-yl]-amide trifluoroacetate

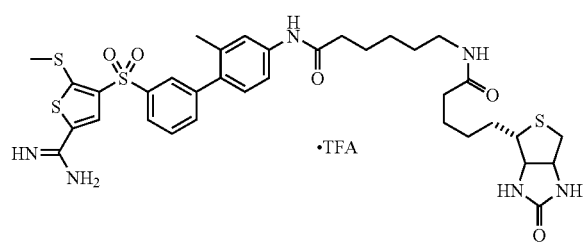

Following the same procedure described for Example 223, but substituting N-(+)-biotinyl-6-aminocaproic acid N-succinimidyl ester for Boc-gly-N-hydroxysuccinimide ester, provided the title compound as a white solid in 11% yield. $^1$H-NMR (CD$_3$OD, 400 MHz): δ 8.33 (s, 1H), 7.99–8.02, (m, 1H), 7.95–7.97 (m, 1H), 7.66–7.69 (m, 2H), 7.49–7.53 (m, 2H), 7.17 (d, 1H, J=8.4 Hz), 4.47 (dd, 1H, J=7.9, 4.2 Hz), 4.27 (dd, 1H, J=7.8, 4.2 Hz), 3.15–3.22 (m, 4H), 2.91 (dd, 1H, J=12.6, 4.9 Hz), 2.73 (s, 3H), 2.41 (t, 2H, J=7.6 Hz), 2.23 (s, 3H), 2.19 (t, 2 H, J=7.4 Hz), 1.35–1.80 (m, 12H). ESI-MS (m/z): Calcd. for C$_{35}$H$_{44}$N$_6$O$_5$S$_4$: 757.2 (M+H); found: 757.3

Example 231

4-Amino-4-[3'-(5-carbamimidoyl-2-methylsulfanyl-thiophene-3-sulfonyl)-2-methyl-biphenyl-4-ylcarbamoyl]-butyric acid bis-trifluoroacetate

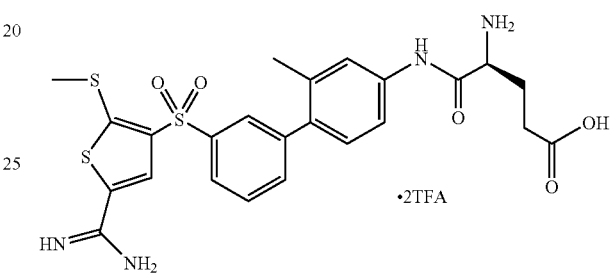

Following the same procedure described for Example 223, but substituting Boc-L-glu(OtBu)-OSu for Boc-gly-N-hydroxysuccinimide ester, provided the title compound as a white solid in 64% yield. $^1$H-NMR (CD$_3$OD, 400 MHz): δ 8.34 (s, 1H), 7.99–8.05 (m, 2H), 7.67–7.73 (m, 2H), 7.56–7.61 (m, 2H), 7.23 (d, 1H, J=8.1 Hz), 4.10 (t, 1H, J=6.0 Hz), 2.74 (s, 3H), 2.58 (t, 2H, J=7.4 Hz), 2.26 (s, 3H), 2.20–2.35 (m, 2H). ESI-MS (m/z): Calcd. for C$_{24}$H$_{26}$N$_4$O$_5$S$_3$: 547.1 (M+H); found: 547.1.

Example 232

2-Amino-N-[3'-(5-carbamimidoyl-2-methylsulfanyl-thiophene-3-sulfonyl)-2-methyl-biphenyl-4-yl]-4-methanesulfonyl-butyramide bis-trifluoroacetate

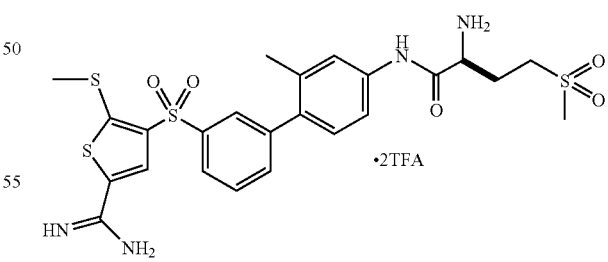

In a scintillation vial, Boc-L-methionine sulfone (124 mg, 0.44 mmol, Chem-Impex, International, INC., Wood Dale, Ill.) was dissolved in DMF (2 mL). To the solution was added HBTU (159 mg, 0.42 mmol), HOBT (60 mg, 0.44 mmol), and DIEA (400 µL, 2.1 mmol). After 10 min of vigorous stirring (solution turned pale yellow), the mixture was transferred to a reaction vial charged with a stir bar and {4-(4'-amino-2'-methyl-biphenyl-3-sulfonyl)-5-methylsulfanyl-thiophene-2-yl]-imino-methyl}-carbamic acid tert-butyl ester (73 mg, 0.14 mmol, as prepared in Step 220, step b). The resulting mixture was stirred overnight at rt. Analogous work up as described for Example 223 followed by TFA treatment and RP-HPLC provided 58 mg (72%) of the title compound as the bis-trifluoroacetate salt. $^1$H-NMR (CD$_3$OD, 400 MHz): δ 8.33 (s, 1H), 7.97–8.03 (m, 2H), 7.66–7.71 (m, 2H), 7.57–7.62 (m, 2H), 7.23 (d, 1H, J=8.1 Hz), 4.24 (t, 1H, J=6.4 Hz), 3.25–3.39 (m, 2H), 3.06 (s, 3H), 2.72 (s, 3H), 2.40–2.56 (m, 2H), 2.25 (s, 3H). ESI-MS (m/z): Calcd. for C$_{24}$H$_{28}$N$_4$O$_5$S$_4$: 581.1 (M+H); found: 581.0.

Example 233

4-[4'-(4,5-Dihydro-1H-imidazol-2-ylamino)-2'-methyl-biphenyl-3-sulfonyl]-5-methylsulfanyl-thiophene-2-carboxamidine bis-trifluoroacetate

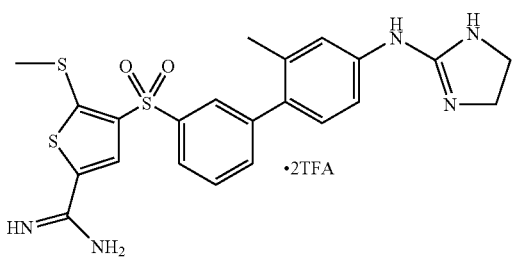

a) 2-Methylsulfanyl-4,5-dihydro-imidazole-1-carboxylic acid tert-butyl ester 4,5-Dihydro-2-methylthioimidazole hydroiodide (3 gm, 12 mmol, Aldrich Chemical Company), di-tert-butyl-dicarbonate (5.4 gm, 24.8 mmol), Et$_3$N (5 mL, 36 mmol), and DMAP (70 mg, 0.57 mmol) were dissolved in DCM (35 mL). The reaction was stirred at rt for 16 h then diluted with more DCM and washed with water and saturated NaHCO$_3$. The organic layer was dried (MgSO$_4$), filtered, and evaporated in vacuo to give 1 gm (38%) of the title compound as a white crystalline solid. $^1$H-NMR (CDCl$_3$; 400 MHz): δ 3.82–3.86 (m, 4H), 2.39 (s, 3H), 1.51 (s, 9H). ESI-MS (m/z): Calcd. for C$_9$H$_{16}$N$_2$O$_2$S: 217.1 (M+H); found: 216.8, 161.0, 117.2 (M–Boc).

b) 4-[4'-(4,5-Dihydro-1H-imidazol-2-ylamino)-2'-methyl-biphenyl-3-sulfonyl]-5-methylsulfanyl-thiophene-2-carboxamidine bis-trifluoroacetate According to a procedure by Mundla et al. (*Tetrahedron Lett.* 2000, 41, 6563–6566), {4-(4'-amino-2'-methyl-biphenyl-3-sulfonyl)-5-methylsulfanyl-thiophene-2-yl]-imino-methyl}-carbamic acid tert-butyl ester (18 mg, 0.035 mmol, as prepared in Example 220, step b) and 2-methylsulfanyl-4,5-dihydro-imidazole-1-carboxylic acid tert-butyl ester (23 mg, 0.1 mmol, as prepared in Example 233, step a) were dissolved in a MeOH/Acetic acid mixture (10:1, 1 mL). The reaction mixture was stirred overnight at 55° C. and then concentrated to dryness. The resulting residue was treated with TFA and purified using C$_{18}$-HPLC as described in Example 220, step c to afford 12 mg (70%) of the title compound as a white solid. $^1$H-NMR (CD$_3$OD; 400 MHz): δ 8.00–8.05 (m, 2H), 7.66–7.73 (m, 2H), 7.19–7.33 (m, 3H), 3.84 (s, 4H), 2.72 (s, 3H), 2.27 (s, 3H). ESI-MS (m/z): Calcd. for C$_{22}$H$_{23}$N$_5$O$_2$S$_3$: 486.1 (M+H); found: 486.1.

Example 234

2-{[3'-(5-Carbamimidoyl-2-methylsulfanyl-thiophene-3-sulfonyl)-2-methyl-biphenyl-4-ylcarbamoyl]-methylsulfanyl}-acetamide trifluoroacetate

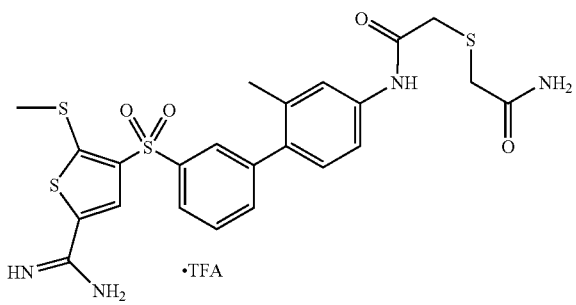

a) ({4-[4'-(2-Bromo-acetylamino)-2'-methyl-biphenyl-3-sulfonyl]-5-methylsulfanyl-thiophen-2-yl}-imino-methyl)-carbamic acid tert-butyl ester {4-(4'-Amino-2'-methyl-biphenyl-3-sulfonyl)-5-methylsulfanyl-thiophene-2-yl]-imino-methyl}-carbamic acid tert-butyl ester (110 mg, 0.21 mmol, as prepared in Example 220, step b), bromoacetyl bromide (19 μL, 0.21 mmol), and Et$_3$N (33 μL, 0.23 mmol) were dissolved in chloroform (2 mL) and the reaction was stirred for 3 h at rt. As TLC indicated small amount of aniline remaining in the reaction mixture, 4 μL of bromoacetyl bromide were added and the reaction was stirred for 2 more hours. The volatiles were removed in vacuo and the residue was partitioned between EtOAc and 20% citric acid. The organic layer was washed with saturated NaHCO$_3$, water, and brine, then dried (MgSO$_4$), and concentrated in vacuo to give 135 mg (100%) of crude product as a tan solid. Purification of this material using PTLC (1:1 EtOAc/hexanes, 2×1500μ SiO$_2$ plate) provided the title compound in 89% yield as a pale yellow solid. $^1$H-NMR (CDCl$_3$, 400 MHz): δ 8.24 (s, 1H), 8.00 (dt, 1H, J=7.3, 1.8 Hz), 7.96 (br s, 1H), 7.92 (m, 1H), 7.55–7.62 (m, 2H), 7.41–7.47 (m, 2H), 7.19 (d, 1H, J=8.1 Hz), 4.09 (s, 2H), 2.52 (s, 3H), 2.25 (s, 3H), 1.54 (s, 9H). ESI-MS (m/z): Calcd. for C$_{24}$H$_{27}$N$_3$O$_4$S$_3$: 517.7; found: 517.7, 418.1 (M–Boc).

b) 2-{[3'-(5-Carbamimidoyl-2-methylsulfanyl-thiophene-3-sulfonyl)-2-methyl-biphenyl-4-ylcarbamoyl]-methylsulfanyl}-acetamide trifluoroacetate To a solution of ({4-[4'-(2-bromo-acetylamino)-2'-methyl-biphenyl-3-sulfonyl]-5-methylsulfanyl-thiophen-2-yl}-imino-methyl)-carbamic acid tert-butyl ester (44 mg, 0.069 mmol, as prepared in Example 234, step a) in MeOH (0.6 mL) was added 2-mercapto acetamide (100 μL of 10% methanolic solution, Maybridge plc) and Et$_3$N (30 μL, 0.21 mmol). The reaction mixture was stirred at rt for 0.5 h and then concentrated in vacuo. The residue was treated with TFA and purified using C$_{18}$-HPLC as described in Example 220, step c to afford 32 mg (84%) of the title compound as a white solid. $^1$H-NMR (CD$_3$OD; 400 MHz): δ 8.32 (s, 1H), 7.99–8.02 (m, 1H), 7.95–7.97 (m, 1H), 7.66–7.68 (m, 2H), 7.51–7.55 (m, 2H), 7.17 (d, 1H, J=8.1 Hz), 3.48 (s, 2H), 3.37 (s, 2H), 2.72 (s, 3H), 2.23 (s, 3H). ESI-MS (m/z): Calcd. for C$_{24}$H$_{25}$N$_3$O$_5$S$_4$: 664.1 (M+H); found: 564.1.

Example 235

2-{[3'-(5-Carbamimidoyl-2-methylsulfanyl-thiophene-3-sulfonyl)-2-methyl-biphenyl-4-ylcarbamoyl]-methylsulfanyl}-succinic acid trifluoroacetate

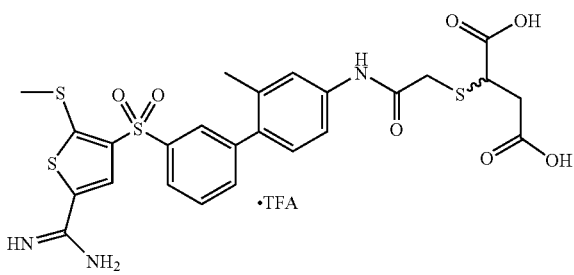

Following the same procedure as described in Example 234, step b, reaction of ({4-[4'-(2-bromo-acetylamino)-2'-methyl-biphenyl-3-sulfonyl]-5-methylsulfanyl-thiophen-2-yl}-imino-methyl)-carbamic acid tert-butyl ester (17 mg, 0.027 mmol, as prepared in Example 234, step a), mercaptosuccinate (6 mg, 0.04 mmol), Et$_3$N (12 μL, 0.08 mmol), and MeOH (3 mL) provided 12 mg (75%) of the title compound as a white solid after RP-HPLC purification. $^1$H-NMR (CD$_3$OD; 400 MHz): δ 8.34 (s, 1H), 7.99–8.00–8.05 (m, 1H), 7.97–7.99 (m, 1H), 7.68–7.70 (m, 2H), 7.54–7.58 (m, 2H), 7.19 (d, 1H, J=7.9 Hz), 3.85 (dd, 1H, J=9.5, 5.6 Hz), 3.56 and 3.69 (AB quartet, 2H, J=15.1 Hz), 2.97 (dd, 1H, J=17.2, 9.8 Hz), 2.76 (dd, 1H, J=17.0, 5.6 Hz), 2.74 (s, 3H), 2.25 (s, 3H). ESI-MS (m/z): Calcd. for C$_{25}$H$_{25}$N$_3$O$_7$S$_4$: 608.1 (M+H); found: 608.1.

Example 236

4-(4'-Guanidino-2'-methyl-6'-nitro-biphenyl-3-sulfonyl)-5-methylsulfanyl-thiophene-2-carboxamidine bis-trifluoroacetate

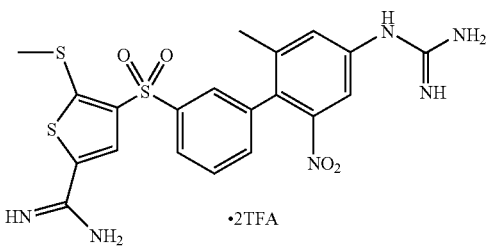

a) {[4-(4'-Amino-2'-methyl-6'-nitro-biphenyl-3-sulfonyl)-5-methylsulfanyl-thiophen-2-yl]-imino-methyl}-carbamic acid tert-butyl ester Following the procedure used for Example 295, step h, reaction of 4-bromo-3-methyl-5-nitro-phenylamine (350 mg, 1.5 mmol, as prepared in Example 135, step a), {[4-(3-dihydroxyboranyl-benzenesulfonyl)-5-methylsulfanyl-thiophen-2-yl]-imino-methyl}-carbamic acid tert-butyl ester (1.0 gm, 2.27 mmol, as prepared in Example 140, step a), tetrakis(triphenylphosine)palladium(0) (433 mg, 0.375 mmol, Strem Chemicals Inc, Newburyport, Mass.), Na$_2$CO$_3$ (6 mL, 2M), and toluene/EtOH mixture (2:1, 18 mL) at 80° C. for 24 h afforded 250 mg (30%) after purification (SiO$_2$, flash elution: 5% to 50% EtOAc in hexanes) of the title compound as a yellow solid. ESI-MS (m/z): Calcd. for C$_{24}$H$_{26}$N$_4$O$_6$S$_3$: 563.1 (M+H); found: 562.8, 463.1 (M–Boc).

b) ({4-[4'-(N,N'-Bis-tert-butoxycarbonyl)-guanidino-2'-methyl-6'-nitro-biphenyl-3-sulfonyl]-5-methylsulfanyl-thiophen-2-yl}-imino-methyl)-carbamic acid tert-butyl ester According to a previously published procedure (Bergerson et al., J. Org. Chem. 1987, 52, 1700–1703; WO 99/20608), mercury (II) chloride (190 mg, 0.7 mmol) was added in one portion to a stirred mixture of {[4-(4'-amino-2'-methyl-6'-nitro-biphenyl-3sulfonyl)-5-methylsulfanyl-thiophen-2-yl]-imino-methyl}-carbamic acid tert-butyl ester (130 mg, 0.23 mmol, as prepared in Example 236, step a), N,N'-bis(tert-butoxycarbonyl)-S-methylisothiourea (203 mg, 0.7 mmol, Aldrich Chemical Company), and Et$_3$N (173 μL, 1.15 mmol) in DCM (3 mL). The mixture was stirred for 24 h at rt and then purified using flash chromatography (Biotage Flash System—40 M SiO$_2$ column, 10% to 30% EtOAc in hexanes) to afford 145 mg (78%) of the title compound as a clear oil. ESI-MS (m/z): Calcd. for C$_{35}$H$_{44}$N$_6$O$_{10}$S$_3$: 805.2 (M+H); found: 804.7, 704.9, 604.9, 505.1 (M−3×Boc).

c) 4-(4'-Guanidino-2'-methyl-6'-nitro-biphenyl-3-sulfonyl)-5-methylsulfanyl-thiophene-2-carboxamidine bis-trifluoroacetate ({4-[4'-(N,N'-Bis-tert-butoxycarbonyl)-guanidino-2'-methyl-6'-nitro-biphenyl-3-sulfonyl]-5-methylsulfanyl-thiophen-2-yl}-imino-methyl)-carbamic acid tert-butyl ester (10 mg, 12.4 μmol, as prepared in Example 236, step b) was treated with TFA and purified using C$_{18}$-HPLC as described in Example 220, step c to afford 1.1 mg (17%) of the title compound as a white solid. $^1$H-NMR (CD$_3$OD; 400 MHz): δ 8.34 (s, 1H), 8.04 (ddd, 1H, J=7.9, 1.9, 1.2 Hz), 7.92–7.94 (m, 1H), 7.72–7.79 (m, 2H), 7.62 (ddd, 1H, J=7.7, 1.6, 1.2 Hz), 7.60 (dd, 1H, J=2.1, 0.7 Hz), 2.72 (s, 3H), 2.18 (s, 3H). ESI-MS (m/z): Calcd. for C$_{20}$H$_{20}$N$_6$O$_4$S$_3$: 505.1 (M+H); found: 505.1.

Example 237

4-(6'-Amino-4'-guanidino-2'-methyl-biphenyl-3-sulfonyl)-5-methylsulfanyl-thiophene-2-carboxamidine bis-trifluoroacetate

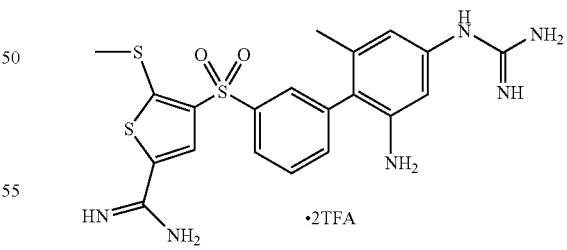

a) {[4-(2',4'-Diamino-6'-methyl-biphenyl-3-sulfonyl)-5-methylsulfanyl-thiophen-2-yl]-imino-methyl}-carbamic acid tert-butyl ester {2-Amino-3'-[5-(tert-butoxycarbonylamino-imino-methyl)-2-methylsulfanyl-thiophene-3-sulfonyl]-6-methyl-biphenyl-4-yl}-carbamic acid 2-trimethylsilanyl-ethyl ester (1000 mg, 1.48 mmol, Example 294, step f) was dissolved into THF (25 mL). To this was added TBAF (1M, 1.62 mL, 1.62 mmol) and the reaction was warmed to 40° C. with stirring for 3 hours. Additional TBAF (1.48 mL, 1.48 mmol) was added and the reaction was stirred at rt overnight. The solvents were removed in vacuo, the residue was dissolved into EtOAc and washed with water several times (5 washes). The combined organic layers were dried (MgSO$_4$) and the solvents were removed in vacuo resulting in the title compound as a yellow solid (800 mg, 100%). $^1$H-NMR (CDCl$_3$): δ: 8.03 (s, 1H), 7.95–7.93 (m, 1H), 7.89–7.88 (m, 1H), 7.59–7.53 (m, 2H), 6.08 (m, 1H), 5.99 (m, 1H), 2.55 (s, 3H), 1.85 (s, 3H), 1.52 (s, 9H).

b) 4-{4'-[N',N"-Bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester {[4-(2',4'-Diamino-6'-methyl-biphenyl-3-sulfonyl)-5-methylsulfanyl-thiophen-2-yl]-imino-methyl}-carbamic acid tert-butyl ester (342 mg, 0.64 mmol, Example 237, step a) was dissolved into MeOH (4 mL) and acetic acid (200 μL). To this was added 1,3-bis(tert-butoxycarbonyl)-2-methyl-2-thiopseudourea (203 mg, 0.70 mmol) slowly as a suspension in MeOH and the reaction was stirred at rt overnight. The solvents were removed in vacuo followed by flash column chromatography purification (SiO$_2$) (40% EtOAc in hexanes) that yielded the title compound (235 mg, 47%) as a white solid. ESI-MS (m/z): Calcd. for C$_{35}$H$_{46}$N$_6$O$_8$S$_3$: 775.3 (M+1); found: 774.8.

c) 4-(6'-Amino-4'-guanidino-2'-methyl-biphenyl-3-sulfonyl)-5-methylsulfanyl-thiophene-2-carboxamidine bis-trifluoroacetate 4-{4'-[N',N"-Bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester (10 mg, 12.9 μmol, as prepared in Example 237, step b) was treated with TFA and purified using C$_{18}$-HPLC as described in Example 220, step c to afford 3 mg (50%) of the title compound as a white solid. $^1$H-NMR (CD$_3$OD; 400 MHz): δ 8.35 (s, 1H), 8.04 (ddd, 1H, J=7.9, 1.9, 1.1 Hz), 7.92–7.95 (m, 1H), 7.75 (t, 1H, J=7.8 Hz), 7.58 (dt, 1H, J=7.6, 1.1 Hz), 6.65–6.63 (m, 2H), 2.71 (s, 3H), 1.94 (s, 3H). ESI-MS (m/z): Calcd. for C$_{20}$H$_{22}$N$_6$O$_2$S$_3$: 475.1 (M+H); found: 475.1.

Example 238

3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid methyl ester bis-trifluoroacetate

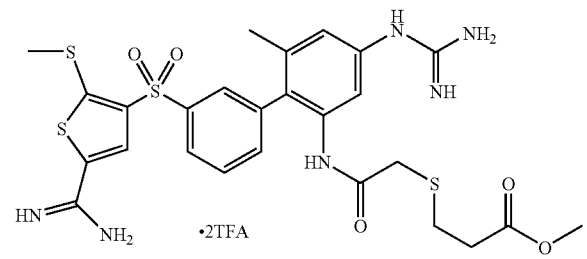

a) ({4-[6'-(2-Hydroxy-acetylamino)-2'-methyl-4'-nitro-biphenyl-3-sulfonyl]-5-methyl sulfanyl-thiophen-2-yl}-imino-methyl)-carbamic acid tert-butyl ester To a solution of {[4-(6'-amino-2'-methyl-4'-nitro-biphenyl-3-sulfonyl)-5-methylsulfanyl-thiophen-2-yl]-imino-methyl}-carbamic acid tert-butyl ester (216 mg, 0.384 mmol, as prepared in Example 295, step h) in DCM (2 mL) was added DIEA (212 μL, 1.15 mmol) and acetoxyacetyl chloride (54 mL, 0.5 mmol). The solution was stirred at rt for 3 hr. The reaction mixture was diluted with EtOAc and washed with saturated NaHCO$_3$, water, and brine. The organic layer was dried over MgSO$_4$, filtered, and concentrated in vacuo to provide 256 mg of a crude oil that was used without further purification. ESI-MS (m/z): Calcd. for C$_{28}$H$_{30}$N$_4$O$_9$S$_3$: 663.1 (M+H); found: 662.7, 563.0 (M−Boc). To a solution of the crude intermediate obtained above in MeOH (2.5 mL) was added 1 N NaOH (2.5 mL) and the mixture was stirred at rt for 45 min at which time TLC was consistent with complete conversion. The reaction mixture was neutralized with acetic acid, concentrated in vacuo, and the residue partitioned between EtOAc and saturated NaHCO$_3$. The organic layer was washed with water and brine, dried over MgSO$_4$, filtered, and concentrated in vacuo to give 220 mg (92%, crude yield over two steps) of the title compound which was used without further purification. ESI-MS (m/z): Calcd. for C$_{26}$H$_{28}$N$_4$O$_8$S$_3$: 621.1 (M+H); found: 620.7, 521.0 (M−Boc).

b) ({4-[4'-(N,N'-Bis-tert-butoxycarbonyl)-guanidino-6'-(2-hydroxy-acetylamino)-2'-methyl-biphenyl-3-sulfonyl]-5-methylsulfanyl-thiophen-2-yl}-imino-methyl)-carbamic acid tert-butyl ester To a solution of ({4-[6'-(2-hydroxy-acetylamino)-2'-methyl-4'-nitro-biphenyl-3-sulfonyl]-5-methylsulfanyl-thiophen-2-yl}-imino-methyl)-carbamic acid tert-butyl ester (220 mg, 0.354 mmol, as prepared in Example 237, step a) in EtOH (2.2 mL) was added a solution of NH$_4$Cl (1.1 mL, 3.2 M, 3.54 mmol). The mixture was stirred vigorously at 50° C. for 30-min. Iron powder (100 mg, 1.77 mmol) was added and the mixture was heated to 80° C. for 3.5 h. The reaction mixture was filtered (0.2μ, Wheaton syringe filter) and the filtrate was concentrated to a solid that was partitioned between EtOAc and 1 N Na$_2$CO$_3$. The organic layer was washed with another portion of Na$_2$CO$_3$, dried (MgSO$_4$), filtered, and concentrated to give the crude desired product. Purification using PTLC (4×1500μ plate, 5% MeOH in DCM) provided 58 mg of the desired aniline. ESI-MS (m/z): Calcd. for C$_{26}$H$_{30}$N$_4$O$_6$S$_3$: 591.1 (M+H); found: 591.0, 491.0 (M−Boc). To a solution of this aniline (55 mg, 0.09 mmol) in McOH/AcOH (10:1, 5 mL), N,N'-bis(tert-butoxycarbonyl)-S-methylisothiourea (78 mg, 0.27 mmol, Aldrich Chemical Company) was added. The reaction mixture was warmed to 40° C. and stirred for 3 h. The mixture was concentrated in vacuo to a solid that was purified on PTLC (2×1000μ plate, 1:1 EtOAc/hexanes) to give 45 mg (60%) of the title compound as a clear oil. $^1$H-NMR (CDCl$_3$; 400 MHz): δ 11.60 (s, 1H), 10.27 (s, 1H), 8.20 (m, 2H), 8.04 (d, 1H, J=6.7 Hz), 7.90 (br s, 1H), 7.64 (t, 1H, J=7.8 Hz), 7.40–7.45 (m, 2H), 4.42 (br s, 1H), 3.84 and 3.99 (AB quartet, 2H, J=15.4 Hz), 2.55 (s, 3H), 1.93 (s, 3H), 1.57 (s, 9H), 1.53 (s, 9H), 1.48 (s, 9H). ESI-MS (m/z): Calcd. for C$_{37}$H$_{48}$N$_6$O$_{10}$S$_3$: 833.2 (M+H); found: 832.8, 732.8, 632.9, 533.1.

c) Methanesulfonic acid {3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-ylcarbamoyl}-methyl ester To a solution of ({4-[4'-(N,N'-bis-tert-butoxycarbonyl)-guanidino-6'-(2-hydroxy-acetylamino)-2'-methyl-biphenyl-3-sulfonyl]-5-methylsulfanyl-thiophen-2-yl}-imino-methyl)-carbamic acid tert-butyl ester (40 mg, 48 µmmol, as prepared in Example 238, step b) and diisopropyl ethylamine (100 µL, 192 µmol) in DCM (1 mL) at 0° C. was added methanesulfonyl chloride (10 µL, 130 µmol). The solution was stirred at 0° C. for 30 min and then allowed to warm up and stirred at rt for 5 h. The reaction mixture was concentrated in vacuo and the residue was chromatographed (PTLC, 1:1 EtOAc/hexanes, 1000µ SiO₂ plate) to afford 40 mg (97%) of the desired title compound as a glassy solid. ESI-MS (m/z): Calcd. for $C_{38}H_{50}N_6O_{12}S_4$: 911.2 (M+H); found: 910.7, 810.8, 710.8, 611.1.

d) 3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid methyl ester bis-trifluoroacetate Methyl 3-mercapto propionate (large molar excess) was added to a solution of (Methanesulfonic acid {3'-[5-(tert-butoxycarbonylamino-imino-methyl)-2-methylsulfanyl-thiophene-3-sulfonyl]-4-(N,N'-Bis-tert-butoxycarbonyl)-guanidino-6-methyl-biphenyl-2-ylcarbamoyl}-methyl ester (7 mg, 7.7 mol, as prepared in Example 238, step c) and Et₃N (20 µL) in DCM (200 µL). The solution was stirred for 1 hr at rt then concentrated in vacuo. The resulting residue was treated with TFA and purified using $C_{18}$-HPLC as described in Example 220, step c to afford 3 mg (45%) of the title compound as a white solid. ¹H-NMR (CD₃OD; 400 MHz): δ 8.32 (s, 1H), 8.08 (ddd, 1H, J=8.0, 2.0, 1.2 Hz), 7.92 (t, 1H, J=1.6 Hz), 7.74 (t, 1H, J=8.0 Hz), 7.57 (dt, 1H, J=7.6, 1.6 Hz), 7.45 (d, 1H, J=2.3 Hz), 7.20 (dd, 1H, J=2.3, 0.7 Hz), 3.67 (s, 3H), 3.05 and 3.10 (AB quartet, 2H, J=15.5 Hz), 2.73 (s, 3H), 2.40–2.44 (m, 2H), 2.27–2.33 (m, 2H), 2.08 (s, 3H). ESI-MS (m/z): Calcd. for $C_{26}H_{30}N_6O_5S_4$: 635.1 (M+H); found: 635.1.

Example 239

3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid bis-trifluoroacetate

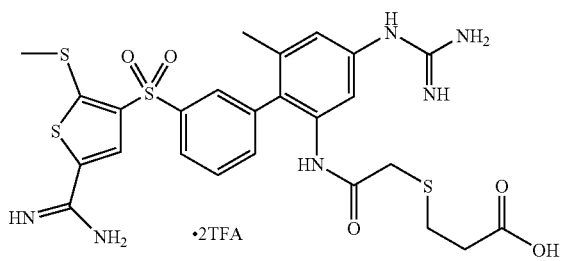

3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid methyl ester bis-trifluoroacetate (5.7 mg, 6.3 µmol, as prepared in Example 238, step d), dissolved in MeOH (200 µL), was treated with 1 N NaOH (200 µL) at rt for 2 hr. The reaction was acidified with acetic acid and the crude product was purified using $C_{18}$-HPLC as described in Example 220, step c to provide 4 mg (75%) of the title compound as a white solid. ¹H-NMR (CD₃CN; 400 MHz): δ 9.67 (br s, 1H), 9.44 (br s, 2H), 8.36 (s, 1H), 8.19 (s, 1H), 8.12 (ddd, 1H, J=8.1, 1.9, 1.1 Hz), 7.88 (t, 1H, J=1.6 Hz), 7.75–7.81 (m, 3H), 7.55 (dt, 1H, J=7.7, 1.5 Hz), 7.10 (d, 1H, J=1.9 Hz), 6.84 (br s, 4H), 3.01 and 3.08 (AB quartet, 2H, J=16.2 Hz), 2.69 (s, 3H), 2.24–2.36 (m, 4H), 2.04 (s, 3H). ESI-MS (m/z): Calcd. for $C_{25}H_{28}N_6O_5S_4$: 621.1 (M+H); found: 621.0.

Example 240

6-{3-[3'-(5-Carbamimidoyl-2-methylsulfanyl-thiophene-3-sulfonyl)-6-methyl-biphenyl-2-yl]-ureido}-hexanoic acid trifluoroacetate

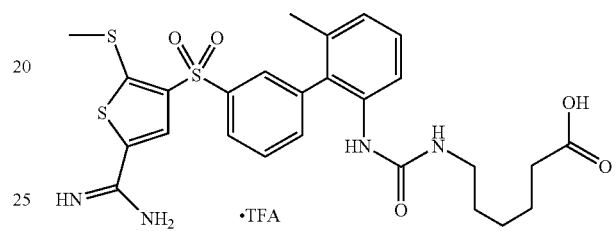

To a solution of {[4-(6'-amino-2'-methyl-biphenyl-3-sulfonyl)-5-methylsulfanyl-thiophen-2-yl]-imino-methyl}-carbamic acid tert-butyl ester (23 mg, 0.044 mmol, as prepared in Example 25, step c) and Et₃N (50 µL, 0.36 mmol) in DCM (2 mL) was added 6-isocyanato-hexanoic acid ethyl ester (40 µL, 0.22 mmol) and the mixture was stirred for 3 h at rt. The reaction mixture was diluted with EtOAc and then washed with water and saturated NaHCO₃. The organic layer was dried over MgSO₄, filtered, and concentrated in vacuo. The resulting crude product was taken up in MeOH (3 mL) and treated with 1 N NaOH (3 mL) at rt for 2 h. The reaction was acidified with acetic acid, concentrated in vacuo, and the residue was subjected to TFA treatment followed by $C_{18}$-HPLC purification as described in Example 220, step c to afford the title compound as a white solid. ¹H-NMR (CD₃OD; 400 MHz) δ 8.30 (s, 1H), 8.05 (ddd, 1H, J=7.9, 1.9, 1.2 Hz), 7.89 (t, 1H, J=1.6 Hz), 7.71 (t, 1H, J=7.8 Hz), 7.54–7.58 (m, 1H), 7.43 (d, 1H, J=7.7 Hz), 7.28 (t, 1H, J=7.8 Hz), 7.10–7.14 (m, 1H), 2.97 (td, 2H, J=6.8, 2.2 Hz), 2.72 (s, 3H), 2.26 (t, 2H, J=7.4 Hz), 2.00 (s, 3H), 1.51–1.59 (m, 2H), 1.19–1.36 (m, 4H). ESI-MS (m/z): Calcd. for $C_{26}H_{30}N_4O_5S_3$: 575.1 (M+H); found: 575.1.

Example 241

3-(2-{2-[2-(2-{3-[3'-(5-Carbamimidoyl-2-methylsulfanyl-thiophene-3-sulfonyl)-6-methyl-biphenyl-2-yl]-ureido}-ethoxy)-ethoxy]-ethoxy}-ethoxy)-propionic acid trifluoroacetate

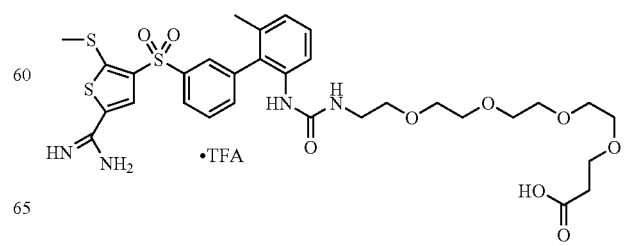

As described in Example 194, step a, {[4-(6'-amino-2'-methyl-biphenyl-3-sulfonyl)-5-methylsulfanyl-thiophen-2-yl]-imino-methyl}-carbamic acid tert-butyl ester (75 mg, 0.145 mmol, as prepared in Example 25, step c), p-nitrophenyl chloroformate (31 mg, 0.152 mmol), pyridine (40 µL, 0.435 mmol) in DCM (1 mL) were stirred at rt for 3 h. To the mixture was added amino-dPEG$_4$-™-t-butyl ester (93 mg, 0.29 mmol, Quanta Biodesign, Powell, Ohio) and the reaction was stirred for another 16 h at rt. The mixture was concentrated and the residue was subjected to TFA treatment followed by C$_{18}$-HPLC purification as described in Example 220, step c to afford 25 mg (24%) of the title compound as a glassy solid. $^1$H-NMR (CD$_3$OD; 400 MHz) δ 8.31 (s, 1H), 8.07 (ddd, 1H, J=7.9, 1.9, 1.1 Hz), 7.87–7.90 (m, 1H), 7.72 (t, 1H, J=7.8 Hz), 7.55–7.58 (m, 1H), 7.45 (d, 1H, J=8.1 Hz), 7.28, (t, 1H, J=7.8 Hz), 7.12 (d, 1H, J=7.3 Hz), 3.68 (t, 2H, J=6.3 Hz), 3.50–3.62 (m, 12H) 3.39 (t, 2H, J=5.2 Hz), 3.16 (t, 2H, J=5.3 Hz), 2.72 (s, 3H), 2.50 (t, 2H, J=6.3 Hz), 2.00 (s, 3H). ESI-MS (m/z): Calcd. for C$_{31}$H$_{40}$N$_4$O$_9$S$_3$: 709.2 (M+H); found: 709.2.

Example 242

4-[2'-Methyl-6'-(3-phenethyl-ureido)-biphenyl-3-sulfonyl]-5-methylsulfanyl-thiophene-2-carboxamidine trifluoroacetate

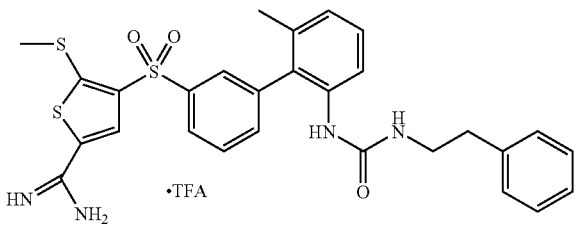

To a solution of {[4-(6'-amino-2'-methyl-biphenyl-3-sulfonyl)-5-methylsulfanyl-thiophen-2-yl]-imino-methyl}-carbamic acid tert-butyl ester (30 mg, 0.058 mmol, as prepared in Example 25, step c) and DIEA (100 µL, 0.57 mmol) in DCM (1.5 mL) was added (2-Isocyanato-ethyl)-benzene (100 µL, 0.68 mmol) and the mixture was stirred for 4 h at rt. The reaction mixture was diluted with EtOAc and then washed with water and saturated NaHCO$_3$. The organic layer was dried over MgSO$_4$, filtered, and concentrated in vacuo. The resulting residue was subjected to TFA treatment followed by C$_{18}$-HPLC purification as described in Example 220, step c to afford 20 mg (62%) of the title compound as a white solid. $^1$H-NMR (CD$_3$OD; 400 MHz) δ 8.30 (s, 1H), 8.08 (ddd, 1H, J=7.9, 1.9, 1.1 Hz), 7.90 (t, 1H, J=1.6 Hz), 7.71 (t, 1H, J=7.8 Hz), 7.51–7.55 (m, 1H), 7.36–7.39 (m, 1H), 7.22–7.30 (m, 3H), 7.12–7.19 (m, 2H), 7.02–7.06 (m, 2H), 3.14–3.24 (m, 2H), 2.64 (s, 3H), 2.52–2.62 (m, 2H), 2.00 (s, 3H). ESI-MS (m/z): Calcd. for C$_{28}$H$_{28}$N$_4$O$_3$S$_3$: 565.1 (M+H); found: 565.1.

Example 243

{3-[3'-(5-Carbamimidoyl-2-methylsulfanyl-thiophene-3-sulfonyl)-6-methyl-biphenyl-2-yl]-ureido}-acetic acid ethyl ester trifluoroacetate

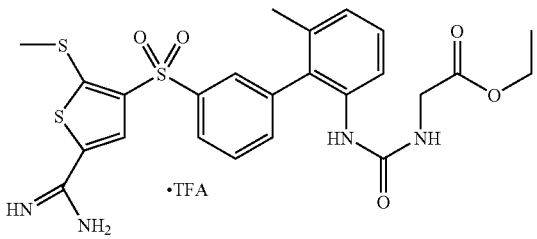

To a solution of {[4-(6'-amino-2'-methyl-biphenyl-3-sulfonyl)-5-methylsulfanyl-thiophen-2-yl]-imino-methyl}-carbamic acid tert-butyl ester (15 mg, 0.029 mmol, as prepared in Example 25, step c) and Et$_3$N (20 µL, 0.15 mmol) in DCM (1.0 mL) was added isocyanato-acetic acid ethyl ester (10 µL, 0.087 mmol) and the mixture was stirred for 4 h at rt. The reaction mixture was diluted with EtOAc and then washed with water and saturated NaHCO$_3$. The organic layer was dried over MgSO$_4$, filtered, and concentrated in vacuo. The resulting crude product was split in two equal portions. One portion was subjected to TFA treatment followed by C$_{18}$-HPLC purification as described in Example 220, step c to afford the title compound as a white solid. $^1$H-NMR (CD$_3$OD; 400 MHz): δ 8.31 (s, 1H), 8.07 (ddd, 1H, J=7.9, 1.9, 1.2 Hz), 7.90 (t, 1H, J=1.6 Hz), 7.72 (t, 1H, J=7.8 Hz), 7.56–7.60 (m, 1H), 7.46–7.50 (m, 1H), 7.30 (t, 1H, J=7.8 Hz), 7.12–7.16 (m, 1H), 4.16 (q, 2H, J=7.2 Hz), 3.76 (d, 2H, J=4.2 Hz), 2.72 (s, 3H), 2.01 (s, 3H), 1.26 (t, 3H, J=7.2 Hz). ESI-MS (m/z): Calcd. for C$_{24}$H$_{26}$N$_4$O$_5$S$_3$: 547.1 (M+H); found: 547.1.

Example 244

{3-[3'-(5-Carbamimidoyl-2-methylsulfanyl-thiophene-3-sulfonyl)-6-methyl-biphenyl-2-yl]-ureido}-acetic acid trifluoroacetate

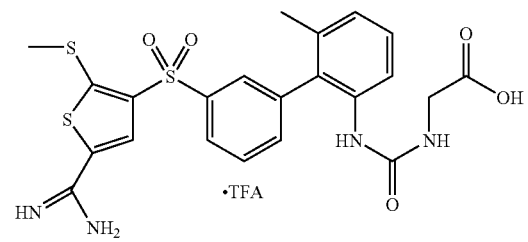

The other portion of the crude ethyl ester obtained in Example 244 was saponified by treatment with a mixture of MeOH/1 N NaOH (1:1, 2 mL) at rt for 4 h. The crude reaction mixture was acidified with acetic acid, concentrated in vacuo, and the residue was subjected to TFA treatment followed by C$_{18}$-HPLC purification as described in Example 220, step c to afford the title compound as a white solid. $^1$H-NMR (CD$_3$OD; 400 MHz): δ 8.31 (s, 1H), 8.07 (ddd, 1H, J=7.9, 1.9, 1.2 Hz), 7.88 (t, 1H, J=1.8 Hz), 7.72 (t, 1H, J=7.8 Hz), 7.56–7.60 (m, 1H), 7.47–7.51 (m, 1H), 7.30 (t, 1H, J=7.9 Hz), 7.12–7.15 (m, 1H), 3.68–3.80 (m, 2H), 2.72 (s, 3H), 2.01 (s, 3H). ESI-MS (m/z): Calcd. for C$_{22}$H$_{22}$N$_4$O$_5$S$_3$: 519.1 (M+H); found: 519.1.

Example 245

{[3'-(5-Carbamimidoyl-2-methylsulfanyl-thiophene-3-sulfonyl)-6-methyl-biphenyl-2-ylcarbamoyl]-methoxy}-acetic acid trifluoroacetate

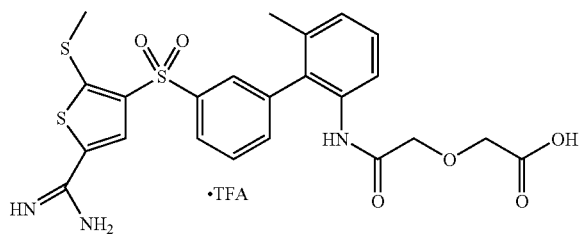

Following the same procedure as in Example 227, reaction of {[4-(6'-amino-2'-methyl-biphenyl-3-sulfonyl)-5-methylsulfanyl-thiophen-2-yl]-imino-methyl}-carbamic acid tert-butyl ester (28 mg, 0.054 mmol, as prepared in Example 25, step c), Et$_3$N (45 μL, 0.32 mmol), and diglycolic anhydride (20 mg, 0.16 mmol) in DCM (2 mL) followed by analogous work up and purification provided the title compound (50% yield over two steps). $^1$H-NMR (CD$_3$OD; 400 MHz): δ 8.28 (s, 1H), 8.08 (ddd, 1H, J=7.9, 1.9, 1.2 Hz), 7.85 (t, 1H, J=1.5 Hz), 7.72 (t, 1H, J=7.8 Hz), 7.56–7.60 (m, 1H), 7.53 (d, 1H, J=8.1 Hz), 7.36 (t, 1H, J=7.8 Hz), 7.26 (d, 1H, J=7.7 Hz), 3.70–3.91 (m, 4H), 2.72 (s, 3H), 2.08 (s, 3H). ESI-MS (m/z): Calcd. for C$_{23}$H$_{23}$N$_3$O$_6$S$_3$: 534.1 (M+H); found: 534.1.

Example 246

2-{[3'-(5-Carbamimidoyl-2-methylsulfanyl-thiophene-3-sulfonyl)-6-methyl-biphenyl-2-ylcarbamoyl]-methylsulfanyl}-acetamide trifluoroacetate

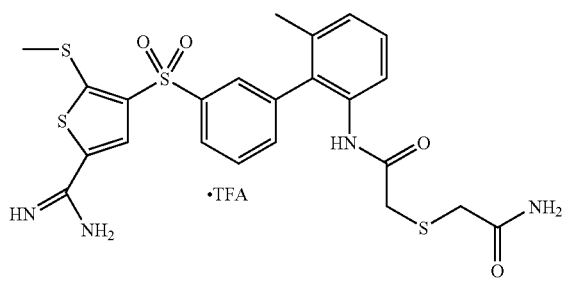

a) ({4-[6'-(2-Bromo-acetylamino)-2'-methyl-biphenyl-3-sulfonyl]-5-methylsulfanyl-thiophen-2-yl}-imino-methyl)-carbamic acid tert-butyl ester Following the procedure described for Example 234, step a, reaction of {[4-(6'-amino-2'-methyl-biphenyl-3-sulfonyl)-5-methylsulfanyl-thiophen-2-yl]-imino-methyl}-carbamic acid tert-butyl ester (137 mg, 0.265 mmol, as prepared in Example 25, step c), bromoacetyl bromide (28 μL, 0.32 mmol), and DIEA (70 μL, 0.40 mmol) in chloroform (3 mL) afforded 129 mg (76%) of the title compound as a yellow foamy solid after chromatography (PTLC, 10% EtOAc in DCM, 2×1500μ SiO$_2$ plate). $^1$H-NMR (CDCl$_3$; 400 MHz): δ 8.05–8.10 (m, 1H), 7.85–7.95 (m, 2H), 7.65–7.73 (m, 2H), 7.46–7.51 (m, 1H), 7.35 (t, 1H, J=7.9 Hz), 7.16 (d, 1H, J=7.7 Hz), 3.64 and 3.74 (AB quartet, 2H, J=14.0 Hz), 2.60 (s, 3H), 2.03 (s, 3H), 1.52 (s, 9H). ESI-MS (m/z): Calcd. for C$_{26}$H$_{28}$BrN$_3$O$_5$S$_3$: 637.0 (M+H); found: 637.8, 639.8, 538.0, 540.0 (M–Boc).

b) 2-{[3'-(5-Carbamimidoyl-2-methylsulfanyl-thiophene-3-sulfonyl)-6-methyl-biphenyl-2-ylcarbamoyl]-methylsulfanyl}-acetamide trifluoroacetate To a solution of ({4-[6'-(2-bromo-acetylamino)-2'-methyl-biphenyl-3-sulfonyl]-5-methylsulfanyl-thiophen-2-yl}-imino-methyl)-carbamic acid tert-butyl ester (9 mg, 0.014 mmol, as prepared in Example 246, step a) in MeOH (0.1 mL) was added 2-mercapto acetamide (20 μL of 10% methanolic solution, Maybridge plc) and Et$_3$N (6 μL, 0.042 mmol). The reaction mixture was stirred at rt for 0.5 h and then concentrated in vacuo. The residue was treated with TFA as described in Example 220, step c and then purified using C$_{18}$-HPLC (10–60% CH$_3$CN in H$_2$O with 0.1% TFA) to afford 8.7 mg (94%) of the title compound as a clear glassy solid. $^1$H-NMR (CD$_3$OD; 400 MHz): δ 8.30 (s, 1H), 8.09 (ddd, 1H, J=7.9, 1.9, 1.2 Hz), 7.88 (t, 1H, J=1.6 Hz), 7.72 (t, 1H, J=7.9 Hz), 7.57–7.60 (m, 1H), 7.35–7.40 (m, 2H), 7.27–7.31 (m, 1H), 3.05 and 3.11 (AB quartet, 2H, J=14.9 Hz), 2.78 and 2.85 (AB quartet, 2H, J=14.9 Hz), 2.74 (s, 3H), 2.08 (s, 3H). ESI-MS (m/z): Calcd. for C$_{23}$H$_{24}$N$_4$O$_4$S$_4$: 549.1 (M+H); found: 549.1.

Example 247

3-{[3'-(5-Carbamimidoyl-2-methylsulfanyl-thiophene-3-sulfonyl)-6-methyl-biphenyl-2-ylcarbamoyl]-methylsulfanyl}-propionic acid trifluoroacetate

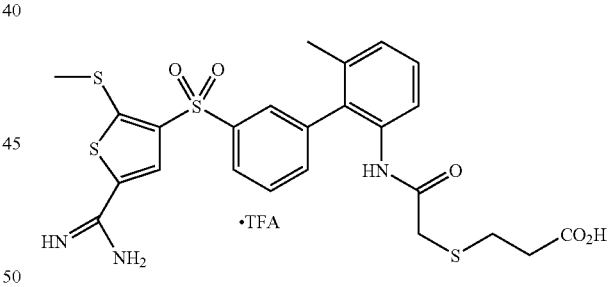

Following the same procedure as described in Example 246, step b, reaction of ({4-[6'-(2-bromo-acetylamino)-2'-methyl-biphenyl-3-sulfonyl]-5-methylsulfanyl-thiophen-2-yl}-imino-methyl)-carbamic acid tert-butyl ester (15.2 mg, 0.029 mmol, as prepared in Example 246, step a), 3-mercaptopropionate (8 μL, 0.09 mmol), Et$_3$N (20 μL, 0.12 mmol), in MeOH (1 mL) for 1 h afforded 9 mg (56%) of the title compound as a white solid after TFA treatment and RP-HPLC purification. $^1$H-NMR (CD$_3$OD; 400 MHz): δ 8.28 (s, 1H), 8.06–8.09 (m, 1H), 7.88 (t, 1H, J=1.9 Hz), 7.70 (t, 1H, J=7.8 Hz), 7.53–7.57 (m, 1H), 7.33–7.38 (m, 2H), 7.25–7.29 (m, 1H), 2.95 and 3.04 (AB quartet, 2H, J=15.4 Hz), 2.73 (s, 3H), 2.31–2.36 (m, 2H), 2.16–2.20 (m, 2H), 2.04 (s, 3H). ESI-MS (m/z): Calcd. for C$_{24}$H$_{25}$N$_3$O$_5$S$_4$: 564.1 (M+H); found: 564.1.

Example 248

2-{[3'-(5-Carbamimidoyl-2-methylsulfanyl-thiophene-3-sulfonyl)-6-methyl-biphenyl-2-ylcarbamoyl]-methylsulfanyl}-succinic acid trifluoroacetate

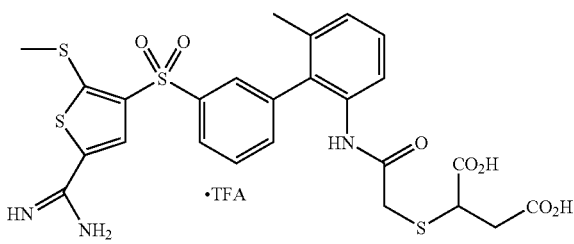

Following the same procedure as described in Example 246, step b, reaction of ({4-[6'-(2-bromo-acetylamino)-2'-methyl-biphenyl-3-sulfonyl]-5-methylsulfanyl-thiophen-2-yl}-imino-methyl)-carbamic acid tert-butyl ester (15.3 mg, 0.03 mmol, as prepared in Example 246, step a), mercaptosuccinate (14 mg, 0.09 mmol), $Et_3N$ (20 µL, 0.12 mmol), and MeOH (1 mL) for 2 h provided 12 mg (67%) of the title compound as a white solid after TFA treatment and RP-HPLC purification. $^1$H-NMR ($CD_3OD$; 400 MHz, (+) and (−) enantiomers appear as two distinct diastereomers on NMR presumably due to conformational restriction around o-methyl-biphenyl ring system): δ 8.27 (s, 1H), 8.04–8.09 (m, 1H), 7.84–7.88 (m, 1H), 7.66–7.73 (m, 1H), 7.53–7.57 (m, 1H), 7.32–7.44 (m, 2H), 7.27 (t, 1H, J=6.7 Hz), 3.38–3.42 (m, 0.5H), 3.09–3.29 (m, 2H), 2.62–2.79 (m, 2.5H), 2.75 (s, 3H), 2.44–2.50 (m, 0.5H), 2.22–2.28 (m, 0.5H), 2.06 (s, 3H). ESI-MS (m/z): Calcd. for $C_{25}H_{25}N_3O_7S_4$: 608.1 (M+H); found: 608.1.

Example 249

2-Bromo-N-[3'-(5-carbamimidoyl-2-methylsulfanyl-thiophene-3-sulfonyl)-6-methyl-biphenyl-2-yl]-acetamide trifluoroacetate

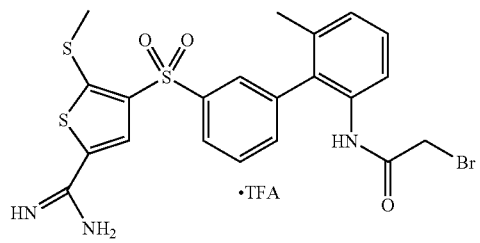

({4-[6'-(2-bromo-acetylamino)-2'-methyl-biphenyl-3-sulfonyl]-5-methylsulfanyl-thiophen-2-yl}-imino-methyl)-carbamic acid tert-butyl ester (22 mg, 0.034 mmol, as prepared in Example 246, step a) was stirred in a mixture of TFA/DCM (1:1, 4 mL) for 1 h at rt. The reaction was concentrated in vacuo and the resulting residue was purified using RP-HPLC (10–50% $CH_3CN$ in $H_2O$ with 0.1% TFA over 30 min) to afford 15 mg (68%) of the title compound as a clear glassy solid (purity>99.9% by analytical RP-HPLC). ESI-MS (m/z): Calcd. for $C_{21}H_{20}BrN_3O_3S_3$: 538.0 (M+H); found: 538.0 and 540.0

Example 250

2-Acetylamino-3-{[3'-(5-carbamimidoyl-2-methylsulfanyl-thiophene-3-sulfonyl)-6-methyl-biphenyl-2-ylcarbamoyl]-methylsulfanyl}-3-methyl-butyric acid trifluoroacetate

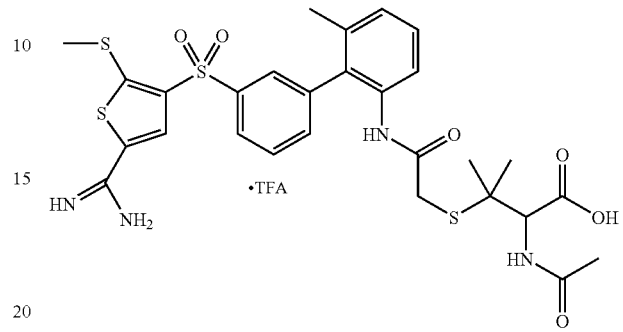

N-Acetyl-penicillamine (3.0 mg, 0.0154 mmol, racemic) and DIEA (7 µL, 0.04 mmol) were dissolved in DMSO (223 µL) and then transferred to a solution of 2-bromo-N-[3'-(5-carbamimidoyl-2-methylsulfanyl-thiophene-3-sulfonyl)-6-methyl-biphenyl-2-yl]-acetamide trifluoroacetate (20 mM in DMSO, 230 µL, 0.0046 mmol, prepared from the title compound described in Example 249). The reaction was mixed on a shaker for 1 h at rt. Bromomethyl wang resin (16 mg, 1.47 mmol/gm) was added to scavenge the excess thiol. After 2 h of shaking, the resin was filtered and the filtrate was directly purified using RP-HPLC as previously described in Example 246, step b, to afford 1.5 mg (50%, single peak on analytical RP-HPLC) of the title compound as a glassy solid. ESI-MS (m/z): Calcd. for $C_{28}H_{32}N_4O_6S_4$: 649.1 (M+H); found: 649.1.

Example 251

2-Acetylamino-3-{[3'-(5-carbamimidoyl-2-methylsulfanyl-thiophene-3-sulfonyl)-6-methyl-biphenyl-2-ylcarbamoyl]-methylsulfanyl}-propionic acid trifluoroacetate

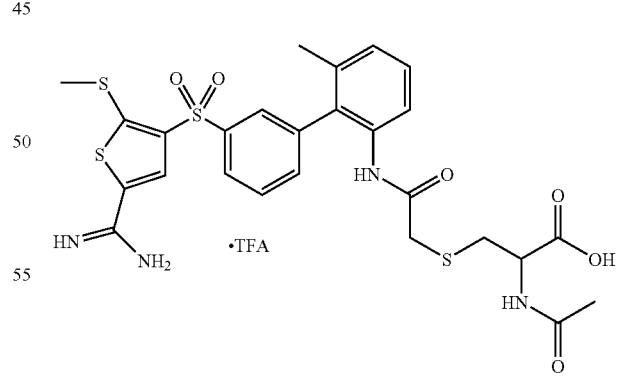

Following the same procedure as described in Example 246, step b, reaction of ({4-[6'-(2-bromo-acetylamino)-2'-methyl-biphenyl-3-sulfonyl]-5-methylsulfanyl-thiophen-2-yl}-imino-methyl)-carbamic acid tert-butyl ester (10 mg, 0.016 mmol, as prepared in Example 246, step a), (L)-N-acetylcysteine (22 mg, 0.135 mmol), $Et_3N$ (50 µL, 0.12 mmol), and DCM (0.5 mL) for 2 h provided 7 mg (71%) of the title compound as a white solid after TFA treatment and RP-HPLC purification. ¹H-NMR (CD₃OD; 400 MHz): δ 8.30 (s, 1H), 8.06–8.09 (m, 1H), 7.87 (t, 1H, J=1.6 Hz), 7.68–7.73 (m, 1H), 7.54–7.59 (m, 1H), 7.34–7.39 (m, 2H), 7.26–7.30 (m, 1H), 4.41–4.48 (m, 1H), 2.94–3.10 (m, 2H), 2.74 (s, 3H), 2.59–2.64 (m, 1H), 2.43–2.49 (m, 1H), 2.06 (s, 3H). 2.00 (d, 3H, 2.1 J=2.1 Hz). ESI-MS (m/z): Calcd. for C₂₆H₂₈N₄O₆S₄: 621.1 (M+H); found: 621.1.

Example 252

3-{[3'-(5-Carbamimidoyl-2-methylsulfanyl-thiophene-3-sulfonyl)-4-methoxy-6-methyl-biphenyl-2-ylcarbamoyl]-methylsulfanyl}-propionic acid trifluoroacetate

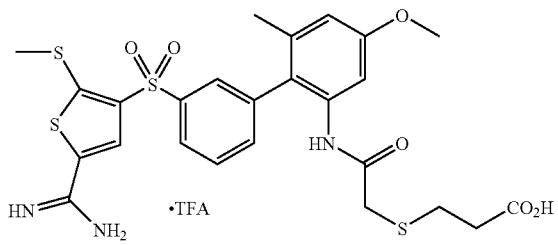

a) ({4-[6'-(2-Bromo-acetylamino)-4'-methoxy-2'-methyl-biphenyl-3-sulfonyl]-5-methylsulfanyl-thiophen-2-yl}-imino-methyl)-carbamic acid tert-butyl ester Following the procedure described for Example 234, step a, reaction of {[4-(6'-amino-4'-methoxy-2'-methyl-biphenyl-3-sulfonyl)-5-methylsulfanyl-thiophen-2-yl]-imino-methyl}-carbamic acid tert-butyl ester (204 mg, 0.37 mmol, as prepared in Example 198, step e), bromoacetyl bromide (39 µL, 0.45 mmol), and Et₃N (77 µL, 0.56 mmol) in DCM (5 mL) afforded 170 mg (69%) of the title compound as a yellow foamy solid after chromatography (PTLC, 50% EtOAc in hexanes, 4×1000µ SiO₂ plate). ¹H-NMR (CDCl₃; 400 MHz): δ 8.02–8.05 (m, 1H), 7.91 (s, 1H), 7.87 (t, 1H, J=1.6 Hz), 7.73 (br s, 1H), 7.63–7.67 (m, 2H), 7.45–7.49 (m, 1H), 6.69 (d, 1H, J=2.1 Hz), 3.85 (s, 3H), 3.69 and 3.74 (AB quartet, 2H, J=14.1 Hz), 2.59 (s, 3H), 2.00 (s, 3H), 1.52 (s, 9H). ESI-MS (m/z): Calcd. for C₂₇H₃₀BrN₃O₆S₃: 668.0 (M+H); found: 669.6, 667.6, 570.0, 568.0 (M–Boc).

b) 3-{[3'-(5-Carbamimidoyl-2-methylsulfanyl-thiophene-3-sulfonyl)-4-methoxy-6-methyl-biphenyl-2-ylcarbamoyl]-methylsulfanyl}-propionic acid trifluoroacetate Following the same procedure as described in Example 246, step b, reaction of ({4-[6'-(2-bromo-acetylamino)-4'-methoxy-2'-methyl-biphenyl-3-sulfonyl]-5-methylsulfanyl-thiophen-2-yl}-imino-methyl)-carbamic acid tert-butyl ester (12 mg, 0.018 mmol, as prepared in Example 252, step a), 3-mercaptopropionate (8 µL, 0.09 mmol), Et₃N (20 µL, 0.12 mmol), in MeOH (1 mL) for 1 h afforded 9.3 mg (62%) of the title compound as a white solid after TFA treatment and RP-HPLC purification. ¹H-NMR (CD₃OD; 400 MHz): δ 8.29 (s, 1H), 8.07 (ddd, 1H, J=7.9, 1.9, 1.2 Hz), 7.87 (t, 1H, J=1.6 Hz), 7.70 (t, 1H, J=7.8 Hz), 7.53–7.57 (m, 1H), 7.05 (d, 1H, J=2.5 Hz), 6.84 (d, 1H, J=2.5 Hz), 3.83 (s, 3H), 2.98 and 3.06 (AB quartet, 2H, J=15.4 Hz), 2.73 (s, 3H), 2.32–2.36 (m, 2H), 2.19–2.23 (m, 2H), 2.02 (s, 3H). ESI-MS (m/z): Calcd. for C₂₅H₂₇N₃O₆S₄: 594.1 (M+H); found: 594.0.

Example 253

3-{[3'-(5-Carbamimidoyl-2-methylsulfanyl-thiophene-3-sulfonyl)-4-methoxy-6-methyl-biphenyl-2-ylcarbamoyl]-methylsulfanyl}-propionic acid methyl ester trifluoroacetate

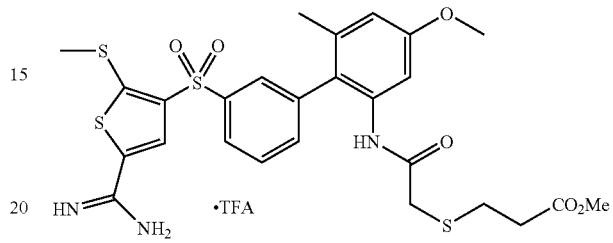

Following the same procedure as described in Example 246, step b, reaction of ({4-[6'-(2-bromo-acetylamino)-4'-methoxy-2'-methyl-biphenyl-3-sulfonyl]-5-methylsulfanyl-thiophen-2-yl}-imino-methyl)-carbamic acid tert-butyl ester (22 mg, 0.04 mmol, as prepared in Example 252, step a), methyl 3-mercaptopropionate (10 µL, 0.09 mmol), Et₃N (20 µL, 0.12 mmol), in MeOH (1 mL) for 1 h afforded the title compound as a white solid after TFA treatment and RP-HPLC purification. ¹H-NMR (CD₃OD; 400 MHz): δ 8.31 (s, 1H), 8.07 (ddd, 1H, J=7.9, 1.9, 1.2 Hz), 7.87 (t, 1H, J=1.6 Hz), 7.70 (t, 1H, J=7.8 Hz), 7.53–7.57 (m, 1H), 7.06 (d, 1H, J=2.4 Hz), 6.85 (d, 1H, J=2.4 Hz), 3.84 (s, 3H), 3.68 (s, 3H), 3.00 and 3.07 (AB quartet, 2H, J=15.4 Hz), 2.74 (s, 3H), 2.39–2.42 (m, 2H), 2.23–2.27 (m, 2H), 2.03 (s, 3H). ESI-MS (m/z): Calcd. for C₂₆H₂₉N₃O₆S₄: 608.1 (M+H); found: 608.1.

Example 254

N-[3'-(5-Carbamimidoyl-2-methylsulfanyl-thiophene-3-sulfonyl)-4-methoxy-6-methyl-biphenyl-2-yl]-2-methanesulfonyl-acetamide trifluoroacetate

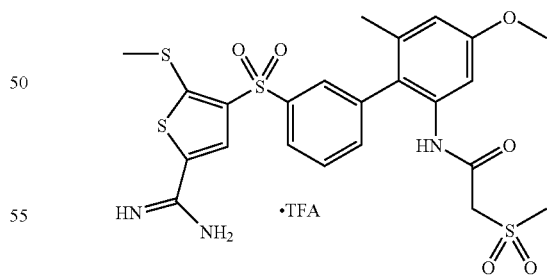

Following the same procedure as described in Example 257, reaction of ({4-[6'-(2-bromo-acetylamino)-4'-methoxy-2'-methyl-biphenyl-3-sulfonyl]-5-methylsulfanyl-thiophen-2-yl}-imino-methyl)-carbamic acid tert-butyl ester (37 mg, 0.065 mmol, as prepared in Example 252, step a) and sodium methanesulfinate (25 mg, 0.195 mmol, Aldrich Chemical Company) in EtOH/CH₃CN (1:1, 2 mL) provided 29 mg (66%) of the title compound as a white solid after TFA treatment and RP-HPLC purification. ¹H-NMR (CD₃OD; 400 MHz): δ 8.30 (s, 1H), 8.03 (ddd, 1H, J=7.9, 1.9, 1.2 Hz), 7.84 (t, 1H, J=1.6 Hz), 7.66 (t, 1H, J=7.8 Hz), 7.51–7.54 (m, 1H), 6.99 (d, 1H, J=2.6 Hz), 6.84 (d, 1H, J=2.6 Hz), 3.89 and 3.93 (AB quartet, 2H, J=14.1 Hz), 3.82 (s, 3H), 2.86 (s, 3H), 2.72 (s, 3H), 2.01 (s, 3H). ESI-MS (m/z): Calcd. for $C_{23}H_{25}N_3O_6S_4$: 568.1 (M+H); found: 568.0.

Example 255

6-Methanesulfonyl-hexanoic acid[3'-(5-carbamimidoyl-2-methylsulfanyl-thiophene-3-sulfonyl)-4-methoxy-6-methyl-biphenyl-2-yl]-amide trifluoroacetate

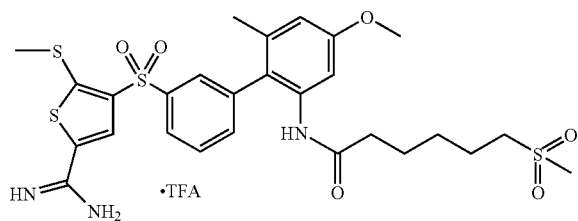

Following the procedure described for Example 234, step a, reaction of {[4-(6'-amino-4'-methoxy-2'-methyl-biphenyl-3-sulfonyl)-5-methylsulfanyl-thiophen-2-yl]-imino-methyl}-carbamic acid tert-butyl ester (60 mg, 0.11 mmol, as prepared in Example 198, step e), 6-bromo-hexanoyl chloride (26 μL, 0.17 mmol), and Et₃N (79 μL, 0.55 mmol) in DCM (1 mL) afforded the title compound as a crude oil after aqueous work up. ESI-MS (m/z): Calcd. for $C_{31}H_{38}BrN_3O_6S_3$: 724.1 (M+H); found: 626.1, 624.1 (M–Boc). The crude bromide intermediate obtained above was suspended in a EtOH-water mixture (1:1, 3 mL) and to the mixture was added sodium methanesulfinate (45 mg, 0.33 mmol, Aldrich Chemical Company). The reaction mixture was heated at 50° C. for 48 h and then concentrated in vacuo. The residue was treated with TFA as described in Example 220, step c and then purified using $C_{18}$-HPLC (10–60% CH₃CN in H₂O with 0.1% TFA) to afford 12 mg (18% from the aniline) of the title compound as a clear glassy solid. ¹H-NMR (CD₃OD; 400 MHz): δ 8.30 (s, 1H), 8.02 (ddd, 1H, J=7.9, 1.9, 1.1 Hz), 7.86 (t, 1H, J=1.6 Hz), 7.67 (t, 1H, J=7.9 Hz), 7.52 (dt, 1H, J=7.7, 1.2 Hz), 6.85 (d, 1H, J=2.5 Hz), 6.77 (d, 1H, J=2.5 Hz), 3.82 (s, 3H), 2.98–3.04 (m, 2H), 2.96 (s, 3H), 2.72 (s, 3H), 1.99–2.04 (m, 2H), 2.03 (s, 3H), 1.57–1.66 (m, 2H), 1.05–1.25 (m, 4H). ESI-MS (m/z): Calcd. for $C_{27}H_{33}N_3O_6S_4$: 624.1 (M+H); found: 624.1

Example 256

N-[3'-(5-Carbamimidoyl-2-methylsulfanyl-thiophene-3-sulfonyl)-4-methoxy-6-methyl-biphenyl-2-yl]-3-methanesulfonyl-propionamide trifluoroacetate

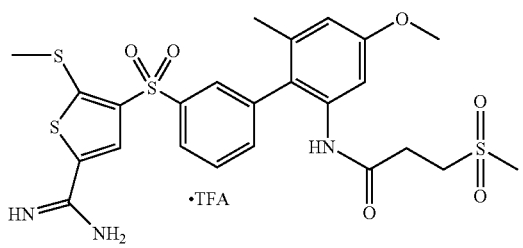

Following the procedure described for Example 234, step a, reaction of {[4-(6'-amino-4'-methoxy-2'-methyl-biphenyl-3-sulfonyl)-5-methylsulfanyl-thiophen-2-yl]-imino-methyl}-carbamic acid tert-butyl ester (60 mg, 0.11 mmol, as prepared in Example 198, step e), acryloyl chloride (22 μL, 0.22 mmol), and Et₃N (80 μL, 0.55 mmol) in THF (1 mL) afforded the title compound as a crude oil after aqueous work up. ESI-MS (m/z): Calcd. for $C_{28}H_{31}N_3O_6S_3$: 602.1 (M+H); found: 601.9, 502.1 (M–Boc). The crude acrylamide intermediate obtained above was suspended in a EtOH-water mixture (1:1, 3 mL) and to the mixture was added sodium methanesulfinate (45 mg, 0.33 mmol, Aldrich Chemical Company). The reaction mixture was heated at 50° C. for 48 h and then concentrated in vacuo. The residue was treated with TFA as described in Example 220, step c and then purified using $C_{18}$-HPLC (10–60% CH₃CN in H₂O with 0.1% TFA) to give 15 mg (23% from the aniline) of the title compound as a white solid. ¹H-NMR (CD₃OD; 400 MHz): δ 8.30 (s, 1H), 8.03 (ddd, 1H, J=7.9, 1.9, 1.1 Hz), 7.83 (t, 1H, J=1.6 Hz), 7.67 (t, 1H, J=7.8 Hz), 7.54 (dt, 1H, J=7.7, 1.3 Hz), 6.84–6.87 (m, 2H), 3.82 (s, 3H), 3.07 (t, 2H, J=7.8 Hz), 2.86 (s, 3H), 2.73 (s, 3H), 2.44–2.51 (m, 2H), 2.06 (s, 3H). ESI-MS (m/z): Calcd. for $C_{24}H_{27}N_3O_6S_4$: 582.1 (M+H); found: 582.1.

Example 257

N-[3'-(5-Carbamimidoyl-2-methylsulfanyl-thiophene-3-sulfonyl)-6-methyl-biphenyl-2-yl]-2-methanesulfonyl-acetamide trifluoroacetate

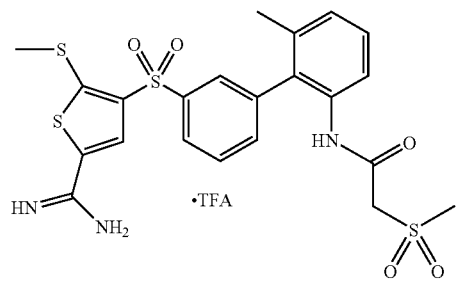

To a solution of ({4-[6'-(2-bromo-acetylamino)-2'-methyl-biphenyl-3-sulfonyl]-5-methylsulfanyl-thiophen-2-yl}-imino-methyl)-carbamic acid tert-butyl ester (8 mg, 0.0125 mmol, as prepared in Example 246, step a) in EtOH (1.0 mL) was added sodium methanesulfinate (13 mg, 0.127 mmol, Aldrich Chemical Company) and the reaction was stirred overnight and monitored by MS and TLC. After 16 h at rt, the starting material had disappeared and the reaction was concentrated in vacuo to give an oil. Treatment of this intermediate with trifluoroacetic acid for 2 h followed by RP-HPLC purification afforded 5.2 mg (78%) of the title compound as a white solid. ¹H-NMR (CD₃OD; 400 MHz): δ 8.31 (s, 1H), 8.05 (ddd, 1H, J=7.9, 1.9, 1.2 Hz), 7.87 (t, 1H, J=1.6 Hz), 7.68 (t, 1H, J=8.0 Hz), 7.53–7.56 (m, 1H), 7.33–7.37 (m, 2H), 7.26–7.30 (m, 1H), 3.85–3.94 (m, 2H) 2.84 (s, 3H), 2.72 (s, 3H), 2.04 (s, 3H). ESI-MS (m/z): Calcd. for $C_{22}H_{23}N_3O_5S_4$: 538.0 (M+H); found: 538.0.

Example 258

N-[3'-(5-Carbamimidoyl-2-methylsulfanyl-thiophene-3-sulfonyl)-6-methyl-biphenyl-2-yl]-2-methanesulfonyl-propionamide trifluoroacetate

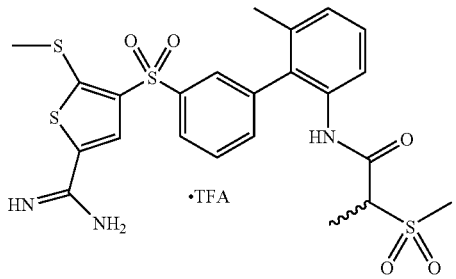

a) ({4-[6'-(2-Bromo-propionylamino)-2'-methyl-biphenyl-3-sulfonyl]-5-methylsulfanyl-thiophen-2-yl}-imino-methyl)-carbamic acid tert-butyl ester Following the procedure described for Example 234, step a, reaction of {[4-(6'-amino-2'-methyl-biphenyl-3-sulfonyl)-5-methylsulfanyl-thiophen-2-yl]-imino-methyl}-carbamic acid tert-butyl ester (65 mg, 0.126 mmol, as prepared in Example 25, step c), racemic 2-bromo-propionyl bromide (19 μL, 0.189 mmol), and Et₃N (52 μL, 0.378 mmol) in DCM (2 mL) afforded 55 mg (67%) of the title compound as a glassy solid after chromatography (PTLC, 10% EtOAc in DCM, 2×1500μ SiO₂ plate). ESI-MS (m/z): Calcd. for $C_{27}H_{30}BrN_3O_5S_3$: 652.0 (M+H); found: 653.6, 651.7, 553.9, 552.0 (M−Boc).

b) N-[3'-(5-Carbamimidoyl-2-methylsulfanyl-thiophene-3-sulfonyl)-6-methyl-biphenyl-2-yl]-2-methanesulfonyl-propionamide trifluoroacetate lp;1pFollowing the procedure described for Example 257, reaction of ({4-[6'-(2-bromo-propionylamino)-2'-methyl-biphenyl-3-sulfonyl]-5-methylsulfanyl-thiophen-2-yl}-imino-methyl)-carbamic acid tert-butyl ester (30 mg, 0.046 mmol, as prepared in Example 258, step a) and sodium methanesulfinate (48 mg, 0.46 mmol, Aldrich Chemical Company) in EtOH (1 mL) provided 18 mg (72%) of the title compound as a white solid after TFA treatment and RP-HPLC purification. ¹H-NMR (CD₃OD; 400 MHz, (+) and (−) enantiomers appear as two distinct diastereomers on NMR presumably due to conformational restriction around o-methyl-biphenyl ring system): δ 8.32, 8.31 (2×s, 1H), 8.05–8.08 (m, 1H), 7.87–7.88 (m, 1H), 7.69 (t, 1H, J=7.8 Hz), 7.52–7.55 (m, 1H), 7.27–7.39 (m, 3H), 3.67–3.74 (m, 1H), 2.78, 2.724, 2.718, 2.16 (4×s, 6H), 2.06, 2.03 (2×s, 3H), 1.30, 1.28, 1.17, 1.15 (4×s, 3H). ESI-MS (m/z): Calcd. for $C_{23}H_{25}N_3O_5S_4$: 552.1 (M+H); found: 652.0.

Example 259

6-{3-[3'-(5-Carbamimidoyl-2-methylsulfanyl-thiophene-3-sulfonyl)-4-guanidino-biphenyl-2-yl]-ureido}-hexanoic acid

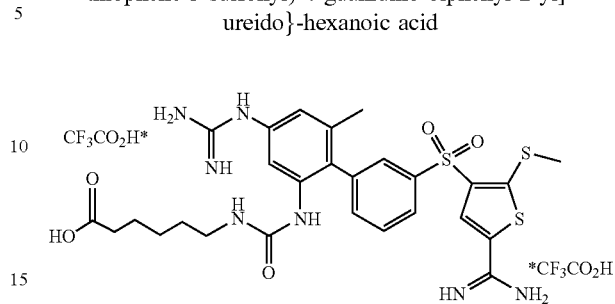

a) 6-{3-[3'-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ethyl ester A solution of {2-amino-3'-[5-(imino-methoxycarbonylamino-methyl)-2-methylsulfanyl-thiophene-3-sulfonyl]-6-methyl-biphenyl-4-yl}-carbamic acid 2-trimethylsilanyl-ethyl ester ((Example 294: step f) 0.020 g, 0.030 mmol) in dry CH₂Cl₂ (3 mL) was treated with 6-isocyanato-hexanoic acid ethyl ester (5.30 μL, 0.030 mmol) and stirred at room temperature 40 min. The reaction mixture was diluted with CH₂Cl₂ and washed with water (1×15 mL). The organic layer was dried over MgSO₄ and concentrated in vacuo to afford the product 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ethyl ester (0.025 g, 98%) as an off-white solid. ¹H NMR (CD₃OD): δ 8.217 (s, 1H), 8.062 (d, 1H, J=8.0 Hz), 7.920 (t, 1H, J=1.6 Hz), 7.718 (t, 1H, J=8.0 Hz), 7.647 (d, 1H, J=1.6 Hz), 7.556 (d, 1H, J=7.6 Hz), 7.282 (s, 1H), 4.292 (dd, 2H, J=8.4 Hz, J=1.6 Hz), 3.063–3.002 (m, 2H), 2.699 (s, 3H), 2.327 (t, 2H, J=7.2 Hz), 2.011 (s, 3H), 1.604 (quint, 2H, J=7.2 Hz), 1.538 (s, 9H), 1.403–1.362 (m, 2H), 1.124 (dd, 2H, J=7.2 Hz, J=1.6 Hz), 1.281 (t, 3H, J=7.2 Hz). ESI-MS (m/z): Calcd. for $C_{39}H_{55}N_5O_9S_3Si$ (M+H): 862.3; found 861.90.

b) 6-{3-[3'-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid A solution of 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ethyl ester ((Example 259: step a) 0.437 g, 0.507 mmol) in THF:water (2:1, 15 mL) was treated with solid LiOH (0.097 g, 4.06 mmol) and stirred at room temperature 18.5 h. The THF was removed in vacuo, and the remaining aqueous solution was acidified to pH 5 with glacial acetic acid. The solution was extracted with CH₂Cl₂ (3×50 mL). The combined organic layers were dried over MgSO₄ and concentrated in vacuo to afford the title compound (0.4222 g, 99%) as an off-white solid. ESI-MS (m/z): Calcd. for $C_{37}H_{51}N_5O_9S_3Si$ (M+H): 834.3; 834.2.

c) 6-(3-{4-Amino-3'-[5-(tert-butoxycarbonylamino-imino-methyl)-2-methylsulfanyl-thiophene-3-sulfonyl]-6-methyl-biphenyl-2-yl}-ureido)-hexanoic acid A solution of 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ((Example 259: step b) 0.422 g, 0.506 mmol) in dry THF (20 mL) was treated with tetrabutylammonium fluoride (1 M in hexanes, 3.39 mL, 3.39 mmol) and stirred at 40° C. 4 h. Solvents were evaporated in vacuo. The residue was taken up in $CH_2Cl_2$ and washed with water (4×50 mL). The organic layer was dried over $MgSO_4$ and concentrated in vacuo. Silica gel chromatography (4% MeOH in $CH_2Cl_2$) afforded the product 6-(3-{4-amino-3'-[5-(tert-butoxycarbonylamino-imino-methyl)-2-methylsulfanyl-thiophene-3-sulfonyl]-6-methyl-biphenyl-2-yl}-ureido)-hexanoic acid (0.200 g, 57%) as an off-white solid. The material was combined with 1,3-bis(tert-butoxycarbonyl)-2-methyl-2-thiopseudourea (0.252 g, 0.870 mmol) and acetic acid (0.5 mL) in MeOH (10 mL) and was stirred at 40° C. 2 h. The solvent was removed in vacuo. Silica gel chromatography (4% MeOH in $CH_2Cl_2$ then 10% MeOH in $CH_2Cl_2$) afforded the title compound (0.215 g, 80%) as a white solid. $^1$H-NMR ($CD_3OD$): δ 8.22 (s, 1H), 8.06 (m, 1H), 7.89 (m, 1H), 7.72 (m, 1H), 7.69 (m, 1H), 7.53 (m, 1H), 7.32 (m, 1H), 3.01 (m, 2H), 2.66 (s, 3H), 2.27 (t, 2H, 7.4 Hz), 1.97 (s, 3H), 1.57 (m, 2H), 1.54 (s, 18H), 1.51 (s, 9H), 1.37 (m 2H), 1.27 (m, 2H).

d) 6-{3-[3'-(5-Carbamimidoyl-2-methylsulfanyl-thiophene-3-sulfonyl)-4-guanidino-biphenyl-2-yl]-ureido}-hexanoic acid bis-trifluoroacetate The reaction conditions used in Example 1: step d were followed using 6-(3-{3'-[5-(tert-butoxycarbonylamino-imino-methyl)-2-methylsulfanyl-thiophene-3-sulfonyl]-4-(N',N''-bis-tert-butoxycarbonyl-guanidino)-6-methyl-biphenyl-2-yl}-ureido)-hexanoic acid ((Example 259: step c) 80 mg, 0.086 mmol). Analogous purification by HPLC yielded the title compound as a white solid (70 mg, 95%). $^1$H-NMR ($CD_3CN/D_2O$): δ 8.23 (s, 1H), 8.04 (m, 1H), 7.83 (m, 1H), 7.74 (m, 1H), 7.55 (m, 1H), 7.48 (m, 1H), 6.99 (m, 1H), 2.92 (m, 2H), 2.66 (s, 3H), 2.24 (t, 2H, 7.4 Hz), 1.95 (s, 3H), 1.48 (m, 2H), 1.27 (m, 2H), 1.25 (m, 2H). ESI-MS (m/z): Calcd. for $C_{27}H_{33}N_7O_5S_3$ (M+H): 632.2; found: 632.1.

Example 260

N-[3'-(5-Carbamimidoyl-2-methylsulfanyl-thiophene-3-sulfonyl)-4-guanidino-6-methyl-biphenyl-2-yl]-4-methanesulfonyl-butyramide bis-trifluoroacetate

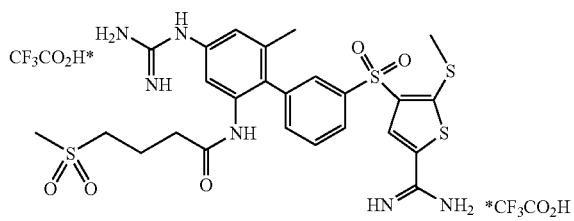

({4-[4'-Amino-6'-(4-methanesulfonyl-butyrylamino)-2'-methyl-biphenyl-3-sulfonyl]-5-methylsulfanyl-thiophen-2-yl}-imino-methyl)-carbamic acid tert-butyl ester The procedure in Example 261: step b was followed using 4-methanesulfonyl-butyryl chloride (Example 209: step a) (53 mg, 0.29)), {[4-(6'-amino-2'-methyl-4'-nitro-biphenyl-3-sulfonyl)-5-methylsulfanyl-thiophen-2-yl]-imino-methyl}-carbamic acid tert-butyl ester ((Example 295: step h) 130 mg, 0.23 mmol), and $Et_3N$ (192 µL, 1.38 mmol) in DCM (5 mL). After stirring for 1 h, starting material remained and an additional 20 mg of acid chloride was added. The solution was partitioned between EtOAc (70 mL) and aq $NH_4Cl$ (30 mL) and the layers were separated. The organic layer was washed with $NaHCO_3$ (20 mL) and brine (30 mL) and was dried over sodium sulfate. The solution was concentrated and the residue was purified by $SiO_2$ flash column chromatography to yield 126 mg of the amide product. The residue dissolved in EtOH (5 mL). Saturated aqueous $NH_4Cl$ (1.5 mL) was added followed by iron powder (110 mg, 2 mmol). The mixture was vigorously stirred at 80° C. for 30 min. The solution was filtered through a 0.22 µm filter and was then partitioned between EtOAc (70 mL) and water (20 mL). The layers were separated, the organic solution was dried over sodium sulfate, and the solution was concentrated to give the crude title compound which was used without further purification. $^1$HMR ($CDCl_3$): δ 7.99 (s, 1H), 7.96 (m, 2H), 7.77 (s, 1H), 7.57 (t, 1H, J=7.9 Hz), 7.43 (dt, 1H, J=1.3, 7.7 Hz), 7.10 (br s, 1H), 7.04 (br s, 1H), 6.43 (br s, 1H), 3.85 (br s, 2H), 2.92 (m, 2H), 2.88 (s, 3H), 2.56 (s, 3H), 2.20 (t, 2H, J=6.7 Hz), 1.98 (m, 2H), 1.90 (s, 3H), 1.50 (s, 9H).

b) N-[3'-(5-Carbamimidoyl-2-methylsulfanyl-thiophene-3-sulfonyl)-4-guanidino-6-methyl-biphenyl-2-yl]-4-methanesulfonyl-butyramide bis-trifluoroacetate Acetic acid (500 µL) was added to a solution of ({4-[4'-amino-6'-(4-methanesulfonyl-butyrylamino)-2'-methyl-biphenyl-3-sulfonyl]-5-methylsulfanyl-thiophen-2-yl}-imino-methyl)-carbamic acid tert-butyl ester ((Example 260: step a) 136 mg, 0.2 mmol) and 1,3-bis-(tert-butoxycarbonyl)-2-methyl-2-thiopseudourea (145 mg, 0.5 mmol) in MeOH (10 mL). The solution was stirred for 16 h at 40° C., then was partitioned between EtOAc (80 mL) and water (40 mL). The layers were separated and the organic layer was washed with aq $NaHCO_3$ (2×30 mL) and brine (30 mL) and was dried over sodium sulfate. After concentration, the residue was purified by preparative TLC. The residue was treated with 1:1 TFA/DCM as in Example 1: step d and analogously purified by HPLC to yield the title compound (47 mg, 23%) as a white solid. $^1$H-NMR ($CD_3OD$): δ 8.39 (s, 1H), 8.09 (ddd, 1H, J=0.9, 1.9, 8.1 Hz), 7.92 (t, 1H, J=1.6 Hz), 7.74 (t, 1H, J=7.7 Hz) 7.58 (m, 1H), 7.24 (m, 2H), 2.94 (s, 3H), 2.86 (t, 2H, J=7.7 Hz), 2.76 (s, 3H), 2.24 (m, 2), 2.12 (s, 3H), 1.80 (m, 2H). ESI-MS (m/z): Calcd. for $C_{25}H_{30}N_6O_5S_4$ (M+H): 623.1; found: 623.1.

Example 261

5-[3'-(5-Carbamimidoyl-2-methylsulfanyl-thiophene-3-sulfonyl)-4-guanidino-6-methyl-biphenyl-2-ylcarbamoyl]-pentanoic acid bis-trifluoroacetate

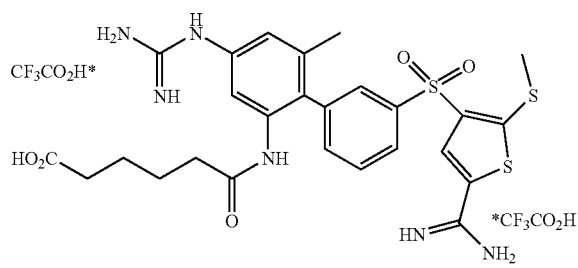

a) 5-{4-Amino-3'-[5-(tert-butoxycarbonylamino-imino-methyl)-2-methylsulfanyl-thiophene-3-sulfonyl]-6-methyl-biphenyl-2-ylcarbamoyl}-pentanoic acid methyl ester To a solution of {[4-(6'-amino-2'-methyl-4'-nitro-biphenyl-3-sulfonyl)-5-methylsulfanyl-thiophen-2-yl]-imino-methyl}-carbamic acid tert-butyl ester ((Example 295: step h) 130 mg, 0.23 mmol), and Et$_3$N (192 µL, 1.38 mmol) in DCM (5 mL) at 0° C. was added 5-chlorocarbonyl-pentanoic acid methyl ester (53 mg, 0.29). After stirring for 1 h, the solution was partitioned between EtOAc (70 mL) and aq NH$_4$Cl (30 mL) and the layers were separated. The organic layer was washed with NaHCO$_3$ (20 mL) and brine (30 mL) and was dried over sodium sulfate. The solution was concentrated and the residue was purified by SiO$_2$ flash column chromatography to yield 36 mg of the amide product. The residue dissolved in EtOH (5 mL). Saturated aqueous NH$_4$Cl (1.5 mL) was added followed by iron powder (110 mg, 2 mmol). The mixture was vigorously stirred at 80° C. for 30 min. The solution was filtered through a 0.22 µm filter and was then partitioned between EtOAc (70 mL) and water (20 mL). The layers were separated, the organic solution was dried over sodium sulfate, and the solution was concentrated to give the crude title compound which was used without further purification. $^1$H-NMR (CDCl$_3$): δ 8.0 (m, 2H), 7.84 (s, 1H), 7.96 (m, 2H), 7.59 (t, 1H, J=7.7 Hz), 7.43 (m, 1H), 7.23 (br s, 1H), 6.86 (br s, 1H), 6.45 (br s, 1H), 3.85 (br s, 2H), 3.65 (s, 3H), 2.60 (m, 3H), 2.35 (m, 2H), 2.00 (m, 2H), 1.90 (s, 3H), 1.67 (m, 2H), 1.90 (s, 3H), 1.53 (s, 9H).

b) 5-[3'-(5-Carbamimidoyl-2-methylsulfanyl-thiophene-3-sulfonyl)-4-guanidino-6-methyl-biphenyl-2-ylcarbamoyl]-pentanoic acid bis-trifluoroacetate Acetic acid (500 µL) was added to a solution of 5-{4-amino-3'-[5-(tert-butoxycarbonylamino-imino-methyl)-2-methylsulfanyl-thiophene-3-sulfonyl]-6-methyl-biphenyl-2-ylcarbamoyl}-pentanoic acid methyl ester ((Example 260: step b) 136 mg, 0.2 mmol) and 1,3-bis-(tert-butoxycarbonyl)-2-methyl-2-thiopseudourea (145 mg, 0.5 mmol) in MeOH (10 mL). The solution was stirred for 16 h at 40° C., then was partitioned between EtOAc (80 mL) and water (40 mL). The layers were separated and the organic layer was washed with aq NaHCO$_3$ (2×30 mL) and brine (30 mL) and was dried over sodium sulfate. After concentration, the residue was purified by preparative TLC. The residue was dissolved in MeOH (10 mL) and 1N NaOH was added (400 µL, 0.4 mmol). After stirring for 6 h, the solution was neutralized with AcOH (100 µL) and the solvent was removed in vacuo. The residue was treated with 1:1 TFA/DCM as in Example 1: step d and analogously purified by HPLC to yield the title compound (12 mg, 19%) as a white solid. $^1$H-NMR (CD$_3$OD): δ 8.30 (s, 1H), 8.09 (ddd, 1H, J=1.2, 2.1, 7.9 Hz), 7.88 (t, 1H, J=1.6 Hz), 7.70 (t, 1H, J=7.7 Hz) 7.52 (m, 1H), 7.22 (m, 1H), 7.17 (m, 1H), 2.72 (s, 3H), 2.12 (m, 2H), 2.08 (s, 3H), 2.02 (m, 2H), 1.25 (m, 2H). ESI-MS (m/z): Calcd. for C$_{26}$H$_{30}$N$_6$O$_5$S$_3$ (M+H): 603.1; found: 603.2.

Example 262

4-[2'-Methyl-4'-(N-methyl-guanidino)-biphenyl-3-sulfonyl]-5-methylsulfanyl-thiophene-2-carboxamidine bis-trifluoroacetate

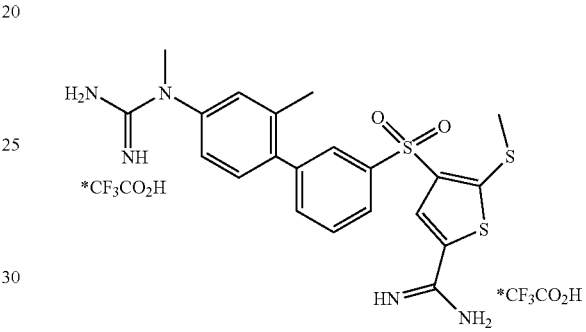

a) (4-Bromo-3-methyl-phenyl)-methyl-amine

A solution of 4-bromo-3-methylaniline (3.72 g, 20 mmol) in formic acid (15 mL) was heated at 100° C. for 8 h. The solvent was removed in vacuo and the residue was partitioned between EtOAc (100 mL) and aq NaHCO$_3$ (50 mL). The layers were separated and the organic layers was dried (Na$_2$SO$_4$) and concentrated. The residue was dissolved in THF (80 mL) and cooled to 0° C. Lithium aluminum hydride (1.52 g, 40 mmol) was added portionwise over 10 min. The mixture was stirred at rt for 8 h and an additional equivalent (750 mg) of LAH was added. After 16 h, the mixture was quenched with EtOAc and MeOH and the solids were filtered. The material was purified by SiO$_2$ flash column chromatography to yield the title compound (2.56 g, 64%) as a colorless oil. $^1$H-NMR (CDCl$_3$): δ 7.29 (d, 1H, J=8.6 Hz), 6.33 (dd, 1H, J=2.8 Hz), 7.29 (d, 1H, J=2.8, 8.6 Hz), 3.66 (s, 2H), 2.81 (d, 1H, J=5.4 Hz), 2.33 (s, 3H).

b) {Imino-[4-(2'-methyl-4'-methylamino-biphenyl-3-sulfonyl)-5-methylsulfanyl-thiophen-2-yl]-methyl}-carbamic acid tert-butyl ester The procedure in Example 294: step e was followed using (4-bromo-3-methyl-phenyl)-methyl-amine ((Example 262: step a) 600 mg, 3 mmol), palladium acetate (34 mg, 0.15 mmol), and 2-(dicyclohexylphosphino)biphenyl (210 mg, 0.6 mmol) in dioxane (20 mL). Analogous workup yielded the crude pinacolboronate ester (720 mg, 98%) which was used without further purification. Following the procedure in Example 294: step f the crude boronate (540 mg, 2.18 mmol) was reacted with {[4-(3-bromo-benzenesulfonyl)-5-methyl-sulfanyl-thiophen-2-yl]-imino-methyl}-carbamic acid tert-butyl ester ((Example 27: step c) 715 mg, 1.46 mmol), aq Na$_2$CO$_3$ (2M, 4.4 mL, 8.8 mL), and Pd(PPh$_3$)$_4$ (407 mg, 0.37 mmol) in ethanol (4.4 mL) and toluene (8.8 mL). Analogous workup and SiO$_2$ flash column chromatography yielded the title compound (482 mg, 62%) as a yellow glass. $^1$H-NMR (CDCl$_3$): δ 8.0 (s, 1H), 7.95 (m, 1H), 7.90 (m, 1H), 7.55 (m, 1H), 7.51 (m, 1H), 7.05 (m, 1H), 6.53 (m, 2H), 2.9 (s, 3H), 2.56 (s, 3H), 2.56 (s, 3H), 2.22 (s, 3H), 1.52 (s, 9H).

c) 4-[2'-Methyl-4'-(N-methyl-guanidino)-biphenyl-3-sulfonyl]-5-methylsulfanyl-thiophene-2-carboxamidine bis-trifluoroacetate The procedure in Example 314 was followed using {imino-[4-(2'-methyl-4'-methylamino-biphenyl-3-sulfonyl)-5-methylsulfanyl-thiophen-2-yl]-methyl}-carbamic acid tert-butyl ester ((Example 262: step b) 106 mg, 0.2 mmol), HgCl$_2$ (109 mg, 0.4 mmol), 1,3-bis-(tert-butoxycarbonyl)-2-methyl-2-thiopseudourea (116 mg, 0.4 mmol), and DIEA (350 μL, 2 mmol) in DMF (3 mL) at 50° C. After analogous workup and purification by SiO$_2$ flash column chromatography, the material was treated with 1:1 TFA/DCM as in Example 1: step d. Purification by HPLC yielded the title compound as a white solid. $^1$H-NMR (CD$_3$OD): δ 8.35 (s, 1H), 8.04 (m, 2H), 7.72 (m, 2H), 7.39 (m, 2H), 7.31 (m, 1H), 3.40 (s, 3H), 2.72 (s, 3H), 2.29 (s, 3H). ESI-MS (m/z): Calcd. for C$_{21}$H$_{23}$N$_5$O$_2$S$_3$ (M+H): 474.1; found: 474.1.

Example 263

6-{N'-[3'-(5-Carbamimidoyl-2-methylsulfanyl-thiophene-3-sulfonyl)-2-methyl-biphenyl-4-yl]-guanidino}-hexanoic acid

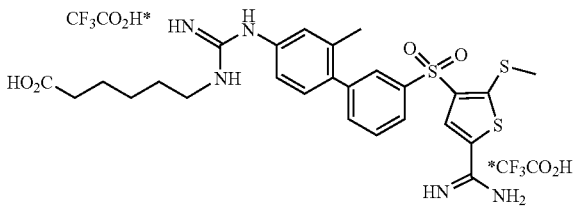

a) 1,3-bis-(tert-butoxycarbonyl)-1-(trimethylsilyl-ethyl-6-hexanoate)-2-methyl-2-thiopseudourea Diisopropylcarbodiimide (1.72 mL, 11 mmol) was added dropwise to a 0° C. solution of 6-bromohexanoic acid (1.95 g, 10 mmol), trimethylsilylethanol (2.4 g, 20 mmol), and DMAP (122 mg, 1 mmol) in DCM (20 mL). The mixture warmed to rt over 1 h and was allowed to stir at rt for 16 h. The solvent was removed in vacuo, the residue was dissolved in EtOAc (100 mL), and the solution was filtered. The solution was extracted with 5% citric acid (3×20 mL), NaHCO$_3$ (3×20 mL), and brine (30 mL), then was dried over sodium sulfate. Concentration of the solution in vacuo yielded the TMSE ester as a non-viscous oil (2.25 g, 76%) which was used without further purification. $^1$H-NMR (CDCl$_3$): δ 4.16 (m, 2H), 2.41 (s, 3H), 3.41 (t, 2H, J=6.75 Hz), 2.30 (t, 2H, J=6.75 Hz), 1.88 (m, 2H), 1.65 (m, 2H), 1.47 (m, 2H).

Sodium hydride was added to a 0° C. solution of 1,3-bis-(tert-butoxycarbonyl)-2-methyl-2-thiopseudourea (581 mg, 2 mmol) in DMF (10 mL). After stirring for 30 min at 0° C., a solution of 2-trimethylsilyethyl-6-bromohexanoate (738 mg, 2.5 mmol) was added and the reaction was warmed to rt. The reaction was stirred at rt for 2 h, 60° C. for 1 h, then at 80° C. for 18 h. The solution was partitioned between EtOAc (120 mL) and water (50 mL) and the layers were separated. The organic layer was extracted with water (8×30 mL) and brine (50 mL), then was dried over sodium sulfate. Concentration of the solution followed by SiO$_2$ flash column chromatography yielded the title compound (526 mg, 52%). $^1$H-NMR (CDCl$_3$): δ 4.13 (m, 2H), 2.41 (s, 3H), 2.30 (t, 2H, J=7.4 Hz), 1.69 (m, 4H), 1.53 (s, 9H), 1.50 (s, 9H), 1.34 (m, 4H), 1.00 (m, 2H).

b) 6-{N'-[3'-(5-Carbamimidoyl-2-methylsulfanyl-thiophene-3-sulfonyl)-2-methyl-biphenyl-4-yl]-guanidino}-hexanoic acid Acetic acid (0.5 mL) was added to a solution of {[4-(4'-amino-2'-methyl-biphenyl-3-sulfonyl)-5-methylsulfanyl-thiophen-2-yl]-imino-methyl}-carbamic acid tert-butyl ester ((Example 220: step b) 130 mg, 0.25 mmol) and 1,3-bis-(tert-butoxycarbonyl)-1-(trimethylsilylethyl-6-hexanoate)-2-methyl-2-thiopseudourea ((Example 263: step a) 245 mg, 0.5 mmol) in MeOH (10 mL). The solution was heated at 40° C. for 24 h. The solvent was removed in vacuo and the residue was purified by SiO$_2$ flash column chromatography to yield the protected guanidine (112 mg, 46%). A portion of the material (15 mg) was treated with 1:1 TFA/DCM as in Example 1: step d. Purification by HPLC yielded the title compound (9.3 mg, 75%) as a white solid. $^1$H-NMR (CD$_3$OD): δ 8.36 (s, 1H), 8.04 (m, 2H), 7.71 (m, 2H), 7.35 (d, 1H, J=8.1 Hz), 7.27 (d, 1H, J=1.9 Hz), 7.22 (dd, 1H, J=1.9, 8.1 Hz), 3.34 (m, 2H), 2.74 (s, 3H), 2.36 (t, 2H, J=7.4 Hz), 2.29 (s, 3H), 1.70 (m, 4H), 1.48 (m, 2H). ESI-MS (m/z): Calcd. for C$_{26}$H$_{31}$N$_5$O$_4$S$_3$ (M+H): 574.2; found: 574.2.

Example 264

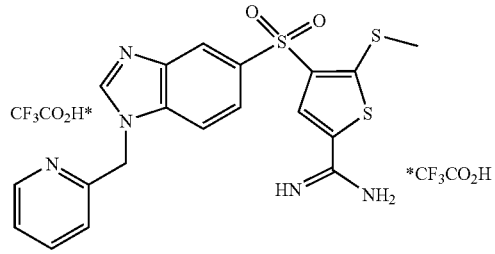

a) 4-(4-Amino-3-nitro-benzenesulfonyl)-5-methylsulfanyl-thiophene-2-carboxylic acid methyl ester Sodium sulfite (1.5 g, 11.9 mmol) and NaHCO$_3$ (1.12 g, 13.3 mmol) were dissolved in water (30 mL) and 4-acetylamino-3-nitro-benzenesulfonyl chloride (1.94 g, 7 mmol) was added. Ethanol (10 mL) and the mixture was stirred for 6 h at rt. Aqueous NaOH (10N, 6 mL, 60 mmol) was added and the reaction was heated to 80° C. for 2 h. The solution was brought to pH~8 with conc. HCl, and the solvent was removed in vacuo. DMF (15 mL) was added, the mixture was stirred for 15 min, and the inorganic salts were then allowed to settle. The DMF was removed via syringe, the salts were washed with a second portion of DMF (10 mL), and the combined DMF solution was slowly added to a 0° C. solution of 4-bromo-5-nitro-thiophene-2-carboxylic acid methyl ester ((Example 114, step c) 931 mg, 3.5 mmol) in DMF (15 mL). The solution was stirred for 0° C. for 1 h then overnight at rt. The DMF was removed in vacuo and the residue was partitioned between EtOAc (100 mL) and aq NaHCO$_3$ (30 mL). The layers were separated and the organic layer was washed with aq NaHCO$_3$ (2×20 mL), water (30 mL), and brine (30 mL), then dried over sodium sulfate. The solution was concentrated and the residue was dissolved in THF (20 mL) and cooled to −78° C. A solution of sodium methoxide in methanol (1M, 7 mL, 7 mmol) was added dropwise and the reaction was stirred for 30 min. Acetic acid (500 μL) was added followed by EtOAc (100 mL). The solution was washed with NaHCO$_3$ (3×30 mL), brine (40 mL), and was dried over sodium sulfate. Concentration and chromatography of the residue yielded the title compound (381 mg, 28%) as a yellow solid. $^1$H-NMR (CDCl$_3$): δ 10.56 (br s, 2H), 9.04 (d, 1H, J=8.8 Hz), 8.89 (d, 1H, J=2.3 Hz), 8.22 (dd, 1H, J=2.3, 9.1 Hz), 8.04 (s, 1H), 3.90 (s, 3H), 2.64 (s, 3H), 2.35 (s, 3H).

b) 4-(4-Bromo-3-nitro-benzenesulfonyl)-5-methyl-sulfanyl-thiophene-2-carboxylic acid methyl ester The procedure used in Example 318: part c was followed using 4-(4-amino-3-nitro-benzenesulfonyl)-5-methylsulfa-nyl-thiophene-2-carboxylic acid methyl ester ((Example 264: step a) 100 mg, 0.26 mmol), CuBr$_2$ (73 mg, 0.31 mmol), and tert-butylnitrite (46 μL, 0.39 mmol) in acetoni-trile (8 mL total). The title compound (118 mg, 100%) was used without further purification. $^1$H-NMR (CDCl$_3$): δ 8.46 (m, 1H), 8.03 (m, 2H), 7.94 (d, 1H, J=8.4 Hz), 3.90 (s, 3H), 2.65 (s, 3H).

c) 5-Methylsulfanyl-4-{3-nitro-4-[(pyridin-2-ylm-ethyl)-amino]-benzenesulfonyl}-thiophene-2-car-boxylic acid methyl ester Pyridin-2-yl-methylamine (60 μL), DIEA (175 μL, 1 mmol), and 4-(4-bromo-3-nitro-benzenesulfonyl)-5-methyl-sulfanyl-thiophene-2-carboxylic acid methyl ester ((Ex-ample 264: step b) 56 mg, 0.12 mmol) were heated at 60° C. in THF (3 mL) for 30 min. The solvent was removed in vacuo and the residue was purified by SiO$_2$ flash column chromatography to yield the title compound (41 mg, 69%). $^1$H-NMR (CDCl$_3$): δ 9.46 (m, 1H), 8.90 (m, 1H), 8.64 (m, 1H), 8.01 (d, 1H, J=2.6 Hz), 7.94 (m, 1H), 8.03 (m, 2H), 7.71 (dt, 1H, J=1.9, 7.7 Hz), 7.28 (m, 2H), 6.95 (d, 1H, J=9.0 Hz), 4.67 (d, 1H, J=5.1 Hz), 3.87 (s, 3H), 2.60 (s, 3H).

d) 5-Methylsulfanyl-4-(1-pyridin-2-ylmethyl-1H-benzoimidazole-5-sulfonyl)-thiophene-2-carboxylic acid methyl ester The procedure in Example 318: part e was followed using 5-methylsulfanyl-4-{3-nitro-4-[(pyridin-2-ylmethyl)-amino]-benzenesulfonyl}-thiophene-2-carboxylic acid methyl ester ((Example 264: step c) 41 mg, 0.08 mmol), iron (110 mg, 2 mmol), and EtOH/aq. AcOH, followed by treatment with formic acid to yield the title compound. $^1$H-NMR (CD$_3$OD): δ 8.50 (m, 1H), 8.42 (s, 1H), 8.08 (m, 1H), 7.97 (d, 1H, J=2.5 Hz), 7.85 (m, 1H), 7.72 (m, 1H), 7.71 (dt, 1H, J=1.9, 7.7 Hz), 7.57 (m, 1H), 7.29 (m, 1H), 7.22 (d, 1H J=7.8 Hz), 6.95 (d, 1H, J=9.0 Hz), 5.57 (s, 2H), 3.82 (s, 3H), 2.56 (s, 3H).

e) 5-Methylsulfanyl-4-(1-pyridin-2-ylmethyl-1H-benzoimidazole-5-sulfonyl)-thiophene-2-carboxami-dine bis-trifluoroacetate The procedure in Example 12: step f was followed using 5-methylsulfanyl-4-(1-pyridin-2-ylmethyl-1H-benzoimida-zole-5-sulfonyl)-thiophene-2-carboxylic acid methyl ester ((Example 264: step d) 36 mg) and 5 mL (5 mmol) of dimethylaluminum amide solution. Analogous workup and purification yielded the title compound (13.2 mg, 23%) as a white solid. $^1$H-NMR (CD$_3$OD): δ 8.63 (ddd, 1H, J=0.9, 1.6, 5.35 Hz), 8.58 (m, 1H), 8.34 (s, 1H), 8.19 (dt, 1H, J=1.6, 7.8 Hz), 8.08 (dd, 1H, J=1.6, 8.7 Hz), 7.85 (d, 1H, J=8.7 Hz), 7.69 (m, 1H), 7.66 (m, 1H), 5.98 (s, 1H), 2.72 (s, 3H). ESI-MS (m/z): Calcd. for $C_{19}H_{17}N_5O_2S_3$ (M+H): 444.1; found: 444.1.

Examples 265–266

4-(3-Benzyl-7-bromo-3H-benzoimidazole-5-sulfo-nyl)-5-methylsulfanyl-thiophene-2-carboxamidine trifluoroacetate and 4-(1-Benzyl-7-bromo-1H-ben-zoimidazole-5-sulfonyl)-5-methylsulfanyl-thiophene-2-carboxamidine trifluoroacetate

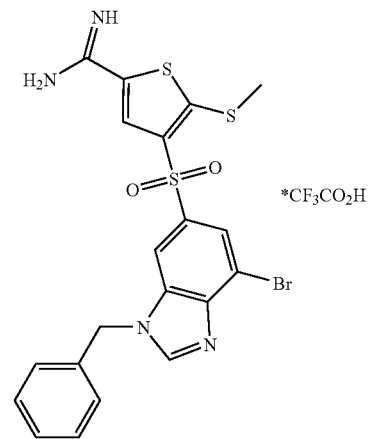

265

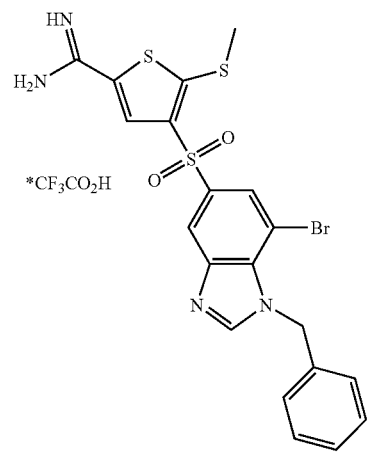

266 a) 4-(3-Benzyl-7-bromo-3H-benzoimidazole-5-sulfonyl)-5-methylsulfanyl-thiophene-2-carboxylic acid methyl ester and 4-(1-Benzyl-7-bromo-1H-benzoimidazole-5-sulfonyl)-5-methylsulfanyl-thiophene-2-carboxylic acid methyl ester The procedure as in Example 39: step a was followed using 4-(7-bromo-3H-benzoimidazole-5-sulfonyl)-5-methylsulfanyl-thiophene-2-carboxylic acid methyl ester (20 mg, 44.7 μmol, Example 38: step e), benzyl bromide (5.3 μL, 44.7 μmol), $K_2CO_3$ (12.4 mg, 89.4 μmol), and DMF (1.5 mL). Removal of the solvents in vacuo was followed by preparative TLC (2–4% 2.0 M $NH_3$ in methanol/$CH_2Cl_2$) to afford a mixture of 4-(3-benzyl-7-bromo-3H-benzoimidazole-5-sulfonyl)-5-methylsulfanyl-thiophene-2-carboxylic acid methyl ester and 4-(1-benzyl-7-bromo-1H-benzoimidazole-5-sulfonyl)-5-methylsulfanyl-thiophene-2-carboxylic acid methyl ester compound as a brown oil (27.7 mg, quantitative). This mixture was used directly in the following step. ESI-MS (m/z): Calcd. for $C_{21}H_{17}BrN_2O_4S_3$: 536 (M+1); found: 538.9.

b) 4-(3-Benzyl-7-bromo-3H-benzoimidazole-5-sulfonyl)-5-methylsulfanyl-thiophene-2-carboxamidine trifluoroacetate and 4-(1-Benzyl-7-bromo-1H-benzoimidazole-5-sulfonyl)-5-methylsulfanyl-thiophene-2-carboxamidine trifluoroacetate The mixture from Examples 265–266: step a (27.7 mg, 44.7 μmmol) was converted to the amidine and purified as described in Examples 39–40: step a to afford the 2 regioisomers: the 3-benzyl (1.6 mg, beige solid) and the 1-benzyl (2.0 mg, white solid). $^1$H-NMR ($CD_3OD$, 3-benzyl): δ 9.08 (s, 1H), 8.27 (s, 1H), 8.23 (s, 1H), 8.10 (s, 1H), 7.35–7.45 (m, 5H), 5.70 (s, 2H), 2.58 (s, 3H). ESI-MS (m/z): Calcd. for $C_{20}H_{17}BrN_4O_2S_3$: 521.0 (M+1); found: 523.0. $^1$H-NMR ($CD_3OD$, 1-benzyl): δ 8.73 (s, 1H), 8.44 (s, 1H), 8.32 (s, 1H), 8.10 (s, 1H), 7.27–7.37 (m, 3H), 7.06–7.11 (m, 2H), 5.93 (s, 2H), 2.72 (s, 3H). ESI-MS (m/z): Calcd. for $C_{20}H_{17}BrN_4O_2S_3$: 521.0 (M+1); found: 523.0.

Example 267–268

4-(3-Allyl-7-bromo-3H-benzoimidazole-5-sulfonyl)-5-methylsulfanyl-thiophene-2-carboxamidine trifluoroacetate and 4-(1-Allyl-7-bromo-3H-benzoimidazole-5-sulfonyl)-5-methylsulfanyl-thiophene-2-carboxamidine trifluoroacetate

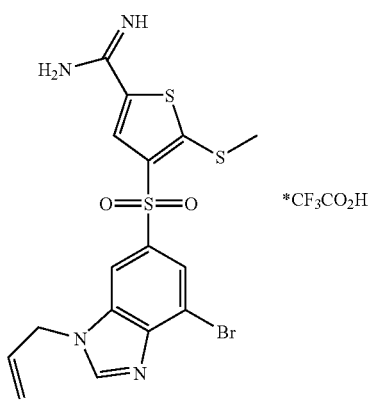

267

*$CF_3CO_2H$

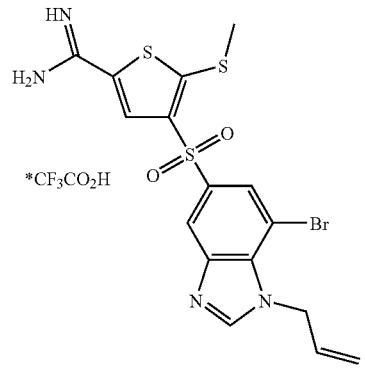

268

*$CF_3CO_2H$ a) 4-(3-Allyl-7-bromo-3H-benzoimidazole-5-sulfonyl)-5-methylsulfanyl-thiophene-2-carboxylic acid methyl ester and 4-(1-Allyl-7-bromo-1H-benzoimidazole-5-sulfonyl)-5-methylsulfanyl-thiophene-2-carboxylic acid methyl ester The procedure as in Example 39: step a was followed using 4-(7-bromo-3H-benzoimidazole-5-sulfonyl)-5-methylsulfanyl-thiophene-2-carboxylic acid methyl ester (20 mg, 44.7 μmol, Example 38: step e), allyl bromide (3.9 μL, 44.7 μmol), $K_2CO_3$ (12.4 mg, 89.4 μmol), and DMF (1.5 mL). The crude was purified by preparative TLC (2–4% 2.0 M $NH_3$ in methanol/$CH_2Cl_2$) to afford a mixture of 4-(3-allyl-7-bromo-3H-benzoimidazole-5-sulfonyl)-5-methylsulfanyl-thiophene-2-carboxylic acid methyl ester and 4-(1-allyl-7-bromo-1H-benzoimidazole-5-sulfonyl)-5-methylsulfanyl-thiophene-2-carboxylic acid methyl ester as a brown oil (22.4 mg, quantitative). This mixture was used directly in the following step. ESI-MS (m/z): Calcd. for $C_{17}H_{15}BrN_2O_4S_3$: 486.9 (M+1); found: 488.9.

b) 4-(3-Allyl-7-bromo-3H-benzoimidazole-5-sulfonyl)-5-methylsulfanyl-thiophene-2-carboxamidine trifluoroacetate and 4-(3-Allyl-7-bromo-3H-benzoimidazole-5-sulfonyl)-5-methylsulfanyl-thiophene-2-carboxamidine trifluoroacetate The mixture from Example 267–268: step a (22.4 mg, 44.7 μmol) was converted to the amidine and purified as described in Example 20: step b to afford the 2 regioisomers: the 3-allyl (1.0 mg, beige solid) and the 1-allyl (2.5 mg, beige solid). $^1$H-NMR ($CD_3OD$, 3-allyl): δ 8.54 (s, 1H), 8.31–8.34 (m, 2H), 8.04–8.05 (m, 1H), 6.05–6.14 (m, 1H), 5.33–5.36 (m, 1H), 5.21–5.26 (m, 1H), 5.05–5.08 (m, 2H), 2.71 (s, 3H). ESI-MS (m/z): Calcd. for $C_{16}H_{15}BrN_4O_2S_3$: 471.0 (M+1); found: 473.0. $^1$H-NMR ($CD_3OD$, 1-allyl): δ 8.31–8.55 (m, 3H), 8.05–8.11 (m, 1H), 6.10–6.22 (m, 1H), 4.92–5.32 (m, 4H), 2.72 (s, 3H). ESI-MS (m/z): Calcd. for $C_{16}H_{15}BrN_4O_2S_3$: 471.0 (M+1); found: 473.0.

Example 269

4-(7-Bromo-3-phenyl-3H-benzoimidazole-5-sulfonyl)-5-methylsulfanyl-thiophene-2-carboxamidine trifluoroacetate

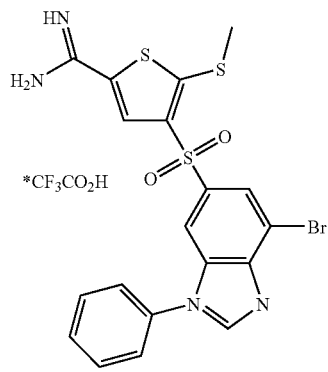

a) 4-(7-Bromo-3-phenyl-3H-benzoimidazole-5-sulfonyl)-5-methylsulfanyl-thiophene-2-carboxylic acid methyl ester 4-(7-Bromo-3-phenyl-3H-benzoimidazole-5-sulfonyl)-5-methylsulfanyl-thiophene-2-carboxylic acid methyl ester was prepared according to literature (Lam, P. Y. S. et al., *Tetrahedron Letters*, 42:3415 (2001)) using 4-(7-bromo-3H-benzoimidazole-5-sulfonyl)-5-methylsulfanyl-thiophene-2-carboxylic acid methyl ester (20 mg, 44.7 μmol, Example 38: step e), phenylboronic acid (11.4 mg, 93.5 μmol), Cu(OAc)$_2$ (8.5 mg, 46.8 μmol), pyridine N-oxide (4.7 mg, 49.2 μmol), triethylamine (13 μL, 93.3 μmol), and CH$_2$Cl$_2$ (1.5 mL) in a loosely-capped, 1-dram vial. The reaction mixture was diluted in CH$_2$Cl$_2$ and washed with water and brine. The organic layer was dried over magnesium sulfate. Removal of solvents in vacuo followed by preparative TLC afforded the title compound as a brown oil (12 mg, 51%). ESI-MS (m/z): Calcd. for C$_{20}$H$_{15}$BrN$_2$O$_4$S$_3$: 522.9 (M+1); found: 525.0.

b) 4-(7-Bromo-3-phenyl-3H-benzoimidazole-5-sulfonyl)-5-methylsulfanyl-thiophene-2-carboxamidine trifluoroacetate 4-(7-Bromo-3-phenyl-3H-benzoimidazole-5-sulfonyl)-5-methylsulfanyl-thiophene-2-carboxylic acid methyl ester (12 mg, 22.9 μmol) was converted to the amidine and purified as described in Example 20: step f to afford the title compound as a beige solid (1.6 mg, 14%). $^1$H-NMR (CD$_3$OD): δ 8.80 (s, 1H), 8.13–8.32 (m, 3H), 7.63–7.74 (m, 5H), 2.73 (s, 3H). ESI-MS (m/z): Calcd. for C$_{19}$H$_{15}$BrN$_4$O$_2$S$_3$: 507.0 (M+1); found: 509.0.

Example 270–271

4-(7-Bromo-3-cyclopropylmethyl-3H-benzoimidazole-5-sulfonyl)-5-methylsulfanyl-thiophene-2-carboxamidine trifluoroacetate and 4-(7-Bromo-1-cyclopropylmethyl-1H-benzomidazole-5-sulfonyl)-5-methylsulfanyl-thiophene-2-carboxamidine trifluoroacetate

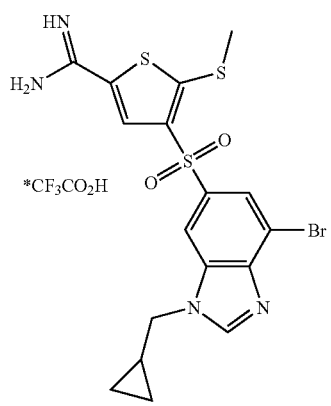

270

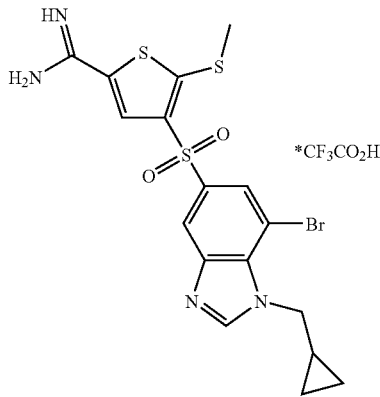

271 a) 4-(7-Bromo-3-cyclopropylmethyl-3H-benzoimidazole-5-sulfonyl)-5-methylsulfanyl-thiophene-2-carboxylic acid ethyl ester The procedure as in Example 39: step a was followed using 4-(7-bromo-3H-benzoimidazole-5-sulfonyl)-5-methylsulfanyl-thiophene-2-carboxylic acid ethyl ester (100 mg, 0.217 mmol, Example 38: step e), (bromomethyl)cyclopropane (21 μL, 0.217 mmol), K$_2$CO$_3$ (60 mg, 0.434 mmol), and DMF (3 mL). The crude was purified by preparative TLC (2–4% 2.0 M NH$_3$ in methanol/CH$_2$Cl$_2$) to afford a mixture of 4-(7-bromo-3-cyclopropylmethyl-3H-benzoimidazole-5-sulfonyl)-5-methylsulfanyl-thiophene-2-carboxylic acid ethyl ester and 4-(7-bromo-1-cyclopropylmethyl-1H-benzoimidazole-5-sulfonyl)-5-methylsulfanyl-thiophene-2-carboxylic acid ethyl ester as a brown oil (72 mg, 64%). This mixture was used directly in the following step. ESI-MS (m/z): Calcd. for C$_{18}$H$_{17}$BrN$_2$O$_4$S$_3$: 515 (M+1); found: 516.9.

b) 4-(7-Bromo-3-cyclopropylmethyl-3H-benzoimidazole-5-sulfonyl)-5-methylsulfanyl-thiophene-2-carboxamidine trifluoroacetate and 4-(7-Bromo-1-cyclopropylmethyl-1H-benzoimidazole-5-sulfonyl)-5-methylsulfanyl-thiophene-2-carboxamidine trifluoroacetate

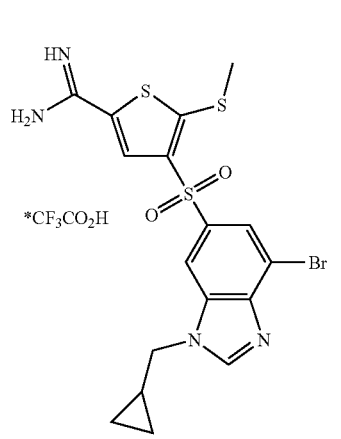

270

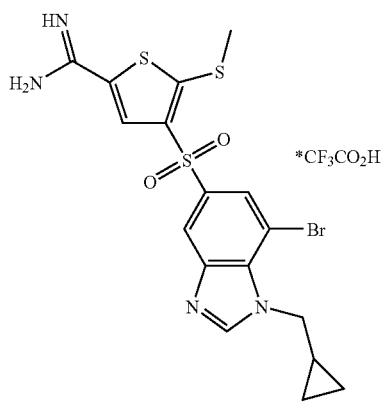

271

The mixture from Examples 270–271: step a (72 mg, 0.14 mmol) was converted to the amidine and purified as described in Examples 39–40: step b to afford 2 regioisomers: the 3-cyclopropylmethyl (3-CPM) (2.8 mg, beige solid) and the 1-cyclopropylmethyl (1-CPM) (3.3 mg, beige solid). $^1$H-NMR (CD$_3$OD, 3-CPM): δ 8.63 (s, 1H), 8.40 (d, 1H, J=1.40 Hz), 8.35 (s, 1H), 8.05 (d, 1H, J=1.40 Hz), 4.27 (d, 2H, J=7.21 Hz), 2.72 (s, 3H), 1.35–1.42(m, 1H), 0.68–0.73 (m, 2H), 0.5–0.54 (m, 2H). ESI-MS (m/z): Calcd. for C$_{17}$H$_{17}$BrN$_4$O$_2$S$_3$: 485.0 (M+1); found: 487.0. $^1$H-NMR (CD$_3$OD, 1-CPM): δ 8.55 (s, 1H), 8.37–8.38 (m, 1H), 8.34 (s, 1H), 8.10–8.11 (m, 1H), 4.52 (d, 2H, J=7.21 Hz), 2.72 (s, 3H), 1.43–1.51 (m, 1H), 0.62–0.67 (m, 2H), 0.47–0.52 (m, 2H). ESI-MS (m/z): Calcd. for C$_{17}$H$_{17}$BrN$_4$O$_2$S$_3$: 485.0 (M+1); found: 487.0.

Examples 272–273

4-[7-Bromo-3-(2,6-dichloro-benzyl)-3H-benzoimidazole-5-sulfonyl]-5-methylsulfanyl-thiophene-2-carboxamidine trifluoroacetate and 4-[7-Bromo-1-(2,6-dichloro-benzyl)-1H-benzoimidazole-5-sulfonyl]-5-methylsulfanyl-thiophene-2-carboxamidine tifluoroacetate

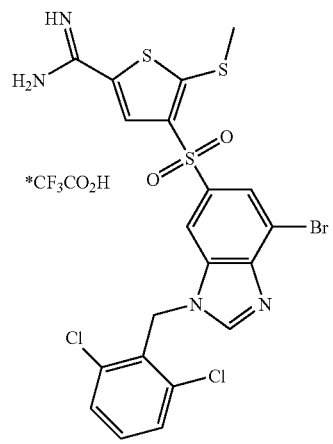

272

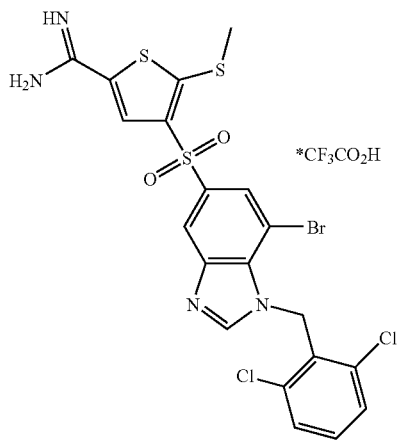

273 a) 4-[7-Bromo-3-(2,6-dichloro-benzyl)-3H-benzoimidazole-5-sulfonyl]-5-methylsulfanyl-thiophene-2-carboxylic acid ethyl ester and 4-[7-Bromo-1-(2,6-dichloro-benzyl)-1H-benzoimidazole-5-sulfonyl]-5-methylsulfanyl-thiophene-2-carboxylic acid ethyl ester The procedure as in Example 39: step a was followed using 4-(7-bromo-3H-benzoimidazole-5-sulfonyl)-5-methylsulfanyl-thiophene-2-carboxylic acid ethyl ester (100 mg, 0.217 mmol, Example 38: step e), 2-bromomethyl-1,3-dichloro-benzene (52 mg, 0.217 mmol), K$_2$CO$_3$ (60 mg, 0.434 mmol), and DMF (3 mL). The crude was purified by preparative TLC (2–4% 2.0 M NH$_3$ in methanol/CH$_2$Cl$_2$) to afford a mixture of 4-[7-bromo-3-(2,6-dichloro-benzyl)-3H-benzoimidazole-5-sulfonyl]-5-methylsulfanyl-thiophene-2-carboxylic acid ethyl ester and 4-[7-bromo-1-(2,6-dichloro-benzyl)-1H-benzoimidazole-5-sulfonyl]-5-methylsulfanyl-thiophene-2-carboxylic acid ethyl ester as brown oil (70 mg, 52.2%). This mixture was used directly in the following step. ESI-MS (m/z): Calcd. for C$_{21}$H$_{15}$BrCl$_2$N$_2$O$_4$S$_3$: 618.9 (M+1); found: 620.9.

b) 4-[7-Bromo-3-(2,6-dichloro-benzyl)-3H-benzoimidazole-5-sulfonyl]-5-methylsulfanyl-thiophene-2-carboxamidine trifluoroacetate and 4-[7-Bromo-1-(2,6-dichloro-benzyl)-1H-benzoimidazole-5-sulfonyl]-5-methylsulfanyl-thiophene-2-carboxamidine tifluoroacetate The mixture from Examples 272–273: step a (70 mg, 0.11 mmol) was converted to the amidine and purified as described in Examples 39–40: step b to afford 2 regioisomers: the 3-(2,6-dichlorobenzyl) (3-DCB) (2.5 mg, beige solid) and the 1-(2,6-dichlorobenzyl) (1-DCB) (2.2 mg, beige solid). $^1$H-NMR (CD$_3$OD, 3-DCB): δ 8.58 (s, 1H), 8.30–8.33 (m, 2H), 8.00 (d, 1H, J=1.63 Hz), 7.55–7.58 (m, 2H), 7.44–7.49 (m, 1H), 5.90 (s, 2H), 2.64 (s, 3H). ESI-MS (m/z): Calcd. for C$_{20}$H$_{15}$BrCl$_2$N$_4$O$_2$S$_3$: 588.9 (M+1); found: 590.9. $^1$H-NMR (CD$_3$OD, 1-DCB): δ 8.34–8.40 (m, 2H), 8.16–8.18 (m, 1H), 7.86–7.90 (m, 1H), 7.46–7.60 (m, 3H), 6.22 (s, 2H), 2.64 (s, 3H). ESI-MS (m/z): Calcd. for C$_{20}$H$_{15}$BrCl$_2$N$_4$O$_2$S$_3$: 588.9 (M+1); found: 590.9.

Examples 274–275

4-[7-Bromo-3-(2,5-difluoro-benzyl)-3H-benzoimidazole-5-sulfonyl]-5-methylsulfanyl-thiophene-2-carboxamidine trifluoroacetate and 4-[7-Bromo-1-(2,5-difluoro-benzyl)-1H-benzoimidazole-5-sulfonyl]-5-methylsulfanyl-thiophene-2-carboxamidine trifluoroacetate

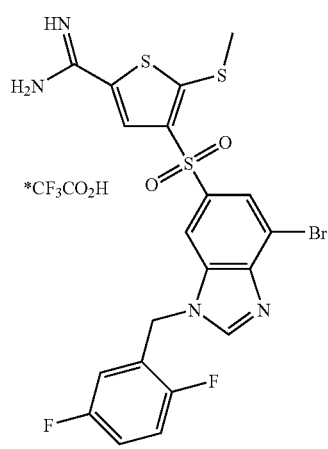

274

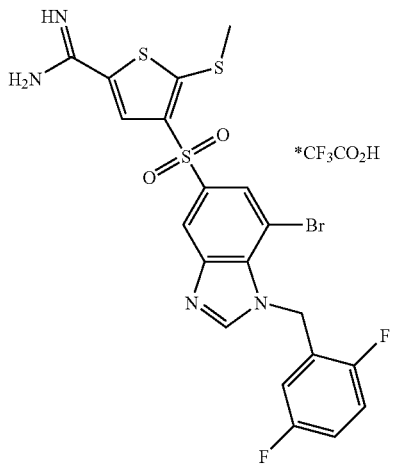

275 a) 4-[7-Bromo-3-(2,5-difluoro-benzyl)-3H-benzoimidazole-5-sulfonyl]-5-methylsulfanyl-thiophene-2-carboxylic acid ethyl ester and 4-[7-Bromo-1-(2,5-difluoro-benzyl)-1H-benzoimidazole-5-sulfonyl]-5-methylsulfanyl-thiophene-2-carboxylic acid ethyl ester The procedure as in Example 39: step a was followed using 4-(7-bromo-3H-benzoimidazole-5-sulfonyl)-5-methylsulfanyl-thiophene-2-carboxylic acid ethyl ester (100 mg, 0.217 mmol, Example 38: step e), 2-bromomethyl-1,4-difluoro-benzene (28 μL, 0.217 mmol), K$_2$CO$_3$ (60 mg, 0.434 mmol), and DMF (3 mL). The crude was purified by preparative TLC (2–4% 2.0 M NH$_3$ in methanol/CH$_2$Cl$_2$) to afford a mixture of 4-[7-bromo-3-(2,5-difluoro-benzyl)-3H-benzoimidazole-5-sulfonyl]-5-methylsulfanyl-thiophene-2-carboxylic acid ethyl ester and 4-[7-bromo-1-(2,5-difluoro-benzyl)-1H-benzoimidazole-5-sulfonyl]-5-methylsulfanyl-thiophene-2-carboxylic acid ethyl ester as a brown oil (70 mg, 55%). This mixture was used directly in the next step. ESI-MS (m/z): Calcd. for C$_{21}$H$_{15}$BrF$_2$N$_2$O$_4$S$_3$: 586.0 (M+1); found: 588.9.

b) 4-[7-Bromo-3-(2,5-difluoro-benzyl)-3H-benzoimidazole-5-sulfonyl]-5-methylsulfanyl-thiophene-2-carboxamidine trifluoroacetate and 4-[7-Bromo-1-(2,5-difluoro-benzyl)-1H-benzoimidazole-5-sulfonyl]-5-methylsulfanyl-thiophene-2-carboxamidine trifluoroacetate The mixture from Examples 274–275: step a (70 mg, 0.12 mmol) was converted to the amidine and purified as described in Examples 39–40: step b to afford 2 regioisomers: the 3-(2,5-difluorobenzyl) (3-DFB) (3.0 mg, white solid) and the 1-(2,5-difluorobenzyl) (1-DFB) (3.2 mg, white solid). $^1$H-NMR (CD$_3$OD, 3-DFB): δ 8.58 (s, 1H), 8.30–8.33 (m, 2H), 8.00 (d, 1H, J=1.63 Hz), 7.55–7.58 (m, 2H), 7.44–7.49 (m, 1H), 5.90 (s, 2H), 2.64 (s, 3H). ESI-MS (m/z): Calcd. for C$_{20}$H$_{15}$BrCl$_2$N$_4$O$_2$S$_3$: 588.9 (M+1); found: 590.9. $^1$H-NMR (CD$_3$OD, 1-DFB): δ 8.57 (s, 1H), 8.41–8.45 (m, 1H), 8.32–8.36 (m, 1H), 8.07-8.11 (m, 1H), 7.05–7.27 (m, 2H), 6.43–6.54 (m, 1H), 5.94 (s, 2H), 2.72 (s, 3H). ESI-MS (m/z): Calcd. for C$_{20}$H$_{15}$BrCl$_2$N$_4$O$_2$S$_3$: 588.9 (M+1); found: 590.9.

Examples 276–277

4-[7-Bromo-3-(2,6-difluoro-benzyl)-3H-benzoimidazole-5-sulfonyl]-5-methylsulfanyl-thiophene-2-carboxamidine trifluoroacetate and 4-[7-Bromo-1-(2,6-difluoro-benzyl)-1H-benzoimidazole-5-sulfonyl]-5-methylsulfanyl-thiophene-2-carboxamidine trifluoroacetate

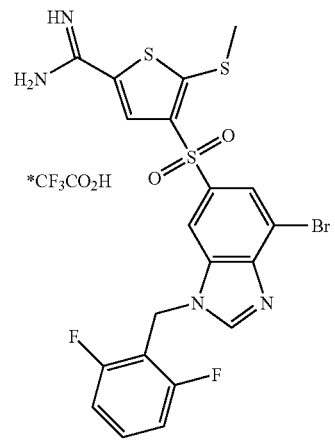

276

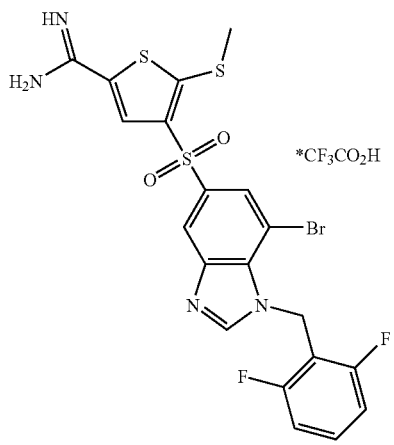

277 a) 4-[7-Bromo-3-(2,6-difluoro-benzyl)-3H-benzoimidazole-5-sulfonyl]-5-methylsulfanyl-thiophene-2-carboxylic acid methyl ester and 4-[7-Bromo-1-(2,6-difluoro-benzyl)-1H-benzoimidazole-5-sulfonyl]-5-methylsulfanyl-thiophene-2-carboxylic acid methyl ester The procedure as in Example 39: step a was followed using 4-(7-bromo-3H-benzoimidazole-5-sulfonyl)-5-methylsulfanyl-thiophene-2-carboxylic acid methyl ester (50 mg, 0.11 mmol, Example 38: step e), 2-bromomethyl-1,3-difluoro-benzene (23 mg, 0.11 mmol), $K_2CO_3$ (31 mg, 0.22 mmol), and DMF (1.5 mL). The crude was purified by preparative TLC (2–4% 2.0 M $NH_3$ in methanol/$CH_2Cl_2$) to afford a mixture of 4-[7-bromo-3-(2,6-difluoro-benzyl)-3H-benzoimidazole-5-sulfonyl]-5-methylsulfanyl-thiophene-2-carboxylic acid methyl ester and 4-[7-bromo-1-(2,6-difluoro-benzyl)-1H-benzoimidazole-5-sulfonyl]-5-methylsulfanyl-thiophene-2-carboxylic acid methyl ester as a brown oil (67 mg, quantitative). ESI-MS (m/z): Calcd. for $C_{21}H_{15}BrF_2N_2O_4S_3$: 572.9 (M+1); found: 574.9.

b) 4-[7-Bromo-3-(2,6-difluoro-benzyl)-3H-benzoimidazole-5-sulfonyl]-5-methylsulfanyl-thiophene-2-carboxamidine trifluoroacetate and 4-[7-Bromo-1-(2,6-difluoro-benzyl)-1H-benzoimidazole-5-sulfonyl]-5-methylsulfanyl-thiophene-2-carboxamidine trifluoroacetate The mixture from Examples 276–277: step a (67 mg, 0.11 mmol) was converted to the amidine and purified as described in Example 39–40: step a to afford 2 regioisomers: the 3-(2,6-difluorobenzyl) (3-DFB) (3.5 mg, beige solid) and the 1-(2,6-difluorobenzyl) (1-DFB) (1.6 mg, white solid). $^1$H-NMR ($CD_3OD$, 3-DFB): δ 8.64 (s, 1H), 8.31–8.35 (m, 2H), 8.02 (s, 1H), 7.45–7.54 (m, 1H), 7.08–7.14 (m, 2H), 5.74 (s, 2H), 2.65 (s, 3H). ESI-MS (m/z): Calcd. for $C_{20}H_{15}BrF_2N_4O_2S_3$: 556.0 (M+1); found: 559.0. $^1$H-NMR ($CD_3OD$, 1-DFB): δ 8.42 (s, 1H), 8.35–8.37 (m, 1H), 8.32 (s, 1H), 7.39–7.48 (m, 1H), 6.99–7.06 (m, 1H), 7.03 (t, 2H, J=8.34), 6.02 (s, 2H), 2.71 (s, 3H). ESI-MS (m/z): Calcd. for $C_{20}H_{15}BrF_2N_4O_2S_3$: 556.0 (M+1); found: 559.0.

Example 278

6-{3-[3'-(5-Carbamimidoyl-2-methylsulfanyl-thiophene-3-sulfonyl)-2-(4-carboxy-butyrylamino)-6-methyl-biphenyl-4-yl]-ureido}-hexanoic acid trifluoroacetate

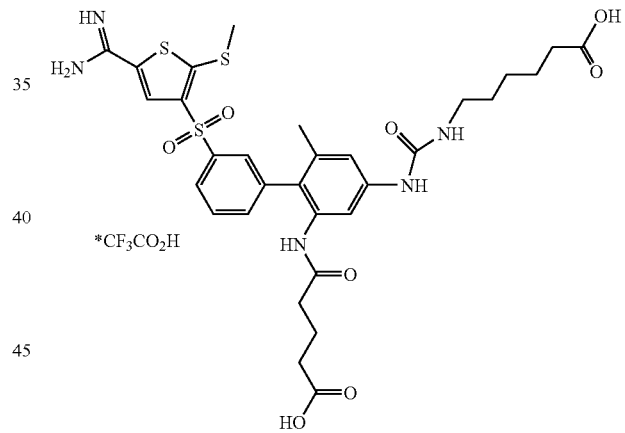

a) 6-[3-(4-Bromo-3-methyl-5-nitro-phenyl)-ureido]-hexanoic acid ethyl ester

6-Isocyanato-hexanoic acid ethyl ester (370 μL, 2.16 mmol) was added to a solution of 4-bromo-3-methyl-5-nitro-phenylamine (250 mg, 1.08 mmol, Example 135: step a) in $CH_2Cl_2$ (5 mL, anhydrous) at rt. The reaction mixture was stirred overnight, then diluted in EtOAc and washed with saturated $NH_4Cl$ solution, water, and brine. The organic layer was dried over magnesium sulfate. Removal of solvents in vacuo was followed by flash chromatography (50–75% EtOAc/hexanes) to afford the title compound as a brown oil (162 mg, 36%). $^1$H-NMR ($CDCl_3$): δ 7.59 (d, 1H, J=2.56 Hz), 7.42–7.48 (m, 1H), 4.10–4.17 (m, 2H), 3.20–3.28 (m, 2H), 2.39 (s, 3H), 2.29–2.35 (m, 2H), 1.47–1.68 (m, 4H), 1.23–1.41 (m, 5H).

b) 6-(3-{3'-[5-(tert-Butoxycarbonylamino-imino-methyl)-2-methylsulfanyl-thiophene-3-sulfonyl]-6-methyl-2-nitro-biphenyl-4-yl}-ureido)-hexanoic acid ethyl ester A 25 mL round bottom flask was charged with 6-[3-(4-bromo-3-methyl-5-nitro-phenyl)-ureido]-hexanoic acid ethyl ester (110 mg, 0.264 mmol, Example 278: step a), {[4-(3-dihydroxyboranyl-benzenesulfonyl)-5-methylsulfanyl-thiophen-2-yl]-imino-methyl}-carbamic acid tert-butyl ester (234 mg, 0.529 mmol, Example 140: step a), aqueous Na$_2$CO$_3$ (2M, 1.06 mL, 2.12 mmol), ethanol (1.06 mL, anhydrous) and toluene (2.11 mL, anhydrous). A stir bar was added, the solution was degassed for 10 min, and Pd(PPh$_3$)$_4$ (76 mg, 65.8 µmol) was added. The reaction mixture was stirred under Ar at 80° C. for 5 hrs, then cooled to rt. The solvents were removed in vacuo. The residue was diluted in EtOAc, washed with brine, and dried over magnesium sulfate. Removal of solvents in vacuo followed by preparative TLC (50–100% EtOAc/hexanes) afforded the title compound as a brown oil (74 mg, 37%). ESI-MS (m/z): Calcd. for C$_{33}$H$_{41}$N$_5$O$_9$S$_3$: 748.2 (M+1); found: 747.8.

c) 6-(3-{2-Amino-3'-[5-(tert-butoxycarbonylamino-imino-methyl)-2-methylsulfanyl-thiophene-3-sulfonyl]-6-methyl-biphenyl-4-yl}-ureido)-hexanoic acid ethyl ester 6-(3-{3'-[5-(tert-Butoxycarbonylamino-imino-methyl)-2-methylsulfanyl-thiophene-3-sulfonyl]-6-methyl-2-nitro-biphenyl-4-yl}-ureido)-hexanoic acid ethyl ester (74 mg, 98.9 µmol, Example 278: step b) in EtOH (5 mL) was reduced as in Example 20: step c using Fe (28 mg, 0.50 mmol) and aqueous NH$_4$Cl solution (50 mg, 0.93 mmol, 10 mL). The solvents were removed from the filtrate in vacuo. The crude was diluted in EtOAc and washed with water and brine. The organic layer was dried over magnesium sulfate. The solvents were removed in vacuo to yield the title compound as a brown oil (70.8, quantitative). ESI-MS (m/z): Calcd. for C$_{33}$H$_{43}$N$_5$O$_7$S$_3$: 718.2 (M+1); found: 718.1.

d) 6-{3-[3'-[5-(tert-Butoxycarbonylamino-imino-methyl)-2-methylsulfanyl-thiophene-3-sulfonyl]-2-(4-methoxycarbonyl-butyrylamino)-6-methyl-biphenyl-4-yl]-ureido}-hexanoic acid ethyl ester 4-Chlorocarbonyl-butyric acid methyl ester (20.4 µL, 0.148 mmol) was added to a solution of 6-(3-{2-amino-3'-[5-(tert-butoxycarbonylamino-imino-methyl)-2-methylsulfanyl-thiophene-3-sulfonyl]-6-methyl-biphenyl-4-yl}-ureido)-hexanoic acid ethyl ester (70.8 mg, 96.4 µmol, Example 278: step c) and triethylamine (41.2 µL, 0.296 mmol) in CH$_2$Cl$_2$ (5 mL, anhydrous) at rt. The reaction mixture was stirred overnight at rt, then diluted in EtOAc, washed with water and brine, and dried over magnesium sulfate. Removal of solvents in vacuo followed by flash chromatography (75–100% EtOAc/hexanes) yielded the title compound as a brown oil (45.5 mg, 54.5%). ESI-MS (m/z): Calcd. for C$_{39}$H$_{51}$N$_5$O$_{10}$S$_3$: 846.3 (M+1); found: 845.9.

e) 6-{3-[3'-[5-(tert-Butoxycarbonylamino-imino-methyl)-2-methylsulfanyl-thiophene-3-sulfonyl]-2-(4-carboxy-butyrylamino)-6-methyl-biphenyl-4-yl]-ureido}-hexanoic acid Lithium hydroxide (53.8 µL, 0.215 mmol, 4N aqueous) was added to a solution of 6-{3-[3'-[5-(tert-butoxycarbonylamino-imino-methyl)-2-methylsulfanyl-thiophene-3-sulfonyl]-2-(4-methoxycarbonyl-butyrylamino)-6-methyl-biphenyl-4-yl]-ureido}-hexanoic acid ethyl ester (45.5 mg, 53.8 µmol, Example 278: step d) in MeOH/H$_2$O (10 mL, 2:1) at 0° C. The reaction mixture was warmed to rt and stirred overnight. The solvents were removed in vacuo to afford the title compound as a yellow solid (50 mg, quantitative). ESI-MS (m/z): Calcd. for C$_{36}$H$_{45}$N$_5$O$_1$OS$_3$: 804.2 (M+1); found: 803.9.

f) 6-{3-[3'-(5-Carbamimidoyl-2-methylsulfanyl-thiophene-3-sulfonyl)-2-(4-carboxy-butyrylamino)-6-methyl-biphenyl-4-yl]-ureido}-hexanoic acid trifluoroacetate 6-{3-[3'-[5-(tert-Butoxycarbonylamino-imino-methyl)-2-methylsulfanyl-thiophene-3-sulfonyl]-2-(4-carboxy-butyrylamino)-6-methyl-biphenyl-4-yl]-ureido}-hexanoic acid (43.2 mg, 53.7 µmol, Example 278: step e) was deprotected and purified as in Example 1: step d to afford the title compound as a white solid (15 mg, 40%). $^1$H-NMR (CD$_3$OD): δ 8.27 (s, 1H), 8.00–8.04 (m, 1H), 7.87–7.89 (m, 1H), 7.63–7.71 (m, 1H), 7.49–7.54 (m, 1H), 7.32–7.35 (m, 1H), 7.25–7.26 (m, 1H), 3.22 (t, 2H, J=6.98 Hz), 2.73 (s, 3H), 2.34 (t, 2H, J=7.44 Hz), 2.05 (s, 3H), 1.88–2.03 (m, 4H), 1.54–1.71 (m, 4H), 1.34–1.48 (m, 4H). ESI-MS (m/z): Calcd. for C$_{31}$H$_{37}$N$_5$O$_8$S$_3$: 704.2 (M+1); found: 704.1.

Example 279

6-{3-[3'-(5-Carbamimidoyl-2-methylsulfanyl-thiophene-3-sulfonyl)-2-(4-methanesulfonyl-butyrylamino)-6-methyl-biphenyl-4-yl]-ureido}-hexanoic acid trifluoroacetate

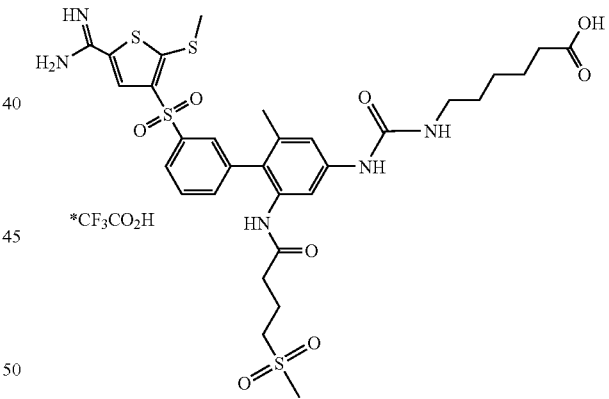

a) 6-{3-[3'-[5-(tert-Butoxycarbonylamino-imino-methyl)-2-methylsulfanyl-thiophene-3-sulfonyl]-2-(4-methanesulfonyl-butyrylamino)-6-methyl-biphenyl-4-yl]-ureido}-hexanoic acid ethyl ester The procedure as in Example 278: step d was followed using 6-{3-[3'-[5-(tert-butoxycarbonylamino-imino-methyl)-2-methylsulfanyl-thiophene-3-sulfonyl]-2-(4-methanesulfonyl-butyrylamino)-6-methyl-biphenyl-4-yl]-ureido}-hexanoic acid ethyl ester (39 mg, 54.3 µmol, Example 278: step b), triethylamine (22.7 µL, 0.163 mmol), 4-methanesulfonyl-butyryl chloride (15 mg, 81.5 µmol, Example 209: step a), and CH$_2$Cl$_2$ (3 mL, anhydrous). The reaction mixture was diluted in EtOAc, washed with water and brine, and dried over magnesium sulfate. The solvents were removed in vacuo to afford the title compound as a brown oil (48 mg, quantitative). ESI-MS (m/z): Calcd. for $C_{38}H_{51}N_5O_{10}S_4$: 866.3 (M+1); found: 865.8.

b) 6-{3-[3'-[5-(tert-Butoxycarbonylamino-imino-methyl)-2-methylsulfanyl-thiophene-3-sulfonyl]-2-(4-methanesulfonyl-butyrylamino)-6-methyl-biphenyl-4-yl]-ureido}-hexanoic acid The procedure as in Example 278: step e was followed using 6-{3-[3'-[5-(tert-butoxycarbonylamino-imino-methyl)-2-methylsulfanyl-thiophene-3-sulfonyl]-2-(4-methanesulfonyl-butyrylamino)-6-methyl-biphenyl-4-yl]-ureido}-hexanoic acid ethyl ester (48 mg, 54.3 µmol, Example 279: step a) in a MeOH/$H_2O$ (2:1) solution and 4N LiOH (54.3 µL, 0.217 mmol). The crude was taken on directly to the next step. ESI-MS (m/z): Calcd. for $C_{36}H_{47}N_5O_{10}S_4$: 838.2 (M+1); found: 837.8.

c) 6-{3-[3'-(5-Carbamimidoyl-2-methylsulfanyl-thiophene-3-sulfonyl)-2-(4-methanesulfonyl-butyrylamino)-6-methyl-biphenyl-4-yl]-ureido}-hexanoic acid trifluoroacetate 6-{3-[3'-[5-(tert-Butoxycarbonylamino-imino-methyl)-2-methylsulfanyl-thiophene-3-sulfonyl]-2-(4-methanesulfonyl-butyrylamino)-6-methyl-biphenyl-4-yl]-ureido}-hexanoic acid (45.5 mg, 54.3 µmol, Example 279: step b) was deprotected and purified as in Example 1: step d to afford the title compound as a beige solid (10 mg, 25%). $^1$H-NMR (CD$_3$OD): δ 8.30 (s, 1H), 8.01–8.05 (m, 1H), 7.86–7.89 (m, 1H), 7.68 (t, 1H, J=7.91 Hz), 7.52–7.57 (m, 1H), 7.23–7.37 (m, 2H), 3.23 (t, 2H, J=6.98 Hz), 2.92 (s, 3H), 2.8 (t, 2H, J=7.68 Hz), 2.74 (s, 3H), 2.34 (t, 2H, J=7.44 Hz), 2.18 (t, 2H, J=7.21Hz), 2.05 (s, 3H), 1.72–1.79 (m, 2H), 1.63–1.71 (m, 2H), 1.54–1.62 (m, 2H), 1.39–1.47 (m, 2H). ESI-MS (m/z): Calcd. for $C_{31}H_{39}N_5O_8S_4$: 738.2 (M+1); found: 738.1.

Example 280

4-{2'-Methyl-4'-[N'-(3-phenyl-propyl)-guanidino]-biphenyl-3-sulfonyl}-5-methylsulfanyl-thiophene-2-carboxamidine bistrifluoroacetate

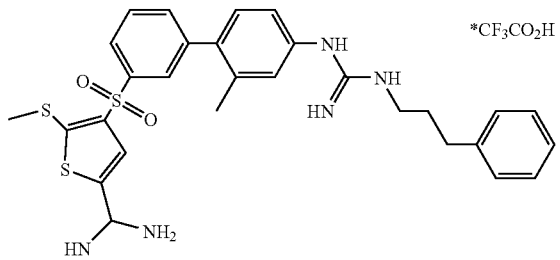

a) 1,3-bis(tert-butoxycarbonyl)-3-(3-phenylpropyl)-2-methyl-2-thiopseudourea

Sodium hydride (95.8 mg, 2.40 mmol, 60% dispersion in mineral oil) was added to a solution of 1,3-bis(tert-butoxycarbonyl)-2-methyl-2-thiopseudourea (580 mg, 2.0 mmol) in DMF (4 mL, anhydrous) at 0° C. in 2 portions. The reaction mixture was stirred for 10 min. at 0° C., then (3-bromo-propyl)-benzene (607 µL, 3.99 mmol) was added and the reaction mixture was heated to 60° C. for 16 hr. The reaction mixture was cooled to rt, diluted in EtOAc, and washed with water and brine. The organic layer was dried over magnesium sulfate. Removal of solvents in vacuo was followed by preparatory TLC (5–10% EtOAc/hexanes) to afford the title compound as a pale yellow oil (310 mg, 38%). $^1$H-NMR (CDCl$_3$): δ 7.16–7.30 (m, 5H), 3.53–3.58 (m, 2H), 2.62–2.66 (m, 2H), 2.38 (s, 3H), 1.95–2.05 (m, 2H), 1.5 (s, 9H), 1.46 (s, 9H).

b) 4-{4'-[N',N''-bis(tert-butoxycarbonyl)-N'-(3-phenyl-propyl)-guanidino]-2'-methyl-biphenyl-3-sulfonyl}-N-methyl-5-methylsulfanyl-thiophene-2-carboxamidine {[4-(4'-Amino-2'-methyl-biphenyl-3-sulfonyl)-5-methylsulfanyl-thiophen-2-yl]-imino-methyl}-carbamic acid tert-butyl ester (40 mg, 77.3 µmol, Example 220: step b) and 1,3-bis(tert-butoxycarbonyl)-3-(3-phenylpropyl)-2-methyl-2-thiopseudourea (63 mg, 0.154 mmol, Example 280: step a) were dissolved in 5% acetic acid/MeOH (1.5 mL) solution and heated to 40° C. overnight. The reaction mixture was cooled to rt and the solvents were removed in vacuo. The crude was purified by preparative TLC (5–10% EtOAc/$CH_2Cl_2$) to afford the title compound as a red oil (26.9 mg, 40%). ESI-MS (m/z): Calcd. For $C_{44}H_{55}N_5O_8S_3$: 878.3 (M+1); found: 877.9.

c) 4-{2'-Methyl-4'-[N'-(3-phenylpropyl)-guanidino]-biphenyl-3-sulfonyl}-5-methylsulfanyl-thiophene-2-carboxamidine bistrifluoroacetate 4-{4'-[N',N''-bis(tert-Butoxycarbonyl)-N'-(3-phenyl-propyl)-guanidino]-2'-methyl-biphenyl-3-sulfonyl}-N-methyl-5-methylsulfanyl-thiophene-2-carboxamidine (26.9 mg, 30.6 µmol, Example 280: step b) was deprotected and purified as in Example 1: step d to afford the title compound as a white solid (11 mg, 62%). $^1$H-NMR (CD$_3$OD): δ 8.34 (s, 1H), 8.00–8.04 (m, 2H), 7.69–7.73 (m, 2H), 7.17–7.34 (m, 8H), 3.30–3.34 (m, 2H), 2.71–2.76 (m, 5H), 2.27 (s, 3H), 1.93–2.02 (m, 2H). ESI-MS (m/z): Calcd. for $C_{29}H_{31}N_5O_2S_3$: 578.2 (M+1); found: 578.2.

Example 281

4-[2'-Methyl-4'-(N'-phenethyl-guanidino)-biphenyl-3-sulfonyl]-5-methylsulfanyl-thiophene-2-carboxamidine bistrifluoroacetate

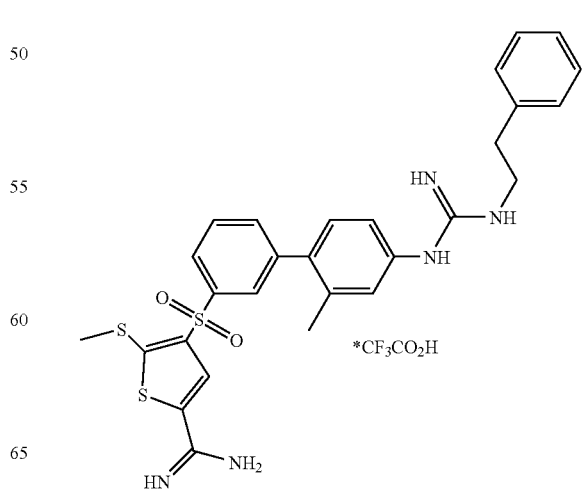

a) 1,3-bis(tert-butoxycarbonyl)-3-(3-phenylethyl)-2-methyl-2-thiopseudourea

The procedure as in Example 280: step a was followed using 1,3-bis(tert-butoxycarbonyl)-2-methyl-2-thiopseudourea (580 mg, 2.0 mmol), NaH (95.8 mg, 2.40 mmol, 60% dispersion in mineral oil), (2-iodo-ethyl)-benzene (578 μL, 3.99 mmol), and DMF (4 mL, anhydrous). The reaction mixture was cooled to rt, diluted in EtOAc, and washed with water and brine. The organic layer was dried over magnesium sulfate. Removal of solvents in vacuo was followed by preparatory TLC (5–10% EtOAc/hexanes) to afford the title compound as a pale yellow oil (146 mg, 19%). $^1$H-NMR (CDCl$_3$): δ 7.18–7.33 (m, 5H), 3.71–3.75 (m, 2H), 2.96–3.01 (m, 2H), 2.37 (s, 3H), 1.51 (s, 9H), 1.49 (s, 9H).

b) ({4-[4'-(N',N''-bis(tert-butoxycarbonyl)-N'-phenethyl-guanidino)-2'-methyl-biphenyl-3-sulfonyl]-5-methylsulfanyl-thiophen-2-yl}-imino-methyl)-carbamic acid tert-butyl ester The procedure as in Example 280: step b was followed using {[4-(4'-amino-2'-methyl-biphenyl-3-sulfonyl)-5-methylsulfanyl-thiophen-2-yl]-imino-methyl}-carbamic acid tert-butyl ester (40 mg, 77.3 μmol, Example 220: step b), 1,3-bis(tert-butoxycarbonyl)-3-(3-phenylethyl)-2-methyl-2-thiopseudourea (61 mg, 0.155 mmol, Example 281: step a), and 5% acetic acid/MeOH (1.5 mL) solution. The reaction mixture was cooled to rt, then concentrated in vacuo. The crude was purified by preparative TLC (5–10% EtOAc/CH$_2$Cl$_2$) to afford the title compound as a red oil (31.5 mg, 47%). ESI-MS (m/z): Calcd. for C$_{43}$H$_{53}$N$_5$O$_8$S$_3$: 864.3 (M+1); found: 863.9.

c) 4-[2'-Methyl-4'-(N'-phenethyl-guanidino)-biphenyl-3-sulfonyl]-5-methylsulfanyl-thiophene-2-carboxamidine bistrifluoroacetate ({4-[4'-(N',N''-bis(tert-butoxycarbonyl)-N'-phenethyl-guanidino)-2'-methyl-biphenyl-3-sulfonyl]-5-methylsulfanyl-thiophen-2-yl}-imino-methyl)-carbamic acid tert-butyl ester (31.5 mg, 36.5 μmol, Example 281: step b) was deprotected and purified as in Example 1: step d to afford the title compound as a white solid (14.2 mg, 68.9%). $^1$H-NMR (CD$_3$OD): δ 8.34 (s, 1H), 7.99–8.05 (m, 2H), 7.65–7.72 (m, 2H), 7.24–7.39 (m, 6H), 7.03–7.09 (m, 2H), 3.60 (t, 2H, J=7.02 Hz), 2.96 (t, 2H, J=7.02 Hz), 2.72 (s, 3H), 2.23 (s, 3H). ESI-MS (m/z): Calcd. for C$_{28}$H$_{29}$N$_5$O$_2$S$_3$: 564.2 (M+1); found: 564.2.

Example 282

4-{2'-Methyl-4'-[N'-(3-methyl-butyl)-guanidino]-biphenyl-3-sulfonyl}-5-methylsulfanyl-thiophene-2-carboxamidine bistrifluoroacetate

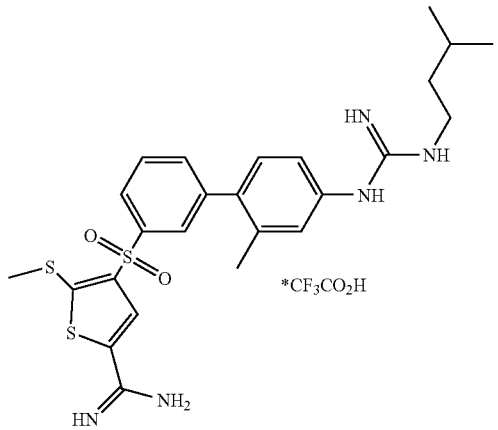

*CF$_3$CO$_2$H a) 1,3-bis(tert-butoxycarbonyl)-3-(3-phenylethyl)-2-methyl-2-thiopseudourea

The procedure as in Example 280: step a was followed using 1,3-bis(tert-butoxycarbonyl)-2-methyl-2-thiopseudourea (580 mg, 2.0 mmol), NaH (95.8 mg, 2.40 mmol, 60% dispersion in mineral oil), 1-iodo-3-methylbutane (528 μL, 3.99 mmol), and DMF (4 mL, anhydrous). The reaction mixture was cooled to rt, diluted in EtOAc, and washed with water and brine. The organic layer was dried over magnesium sulfate. Removal of solvents in vacuo was followed by preparatory TLC (5–10% EtOAc/hexanes) to afford the title compound as a pale yellow oil (235 mg, 33%). $^1$H-NMR (CDCl$_3$): δ 3.49–3.56 (m, 2H), 2.39 (s, 3H), 1.52–1.60 (m, 3H), 1.51 (s, 9H), 1.48 (s, 9H), 0.89–0.94 (m, 6H).

b) 4-{4'-[N',N''-bis(tert-butoxycarbonyl)-N'-(3-methyl-butyl)-guanidino]-2'-methyl-biphenyl-3-sulfonyl}-N-tert-butoxycarbonyl-5-methylsulfanyl-thiophene-2-carboxamidine The procedure as in Example 280: step b was followed using {[4-(4'-amino-2'-methyl-biphenyl-3-sulfonyl)-5-methylsulfanyl-thiophen-2-yl]-imino-methyl}-carbamic acid tert-butyl ester (40 mg, 77.3 μmol, Example 220: step b), 1,3-bis(tert-butoxycarbonyl)-1-(3-methylbutyl)-2-methyl-2-thiopseudourea (56 mg, 0.155 mmol, Example 282: step a), and 5% acetic acid/MeOH (1.5 mL) solution. The reaction mixture was cooled to rt, then concentrated in vacuo. The crude was purified by preparative TLC (5–10% EtOAc/CH$_2$Cl$_2$) to afford the title compound as a red oil (29.2 mg, 46%). ESI-MS (m/z): Calcd. for C$_{40}$H$_{55}$N$_5$O$_8$S$_3$: 830.3 (M+1); found: 829.9.

c) 4-{2'-Methyl-4'-[N'-(3-phenyl-propyl)-guanidino]-biphenyl-3-sulfonyl}-5-methylsulfanyl-thiophene-2-carboxamidine bistrifluoroacetate 4-{4'-[N',N''-bis(tert-Butoxycarbonyl)-N'-(3-methyl-butyl)-guanidino]-2'-methyl-biphenyl-3-sulfonyl}-N-tert-butoxycarbonyl-5-methylsulfanyl-thiophene-2-carboxamidine (29.2 mg, 35.2 µmol, Example 282: step b) was deprotected and purified as in Example 1: step d to afford the title compound as a white solid (13.6 mg, 73%). $^1$H-NMR (CD$_3$OD): δ 8.34 (s, 1H), 8.00–8.05 (m, 2H), 7.67–7.73 (m, 2H), 7.18–7.34 (m, 3H), 3.30–3.34 (m, 2H), 2.72 (s, 3H), 2.27 (s, 3H), 1.66–1.79 (m, 1H), 1.52–1.59 (m, 2H), 0.99 (d, 6H, J=6.64 Hz). ESI-MS (m/z): Calcd. for C$_{25}$H$_{31}$N$_5$O$_2$S$_3$: 530.2 (M+1); found: 530.2.

Example 283

4-(5-{3-[3'-(5-Carbamimidoyl-2-methylsulfanyl-thiophene-3-sulfonyl)-4-guanidino-6-methyl-biphenyl-2-yl]-ureido}-pentyloxy)-benzoic acid bistrifluoroacetate

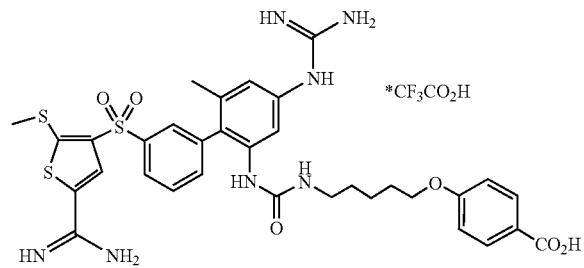

a) 4-[5-(1,3-Dioxo-1,3-dihydro-isoindol-2-yl)-pentyloxy]-benzoic acid methyl ester A mixture of 4-hydroxy-benzoic acid methyl ester (3.01 g, 19.8 mmol), 2-(5-bromo-pentyl)-isoindole-1,3-dione (3.9 g, 13.2 mmol), and K$_2$CO$_3$ (1.82 g, 13.2 mmol) in acetone (150 mL) was heated to reflux for 24 hrs. The reaction mixture was cooled to rt and the solvents were removed in vacuo. The crude was diluted in EtOAc and washed with 1N NaOH and brine. The organic layer was dried over sodium sulfate. The solvents were removed in vacuo. The crude was recrystallized from EtOAc to afford the title compound as a white solid (4 g, 83%). $^1$H-NMR (CDCl$_3$): δ 7.95–7.98 (m, 2H), 7.83–7.86 (m, 2H), 7.70–7.73 (m, 2H), 6.86–6.89 (m, 2H), 4.00 (t, 2H, J=6.22 Hz), 3.88 (s, 3H), 3.73 (t, 2H, J=7.29 Hz), 1.82–1.89 (m, 2H), 1.73–1.81 (m, 2H), 1.50–1.57 (m, 2H).

b) 4-(5-Amino-pentyloxy)-benzoic acid methyl ester

A suspension of 4-[5-(1,3-dioxo-1,3-dihydro-isoindol-2-yl)-pentyloxy]-benzoic acid methyl ester (1 g, 2.72 mmol, Example 283. step a) and hydrazine (98.4 µL, 3.13 mmol) in MeOH:H2O (10 mL, 4:1) was heated to 65° C. for 2 hrs. Additional hydrazine was added (171 µL, 5.44 mmol) to the reaction mixture at rt. The reaction mixture was heated to 70° C. for 2 hrs then stirred overnight at rt. Potassium carbonate (30 mL, 1N aqueous) and methylene chloride (200 mL) were added to the reaction. The organic layer was dried over magnesium sulfate. The solvents were removed in vacuo to afford the title compound as a white solid (500 mg, 77%). $^1$H-NMR (CDCl$_3$): δ 7.95–8.00 (m, 2H), 6.88–6.92 (m, 2H), 4.02 (t, 2H, J=6.43 Hz), 3.88 (s, 3H), 2.71–2.76 (m, 2H), 1.79–1.86 (m, 2H), 1.49–1.56 (m, 4H).

c) 4-(5-{3-[3'-[5-(tert-Butoxycarbonylamino-iminomethyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid methyl ester 4-Nitrophenyl chloroformate (99.2 mg, 0.49 mmol) was added to a solution of {2-amino-3'-[5-(tert-butoxycarbonylamino-imino-methyl)-2-methylsulfanyl-thiophene-3-sulfonyl]-6-methyl-biphenyl-4-yl}-carbamic acid 2-trimethylsilanyl-ethyl ester (303 mg, 0.45 mmol, Example 294: step f) and pyridine (39.8 µL, 0.49 mmol) in methylene chloride (5 mL) at rt. The reaction mixture was stirred for 2 hrs at rt. 4-(5-Amino-pentyloxy)-benzoic acid methyl ester (117 mg, 0.49 mmol, Example 283: step b) and triethylamine were added to the reaction mixture and stirred for 2 hrs at rt. The reaction mixture was diluted in EtOAc, washed with water and brine, and dried over magnesium sulfate. Removal of solvents in vacuo was followed by flash chromatography (50–60% EtOAc/hexanes) to afford the title compound as a yellow solid (280 mg, 66.5%). ESI-MS (m/z): Calcd. for C$_{44}$H$_{57}$N$_5$O$_{10}$S$_3$Si: 940.3 (M+1); found: 939.9.

d) 4-(5-{3-[3'-[5-(tert-Butoxycarbonylamino-iminomethyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid Lithium hydroxide (45.8 mg, 2.08 mmol) was added to a solution of 4-(5-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid methyl ester (280 mg, 0.298 mmol, Example 283: step c) in 1,4-dioxane:water (10 mL, 2:1) over 2 days at rt. The solvents were removed in vacuo. The residue was diluted in water, acidified to pH~5 with acetic acid, and extracted with EtOAc. The organic layer was washed with brine and dried over magnesium sulfate. The solvents were removed in vacuo to afford the title compound as a yellow solid (276 mg, quantitative). $^1$H-NMR (CDCl$_3$/CD$_3$OD): δ 7.93–7.99 (m, 3H), 7.83–7.86 (m, 2H), 7.52–7.59 (m, 2H), 7.15–7.20 (m, 2H), 6.85–6.89 (m, 2H), 4.21–4.26 (m, 2H), 3.99 (t, 2H, J=6.43 Hz), 3.13–3.24 (m, 2H), 2.61 (s, 3H), 2.02 (s, 3H), 1.75–1.83 (m, 2H), 1.43–1.56 (m, 13H), 1.02–1.08 (m, 2H), 0.07 (s, 9H).

e) 4-[5-(3-{4-Amino-3'-[5-(tert-butoxycarbonylamino-imino-methyl)-2-methylsulfanyl-thiophene-3-sulfonyl]-6-methyl-biphenyl-2-yl}-ureido)-pentyloxy]-benzoic acid Tetrabutyl ammonium fluoride solution (2.38 mL, 1M in THF) was added to a solution of 4-(5-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid (276 mg, 0.298 mmol, Example 283: step d) in THF (10 mL) over 2 days at 35° C. The solvents were removed in vacuo. The residue was diluted in EtOAc, washed with water and brine, and dried over magnesium sulfate. The solvents were removed in vacuo to afford the title compound as a brown solid (300 mg, quantitative). ESI-MS (m/z): Calcd. for C$_{37}$H$_{44}$N$_5$O$_8$S$_3$: 782.2 (M+1); found: 781.8.

f) 4-(5-{3-[3'-[5-(tert-Butoxycarbonylamino-imino-methyl)-2-methylsulfanyl-thiophene-3-sulfonyl]-4-(N',N''-bis(tertbutoxycarbonyl)-guanidino)-6-methyl-biphenyl-2-yl]-ureido}-pentyloxy)-benzoic acid 1,3-bis(tert-Butoxycarbonyl)-2-methyl-2-thiopseudourea (433 mg, 1.49 mmol) was added to a solution of 4-[5-(3-{4-amino-3'-[5-(tert-butoxycarbonylamino-imino-methyl)-2-methylsulfanyl-thiophene-3-sulfonyl]-6-methyl-biphenyl-2-yl}-ureido)-pentyloxy]-benzoic acid (233 mg, 0.298 mmol, Example 283: step e) in 5% AcOH/MeOH (10 mL) over 2 days at 35° C. The solvents were removed in vacuo and the residue was purified by flash chromatography (1–6% MeOH/methylene chloride) to afford the title compound as a yellow solid (70 mg, 23%). ESI-MS (m/z): Calcd. for $C_{48}H_{61}N_7O_{12}S_3$: 1024.4 (M+1); found: 1024.0.

g) 4-(5-{3-[3'-(5-Carbamimidoyl-2-methylsulfanyl-thiophene-3-sulfonyl)-4-guanidino-6-methyl-biphenyl-2-yl]-ureido}-pentyloxy)-benzoic acid bistrifluoroacetate 4-(5-{3-[3'-[5-(tert-Butoxycarbonylamino-imino-methyl)-2-methylsulfanyl-thiophene-3-sulfonyl]-4-(N',N''-bis(tert-butoxycarbonyl)-guanidino)-6-methyl-biphenyl-2-yl]-ureido}-pentyloxy)-benzoic acid (15 mg, 14.6 µmol, Example 283: step f) was deprotected and purified as in Example 1: step d to afford the title compound as a white solid (4.2 mg, 39.6%). $^1$H-NMR (CD$_3$CN/D$_2$O): δ 8.19 (s, 1H), 7.98–8.03 (m, 1H), 7.90–7.95 (m, 2H), 7.80–7.83 (m, 1H), 7.69–7.74 (m, 1H), 7.49–7.55 (m, 2H), 6.93–6.97 (m, 3H), 4.01 (t, 2H, J=6.43 Hz), 2.88–3.03 (m, 2H), 2.64 (s, 3H), 1.94–1.97 (m, 3H), 1.66–1.73 (m, 2H), 1.29–1.37 (m, 4H). ESI-MS (m/z): Calcd. for $C_{33}H_{37}N_7O_6S_3$: 724.2 (M+1); found: 724.2.

Example 284

4-(4-Amino-3-bromo-benzenesulfonyl)-5-methylsulfanyl-thiophene-2-carboxamidine

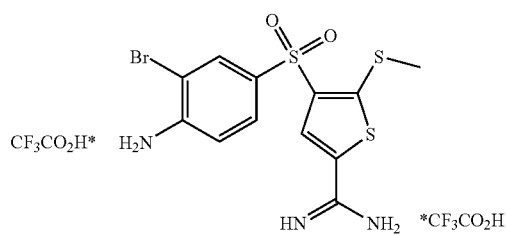

The reaction conditions in Example 12: step f were followed using 4-(4-amino-3-bromo-benzenesulfonyl)-5-methylsulfanyl-thiophene-2-carboxylic acid amide ((Example 319: step d) 50 mg, 0.12 mmol) and dimethylaluminum amide reagent (5 mL). Analogous workup and HPLC purification yielded the title compound as an off-white solid (26 mg, 34%). $^1$H-NMR (CD$_3$OD): δ 8.23 (s, 1H), 7.96 (d, 1H, J=2.1 Hz), 7.67 (dd, 1H, J=2.1, 8.6 Hz), 6.85 (d, 1H, J=8.6 Hz), 2.71 (s, 3H). ESI-MS (m/z): Calcd. for $C_{12}H_{12}BrN_3O_2S_3$ (M+H): 405.9; found: 405.9, 407.9 (m+2).

Example 285

[3'-(5-Carbamimidoyl-2-methylsulfanyl-thiophene-3-sulfonyl)-2,6-dimethyl-biphenyl-4-yloxymethyl]-phosphonic acid

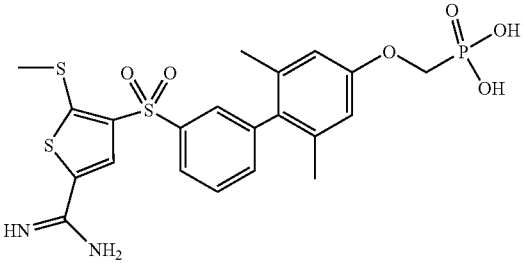

To a flask containing {[4-(4'-hydroxy-2',6'-dimethyl-biphenyl-3-sulfonyl)-5-methylsulfanyl-thiophen-2-yl]-iminomethyl}-carbamic acid tert-butyl ester ((Example 224: step b) 233 mg, 0.42 mmol), Cs$_2$CO$_3$ (137 mg, 0.42 mmol), DMF (2 mL), and trifluoro-methanesulfonic acid diethoxy-phosphorylmethyl ester (200 mg, 0.67 mmol, (Xu, Y. et al J. Org. Chem. 61, 7697 (1996); Phillion, D. et al Tetrahedron Lett. 27, 1477 (1986)) were added and heated to 50 C. This mixture was heated and stirred for 18 h under an Ar atmosphere. DMF was removed under vacuum and the residue was taken in EtOAc and washed with water and saturated NaCl. The EtOAc layer was separated dried over Na$_2$SO$_4$ and evaporated under vacuum to give an oil. This was purified by preparative thin-layer chromatography (EtOAc/Hexane) to give 94 (33%) of {3'-[5-(tert-butoxycarbonylamino-imino-methyl)-2-methylsulfanyl-thiophene-3-sulfonyl]-2,6-dimethyl-biphenyl-4-yloxymethyl}-phosphonic acid diethyl ester as a white solid. This solid was dissolved in dichloromethane (2 mL), and cooled in an ice bath. To this iodotrimethylsilane (Aldrich Chemical Company, 60 µL) was added and the mixture was stirred for 1 h at which time the dichloromethane was removed and the residue was taken in MeOH and treated with 6N HCl. This mixture was stirred for 3 h and the solvents were removed under high vacuum. To this residue a 50% solution of TFA in dichloromethane was added and the mixture was stirred for 1 h. TFA and dichloromethane were removed under vacuum and the residue was purified by preparative HPLC (Rev. Phase acetonitrile/water) which yielded the title compound as a white solid (30 mg, 33%). $^1$H-NMR (CD$_3$OD): δ 7.8–7.7 (m, 2H), 7.62 (s, 1H), 7.5–7.3 (m, 2H), 6.7 (s, 2H), 3.77 (d, 2H, J=9.8 Hz), 2.44 (s, 3H), 1.74 (s, 6 H). ESI-MS (m/z): Calcd. for $C_{21}H_{23}N_2O_6PS_3$: 527.1 (M+H); found: 527.1.

Example 286

5-Methylsulfanyl-4-(3-piperidin-1-yl-benzenesulfonyl)-thiophene-2-carboxamidine

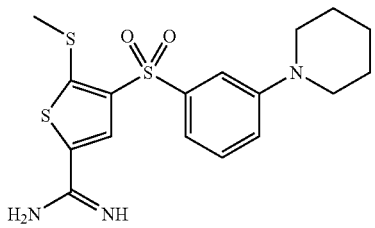

a) 4-Bromo-5-nitro-thiophene-2-carbaldehyde

A solution of potassium nitrate (110 g, 1.09 mol) in $H_2SO_4$ (550 mL, conc.) was added to a solution of 4-bromo-thiophene-2-carbaldehyde (207.6 g, 1.08 mol) in $H_2SO_4$ (1.1 L, conc.) at $CH_2Cl_2$ (5 mL, anhydrous) at 0° C. over a 45 minute period. The reaction mixture was stirred 0° C. for 2 hrs, then stirred overnight at rt. The reaction mixture was poured over ice, filtered, and washed with water and hexanes. The yellow solid was dried overnight to afford the title compound (251.4 g, 98.6%). $^1$H-NMR (DMSO-$d_6$): δ 9.90 (s, 1H), 8.56 (s, 1H).

b) 4-Bromo-5-nitro-thiophene-2-carbaldehyde oxime

Hydroxylamine hydrochloride (85 g, 1.2 mol) was added to a solution of 4-bromo-5-nitro-thiophene-2-carbaldehyde (234 mg, 0.529 mmol, Example 286: step a) in EtOH (7.5 mL, 200 proof—anhydrous):pyridine (100 mL, anhydrous) at rt over 5 min. The reaction mixture was heated to reflux overnight, then cooled to rt. The solvents were removed in vacuo resulting in a solid residue that was washed with water and filtered. The solid was dried overnight under high vacuum to afford the title compound as a yellow solid (225 g, 88%). The solid was used for the next step without further characterization.

c) 4-Bromo-5-nitro-thiophene-2-carbonitrile

A mixture of 4-bromo-5-nitro-thiophene-2-carbaldehyde oxime (216 g, 0.86 mol, Example 286: step b) and acetic anhydride (1 L, 10.6 mol) was heated to reflux for 4 hrs. The reaction mixture was cooled to rt and the solvents were removed in vacuo. The crude reaction mixture was diluted in methylene chloride and washed with water. The organic layer was dried over magnesium sulfate and concentrated in vacuo resulting in a residue, which was stirred in diethyl ether/hexanes and filtered to afford the title compound as a yellow solid (170.2 g, 85%). $^1$H-NMR (DMSO-$d_6$): δ 8.25 (s, 1H).

d) 4-(3-Bromo-phenylsulfanyl)-5-nitro-thiophene-2-carbonitrile

Triethylamine (104 mL, 0.75 mol) was slowly added to a solution of 4-bromo-5-nitro-thiophene-2-carbonitrile (165 g, 0.708 mol, Example 286: step c) and 3-bromo-benzenethiol (78 mL, 0.76 mmol) in THF (1.2 L) at rt for 2 days. The solvents were removed in vacuo and the resulting residue was diluted in EtOAc, washed with saturated $Na_2CO_3$ solution, and dried over magnesium sulfate. The solvents were removed in vacuo and the residue was stirred in diethyl ether :hexanes (1:5) and filtered to afford the title compound as a yellow solid (232.7 g, 96%). $^1$H-NMR (DMSO-$d_6$): δ 7.88–7.92 (m, 1H), 7.65–7.81 (m, 2H), 7.48–7.54 (m, 1H), 7.22 (s, 1H).

e) 4-(3-Bromo-benzenesulfonyl)-5-nitro-thiophene-2-carbonitrile

A solution of mCPBA (26.3 g, 11.7 mol, 77%) in 1,2-dichloroethane was added to a solution of 4-(3-bromo-phenylsulfanyl)-5-nitro-thiophene-2-carbonitrile (10 g, 29.3 mmol, Example 286: step d) in 1,2-dichloroethane (200 mL) at rt over 30 min. The reaction mixture was heated to reflux for 2.5 hrs then cooled to rt. The reaction mixture was washed with 0.5 N NaOH and water and the organic layers were dried over magnesium sulfate. The solvents were removed in vacuo. The residue was stirred in diethyl ether, filtered, and dried under high vacuum to afford the title compound as a yellow solid (6.9 g, 63%). $^1$H-NMR (DMSO-$d_6$): δ 8.53 (s, 1H), 8.14–8.16 (m, 1H), 7.98–8.05 (m, 2H), 7.62–7.67 (m, 1H).

f) 4-(3-Bromo-benzenesulfonyl)-5-methylsulfanyl-thiophene-2-carbonitrile

A solution of sodium thiomethoxide (1.87 g, 26.8 mmol) in EtOH (26.8 mL, anhydrous) was added to a suspension of 4-(3-bromo-benzenesulfonyl)-5-nitro-thiophene-2-carbonitrile (10 g, 26.8 mmol, Example 286: step e) in THF (67 mL, anhydrous) portionwise at −78° C. The temperature of the reaction was maintained at −78° C. with stirring for 1 hour. The reaction was quenched with acetic acid (2 mL, 34.9 mmol) at −78° C. followed by warming the reaction mixture to rt and then filtered. The yellow solids were washed with diethyl ether and saved. The filtrate was concentrated in vacuo resulting in a residue that was suspended in diethyl ether and stirred at rt overnight. The solids were filtered from the suspension. The combined yellow solids were dried under high vacuum to afford the title compound (8.77 g, 87.4%). $^1$H-NMR (DMSO-$d_6$): δ 8.45 (s, 1H), 7.97–8.16 (m, 3H), 7.62–7.67 (m, 1H), 2.71 (s, 3H).

g) 5-Methylsulfanyl-4-(3-piperidin-1-yl-benzenesulfonyl)-thiophene-2-carbonitrile A mixture of 4-(3-Bromo-benzenesulfonyl)-5-methylsulfanyl-thiophene-2-carbonitrile (Example 286: step f, 200 mg, 0.534 mmol), piperidine (56 mg, 0.64 mmol), Pd(OAc)$_2$ (24 mg, 0.11 mmol), BINAP (100 mg, 0.16 mmol) and Cs$_2$CO$_3$ in 2 mL of toluene under Ar was stirred at 150° C. for 16 h, then cooled to RT. The mixture was purified directly by PTLC (30% EtOAc/hexane) to give 20 mg of product as a light yellow oil: $^1$H-NMR (CDCl$_3$; 400 MHz) δ 7.68 (m, 1H), 7.67 (s, 1H), 7.54–7.52 (m, 1H), 7.39–7.32 (m, 2H), 3.16–3.12 (m, 4H), 2.45 (s, 3H), 1.64–1.59 (m, 4H), 1.55–1.50 (m, 2H). Mass spectrum (ESI, m/z): Calcd. for $C_{17}H_{18}N_2O_2S_3$, 379.1 (M+H), found 379.3.

h) {Imino-[5-methylsulfanyl-4-(3-piperidin-1-yl-benzenesulfonyl)-thiophen-2-yl]-methyl}-carbamic acid tert-butyl ester To a solution of carbamic acid tert-butyl ester (8 mg, 0.069 mmol, Aldrich Chemical Company) in 1 mL of THF at −78° C. was added 35 μL of n-BuLi under Ar. The mixture was stirred at −78° C. for 15 min. A solution of 5-methylsulfanyl-4-(3-piperidin-1-yl-benzenesulfonyl)-thiophene-2-carbonitrile (20 mg, 0.053 mmol, Example 286: step g) in 1 mL of THF was added. The resulting mixture was stirred at RT for 5 h, then at 50° C. overnight. Cooled to RT, the mixture was purified directly by PTLC (20% EtOAc/hexane) to give 10 (38%) of product as colorless oil: $^1$H-NMR (CDCl$_3$; 400 MHz) δ 8.42 (s, 1H), 7.74 (dd, 1H, J=1.6, 1.6 Hz), 7.67 (s, 1H), 7.62 (ddd, 1H, J=7.5, 1.6, 1.6 Hz), 7.57 (d, 1H, J=7.5, 1.6, 1.6 Hz), 7.52 (dd, 1H, J=7.5, 7.5), 3.42–3.40 (m, 4H), 2.54 (s, 3H), 1.64 (br s, 6H), 1.61 (s, 9H). Mass spectrum (ESI, m/z): Calcd. for $C_{22}H_{29}N_3O_4S_3$, 496.1 (M+H), found 495.9.

i) 5-Methylsulfanyl-4-(3-piperidin-1-yl-benzene-sulfonyl)-thiophene-2-carboxamidine To a solution of 5-methylsulfanyl-4-(3-piperidin-1-yl-benzenesulfonyl)-thiophene-2-carboxamidine (10 mg, 0.020 mmol, Example 286: step h) in 1 mL of $CH_2Cl_2$ under Ar at 0° C. was added 5 drops (~200 ul) of TFA. The mixture was stirred at 0° C. for 1 h. Removal of the solvent under reduced pressure followed by flash chromatography of the residue on silica gel (5% $MeOH/CH_2Cl_2$) gave 7.5 (77%) of product as colorless oil: $^1$H-NMR ($CD_3OD$, 400 MHz) δ 8.25 (s, 1H), 7.76 (dd, 1H, J=1.6, 1.6 Hz), 7.62 (ddd, 1H, J=7.5, 1.6, 1.6 Hz), 7.56 (ddd, 1H, J=7.5, 1.6, 1.6 Hz), 7.51 (dd, 1H, J=7.5, 7.5), 3.31–3.30 (m, 4H), 2.54 (s, 3H), 1.57–1.56 (m, 6H). Mass spectrum (ESI, m/z): Calcd. for $C_{17}H_{21}N_3O_2S_3$ mg, 396.1 (M+H), found 396.2.

Example 287

5-Methylsulfanyl-4-{3-[5-methyl-1-(2-trimethylsilanyl-ethoxymethyl)-1H-benzoimidazol-4-yl]-benzenesulfonyl}-thiophen-2-carboxamidine

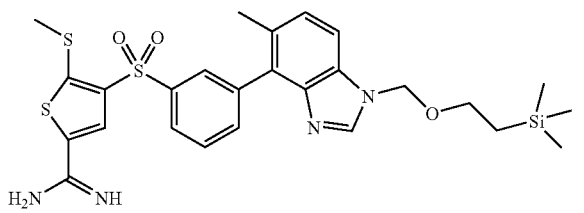

a) 4-Iodo-5-methyl-1H-benzoimidazole

A solution of 5-methyl-1H-benzoimidazole (132 mg, 1.0 mmol) and NIS (248 mg, 1.10 mmol) in 1 mL of TFA was reflux for 1 hr and then cooled to RT. Treated with 30 mL of EtOAc, the mixture was neutralized with sat. $NaHCO_3$ solution. The organic layer was washed with $H_2O$ (10 mL), brine (10 mL) and dried ($Na_2SO_4$). Removal of the solvent under reduced pressure followed by flash chromatography of the residue on silica gel (5% $MeOH/CH_2Cl_2$) gave 78 (30%) of product as a white solid: $^1$H-NMR ($CDCl_3$; 400 MHz) δ 8.07 (d, 1H), 7.57 (br s, 1H), 7.22 (d, 1H, J=8.4 Hz), 2.59 (s, 3H). Mass spectrum (ESI, m/z): Calcd. for $C_8H_7IN_2$, 259.0 (M+H), found 259.2.

b) 4-Iodo-5-methyl-1-(2-trimethylsilanyl-ethoxymethyl)-1H-benzoimidazole

To a solution of 4-Iodo-5-methyl-1H-benzoimidazole (100 mg, 0.39 mmol, Example 287: step a) and SEMCl (71 mg 0.43 mmol) in 2 mL of DMF under Ar was added NaH (11 mg, 0.43 mmol). The mixture was stirred at RT for 4 h and purified directly by PTLC (25% EtOAc/hexane) to give 122 mg (81%) of product as a colorless oil: $^1$HMR ($CDCl_3$; 400 MHz) δ 7.95 (s, 1H), 7.37 (d, 1H, J=8.4 Hz), 7.21 (d, 1H, J=8.4 Hz), 5.48 (s, 2H), 3.47 (t, 2H, J=8.3 Hz), 2.59 (s, 3H), 0.89 (t, 2H, J=8.3 Hz), –0.06 (s, 9H). Mass spectrum (ESI, m/z): Calcd. for $C_{14}H_{21}IN_2OSi$, 389.1 (M+H), found 389.0.

c) [Imino-(5-methylsulfanyl-4-{3-[5-methyl-1-(2-trimethylsilanyl-ethoxymethyl)-1H-benzoimidazol-4-yl]-benzenesulfonyl}-thiophen-2-yl)-methyl]-carbamic acid tert-butyl ester A mixture of {[4-(3-dihydroxyboranyl-benzenesulfonyl)-5-methylsulfanyl-thiophen-2-yl]-imino-methyl}-carbamic acid tert-butyl ester. (20 mg, 0.044 mmol, Example 140: step a), 4-Iodo-5-methyl-1-(2-trimethylsilanyl-ethoxymethyl)-1H-benzoimidazole (21 mg, 0.054 mmol, Example 287: step b) and $Pd(PPh_3)_4$ in 1.2 mL of 1:1:2 $EtOH/2M\ Na_2CO_3$/toluene was stirred at 90° C. for 5 h, the cooled to RT. Treated with 3 mL of $H_2O$, the mixture was extracted with EtOAc (3×5 mL)/Removal of the solvent under reduced pressure followed by flash chromatography of the residue on silica gel (30% EtOAc/hexane) gave 21 (71%) of product as a light yellow solid: $^1$H-NMR ($CDCl_3$; 400 MHz) δ 8.42 (s, 1H). 8.08 (s, 1H), 8.05 (s, 1H), 8.01 (ddd, 1H, J=7.2, 1.8, 1.7 Hz), 7.71–7.67 (m, 2H), 7.57 (d, 1H, J=8.4 Hz), 7.39 (d, 1H, J=8.7 Hz), 5.64 (s, 2H), 3.57 (t, 2H, J=8.3 Hz), 2.61 (s, 3H), 2.33 (s, 3H), 1.51 (s, 9H), 0.95 (t, 2H, J=8.3), –0.03 (s, 9H).). Mass spectrum (ESI, m/z): Calcd. for $C_{31}H_{40}N_4O_5S_3Si$, 673.2, (M+H), found 672.9.

d) 5-Methylsulfanyl-4-{3-[5-methyl-1-(2-trimethylsilanyl-ethoxymethyl)-1H-benzoimidazol-4-yl]-benzenesulfonyl}-thiophen-2-carboxamidine To a solution of [Imino-(5-methylsulfanyl-4-{3-[5-methyl-1-(2-trimethylsilanyl-ethoxymethyl)-1H-benzoimidazol-4-yl]-benzenesulfonyl}-thiophen-2-yl)-methyl]-carbamic acid tert-butyl ester (7 mg, 0.01 mmol, Example 287: step c) in 0.7 mL of $CH_2Cl_2$ was added 0.3 mL of TFA. The resulting solution was stirred at RT for 1 h. Removal of the solvent under reduced pressure followed by flash chromatography of the residue on silica gel (5–10% $MeOH/CH_2Cl_2$) gave 6 (84%) of product as colorless oil: $^1$H-NMR ($CD_3OD$; 400 MHz) δ 8.84 (s, 1H). 8.32 (s, 1H), 8.14 (ddd, 1H, J=7.6, 1.6, 1.6 Hz). 8.08 (s, 1H), 7.83–7.77 (m, 3H), 7.52 (d, 1H, J=8.4 Hz), 5.79 (s, 2H), 3.65 (t, 2H, J=8.0 Hz), 2.72 (s, 3H), 2.29 (s, 3H), 0.93 (t, 2H, J=8.0 Hz), –0.04 (s, 9H). Mass spectrum (ESI, m/z): Calcd. for $C_{26}H_{32}N_4O_3S_3Si$, 573.1, (M+H), found 573.0.

Example 288

4-[3-(5-Methyl-1H-benzoimidazol-4-yl)-benzenesulfonyl]-5-methylsulfanyl-thiophene-2-carboxamidine A solution of [Imino-(5-methylsulfanyl-4-{3-[5-methyl-1-(2-trimethylsilanyl-ethoxymethyl)-1H-benzoimidazol-4-yl]-benzenesulfonyl}-thiophen-2-yl)-methyl]-carbamic acid tert-butyl ester (14 mg, 0.021 mmol, Example 287: step c) in 1 mL of TFA was heated at 50° C. for 2 h under Ar, cooled to RT. Removal of the solvent under reduced pressure followed by flash chromatography of the residue on silica gel (10–15% $MeOH/CH_2Cl_2$) gave 14 (100%) of product as colorless oil: $^1$H-NMR ($CD_3OD$; 400 MHz) δ 9.28 (s, 1H). 8.35 (s, 1H), 8.20 (d, 1H, J=7.6 Hz). 8.11 (s, 1H), 7.86 (dd, 1H, J=7.7, 7.7), 7.80 (m, 2H), 7.63 (d, 1H, J=8.6 Hz), 2.72 (s, 3H), 2.30 (s, 3H). Mass spectrum (ESI, m/z): Calcd. for $C_{20}H_{18}N_4O_2S_3$, 443.1.00 (M+H), found 443.1.

Example 289

4-[3-(3-Methyl-5-nitro-pyridin-2-yl)-benzenesulfonyl]-5-methylsulfanyl-thiophene-2-carboxamidine. TFA Salt a) (Imino-{4-[3-(3-methyl-5-nitro-pyridin-2-yl)-benzenesulfonyl]-5-methylsulfanyl-thiophen-2-yl}-methyl)-carbamic acid tert-butyl ester A solution of {[4-(3-dihydroxyboranyl-benzenesulfonyl)-5-methylsulfanyl-thiophen-2-yl]-imino-methyl}-carbamic acid tert-butyl ester (0.058 mmol, 40 mg, Example 140: step a), 2-iodo-3-methyl-5-nitropyridine (0.08 mmol, 21.1), CuI (0.01 mmol, 2.2) and (Ph$_3$P)$_4$Pd (0.006 mmol) in DMF (0.6 mL) was heated at 100° under Ar for 3 hr. The reaction mixture was allowed to cool to RT and poured in to water (20 mL). The product was extracted with CH$_2$Cl$_2$ (3×10 mL). CH$_2$Cl$_2$ extracts were combined, dried (Na$_2$SO$_4$) and concentrated in vaccuo. The resulting residue was purified on silica (30% EtOAc:Hexane) to obtain (Imino-{4-[3-(3-methyl-5-nitro-pyridin-2-yl)-benzenesulfonyl]-5-methylsulfanyl-thiophen-2-yl}-methyl)-carbamic acid tert-butyl ester. Yield: 48%; $^1$H NMR (CDCl$_3$) δ 9.36 (br, 1H), 8.37 and 8.25 (s, 1H each), 8.1 and 7.8 (d, J=2.4 Hz, 1H each), 7.93 (s, 1H), 7.74 (t, J=6.8 Hz, 1H), 2.7 and 2.5 (s, 3H each), 1.35 (s, 9H)

b) 4-[3-(3-Methyl-5-nitro-pyridin-2-yl)-benzenesulfonyl]-5-methylsulfanyl-thiophene-2-carboxamidine. TFA Salt (Imino-{4-[3-(3-methyl-5-nitro-pyridin-2-yl)-benzenesulfonyl]-5-methylsulfanyl-thiophen-2-yl}-methyl)-carbamic acid tert-butyl ester (20 mg, Example 289: step a) was then dissolved in 1:1 mixture of CH$_2$Cl$_2$ and TFA (1 mL). The resulting solution was stirred at RT for 1 hr. and concentrated in vaccuo to obtain a yellow oil which was dried in a high vaccum. Ether (10 mL) was then added and the precipitate formed was collected by suction filtration to yield 4-[3-(3-Methyl-5-nitro-pyridin-2-yl)-benzenesulfonyl]-5-methylsulfanyl-thiophene-2-carboxamidine. TFA salt.

Yield: 78%; $^1$H NMR (DMSO) δ 9.36 (br, 2H), 9.31 (d, J=2.4 Hz, 1H), 8.75 (brs, s), 8.65 (d, J=2.4 Hz, 1H), 8.45 (s, 1H), 8.20 (m, 1H), 8.13 and 8.06 (d, J=6.6 Hz, 1H each), 7.84 (t, J=6.7 Hz, 1H), 2.7 and 2.4 (s, 3H each); MS 448.03 (M$^+$) calculated for C$_{18}$H$_{16}$N$_4$O$_4$S$_3$; found 449.1 (M$^+$+1)

Example 290

4-[3-(5-Amino-3 methyl-pyridin-2-yl)-benzenesulfonyl]-5-methylsulfanyl-thiophene-2-carboxamidine. TFA Salt

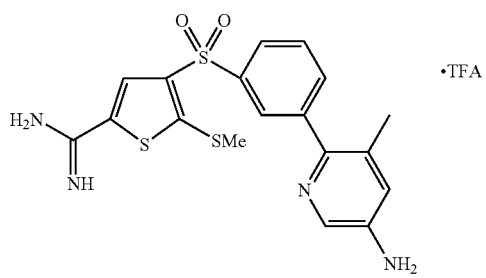

A solution of {[4-(3-dihydroxyboranyl-benzenesulfonyl)-5-methylsulfanyl-thiophen-2-yl]-imino-methyl}-carbamic acid tert-butyl ester (0.058 mmol, 40 mg, Example 140: step a), 2-iodo-3-methyl-5-nitropyridine (0.08 mmol, 21.1), CuI (0.01 mmol, 2.2 mg) and (Ph$_3$P)$_4$Pd (0.006 mmol) in DMF (0.6 mL) was heated at 100° under Ar for 3 hr. The reaction mixture was allowed to cool to RT and poured in to water (20 mL). The product was extracted with CH$_2$Cl$_2$ (3×10 mL). CH$_2$Cl$_2$ extracts were combined, dried (Na$_2$SO$_4$) and concentrated in vaccuo. The resulting residue was purified on silica (30% EtOAc:Hexane) to obtain the expected coupling product. The product (54.8 mg, 0.1 mmol) was suspended in EtOH:water (2:1, 10 mL) and NH$_4$Cl (53.5 mg, 1 mmol) and Fe powder (28 mg, 0.5 mmol) were added. The resulting mixture was heated at reflux for 2 hr. The reaction mixture was cooled to RT and poured in to Std. Na$_2$CO$_3$ solution and the product was extracted with CH$_2$Cl$_2$ (3×10 mL). CH$_2$Cl$_2$ extracts were combined, dried (Na$_2$SO$_4$) and concentrated in vaccuo to obtain a brownish yellow oil. This compound (29 mg) was then dissolved in 1:1 mixture of CH$_2$Cl$_2$ and TFA (1 mL). The resulting solution was stirred at RT for 1 hr. and concentrated in vaccuo to obtain a yellow oil which was dried in a high vaccum. Ether (10 mL) was then added and the precipitate formed was collected by suction filtration to yield the title compound.

Yield: 28%; $^1$H NMR (DMSO) δ 9.37 (br, 2H), 9.07 (br, 2H), 8.4 ( s, 1H), 8.05 (s, 1H), 7.9 (d, J=2.6 Hz, 1H), 7.85 (m, 2H), 7.74 (t, J=6.7 Hz, 1H), 7.1 ( s, 1H), 2.6 and 2.2 (s, 3H each); MS 418.06 (M$^+$) calculated for C$_{18}$H$_{16}$N$_4$O$_2$S$_3$; found 419.1 (M$^+$+1)

Example 291

4-[3-(3-Methyl-pyrazin-2-yl)-benzenesulfonyl]-5-methylsulfanyl-thiophene-2-carboxamidine TFA salt

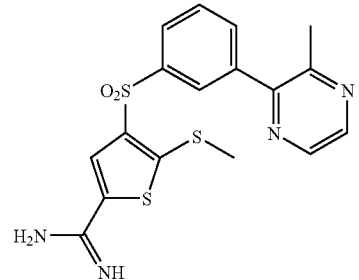

a) (Imino-{4-{3-(3-methyl-pyrazine-2-yl)-benzenesulfanyl-thiophene-2-yl}-methyl)-carbamic acid tert-butyl ester To a flask containing {Imino-[5-methylsulfanyl-4-(3-tributylstannanyl-benzenesulfonyl)-thiophen-2-yl]-methyl}-carbamic acid tert-butyl ester (22.3 mg, 0.031 mmol, Example 152: step a), methyl-iodopyrazine (8.3 mg, 0.038 mmol), Pd(PPh3)4 (10 mol %, 3.6 mg), and CuI (20 mol %, 1.2 mg) was added 0.5 mL of DMF. The flask was purged with Ar, and then heated to 100° C. for 16 h in an oil bath. The result was concentrated in vacuo and purified by preparative TLC (80% EtOAc-Hexanes) to give the 7.2 mg (46%) of the product as a yellow solid contaminated with a small amount of tin. Mass spectrum (ESI, m/z) calcd. for C$_{22}$H$_{24}$N$_4$O$_4$S3, 505.1 (M+H), found 405.1 (M+H–BOC).

¹H NMR (CDCl₃, 400 MHz): d 1.53 (s, 9H), 2.60 (s, 3H), 2.65 (s, 3H), 7.70 (t, 1H, J=8.8 Hz), 7.87–7.89 (m, 2H), 8.10 (d, 1H, J=8.8 Hz), 8.25 (s, 1H), 8.53 (m, 2H);

b) 4-[3-(3-Methyl-pyrazin-2-yl)-benzenesulfonyl]-5-methylsulfanyl-thiophene-2-carboxamidine TFA salt To a solution of 7 mg of (Imino-{4-{3-(3-methyl-pyrazine-2-yl)-benzenesulfanyl-thiophene-2-yl}-methyl)-carbamic acid tert-butyl ester (Example 291: step a) in 0.3 mL of CH₂Cl₂ at 0° C. was added 0.3 mL of TFA containing 10 μL H₂O. The reaction was allowed to warm to ambient temperature. After 1 h, the solution was concentrated in vacuo with azeotropic removal using toluene (2×5 mL). The orange-brown solid was treated with 0.2 mL hexanes/0.5 mL CHCl₃ and finely divided using sonication. The supernatant was removed via pipette. The solids were dried giving 4.8 mg (71%) of 4-[3-(3-Methyl-pyrazin-2-yl)-benzenesulfonyl]-5-methylsulfanyl-thiophene-2-carboxamidine TFA salt as a yellow film.

Mass spectrum (ESI, m/z) calcd. for $C_{17}H_{16}N_4O_2S_3$, 404.5. (M+H), found 405.1; ¹H NMR (CD₃OD, 400 MHz): d 2.62 (s, 3H), 2.74 (s, 3H), 7.79 (t, 1H, J=8.9 Hz), 7.99–8.01 (m, 1H), 8.17–8.19 (m, 1H), 8.29 (t, 1H, J=1.7 Hz), 8.35 (s, 1H), 8.56–8.58 (m, 2H);

Example 292

4-[3-(4-Piperazin-1-yl)-benzenesulfonyl]-5-methylsulfanyl-thiophene-2-carboxamidine

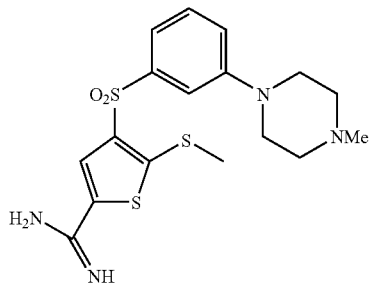

a) 4-[3-(4-Methyl-piperazin-1-yl)-benzenesulfonyl]-5-methylsufanyl-thiophene-2-carbonitrile To a flask containing 0.15 g (0.4 mmol) of 4-(3-bromo-benzenesulfonyl)-5-methylsulfanyl-thiophene-2-carbonitrile (Example 286: step f), 44.1 μL (0.4 mmol) of N-methylpipirazine, 4.5 mg (0.02 mmol) of Pd(OAc)₂, 24.8 mg (0.04 mmol) of BINAP, and 195 mg (0.6 mmol) of CsCO₃ was added 2.5 mL of toluene. The flask was purged with Ar, and heated to 100° C. for 16 h. The reaction was then concentrated in vacuo and purified by preparative TLC (50% EtOAc-Hexane), isolating the low R_f material, which was subjected to preparative TLC again (10% MeOH—CHCl₃) to give 15.5 mg (10% yield) of 4-[3-(4-methyl-piperazin-1-yl)-benzenesulfonyl]-5-methylsufanyl-thiophene-2-carbonitrile in greater than 98% purity.

Mass spectrum (ESI, m/z) calcd. for $C_{17}H_{19}N_3O_2S_3$, 394.06 (M+H), found 394.1; ¹H NMR (CDCl₃, 400 MHz): d 2.36 (s, 3H), 2.57–2.59 (m, 4H), 2.62 (s, 3H), 3.29 (m, 4H), 7.11–7.13 (m, 1H), 7.38–7.40 (m, 2H), 7.49 (d, 1H, J=1.2 Hz), 7.84 (s, 1H);

b) 4-[3-(4-Methyl-piperazin-1-yl)-benzenesulfonyl]-5-methylsulfanyl-thiophene-2-carboximidic acid methyl ester To a flask containing 15 mg (0.03 mmol) of 4-[3-(4-methyl-piperazin-1-yl)-benzenesulfonyl]-5-methylsufanyl-thiophene-2-carbonitrile (Example 292: step a) was added 1 mL of MeOH and the resultant solution was treated with 1 mL 2M NaOMe in MeOH (2 mmol) at room temperature. The reaction was heated to 50° C. for 2 h. At this time it was cooled to room temperature and 2 drops of H₂O was added. Concentration of the mixture in vacuo followed by purification by preparative TLC (5% MeOH—CHCl₃) yielded 12 mg (74%) of 4-[3-(4-methyl-piperazin-1-yl)-benzenesulfonyl]-5-methylsulfanyl-thiophene-2-carboximidic acid methyl ester as a yellow solid.

Mass spectrum (ESI, m/z) calcd. for $C_{18}H_{23}N_3O_3S_3$, 426.09 (M+H), found 426.2; ¹H NMR (CDCl₃, 400 MHz): d 2.36 (s, 3H), 2.56–2.58 (m, 7H), 3.27–3.30 (m, 4H), 3.88 (s, 3H), 7.09–7.11 (m, 1H), 7.35–7.43 (m, 2H), 7.45 (s, 1H), 7.57 (s, 1H), 7.71 (s, 1H);

c) 4-[3-(4-Piperazin-1-yl)-benzenesulfonyl]-5-methylsulfanyl-thiophene-2-carboxamidine 4-[3-(4-Methyl-piperazin-1-yl)-benzenesulfonyl]-5-methylsulfanyl-thiophene-2-carboximidic acid methyl ester (10 mg, 0.023 mmol, Example 292: step b)), NH₄OAc (10 mg, 0.6 mmol) and 1 mL of 2M NH₃ in MeOH were heated in a sealed tube at 60° C. for 3 h. The reaction was then concentrated in vacuo and purified by preparative TLC (10% MeOH—CHCl₃-sat'd NH₃) to give 8.7 mg (94%) of 4-[3-(4-Piperazin-1-yl)-benzenesulfonyl]-5-methylsulfanyl-thiophene-2-carboxamidine as a yellow solid.

Mass spectrum (ESI, m/z) calcd. for $C_{18}H_{23}N_3O_3S_3$, 411.09 (M+H), found 411.2. ¹H NMR (CD₃OD, 400 MHz): δ 2.36 (s, 3H), 2.61–2.64 (m, 4H), 2.67 (s, 3H), 3.28–3.31 (m, 4H), 7.24–7.27 (m, 1H), 7.42–7.44 (m, 2H), 7.54 (d, 1H, J=1.3 Hz), 8.00 (s, 1H);

Example 293

4-[3-(4-Methyl-pyrimidin-5-yl)-benzenesulfonyl]-5-methylsulfanyl-thiophene-2-carboxamidine

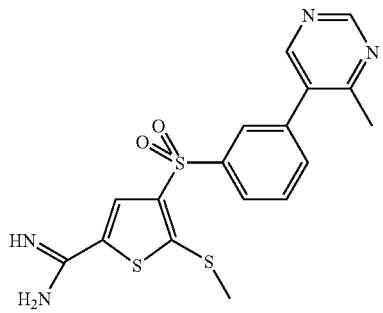

a) (Imino-{4-[3-(4-methyl-pyrimidin-5-yl)-benzenesulfonyl]-5-methylsulfanyl-thiophen-2-yl}-methyl)-carbamic acid tert-butyl ester To a flask with a reflux condenser under argon was added 5-Bromo-4-methyl-pyrimidine (9 mg, 0.044 mmol), prepared according to the procedure of Yamanaka, Sakamoto, Nishimura, and Sagi, Chem. Pharm. Bull. 35(8), 3119–3126

(1987). {[4-(3-dihydroxyboranyl-benzenesulfonyl)-5-methylsulfanyl-thiophen-2-yl]-imino-methyl}-carbamic acid tert-butyl ester (20 mg, 0.044 mmol, Example 140: step a), Na$_2$CO$_3$ (2M, 0.220 mL, 0.44 mmol), Pd(PPh$_3$)$_4$ (8 mg, 0.007 mmol), ethanol (0.220 mL) and toluene (0.440 mL). PdCl$_2$(PPh$_3$)$_2$ (42 mg, 0.06 mmol), dioxane (4 mL), and triethylamine (420 μL, 3 mmol) and the mixture was stirred for 2 h 15 min at 90° C. After cooling to rt, EtOAc (2 mL) and NaHCO$_3$ (saturated, 2 mL) were added and the layers were separated. The organic layer concentrated in vacuo followed by purification of the crude material by preparative TLC (5% methanol in dichloromethane) to yield the title compound (19 mg, 87%) as a white solid. $^1$H-NMR (CDCl$_3$): δ 9.12 (s, 1H), 8.54 (s, 1H), 8.10–7.29 (m, 7H), 2.59 (s, 3H), 2.50 (s, 3H), 1.51 (s, 9H). ESI-MS (m/z): Calcd. for C$_{22}$H$_{24}$N$_4$O$_4$S$_3$: 504.1 (M−BOC)+H; found: 405.1.

b) 4-[3-(4-Methyl-pyrimidin-5-yl)-benzenesulfonyl]-5-methylsulfanyl-thiophene-2-carboxamidine The (imino-{4-[3-(4-methyl-pyrimidin-5-yl)-benzenesulfonyl]-5-methylsulfanyl-thiophen-2-yl}-methyl)-carbamic acid tert-butyl ester ((Example 293: step a) 15 mg, 0.03 mmol) was dissolved in dichloromethane (1 mL), water (1 drop) was added, followed by trifluoroacetic acid (1 mL). The solution was stirred for 1 h 40 min at rt. The solvents were removed in vacuo, the residue was co-evaporated with dichloromethane and methanol, then purified by preparative TLC (10% methanol in dichloromethane) which yielded the title compound as a pale yellow glass (4 mg, 32%). $^1$H-NMR (CD$_3$OD): δ 9.05 (s, 1H), 8.61 (s, 1H), 8.13–8.08 (m, 2H), 8.04 (s, 1H), 7.78–7.76 (m, 2H), 2.66 (s, 3H), 2.49 (s, 3H). ESI-MS (m/z): Calcd. for C$_{17}$H$_{16}$N$_4$O$_2$S$_3$: 404.5 (M+H); found: 405.1.

Example 294

4-{4',6'-Bis-[3-(3-methanesulfonyl-propyl)-uredo]-2'-methyl-biphenyl-3-sulfonyl}-5-methylsulfanyl-thiophene-2-carboxamidine trifluoroacetate a) 4-Bromo-5-methyl-3-nitrobenzoic acid methyl ester 4-Bromo-3-methylbenzoic acid methyl ester (10.13 g, 44 mmol) was dissolved in a mixture of H$_2$SO$_4$ 120 mL and TFA (15 mL) at room temperature. The solution was cooled on an ice bath and KNO$_3$ (4.65 g, 46 mmol) was added portionwise over 30 min. The mixture was stirred at ambient temperature for 4 hours during which it warmed to rt. TLC analysis (after mini aqueous workup) showed total disappearance of starting material (30% EtOAc/Hex). The solution was poured onto ice and the aqueous slurry was extracted with EtOAc (3×150 mL). The organic layer was washed with 5% Na$_2$CO$_3$ (3×75 mL), NaHCO$_3$ (3×50 mL), water (2×100 mL), brine (100 mL), then was dried over sodium sulfate. Concentration of the solution yielded a yellowish solid/gel substance (11.6 g) which was one spot by TLC. $^1$H NMR analysis shows two (major) products in ~2:1 ratio, corresponding to the o- and m-nitrobenzoate derivatives. The material was carried onto the next step without further purification.

b) 4-Bromo-5-methyl-3-nitrobenzoic acid

4-Bromo-5-methyl-3-nitrobenzoic acid methyl ester ((Example 294: step a (11.6 g, 42.3 mmol) was dissolved in MeOH (400 mL) at rt and 2N NaOH (43 mL) was added dropwise over 30 min via addition funnel. The solution was stirred for 12 hr during which, precipitate appeared, and sm disappeared (TLC shows only baseline spot in 30% EtOAc). The pH was adjusted to ~2 with conc HCl and the methanol was removed in vacuo. EtOAc (300 mL) was added to the aqueous slurry and the layers were separated. The aqueous layer was extracted with EtOAc (2×50 mL) and then discarded. TLC analysis of the combined organic extracts showed two products (40% EtOAc in Hexanes, 4% AcOH). The combined organic extracts were washed with a 3:1 solution of 0.5N NaH$_2$PO$_4$/0.5N NaOAc (~30×50 mL portions) until removal of the o-nitrobenzoic acid (lower spot on TLC, 40% EtOAc in Hex, 4% AcOH) was complete. The organic layer was then washed with brine and dried over sodium sulfate. Concentration of the solution yielded 5.4 g (47%) of a white solid. $^1$H NMR (CD$_3$OD) δ 8.10 (m, 2H), 2.54 (s, 3H).

c) (4-Bromo-3-methyl-5-nitro-phenyl)-carbamic acid 2-trimethylsilanyl-ethyl ester Diphenylphosphorylazide (4.31 mL, 20 mmol) was added to a stirred solution of 4-bromo-3-methyl-5-nitro-benzoic acid (Example 294: step b (5.2 g, 20 mmol)) and diisopropylethylamine (3.66 mL, 21 mmol) in 1,4-dioxane (80 mL) at rt. After 30 minutes at rt, the reaction was heated to 90° C. for 5 min. Trimethylsilylethanol (5.73 mL, 40 mmol) was added and the solution was stirred for 16 h at 95° C. The solvents were removed in vacuo and the residue was partitioned between EtOAc (100 mL) and water (30 mL). The organic layer was further extracted with aq citric acid (3×30 mL), NaHCO$_3$, (2×30 mL) and brine (50 mL). Purification by column chromatography (9:1 Hex/EtOAc) yielded the title compound as a yellow solid. $^1$H NMR (CDCl$_3$) δ 7.73 (d, 1H, J=2.4 Hz), 7.41 (br d, 1H, J=1.7 Hz), 7.01 (s, 1H), 4.24 (m, 2H), 2.43 (s, 3H), 1.02 (m, 2H), 0.04 (s, 9H).

d) (3-Amino-4-bromo-5-methyl-phenyl)-carbamic acid 2-trimethylsilanyl-ethyl ester Iron powder (6.1 g, 109 mmol) was added to a suspension of (4-bromo-3-methyl-5-nitro-phenyl)-carbamic acid 2-trimethylsilanyl-ethyl ester (Example 294: step c (4.1 g, 10.9 mmol)) and NH$_4$Cl (5.84 g, 109 mmol) in EtOH (27 mL) and water (54 mL). The reaction was heated at 85° C. for 14 h. The cooled mixture was filtered through celite and the solids were washed with 1:1 EtOAc/MeOH (200 mL). The filtrate was concentrated in vacuo and the residue was partitioned between EtOAc (100 mL) and H$_2$O (30 mL). The organic solution was washed with water (30 mL), and brine (50 mL). Drying and concentration of the solution yielded the title compound (3.24 g, 86%) as a brown solid which was used without further purification. $^1$H NMR (CDCl$_3$) δ 6.96 (s, 1H), 6.54 (s, 1H), 6.39 (s, 1H), 4.26 (m, 2H), 4.16 (s, 2H), 2.35 (s, 3H), 1.06 (m, 2H), 0.08 (s, 9H).

e) [3-Amino-5-methyl-4-(4,4,5,5-tetramethyl-[1,3,2]dioxaborolan-2-yl)-phenyl]-carbamic acid 2-trimethylsilanyl-ethyl ester Palladium acetate (106 mg, 0.47 mmol), 2-(dicyclohexylphosphino)biphenyl (658 mg, 1.88 mmol), (3-amino-4-bromo-5-methyl-phenyl)-carbamic acid 2-trimethylsilanyl-ethyl ester (Example 294: step d (3.24 g, 9.38 mmol)) were combined in a flask and placed under an argon atmosphere. p-Dioxane (40 mL) was added, followed by triethylamine (5.23 mL, 38 mmol) and pinacolborane (4.08 mL, 28 mmol). The solution was stirred at 80° C. for 1 h during which a precipitate appeared. The solvent was removed in vacuo and the residue was partitioned between EtOAc (100 mL) and aq. NH$_4$Cl (50 mL). The organic layer was further extracted with NH$_4$Cl (2×30 mL), NaHCO$_3$ (30 mL), and brine (50 mL). The organic layer was dried (MgSO$_4$), concentrated in vacuo, and the residue was purified by SiO$_2$ flash column chromatography (8:2 Hex/EtOAc) to afford the product (2.44 g, 66%) as a brown solid. $^1$H NMR (CDCl$_3$) δ 6.77 (s, 1H), 6.38 (s, 1H), 6.28 (d, 1H, J=1.9 Hz), 4.91 (s, 2H), 4.23 (m, 2H), 2.42 (s, 3H), 1.32 (s, 12H), 1.03 (m, 2H), 0.05 (s, 9H).

f) {6-Amino-3'-[5-(tert-butoxycarbonylamino-imino-methyl)-2-methylsulfanyl-thiophene-3-sulfonyl]-2-methyl-biphenyl-4-yl}-carbamic acid 2-trimethylsilanyl-ethyl ester A flask with a stirbar was charged with [3-amino-5-methyl-4-(4,4,5,5-tetramethyl-[1,3,2]dioxaborolan-2-yl)-phenyl]-carbamic acid 2-trimethylsilanyl-ethyl ester ((Example 294: step e) 2.34 g, 5.96 mmol), {[4-(3-bromo-benzenesulfonyl)-5-methylsulfanyl-thiophen-2-yl]-imino-methyl}-carbamic acid tert-butyl ester ((Example 27: step c) 2.93 g, 5.96 mmol), aqueous Na$_2$CO$_3$ (2M, 11.9 mL, 23.8 mmol), ethanol (12 mL) and toluene (24 mL). The solution was sparged with argon for 10 min and Pd(PPh$_3$)$_4$ (689 mg, 0.6 mmol) was added. The biphasic solution was vigorously stirred under inert atmosphere at 80° C. for 16 h, then was cooled to rt. EtOAc (80 mL) and water (20 mL) were added and the layers were separated. The organic layer was washed with saturated NaHCO$_3$ (2×20 mL), brine (20 mL) and was dried over sodium sulfate. Removal of the solvents in vacuo followed by column chromatography (85:15 DCM/EtOAc) of the residue yielded the title compound (2.24 g, 55%) as a light brown solid. $^1$H-NMR (CDCl$_3$): δ 7.98 (ddd, 1H, J=1.3, 1.9, 7.8 Hz), 7.89 (m, 2H), 7.61 (t, 1H, J=7.7 Hz), 7.5 (dt, 1H, J=1.3, 7.7 Hz), 6.88 (s, 1H), 6.55 (d, 1H, J=1.7 Hz), 6.47 (s, 1H), 4.26 (m, 2H), 3.42 (s, 2H), 2.56 (s, 3H), 1.9 (s, 3H), 1.52 (s, 9H), 1.06 (m, 2H), 0.08 (s, 9H).

g) {[4-(4',6'-Diamino-2'-methyl-biphenyl-3-sulfonyl)-5-methylsulfanyl-thiophen-2-yl]-imino-methyl}-carbamic acid tert-butyl ester A solution of tetrabutylammonium fluoride (1M in THF, 1 mL, 1 mmol) was added to a solution of {6-amino-3'-[5-(tert-butoxycarbonylamino-imino-methyl)-2-methylsulfanyl-thiophene-3-sulfonyl]-2-methyl-biphenyl-4-yl}-carbamic acid 2-trimethylsilanyl-ethyl ester ((Example 294: step f) 86 mg, 0.11 mmol) in THF (1 mL). The solution was heated at 50° C. for 12 h, then the solution was partitioned between EtOAc (50 mL) and water (20 mL). The layers were separated and the organic layer was further extracted with water (5×10 mL) and brine (20 mL). The solution was dried over sodium sulfate and concentrated in vacuo to yield the title compound (71 mg, 84%) which was used without further purification. ESI-MS (m/z): Calcd. for C$_{24}$H$_{28}$N$_4$O$_4$S$_3$ (M+H): 533.1; found: 532.7.

h) 4-{4',6'-Bis-[3-(3-methanesulfonyl-propyl)-ureido]-2'-methyl-biphenyl-3-sulfonyl}-5-methylsulfanyl-thiophene-2-carboxamidine trifluoroacetate The procedure in Example 296 was followed using {[4-(4',6'-diamino-2'-methyl-biphenyl-3-sulfonyl)-5-methylsulfanyl-thiophen-2-yl]-imino-methyl}-carbamic acid tert-butyl ester (71 mg, 0.13 mmol), diphenylphosphoryl azide (250 µL, 1 mmol), 4-methanesulfonyl-butyric acid (166 mg, 1 mmol), and DIEA (183 µL, 1.05 mmol) in dioxane (4 mL). Analogous treatment of the crude intermediate with TFA/DCM and HPLC purification yielded the product (8 mg, 7%). $^1$H-NMR (CD$_3$OD): δ 8.30 (s, 1H), 8.04 (ddd, 1H, J=1.1, 2.1, 8.1 Hz), 7.90 (t, 1H, J=1.6 Hz), 7.73 (t, 1H, J=7.9 Hz), 7.58 (m, 1H), 7.49 (m, 1H), 7.23 (dd, 1H, J=0.6, 2.1 Hz), 3.38 (t, 2H, J=6.8 Hz), 3.20 (m, 4H), 3.0 (m, 2H), 3.01 (s, 3H), 2.97 (s, 3H), 2.74 (s. 3H), 2.05 (m, 2H), 2.02 (s, 3H), 1.87 (m, 2H). ESI-MS (m/z): Calcd. for C$_{27}$H$_{32}$N$_4$O$_4$S$_3$ (M+H): 759.1; found: 759.1, 781.1 (M+Na).

Example 295

11-[3'-(5-Carbamimidoyl-2-methylsulfanyl-thiophene-3-sulfonyl)-4-guanidino-6-methyl-biphenyl-2-ylcarbamoyl]-undecanoic acid bis-trifluoroacetate

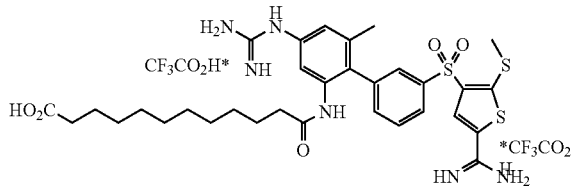

a) 8-Methyl-1H-benzo[d][1,3]oxazine-2,4-dione

To a solution of 2-amino-3-methylbenzoic acid (9.07 g, 60 mmol) in THF (60 mL) was added simultaneously diisopropylethylamine (20.9 mL) and a solution of triphosgene (5.94 g, 20 mmol) in dichloromethane (60 mL) over 30 minutes period. After the addition was completed, the mixture stirred at ambient temperature for 16 hours. Solid was filtered and washed with ether (2×100 mL) and H$_2$O (3×50 mL), and dried in high vacuum to afford the title compound (10.02 g, 94% yield) as a white solid. $^1$H NMR (DMSO) δ 11.02 (s, 1H), 7.76 (d, 1H, J=7.7 Hz), 7.57 (d, 1H, J=7.5 Hz), 7.17–7.13 (m, 1H), 2.32 (s, 3H).

b) 8-Methyl-6-nitro-1H-benzo[d][1,3]oxazine-2,4-dione

To a flask charged with 8-methyl-1H-benzo[d][1,3]oxazine-2,4-dione ((Example 295: step a) 9.27 g, 52.4 mmol) in an ice-water bath was added concentrated H$_2$SO$_4$ (90 mL) over 5 minutes period. After stirring for 10 minutes, fuming HNO$_3$ (2.9 mL) was added over 15 minutes. The reaction mixture was stirred for further 30 minutes in the ice-water bath, 30 minutes at ambient temperature, then slowly poured into ice with stirring. The solid was collected, washed with H$_2$O (3×50 mL), and dried in high vacuum to give the title compound (10.4 g, 89% yield) as a yellow solid. $^1$H NMR (DMSO) δ 11.65 (br s, 1H), 8.46–8.43 (m, 2H), 2.44 (s, 3H).

c) 2-Amino-3-methyl-5-nitro-benzoic acid methyl ester

To a suspension of 8-methyl-6-nitro-1H-benzo[d][1,3] oxazine-2,4-dione ((Example 295: step b) 1.04 g, 4.68 mmol) in methanol (30 mL) was added a solution of sodium methoxide (0.5 M, 0.94 mL, 4.7 mmol) in methanol. The mixture was stirred at ambient temperature for 1 hour and neutralized by addition of saturated NH₄Cl. Methanol was removed under reduced pressure and the resulting mixture was filtered. The solids were washed with H₂O (twice), dried in high vacuum to give the product (0.97 g, 99% yield) as a yellow solid. ¹H NMR (DMSO) δ 8.48 (d, 1H, J=2.7 Hz), 8.02–8.01 (m, 1H), 7.75 (br s, 2H), 3.86 (s, 3H), 2.20 (s, 3H).

d) 2-Bromo-3-methyl-5-nitro-benzoic acid methyl ester

To a flask charged with copper (II) bromide (7.40 g, 33.1 mmol) was added a solution of t-butyl nitrite (4.50 mL, 37.9 mmol) in MeCN (30 mL) at ambient temperature. After stirring for 5 minutes, a suspension of 2-amino-3-methyl-5-nitro-benzoic acid methyl ester ((Example 295: step c) 4.97 g, 23.7 mmol) in MeCN (50 mL) was added. The mixture was stirred at ambient temperature for 15 minutes, 65° C. for 20 minutes, then cooled back to ambient temperature. The reaction was filtered and the filtrate was concentrated to give a dark brown solid. The solid was triturated with hexane, filtered off, and washed with hexane (4×50 mL). All hexane layers were combined and concentrated to give the title product (5.7 g, 88% yield) as a pale yellow solid. ¹H NMR (CDCl₃) δ 8.35 (d, 1H, J=2.5 Hz), 8.21 (d, 1H, J=2.9 Hz), 3.99 (s, 3H), 2.59 (s, 3H).

e) 2-Bromo-3-methyl-5-nitro-benzoic acid

To a solution of 2-bromo-3-methyl-5-nitro-benzoic acid methyl ester ((Example 295: step d) 5.04 g) in ethanol (50 mL) was added a solution of aq NaOH (4M, 1.62 g, 40.5 mmol) and stirred at ambient temperature for 16 h. The resulting red colored solution was concentrated to dryness, dissolved in a minimum amount of H₂O, and acidified with 1 N HCl to pH 3–4. The solid was filtered, washed with H₂O (3×50 mL) dried under high vacuum to afford the title compound (4.5 g, 94% yield) as a pale yellow solid. ¹H NMR (DMSO) δ 8.36–8.35 (m, 1H), 8.24–8.23 (m, 1H), 2.53 (s, 3H).

f) (2-Bromo-3-methyl-5-nitro-phenyl)-carbamic acid tert-butyl ester

Diphenylphosphorylazide (453 μL, 2.1 mmol) was added to a stirred solution of 2-bromo-3-methyl-5-nitro-benzoic acid ((Example 295: step e) 520 mg, 2 mmol) and triethylamine (1.4 mL, 2.1 mmol) in tert-butanol (25 mL) at rt. After 15 minutes, the reaction was heated to 80° C. for 16 h. EtOAc (100 mL) was added and the solution was extracted with solutions of citric acid (3×30 mL), NaHCO₃, (2×30 mL) and brine (50 mL). Purification by column chromatography yielded the title compound as a white solid. ¹H NMR (CDCl₃) δ 8.93 (d, 1H, J=2.6 Hz), 7.77 (app dd, 1H, J=0.7, 2.8 Hz), 7.26 (br s, 1H), 2.51 (s, 3H), 1.55 (s, 9H).

g) 2-Bromo-3-methyl-5-nitro-phenylamine

2-Bromo-3-methyl-5-nitro-phenyl)-carbamic acid tert-butyl ester ((Example 295: step d) 435 mg, 1.32 mmol) was dissolved in 10 mL of a 1:1 mixture of trifluoroacetic acid and DCM (10 mL total). After stirring for 1 h, the solvent was removed in vacuo and the yellow solid residue (306 mg) was used without further purification. ¹H NMR (CDCl₃) δ 7.46 (d, 1H, J=2.8 Hz), 7.42 (d, 1H J=2.8 Hz), 6.62 (br s, 2H), 2.42 (s, 3H).

h) {[4-(6'-Amino-2'-methyl-4'-nitro-biphenyl-3-sulfonyl)-5-methylsulfanyl-thiophen-2-yl]-imino-methyl}-carbamic acid tert-butyl ester A flask with a stirbar was charged with {[4-(3-dihydroxyboranyl-benzenesulfonyl)-5-methylsulfanyl-thiophen-2-yl]-imino-methyl}-carbamic acid tert-butyl ester ((Example 140: step a (752 mg, 1.65 mmol), 2-bromo-3-methyl-5-nitro-phenylamine ((Example 295: step g) 306 mg, 1.32 mmol), aqueous Na₂CO₃ (2M, 4 mL, 8 mmol), ethanol (4 mL) and toluene (8 mL). The solution was sparged with argon for 10 min and Pd(PPh₃)₄ (294 mg, 0.25 mmol) was added. The biphasic solution was vigorously stirred under inert atmosphere at 80° C. for 16 h, then was cooled to rt. EtOAc (40 mL) and water (20 mL) were added and the layers were separated. The organic layer was washed with saturated NaHCO₃ (2×20 mL), brine (20 mL) and was dried over sodium sulfate. Removal of the solvents in vacuo followed by column chromatography (10–40% EtOAc in hexanes) of the residue yielded the title compound (245 mg, 33%) as a yellow solid. ¹H-NMR (CDCl₃): δ 8.03 (ddd, 1H, J=1.2, 2.1, 8.1 Hz), 7.91 (s, 1H), 7.90 (t, 1H, J=1.6 Hz), 7.69 (t, 1H, J=7.9 Hz), 7.53 (app dd, 1H, J=0.7, 2.3 Hz), 7.50 (dt, 1H, J=1.4, 7.7 Hz), 7.44 (app dd, 1H, J=0.5, 2.3 Hz), 3.70 (s, 2H), 2.59 (s, 3H), 2.00 (s, 3H), 1.51 (s, 9H).

i) 11-{4-Amino-3'-[5-(tert-butoxycarbonylamino-imino-methyl)-2-methylsulfanyl-thiophene-3-sulfonyl]-6-methyl-biphenyl-2-ylcarbamoyl}-undecanoic acid methyl ester Triethylamine (139 μL, 1 mmol) was added to a solution of {[4-(6'-amino-2'-methyl-4'-nitro-biphenyl-3-sulfonyl)-5-methylsulfanyl-thiophen-2-yl]-imino-methyl}-carbamic acid tert-butyl ester ((Example 295: step h) 118 mg, 0.21 mmol) in DCM (10 mL). 11-chlorocarbonyl-undecanoic acid ethyl ester (73 mg, 0.26 mmol) was added dropwise over 5 min. After 30 minutes of stirring, the reaction was not complete. Additional portions of acid chloride (3×1 eq) were added in a similar manner, until the reaction was complete. Addition of EtOAc (40 mL) followed by aqueous workup with NaHCO₃ (2×20 mL) and brine (30 mL) yielded the crude amide (206 mg) as a glass. The residue was dissolved in EtOH (5 mL) and 4M aq NH₄Cl (1 mL) was added. Iron powder (165 mg, 3 mmol) was added and the reaction was heated at 75° C. for 1 h. The cooled mixture was filtered through a 0.22 μm filter and solids washed with 5 mL portions of MeOH and EtOAc. Additional EtOAc (80 mL) was added and the organic solution was washed with citric acid (2×20 mL), NaHCO₃ (2×30 mL), water (30 mL), and brine (50 mL). Drying and concentration of the solution yielded the title compound (165 mg) which was used without further purification.

j) 11-{3'-[5-(tert-Butoxycarbonylamino-imino-methyl)-2-methylsulfanyl-thiophene-3-sulfonyl]-4-(N,N-bis-(tert-Butoxycarbonylamino))guanidino-6-methyl-biphenyl-2-ylcarbamoyl}-undecanoic acid Sodium hydroxide (1M, 1 mL) was added to a solution of 11-{4-amino-3'-[5-(tert-butoxycarbonylamino-imino-methyl)-2-methylsulfanyl-thiophene-3-sulfonyl]-6-methyl-biphenyl-2-ylcarbamoyl}-undecanoic acid methyl ester ((Example 295: step i) 122 mg, 0.16 mmol) in MeOH (10 mL). The solution was stirred for 18 h at rt, the solution was quenched with AcOH (500 μL), and the solvent was removed in vacuo. The residue was dissolved in MeOH (10 mL), AcOH (500 μL), and N,N-bis(tert-butoxycarbonyl)-S-methyl-isothiourea (145 mg, 0.5 mmol) was added. The solution was stirred at 40° C. for 16 h and the solvent removed in vacuo. The residue was partitioned between EtOAc (50 mL) and water (20 mL) and the organic layer was washed with brine (20 mL). Drying and concentration of the solution yielded a residue which was purified by $SiO_2$ flash column chromatography (6:4 Hex/EtOAc, then 25:75:5 Hex/EtOAc/MeOH). The residue was further purified by RP-HPLC (C-18 column, $CH_3CN/H_2O$) to yield 115 mg of product). $^1H$-NMR ($CD_3OD$): δ 8.16 (s, 1H), 8.01(ddd, 1H, J=1.2, 1.9, 7.9 Hz), 7.87 (t, 1H, J=1.6 Hz), 7.65 (t, 1H, J=7.9 Hz), 7.53 (m, 1H), 7.50 (dt, 1H, J=1.4, 7.7 Hz), 7.39 (m, 1H), 2.66 (s, 3H), 2.29 (t, 2H, J=7.4 Hz), 2.05 (s, 3H), 1.93 (m, 2H), 1.61 (m, 2H), 1.53 (s, 18H), 1.49 (s, 9H), 1.0–1.40 (m, 12H), 0.94 (m, 2H).

k) 11-[3'-(5-Carbamimidoyl-2-methylsulfanyl-thiophene-3-sulfonyl)-4-guanidino-6-methyl-biphenyl-2-ylcarbamoyl]-undecanoic acid bis trifluoroacetate The procedure in Example 260: step b was followed using 11-{3'-[5-(tert-butoxycarbonylamino-imino-methyl)-2-methylsulfanyl-thiophene-3-sulfonyl]-4-(N,N-bis-(tert-butoxycarbonylamino))guanidino-6-methyl-biphenyl-2-ylcarbamoyl}-undecanoic acid ((Example 295: step j) 15 mg, 0.015 mmol) and 1:1 TFA/DCM (10 mL). Purification by HPLC yielded the product (8.2 mg, 55%) as an opaque glass. $^1H$-NMR ($CD_3CN/D_2O$): δ 8.16 (s, 1H), 7.79 (ddd, J=1.2, 2.1, 7.9 Hz), 7.82 (m, 1H), 7.67 (t, 1H, J=7.9 Hz), 7.49 (m, 1H), 7.18 (m, 1H), 7.14 (m, 1H), 2.65 (s, 3H), 2.26 (t, 2H, J=7.4 Hz), 2.02 (s, 3H), 1.85 (m, 2H), 1.55 (m, 1H), 0.9–1.3 (m, 12H), 0.80 (m, 2H). ESI-MS (m/z): Calcd. for $C_{32}H_{42}N_6O_5S_3$ (M+H): 687.2; found: 687.2.

Example 296

4-{4'-[3-(3-Methanesulfonyl-propyl)-ureido]-2'-methyl-biphenyl-3-sulfonyl}-5-methylsulfanyl-thiophene-2-carboxamidine trifluoroacetate

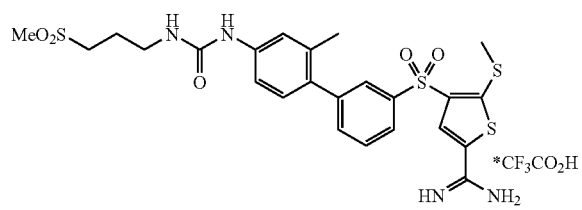

Diphenylphosphoryl azide (250 μL, 1 mmol) was added to a solution of 4-methanesulfonyl-butyric acid ((Example 209: part a) 166 mg, 1 mmol) and DIEA (183 μL, 1.05 mmol) in dioxane (4 mL). The solution was stirred at rt for 15 min, then stirred at 90° C. for 3 h. The solution was cooled, then an aliquot (250 μL) was added to a solution of {[4-(4'-amino-2'-methyl-biphenyl-3-sulfonyl)-5-methylsulfanyl-thiophen-2-yl]-imino-methyl}-carbamic acid tert-butyl ester ((Example 220: step b) 76 mg) in DCM (2 mL). The reaction was stirred overnight and the solvent was removed in vacuo. The residue was partially purified by $SiO_2$ flash column chromatography. The impure urea was treated with 1:1 TFA/DCM as described in Example 1: step d and was purified by HPLC to yield the title compound (31 mg, 19%). $^1H$-NMR ($CD_3OD$): δ 8.32 (s, 1H), 8.0 (m, 1H), 7.97 (m, 1H), 7.67 (m, 2H), 7.33 (m, 2H), 7.13 (d, 1H, J=8.1 Hz), 3.37 (t, 2H, J=6.8 Hz), 3.20 (m, 2H), 3.0 (s, 3H), 2.73 (s, 3H), 2.22 (s, 3H), 2.05 (m, 2H). ESI-MS (m/z): Calcd. for $C_{24}H_{28}N_4O_5S_4$ (M+H): 581.1; found: 581.1.

Example 297

4-[2'-Methyl-6'-(4-methyl-piperazin-1-ylmethyl)-biphenyl-3-sulfonyl]-5-methylsulfanyl-thiophene-2-carboxamidine bis-trifluoroacetate

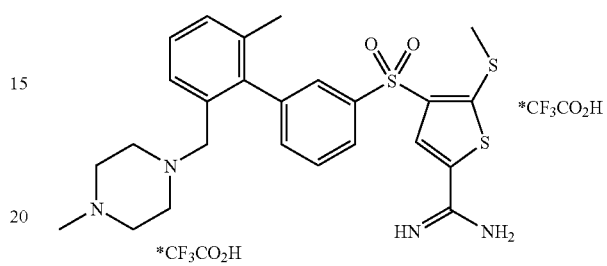

Methanesulfonyl chloride (100 μL) was added over 1 min to a 0° C. solution of {[4-(6'-hydroxymethyl-2'-methyl-biphenyl-3-sulfonyl)-5-methylsulfanyl-thiophen-2-yl]-imino-methyl}-carbamic acid tert-butyl ester ((Example 5: step c) (30 mg, 0.06 mmol) and diisopropylethylamine (0.25 mL) in DCM (10 mL). The solution was stirred for 1 h at 0° C. and warmed to rt. 1-Methylpiperazine was added (0.25 mL) and the solution was stirred for 3 h at rt. The volatile components were removed in vacuo and the residue was treated with 1:1 TFA/DCM (10 mL) for 2 h at rt. The solvent was removed in vacuo the residue was purified via preparative HPLC ($C_{18}$-column, 10–70% $CH_3CN$ over 30 min) which yielded the title compound as a opaque glass (8.2 mg). $^1H$-NMR ($CD_3OD$): δ 8.38 (s, 1H), 8.02 (ddd, 2H, J=1.2, 1.9, 7.9 Hz), 7.98 (t, 1H, J=1.6 Hz), 7.72 (t, 1H, J=7.9 Hz), 7.57 (dt, 1H, J=1.4, 7.7 Hz), 7.26–7.35 (m, 3H), 3.39 (d, 1H, J=12.9 Hz), 3.21 (d, 1H, J=12.9 Hz), 3.20 (br s, 4H), 2.87 (s, 3H), 2.75 (s, 3H), 2.50 (br s, 4H), 1.98 (s, 3H). ESI-MS (m/z): Calcd. for $C_{25}H_{30}N_4O_2S_3$ (M+H): 515.2; found: 515.2.

Example 298

4-(2'-Methyl-6'-morpholin-4-ylmethyl-biphenyl-3-sulfonyl)-5-methylsulfanyl-thiophene-2-carboxamidine

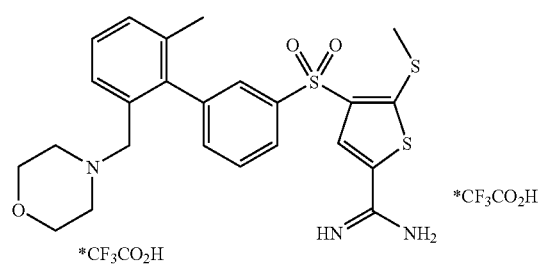

Methanesulfonyl chloride (100 μL) was added over 1 min to a 0° C. solution of {[4-(6'-hydroxymethyl-2'-methyl-biphenyl-3-sulfonyl)-5-methylsulfanyl-thiophen-2-yl]-imino-methyl}-carbamic acid tert-butyl ester (Example 5: step c) (30 mg)) and diisopropylethylamine (0.25 mL) in DCM (10 mL). The solution was stirred for 1 h at 0° C. and warmed to rt. 4-Methylmorpholine (0.5 mL) was added and the solution was stirred for 3 h at rt. The volatile components were removed in vacuo and the residue was treated with 1:1 TFA/DCM (10 mL) for 2 h at rt. The solvent was removed in vacuo and the residue was purified by preparative HPLC ($C_{18}$-column, 10–70% $CH_3CN$ over 30 min) which yielded the title compound as a opaque glass (6.8 mg). $^1$H-NMR ($CD_3OD$): δ 8.40 (s, 1H), 8.13 (ddd, 1H, J=1.2, 1.9, 7.9 Hz), 7.97 (t, 1H, J=1.6 Hz), 7.82 (t, 1H, J=7.9 Hz), 7.61 (m, 2H), 7.49 (m, 2H), 4.15 (d, 1H, J=13.5 Hz), 4.07 (d, 1H, J=13.5 Hz), 3.82 (br s, 4H), 2.75 (s, 3H), 2.18 (s, 2H), 2.03 (s, 3H), 1.31 (s, 2H). ESI-MS (m/z): Calcd. for $C_{24}H_{27}N_3O_3S_3$ (M+H): 502.1; found: 502.1.

Example 299

[3'-(5-Carbamimidoyl-2-methylsulfanyl-thiophene-3-sulfonyl)-6-methyl-biphenyl-2-ylmethoxy]-acetic acid trifluoroacetate

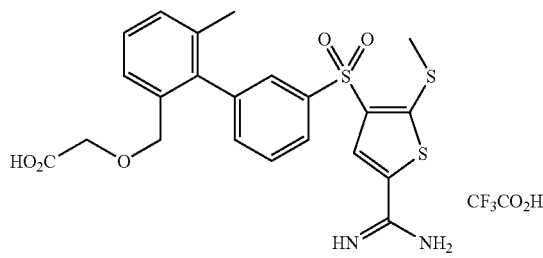

a) (2-Iodo-3-methyl-benzyloxy)-acetic acid tert-butyl ester

Sodium hydride (53 mg, 2.2 mmol) was added to a 0° C. solution of 2-iodo-3-methyl-phenyl-methanol ((Example 5: step a) 492 mg, 2 mmol) in DMF (20 mL). The solution was stirred at 0° C. for 30 min and tert-butyl bromoacetate (0.4 mL, 2.5 mmol) was added. The solution was warmed to rt over 15 min and stirred for 3 h at rt. EtOAc (80 mL) and water (40 mL) were added, the layers were separated, and the organic layer was washed with water (6×20 mL), brine (30 mL), and was dried over sodium sulfate. Concentration of the solution followed by $SiO_2$ flash column chromatography (5–10% EtOAc in hexanes) yielded the title compound (0.571 g, 79%) as an oil. $^1$H-NMR ($CDCl_3$): δ 7.36 (dd, 1H, J=1.4, 7.4 Hz), 7.30 (t, 1H, 7.4 Hz), 7.24 (dd, 1H, J=1.4, 7.4 Hz), 4.72 (s, 2H), 4.15 (s, 2H), 2.53 (s, 3H), 1.56 (s, 9H).

b) [3-Methyl-2-(4,4,5,5-tetramethyl-[1,3,2]dioxaborolan-2-yl)-benzyloxy]-acetic acid tert-butyl ester The procedure used in Example 3: step b was followed using (2-iodo-3-methyl-benzyloxy)-acetic acid tert-butyl ester ((Example 299: step a) 571 mg, 1.6 mmol), $PdCl_2(PPh_3)_2$ (55 mg, 0.08 mmol), triethylamine (1.25 mL, 9.4 mmol), and 4,4,5,5-tetramethyl-[1,3,2]dioxaborolane (0.91 mL, 6.4 mmol) in dioxane (5 mL) at a reaction temperature of 80° C. Analogous aqueous workup and purification by $SiO_2$ flash column chromatography yielded the title compound contaminated with the product resulting from halide reduction (542 mg, 95%). The material was used without further purification. $^1$H-NMR ($CDCl_3$): δ 7.20 (t, 1H, 7.4 Hz), 7.11 (d, 1H, J=7.4 Hz), 7.07 (d, 1H, J=7.4 Hz), 4.72 (s, 2H), 3.86 (s, 2H), 2.43 (s, 3H), 1.46 (s, 9H), 1.39 (s, 12H).

c) [3'-(5-Carbamimidoyl-2-methylsulfanyl-thiophene-3-sulfonyl)-6-methyl-biphenylyl-methoxy]-acetic acid trifluoroacetate The procedure used in Example 1: step c was followed using {[4-(3-bromo-benzenesulfonyl)-5-methylsulfanyl-thiophen-2-yl]-imino-methyl}-carbamic acid tert-butyl ester ((Example 27: step c) 123 mg, 0.25 mmol), [3-methyl-2-(4,4,5,5-tetramethyl-[1,3,2]dioxaborolan-2-yl)-benzyloxy]-acetic acid tert-butyl ester ((Example 299: step c) 270 mg, 0.75 mmol), $Na_2CO_3$ (2M, 1.5 mL, 3 mmol), $Pd(PPh_3)_4$ (66 mg, 0.06 mmol), ethanol (1.5 mL) and toluene (3 mL). Analogous aqueous workup yielded 417 mg of crude material which was treated with 1:1 TFA/DCM as described in Example 1: step d. Analogous purification by $C_{18}$-HPLC yielded the title compound (26.8 mg, 22%) as a white solid. $^1$H-NMR ($CD_3OD$): δ 8.35 (s, 1H), 8.07 (ddd, 1H, J=1.2, 1.9, 7.9 Hz), 7.86 (t, 1H, J=1.6 Hz), 7.71 (t, 1H, J=7.9 Hz), 7.10–7.43 (m, 3H), 4.25 (m, 2H), 4.07 (br s, 1H), 3.78 (br s, 1H), 2.73 (s, 3H), 2.35 (s, 3H), 2.02 (s, 3H). ESI-MS (m/z): Calcd. for $C_{22}H_{22}N_2O_5S_3$ (M+H): 490.1; found: 490.1.

Example 300

[3'-(5-Carbamimidoyl-2-methylsulfanyl-thiophene-3-sulfonyl)-6-methyl-biphenyl-3-ylmethoxy]-acetic acid

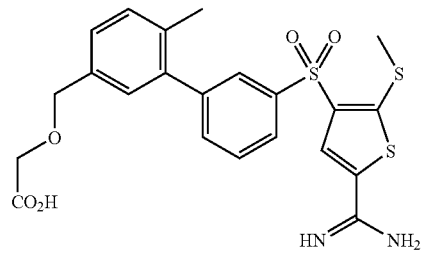

a) (3-Iodo-4-methyl-benzyloxy)-acetic acid tert-butyl ester

The procedure used in Example 299: step a was followed using sodium hydride (53 mg, 2.2 mmol), 3-iodo-4-methyl-benzyl alcohol (992 mg, 4 mmol), tert-butyl bromoacetate (0.4 mL, 2.5 mmol) in DMF (10 mL). Analogous aqueous workup and purification by $SiO_2$ flash column chromatography yielded the title compound (1.30 g, 89%) as an oil. $^1$H-NMR ($CDCl_3$): δ 7.84 (d, 1H, J=1.4 Hz), 7.27 (d, 1H, J=1.4 Hz), 7.23 (d, 1H, J=7.7 Hz), 4.55 (s, 2H), 3.99 (s, 2H), 2.44 (s, 3H), 1.51 (s, 9H).

b) [4-Methyl-3-(4,4,5,5-tetramethyl-[1,3,2]dioxaborolan-2-yl)-benzyloxy]-acetic acid tert-butyl ester The procedure used in Example 3: step b was followed using (3-iodo-4-methyl-benzyloxy)-acetic acid tert-butyl ester ((Example 300: step a) 600 mg, 1.65 mmol), $PdCl_2(PPh_3)_2$ (58 mg, 0.08 mmol), triethylamine (1.25 mL, 9.4 mmol), and 4,4,5,5-tetramethyl-[1,3,2]dioxaborolane (0.91 mL, 6.4 mmol) in dioxane (5 mL). Analogous aqueous workup and purification by SiO$_2$ flash column chromatography yielded the title compound contaminated with the product resulting from halide reduction (569 mg, 95%). The material was used without further purification. $^1$H-NMR (CDCl$_3$): δ 7.73 (d, 1H, J=1.9 Hz), 7.38 (dd, 1H, J=2.1, 7.9 Hz), 7.18 (d, 1H, J=7.9 Hz), 4.61 (s, 2H), 3.97 (s, 2H), 2.55 (s, 3H), 1.50 (s, 9H), 1.37 (s, 9H).

c) [3'-(5-Carbamimidoyl-2-methylsulfanyl-thiophene-3-sulfonyl)-6-methyl-biphenyl-2-yl-methoxy]-acetic acid trifluoroacetate The procedure used in Example 1: step c was followed using {[4-(3-bromo-benzenesulfonyl)-5-methylsulfanyl-thiophen-2-yl]-imino-methyl}-carbamic acid tert-butyl ester ((Example 27: step c) (239 mg, 0.24 mmol)), [4-methyl-3-(4,4,5,5-tetramethyl-[1,3,2]dioxaborolan-2-yl)-benzyloxy]-acetic acid tert-butyl ester ((Example 300: step c) 530 mg, 1.46 mmol), Na$_2$CO$_3$ (2M, 3 mL, 6 mmol), Pd(PPh$_3$)$_4$ (70 mg, 0.06 mmol), ethanol (3 mL) and toluene (6 mL). Analogous aqueous workup yielded 629 mg of crude material which was treated with 1:1 TFA/DCM as described in Example 1: step d. Analogous purification by C$_{18}$-HPLC yielded the title compound (47 mg, 38%) as a white solid. RP-HPLC (5 to 100% ACN over 8 min) analytical purity=100%. ESI-MS (m/z): Calcd. for C$_{22}$H$_{22}$N$_2$O$_5$S$_3$ (M+H): 491.1; found: 491.1.

Example 301

3'-(5-Carbamimidoyl-2-methylsulfanyl-thiophene-3-sulfonyl)-6-methyl-biphenyl-3-carboxylic acid (3-morpholin-4-yl-propyl)-amide bis trifluoroacetamide

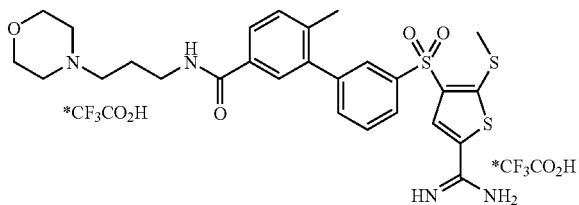

a) 3-Iodo-4-methyl-N-(3-morpholin-4-yl-propyl)-benzamide

Thionyl chloride (5.6 mL) was added over 1 min to a 0° C. solution of 3-iodo-4-methyl benzoic acid (5 g, 19.1 mmol) in THF (30 mL). The solution was stirred for 24 h at rt and the volatile components were removed in vacuo. A portion of the crude acid chloride (1 g, 3.57 mmol) was dissolved in DCM (10 mL) and was cooled to 0° C. Diisopropylethylamine (0.78 mL, 4.46 mmol) was added followed by 3-morpholin-4-yl-propylamine (0.52 mL, 3.56 mmol) and the reaction was stirred for 1 h at rt. EtOAc (80 mL) and aq. NH$_4$Cl (20 mL) was added and the layers were separated. The organic layer was washed with aq NH$_4$Cl (2×10 mL), NaOH (1N, 3×20 mL), water (20 mL), brine (50 mL) and was dried over sodium sulfate. Concentration of the solution and SiO$_2$ flash column chromatography of the residue (0–10% MeOH in DCM) yielded the product (695 mg, 50%) as a yellow glass.

b) 4-Methyl-N-(3-morpholin-4-yl-propyl)-3-(4,4,5,5-tetramethyl-[1,3,2]dioxaborolan-2-yl)-benzamide The procedure used in Example 3: step b was followed using 3-iodo-4-methyl-N-(3-morpholin-4-yl-propyl)-benzamide ((Example 301: step a) 695 mg, 1.79 mmol), PdCl$_2$(PPh$_3$)$_2$ (63 mg, 0.09 mmol), triethylamine (1.25 mL, 9.4 mmol), and 4,4,5,5-tetramethyl-[1,3,2]dioxaborolane (0.91 mL, 6.4 mmol) in dioxane (5 mL). Analogous aqueous workup and purification by SiO$_2$ flash column chromatography (0–10% MeOH in DCM) yielded the title compound contaminated with the product resulting from halide reduction (653 mg, 94%). The material was used without further purification.

c) 3'-(5-Carbamimidoyl-2-methylsulfanyl-thiophene-3-sulfonyl)-6-methyl-biphenyl-3-carboxylic acid (3-morpholin-4-yl-propyl)-amide bis trifluoroacetamide The procedure used in Example 1: step c was followed using {[4-(3-bromo-benzenesulfonyl)-5-methylsulfanyl-thiophen-2-yl]-imino-methyl}-carbamic acid tert-butyl ester ((Example 27: step c) (237 mg, 0.24 mmol)), 4-methyl-N-(3-morpholin-4-yl-propyl)-3-(4,4,5,5-tetramethyl-[1,3,2]dioxaborolan-2-yl)-benzamide ((Example 301: step b) 563 mg, 1.45 mmol), Na$_2$CO$_3$ (2M, 3 mL, 6 mmol), Pd(PPh$_3$)$_4$ (67 mg, 0.06 mmol), ethanol (3 mL) and toluene (6 mL). Analogous aqueous workup followed by SiO$_2$ flash column chromatography (0–10% MeOH in DCM) yielded 605 mg of material which was treated with 1:1 TFA/DCM as described in Example 1: step d. Analogous purification by C$_{18}$-HPLC yielded the title compound (92 mg, 48%) as a white solid. RP-HPLC (5 to 100% ACN over 8 min) analytical purity=100%. ESI-MS (m/z): Calcd. for C$_{27}$H$_{32}$N$_4$O$_4$S$_3$ (M+H): 573.2; found: 573.2.

Example 302

3'-(5-Carbamimidoyl-2-methylsulfanyl-thiophene-3-sulfonyl)-6-methyl-biphenyl-2-carboxylic acid (3-morpholin-4-yl-propyl)-amide bis trifluoroacetamide

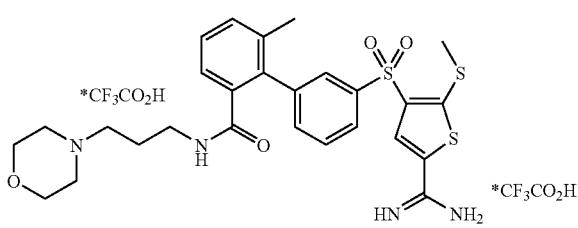

a) 2-Iodo-3-methyl-N-(3-morpholin-4-yl-propyl)-benzamide

The procedure and scale used in Example 301: step a was followed using 2-iodo-3-methyl benzoic acid. Concentration of the solution and SiO$_2$ flash column chromatography of the residue (0–10% MeOH in DCM) yielded the product (878 mg, 63%) as a yellow glass.

b) 3'-(5-Carbamimidoyl-2-methylsulfanyl-thiophene-3-sulfonyl)-6-methyl-biphenyl-2-carboxylic acid (3-morpholin-4-yl-propyl)-amide bis trifluoroacetamide The procedure used in Example 295: step h was followed using 2-iodo-3-methyl-N-(3-morpholin-4-yl-propyl)-benzamide ((Example 302: step a) 150 mg, 0.39 mmol), {[4-(3-dihydroxyboranyl-benzenesulfonyl)-5-methylsulfanyl-thiophen-2-yl]-imino-methyl}-carbamic acid tert-butyl ester ((Example 140: step a (25 mg, 0.05 mmol), $Na_2CO_3$ (2M, 1 mL, 2 mmol), Pd(PPh$_3$)$_4$ (30 mg, 0.03 mmol), ethanol (1 mL) and toluene (2 mL). Analogous aqueous workup followed by $SiO_2$ flash column chromatography (0–10% MeOH in DCM) yielded 60 mg of material which was treated with 1:1 TFA/DCM as described in Example 1: step d. Analogous purification by $C_{18}$-HPLC yielded the title compound (22 mg, 55%) as a white solid. $^1$H-NMR (CD$_3$OD): δ 8.35 (s, 1H), 8.05 (ddd, 1H, J=1.2, 1.9, 7.9 Hz), 7.96 (t, 1H, J=1.6 Hz), 7.72 (t, 1H, J=7.9 Hz), 7.66 (dt, 1H, 1.4, 7.7 Hz), 7.46 (m, 1H), 7.40 (m, 1H), 4.06 (m, 2H), 3.73 (m, 2H), 3.35 (m, 2H), 3.20 (m, 2H), 3.08 (m, 2H), 2.94 (m, 2H), 2.73 (s, 3H), 2.09 (s, 3H), 1.75 (m, 2H). ESI-MS (m/z): Calcd. for $C_{27}H_{32}N_4O_4S_3$ (M+H): 573.2; found: 573.2.

Example 303

4-[3-(6-Formyl-pyridin-2-yl)-benzenesulfonyl]-5-methylsulfanyl-thiophene-2-carboxamidine

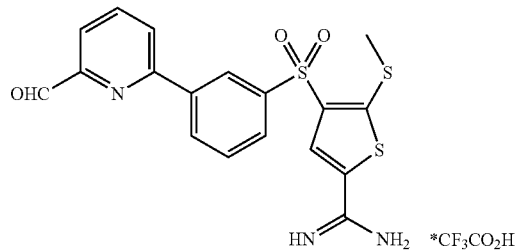

a) 2-Bromo-6-dimethoxymethyl-pyridine

The procedure in Example 6: step b was followed using 6-bromo-pyridine-2-carbaldehyde (600 mg, 3.23 mmol), trimethyl orthoformate (8 mL), and toluenesulfonic acid (100 mg) in MeOH (50 mL). Analogous aqueous workup yielded the product (743 mg) which was used without further purification.

b) 4-[3-(6-Formyl-pyridin-2-yl)-benzenesulfonyl]-5-methylsulfanyl-thiophene-2-carboxamidine To a slurry of Rieke Zinc (370 mg, 5.64 mmol) in THF (7.4 mL) was added a solution of 2-bromo-6-dimethoxymethyl-pyridine (400 mg, 1.7 mmol) in THF (2.6 mL). The suspension was heated to 65° C. for 2 h and the solution was filtered through a 0.23 μm syringe filter into a THF solution of {[4-(3-bromo-benzenesulfonyl)-5-methylsulfanyl-thiophen-2-yl]-imino-methyl}-carbamic acid tert-butyl ester ((Example 27: step c) (250 mg, 0.5 mmol)) and Pd(PPh$_3$)$_4$ (0.112 mg, 0.1 mmol). The reaction was heated at 80° C. for 30 min, cooled, and was poured into aqueous NaHCO$_3$. EtOAc (70 mL) was added and the layers were separated. The organic layer was washed with NH$_4$Cl (2×20 mL), NaHCO$_3$ (20 mL) and brine (30 mL) and was dried over sodium sulfate. Concentration of the solution followed by $SiO_2$ flash column chromatography of the residue yielded 200 mg of the title compound which was contaminated with 2-dimethoxymethyl-pyridine. The material was treated with 1:1 TFA/DCM as described in Example 1: step d. Analogous purification by $C_{18}$-HPLC yielded the title compound (118 mg, 38%) as a white solid. $^1$H-NMR (CD$_3$OD) (aldehyde exists in hydrated form (acetal)) δ 8.60 (m, 2H), 8.44 (s, 1H), 8.33 (d, 1H, J=7.9), 8.27 (d, 1H, J=7.7), 8.23 (d, 1H, J=7.7), 8.12 (d, 1H, J=7.9), 7.9 (t, 1H, J=7.7), 5.82 (s, 1H), 2.74 (s, 3H). ESI-MS (m/z) (sample in MeOH): Calcd. for $C_{18}H_{15}N_3O_3S_3$ (M+H): 418.0; found: 449.9 (MeOH adduct).

Example 304

4-[3-(6-Methyl-benzo[1,3]dioxol-5-yl)-benzenesulfonyl]-5-methylsulfanyl-thiophene-2-carboxamidine trifluoroacetate

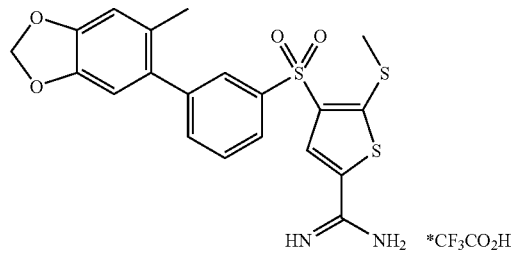

a) 5-bromo-6-methyl-benzo[1,3]dioxole

Bromine (3.36 g, 21 mmol) was added to a solution of piperonal alcohol (3.0 g, 20 mmol) in chloroform (15 mL). The solution was heated to 60° C. for 12 h. After cooling, DCM (60 mL) was added and the solution was extracted with aq NaHCO$_3$ (2×20 mL), brine (20 mL), and was dried over sodium sulfate. After concentration, the residue 5-bromo-6-bromomethyl-benzo[1,3]dioxole (5.88 g, 100%), solidified upon standing. A portion of the crude solid (2.44 g, 8.33 mmol) was dissolved in THF and cooled to –78° C. Lithium aluminum hydride (348 mg, 9.16 mmol) was added and the solution was stirred for 3 h. An additional portion of LAH (80 mg, 2.03 mmol) was added and the reaction was stirred an additional hour. EtOAc was added carefully to quench the excess LAH, followed by addition of MeOH (20 mL). The salts were filtered and the filtrate was concentrated in vacuo, to yield the title compound (1.76 g, 99%) which was used without further purification. $^1$H-NMR (CDCl$_3$): δ 7.01 (s, 1H), 6.73 (s, 1H), 5.95 (s, 2H), 2.32 (s, 3H).

b) 4-[3-(6-Methyl-benzo[1,3]dioxol-5-yl)-benzenesulfonyl]-5-methylsulfanyl-thiophene-2-carboxamidine trifluoroacetate Butyllithium (2.5 M, 2.4 mL, 6 mmol) was added dropwise to a –78° C. solution of 5-bromo-6-methyl-benzo[1,3]dioxole ((Example 304: step a) 648 mg, 3 mmol) in Et$_2$O (12 mL). The solution was stirred for 4 h maintaining the temperature between –20 and –40° C. The solution was cooled to –78° C. and trimethylborate (5 mL, 44 mmol) was quickly added in one portion. The solution was warmed to rt over 15 min and stirred for 1 h at rt (appearance of gelatin-like ppt). The volatile components were removed in vacuo to give the crude arylboronic acid as a yellow solid. A portion of the crude arylboronic acid (99 mg, 0.4 mmol) was combined with {[4-(3-bromo-benzenesulfonyl)-5-methylsulfanyl-thiophen-2-yl]-imino-methyl}-carbamic acid tert-butyl ester ((Example 27: step c) (50 mg, 0.1 mmol)), aq Na$_2$CO$_3$ (2M, 0.8 mL, 1.6 mmol), ethanol (0.8 mL), and toluene (1.6 mL). The procedure used in Example 1: step c was followed, and analogous workup yielded the product which was purified by preparative TLC. The purified material was treated with 1:1 TFA/DCM as described in Example 1: step d. Analogous purification by C$_{18}$-HPLC yielded the title compound (25 mg, 45%) as a white solid. $^1$H-NMR (CD$_3$OD): δ 8.32 (s, 1H), 7.99 (m, 1H), 7.93 (m, 1H), 7.64 (m, 2H), 6.79 (s, 1H), 6.68 (s, 1H), 2.72 (s, 3H), 2.12 (s, 3H),. ESI-MS (m/z): Calcd. for C$_{20}$H$_{18}$N$_2$O$_4$S$_3$ (M+H): 447.0; found: 447.2.

Example 305–306

4-[7-Bromo-3-(3-methyl-but-2-enyl)-3H-benzoimidazole-5-sulfonyl]-5-methylsulfanyl-thiophene-2-carboxamidine bis-trifluoroacetate

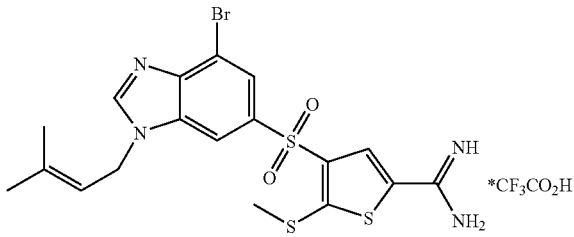

4-[7-Bromo-1-(3-methyl-but-2-enyl)-1H-benzoimidazole-5-sulfonyl]-5-methylsulfanyl-thiophene-2-carboxamidine bis-trifluoroacetate A mixture of {[4-(7-bromo-1H-benzoimidazole-5-sulfonyl)-5-methylsulfanyl-thiophen-2-yl]-imino-methyl}-carbamic acid tert-butyl ester ((Example 187–188: step c) 30 mg, 0.061 mmol), K$_2$CO$_3$ (10 mg, 0.072 mmol), and 1-bromo-3-methyl-but-2-ene (60 µL, 0.5 mmol) were stirred in DMF (2.5 mL for 16 h at rt. EtOAc (50 mL) was added and the organic solution was washed with water (8×20 mL) and brine (20 mL) and was dried over sodium sulfate. Removal of the solvent in vacuo yielded 22 mg of material which was treated with 1:1 TFA/DCM as described in Example 1: step d. Analogous purification by C$_{18}$-HPLC (10–55% CH$_3$CN over 30 min) yielded the title compounds as white solids.

4-[7-Bromo-3-(3-methyl-but-2-enyl)-3H-benzoimidazole-5-sulfonyl]-5-methylsulfanyl-thiophene-2-carboxamidine bis-trifluoroacetate. $^1$H-NMR (CDCl$_3$): δ 8.55 (s, 1H), 8.34 (s, 1H), 8.27 (m, 1H), 8.06 (m, 1H), 5.44 (m, 1H), 5.01 (m, 2H), 2.72 (s, 3H), 1.96 (s, 3H), 1.83 (s, 3H). ESI-MS (m/z): Calcd. for C$_{18}$H$_{19}$BrN$_4$O$_2$S$_3$ (M+H): 499.0; found: 498.9, 500.9 (m+2).

4-[7-Bromo-]-(3-methyl-but-2-enyl)-1H-benzoimidazole-5-sulfonyl]-5-methylsulfanyl-thiophene-2-carboxamidine bis-trifluoroacetate. $^1$H-NMR (CDCl$_3$): δ 8.50 (br s, 1H), 8.37 (br s, 1H), 8.32 (s, 1H), 8.09 (s, 1H), 5.43 (m, 1H), 5.27 (m, 2H), 2.72 (s, 3H), 1.85 (s, 3H), 1.77 (s, 3H). ESI-MS (m/z): Calcd. for C$_{18}$H$_{19}$BrN$_4$O$_2$S$_3$ (M+H): 499.0; found: 498.9, 500.9 (m+2).

Example 307–308

4-(3-Benzyl-3H-benzoimidazole-5-sulfonyl)-5-methylsulfanyl-thiophene-2-carboxamidine bis-trifluoroacetate

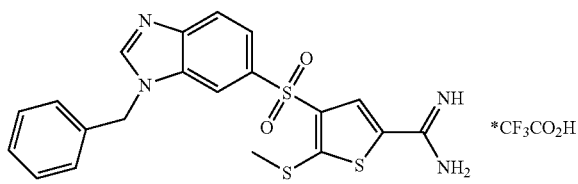

4-(1-Benzyl-1H-benzoimidazole-5-sulfonyl)-5-methylsulfanyl-thiophene-2-carboxamidine bis-trifluoroacetate

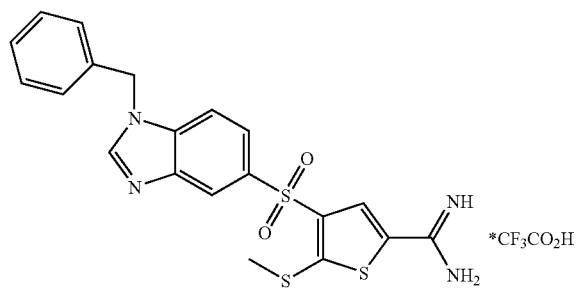

The procedure in Example 318: step e was followed using 4-(4-amino-3-nitro-benzenesulfonyl)-5-methylsulfanyl-thiophene-2-carboxylic acid methyl ester ((Example 264: step a) 40 mg, 0.1 mmol) to yield the benzimidazole intermediate which was used without further purification. ESI-MS (m/z): Calcd. for C$_{14}$H$_{12}$N$_2$O$_4$S$_3$ (M+H): 369.00; found: 369.1.

The procedure in Example 305/306 was followed using 4-(3H-benzoimidazole-5-sulfonyl)-5-methylsulfanyl-thiophene-2-carboxylic acid methyl ester ((Example 187–188: step c) 20 mg, 0.037 mmol), K$_2$CO$_3$ (25 mg, 0.18 mmol), and benzyl bromide (30 mg, 0.175 mmol) in DMF (2.5 mL). After analogous workup, the isomeric mixture of compounds was treated with dimethylaluminum amide reagent (5 mL) following the procedure in Example 12: step f. Analogous workup and purification by HPLC yielded the title compounds each as a white solid.

3-benzyl isomer: $^1$H-NMR (CD$_3$OD): δ 8.80 (br s, 1H), 8.26 (s, 1H), 8.20 (br s, 1H), 7.88 (s, 2H), 7.36 (m, 5H), 5.66 (s, 2H), 2.56 (s, 3H). ESI-MS (m/z): Calcd. for C$_{20}$H$_{18}$N$_4$O$_2$S$_3$ (M+H): 443.0; found: 443.1.

1-benzyl isomer: $^1$H-NMR (CD$_3$OD): δ 8.62 (br s, 1H), 8.44 (s, 1H), 8.32 (br s, 1H), 7.94 (dd, 1H, J=1.6, 8.8 Hz), 7.88 (s, 2H), 7.70 (d, 1H, J=8.8 Hz), 7.34 (m, 5H), 5.58 (s, 2H), 2.72 (s, 3H). ESI-MS (m/z): Calcd. for C$_{20}$H$_{18}$N$_4$O$_2$S$_3$ (M+H): 443.0; found: 443.1.

Example 309

4-[7-Bromo-1R-(1-phenyl-ethyl)-1H-benzoimidazole-5-sulfonyl]-5-methylsulfanyl-thiophene-2-carboxamidine bis-trifluoracetate

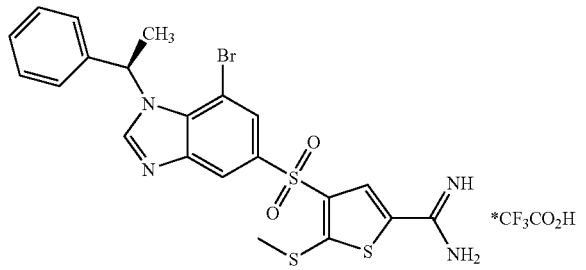

The procedures used in Example 318: parts d–f were followed using with 4-(3-bromo-4-chloro-5-nitro-benzenesulfonyl)-5-methylsulfanyl-thiophene-2-carboxylic acid methyl ester ((Example 318: part c) 35 mg, 0.072 mmol), 1R-phenyl-ethylamine (50 mg), and DIEA (100 uL). All other reagent amounts, reaction conditions, and purifications were identical to Example 318 d–f $^1$H-NMR (CD$_3$OD): δ 8.86 (s, 1H), 8.23 (s, 1H), 8.01 (d, 1H, J=1.4 Hz), 7.96 (d, 1H, J=1.4 Hz), 7.35 (m, 5H), 5.95 (q, 1H, J=7.2 Hz), 2.56 (s, 3H), 2.07 (d, 3H, J=7.2 Hz). ESI-MS (m/z): Calcd. for C$_{21}$H$_{19}$BrN$_4$O$_2$S$_3$ (M+H): 535.0; found: 534.9, 536.9 (m+2).

Example 310

4-[7-Bromo-1S-(1-phenyl-ethyl)-1H-benzoimidazole-5-sulfonyl]-5-methylsulfanyl-thiophene-2-carboxamidine bis-trifluoracetate

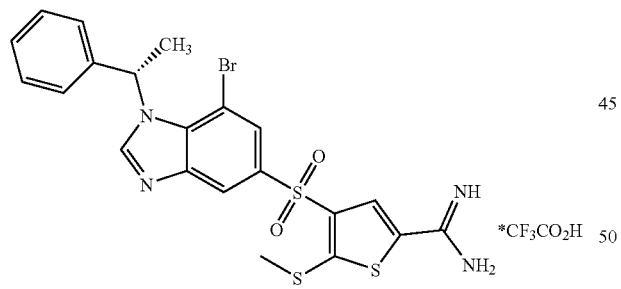

The procedures used in Example 318: parts d–f were followed using with 4-(3-bromo-4-chloro-5-nitro-benzenesulfonyl)-5-methylsulfanyl-thiophene-2-carboxylic acid methyl ester ((Example 318: part c) 35 mg, 0.072 mmol), 1S-phenyl-ethylamine (50 mg), and DIEA (100 uL). All other reagent amounts, reaction conditions, and purifications were identical to Example 318 d–f $^1$H-NMR (CD$_3$OD): δ 8.86 (s, 1H), 8.23 (s, 1H), 8.01 (d, 1H, J=1.4 Hz), 7.96 (d, 1H, J=1.4 Hz), 7.35 (m, 5H), 5.95 (q, 1H, J=7.2 Hz), 2.56 (s, 3H), 2.07 (d, 3H, J=7.2 Hz). ESI-MS (m/z): Calcd. for C$_{21}$H$_{19}$BrN$_4$O$_2$S$_3$ (M+H): 535.0; found: 534.9, 536.9 (m+2).

Example 311

6-{3-[3'-(5-Carbamimidoyl-2-methylsulfanyl-thiophene-3-sulfonyl)-2-methyl-biphenyl-4-yl]-ureido}-hexanoic acid ethyl ester trifluoroacetate

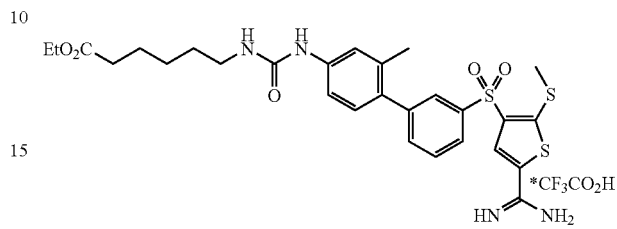

a) 6-(3-{3'-[5-(tert-Butoxycarbonylamino-iminomethyl)-2-methylsulfanyl-thiophene-3-sulfonyl]-2-methyl-biphenyl-4-yl}-ureido)-hexanoic acid ethyl ester Diisopropylethylamine (35 μL, 0.2 mmol), 6-isocyanato-hexanoic acid ethyl ester (40 μL, 0.2 mmol), and {[4-(4'-amino-2'-methyl-biphenyl-3-sulfonyl)-5-methylsulfanyl-thiophen-2-yl]-imino-methyl}-carbamic acid tert-butyl ester ((Example 220: step b) 20 mg, 0.04 mmol) were stirred for 24 h in DCM (1 mL). The solution was partitioned between EtOAc (40 mL) and 0.1 N HCl (10 mL) and was washed with additional 0.1N HCl (2×10 mL), NaHCO$_3$ (10 mL), and brine (20 mL). The solution was dried, concentrated in vacuo, and purified by SiO$_2$ preparative TLC to yield the product (12 mg, 43%). $^1$H-NMR (CDCl$_3$): δ 8.06 (s, 1H), 7.94 (m, 1H), 7.81 (m, 1H), 7.46 (m, 2H), 7.23 (br t, 1H, J=5.4 Hz), 7.15 (m, 1H), 7.07 (m, 2H), 6.97 (m, 1H), 5.32 (br t, 1H), 4.15 (q, 2H, J=7.2 Hz), 2.40 (s, 3H), 2.30 (t, 2H, J=7.3 Hz), 2.11 (s, 3H), 1.54–1.70 (m, 4H), 1.51 (s, 9H) 1.35 (m, 2H), 1.25 (t, 3H, J=7.3 Hz).

b) 6-{3-[3'-(5-Carbamimidoyl-2-methylsulfanyl-thiophene-3-sulfonyl)-2-methyl-biphenyl-4-yl]-ureido}-hexanoic acid ethyl ester trifluoroacetate Following the procedure in Example 1: step d, 6-(3-{3'-[5-(tert-butoxycarbonylamino-imino-methyl)-2-methylsulfanyl-thiophene-3-sulfonyl]-2-methyl-biphenyl-4-yl}-ureido)-hexanoic acid ethyl ester ((Example 311: step a) 12 mg) was treated with 1:1 TFA/DCM. Purification by HPLC yielded the product (8.3 mg) as a white solid. $^1$H-NMR (CD$_3$OD): δ 8.31 (s, 1H), 7.97 (m, 1H), 7.94 (m, 1H), 7.65 (m, 2H), 7.29 (m, 2H), 7.09 (m, 1H), 4.10 (q, 2H, 7.2 Hz), 3.20 (t, 2H, 7.0 Hz), 2.71 (s, 3H), 2.33 (t, 2H, J=7.3 Hz), 2.19 (s, 3H), 1.65 (m, 2H), 1.55 (m, 2H), 1.40 (m, 2H), 1.23 (t, 3H, J=7.2 Hz). ESI-MS (m/z): Calcd. for C$_{28}$H$_{34}$N$_4$O$_5$S$_3$ (M+H): 603.2; found: 603.2.

Example 312

6-{3'-[3'-(5-Carbamimidoyl-2-methylsulfanyl-thiophene-3-sulfonyl)-2-methyl-biphenyl-4-yl]-ureido}-hexanoic acid trifluoroacetate

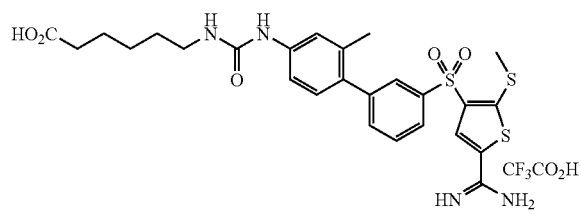

Aqueous sodium hydroxide (1M, 0.75 µL), was added to a solution of 6-(3-{3'-[5-(tert-butoxycarbonylamino-iminomethyl)-2-methylsulfanyl-thiophene-3-sulfonyl]-2-methyl-biphenyl-4-yl}-ureido)-hexanoic acid ethyl ester (Example 311: step a) 52 mg, 0.07 mmol) in MeOH. The solution was stirred for 6 h at rt, AcOH was added (100 µL) and the solvent was removed in vacuo. The residue was treated with 1:1 TFA/DCM as in Example : step d and analogously purified via RP-HPLC to yield a white solid (26 mg, 54%). $^1$H-NMR (CD$_3$OD): δ 8.34 (s, 1H), 8.00 (m, 1H), 7.95 (m, 1H), 7.67 (m, 2H), 7.32 (m, 2H), 7.11 (d, 1H, J=8.4 Hz), 3.24 (t, 2H, 7.0 Hz), 2.74 (s, 3H), 2.34 (t, 2H, J=7.3 Hz), 2.22 (s, 3H), 1.68 (m, 2H), 1.59 (m, 2H), 1.44 (m, 2H). ESI-MS (m/z): Calcd. for C$_{26}$H$_{30}$N$_4$O$_5$S$_3$ (M+H): 575.1; found: 575.1.

Example 313

6–3-[3'-(5-Carbamimidoyl-2-methylsulfanyl-thiophene-3-sulfonyl)-6-methyl-biphenyl-2-yl]-ureido}-hexanoic acid ethyl ester trifluoroacetate

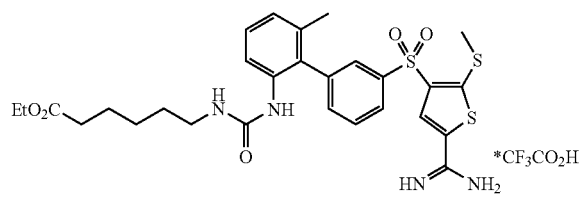

The procedure used in Example 311: step a was followed using {[4-(6'-amino-2'-methyl-biphenyl-3-sulfonyl)-5-methylsulfanyl-thiophen-2-yl]-imino-methyl}-carbamic acid tert-butyl ester ((Example 25: step c) 60 mg, 0.12 mmol), 6-isocyanato-hexanoic acid ethyl ester (28 mg, 0.15 mmol), and DIEA (89 µL, 0.5 mmol). After analogous workup and purification, the crude material was treated with 1:1 TFA/DCM as in Example 1: step d. Analogous HPLC purification yielded the product (20 mg, 24%) as a white solid. $^1$H-NMR (CD$_3$OD): δ 8.31 (s, 1H), 8.06 (ddd, 1H, J=1.2, 1.9, 7.9 Hz), 7.90 (t, 1H, J=1.6 Hz), 7.72 (t, 1H, J=7.9 Hz), 7.13 (m, 1H), 4.11 (q, 2H, 7.2 Hz), 2.99 (m, 2H), 2.73 (s, 3H), 2.29 (t, 2H, J=7.4 Hz), 2.01 (s, 3H), 1.65 (m, 2H), 1.55 (m, 2H), 1.35 (m, 2H), 1.23 (t, 3H, J=7.2 Hz). ESI-MS (m/z): Calcd. for C$_{28}$H$_{34}$N$_4$O$_5$S$_3$ (M+H): 603.2; found: 603.2.

Example 314

4-(4'-Guanidino-2'-methyl-biphenyl-3-sulfonyl)-5-methylsulfanyl-thiophene-2-carboxamidine bis-trifluoroacetate

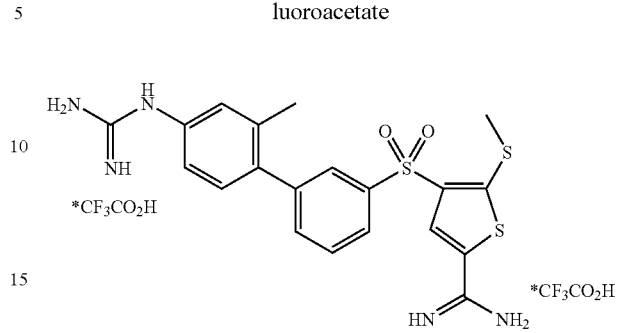

DIEA (89 µL, 0.5 mmol) was added to solution of {[4-(4'-amino-2'-methyl-biphenyl-3-sulfonyl)-5-methylsulfanyl-thiophen-2-yl]-imino-methyl}-carbamic acid tert-butyl ester ((Example 220: step b) 26 mg, 0.05 mmol), 1,3-bis-(tert-butoxycarbonyl)-2-methyl-2-thiopseudourea (29 mg, 0.1 mmol) and HgCl$_2$ (27 mg, 0.1 mmol) in DMF (2 mL). The solution became hazy after stirring for 5 min at rt. The solution was stirred for 24 h at rt and then was partitioned between EtOAc (40 mL) and water (20 mL). The layers were separated and the organic layer was extracted with citric acid (2×10 mL), NaHCO$_3$ (20 mL), water (6×10 mL), and brine (20 mL). After drying (Na$_2$SO$_4$) and concentration in vacuo the residue was purified by preparative TLC. The protected guanidine was treated 1:1 TFA/DCM as in Example 1: step d. Analogous HPLC purification yielded the product (8 mg, 24%) as a white solid. $^1$H-NMR (CD$_3$OD): δ 8.35 (s, 1H), 8.04 (m, 2H), 7.71 (m, 2H), 7.35 (d, 1H, J=8.1 Hz), 7.28 (d, 1H, J=2.3 Hz), 7.23 (dd, 1H, J=2.3, 8.1 Hz), 2.74 (s, 3H), 2.28 (s, 3H). ESI-MS (m/z): Calcd. for C$_{20}$H$_{21}$N$_5$O$_2$S$_3$ (M+H): 460.1; found: 460.2, 230.1 (m/2).

Example 315

4-[2'-Methyl-4'-(N'-methoxyl-guanidino)-biphenyl-3-sulfonyl]-5-methylsulfanyl-thiophene-2-carboxamidine bis-trifluoroacetate

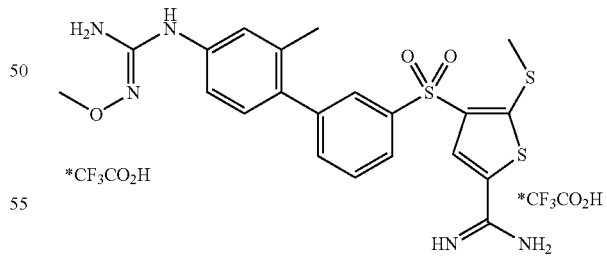

a) {Imino-[4-(4'-isothiocyanato-2'-methyl-biphenyl-3-sulfonyl)-5-methylsulfanyl-thiophen-2-yl]-methyl}-carbamic acid tert-butyl ester A solution of 1,1'-thiocarbonyldi-2(1H)-pyridone in DCM (0.25 M, 300 µL, 0.075 mmol) was added to {[4-(4'-amino-2'-methyl-biphenyl-3-sulfonyl)-5-methylsulfanyl-thiophen-2-yl]-imino-methyl}-carbamic acid tert-butyl ester ((Example 220: step b) 26 mg, 0.05 mmol) at rt. The orange color of the thiourea dissipated as the reagent was added, and a new higher spot appeared on TLC. The solvent was removed in vacuo and the residue was purified by preparative TLC to yield 23 mg of product. ¹H-NMR (CDCl₃): δ 8.01 (br s, 1H), 7.96 (d, 1H, J=7.4 Hz), 7.87 (s, 1H), 7.53 (m, 2H), 7.10 (d, 1H, J=7.9 Hz), 6.93 (br s, 1H), 6.87 (d, 1H, J=7.9 Hz), 2.51 (s, 3H), 2.17 (s, 3H), 1.50 (s, 9H).

b) 4-[2'-Methyl-4'-(N'-methoxyl-guanidino)-biphenyl-3-sulfonyl]-5-methylsulfanyl-thiophene-2-carboxamidine bis-trifluoroacetate Methoxylamine hydrochloride (30 mg, 0.36 mmol), {imino-[4-(4'-isothiocyanato-2'-methyl-biphenyl-3-sulfonyl)-5-methylsulfanyl-thiophen-2-yl]-methyl}-carbamic acid tert-butyl ester (Example 315: step a), 21 mg, 0.038 mmol), and triethylamine (100 μL) were stirred in DCM (2 mL)/CH₃CN (1 mL), was stirred for 1 h at rt. The solution was partitioned between EtOAc (40 mL) and water (20 mL) and the layers were separated. The organic layer was extracted with citric acid (3×10 mL), NaHCO₃ (20 mL), and brine (20 mL). After drying (Na₂SO₄) and concentration in vacuo, the residue was purified by preparative TLC. The purified material was dissolved in ammonia in MeOH (2M, 10 mL) and mercuric oxide (100 mg) was added. The mixture was stirred overnight at rt and at 40° C. for 3 h. The solution was filtered and the filtrate was concentrated in vacuo. The residue purified by preparative TLC and the product was treated with 1:1 TFA/DCM as in Example 1: step d. Purification by HPLC yielded the product (6 mg, 23%) as a white solid. ¹H-NMR (CD₃OD): δ 8.36 (s, 1H), 8.05 (m, 2H), 7.72 (m, 2H), 7.30 (m, 1H), 7.25 (ddd, 1H, J=0.45, 2.3, 8.1 Hz), 7.36 (d, 1H, J=8.1 Hz), 3.84 (s, 3H), 2.74 (s, 3H), 2.29 (s, 3H). ESI-MS (m/z): Calcd. for C₂₁H₂₃N₅O₃S₃ (M+H): 490.1; found: 490.1.

Example 316

4-[7-Bromo-3-(3,5-dimethyl-isoxazol-4-ylmethyl)-3H-benzoimidazole-5-sulfonyl]-5-methylsulfanyl-thiophene-2-carboxamidine bis-trifluoroacetate

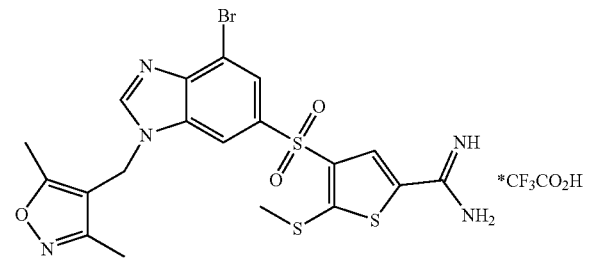

Example 317

4-[7-Bromo-1-(3,5-dimethyl-isoxazol-4-ylmethyl)-1H-benzoimidazole-5-sulfonyl]-5-methylsulfanyl-thiophene-2-carboxamidine bis-trifluoroacetate

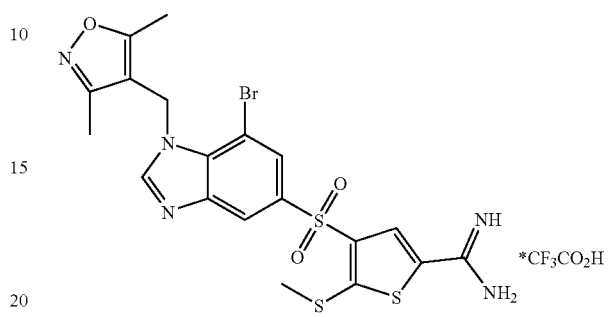

The procedure in Example 305–306 was followed using {[4-(7-bromo-1H-benzoimidazole-5-sulfonyl)-5-methylsulfanyl-thiophen-2-yl]-imino-methyl}-carbamic acid tert-butyl ester ((Example 187–188: step c) 20 mg, 0.037 mmol), K₂CO₃ (25 mg, 0.18 mmol), and 4-chloromethyl-3,5-dimethyl-isoxazole (25 μL, 0.15 mmol) in DMF (2.5 mL). The title compounds were isolated as white solids.

Example 316: ¹H-NMR (CDCl₃): δ 8.69 (s, 1H), 8.33 (s, 1H), 8.10 (d, 1H, J=1.6 Hz), 7.98 (d, 1H, J=1.6 Hz), 5.52 (s, 2H), 2.67 (s, 3H), 2.55 (s, 3H), 2.02 (s, 3H). ESI-MS (m/z): Calcd. for C₁₉H₁₈BrN₅O₃S₃ (M+H): 540.0; found: 540.0, 542.0 (m+2).

Example 317: ¹H-NMR (CDCl₃): δ 8.43 (br s, 1H), 8.40 (d, 1H, J=1.6 Hz), 8.35 (s, 1H), 8.13 (d, 1H, J=1.6 Hz), 5.73 (s, 2H), 5.27 (m, 2H), 2.73 (s, 3H), 2.19 (s, 3H), 2.03 (s, 3H). ESI-MS (m/z): Calcd. for C₁₉H₁₈BrN₅O₃S₃ (M+H): 540.0; found: 540.0, 542.0 (m+2).

Example 318

4-(7-Bromo-1-phenyl-1H-benzoimidazole-5-sulfonyl)-5-methylsulfanyl-thiophene-2-carboxamidine trifluoroacetate

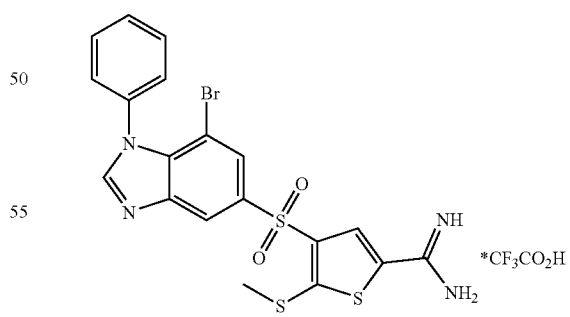

a) 4-Amino-3-bromo-5-nitro-benzenesulfonyl chloride

4-Amino-3-bromo-5-nitrobenzenesulfonamide ((U.S. Pat. No. 3,987,199) 1 g, 3.17 mmol) was heated at 95° C. for 3 h in chlorosulfonic acid (10 mL). The solution was cooled then poured onto ice and then filtered. The solid was redissolved in DCM and dried over sodium sulfate. Removal of the solvent yielded the product (960 mg) which was used without further purification.

b) 4-(4-Amino-3-bromo-5-nitro-benzenesulfonyl)-5-methylsulfanyl-thiophene-2-carboxylic acid methyl ester Sodium sulfite (643 mg, 5.1 mmol) and NaHCO$_3$ (480 mg, 5.7 mmol) were dissolved in water (20 mL) and 4-amino-3-bromo-5-nitrobenzenesulfonyl chloride ((Example 318: step b) 940 mg, 3 mmol) was added. The suspension was stirred for 1 h at rt and 5 mL of EtOH was added to aid dissolution. The mixture was stirred for 4 h at rt, during which nearly all of the sulfonyl chloride had dissolved and the major spot on TLC was at the baseline. The solvent was removed in vacuo and DMF was added (10 mL). The mixture was stirred for 15 min and the inorganic salts were allowed to settle. The DMF was removed via syringe, the salts were washed with a second portion of DMF (10 mL), and the combined DMF solution was slowly added to a 0° C. solution of 4-bromo-5-nitro-thiophene-2-carboxylic acid methyl ester ((Example 114: step c) 800 mg, 3 mmol) in DMF (20 mL). The solution was stirred for 0° C. for 1 h then overnight at rt. The DMF was removed in vacuo and the residue was partitioned between EtOAc (100 mL) and aq NaHCO$_3$ (30 mL). The layers were separated and the organic layer was washed with aq NaHCO$_3$ (2×20 mL), water (30 mL), and brine (30 mL), then dried over sodium sulfate. The solution was concentrated and the residue was dissolved in THF (20 mL) and cooled to −78° C. A solution of sodium methoxide in methanol (1M, 3.75 mL, 3.75 mmol) was added dropwise and the reaction was stirred for 30 min. Acetic acid (500 µL) was added followed by EtOAc (100 mL). The solution was washed with NaHCO$_3$ (3×30 mL), brine (40 mL), and was dried over sodium sulfate. Concentration and chromatography of the residue yielded the product (430 mg). $^1$H-NMR (CDCl$_3$): δ 8.88 (d, 1H, J=2.1 Hz), 8.27 (d, 1H, J=2.1 Hz), 8.06 (s, 1H), 3.93 (s, 3H), 2.67 (s, 3H).

c) 4-(3-Bromo-4-chloro-5-nitro-benzenesulfonyl)-5-methylsulfanyl-thiophene-2-carboxylic acid methyl ester To a mixture of CuCl$_2$ (142 mg, 1.06 mmol), and tert-butylnitrite (157 µL, 1.32 mmol) in CH$_3$CN (10 mL) was added a solution of 4-(4-amino-3-bromo-5-nitro-benzenesulfonyl)-5-methylsulfanyl-thiophene-2-carboxylic acid methyl ester ((Example 318: step b) 410 mg, 0.88 mmol) in CH$_3$CN (10 mL), dropwise over 5 min. After 1.5 h, extra CuCl$_2$ (142 mg), and tert-butylnitrite (157 µL) were added and the reaction was stirred an additional 1.5 h. The solution was cooled then partitioned between EtOAc (120 mL) and water (50 mL). The organic layer was washed with water (2×20 mL) and brine (30 mL) then was dried over sodium sulfate. Concentration of the solution followed by chromatography yielded an impure product (285 mg, 68%) that was used without further purification. $^1$H-NMR (CDCl$_3$): δ 8.43 (d, 1H, J=2.1 Hz), 8.34 (d, 1H, J=2.1 Hz), 8.02 (s, 1H), 3.90 (s, 3H), 2.66 (s, 3H).

d) 4-(3-Bromo-5-nitro-4-phenylamino-benzenesulfonyl)-5-methylsulfanyl-thiophene-2-carboxylic acid methyl ester A mixture of aniline (112 mg, 1.35 mmol), 4-(3-bromo-4-chloro-5-nitro-benzenesulfonyl)-5-methylsulfanyl-thiophene-2-carboxylic acid methyl ester ((Example 318: step c) 53 mg, 0.11 mmol), and sodium acetate (16.5 mg, 0.2 mmol) in dioxane (3 mL) was heated at 80° C. for 24 h. The mixture was partitioned between EtOAc (50 mL) and 0.5 N HCl (10 mL) and the organic layer was further extracted with 0.5 N HCl (2×10 mL), NaHCO$_3$ (10 mL), and brine (20 mL). Drying of the solution over sodium sulfate followed by concentration yielded the product (58 mg) which was used without further purification. $^1$H-NMR (CDCl$_3$): δ 8.04 (s, 1H), 7.64 (d, 1H, J=2.1 Hz), 7.32 (d, 1H, J=1.9 Hz), 7.25 (m, 2H), 6.95 (m, 1H), 6.69 (m, 2H), 5.70) (s, 1H), 3.90 (s, 3H), 2.66 (s, 3H).

e) 4-(7-Bromo-1-phenyl-1H-benzoimidazole-5-sulfonyl)-5-methylsulfanyl-thiophene-2-carboxylic acid methyl ester Iron powder (110 mg, 2 mmol) was added to a solution of 4-(3-bromo-5-nitro-4-phenylamino-benzenesulfonyl)-5-methylsulfanyl-thiophene-2-carboxylic acid methyl ester (Example 318: step d) in EtOH (4 mL) and 50% aqueous AcOH (1 mL). The reaction was stirred for 30 min at 60° C. during which a new lower spot became evident by TLC analysis. EtOAc (10 mL) was added and the mixture was filtered through a 0.22 µm polypropylene syringe filter. Additional EtOAc (30 mL) was added and the solution was extracted with aq NaHCO$_3$ (3×10 mL) and brine (20 mL). The solution was dried and concentrated in vacuo. One-half of the residue (26 mg) was suspended in formic acid (3 mL) and was heated at 95° C. for 4 h. The formic acid was removed in vacuo and the residue was purified by chromatography to yield the product (23 mg). $^1$H-NMR (CDCl$_3$): δ 8.56 (d, 1H, J=1.6 Hz), 8.13 (s, 1H), 8.07 (d, 1H, J=1.6 Hz), 8.04 (s, 1H), 7.55 (m, 3H, 7.41 (m, 2H), 3.87 (s, 3H), 2.61 (s, 3H).

f) 4-(7-Bromo-1-phenyl-1H-benzoimidazole-5-sulfonyl)-5-methylsulfanyl-thiophene-2-carboxamidine trifluoroacetate The procedure in Example 12: step f was followed using 4-(7-bromo-1-phenyl-1H-benzoimidazole-5-sulfonyl)-5-methylsulfanyl-thiophene-2-carboxylic acid methyl ester ((Example 318: step e) 23 mg, 0.044 mmol) and dimethylaluminum amide reagent (5 mL). Analogous workup and purification by HPLC yielded the title compound as a white solid (16 mg, 49%). $^1$H-NMR (CD$_3$OD): δ 8.53 (s, 1H), 8.47 (d, 1H, J=1.6 Hz), 8.37 (s, 1H), 8.10 (d, 1H, J=1.6 Hz), 7.53–7.65 (m, 5H), 2.73 (s, 3H). ESI-MS (m/z): Calcd. for C$_{19}$H$_{15}$BrN$_4$O$_2$S$_3$ (M+H): 507.0; found: 507.1, 509.1 (m+2).

Example 319

4-(6-Amino-2'-methyl-biphenyl-3-sulfonyl)-5-methylsulfanyl-thiophene-2-carboxamidine

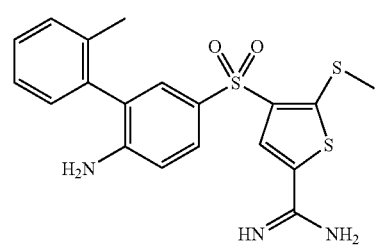

a) 3-Bromo-4-fluoro-phenylamine

Sodium chlorite (6.78 g, 75 mmol) and 4-fluoro-3-bromobenzaldehyde (24.63 mmol) were dissolved in 1:1 THF/water (100 mL) and stirred vigorously at 50° C. for 5 h. EtOAc (250 mL) and 1N HCl (50 mL) was added and the layers were separated. The organic layer was washed with water (3×50 mL), then was extracted with 0.5M $Na_2CO_3$ (10×50 mL). The combined basic aqueous layers were slowly acidified with concentrated HCl while stirring, to precipitate the carboxylic acid product. The solid was collected via filtration and dried under high vacuum overnight (4.93 g, 91%). A portion of the solid carboxylic acid was dissolved in chloroform (30 mL) and concentrated sulfuric acid was added. A reflux condenser was attached to the flask and the solution was heated to 55° C. Sodium azide (2.36 g, 36.45 mmol) was added in 3 portions over 1 h. After 4 h, additional sulfuric acid (10 mL) and sodium azide (1 g) were added and the reaction was stirred at 55° C. for 16 h. The mixture was transferred to a large cooled flask and the sulfuric acid was slowly quenched with 5N sodium hydroxide. The solution was adjusted to pH~8 and the aqueous solution was extracted with DCM (5×30 mL). The organic extracts were dried over sodium sulfate and concentrated in vacuo to yield a dark brown oil (2.2 g, 95%) that solidified upon standing. $^1$H-NMR (CDCl$_3$): δ 6.94 (t, 8.4 Hz), 6.88 (dd, 1H, J=2.8, 5.6 Hz), 6.58 (m, 1H), 3.62 (s, 2H).

b) 3-Bromo-4-fluoro-benzenesulfonyl chloride

Concentrated HCl (1.93 mL, 23.16 mmol) was added to a solution of 3-bromo-4-fluoro-phenylamine ((Example 265: part a) 2.2 g, 11.58 mmol) in 18 mL of 2:1 DCM/MeOH. A precipitate appeared and another 9 mL of 2:1 DCM/MeOH was added. The solution was cooled to −5° C. and tert-butylnitrate (2.71 mL, 23.16 mmol) was added dropwise over 8 min. After stirring for 15 min, sulfur dioxide (~5 mL) was condensed into the reaction, followed by addition of copper (II) chloride (592 mg, 3.47 mmol) (gas evolution). The solvent was removed in vacuo and the residue was purified by SiO$_2$ flash column chromatography to yield the title compound (1.9 g, 59%). $^1$H-NMR (CDCl$_3$): δ 8.31 (dd, 1H, J=2.3, 5.8 Hz), 8.04 (ddd, 1H, J=2.6, 4.1, 8.8 Hz), 7.39 (dd, 1H, J=7.7, 8.8 Hz).

c) 4-(3-Bromo-4-fluoro-benzenesulfonyl)-5-methylsulfanyl-thiophene-2-carboxylic acid methyl ester 3-Bromo-4-fluoro-benzenesulfonyl chloride ((Example 319: part b) 1.9 g, 6.83 mmol) and sodium bicarbonate (1.15 g, 13.66 mmol) was suspended in 16 mL of water at 70° C. A solution of sodium sulfite (1.64 g, 13 mmol) in 15 mL of water was added in 3 portions over 3 h. The mixture was stirred for 16 h, and the solvent was removed in vacuo. DMF (15 mL) was added, the mixture was stirred for 15 min, and the inorganic salts were then allowed to settle. The DMF was removed via syringe, the salts were washed with a second portion of DMF (10 mL), and the combined DMF solution was slowly added to a 0° C. solution of 4-bromo-5-nitro-thiophene-2-carboxylic acid methyl ester ((Example 114, step c) 931 mg, 3.5 mmol) in DMF (15 mL). The solution was stirred for 0° C. for 1 h. The DMF was removed in vacuo and the residue was partitioned between EtOAc (100 mL) and aq NaHCO$_3$ (30 mL). The layers were separated and the organic layer was washed with aq NaHCO$_3$ (2×20 mL), water (30 mL), and brine (30 mL), then dried over sodium sulfate. The solution was concentrated and the residue (1.42 g) was dissolved in THF (20 mL) and cooled to −78° C. A solution of sodium methoxide in methanol (1M, 5 mL, 5 mmol) was added dropwise and the reaction was stirred for 30 min at −78° C. Acetic acid (500 μL) was added followed by EtOAc (100 mL). The solution was washed with NaHCO$_3$ (3×30 mL), brine (40 mL), and was dried over sodium sulfate. Concentration and chromatography of the residue yielded the title compound (502 mg, 17%) as a yellow solid. $^1$H-NMR (CDCl$_3$): δ 8.16 (dd, 1H, J=2.3, 6.3 Hz), 7.94 (s, 1H), 7.91 (ddd, 1H, J=2.6, 4.4, 8.6 Hz), 7.39 (dd, 1H, J=5.3, 8.6 Hz).

d) 4-(4-Amino-3-bromo-benzenesulfonyl)-5-methylsulfanyl-thiophene-2-carboxylic acid amide The procedure in Example 124: step a was followed using 4-(3-bromo-4-fluoro-benzenesulfonyl)-5-methylsulfanyl-thiophene-2-carboxylic acid methyl ester ((Example 319: part c) 100 mg, 0.24 mmol). After 24 h, the ammonia was allowed to evaporate and the solid product was used without further purification. $^1$H-NMR (CDCl$_3$): δ 7.73 (d, 1H, J=2.1 Hz), 7.69 (s, 1H), 7.42 (dd, 1H, J=2.1, 8.6 Hz), 6.57 (d, 1H), 3.14 (s, 2H), 2.36 (s, 3H).

e) 4-(6-Amino-2'-methyl-biphenyl-3-sulfonyl)-5-methylsulfanyl-thiophene-2-carboxylic acid amide The procedure used in Example 1: step c was followed using 4-(4-amino-3-bromo-benzenesulfonyl)-5-methylsulfanyl-thiophene-2-carboxylic acid amide ((Example 319: part d) 44 mg, 0.11 mmol), 2-methylphenylboronic acid (54 mg, 0.4 mmol), aq Na$_2$CO$_3$ (2M, 800 μL, 1.6 mmol), and Pd(PPh$_3$)$_4$ (29 mg, 0.025 mmol). Analogous workup and purification by preparative TLC yielded the title compound (24 mg, 56%). $^1$H-NMR (CDCl$_3$): δ 7.97 (s, 1H), 7.76 (dd, 1H, J=2.3, 8.6 Hz), 7.67 (d, 1H, J=2.3 Hz), 7.32 (m, 2H), 7.28 (m, 1H), 7.16 (m, 1H), 6.76 (d, 1H, J=8.6 Hz), 4.11 (s, 2H), 2.58 (s, 3H), 2.13 (s, 3H).

f) 4-(6-Amino-2'-methyl-biphenyl-3-sulfonyl)-5-methylsulfanyl-thiophene-2-carboxamidine bis-trifluoroacetate The reaction conditions in Example 12: step f were followed using 4-(6-amino-2'-methyl-biphenyl-3-sulfonyl)-5-methylsulfanyl-thiophene-2-carboxylic acid amide ((Example 319: part e) 24 mg, 0.06 mmol) and dimethylaluminum amide reagent (5 mL). Analogous workup and HPLC purification yielded the title compound as an off-white solid (8.8 mg, 24%). $^1$H-NMR (CD$_3$OD): δ 8.24 (s, 1H), 7.72 (dd, 1H, J=2.3, 8.8 Hz), 7.52 (d, 1H, J=2.3 Hz), 7.33 (m, 2H), 7.28 (m, 1H), 7.12 (m, 1H), 6.85 (d, 1H, J=8.8 Hz), 2.71 (s, 3H), 2.10 (s, 3H). ESI-MS (m/z): Calcd. for C$_{19}$H$_{19}$N$_3$O$_2$S$_3$ (M+H): 418.1; found: 418.1.

Example 320

4-(6'-Methanesulfonylamino-2'-methyl-biphenyl-3-sulfonyl)-5-methylsulfanyl-thiophene-2-carboxamidine trifluoroacetate

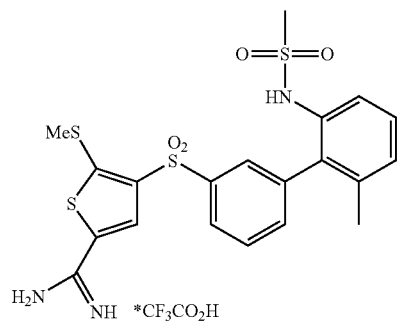

{[4-(2'-Amino-6'-methyl-biphenyl-3-sulfonyl)-5-methyl-sulfanyl-thiophen-2-yl]-imino-methyl}-carbamic acid tert-butyl ester (20 mg, 0.04 mmol, Example 25: step c) and methane sulphonyl chloride (5 mg, 0.04 mmol) were dissolved into toluene (1 mL) and heated to 100° C. for 48 hours. The solvents were removed in vacuo resulting in the desired product with loss of the tert-butyl protection group. The resulting compound was purified as in Example 1: step d, yielding the title compound as an off-white solid (1.3 mg). $^1$H-NMR (CD$_3$OD): δ 8.29 (s, 1H), 8.07–8.05 (d, 1H, J=7.21 Hz), 7.90 (m, 1H), 7.72–7.68 (t, 1H, J=8.14 Hz, J=7.67 Hz), 7.57–7.55 (d, 1H, J=7.67 Hz) 7.35 (m, 2H), 7.26 (m, 1H), 2.75 (s, 3H), 2.50 (s, 3H), 1.30 (s, 3H). ESI-MS (m/z): Calcd. for $C_{20}H_{21}N_3O_3S_4$: 496.0 (M+1); found: 496.1.

Examples 321–334

Example 335

Tablet Preparation

Tablets containing 25.0, 50.0, and 100.0 mg, respectively, of an active compound are prepared as illustrated below:

Tablet for Doses Containing from 25–100 mg of the Active Compound

|  | Amount-mg | | |
| --- | --- | --- | --- |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the cornstarch are mixed and granulated to 10% corn starch paste. The resulting granulation is sieved, dried and blended

| Ex. No. | Compound | Formula | ESI-MS (m/z) Calcd. (M + H) | Found |
| --- | --- | --- | --- | --- |
| 321 | 4-[4-Fluoro-3-(3-methyl-pyridin-2-yl)-benzenesulfonyl]-5-methylsulfanyl-thiophene-2-carboxamidine | $C_{18}H_{16}FN_3O_2S_3$ | 422.04 | 422.1 |
| 322 | 4-(3-Chloro-4-fluoro-benzenesulfonyl)-5-methylsulfanyl-thiophene-2-carboxamidine | $C_{12}H_{10}ClFN_2O_2S_3$ | 364.96 | 365.1, 367.1 (m + 2) |
| 323 | 4-(6H-Benzo[c]chromene-2-sulfonyl)-5-methylsulfanyl-thiophene-2-carboxamidine | $C_{19}H_{16}N_2O_3S_3$ | 417.03 | 417.1 |
| 324 | 4-[3-(2-Methoxymethyl-6-methyl-1H-benzoimidazol-5-yl)-benzenesulfonyl]-5-methylsulfanyl-thiophene-2-carboxamidine | $C_{22}H_{22}N_4O_3S_3$ | 487.09 | 487.1 |
| 325 | 4-[3-(3-Chloro-5-trifluoromethyl-pyridin-2-yl)-benzenesulfonyl]-5-methylsulfanyl-thiophene-2-carboxamidine | $C_{18}H_{13}ClF_3N_3O_2S_3$ | 491.98 | 492 |
| 326 | 4-[3-(2,6-Dimethyl-1H-benzoimidazol-5-yl)-benzenesulfonyl]-5-methylsulfanyl-thiophene-2-carboxamidine | $C_{21}H_{20}N_4O_2S_3$ | 457.07 | 457.1 |
| 327 | 4-[3-(1,6-Dimethyl-1H-benzoimidazol-5-yl)-benzenesulfonyl]-5-methylsulfanyl-thiophene-2-carboxamidine | $C_{21}H_{20}N_4O_2S_3$ | 457.07 | 457.1 |
| 328 | 2-Bromo-N-[3'-(5-carbamimidoyl-2-methylsulfanyl-thiophene-3-sulfonyl)-2-methyl-biphenyl-4-yl]-acetamide | $C_{21}H_{20}BrN_3O_3S_3$ | 538.0 | 540.0 |
| 329 | {[3'-(5-Carbamimidoyl-2-methylsulfanyl-thiophene-3-sulfonyl)-2-methyl-biphenyl-4-ylcarbamoyl]-methyl}-triethyl-ammonium | $C_{27}H_{35}N_4O_3S_3+$ | 560.19 | 560.0 |
| 330 | {[3'-(5-Carbamimidoyl-2-methylsulfanyl-thiophene-3-sulfonyl)-6-methyl-biphenyl-2-ylcarbamoyl]-methoxy}-acetic acid methyl ester | $C_{24}H_{25}N_3O_6S_3$ | 548.09 | 548.1 |
| 331 | 4-[3-(1-Methyl-1H-benzoimidazol-5-yl)-benzenesulfonyl]-5-methylsulfanyl-thiophene-2-carboxamidine | $C_{20}H_{18}N_4O_2S_3$ | 443.06 | 443.2 |
| 332 | 2-{[3'-(5-Carbamimidoyl-2-methylsulfanyl-thiophene-3-sulfonyl)-6-methyl-biphenyl-2-ylcarbamoyl]-methoxy}-acetamide | $C_{23}H_{24}N_4O_5S_3$ | 533.09 | 533.1 |
| 333 | 2-{[3'-(5-Carbamimidoyl-2-methylsulfanyl-thiophene-3-sulfonyl)-4-methoxy-6-methyl-biphenyl-2-ylcarbamoyl]-methylsulfanyl}-ethanesulfonic acid | $C_{24}H_{27}N_3O_7S_5$ | 630.05 | 630.0 |
| 334 | 2-Bromo-N-[3'-(5-carbamimidoyl-2-methylsulfanyl-thiophene-3-sulfonyl)-4-methoxy-6-methyl-biphenyl-2-yl]-acetamide | $C_{22}H_{22}BrN_3O_4S_3$ | 568.00 | 568.0 | with the remainder of the corn starch and the magnesium stearate. The resulting granulation is then compressed into tablets containing 25.0, 50.0, and 100.0 mg, respectively, of active ingredient per tablet.

Example 336

Intravenous Solution Preparation

An intravenous dosage form of the above-indicated active compounds is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Example 337

In Vitro Inhibition of C1s

Reagents: All buffer salts were obtained from Sigma Chemical Company (St. Louis, Mo.), and were of the highest purity available. DTNB was purchased from Pierce (Rockford, Ill.). Z-Gly-Arg-S-Bzl was purchased from Enzyme Systems Products (Livermore, Calif.). Activated human C1s was purchased from Calbiochem (La Jolla, Calif.).

$K_i$ Determinations: All assays are based on the ability of the test compound to inhibit the C1s-catalyzed hydrolysis of the substrate Z-Gly-Arg-S-Bzl, which is observed via a secondary reaction with 5,5'-dithio-bis(2-nitrobenzoic acid) (DTNB). In a typical $K_i$ determination, substrate is prepared in DMSO, and diluted into an assay buffer consisting of 50 mM HEPES, 200 mM NaCl, pH 7.5, 0.05% n-octyl-β-D-glucopyranoside. Substrate solutions were prepared at a concentration of 45 µM ($K_m$=190 µM) with DTNB at a concentration of 200 µM in assay buffer. Test compounds are prepared as a 10 µM solution in DMSO. Dilutions are prepared in DMSO yielding 7 final concentrations encompassing a 700-fold concentration range. Purified activated C1s was diluted into assay buffer for a working concentration of 66 nM.

In a typical $K_i$ determination, into each well of a 96-well plate is pipetted 280 µL of substrate solution, 10 µL of test compound solution, and the plate allowed to thermally equilibrate at 37° C. for 15 minutes. Reactions were initiated by the addition of a 10 µL aliquot of the enzyme, and the absorbance increase at 405 nm is continuously recorded for 15 minutes in a Molecular Devices plate reader. Final DMSO concentration was 4.3%. Final reagent concentrations were: [C1s]=2.3 nM, [Z-Gly-Arg-S-Bzl]=45 µM, [DTNB]=200 µM. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

COMPLEMENT INHIBITION DATA

The following compounds have Ki values in the range of 0.006 to 0.023 micromolar (µM) for C1s: Examples 1–13, 15–20, 24–26, 28–30, 32–35, 37, 41–96, 98–110, 114–119, 121, 135–136, 171, 173, 184, 192, 194–195, 203, 207, 209–211, 219–220, 224, 228, 231, 233, 236–239, 240, 242, 246, 252, 254–263, 275, 280, 282, 294–296 and 314–315.

The compound of Example 11 has a Ki value of 0.023 µM for C1s. The compound of Example 61 has a Ki value of 0.006 µM for C1s. The results indicate that the compounds of the present invention are inhibitors of complement, specifically C1s.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

ABBREVIATIONS

| DCM | dichloromethane |
|---|---|
| NaHCO$_3$ | sodium bicarbonate |
| NaOH | sodium hydroxide |
| EtOAc | ethyl acetate |
| THF | tetrahydrofuran |
| HCl | hydrochloric acid |
| Na$_2$CO$_3$ | sodium carbonate |
| Pd(PPh$_3$)$_4$ | tetrakistriphenylphosphine Pd$^0$ |
| Et$_2$O | diethyl ether |
| DMSO | dimethyl sulfoxide |
| MeOH | methanol |
| K$_2$CO$_3$ | potassium carbonate |
| DMAP-resin | 4-dimethylaminopyridine - modified resin |
| CHCl$_3$ | chloroform |
| m-CPBA | m-chloroperbenzoic acid |
| Boc | t-butyloxycarbonyl, also tBoc |
| TBAF | tetrabutyl ammonium fluoride |
| AlMe$_3$ | trimethyl aluminum |
| H$_2$SO$_4$ | sulfuric acid |
| MgSO$_4$ | magnesium sulfate |
| Cs$_2$CO$_3$ | cesium carbonate |

What is claimed is:
1. A compound of having the following formula:

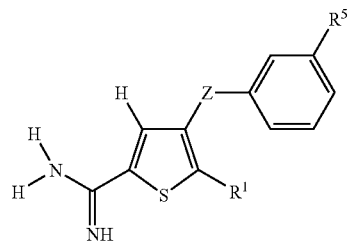

or a solvate, hydrate or pharmaceutically acceptable salt thereof; wherein:

Z is —S(O$_2$)—;

R$^1$ is C$_{1-6}$ alkylthio or methylsulfonyl; and

R$^5$ is phenyl substituted by three substituents;

one of the substituents being $C_{1-4}$ alkyl or halo;

the second substituent being $C_{1-4}$ alkyl, $C_{1-4}$ alkoxy, hydroxyl, amino, nitro, optionally-substituted ureido, or optionally substituted alkylcarbonylamino;

and the third substituent being either optionally-substituted ureido, or optionally-substituted guanidino.

2. The compound of claim 1 in which $R^1$ is methylthio.

3. The compound of claim 2 in which the $C_{1-4}$ alkyl substituent on R5 is methyl.

4. A compound of claim 1, wherein said optionally-substituted ureido has the formula $-N(L^1)-C(O)-N(L^2)-Y^{2a}-X^2-Y^{2b}-Z^2$, wherein:

$L^1$ and $L^2$ are both hydrogen, or $L^1$ and $L^2$ together represent ethylene or trimethylene;

$Y^{2a}$ is a direct covalent bond or an $\alpha,\omega$-diradical of a $C_{1-10}$ straight or branched alkane;

$X^2$ is O or S, or a direct covalent bond;

$Y^{2b}$ is an $\alpha,\omega$-diradical of a $C_{1-10}$ straight or branched alkane, optionally substituted with a carboxy group; and $Z^2$ is carboxy, ($C_{1-6}$ alkoxy)carbonyl, phenoxy, carboxyphenoxy, $C_{1-6}$ alkylsulfonyl, phenyl, benzyloxycarbonylamino, amino, $C_{1-4}$ alkylamino, halophenyl, indolyl, diphenylmethyl, phenylsulfonylamino, N'-(carboxy ($C_{1-4}$)alkyl)ureido, tetrazolyl, phosphono or phenylamino;

or, $Y^{2a}-X^2-Y^{2b}-Z^2$ represents $C_{1-4}$ alkylsulfonyl or $-(CH_2CH_2-O-)_m-(CH_2)_n-C(O)OR$ wherein m is an integer from 2 to 6, n is an integer from 2 to 4, and R is hydrogen or $C_{1-4}$ alkyl.

5. A compound of claim 1, wherein said optionally-substituted guanidino has the formula $-N(L^3)-C(=NL^4)-N(L^5)-Z^3$, wherein:

$L^3$ is hydrogen or $C_{1-4}$ alkyl;

$L^4$ and $L^5$ are both hydrogen, or $L^4$ and $L^5$ together represent ethylene; and $Z^3$ is hydrogen, $C_{1-6}$ alkyl, phenyl($C_{1-6}$)alkyl, carboxy($C_{1-6}$)alkyl, $C_{1-4}$ alkoxy, ($C_{1-4}$ alkyl)carbonyl or $C_{1-4}$ alkylsulfonyl($C_{1-6}$)alkyl.

6. A compound of claim 1 wherein said optionally-substituted alkylcarbonylamino has the formula $-N(H)-C(O)-C(H)(W^1)-Y^{1a}-X^1-Y^{1b}-Z^1$, wherein:

$W^1$ is hydrogen or amino;

$Y^{1a}$ is a direct covalent bond or an $\alpha,\omega$-diradical of a $C_{1-10}$ straight or branched alkane;

$X^1$ is O or S, or a direct covalent bond;

$Y^{1b}$ is an $\alpha,\omega$-diradical of a $C_{1-10}$ straight or branched alkane, optionally substituted with a carboxy group or an amino group; and $Z^1$ is carbamoyl, carboxy, $C_{1-6}$ alkylsulfonyl, ($C_{1-6}$ alkoxy)carbonyl, $C_{2-6}$ alkanoylamino, sulfo, phosphono, phenyl, aminosulfonyl, amino, $C_{1-6}$ haloalkylsulfonylamino, formylamino, $C_{1-6}$ alkylamino, $C_{1-6}$ alkylaminosulfonyl, $C_{1-6}$ alkylsulfonylamino or 2-oxo-hexahydro-thieno[3,4-d]imidazol-6-yl-($C_{1-6}$ alkyl)carbonylamino;

or, $W^1$ is hydrogen and $Y^{1a}-X^1-Y^{1b}-Z^1$ represents hydrogen, halo, amino or tri-($C_{1-4}$ alkyl)ammonio;

provided that, if $Y^{1a}$ is a direct covalent bond and X is O or S, then $W^1$ is hydrogen.

7. A compound of claim 1, wherein $R^5$ is phenyl substituted at the 2'-position by methyl and at the 4'-position by optionally-substituted guanidino, and in the 6' position by amino.

8. A compound of claim 1, wherein $R^5$ is phenyl substituted at the 2'-position by methyl, at the 4'-position by optionally-substituted ureido, and at the 6'-position by amino.

9. A compound of claim 1 wherein:

$R^5$ is phenyl substituted by $C_{1-4}$ alkyl, amino, and guanidino.

10. A compound of claim 1 wherein:

$R^5$ is phenyl substituted by $C_{1-4}$ alkyl, optionally substituted ureido, and optionally substituted guanidino.

11. A compound of claim 10 wherein:

$R^5$ is phenyl substituted by methyl, optionally substituted ureido, and optionally substituted guanidino.

12. A compound of claim 10 wherein:

$R^5$ is phenyl substituted by at the 2'-position with $C_{1-4}$ alkyl, at the 4' position with optionally substituted guanidino, and at the 6' position with optionally substituted ureido.

13. A compound of claim 1 wherein:

$R^5$ is phenyl substituted by three groups which are methyl, amino, and guanidino.

14. The compound of claim 1 which is 4-(4'-Guanidino-2'-methyl-6'-nitro-biphenyl-3-sulfonyl)-5-methylsulfanyl-thiophene-2-carboxamidine bis-trifluoroacetate; or 4-(6'-Amino-4'-guanidino-2'-methyl-biphenyl-3-sulfonyl)-5-methylsulfanyl-thiophene-2-carboxamidine bis-trifluoroacetate.

15. A compound of claim 1, wherein $R^5$ is phenyl substituted at the 2'-position by methyl, at the 4'-position by optionally-substituted guanidino, and at the 6'-position by optionally-substituted alkylcarbonylamino or optionally-substituted ureido.

16. The compound of claim 1 which is 4-{4'-Guanidino-2'-[3-(4-methanesulfonyl-butyl)-ureido]-6'-methyl-biphenyl-3-sulfonyl}-5-methylsulfanyl-thiophene-2-carboxamidine trifluoroacetate.

* * * * *